US011878055B1

(12) United States Patent
Muik et al.

(10) Patent No.: US 11,878,055 B1
(45) Date of Patent: Jan. 23, 2024

(54) CORONAVIRUS VACCINE

(71) Applicant: BioNTech SE, Mainz (DE)

(72) Inventors: Alexander Muik, Seeheim-Jugenheim (DE); Kena Anne Swanson, Pearl River, NY (US); Qi Yang, Orangeburg, NY (US); Hui Cai, Ridgewood, NJ (US); Ugur Sahin, Mainz (DE); Kayvon Modjarrad, Chevy Chase, MD (US)

(73) Assignee: BioNTech SE, Mainz (DE)

( * ) Notice: Subject to any disclaimer, the term of this patent is extended or adjusted under 35 U.S.C. 154(b) by 0 days.

(21) Appl. No.: 18/341,590

(22) Filed: Jun. 26, 2023

Related U.S. Application Data

(60) Provisional application No. 63/469,472, filed on May 29, 2023, provisional application No. 63/465,521, filed on May 10, 2023, provisional application No. 63/452,148, filed on Mar. 14, 2023, provisional application No. 63/486,953, filed on Feb. 24, 2023, provisional application No. 63/425,290, filed on Nov. 14, 2022, provisional application No. 63/422,404, filed on Nov. 3, 2022, provisional application No. 63/417,680, filed on Oct. 19, 2022, provisional application No. 63/402,444, filed on Aug. 30, 2022, provisional application No. 63/394,571, filed on Aug. 2, 2022, provisional application No. 63/358,522, filed on Jul. 5, 2022, provisional application No. 63/357,628, filed on Jun. 30, 2022, provisional application No. 63/355,648, filed on Jun. 26, 2022.

(30) Foreign Application Priority Data

Nov. 29, 2022 (WO) ................. PCT/EP2022/083740

(51) Int. Cl.
| *A61K 9/51* | (2006.01) |
| *A61K 31/7105* | (2006.01) |
| *A61K 31/7115* | (2006.01) |
| *A61K 39/215* | (2006.01) |
| *A61P 31/14* | (2006.01) |
| *C07K 14/005* | (2006.01) |
| *A61K 39/00* | (2006.01) |

(52) U.S. Cl.
CPC .......... *A61K 39/215* (2013.01); *C07K 14/005* (2013.01); *A61K 2039/53* (2013.01); *A61K 2039/545* (2013.01); *A61K 2039/55555* (2013.01); *A61K 2039/70* (2013.01); *C12N 2770/20022* (2013.01); *C12N 2770/20034* (2013.01); *C12N 2770/20071* (2013.01)

(58) Field of Classification Search
CPC .......... A61K 2039/55555; A61K 39/12; A61K 39/215; A61K 2039/53; A61P 31/14
See application file for complete search history.

(56) References Cited

U.S. PATENT DOCUMENTS

| 4,898,278 | A | 2/1990 | Leoncavallo et al. |
| 6,381,981 | B1 | 5/2002 | Yaddgo et al. |
| 7,736,850 | B2 | 6/2010 | Van Der Werf et al. |
| 7,901,708 | B2 | 3/2011 | MacLachlan et al. |
| 8,058,069 | B2 | 11/2011 | Yaworski et al. |
| 8,153,773 | B2 | 4/2012 | Jemielity et al. |
| 8,278,036 | B2 | 10/2012 | Kariko et al. |
| 8,329,070 | B2 | 12/2012 | MacLachlan et al. |
| 8,691,966 | B2 | 4/2014 | Kariko et al. |
| 8,710,200 | B2 | 4/2014 | Schrum et al. |
| 8,748,089 | B2 | 6/2014 | Kariko et al. |
| 8,754,062 | B2 | 6/2014 | de Fougerolles et al. |
| 8,822,663 | B2 | 9/2014 | Schrum et al. |
| 8,835,108 | B2 | 9/2014 | Kariko et al. |
| 8,999,380 | B2 | 4/2015 | Bancel et al. |
| 9,220,755 | B2 | 12/2015 | Chakraborty et al. |
| 9,221,891 | B2 | 12/2015 | Bancel et al. |
| 9,283,287 | B2 | 3/2016 | Chakraborty et al. |
| 9,295,717 | B2 | 3/2016 | Sahin et al. |
| 9,303,079 | B2 | 4/2016 | Chakraborty et al. |
| 9,334,328 | B2 | 5/2016 | Schrum et al. |
| 9,364,435 | B2 | 6/2016 | Yaworski et al. |
| 9,428,535 | B2 | 8/2016 | de Fougerolles et al. |
| 9,464,124 | B2 | 10/2016 | Bancel et al. |
| 9,476,055 | B2 | 10/2016 | Sahin et al. |
| 9,492,386 | B2 | 11/2016 | MacLachlan et al. |
| 9,504,651 | B2 | 11/2016 | MacLachlan et al. |
| 9,512,456 | B2 | 12/2016 | Wang et al. |
| 9,533,047 | B2 | 1/2017 | de Fougerolles et al. |
| 9,597,380 | B2 | 3/2017 | Chakraborty et al. |
| 9,657,295 | B2 | 5/2017 | Schrum et al. |
| 9,669,089 | B2 | 6/2017 | Thess et al. |

(Continued)

FOREIGN PATENT DOCUMENTS

| AU | 2015210364 A1 | 8/2015 |
| AU | 2019264591 A1 | 12/2019 |

(Continued)

OTHER PUBLICATIONS

U.S. Appl. No. 17/988,742.
U.S. Appl. No. 18/071,499.
U.S. Appl. No. 18/186,914.
[No Author Listed] "CureVac Announces Positive Results in Low Dose—1 µg—Rabies Vaccine Clinical Phase 1 Study." Globalnewswire. com. Jan. 7, 2020.
[No Author Listed], 10 Million Doses of mRNA-based COVID-19 Vaccine to be supplied to Taiwan Region, 2 pages (Jul. 12, 2021).

(Continued)

*Primary Examiner* — Barry A Chestnut
(74) *Attorney, Agent, or Firm* — Choate, Hall & Stewart LLP; Brenda Herschbach Jarrell; Rolando Medina

(57) ABSTRACT

This disclosure relates to the field of RNA to prevent or treat coronavirus infection. In particular, the present disclosure relates to methods and agents for vaccination against coronavirus infection and inducing effective coronavirus antigen-specific immune responses such as antibody and/or T cell responses.

30 Claims, 11 Drawing Sheets

Specification includes a Sequence Listing.

(56) References Cited

U.S. PATENT DOCUMENTS

| | | |
|---|---|---|
| 9,737,619 B2 | 8/2017 | Ansell et al. |
| 9,738,593 B2 | 8/2017 | Ansell et al. |
| 9,750,824 B2 | 9/2017 | Kariko et al. |
| 9,850,269 B2 | 12/2017 | DeRosa et al. |
| 9,868,691 B2 | 1/2018 | Benenato |
| 9,868,692 B2 | 1/2018 | Benenato |
| 9,872,900 B2 | 1/2018 | Ciaramella et al. |
| 9,957,499 B2 | 5/2018 | Heartlein et al. |
| 9,970,047 B2 | 5/2018 | Heartlein et al. |
| 10,022,435 B2 | 7/2018 | Ciaramella et al. |
| 10,064,934 B2 | 9/2018 | Ciaramella et al. |
| 10,064,935 B2 | 9/2018 | Ciaramella et al. |
| 10,064,959 B2 | 9/2018 | Schrum et al. |
| 10,106,490 B2 | 10/2018 | Du |
| 10,106,800 B2 | 10/2018 | Sahin et al. |
| 10,124,055 B2 | 11/2018 | Ciaramella et al. |
| 10,166,298 B2 | 1/2019 | Ansell et al. |
| 10,207,010 B2 | 2/2019 | Besin et al. |
| 10,232,055 B2 | 3/2019 | Kariko et al. |
| 10,238,754 B2 | 3/2019 | Guild et al. |
| 10,266,485 B2 | 4/2019 | Benenato |
| 10,272,150 B2 | 4/2019 | Ciaramella et al. |
| 10,273,269 B2 | 4/2019 | Ciaramella |
| 10,286,086 B2 | 5/2019 | Roy et al. |
| 10,350,303 B1 | 7/2019 | Guild et al. |
| 10,385,088 B2 | 8/2019 | Fraley et al. |
| 10,413,618 B2 | 9/2019 | Guild et al. |
| 10,442,756 B2 | 10/2019 | Benenato et al. |
| 10,449,244 B2 | 10/2019 | Ciaramella et al. |
| 10,465,190 B1 | 11/2019 | Chen et al. |
| 10,493,143 B2 | 12/2019 | Ciaramella et al. |
| 10,493,167 B2 | 12/2019 | de Fougerolles et al. |
| 10,494,399 B2 | 12/2019 | Hogrefe et al. |
| 10,519,189 B2 | 12/2019 | Hogrefe et al. |
| 10,526,629 B2 | 1/2020 | Rabideau et al. |
| 10,543,269 B2 | 1/2020 | Ciaramella et al. |
| 10,577,403 B2 | 3/2020 | De Fougerolles et al. |
| 10,583,203 B2 | 3/2020 | De Fougerolles et al. |
| 10,648,017 B2 | 5/2020 | Wochner |
| 10,653,712 B2 | 5/2020 | Hoge et al. |
| 10,653,767 B2 | 5/2020 | Ciaramella et al. |
| 10,695,419 B2 | 6/2020 | Ciaramella et al. |
| 10,702,599 B2 | 7/2020 | Ciaramella et al. |
| 10,702,600 B1 | 7/2020 | Ciaramella et al. |
| 10,703,789 B2 | 7/2020 | De Fougerolles et al. |
| 10,709,779 B2 | 7/2020 | Ciaramella et al. |
| 10,717,982 B2 | 7/2020 | Eberle et al. |
| 10,723,692 B2 | 7/2020 | Ansell et al. |
| 10,738,306 B2 | 8/2020 | Thess |
| 10,760,070 B2 | 9/2020 | Funkner et al. |
| 10,772,975 B2 | 9/2020 | Bancel et al. |
| 10,808,242 B2 | 10/2020 | Kariko et al. |
| 10,857,105 B2 | 12/2020 | Benenato et al. |
| 10,858,647 B2 | 12/2020 | Issa et al. |
| 10,906,944 B2 | 2/2021 | He et al. |
| 10,912,826 B2 | 2/2021 | Thess et al. |
| 10,913,768 B2 | 2/2021 | Hogrefe et al. |
| 10,925,935 B2 | 2/2021 | Chakraborty et al. |
| 10,925,958 B2 | 2/2021 | Ciaramella |
| 10,960,070 B2 | 3/2021 | Graham et al. |
| 10,973,909 B1 | 4/2021 | Csiszovszki et al. |
| 11,040,112 B2 | 6/2021 | Ansell et al. |
| 11,045,540 B2 | 6/2021 | Ciaramella |
| 11,110,166 B2 | 9/2021 | Fotin-Mleczek et al. |
| 11,213,482 B1 | 1/2022 | Gambotto et al. |
| 11,241,493 B2 | 2/2022 | Rauch et al. |
| 11,278,617 B2 | 3/2022 | Mosharraf et al. |
| 11,498,944 B2 | 11/2022 | Langedijk et al. |
| 11,510,977 B2 | 11/2022 | Ying |
| 11,547,673 B1 | 1/2023 | Sahin et al. |
| 11,634,379 B2 | 4/2023 | Ansell et al. |
| 2003/0194759 A1 | 10/2003 | Darzynkiewiz et al. |
| 2005/0002953 A1 | 1/2005 | Herold |
| 2005/0095582 A1 | 5/2005 | Gillim-Ross et al. |
| 2005/0112554 A1 | 5/2005 | Zhao et al. |
| 2005/0178142 A1 | 8/2005 | Perry et al. |
| 2005/0249742 A1 | 11/2005 | Ruprecht et al. |
| 2006/0121580 A1 | 6/2006 | ter Meulen et al. |
| 2006/0196193 A1 | 9/2006 | Byrne |
| 2007/0128217 A1 | 6/2007 | Meulen et al. |
| 2007/0270361 A1 | 11/2007 | Lu et al. |
| 2009/0093433 A1 | 4/2009 | Woolf et al. |
| 2009/0286852 A1 | 11/2009 | Kariko et al. |
| 2010/0017904 A1 | 1/2010 | Abad et al. |
| 2011/0300205 A1 | 12/2011 | Geall et al. |
| 2012/0082693 A1 | 4/2012 | Van Der Werf et al. |
| 2012/0101148 A1 | 4/2012 | Aking et al. |
| 2013/0102034 A1 | 4/2013 | Schrum |
| 2013/0115272 A1 | 5/2013 | de Fougerolles et al. |
| 2013/0236974 A1 | 9/2013 | de Fougerolles |
| 2013/0245103 A1 | 9/2013 | de Fougerolles et al. |
| 2013/0259923 A1 | 10/2013 | Bancel et al. |
| 2013/0266640 A1 | 10/2013 | de Fougerolles et al. |
| 2014/0147432 A1 | 5/2014 | Bancel et al. |
| 2014/0148502 A1 | 5/2014 | Bancel et al. |
| 2014/0193482 A1 | 7/2014 | Bancel et al. |
| 2014/0206752 A1 | 7/2014 | Afeyan et al. |
| 2014/0308304 A1 | 10/2014 | Manoharan et al. |
| 2014/0378538 A1 | 12/2014 | Bancel |
| 2015/0051268 A1 | 2/2015 | Bancel et al. |
| 2015/0056253 A1 | 2/2015 | Bancel et al. |
| 2015/0141499 A1 | 5/2015 | Bancel et al. |
| 2015/0265698 A1 | 9/2015 | Pushko et al. |
| 2015/0307542 A1 | 10/2015 | Roy et al. |
| 2015/0315541 A1 | 11/2015 | Bancel et al. |
| 2015/0376115 A1 | 12/2015 | Ansell et al. |
| 2016/0022580 A1 | 1/2016 | Ramsay et al. |
| 2016/0024140 A1 | 1/2016 | Issa et al. |
| 2016/0024141 A1 | 1/2016 | Issa et al. |
| 2016/0032273 A1 | 2/2016 | Shahrokh et al. |
| 2016/0038612 A1 | 2/2016 | Hoge et al. |
| 2016/0235864 A1 | 8/2016 | Schlake et al. |
| 2016/0243221 A1 | 8/2016 | Hoge et al. |
| 2016/0317647 A1 | 11/2016 | Ciaramella et al. |
| 2017/0043037 A1 | 2/2017 | Kariko et al. |
| 2017/0056528 A1 | 3/2017 | De Fougerolles et al. |
| 2017/0130255 A1 | 5/2017 | Wang et al. |
| 2017/0166905 A1 | 6/2017 | Eberle et al. |
| 2017/0202979 A1 | 7/2017 | Chakraborty et al. |
| 2017/0204152 A1 | 7/2017 | Nelson et al. |
| 2017/0362627 A1 | 12/2017 | Reynders, III et al. |
| 2018/0000953 A1 | 1/2018 | Almarsson et al. |
| 2018/0002393 A1 | 1/2018 | Bancel et al. |
| 2018/0086816 A1 | 3/2018 | Hoge et al. |
| 2018/0112221 A1 | 4/2018 | Schrum et al. |
| 2018/0161422 A1 | 6/2018 | Thess et al. |
| 2018/0237766 A1 | 8/2018 | Heartlein et al. |
| 2018/0237849 A1 | 8/2018 | Thompson |
| 2018/0243225 A1 | 8/2018 | Ciaramella |
| 2018/0243230 A1 | 8/2018 | Smith |
| 2018/0256628 A1 | 9/2018 | Hoge et al. |
| 2018/0256750 A1 | 9/2018 | Butora et al. |
| 2018/0271795 A1 | 9/2018 | Martini et al. |
| 2018/0271970 A1 | 9/2018 | Ciaramella et al. |
| 2018/0273576 A1 | 9/2018 | Hogrefe et al. |
| 2018/0273977 A1 | 9/2018 | Mousavi et al. |
| 2018/0274009 A1 | 9/2018 | Marquardt et al. |
| 2018/0291425 A1 | 10/2018 | Heartlein et al. |
| 2018/0303925 A1 | 10/2018 | Weissman et al. |
| 2018/0303929 A1 | 10/2018 | Ciaramella et al. |
| 2018/0311336 A1 | 11/2018 | Ciaramella et al. |
| 2018/0311343 A1 | 11/2018 | Huang et al. |
| 2018/0318409 A1 | 11/2018 | Valiante et al. |
| 2018/0318446 A1 | 11/2018 | Bancel et al. |
| 2018/0353618 A1 | 12/2018 | Burkhardt et al. |
| 2018/0369374 A1 | 12/2018 | Frederick et al. |
| 2018/0369419 A1 | 12/2018 | Benenato et al. |
| 2018/0371047 A1 | 12/2018 | Ticho et al. |
| 2019/0000959 A1 | 1/2019 | Ciaramella et al. |
| 2019/0002890 A1 | 1/2019 | Martini et al. |
| 2019/0008938 A1 | 1/2019 | Ciaramella et al. |
| 2019/0008948 A1 | 1/2019 | Ciaramella et al. |
| 2019/0015501 A1 | 1/2019 | Ciaramella et al. |
| 2019/0030129 A1 | 1/2019 | Schrum et al. |

(56) References Cited

U.S. PATENT DOCUMENTS

| | | |
|---|---|---|
| 2019/0060458 A1 | 2/2019 | De Fougerolles et al. |
| 2019/0062762 A1 | 2/2019 | Sahin et al. |
| 2019/0071682 A1 | 3/2019 | Orlandini Von Niessen et al. |
| 2019/0078087 A1 | 3/2019 | Butora et al. |
| 2019/0085368 A1 | 3/2019 | Bancel et al. |
| 2019/0100748 A1 | 4/2019 | Issa et al. |
| 2019/0144480 A1 | 5/2019 | DeRosa et al. |
| 2019/0153428 A1 | 5/2019 | Kariko et al. |
| 2019/0160185 A1 | 5/2019 | Schrum et al. |
| 2019/0167811 A1 | 6/2019 | Benenato et al. |
| 2019/0175517 A1 | 6/2019 | Martini et al. |
| 2019/0175727 A1 | 6/2019 | Huang et al. |
| 2019/0192646 A1 | 6/2019 | Cohen et al. |
| 2019/0192653 A1 | 6/2019 | Hoge et al. |
| 2019/0211368 A1 | 7/2019 | Butora et al. |
| 2019/0216951 A1 | 7/2019 | Baumhof |
| 2019/0218546 A1 | 7/2019 | Butora et al. |
| 2019/0225644 A1 | 7/2019 | Butora et al. |
| 2019/0240317 A1 | 8/2019 | Ciaramella et al. |
| 2019/0241633 A1 | 8/2019 | Fotin-Mleczek et al. |
| 2019/0247417 A1 | 8/2019 | Hoge et al. |
| 2019/0255194 A1 | 8/2019 | Roy et al. |
| 2019/0275170 A1 | 9/2019 | Benenato et al. |
| 2019/0298657 A1 | 10/2019 | Martini et al. |
| 2019/0298658 A1 | 10/2019 | Benenato et al. |
| 2019/0300906 A1 | 10/2019 | Martini et al. |
| 2019/0314291 A1 | 10/2019 | Besin et al. |
| 2019/0314292 A1 | 10/2019 | Benenato et al. |
| 2019/0314524 A1 | 10/2019 | Ansell et al. |
| 2019/0336452 A1 | 11/2019 | Brader |
| 2019/0336595 A1 | 11/2019 | Ciaramella |
| 2019/0351040 A1 | 11/2019 | Valiante et al. |
| 2019/0351048 A1 | 11/2019 | Rauch |
| 2019/0382774 A1 | 12/2019 | Hoge et al. |
| 2019/0390181 A1 | 12/2019 | Benenato et al. |
| 2020/0010528 A1 | 1/2020 | Seidel, III et al. |
| 2020/0030432 A1 | 1/2020 | Ciaramella et al. |
| 2020/0030460 A1 | 1/2020 | Kariko et al. |
| 2020/0032274 A1 | 1/2020 | Mauger et al. |
| 2020/0038499 A1 | 2/2020 | Narayanan et al. |
| 2020/0054737 A1 | 2/2020 | Ciaramella et al. |
| 2020/0060971 A1 | 2/2020 | Eber et al. |
| 2020/0061185 A1 | 2/2020 | Graham et al. |
| 2020/0069599 A1 | 3/2020 | Smith et al. |
| 2020/0069793 A1 | 3/2020 | Ciaramella |
| 2020/0069794 A1 | 3/2020 | Ciaramella et al. |
| 2020/0071689 A1 | 3/2020 | Miracco |
| 2020/0085916 A1 | 3/2020 | Martini et al. |
| 2020/0109420 A1 | 4/2020 | Brito et al. |
| 2020/0113832 A1 | 4/2020 | Yaworski et al. |
| 2020/0121809 A1 | 4/2020 | Hope et al. |
| 2020/0123100 A1 | 4/2020 | Benenato et al. |
| 2020/0129445 A1 | 4/2020 | Patel et al. |
| 2020/0129608 A1 | 4/2020 | Ciaramella et al. |
| 2020/0129615 A1 | 4/2020 | Ciaramella et al. |
| 2020/0147176 A1 | 5/2020 | Gieseke et al. |
| 2020/0155706 A1 | 5/2020 | De Fougerolles et al. |
| 2020/0163878 A1 | 5/2020 | Baumhof et al. |
| 2020/0164038 A1 | 5/2020 | De Fougerolles et al. |
| 2020/0206362 A1 | 7/2020 | Besin et al. |
| 2020/0208145 A1 | 7/2020 | Moore et al. |
| 2020/0216878 A1 | 7/2020 | Wochner |
| 2020/0230058 A1 | 7/2020 | Geall et al. |
| 2020/0239869 A1 | 7/2020 | Issa et al. |
| 2020/0247861 A1 | 8/2020 | De Fougerolles et al. |
| 2020/0254086 A1 | 8/2020 | Hoge et al. |
| 2020/0268664 A1 | 8/2020 | MacLachlan et al. |
| 2020/0282046 A1 | 9/2020 | Ciaramella et al. |
| 2020/0282047 A1 | 9/2020 | Ciaramella et al. |
| 2020/0332293 A1 | 10/2020 | Thess |
| 2020/0338214 A1 | 10/2020 | Guild et al. |
| 2020/0354423 A1 | 11/2020 | De Fougerolles et al. |
| 2020/0383922 A1 | 12/2020 | Ketterer et al. |
| 2020/0392518 A1 | 12/2020 | Eberle et al. |
| 2020/0399629 A1 | 12/2020 | Kariko et al. |
| 2020/0405844 A1 | 12/2020 | Ciaramella et al. |
| 2021/0023199 A1 | 1/2021 | Kallen et al. |
| 2021/0030683 A1 | 2/2021 | Eber et al. |
| 2021/0030866 A1 | 2/2021 | Kallen et al. |
| 2021/0040473 A1 | 2/2021 | Funkner et al. |
| 2021/0046173 A1 | 2/2021 | Ciaramella et al. |
| 2021/0060175 A1 | 3/2021 | Fotin-Mleczek et al. |
| 2021/0077634 A1 | 3/2021 | De Fougerolles et al. |
| 2021/0107861 A1 | 4/2021 | Ansell et al. |
| 2021/0128716 A1 | 5/2021 | Thess et al. |
| 2021/0139543 A1 | 5/2021 | He et al. |
| 2021/0163919 A1 | 6/2021 | Issa et al. |
| 2021/0187097 A1 | 6/2021 | Ciaramella et al. |
| 2021/0217484 A1 | 7/2021 | Giessel et al. |
| 2021/0220467 A1 | 7/2021 | Ciaramella et al. |
| 2021/0228707 A1 | 7/2021 | Metkar et al. |
| 2021/0228708 A1 | 7/2021 | Smith et al. |
| 2021/0230578 A1 | 7/2021 | Issa et al. |
| 2021/0246170 A1 | 8/2021 | Langedijk et al. |
| 2021/0251898 A1 | 8/2021 | Baumhof et al. |
| 2021/0261597 A1 | 8/2021 | Hogrefe et al. |
| 2021/0275664 A1 | 9/2021 | Graham et al. |
| 2021/0290756 A1 | 9/2021 | Sullivan et al. |
| 2021/0299244 A1 | 9/2021 | Mosharraf et al. |
| 2021/0299251 A1 | 9/2021 | Mosharraf et al. |
| 2021/0299278 A1 | 9/2021 | Bancel et al. |
| 2021/0308257 A1 | 10/2021 | Kuo et al. |
| 2021/0322541 A1 | 10/2021 | Akahata et al. |
| 2021/0332085 A1 | 10/2021 | Chen |
| 2021/0346493 A1 | 11/2021 | Zhou et al. |
| 2021/0355170 A1 | 11/2021 | Whitehead et al. |
| 2021/0371452 A1 | 12/2021 | Hogrefe et al. |
| 2021/0379181 A1 | 12/2021 | Rauch et al. |
| 2021/0388032 A1 | 12/2021 | Langedijk et al. |
| 2022/0011039 A1 | 1/2022 | Hou et al. |
| 2022/0016234 A1 | 1/2022 | Rice et al. |
| 2022/0040285 A1 | 2/2022 | Weissman et al. |
| 2022/0040292 A1 | 2/2022 | Tang et al. |
| 2022/0048954 A1 | 2/2022 | Pao et al. |
| 2022/0072155 A1 | 3/2022 | Ansell et al. |
| 2022/0105201 A1 | 4/2022 | Guild et al. |
| 2022/0193226 A1 | 6/2022 | Rauch et al. |
| 2022/0202930 A1 | 6/2022 | Roth et al. |
| 2022/0211838 A1 | 7/2022 | Oostvogels et al. |
| 2022/0211841 A1 | 7/2022 | Oostvogels et al. |
| 2022/0218815 A1 | 7/2022 | Rauch et al. |
| 2022/0218816 A1 | 7/2022 | Ying |
| 2022/0249654 A1 | 8/2022 | Oostvogels et al. |
| 2022/0249704 A1 | 8/2022 | Sahin et al. |
| 2022/0273820 A1 | 9/2022 | Sahin et al. |
| 2022/0307040 A1 | 9/2022 | Thess et al. |
| 2022/0323572 A1 | 10/2022 | Metkar et al. |
| 2022/0347097 A1 | 11/2022 | Geall |
| 2022/0347289 A1 | 11/2022 | Chen et al. |
| 2022/0395562 A1 | 12/2022 | Chakraborty et al. |
| 2022/0395570 A1 | 12/2022 | Rauch et al. |
| 2022/0401550 A1 | 12/2022 | Simon-Loriere et al. |
| 2023/0007597 A1 | 1/2023 | Guo et al. |
| 2023/0073461 A1 | 3/2023 | Sahin et al. |
| 2023/0075979 A1 | 3/2023 | Sahin et al. |
| 2023/0167159 A1 | 6/2023 | Mwangi et al. |
| 2023/0173057 A1 | 6/2023 | Zhang et al. |
| 2023/0233665 A1 | 7/2023 | Wei et al. |

FOREIGN PATENT DOCUMENTS

| | | |
|---|---|---|
| AU | 2016253972 B2 | 1/2020 |
| AU | 2015280499 B2 | 3/2020 |
| CN | 107033250 A | 8/2017 |
| CN | 110167587 A | 8/2019 |
| CN | 106795096 B | 5/2020 |
| CN | 111088283 B | 6/2020 |
| CN | 111303254 A | 6/2020 |
| CN | 110951756 B | 8/2020 |
| CN | 110974950 B | 8/2020 |
| CN | 111518175 A | 8/2020 |
| CN | 111592602 A | 8/2020 |
| CN | 111139241 B | 9/2020 |
| CN | 111218459 B | 9/2020 |

(56) References Cited

FOREIGN PATENT DOCUMENTS

| | | |
|---|---|---|
| CN | 111363858 B | 9/2020 |
| CN | 111748557 A | 10/2020 |
| CN | 111778254 A | 10/2020 |
| CN | 111848753 A | 10/2020 |
| CN | 111218458 B | 11/2020 |
| CN | 111876419 A | 11/2020 |
| CN | 111939250 A | 11/2020 |
| CN | 111978377 A | 11/2020 |
| CN | 112023035 A | 12/2020 |
| CN | 112028976 A | 12/2020 |
| CN | 112043825 A | 12/2020 |
| CN | 112048005 A | 12/2020 |
| CN | 112094327 A | 12/2020 |
| CN | 112220920 A | 1/2021 |
| CN | 112226445 A | 1/2021 |
| CN | 112266411 A | 1/2021 |
| CN | 112321688 A | 2/2021 |
| CN | 112358533 A | 2/2021 |
| CN | 112480217 A | 3/2021 |
| CN | 112626089 A | 4/2021 |
| CN | 112794884 A | 5/2021 |
| CN | 113186203 A | 7/2021 |
| DE | 20 2021 003 575 U1 | 1/2022 |
| EP | 1291300 A2 | 3/2003 |
| EP | 1392341 B1 | 3/2005 |
| EP | 1857122 B1 | 12/2010 |
| EP | 2691101 A2 | 2/2014 |
| EP | 2791160 A1 | 10/2014 |
| EP | 2833892 A2 | 2/2015 |
| EP | 2833894 A1 | 2/2015 |
| EP | 1685844 B1 | 3/2015 |
| EP | 3169693 A1 | 5/2017 |
| EP | 3190361 A1 | 7/2017 |
| EP | 2958588 B1 | 8/2017 |
| EP | 3218508 A1 | 9/2017 |
| EP | 2506857 B1 | 2/2018 |
| EP | 3289083 A1 | 3/2018 |
| EP | 2971102 B1 | 6/2018 |
| EP | 3334828 A1 | 6/2018 |
| EP | 3350157 A2 | 7/2018 |
| EP | 3350333 A2 | 7/2018 |
| EP | 3362460 A1 | 8/2018 |
| EP | 3362461 A1 | 8/2018 |
| EP | 3364949 A1 | 8/2018 |
| EP | 3364983 A2 | 8/2018 |
| EP | 3036330 B1 | 9/2018 |
| EP | 3368507 A1 | 9/2018 |
| EP | 3386484 A1 | 10/2018 |
| EP | 3394030 A1 | 10/2018 |
| EP | 2970955 B1 | 11/2018 |
| EP | 2763701 B1 | 12/2018 |
| EP | 3090060 B1 | 2/2019 |
| EP | 3452101 A2 | 3/2019 |
| EP | 3318248 B1 | 4/2019 |
| EP | 3468537 A1 | 4/2019 |
| EP | 2717893 B1 | 5/2019 |
| EP | 3260541 B1 | 5/2019 |
| EP | 3292873 B1 | 5/2019 |
| EP | 3501550 A1 | 6/2019 |
| EP | 1797886 B1 | 7/2019 |
| EP | 3505176 A1 | 7/2019 |
| EP | 3512944 A1 | 7/2019 |
| EP | 3134131 A1 | 8/2019 |
| EP | 3134506 B1 | 8/2019 |
| EP | 3520820 A1 | 8/2019 |
| EP | 3520821 A1 | 8/2019 |
| EP | 3532070 A1 | 9/2019 |
| EP | 3538067 A1 | 9/2019 |
| EP | 3540060 A1 | 9/2019 |
| EP | 3577221 A1 | 12/2019 |
| EP | 3578200 A1 | 12/2019 |
| EP | 3578205 A1 | 12/2019 |
| EP | 3578659 A1 | 12/2019 |
| EP | 3586861 A1 | 1/2020 |
| EP | 3590949 A1 | 1/2020 |
| EP | 3595676 A1 | 1/2020 |
| EP | 3595727 A1 | 1/2020 |
| EP | 3596041 A1 | 1/2020 |
| EP | 3596042 A1 | 1/2020 |
| EP | 3607074 A1 | 2/2020 |
| EP | 3492109 B1 | 3/2020 |
| EP | 3625345 A1 | 3/2020 |
| EP | 3638215 A1 | 4/2020 |
| EP | 3062798 B1 | 5/2020 |
| EP | 3668522 A2 | 6/2020 |
| EP | 3294885 B1 | 7/2020 |
| EP | 3682905 A1 | 7/2020 |
| EP | 3160938 B1 | 9/2020 |
| EP | 3718565 A1 | 10/2020 |
| EP | 3838294 A1 | 6/2021 |
| EP | 3886897 A1 | 10/2021 |
| EP | 3901260 A1 | 10/2021 |
| EP | 3901261 A1 | 10/2021 |
| EP | 3981437 A1 | 4/2022 |
| EP | 4096710 A1 | 12/2022 |
| EP | 4097122 A1 | 12/2022 |
| EP | 4103228 A1 | 12/2022 |
| EP | 4103229 A1 | 12/2022 |
| EP | 4217370 A2 | 8/2023 |
| JP | H10-113117 A | 5/1998 |
| JP | 6594421 B2 | 10/2019 |
| RU | 2731342 C1 | 9/2020 |
| RU | 2731356 C1 | 9/2020 |
| RU | 2733834 C1 | 10/2020 |
| TW | 200515917 A | 5/2005 |
| WO | WO-1998/051278 A2 | 11/1998 |
| WO | WO-1999/14346 A2 | 3/1999 |
| WO | WO-02/098443 A2 | 12/2002 |
| WO | WO-2004/002453 A1 | 1/2004 |
| WO | WO-2004/004743 A1 | 1/2004 |
| WO | WO-2004/096842 A2 | 11/2004 |
| WO | WO-2004/110081 A1 | 12/2004 |
| WO | WO-2005/027963 A2 | 3/2005 |
| WO | WO-2006/138380 A1 | 12/2006 |
| WO | WO-2007/024708 A2 | 3/2007 |
| WO | WO-2007/036366 A2 | 4/2007 |
| WO | WO-2008/016473 A2 | 2/2008 |
| WO | WO-2008/027942 A2 | 3/2008 |
| WO | WO-2008/052770 A2 | 5/2008 |
| WO | WO-2008/157688 A2 | 12/2008 |
| WO | WO-2009/127060 A1 | 10/2009 |
| WO | WO-2009/149253 A2 | 12/2009 |
| WO | WO-2011/015347 A1 | 2/2011 |
| WO | WO-2011/068810 A1 | 6/2011 |
| WO | WO-2012/019168 A2 | 2/2012 |
| WO | WO-2012/045075 A1 | 4/2012 |
| WO | WO-2012/135805 A2 | 10/2012 |
| WO | WO-2012/170930 A1 | 12/2012 |
| WO | WO-2013/052523 A1 | 4/2013 |
| WO | WO-2013/090648 A1 | 6/2013 |
| WO | WO-2013/143699 A1 | 10/2013 |
| WO | WO-2013/151668 A2 | 10/2013 |
| WO | WO-2013/151671 A1 | 10/2013 |
| WO | WO-2013/151672 A2 | 10/2013 |
| WO | WO-2013/151736 A2 | 10/2013 |
| WO | WO-2014/089239 A1 | 6/2014 |
| WO | WO-2014/127917 A1 | 8/2014 |
| WO | WO-2014/144711 A1 | 9/2014 |
| WO | WO-2014/152659 A1 | 9/2014 |
| WO | WO-2014/152966 A1 | 9/2014 |
| WO | WO-2014/159813 A1 | 10/2014 |
| WO | WO-2014/164253 A1 | 10/2014 |
| WO | WO-2015/005253 A1 | 1/2015 |
| WO | WO-2015/024667 A1 | 2/2015 |
| WO | WO-2015/062738 A1 | 5/2015 |
| WO | WO-2015/101416 A1 | 7/2015 |
| WO | WO-2015/130584 A2 | 9/2015 |
| WO | WO-2015/164674 A1 | 10/2015 |
| WO | WO-2015/164773 A1 | 10/2015 |
| WO | WO-2015/199952 A1 | 12/2015 |
| WO | WO-2016/005004 A1 | 1/2016 |
| WO | WO-2016/005324 A1 | 1/2016 |
| WO | WO-2016/010840 A1 | 1/2016 |
| WO | WO-2016/011226 A1 | 1/2016 |

(56) References Cited

FOREIGN PATENT DOCUMENTS

| | | |
|---|---|---|
| WO | WO-2016/045732 A1 | 3/2016 |
| WO | WO-2016/077123 A1 | 5/2016 |
| WO | WO-2016/091391 A1 | 6/2016 |
| WO | WO-2016/164762 A1 | 10/2016 |
| WO | WO-2016/165831 A1 | 10/2016 |
| WO | WO-2016/176330 A1 | 11/2016 |
| WO | WO-2016/180430 A1 | 11/2016 |
| WO | WO-2016/184575 A1 | 11/2016 |
| WO | WO-2016/184576 A2 | 11/2016 |
| WO | WO-2016/193206 A1 | 12/2016 |
| WO | WO-2016/201377 A1 | 12/2016 |
| WO | WO-2017/015457 A1 | 1/2017 |
| WO | WO-2017/025447 A1 | 2/2017 |
| WO | WO-2017/036889 A1 | 3/2017 |
| WO | WO-2017/049245 A2 | 3/2017 |
| WO | WO-2017/049275 A2 | 3/2017 |
| WO | WO-2017/053297 A1 | 3/2017 |
| WO | WO-2017/059902 A1 | 4/2017 |
| WO | WO-2017/060314 A2 | 4/2017 |
| WO | WO-2017/066781 A1 | 4/2017 |
| WO | WO-2017/066789 A1 | 4/2017 |
| WO | WO-2017/066793 A1 | 4/2017 |
| WO | WO-2017/070601 A1 | 4/2017 |
| WO | WO-2017/070618 A1 | 4/2017 |
| WO | WO-2017/070626 A2 | 4/2017 |
| WO | WO-2017/075531 A1 | 5/2017 |
| WO | WO-2017/099823 A1 | 6/2017 |
| WO | WO-2017/112865 A1 | 6/2017 |
| WO | WO-2017/127750 A1 | 7/2017 |
| WO | WO-2017/191274 A2 | 11/2017 |
| WO | WO-2017/201333 A1 | 11/2017 |
| WO | WO-2017/218704 A1 | 12/2017 |
| WO | WO-2018/053209 A1 | 3/2018 |
| WO | WO-2018/075827 A1 | 4/2018 |
| WO | WO-2018/078053 A1 | 5/2018 |
| WO | WO-2018/081318 A1 | 5/2018 |
| WO | WO-2018/081459 A1 | 5/2018 |
| WO | WO-2018/081462 A1 | 5/2018 |
| WO | WO-2018/081480 A1 | 5/2018 |
| WO | WO-2018/089540 A1 | 5/2018 |
| WO | WO-2018/089851 A2 | 5/2018 |
| WO | WO-2018/115527 A2 | 6/2018 |
| WO | WO-2018/144778 A1 | 8/2018 |
| WO | WO-2018/157009 A1 | 8/2018 |
| WO | WO-2018/170245 A1 | 9/2018 |
| WO | WO-2018/170306 A1 | 9/2018 |
| WO | WO-2018/170322 A1 | 9/2018 |
| WO | WO-2018/170336 A1 | 9/2018 |
| WO | WO-2018/170347 A1 | 9/2018 |
| WO | WO-2018/187590 A1 | 10/2018 |
| WO | WO-2018/213789 A1 | 11/2018 |
| WO | WO-2018/232355 A1 | 12/2018 |
| WO | WO-2018/232357 A1 | 12/2018 |
| WO | WO-2019/035998 A1 | 2/2019 |
| WO | WO-2019/036670 A2 | 2/2019 |
| WO | WO-2019/036683 A1 | 2/2019 |
| WO | WO-2019/036685 A1 | 2/2019 |
| WO | WO-2019/092002 A1 | 5/2019 |
| WO | WO-2019/092437 A1 | 5/2019 |
| WO | WO-2019/148101 A1 | 8/2019 |
| WO | WO-2019/209914 A2 | 10/2019 |
| WO | WO-2019/232097 A1 | 12/2019 |
| WO | WO-2020/006242 A1 | 1/2020 |
| WO | WO-2020/025576 A1 | 2/2020 |
| WO | WO-2020/056370 A1 | 3/2020 |
| WO | WO-2020/061284 A1 | 3/2020 |
| WO | WO-2020/061295 A1 | 3/2020 |
| WO | WO-2020/061367 A1 | 3/2020 |
| WO | WO-2020/061457 A1 | 3/2020 |
| WO | WO-2020/072605 A1 | 4/2020 |
| WO | WO-2020/097291 A1 | 5/2020 |
| WO | WO-2020/150152 A1 | 7/2020 |
| WO | WO-2020/160397 A1 | 8/2020 |
| WO | WO-2020/172239 A1 | 8/2020 |
| WO | WO-2020/185811 A1 | 9/2020 |
| WO | WO-2020/190750 A1 | 9/2020 |
| WO | WO-2020/198337 A1 | 10/2020 |
| WO | WO-2020/243561 A1 | 12/2020 |
| WO | WO-2020/263985 A1 | 12/2020 |
| WO | WO-2021/000968 A2 | 1/2021 |
| WO | WO-2021/000969 A2 | 1/2021 |
| WO | WO-2021/04081 A1 | 1/2021 |
| WO | WO-2021/030533 A1 | 2/2021 |
| WO | WO-2021/030701 A1 | 2/2021 |
| WO | WO-2021/050864 A1 | 3/2021 |
| WO | WO-2021/055811 A1 | 3/2021 |
| WO | WO-2021/084282 A1 | 5/2021 |
| WO | WO-2021/123332 A1 | 6/2021 |
| WO | WO-2021/138447 A1 | 7/2021 |
| WO | WO-2021/147025 A1 | 7/2021 |
| WO | WO-2021/154763 A1 | 8/2021 |
| WO | WO-2021/154812 A1 | 8/2021 |
| WO | WO-2021/155243 A1 | 8/2021 |
| WO | WO-2021/155323 A1 | 8/2021 |
| WO | WO-2021/155733 A1 | 8/2021 |
| WO | WO-2021/155760 A1 | 8/2021 |
| WO | WO-2021/156267 A1 | 8/2021 |
| WO | WO-2021/159040 A2 | 8/2021 |
| WO | WO-2021/159118 A2 | 8/2021 |
| WO | WO-2021/159130 A2 | 8/2021 |
| WO | WO-2021/159648 A1 | 8/2021 |
| WO | WO-2021/159985 A1 | 8/2021 |
| WO | WO-2021/160346 A1 | 8/2021 |
| WO | WO-2021/160850 A1 | 8/2021 |
| WO | WO-2021/163365 A1 | 8/2021 |
| WO | WO-2021/163371 A1 | 8/2021 |
| WO | WO-2021/163398 A1 | 8/2021 |
| WO | WO-2021/163427 A1 | 8/2021 |
| WO | WO-2021/163456 A1 | 8/2021 |
| WO | WO-2021/165667 A1 | 8/2021 |
| WO | WO-2021/181100 A1 | 9/2021 |
| WO | WO-2021/188906 A1 | 9/2021 |
| WO | WO-2021/188969 A2 | 9/2021 |
| WO | WO-2021/189056 A2 | 9/2021 |
| WO | WO-2021/191630 A1 | 9/2021 |
| WO | WO-2021/194826 A2 | 9/2021 |
| WO | WO-2021/198705 A1 | 10/2021 |
| WO | WO-2021/198706 A2 | 10/2021 |
| WO | WO-2021/200800 A1 | 10/2021 |
| WO | WO-2021/201612 A1 | 10/2021 |
| WO | WO-2021/202599 A2 | 10/2021 |
| WO | WO-2021/202772 A1 | 10/2021 |
| WO | WO-2021/203017 A2 | 10/2021 |
| WO | WO-2021/203018 A1 | 10/2021 |
| WO | WO-2021/203044 A2 | 10/2021 |
| WO | WO-2021/204179 A1 | 10/2021 |
| WO | WO-2021/205455 A1 | 10/2021 |
| WO | WO-2021/206581 A1 | 10/2021 |
| WO | WO-2021/209824 A1 | 10/2021 |
| WO | WO-2021/210686 A1 | 10/2021 |
| WO | WO-2021/211279 A1 | 10/2021 |
| WO | WO-2021/211688 A1 | 10/2021 |
| WO | WO-2021/211748 A1 | 10/2021 |
| WO | WO/2021-211749 A1 | 10/2021 |
| WO | WO-2021/211760 A1 | 10/2021 |
| WO | WO-2021/212568 A1 | 10/2021 |
| WO | WO-2021/213924 A1 | 10/2021 |
| WO | WO-2021/213945 A1 | 10/2021 |
| WO | WO-2021/214204 A1 | 10/2021 |
| WO | WO-2021/216729 A1 | 10/2021 |
| WO | WO-2021/216738 A2 | 10/2021 |
| WO | WO-2021/216743 A2 | 10/2021 |
| WO | WO-2021/203017 A3 | 11/2021 |
| WO | WO-2021/220319 A1 | 11/2021 |
| WO | WO-2021/221486 A1 | 11/2021 |
| WO | WO-2021/222304 A1 | 11/2021 |
| WO | WO-2021/223647 A1 | 11/2021 |
| WO | WO-2021/224946 A1 | 11/2021 |
| WO | WO-2021/226436 A1 | 11/2021 |
| WO | WO-2021/227401 A1 | 11/2021 |
| WO | WO-2021/231560 A1 | 11/2021 |
| WO | WO-2021/231929 A1 | 11/2021 |
| WO | WO-2021/231963 A1 | 11/2021 |
| WO | WO-2021/237174 A1 | 11/2021 |

(56) References Cited

FOREIGN PATENT DOCUMENTS

| | | |
|---|---|---|
| WO | WO-2021/214081 A3 | 12/2021 |
| WO | WO-2021/239880 A1 | 12/2021 |
| WO | WO-2021/253172 A1 | 12/2021 |
| WO | WO-2022/003119 A1 | 1/2022 |
| WO | WO-2022/005503 A1 | 1/2022 |
| WO | WO-2022/009121 A1 | 1/2022 |
| WO | WO-2022/011092 A1 | 1/2022 |
| WO | WO-2022/011332 A2 | 1/2022 |
| WO | WO-2022/043551 A2 | 3/2022 |
| WO | WO-2022/064494 A2 | 3/2022 |
| WO | WO-2022/073131 A1 | 4/2022 |
| WO | WO-2022/101469 A1 | 5/2022 |
| WO | WO-2022/110099 A1 | 6/2022 |
| WO | WO-2022/131832 A1 | 6/2022 |
| WO | WO-2022/137133 A1 | 6/2022 |
| WO | WO-2022/155530 A1 | 7/2022 |
| WO | WO-2022/191377 A1 | 9/2022 |
| WO | WO-2022/192594 A2 | 9/2022 |
| WO | WO2022/197720 A2 | 9/2022 |
| WO | WO-2022/212659 A1 | 10/2022 |
| WO | WO-2022/221335 A1 | 10/2022 |
| WO | WO-2022/221440 A1 | 10/2022 |
| WO | WO-2022/223617 A1 | 10/2022 |
| WO | WO-2022/234405 A1 | 11/2022 |
| WO | WO-2023/004415 A2 | 1/2023 |
| WO | WO-2023/286076 A1 | 1/2023 |
| WO | WO-2023/042099 A2 | 3/2023 |
| WO | WO-2023/049272 A1 | 3/2023 |
| WO | WO-2023/056911 A1 | 4/2023 |
| WO | WO-2023/064708 A1 | 4/2023 |
| WO | WO-2023/064907 A1 | 4/2023 |
| WO | WO-2023/089071 A1 | 5/2023 |
| WO | WO-2023/094713 A2 | 6/2023 |
| WO | WO-2023/098842 A1 | 6/2023 |
| WO | WO-2023/102448 A2 | 6/2023 |
| WO | WO-2023/111725 A1 | 6/2023 |
| WO | WO-2023/094713 A3 | 7/2023 |
| WO | WO-2023/137550 A1 | 7/2023 |
| WO | WO-2023/142786 A1 | 8/2023 |
| WO | WO-2023/150838 A1 | 8/2023 |
| WO | WO-2023/151172 A1 | 8/2023 |
| WO | WO-2023/151173 A1 | 8/2023 |

OTHER PUBLICATIONS

[No Author Listed], An In Vitro Study Shows Pfizer-BioNTech COVID-19 Vaccine Elicits Antibodies that Neutralize SARS-COV-2 with a Mutation Associated with Rapid Transmission, 3 pages (Jan. 8, 2021).

[No Author Listed], Assessment Report—Comirnaty, 140 pages Jan. 19, 2021.

[No Author Listed], BioNTech and Fosun Pharma Announce Start of Clinical Trial of mRNA-based COVID-19 Vaccine Candidate in China, 2 pages (Aug. 5, 2020).

[No Author Listed], BioNTech and Fosun Pharma Announce the Start of a Phase 2 Clinical Trial of Lead mRNA COVID-19 Vaccine BNT162b2 in China, 2 pages (Nov. 25, 2020).

[No Author Listed], BioNTech and Fosun Pharma form COVID-19 vaccine strategic alliance in China, 2 pages (Mar. 16, 2020).

[No Author Listed], BioNTech and Fosun Pharma Receive Authorization for Emergency Use in Hong Kong for COVID-19 Vaccine, 2 pages (Jan. 25, 2021).

[No Author Listed], BioNTech and Fosun Pharma Receive Special Import Authorization in Macau for COVID-19 Vaccine, 2 pages (Feb. 25, 2021).

[No Author Listed], BioNTech and Fosun Pharma to Potentially Supply 10 Million Doses of BioNTech's NT162 mRNA-based Vaccine Candidate Against SARS-COV-2 to Hong Kong SAR and Macao SAR, 2 pages (Aug. 27, 2020).

[No Author Listed], BioNTech and Fosun Pharma to Supply China with mRNA-based COVID-19 Vaccine, 2 pages (Dec. 16, 2020).

[No Author Listed], BioNTech and Pfizer announce completion of dosing for first cohort of Phase ½ trial of COVID-19 vaccine candidates in Germany, 2 pages (Apr. 29, 2020).

[No Author Listed], BioNTech and Pfizer Announce Nature Publication of German Phase ½ Study Data from mRNA-based Vaccine Candidate BNT162b1 Against SARS-COV-2, 3 pages (Sep. 30, 2020).

[No Author Listed], BioNTech and Pfizer announce regulatory approval from German authority Paul-Ehrlich-Institut to commence first clinical trial of COVID-19 vaccine candidates, 3 pages (Apr. 22, 2020).

[No Author Listed], BioNTech and Pfizer Initiate Rolling Submission to European Medicines Agency for SARS-COV-2 Vaccine Candidate BNT162b2, 3 pages (Oct. 6, 2020).

[No Author Listed], BioNTech and Pfizer Receive Regulatory Approval From Paul-Ehrlich-Institut to commence German Part of Global Phase 2/3 Trial for COVID-19 Vaccine Candidate BNT162b2, 3 pages (Sep. 7, 2020).

[No Author Listed], BioNTech Recognizes Employees and Partners for Their Support in Developing Historic Vaccine, 2 pages (Dec. 31, 2020).

[No Author Listed], BioNTech reports rapid progress on COVID-19 vaccine program to address global public health threat, 2 pages (Mar. 16, 2020).

[No Author Listed], BioNTech to Acquire GMP Manufacturing Site to Expand COVID-19 Vaccine Production Capacity in First Half 2021, 2 pages (Sep. 17, 2020).

[No Author Listed], BioNTech to Hold Press Conference to Provide an Update on COVID-19 Vaccine Development Program, 1 page (Dec. 2, 2020).

[No Author Listed], BioNTech to Hold Press Conference to Provide an Update on COVID-19 Vaccine Development Program, 1 page (Dec. 21, 2020).

[No Author Listed], BioNTech to Hold Webcast to Present Early Positive Data from Ongoing Phase 1/2 Study of mRNA-based Vaccine Candidate Against SARS-COV-2, 1 page (Jul. 1, 2020).

[No Author Listed], BioNTech to Receive up to €375M in Funding from German Federal Ministry of Education and Research to Support COVID-19 Vaccine Program BNT162, 2 pages (Sep. 15, 2020).

[No Author Listed], Canada Exercises Increased Option for 20 Million Doses of mRNA Vaccine Against COVID-19 (mRNA-1273), Moderna Press Release, 2 pages (Sep. 22, 2020).

[No Author Listed], EMA Approves New Storage Option for Pfizer-BioNTech Vaccine, Easing Distribution and Storage of Doses Across European Union, 3 pages (Mar. 26, 2021).

[No Author Listed], Experimental COVID-19 Vaccine Protects Upper and Lower Airways in Nonhuman Primates, NIH News Release, 2 pages (Jul. 28, 2020).

[No Author Listed], Experimental COVID-19 Vaccine Safe, Generates Immune Response, NIH News Release, 2 pages (Jul. 14, 2020).

[No Author Listed], In Vitro Studies Demonstrate Pfizer and BioNTech COVID-19 Vaccine Elicits Antibodies that Neutralize SARS-COV-2 with Key Mutations Present in U.K. and South African Variants, 3 pages (Jan. 27, 2021).

[No Author Listed], In Vitro Study Published in the New England Journal of Medicine Demonstrates Sera from Individuals Immunized with the Pfizer-BioNTech COVID-19 Vaccine Neutralize SARS-COV-2 with South African Variant Spike Mutations, 3 pages (Feb. 17, 2021).

[No Author Listed], Investment Plan for Europe: European Investment Bank to provide BioNTech with up to €100 million in debt financing for COVID-19 vaccine development and manufacturing, 2 pages (Jun. 11, 2020).

[No Author Listed], Moderna Advances Late-Stage Development of its Vaccine (mRNA-1273) Against COVID-19, Moderna Press Release, 3 pages (Jun. 11, 2020).

[No Author Listed], Moderna and Lonza Announce Worldwide Strategic Collaboration to Manufacture Moderna's Vaccine (mRNA-1273) Against Novel Coronavirus, Moderna Press Release, 3 pages (May 1, 2020).

(56) References Cited

OTHER PUBLICATIONS

[No Author Listed], Moderna Announces Award from U.S. Government Agency BARDA for up to $483 Million to Accelerate Development of mRNA Vaccine (mRNA-1273) Against Novel Coronavirus, Moderna Press Release, 3 pages (Apr. 16, 2020).

[No Author Listed], Moderna Announces Expansion of BARDA Agreement to Support Larger Phase 3 Program forVaccine (mRNA-1273) Against COVID-19, Moderna Press Release, 3 pages (Jul. 26, 2020).

[No Author Listed], Moderna Announces First Participant Dosed in NIH-led Phase 1 Study of mRNA Vaccine (mRNA-1273) Against Novel Coronavirus, Moderna Press Release, 2 pages (Mar. 16, 2020).

[No Author Listed], Moderna Announces First Participants in Each Age Cohort Dosed in Phase 2 Study of mRNA Vaccine (mRNA-1273) Against Novel Coronavirus, Moderna Press Release, 2 pages (May 29, 2020).

[No Author Listed], Moderna Announces IND Submitted to U.S. FDA for Phase 2 Study of mRNA Vaccine (mRNA-1273) Against Novel Coronavirus, Moderna Press Release, 3 pages (Apr. 27, 2020).

[No Author Listed], Moderna Announces Phase 3 COVE Study of mRNA Vaccine Against COVID-19 (mRNA-1273) Begins, Moderna Press Release, 3 pages (Jul. 27, 2020).

[No Author Listed], Moderna Announces Positive Interim Phase 1 Data for its mRNA Vaccine (mRNA-1273) Against Novel Coronavirus, Moderna Press Release, 3 pages (May 18, 2020).

[No Author Listed], Moderna Announces Progress Across Broad Portfolio and all Three Clinical Stage Therapeutic Areas at 2020 R&D Day, Moderna Press Release, 4 pages (Sep. 17, 2020).

[No Author Listed], Moderna Announces Publication in the New England Journal of Medicine of Interim Results From Phase 1 Study of Its mRNA Vaccine Against COVID-19 (mRNA-1273), Moderna Press Release, 5 pages (Jul. 14, 2020).

[No Author Listed], Moderna Announces Publication in the New England Journal of Medicine of Non-Human Primate Preclinical Viral Challenge Study of its mRNA Vaccine Against COVID-19 (mRNA-1273), Moderna Press Release, 3 pages (Jul. 28, 2020).

[No Author Listed], Moderna Announces Supply Agreement with U.S. Government for Initial 100 Million Doses of mRNA Vaccine Against COVID-19 (mRNA-1273), Moderna Press Release, 3 pages (Aug. 11, 2020).

[No Author Listed], Moderna Completes Enrollment of Phase 2 Study of its mRNA Vaccine Against COVID-19 (mRNA-1273), Moderna Press Release, 2 pages (Jul. 8, 2020).

[No Author Listed], Moderna Confirms Advanced Discussions with European Commission to Supply Europe with 80 Million Doses of mRNA Vaccine Against COVID-19 (mRNA-1273), Moderna Press Release, 3 pages (Aug. 24, 2020).

[No Author Listed], Moderna Confirms Discussions with the Ministry of Health, Labour and Welfare to Supply Japan with 40 Million Doses of mRNA Vaccine Against COVID-19 (mRNA-1273), Moderna Press Release, 2 pages (Aug. 28, 2020).

[No Author Listed], Moderna Receives FDA Fast Track Designation for mRNA Vaccine (mRNA-1273) Against Novel Coronavirus, Moderna Press Release, 2 pages (May 12, 2020).

[No Author Listed], Moderna Ships mRNA Vaccine Against Novel Coronavirus (mRNA- 1273) for Phase 1 Study, Moderna Press Release, 2 pages (Feb. 24, 2020).

[No Author Listed], Nih Clinical Trial NCT04283461, Safety and Immunogenicity Study of 2019-nCOV Vaccine (mRNA-1273) for Prophylaxis of SARS-COV-2 Infection (COVID-19), 6 pages (Feb. 11, 2021).

[No Author Listed], Nih Clinical Trial NCT04283461, Safety and Immunogenicity Study of 2019-nCOV Vaccine (mRNA-1273) for Prophylaxis of SARS-COV-2 Infection (COVID-19), 8 pages (Apr. 30, 2020).

[No Author Listed], NIH Clinical Trial NCT04283461, Safety and Immunogenicity Study of 2019-nCOV Vaccine (mRNA-1273) for Prophylaxis of SARS-COV-2 Infection (COVID-19), 8 pages (May 28, 2020).

[No Author Listed], Nih Clinical Trial NCT04283461, Safety and Immunogenicity Study of 2019-nCOV Vaccine (mRNA-1273) for Prophylaxis of SARS-COV-2 Infection (COVID-19), First Posted: Feb. 25, 2020, 18 pages, <https://clinicaltrials.gov/ct2/show/NCT04283461>.

[No Author Listed], Nih Clinical Trial NCT04283461, Safety and Immunogenicity Study of 2019-nCOV Vaccine (mRNA-1273) to Treat Novel Coronavirus, 6 pages (Feb. 21, 2020).

[No Author Listed], NIH Clinical Trial of Investigational Vaccine for COVID-19 begins, NIH News Release, 3 pages (Mar. 16, 2020).

[No Author Listed], NIH-Moderna Investigational COVID-19 Vaccine Shows Promise in Mouse Studies, NIH News Release, 2 pages (Aug. 5, 2020).

[No Author Listed], Pfizer and BioNTech Achieve First Authorization in the World for a Vaccine to Combat COVID-19, 3 pages (Dec. 2, 2020).

[No Author Listed], Pfizer and BioNTech Achieve Health Canada Authorization for Their Vaccine to Combat COVID-19, 2 pages (Dec. 9, 2020).

[No Author Listed], Pfizer and BioNTech Announce Agreement with the United Kingdom for 30 Million Doses of mRNA-based Vaccine Candidate Against SARS-COV-2, 3 pages (Jul. 20, 2020).

[No Author Listed], Pfizer and BioNTech Announce an Agreement with U. S. Government for up to 600 Million Doses of mRNA-based Vaccine Candidate Against SARS-COV-2, 3 pages (Jul. 22, 2020).

[No Author Listed], Pfizer and BioNTech Announce Collaboration with Biovac to Manufacture and Distribute COVID-19 Vaccine Doses within Africa, 4 pages (Jul. 21, 2021).

[No Author Listed], Pfizer and BioNTech Announce Data From Preclinical Studies of mRNA-Based Vaccine Candidate Against COVID-19, 3 pages (Sep. 9, 2020).

[No Author Listed], Pfizer and BioNTech Announce Early Positive Data from an Ongoing Phase 1/2 Study of mRNA-based Vaccine Candidate Against SARS-COV-2, 3 pages (Jul. 1, 2020).

[No Author Listed], Pfizer and BioNTech Announce Early Positive Update from German Phase 1/2 COVID-19 Vaccine Study, Including First T Cell Response Data, 3 pages (Jul. 20, 2020).

[No Author Listed], Pfizer and BioNTech Announce Further Details on Collaboration to Accelerate Global COVID-19 Vaccine Development, 2 pages (Apr. 9, 2020).

[No Author Listed], Pfizer and BioNTech Announce New England Journal of Medicine Publication of Phase 1 Data on Lead mRNA Vaccine Candidate BNT162b2 Against COVID-19, 2 pages (Oct. 14, 2020).

[No Author Listed], Pfizer and BioNTech Announce Publication of Peer-Reviewed Data from Ongoing Phase 1/2 study of mRNA-based Vaccine Candidate, BNT162b1, Against SARS-COV-2 in Nature, 4 pages (Aug. 12, 2020).

[No Author Listed], Pfizer and BioNTech Announce Publication of Results from Landmark Phase 3 Trial of BNT162b2 COVID-19 Vaccine Candidate in the New England Journal of Medicine, 3 pages (Dec. 10, 2020).

[No Author Listed], Pfizer and BioNTech Announce Vaccine Candidate Against COVID-19 Achieved Success in First Interim Analysis from Phase 3 Study, 3 pages (Nov. 9, 2020).

[No Author Listed], Pfizer and BioNTech Choose Lead mRNA Vaccine Candidate Against COVID-19 and Commence Pivotal Phase 2/3 Global Study, 3 pages (Jul. 27, 2020).

[No Author Listed], Pfizer and BioNTech Commence Global Clinical Trial to Evaluate COVID-19 Vaccine in Pregnant Women, 3 pages (Feb. 18, 2021).

[No Author Listed], Pfizer and BioNTech Confirm High Efficacy and No. Serious Safety Concerns Through Up to Six Months Following Second Dose in Updated Topline Analysis of Landmark COVID-19 Vaccine Study, 4 pages (Apr. 1, 2021).

[No Author Listed], Pfizer and BioNTech Dose First Participants in the U.S. as Part of Global COVID-19 mRNA Vaccine Development Program, 2 pages (May 5, 2020).

(56) References Cited

OTHER PUBLICATIONS

[No Author Listed], Pfizer and BioNTech Granted FDA Fast Track Designation for Two Investigational mRNA-based Vaccine Candidates Against SARS-COV-2, 2 pages (Jul. 13, 2020).
[No Author Listed], Pfizer and BioNTech Initiate a Study as Part of Broad Development Plan to Evaluate COVID-19 Booster and New Vaccine Variants, 3 pages (Feb. 25, 2021).
[No Author Listed], Pfizer and BioNTech Initiate Rolling Submission of Biologics License Application for U.S. FDA Approval of their COVID-19 Vaccine, 3 pages (May 7, 2021).
[No Author Listed], Pfizer and BioNTech Propose Expansion of Pivotal COVID-19 Vaccine Trial, 2 pages (Sep. 12, 2020).
[No Author Listed], Pfizer and BioNTech Provide Data from German Phase 1/2 Study Further Characterizing Immune Response Following Immunization with Lead COVID-19 Vaccine Candidate BNT162b2, 3 pages (Dec. 14, 2020).
[No Author Listed], Pfizer and BioNTech Publish Data from In Vitro Studies in Nature Medicine Demonstrating COVID-19 Vaccine Elicits Antibodies that Neutralize SARS-COV-2 with Key Mutations Present in U.K. and South African Variants, 3 pages (Feb. 8, 2021).
[No Author Listed], Pfizer and BioNTech Publish Data on COVID-19 Vaccine-Induced Antibodies' Ability to Neutralize SARS-COV-2 U.K. Strain Pseudovirus in Cell Culture in Science, 3 pages (Jan. 29, 2021).
[No Author Listed], Pfizer and BioNTech Publish Preclinical Data from Investigational COVID-19 Vaccine Program in Nature, 3 pages (Feb. 1, 2021).
[No Author Listed], Pfizer and BioNTech Publish Results of Study Showing COVID-19 Vaccine Elicits Antibodies that Neutralize Pseudovirus Bearing the SARS-COV-2 U.K. Strain Spike Protein in Cell Culture, 3 pages (Jan. 20, 2021).
[No Author Listed], Pfizer and BioNTech Reach Agreement with COVAX for Advance Purchase of Vaccine to Help Combat COVID-19, 3 pages (Jan. 22, 2021).
[No Author Listed], Pfizer and BioNTech Reach an Agreement to Supply the EU with 200 Million Doses of Their BNT162b2 mRNA-based Vaccine Candidate against COVID-19, 3 pages (Nov. 11, 2020).
[No Author Listed], Pfizer and BioNTech Receive Authorization in the European Union for COVID-19 Vaccine, 4 pages (Dec. 21, 2020).
[No Author Listed], Pfizer and BioNTech Receive CHMP Positive Opinion for their COVID-19 Vaccine, 3 pages (Dec. 21, 2020).
[No Author Listed], Pfizer and BioNTech Receive Conditional Marketing Authorization by Swissmedic for COVID-19 Vaccine, 3 pages (Dec. 19, 2020).
[No Author Listed], Pfizer and BioNTech Receive FDA Advisory Committee Vote Supporting Potential First Emergency Use Authorization for Vaccine to Combat COVID-19 in the U.S., 3 pages (Dec. 10, 2020).
[No Author Listed], Pfizer and BioNTech Receive First Authorization in European Union for COVID-19 Vaccine in Adolescents, 3 pages (May 28, 2021).
[No Author Listed], Pfizer and BioNTech Receive First U.S. Authorization for Emergency Use of COVID-19 Vaccine in Adolescents, 4 pages (May 11, 2021).
[No Author Listed], Pfizer and BioNTech Receive Health Canada Authorization of COVID-19 Vaccine in Adolescents, 2 pages (May 5, 2021).
[No Author Listed], Pfizer and BioNTech Request Regulatory Agencies Expand Emergency Use of Their COVID-19 Vaccine to Adolescents, 3 pages (Apr. 9, 2021).
[No Author Listed], Pfizer and BioNTech Share Positive Early Data on Lead mRNA Vaccine Candidate BNT162b2 Against COVID-19, 3 pages (Aug. 20, 2020).
[No Author Listed], Pfizer and BioNTech Sign Agreement for Additional Supply to Turkey of 60 Million Doses of their COVID-19 Vaccine, 3 pages (May 20, 2021).

[No Author Listed], Pfizer and BioNTech Submit COVID-19 Vaccine Stability Data at Standard Freezer Temperature to the U.S. FDA, 3 pages (Feb. 19, 2021).
[No Author Listed], Pfizer and BioNTech Submitted Application for Conditional Marketing Authorization for COVID-19 Vaccine to the EMA, 3 pages (Dec. 1, 2020).
[No Author Listed], Pfizer and BioNTech to Co-develop Potential COVID-19 Vaccine, 2 pages (Mar. 17, 2020).
[No Author Listed], Pfizer and BioNTech to Potentially Supply the EU with 200 Million Doses of mRNA-based Vaccine Candidate Against SARS-COV-2, 3 pages (Sep. 9, 2020).
[No Author Listed], Pfizer and BioNTech to Provide 500 Million Doses of COVID-19 Vaccine to U.S. Government for Donation to Poorest Nations, 4 pages (Jun. 10, 2021).
[No Author Listed], Pfizer and BioNTech to Provide COVID-19 Vaccine Doses for Olympic Athletes at the 2020 Tokyo Games, 4 pages (May 6, 2021).
[No Author Listed], Pfizer and BioNTech to Supply Canada with their BNT162 mRNA-Based Vaccine Candidate, 3 pages (Aug. 5, 2020).
[No Author Listed], Pfizer and BioNTech to Supply Japan with 120 Million Doses of Their BNT162 mRNA-Based Vaccine Candidate, 3 pages (Jul. 31, 2020).
[No Author Listed], Pfizer and BioNTech to Supply the U.S. with 100 Million Additional Doses of COVID-19 Vaccine, 3 pages (Dec. 23, 2020).
[No Author Listed], Pfizer and BioNTech to Supply the United States with 100 Million Additional Doses of COVID-19 Vaccine, 3 pages (Feb. 12, 2021).
[No Author Listed], Pfizer And BioNTech to Supply U.S. Government with an Additional 200 Million Doses of COVID-19 Vaccine to Help Meet Continued Need for Vaccine Supply in the U.S., 3 pages (Jul. 23, 2021).
[No Author Listed], Pfizer Canada and BioNTech Initiate Rolling Submission to Health Canada for SARS-COV-2 Vaccine Candidate BNT162b2, 2 pages (Oct. 9, 2020).
[No Author Listed], Pfizer-BioNTech Announce Positive Topline Results of Pivotal COVID-19 Vaccine Study in Adolescents, 3 pages (Mar. 31, 2021).
[No Author Listed], Pfizer-BioNTech's COVID-19 Vaccine Arrives in Rwanda, 3 pages (Mar. 3, 2021).
[No Author Listed], Phase 3 Clinical Trial of Investigational Vaccine for COVID-19 Begins, NIH News Release, 3 pages (Jul. 27, 2020).
[No Author Listed], Real-World Evidence Confirms High Effectiveness of Pfizer-BioNTech COVID-19 Vaccine and Profound Public Health Impact of Vaccination One Year After Pandemic Declared, 4 pages (Mar. 11, 2021).
[No Author Listed], Severe acute respiratory syndrome coronavirus 2 isolate Wuhan-Hu-1, complete genome, Gen Bank: Accession No. 045512, 16 pages (published on Jan. 2020).
[No Author Listed], Severe acute respiratory syndrome coronavirus 2 isolate Wuhan-Hu-1, complete genome, Genbank Accession No. MN908947.3, 11 pages (Mar. 18, 2020).
[No Author Listed], Statement on Voluntary COVID-19 Vaccination for BioNTech Employees and Suppliers to Ensure Undisrupted Manufacturing and Distribution of COVID-19 Vaccine Doses, 1 page (Jan. 11, 2021).
[No Author Listed], U.S. CDC Committee of Independent Health Experts Recommends Vaccination with Pfizer and BioNTech COVID-19 Vaccine for Persons Ages 16 Years and Older, 3 pages (Dec. 12, 2020).
[No Author Listed], U.S. FDA Grants Priority Review for the Biologics License Application for Pfizer-BioNTech COVID-19 Vaccine, 3 pages (Jul. 16, 2021).
[No Author Listed], Update on vaccine production at BioNTech's manufacturing site in Marburg, 2 pages (Feb. 10, 2021).
Abu-Raddad, L. J. et al., Effectiveness of the BNT162b2 Covid-19 Vaccine against the B.1.1.7 and B.1.351 Variants, N. Engl. J. Med., 3 pages (2021).
Adams, P. et al., PHENIX: a comprehensive Python-based system for macromolecular structure solution, Acta Crystallogr D Biol Crystallogr, 66(Pt 2):213-21 (2010).

(56) References Cited

OTHER PUBLICATIONS

Adney, D. et al., Efficacy of an Adjuvanted Middle East Respiratory Syndrome Coronavirus Spike Protein Vaccine in Dromedary Camels and Alpacas, Viruses, 11(3):212 (2019).
Agnihothram, S. et al., Development of a Broadly Accessible Venezuelan Equine Encephalitis Virus Replicon Particle Vaccine Platform, J Virol, 92(11):e00027-18 (2018).
Akinc, A. et al., The onpattro story and the clinical translation of the nanomedicines containing nucleic acid-based drugs, Nature Nanotechnology, 14:1084-1087 (2019).
Al Kahlout, R. et al., Comparative Serological Study for the Prevalence of Anti-MERS Coronavirus Antibodies in High- and Low-Risk Groups in Qatar, J Immunol Res, 2019:1386740, 8 pages (2019).
Al-Amri, S. et al., Immunogenicity of Candidate MERS-CoV DNA Vaccines Based on the Spike Protein, Sci Rep, 7:44875, 8 pages (2017).
Aldrich, C. et al., Proof-of-concept of a low-dose unmodified MRNA-based rabies vaccine formulated with lipid nanoparticles in human volunteers: A phase 1 trial, Vaccine, 39:1310-1318 (2021).
Anderson, E.J. et al., Safety and Immunogenicity of SARS-CoV-2 mRNA-1273 Vaccine in Older Adults, N. Engl. J. Med., 383(25):2427-2438 (2020).
Andries, O. et al., N(I)-methylpseudouridine-incorporated mRNA outperforms pseudouridineincorporated mRNA by providing enhanced protein expression and reduced immunogenicity in mammalian cell lines and mice, J Control Release, 217:337-44 (2015).
Bao, L. et al., Reinfection could not occur in SARS-CoV-2 infected rhesus macaques, bioRXiv, 20 pages (2020).
Bao, L. et al., The Pathogenicity of SARS-CoV-2 in hACE2 Transgenic Mice, bioRxiv, 24 pages (2020).
Battles, M. B. et al., Structure and immunogenicity of pre-fusion-stabilized human metapneumovirus F glycoprotein, Nature Communications, 8(1528):1-11 (2017).
Berger Rentsch, M. and Zimmer, G., A vesicular stomatitis virus replicon-based bioassay for the rapid and sensitive determination of multi-species type I interferon, PLoS One,6(10):e25858, 8 pages (2011).
Bergtold, A. et al., Cell Surface Recycling of Internalized Antigen Permits Dendritic Cell Priming of B Cells, Immunity, 23:503-514 (2005).
Berkhout, B. and Van Hemert, F., On the biased nucleotide composition of the human coronavirus RNA genome, Virus Research, 202:41-47 (2015).
BioNTech and Fosun Pharma Announce Full Regulatory Approval of their Mono- and Bivalent COVID-19 Vaccine COMIRNATY® in Individuals 12 Years and Older in Hong Kong—Dec. 23, 2022.
BioNTech Announces Second Quarter Financial Results and Corporate Update—Aug. 8, 2022.
Boon, S. et al., Temporal-Geographical Dispersion of SARS-CoV-2 Spike Glycoprotein Variant Lineages and Their Functional Prediction Using in Silico Approach, Mbio 12(5), e02687-21, 19 pages (2021).
Boone, L. et al., Selection and interpretation of clinical pathology indicators of hepatic injury in preclinical studies, Vet Clin Pathol., 34(3):182-8 (2005).
Bouloy, M. et al., Both the 7-methyl and the 2'-0-methyl groups in the CAP of mRNA strongly influence its ability to act as primer for influenza virus RNA transcription, Proceedings of the National Academy of Sciences of the USA, 77(7):3952-3956 (1980).
Braathen, R. et al., The Magnitude and IgG Subclass of Antibodies Elicited by Targeted DNA Vaccines Are Influenced by Specificity for APC Surface Molecules, ImmunoHorizons, 2(1):21pgs (2018).
Brooks, M. et al., Non-Lethal Endotoxin Injection: A Rat Model of Hypercoagulability, PLoS One, 12(1):e0169976 (2017).
Brown, E. L. and Essigmann, H. T., Original Antigenic Sin: the Downside of Immunological Memory and Implications for COVID-19, Amer. Soc. Microbio., 6(2):e00056-21, 6 pages (2021).
Bruun, T. et al., Engineering a Rugged Nanoscaffold to Enhance Plug-and-Display Vaccination, ACS Nano, 12(9):8855-8866 (2018).
Cai, Y. et al., Distinct conformational states of SARS-CoV-2 spike protein, Science, 369(6511):1586-1592 (2020).
Callaway, E. and Ledford, H., How to Redesign Covid Vaccines So They Protect Against Variants, 590(7844):15-16 (2021).
Chan, J. et al., Genomic characterization of the 2019 novel human-pathogenic coronavirus isolated from a patient with atypical pneumonia after visiting Wuhan, Emerg Microbes Infect, 9(1):221-236 (2020).
Chan, J. et al., NCBI GenBank: MN938384.1, Severe acute respiratory syndrome coronavirus 2 isolate 2019_nCOV_HKU_SZ_002a_2020, complete genome, NCBI GenBank (Feb. 11, 2020).
Chan, J. F. et al., A familial cluster of pneumonia associated with the 2019 novel coronavirus indicating person-to-person transmission a study of a family cluster, Lancet, 395(10223):514-523 (2020).
Chandrashekar, A. et al., SARS-CoV-2 infection protects against rechallenge in rhesus macaques, Sci. Mag., 12 pages (2020).
Chen, J. et al., Prediction and mitigation of mutation threats to COVID-19 vaccines and anibody therapies, Arxiv. org, Cornell University Library, 28 pages (2021).
Chen, Y. et al., Emerging Coronaviruses: Genome structure, replication, and pathogenesis, J Med Virol., 92:418-423, (2020).
Chi, X. et al., A neutralizing human antibody binds to the N-terminal domain of the Spike protein of SARS-CoV-2, Science, 369(6504):650-655 (2020).
Cohen, A. et al., Mosaic RBD nanoparticles protect against challenge by diverse sarbecoviruses in animal models, Science, retrieved from the Internet: https://www.science.org/doi/pdf/10.1126/science.abf6840, 30 pages (2022).
Cohen, Jon, Scientists are moving at record speed to create new coronavirus vaccines but they may come too late, Science; AAAS, retrieved from the Internet: https://www.sciencemag.org/news/2020/01/scientists-are-moving-record-speed-create-new-coronavirus-vaccines-they-may-come-too, 6 pages (May 25, 2021).
Corbett, K. S. et al., SARS-COV-2 mRNA Vaccine Development Enabled by Prototype Pathogen Preparedness, posted on bioRxiv (Jun. 2020), 39 pages.
Corbett, K.S. et al., Evaluation of mRNA-1273 against SARS-CoV-2 B.1.351 Infection in Nonhuman Primates, posted on bioRxiv (May 2021), 33 pages.
Corbett, K.S. et al., Evaluation of the mRNA-1273 Vaccine against SARS-CoV-2 in Nonhuman Primates, N. Engl. J. Med., 383(16):1544-1555 (2020).
Corbett, K.S. et al., Immune Correlates of Protection by mRNA-1273 Immunization against SARS-CoV-2 Infection in Nonhuman Primates, posted on bioRxiv (Apr. 2021), 33 pages.
Corbett, K.S. et al., SARS-CoV-2mRNA vaccine design enabled by prototype pathogen preparedness, Nature, 586:567-571 (2020).
Cossarizza, A. et al., SARS-CoV-2, the Virus that Causes COVID-19: Cytometry and the New Challenge for Global Health, Cytometry Part A, 4 pages (2020).
Cullis, P. and Hope, M., Lipid Nanoparticle Systems for Enabling Gene Therapies, Mol Ther, 25(7):1467-1475 (2017).
CureVac Provides Update on Phase 2b/3 Trial of First-Generation COVID-19 Vaccine Candidate, CVnCoV, Jun. 16, 2021, press release, <https://www.curevac.com/en/curevac-provides-update-on-phase-2b-3-trial-of-first-generation-covid-19-vaccine-candidate-cvncov/>, 4 pages.
CureVac's COVID-19 vaccine (CVnCoV): Withdrawal from the rolling review process, Oct. 12, 2021, European Medical Agency (EMA), ema.europa.eu/en/medicines/human/withdrawn-applications/curevacs-covid-19-vaccine-cvncov, 3 pages.
Database EMBL [Online] EBI; Jan. 15, 2020 (Jan. 15, 2020), Zhang Y. et al: "Wuhan seafood market pneumonia virus isolate Wuhan-Hu-1, complete genome.", XP055796635, Database accession No. MN908947 the whole document.
Database UniParc, Database accession No. UPI00131F240A, retrieved from UniProt, 4 pages Aug. 23, 2021.
Database UniParc, Database accession No. UPI0013753F0, retrieved from UniProt, one page (Sep. 2, 2021).
De Wit, E. et al., SARS and MERS: recent insights into emerging coronaviruses, Nat Rev Microbiol., 14(8):523-34 (2016).

(56) References Cited

OTHER PUBLICATIONS

Dearlove, B. et al., A SARS-CoV-2 vaccine candidate would likely match all currently circulating variants, PNAS, 117(38):23652-23662 (2020).

Den Dunnon, J.T. and Antonarakis, S.E., Nomenclature for the description of sequence variations, Human Genet., 109(1):121-124 (2001).

Diao, B. et al., Human kidney is a target for novel severe acute respiratory syndrome coronavirus 2 infection, Nat Commun., 12(1):2506, 9 pages (2021).

Doremalen, N. et al., ChAdOx1 nCoV-19 vaccination prevents SARS-CoV-2 pneumonia in rhesus macaques, bioRxiv, 23 pages (2020).

Du, L. et al., Recombinant adeno-associated virus expressing the receptor-binding domain of severe acute respiratory syndrome coronavirus S protein elicits neutralizing antibodies: Implication for developing SARS vaccines, Virology, 353(1):6-16 (2006).

Emsley, P. et al., Features and development of Coot, Acta Crystallogr D Biol Crystallogr, 66(Pt 4):486-501 (2010).

Ennulat, D. et al., Diagnostic performance of traditional hepatobiliary biomarkers of drug-induced liver injury in the rat, Toxicol Sci., 116(2):397-412 (2010).

Fan, X. et al., Cryo-EM analysis of the post-fusion structure of the SARS-CoV spike glycoprotein, Nat Commun., 11(1):3618, 10 pages (2020).

Fang, Z. et al., Omicron-specific mRNA vaccination alone and as a heterogous booster against SARS-CoV-2, Nature Communications, 13:3250, 12 pages (2022).

Faria, N. et al., Genomic characterisation of an emergent SARS-CoV-2 lineage in Manaus: preliminary findings—SARS-COV-2 coronavirus / nCoV-2019 Genomic Epidemiology—Virological, retrieved from the Internet: https//virological.org/t/genomic-characterisation-of-an-emergent-sars-cov-2-lineage-in-manaus-preliminary-findings/586, 6 pages (May 31, 2021).

Farooq, F. et al., Circulating follicular T helper cells and cytokine profile in humans following vaccination with the rVSV-ZEBOV Ebola vaccine, Scientific Reports, 6(27944):1-9 (2016).

Feldstein, L. R. et al., Multisystem Inflammatory Syndrome in U.S. Children and Adolescents, N. Engl. Med., 383(4):334-346 (2020).

Fierz, W. and Walz, B., Antibody Dependent Enhancement Due to Original Antigenic Sin and the Development of SARS, Front. Immun., 11(1120):1-5 (2020).

Folegatti, P. et al., Safety and immunogenicity of the ChAdOx1 nCoV-19 vaccine against SARS-CoV-2: a preliminary report of a phase 1/2, single-blind, randomised controlled trial, Lancet, 396(10249):467-478 (2020).

Follis, K. et al., Furin cleavage of the SARS coronavirus spike glycoprotein enhances cell-cell fusion but does not affect virion entry, Virology, 350(2):358-69 (2006).

Funk, C. et al., A Snapshot of the Global Race for Vaccines Targeting SARS-CoV-2 and the COVID-19 Pandemic, Front Pharmacol., 11:937, 17 pages (2020).

Furuichi, Y. and Shatkin, A., Viral and cellular mRNA capping: past and prospects, Adv Virus Res, 55:135-84 (2000).

Furuichi, Yasuhiro, Caps on Eukaryotic mRNAs, John Wiley & Sons, pp. 1-12 (Jul. 2014).

Gallie, Daniel R., The cap and poly(A) tail function synergistically to regulate mRNA translational efficiency, Genes Dev, 5(11):2108-16 (1991).

Garcia-Doval, C. and Van Raaij, M. J., Structure of the receptor-binding carboxy-terminal domain of bacteriophage T7 tail fibers, PNAS, 109(24):9390-9395 (2012).

Garrido, C. et al., SARS-CoV-2 vaccines elicit durable immune responses in infant rhesus macaques, Sci. Immunol., 23 pages (2021).

Gautam, U. et al., In vivo inhibition of tryptophan catabolism reorganizes the tuberculoma and augments immune-mediated control of *Mycobacterium tuberculosis*, Proc Natl Acad Sci USA, 115(1):E62-E71 (2018).

Gebre, M. S. et al., Optimization of Non-Coding Regions Improves Protective Efficacy of an mRNA SARS-CoV-2 Vaccine in Nonhuman Primates, bioRxiv, 36 pages (2021).

GenBank MN975262.1 "Wuhan seafood market pneumonia virus isolate 2019-nCoV_HKU-SZ-005b_2020, complete genome" (Jan. 24, 2020) [retrieved on Jun. 2, 2021, https://www.ncbi.nlm.nih.gov/nuccore/1800242661 ?sat=48&satkey=350763] whole doc.

GenBank QHN73810.1 "surface glycoprotein [Wuhan seafood market pneumonia virus]" (Jan. 24, 2020) [retrieved on Jun. 2, 2021, https://www.ncbi.nlm.nih.gov/protein/QHN73810.1/] whole doc.

Gomes, A. C. et al., Type of RNA Packed in VLPs Impacts IgG Class Switching-Implications for an Influenza Vaccine Design, MDPI, 7(47):1-13 (2019).

Graham, Barney S., Rapid COVID-19 vaccine development, Science, 368(6494):945-946 (2020).

Grudzen, E. et al., Differential Inhibition of mRNA Degradation Pathways by Novel Cap Analogs, The Journal of Biological Chemistry, 281(4):1857-1867 (2006).

Habjan, M. et al., Sequestration by IFIT1 impairs translation of 2'0-unmethylated capped RNA, PLoS Pathogens, 9(10):e1003663 (2013).

Hahn, S. et al., FDA Statement on Following the Authorized Dosing Schedules for COVID-19 Vaccines, FDA website, Jan. 4, 2021, 3 pages.

Hait, S. H. et al., Early T Follicular Helper Cell Responses and Germinal Center Reactions Are Associated with Viremia Control in Immunized Rhesus Macaques, Journal of Virology, 93(4):1-22 (2019).

Hassett, K. et al., Optimization of Lipid Nanoparticles for Intramuscular Administration of mRNA Vaccines, Mol Ther Nucleic Acids, 15:1-11 (2019).

He, Y. et al., Receptor-binding domain of SARS-CoV spike protein induces highly potent neutralizing antibodies: implication for developing subunit vaccine, Biochem Biophys Res Commun, 324(2):773-81 (2004).

Henderson, R. et al., Controlling the SARS-CoV-2 spike glycoprotein conformation, Nat Struct Mol Biol., 27(10):925-933 (2020).

Hie, B. et al., Learning the language of viral evolution and escape, Science, 371(6526):284-288 (2021).

Hodcroft, Emma, CoVariants: Shared Mutations, Covariants.org, 4 pages (2022).

Hodgson, J., The pandemic pipeline, Nature Biotechnology, 38(5):523-532 (2020).

Hoffman, M. et al., SARS-CoV-2 variants B.1.351 and B.1.1.248: Escape from the therapeutic antibodies and antibodies induced by infection and vaccination, bioRxiv, retrieved from the Internet: https//www.biorxiv.org/content/10.1101/2021.02.11.430787v1.full.pdf (Aug. 23, 2021).

Hoffmann, M. et al., SARS-CoV-2 Cell Entry Depends on ACE2 and TMPRSS2 and Is Blocked by a Clinically Proven Protease Inhibitor, Cell, 181(2):271-280 (2020).

Holdsworth, S. R. et al., Th1 and Th2 T helper cell subsets affect patterns of injury and outcomes in glomerulonephritis, Kidney International, 55:1198-1216 (1999).

Honda-Okubo, Y. et al., Severe Acute Respiratory Syndrome-Associated Coronavirus Vaccines Formulated with Delta Inulin Adjuvants Provide Enhanced Protection while Ameliorating Lung Eosinophilic Immunopathology, Journal of Virology, 89(6):2995-3007 (2015).

Hsieh, C. et al., Structure-based design of prefusion-stabilized SARS-CoV-2 spikes, Science, 369:1501-1505 (2020).

Hsieh, C.. et al., Structure-based Design of Prefusion-stabilized SARS-CoV-2 Spikes, bioRxiv, retrieved from the Internet: https://www.ncbi.nlm.nih.gov/pmc/articles/PMC7302215/pdf/nihpp-2020.5.30.125484.pdf, 39 pages (May 30, 2020).

Huang, C. et al., Clinical features of patients infected with 2019 novel coronavirus in Wuhan, China, Lancet, 395(10223)497-506 (2020).

Huang, Q. et al., A single-dose mRNA vaccine provides a long-term protection for hACE2 transgenic mice from SARS-CoV-2, Nat. Comm., 12(776):1-10 (2021).

(56) References Cited

OTHER PUBLICATIONS

Huang, Y. et al., Structural and functional properties of SARS-CoV-2 spike protein: potential antivirus drug development for COVID-19, Acta Pharma. Sinica, 41:1141-1149 (2020).
Huber, V. C. et al., Distinct Contributions of Vaccine-Induced Immunoglobulin G1 (IgG1) and IgG2a Antibodies to Protective Immunity against Influenza, Clinical and Vaccine Immunology, 13(9):981-990 (2006).
Hui, A. et al., Immunogenicity and safety of BNT162b2 mRNA vaccine in Chinese adults: A phase 2 randomised clinical trial. The Lancet Regional Health-Western Pacific 29 (2022): 100586.
Hulswit, R. et al., Coronavirus Spike Protein and Tropism Changes, Adv Virus Res., 96:29-57 (2016).
Hyde, J. L. et al., A viral RNA structural element alters host recognition of nonself RNA, Science, 343(6172):783-787 (2014).
Hyde, J. L. et al., Supplementary Information, Science, 343(6172):783-787 (2014).
Iadevaia, V. et al., All translation elongation factors and the e, f, and h subunits of translation initiation factor 3 are encoded by 5'-terminal oligopyrimidine (TOP) mRNAs, RNA, 14:1730-1736 (2008).
International Nonproprietary Names for Pharmaceutical Substances (INN), WHO Drug Information, vol. 33, No. 3, 139 pages, (2019).
International Search Report and Written Opinion for Application No. PCT/US2021/015145, 5 pages, dated May 3, 2021.
International Search Report for PCT/EP2021/059947, 6 pages (dated Aug. 5, 2021).
International Search Report for PCT/EP2021/060004, 7 pages (dated Sep. 8, 2021).
International Search Report for PCT/EP2021/060508, 7 pages (dated Aug. 5, 2021).
International Search Report for PCT/EP2022/060417, 6 pages (dated Aug. 4, 2022).
International Search Report for PCT/EP2022/083740, 9 pages (dated Jun. 2, 2023).
Ishikawa, M. et al., Preparation of eukaryotic mRNA having differently methylated adenosine at the 5'-terminus and the effect of the methyl group in translation, Nucleic Acids Symposium Series, Oxford, 53:129-130 (2009).
Ivens, I. et al., PEGylated Biopharmaceuticals: Current Experience and Considerations for Nonclinical Development, Toxicol Pathol., 43(7):959-83 (2015).
Jackson, L.A. et al., An mRNA Vaccine against SARS-CoV-2—Preliminary Report, N. Engl. J. Med., 383:1920-1931 (2020).
Jackson, N. A. C. et al., The promise of mRNA vaccines: a biotech and industrial perspective, NPJ Vaccines, 5(11):1-6 (2020).
Jafarzadeh, H. et al., Contribution of monocytes and macrophages to the local tissue inflammation and cytokine storm in COVID-19: Lessons from SARS and MERS, and potential therapeutic interventions, Life Sci., 257:118102, 16 pages (2020).
Jaimes, J. et al., Phylogenetic Analysis and Structural Modeling of SARS-CoV-2 Spike Protein Reveals an Evolutionary Distinct and Proteolytically Sensitive Activation Loop, J Mol Biol., 432(10):3309-3325 (2020).
Jeong, D. et al., Assemblies-of-putative-SARS-CoV2-spike-encoding-mRNA-sequences-for-vaccines-BNT-162b2- and-mRNA-1273, 4 pages (2021).
Ji, R. et al., BNT162b2 Vaccine Encoding the SARS-CoV-2 P2 S Protects Transgenic hACE2 Mice against COVID-19, Vaccines, 9(324):1-7 (2021).
Jiang, S. et al., Neutralizing Antibodies against SARS-CoV-2 and Other Human Coronaviruses, Trends in Immunology, 41(5):355-359 (2020).
Kaku, C. et al., Recall of pre-existing cross-reactive B cell memory following Omicron BA. 1 breakthrough infection. Science immunology (2022): eabq3511.
Kanekiyo, M. et al., New Vaccine Design and Delivery Technologies, The Journal of Infectious Diseases, 219(S1):S88-96 (2019).
Kauffman, K. et al., Materials for non-viral intracellular delivery of messenger RNA therapeutics, J Control Release, 240:227-234 (2016).

Ke, Z. et al., Structures, conformations and distributions of SARs-CoV-2 spike protein trimers on intact virions, bioRxiv (2020).
Kielian, M. and Rey, F. A., Virus membrane-fusion proteins: more than one way to make a hairpin, Nature Reviews Microbiology, 4:67-76 (2006).
Kim, A. et al., A mouse model of anemia of inflammation: complex pathogenesis with partial dependence on hepcidinm, Blood, 123(8):1129-36 (2014).
Kim, A. et al., Isocitrate treatment of acute anemia of inflammation in a mouse model. Blood Cells Mol Dis., 56(1):31-6 (2016).
Kim, J. et al., Viral Load Kinetics of SARS-CoV-2 Infection in First Two Patients in Korea, J Korean Med Sci., 35(7):e86 (2020).
Kirchdoerfer, R. N. et al., Stabilized coronavirus spikes are resistant to conformational changes induced by receptor recognition or proteolysis, Sci. Repo., 8(15701):1-11 (2018).
Kleine-Weber, H., et al., Functional analysis of potential cleavage sites in the MERS-coronavirus spike protein, Sci Rep., 8(1):16597 (2018).
Klimek, L. et al., Severe allergic reactions after COVID-19 vaccination with the Pfizer/BioNTech vaccine in Great Britain and USA, Allergo J. Int., 5 pages (2021).
Koukhareva I. I. and Lebedev, A. V., Chemical Route to the Capped RNAs, Nucleosides, Nucleotides and Nucleic Acids, 23(10):1667-1780 (2004).
Kozauer, N. et al., Cross-Discipline Team Leader Review, Center for Drug Evaluation and Research 210922, 485 pages (2020).
Kozma, G. T. et al., Pseudo-anaphylaxis to Polyethylene Glycol (PEG)-Coated Liposomes: Roles of Anti-PEG IgM and Complement Activation in a Porcine Model of Human Infusion Reactions, ACS Nano, 13:9315-9324 (2019).
Krarup, A. et al., A highly stable prefusion RSV F vaccine derived from structural analysis of the fusion mechanism, Nature Communications, 6(8143):1-12 (2015).
Kremsner, P. et al., Phase 1 Assessment of the Safety and Immunogenicity of an mRNALipid Nanoparticle Vaccine Candidate Against SARS-CoV-2 in Human Volunteers, medRxiv, pp. 1-38 (2020).
Kuhn, A. et al., Phosphorothioate cap analogs increase stability and translational efficiency of RNA vaccines in immature dendritic cells and induce superior immune responses in vivo, Gene Therapy, 17:961-971 (2010).
Kumar, A. et al., Status Report on COVID-19 Vaccines Development, Current Infectious Disease Reports, 23(6):1-12 (2021).
Kurhade, C. et al., Neutralization of Omicron BA. 1, BA. 2, and BA. 3 SARS-CoV-2 by 3 doses of BNT162b2 vaccine. Nature communications 13.1 (2022): 1-4.
Kurhade, C. et al., Neutralization of Omicron sublineages and Deltacron SARS-CoV-2 by 3 doses of BNT162b2 vaccine or BA. 1 infection. bioRxiv (2022).
Kurimoto, S. et al., PEG-OligoRNA Hybridization of mRNA for Developing Sterically Stable Lipid Nanoparticles toward In Vivo Administration, Molecules, 24(7):1303, 16 pages (2019).
Laczkó, D. et al., A Single Immunization with Nucleoside-Modified mRNA Vaccines Elicits Strong Cellular and Humoral Immune Responses against SARS-CoV-2 in Mice, Immunity, 53(4):724-732 (2020).
Lambert, P.et al., Consensus summary report for CEPI/BC Mar. 12-13, 2020 meeting: Assessment of risk of disease enhancement with COVID-19 vaccines, Vaccine, 38(31):4783-4791 (2020).
Lan, J. et al., Structure of the SARS-CoV-2 spike receptor-binding domain bound to the ACE2 receptor, Nature, 581:215-220 (2020).
Lee, W. S. et al., Antibody-dependent enhancement and SARS-CoV-2 vaccines and therapies, Nature Microbiology, 5:1185-1191 (2020).
Lee, Y. et al., Cross Protection against Influenza A Virus by Yeast-Expressed Heterologous Tandem Repeat M2 Extracellular Proteins, PLoS One, 10(9):e0137822 (15).
Lester, S. et al., Middle East respiratory coronavirus (MERS-CoV) spike (S) protein vesicular stomatitis virus pseudoparticle neutralization assays offer a reliable alternative to the conventional neutralization assay in human seroepidemiological studies, Access Microbiol., 1(9):e000057, 9 pages (2019).
Leung, A. K.K. et al., Lipid Nanoparticles for Short Interfering RNA Delivery, Advances in Genetics 88:71-110 (2014).

(56) References Cited

OTHER PUBLICATIONS

Li, Fang, Structure, Function, and Evolution of Corona virus Spike Proteins, Annu Rev Viral, 3(1):237-261 (2016).

Li, R. et al., The challenge of emerging SARS-CoV-2 mutants to vaccine development, Journal of Genetics and Genomics, 48(2):102-106 (2021).

Limbach, P. A. et al., Summary: the modified nucleosides of RNA, Nucleic Acids Research, 22(12):2183-2196 (1994).

Liu Y. et al., Neutralizing activity of BNT162b2-elicited serum. New England Journal of Medicine 384.15 (2021): 1466-1468.

Liu, J. et al., BNT162b2-elicited neutralization of B. 1.617 and other SARS-CoV-2 variants. Nature 596.7871 (2021): 273-275.

Liu, J. et al., BNT162b2-elicited neutralization of Delta plus, Lambda, Mu, B. 1.1. 519, and Theta SARS-CoV-2 variants. npj Vaccines 7.1 (2022): 1-4.

Liu, Y. et al., BNT162b2-elicited neutralization against new SARS-CoV-2 spike variants. New England Journal of Medicine 385.5 (2021): 472-474.

Liu, Y. et al., Neutralizing Activity of BNT162b2-Elicited Serum, N. Eng. J. Med., 384(15):1-3 (2021).

Lu, R. et al., Genomic characterisation and epidemiology of 2019 novel coronavirus: implications for virus origins and receptor binding, Lancet, 395(10224):565-574 (2020).

Lucey, Daniel R., Moderna to test a "multivalent" COVID vaccine as well as single-valent boosters, retrieved from Internet: https://www.idsociety.org/science-speaks-blog/2021/moderna-to-test-a-multivalent-covid-vaccine-as-well-as-single-valent-boosters/#/+/0/publishedDate_na_dt/desc/, 2 pages (2021).

McCown, P. J. et al., Naturally occurring modified ribonucleosides, WIREs RNA, 11(e1595):1-71 (2020).

McKay, P. et al., Self-amplifying RNA SARS-Co V-2 lipid nanoparticle vaccine candidate induces high neutralizing antibody titers in mice, Nat Commun, 11(1):3523, 7 pages (2020).

McLean, G et al., The impact of evolving SARS-CoV-2 mutations and variants on COVID-19 vaccines. Mbio 13.2 (2022): e02979-21.

Meier, S. et al., Foldon, The Natural Trimerization Domain of T4 Fibritin, Dissociates into a Monomeric A-state Form containing a Stable β-Hairpin: Atomic Details of Trimer Dissociation and Local β-Hairpin Stability from Residual Dipolar Couplings, J. Mol. Biol., 344(4):1051-1069 (2004).

Mishra, S. and Carnahan, R et al., Coronavirus: A new type of vaccine using RNA could help defeat COVID-19, The Conversation, 4 pages (2020).

Moderna TX Clinical Trial, NCT04283461, Safety and Immunogenicity Study of 2019-nCoV Vaccine (mRNA-1273) for Prophylaxis of SARS-CoV-2 Infection (COVID-19), 18 pages (2020).

Muik, A. et al., Exposure to BA. 4/5 S protein drives neutralization of Omicron BA. 1, BA. 2, BA. 2.12. 1, and BA. 4/5 in vaccine-experienced humans and mice. Science Immunology (2022): eade9888.

Muik, A. et al., Exposure to BA. 4/BA. 5 Spike glycoprotein drives pan-Omicron neutralization in vaccine-experienced humans and mice. bioRxiv (2022).

Muik, A. et al., Neutralization of SARS-CoV-2 lineage B. 1.1. 7 pseudovirus by BNT162b2 vaccine-elicited human sera. Science 371.6534 (2021): 1152-1153.

Muik, A. et al., Neutralization of SARS-CoV-2 Omicron by BNT162b2 mRNA vaccine-elicited human sera. Science 375.6581 (2022): 678-680.

Muik, A. et al., Neutralization of SARS-CoV-2 Omicron pseudovirus by BNT162b2 vaccine-elicited human sera. medRxiv (2021).

Muik, A. et al., Omicron BA. 2 breakthrough infection enhances cross-neutralization of BA. 2.12. 1 and Ba. 4/BA. 5. Science Immunology 7.77 (2022): eade2283.

Muik, A. et al., Progressive loss of conserved spike protein neutralizing antibody sites in Omicron sublineages is balanced by preserved T-cell recognition epitopes. bioRxiv (2022).

Mulligan, M. et al., Phase I/II study of COVID-19 RNA vaccine BNT162b1 in adults, Nature, 586(7830):589-593 (2020).

Mulligan, M. J. et al., Phase 1/2 Study to Describe the Safety and Immunogenicity of a COVID-19 RNA Vaccine Candidate (BNT162b1) in Adults 18 to 55 Years of Age: Interim Report, bioRxiv, 586:16pgs (2020).

Munoz-Fontela, C. et al., Animal models for COVID-19, Nature, 586:509-515 (2020).

Munster, et al., Respiratory disease and virus shedding in rhesus macaques inoculated with SARS-CoV-2, bioRxiv (2020).

Muruato, A. et al., A high-throughput neutralizing antibody assay for COVID-19 diagnosis and vaccine evaluation, Nat Commun., 11(1):4059 (2020).

Muthumani, K. et al., A synthetic consensus anti-spike protein DNA vaccine induces protective immunity against Middle East respiratory syndrome coronavirus in nonhuman primates, Science Translational Medicine, 7(301):1-14 (2015).

Nathan, A. et al., Structure-guided T cell vaccine design for SARS-CoV-2 variants and sarbecovriuses, Cell, 184:1-13 (2021).

Nawrat, A., Q&A with CureVac: resolving the ultra-cold chain logistics of Covid-19 mRNA vaccines, Pharmaceutical Technology, Dec. 5, 2020, <https://www.pharmaceutical-technology.com/analysis/mrna-vaccines-covid19-pandemic-curevac/>, 23 pages.

No Author Listed, Messenger RNA encoding the full-length SARS-CoV-2 spike glycoprotein, WHO International Nonproprietary Names Progamme, 4 pages (Jun. 2021).

Nurieva, R. I. et al., Generation of T Follicular Helper Cells is Mediated by Interleukin-21 but Independent of T Helper 1,2, or 17 Cell Lineages, Immunity, 29:138-149 (2008).

Oany, A. et al., Design of an epitope-based peptide vaccine against spike protein of human coronavirus: an in silico approach, Drug Des Devel Ther., 8:1139-49 (2014).

Ogando, N. S. et al., SARS-coronavirus-2 replication in Vero E6 cells: replication kinetics, rapid adaptation and cytopathology, bioRxiv, 40 pages (2020).

Onpattro (patisiran) lipid complex injection, for intravenous use, Initial U.S. Approval: 2018, Highlights of prescribing information, 14 pages, Revised: Jan. 2023.

Orlandini Von Niessen, A. G. et al., Improving mRNA-Based Therapeautic Gene Delivery by Expression-Augmenting 3' UTRs Identified by Cellular Library Screening, Molecular Therapy Original Article, 27(4):824-836 (2019).

Ou, X. et al., Characterization of spike glycoprotein of SARS-CoV-2 on virus entry and its immune cross-reactivity with SARS-CoV, Nat Commun., 11(1):1620, 12 pages (2020).

Pallesen, J. et al., Immunogenicity and structures of a rationally designed prefusion MERS-CoV spike antigen, Proc Natl Acad Sci USA, 114(35):E7348-E7357 (2017).

Pape, K. A. et al., The Humoral Immune Response is Initiated in Lymph Nodes by B Cells that Acquire Soluble Antigen Directly in the Follicles, Immunity, 26:491-502 (2007).

Pardi, et al., Nucleoside-modified mRNA vaccines induce potent T follicular helper and germinal center B cell responses, J. Exp. Med. 215(6):1571-1588 (2018).

Pardi, N. et al., Characterization of HIV-1 Nucleoside-Modified mRNA Vaccines in Rabbits and Rhesus Macaques, Molecular Therapy: Nucleic Acids, 15:36-47 (2019).

Pardi, N. et al., mRNA vaccines—a new era in vaccinology, Nat Rev Drug Discov, 17(4):261-279 (2018).

Pardi, N. et al., Nucleoside-modified mRNA immunization elicits influenza virus hemagglutinin stalk-specific antibodies, Nat Commun., 22;9(1):3361 (2018).

Pardi, N. et al., Zika virus protection by a single low-dose nucleoside-modified mRNA vaccination, Nature, 543(7644):248-251 (2017).

Pardi, Norbert, COVID-19 Symposium: Nucleoside-modified mRNA Vaccines Against SARS-CoV-2, Penn Medicine, 10 pages (2020).

Pardi, Norbert, Developement of nucleoside modified mRNA Vaccines against SARS-CoV-2, Penn Medicine, 10 pages (2020).

Pegu, A. et al., Durability of mRNA-1273-induced antibodies against SARS-CoV-2 variants, posted on bioRxiv (May 2021), 39 pages.

Peng, Y. et al., Broad and strong memory $CD4^+$ and $CD8^+$ T cells induced by SARS-CoV-2 in UK convalescent individuals following COVID-19, Nat. Immun., 21:1336-1345 (2020).

(56) References Cited

OTHER PUBLICATIONS

Pfizer and BioNTech Advance COVID-19 Vaccine Strategy With Study Start of Next-Generation Vaccine Candidate Based on Enhanced Spike Protein Design—Jul. 27, 2022.
Pfizer and BioNTech Announce Data Demonstrating High Immune Response Following a Booster Dose of Their COVID-19 Vaccine in Children 5 Through 11 Years of Age—Apr. 14, 2022.
Pfizer and BioNTech Announce Omicron-Adapted COVID-19 Vaccine Candidates Demonstrate High Immune Response Against Omicron—Jun. 25, 2022.
Pfizer and BioNTech Announce Positive Early Data From Clinical Trial of Omicron BA.4/BA.5-Adapted Bivalent Booster in Individuals 18 Years and Older—Oct. 13, 2022.
Pfizer and BioNTech Announce Updated Clinical Data for Omicron BA.4/BA.5-Adapted Bivalent Booster Demonstrating Substantially Higher Immune Response in Adults Compared to the Original COVID-19 Vaccine—Nov. 4, 2022.
Pfizer and BioNTech Announce Updated COVID-19 Vaccine Data Supporting Efficacy in Children 6 Months through 4 Years of Age—Aug. 23, 2022.
Pfizer and BioNTech Complete Submission to European Medicines Agency for Omicron BA.1 Adapted Bivalent Vaccine Candidate—Jul. 19, 2022.
Pfizer and BioNTech Complete Submission to European Medicines Agency for Omicron BA.4/BA.5 Adapted Bivalent Vaccine—Aug. 26, 2022.
Pfizer and BioNTech Complete Submission to European Medicines Agency for Omicron BA.4/BA.5-Adapted Bivalent Vaccine Booster in Children 5 Through 11 Years of Age—Sep. 28, 2022.
Pfizer and BioNTech Granted FDA Emergency Use Authorization of Omicron BA.4/BA.5-Adapted Bivalent COVID-19 Vaccine Booster for Ages 12 Years and Older—Aug. 31, 2022.
Pfizer and BioNTech Initiate Study to Evaluate Omicron-Based COVID-19 Vaccine in Adults 18 to 55 Years of Age—Jan. 25, 2022.
Pfizer and BioNTech Provide Update on Omicron Variant—Dec. 8, 2021.
Pfizer and BioNTech Provide Update on Rolling Submission to European Medicines Agency for a Potential Variant-Adapted Vaccine—Jun. 15, 2022.
Pfizer and BioNTech Publish Data from Two Laboratory Studies on COVID-19 Vaccine-induced Antibodies Ability to Neutralize SARS-CoV-2 Omicron Variant—Jan. 24, 2022.
Pfizer and BioNTech Receive Positive CHMP Opinion for Omicron BA.1-Adapted Bivalent COVID-19 Vaccine Booster in European Union—Sep. 1, 2022.
Pfizer and BioNTech Receive Positive CHMP Opinion for Omicron BA.4/BA.5-Adapted Bivalent COVID-19 Vaccine Booster for Children 5 Through 11 Years of Age in European Union—Nov. 10, 2022.
Pfizer and BioNTech Receive Positive CHMP Opinion for Omicron BA.4/BA.5-Adapted Bivalent COVID-19 Vaccine Booster in European Union—Sep. 12, 2022.
Pfizer and BioNTech Receive U.S. FDA Emergency Use Authorization for Omicron BA.4/BA.5-Adapted Bivalent COVID-19 Vaccine Booster in Children 5 Through 11 Years of Age—Oct. 12, 2022.
Pfizer and BioNTech Receive U.S. FDA Emergency Use Authorization for Omicron BA.4/BA.5-Adapted Bivalent COVID-19 Vaccine in Children Under 5 Years—Dec. 8, 2022.
Pfizer and BioNTech Report New Data on Omicron BA.4/BA.5-Adapted Bivalent Booster Demonstrating Improved Immune Response Against Emerging Omicron Sublineages—Nov. 18, 2022.
Pfizer and BioNTech Submit Application to U.S. FDA for Emergency Use Authorization of Omicron BA.4/BA.5-Adapted Bivalent COVID-19 Vaccine—Aug. 22, 2022.
Pfizer and BioNTech Submit Application to U.S. FDA for Emergency Use Authorization of Omicron BA.4/BA.5-Adapted Bivalent COVID-19 Vaccine in Children Under 5 Years—Dec. 8, 2022.
Pfizer and BioNTech Submit Application to U.S. FDA for Emergency Use Authorization of Omicron BA.4/BA.5-Adapted Bivalent Vaccine Booster in Children 5 Through 11 Years of Age—Sep. 26, 2022.
Pfizer and BioNTech Submit for U.S. Emergency Use Authorization of an Additional Booster Dose of their COVID-19 Vaccine for Older Adults—Mar. 15, 2022.
Pfizer and BioNTech's Omicron BA.4/BA.5-Adapted Bivalent COVID-19 Vaccine Booster Receives Health Canada Authorization for Individuals 12 Years of Age and Older—Oct. 7, 2022.
Pfizer-BioNTech COVID-19 Vaccine Demonstrates Strong Immune Response, High Efficacy and Favorable Safety in Children 6 Months to Under 5 Years of Age Following Third Dose—May 23, 2022.
Polack, F. P. et al., Safety and Efficacy of the BNT162b2 mRNA Covid-19 Vaccine, N. Engl. J. Med., 383(27):2603-2615 (2020).
Program leaflet of the "1st International mRNA Health Conference".
Qiao, H. et al., Specific single or double proline substitutions in the "spring-loaded" coiled-coil region of the influenza hemagglutinin impair or abolish membrane fusion activity, The Journal of Cell Biology, 141(6):1335-1347 (1998).
Quandt, J. et al., Omicron BA. 1 breakthrough infection drives cross-variant neutralization and memory B cell formation against conserved epitopes. Science Immunology (2022): eabq2427.
Quandt, J. et al., Omicron breakthrough infection drives cross-variant neutralization and memory B cell formation. bioRxiv (2022).
Quinlan, B. D. et al., The SARS-CoV-2 receptor-binding domain elicits a potent neutralizing response without antibody-dependent enhancement, bioRxiv, 24 pages (2020).
Rabaan, A. A. et al., SARS-CoV-2, SARS-CoV, and MERS-CoV: a comparative overview, Le Infezioni in Medicina, 2:174-184 (2020).
Ralph, R. et al., 2019-nCoV (Wuhan virus), a novel Coronavirus: human-to-human transmission, travel-related cases, and vaccine readiness, J Infect Dev Ctries., 14(1):3-17 (2020).
Ramanathan, A. et al., mRNA capping: biological functions and applications, Nucleic Acids Research, 44(16) 7511-7526 (2016).
Rambaut, A. et al., A dynamic nomenclature proposal for SARS-CoV-2 lineages to assist genomic epidemiology, Nat Microbiol., 5(11):1403-1407 (2020).
Rambaut, A. et al., Preliminary genomic characterisation of an emergent SARS-CoV-2 lineage in the UK defined by a novel set of spike mutations—SARS-CoV-2 coronavirus / nCoV-2019 Genomic Epidemiology—Virological, retrieved from Internet: https://virological.org/t/preliminary-genomic-characterisation-of-an-emergent-sars-cov-2-lineage-in-the-uk-defined-by-a-novel-set-of-spike-mutations/563, 9 pages (May 7, 2021).
Rauch, S. et al., mRNA-based SARS-CoV-2 vaccine candidate CVnCoV induces high levels of virus-neutralising antibodies and mediates protection in rodents, NPJ, 57:1-9 (2021).
Rauch, S. et al., New Vaccine Technologies to Combat Outbreak Situations, Frontiers in Immunology, 9(1963):1-24 (2018).
Reichmuth, A. et al., mRNA vaccine delivery using lipid nanoparticles, Ther. Deliv., 7(5):319-334 (2016).
Rohou, A. and Grigorieff, N., CTFFIND4: Fast and accurate defocus estimation from electron micrographs, J Struct Biol., 192(2):216-21 (2015).
Roth, N. et al., CV2CoV, an enhanced mRNA based SARS-CoV-2 vaccine candidate supports higher protein expression and improved immunogenicity in rats, bioRxiv, 12 pages (2021).
Sahin, U. et al., BNT162b2 induces SARS-CoV-2-neutralising antibodies and T cells in humans. MedRxiv (2020).
Sahin, U. et al., BNT162b2 vaccine induces neutralizing antibodies and poly-specific T cells in humans. Nature 595.7868 (2021): 572-577.
Sahin, U. et al., Concurrent human antibody and TH1 type T-cell responses elicited by a COVID-19 RNA vaccine, medRXiv, 27 pages (2020).
Sahin, U. et al., COVID-19 vaccine BNT162b1 elicits human antibody and TH1 T cell responses, Nature, 586(7830):594-599 (2020).
Sahin, U. et al., mRNA-based therapeutics—developing a new class of drugs. Nat Rev Drug Discov., 13(10):759-80 (2014).

(56) References Cited

OTHER PUBLICATIONS

Sanders, R. W. et al., A next-generation cleaved, soluble HIV-1 Env Trimer, BG505 SOSIP.664 gp140, expresses multiple epitopes for broadly neutralizing but not non-neutralizing antibodies, PLoS Pathogens, 9(9):e1003618 (2013).
Scheaffer, S. et al., Bivalent SARS-CoV-2 mRNA vaccines increase breadth of neutralization and protect against the BA.5 Omicron variant, bioRxiv preprint, 39 pages (posted Sep. 13, 2022).
Schlake, T. et al., Developing mRNA-vaccine technologies, RNA Biol, 9(11):1319-30 (2012).
Selisko, B. et al., Biochemical characterization of the (nucleoside-2'O)-methyltransferase activity of dengue virus protein NS5 using purified capped RNA oligonucleotides (7Me)GpppAC(n) and GpppAC(n), Journal of General Virology, 91(Pt1):112-121 (2010).
Sellers, R. et al., Scientific and Regulatory Policy Committee Points to Consider*: Approaches to the Conduct and Interpretation of Vaccine Safety Studies for Clinical and Anatomic Pathologists, Toxicol Pathol., 48(2):257-276 (2020).
Seq ID No. 7 alignments with Seq ID 84 and 86 in U.S. Pat. No. 10,953,089 with Jan. 27, 2020 earliest priority.
Sequence Alignment for Seq ID No. 7, 3 pages (2022).
Sequence Alignment for Seq ID No. 9, 6 pages (2022).
Sesterhenn, F. et al., Structure-based immunogen design—leading the way to the new age of precision vaccines, Current Opinion in Structural Biology, 51:163-169 (2018).
Shang, J. et al., Structural basis of receptor recognition by SARS-CoV-2, Nature, 581(7807):221-224 (2020).
Shi, P. et al., Neutralization of SARS-CoV-2 variants B. 1.617. 1 and B. 1.525 by BNT162b2-elicited sera. (2021).
Singh, D. et al., Responses to acute infection with SARS-CoV-2 in the lungs of rhesus macaques, baboons and marmosets, Nat Microbiol., 6(1):73-86 (2021).
Singh, D. et al., SARS-CoV-2 infection leads to acute infection with dynamic cellular and inflammatory flux in the lung that varies across nonhuman primate species, bioRxiv (2020).
Sinopeg Data Sheet, 10 pages (2022).
Song, E. et al., Divergent and self-reactive immune responses in the CNS of COVID-19 patients with neurological symptoms, Cell Repo. Med., 2(100288):24 pages (2021).
Song, W. et al., Cryo-EM structure of the SARS coronavirus spike glycoprotein in complex with its host cell receptor ACE2, PLoS Pathogens, 1-19 (2018).
Song, Z. et al., From SARS to MERS, Thrusting Coronaviruses into the Spotlight, Viruses, 11(1):59, 28 pages (2019).
Stadler, K. et al., SARS Beginning to Understand a New Virus, Nature Reviews, 1:209-218 (2003).
Stertz, S. et al., The intracellular sites of early replication and budding of SARS-coronavirus, Virology, 361:304-315 (2007).
Tang, X. et al., On the origin and continuing evolution of SARS-CoV-2, National Science Review, 7:1012-1023 (2020).
Tegally, H. et al., Continued Emergence and Evolution of Omicron in South Africa: New BA.4 and BA.5 Lineages, medRxiv, (May 2, 2022), XP093032398, DOI: 10.1101/2022.05.01.22274406 Retrieved from the internet: URL: https://www.medrxiv.org/content/10.1101/2022.05.01.22274406v1.full.pdf [retrieved on Mar. 16, 2023) the whole document.
Tegunov, D. and Cramer, P., Real-time cryo-electron microscopy data preprocessing with Warp, Nat Methods, 16(11):1146-1152 (2019).
Thanh, Le, T. et al., The COVID-19 vaccine development landscape, Nat Rev Drug Discov., 19(5):305-306 (2020).
Tian, J. et al., SARS-CoV-2 spike glycoprotein vaccine candidate NVX-CoV2373 immunogenicity in baboons and protection in mice, Nat Commun, 12(1):372 (2021).
Tseng, C. et al., Immunization with SARS coronavirus vaccines leads to pulmonary immunopathology on challenge with the SARS virus, PLoS One, 7(4):e35421, 13 pages (2012).
Turner, J. S. et al., SARS-CoV-2 mRNA vaccines induce persistent human germinal centre responses, Nat., 25 pages (2021).

UK Health Security Agency: "SARS-CoV-2 Variants of concern and variants under investigation in England: Technical Briefing 29", (Nov. 26, 2021), XP093032319, Retrieved from the internet: URL: https://assets.publishing.service.gov.uk/government/uploads/attachment_data/file/1036501/technical_briefing_29_published_26_november_2021.pdf [retrieved on Mar. 16, 2023] p. 18.
Van Doremalen, N. et al., ChAdOx1 nCoV-19 vaccine prevents SARS-CoV-2 pneumonia in rhesus macaques, Nature, 586(7830):578-582 (2020).
Viner, R. et al., Kawasaki-like disease: emerging complication during the COVID-19 pandemic, Lancet, 395(10239):1741-1743 (2020).
Vogel, A. B. et al., A prefusion SARS-CoV-2 spike RNA vaccine is highly immunogenic and prevents lung infection in non-human primates, posted on bioRxiv (Sep. 2020), 38 pages.
Vogel, A. B. et al., BNT162b vaccines are immunogenic and protect non-human primates against SARS-CoV-2, posted on bioRxiv (Dec. 2020), 71 pages.
Vogel, A. B. et al., BNT162b vaccines protect rhesus macaques from SARS-CoV-2 (with supplementary materials), Nature, 44 pages (2021).
Vogel, A.B. et al., BNT162b vaccines protect rhesus macaques from SARS-CoV-2, Nature, 592:283-289 (Feb. 2021).
Vojdani, A. et al., Reaction of Human Monoclonal Antibodies to SARS-CoV-2 Proteins With Tissue Antigens: Implications for Autoimmune Diseases, Front. Immun., 11(617089):1-16 (2021).
Walls, A. et al., Elicitation of Potent Neutralizing Antibody Responses by Designed Protein Nanoparticle Vaccines for SARS-CoV-2, Cell, 183(5):1367-1382 (2020).
Walsh, E. E. et al., Safety and Immunogenicity of Two RNA-Based Covid-19 Vaccine Candidates, N. Engl. J. Med., 383:2439-2450 (2020).
Wang, F. et al., An Evidence Based Perspective on mRN A-SARS-Co V-2 Vaccine Development, Med Sci Monit, 26:e924701-e924700-8 (2020).
Wang, L. et al., Evaluation of candidate vaccine approaches for MERS-CoV, Nature Communications, 6(7712):1-11 (2015).
Wang, N. et al., Structural Definition of a Neutralization-sensitive Epitope on the MERS-CoV SI-NTD, Cell Rep, 28(13):3395-3405 (2019).
Wang, Z. et al., mRNA vaccine-elicited antibodies to SARS-CoV-2 and circulating variants, Nature, 592(7855):616-622 (2021).
WHO Drug Information 2021, vol. 35, 2 [full issue], WHO Drug Information 35(2):270-605 (2021).
Winkler, E. S. et al., SARS-CoV-2 infection of human ACE2-transgenic mice causes severe lung inflammation and impaired function, Nat. Immun., 21:1327-1335 (2020).
World Health Organization—WHO guidelines on nonclinical evaluation of vaccines, Annex 1 in World Health Organization, WHO technical report series, No. 927, Geneva, Switzerland; World Health Organization; 31-63 (2005).
World Health Organization, Annex 2, Guidelines on nonclinical evaluation of vaccine adjuvants and adjuvanted vaccines, in WHO technical report series No. 987, Geneva, Switzerland; World Health Organization; 59-100 (2014).
Wrapp D. et al., Prefusion 2019-nCOV spike glycoprotein with a single receptor-binding domain up, 78 pages, (Jan. 16, 2021), deposited on Feb. 10, 2020, Retrieved from the Internet: URL:https://www.rcsb.org/structure/6vsb [retrieved on May 21, 2021] the whole document.
Wrapp, D. et al., Cryo-EM structure of the 2019-nCOV spike in the prefusion conformation, Science, 367(6483): 1260-1263 (2020).
Wrapp, D. et al., Cryo-EM structure of the 2019-nCOV spike in the prefusion conformation, Supplementary Materials, Science, 19 pages (2020).
Wrapp, D. et al., Prefusion 2019-nCoV spike glycoprotein with a single receptor-binding domain up, PDB: database, 4 pages (2020).
Written Opinion for PCT/EP2021/059947, 9 pages (dated Aug. 5, 2021).
Written Opinion for PCT/EP2021/060004, 14 pages (dated Sep. 8, 2021).
Written Opinion for PCT/EP2021/060508, 11 pages (dated Aug. 5, 2021).

(56) References Cited

OTHER PUBLICATIONS

Written Opinion for PCT/EP2022/060417, 10 pages (dated Aug. 4, 2022).

Written Opinion for PCT/EP2022/083740, 15 pages (dated Jun. 2, 2023).

Wu, F. et al., A new coronavirus associated with human respiratory disease in China, Nature, 579(7798):265-269 (2020).

Wu, J. et al., Nowcasting and forecasting the potential domestic and international spread of the 2019-nCoV outbreak originating in Wuhan, China: a modelling study, Lancet, 395(10225):689-697 (2020).

Wu, K. et al., mRNA-1273 vaccine induces neutralizing antibodies against spike mutants from global SARS-CoV-2 variants, posted on bioRxiv (Jan. 2021), 20 pages.

Wu, K. et al., Variant SARS-CoV-2 mRNA vaccines confer broad neutralization as primary or booster series in mice, posted on bioRxiv (Apr. 2021), 28 pages.

Wu, Y. et al., A noncompeting pair of human neutralizing antibodies block COVID-19 virus binding to its receptor ACE2, Science, 368(6496):1274-1278 (2020).

Xia, H. et al., Neutralization and durability of 2 or 3 doses of the BNT162b2 vaccine against Omicron SARS-CoV-2. Cell Host & Microbe 30.4 (2022): 485-488.

Xia, H. et al., Neutralization of Omicron SARS-CoV-2 by 2 or 3 doses of BNT162b2 vaccine. bioRxiv (2022).

Xia, X., Detailed Dissection and Critical Evaluation of the Pfizer/BioNTech and Moderna mRNA Vaccines, Vaccines, 9(734):1-19 (2021).

Xie, X. et al., Neutralization of SARS-CoV-2 spike 69/70 deletion, E484K and N501Y variants by BNT162b2 vaccine-elicited sera, Nat. Med., 6 pages (2021).

Xu, J. et al., Antibodies and vaccines against Middle East respiratory syndrome coronavirus, Emerging Microbes and Infections, 8:841-856 (2019).

Yan, R. et al., Structural basis for the recognition of the SARS-CoV-2 by full-length human ACE2, Sci. Mag., 10 pages (2020).

Yang, D. et al., Attenuated Interferon and Proinflammatory Response in SARS-CoV-2-Infected Human Dendritic Cells Is Associated With Viral Antagonism of STAT1 Phosphorylation, J Infect Dis., 222(5):734-745 (2020).

Yang, X. et al., Highly Stable Timers Formed by Human Immunodeficiency Virus Type 1 Envelope Glycoproteins Fused with the Trimeric Motif of T4 Bacteriophage Fibritin, Journal of Virology, 76(9):4634-4642 (2002).

Yi, C. et al., Key residues of the receptor binding motif in the spike protein of SARS-CoV-2 that interact with ACE2 and neutralizing antibodies, Cell Mol Immunol., 17(6):621-630 (2020).

Yong, C. et al., Recent Advances in the Vaccine Development Against Middle East Respiratory Syndrome-Coronavirus, Front Microbiol., 10:1781 (2019).

Yu, F. et al., Measures for diagnosing and treating infections by a novel coronavirus responsible for a pneumonia outbreak originating in Wuhan, China, Microbes Infect., 22(2):74-79 (2020).

Yu, J. et al., DNA vaccine protection against SARS-CoV-2 in rhesus macaques, Sci. Mag., 11 pages (2020).

Yuan, M. et al., A highly conserved cryptic epitope in the receptor binding domains of SARS-CoV-2 and SARS-CoV, Science, 368(6491):630-633 (2020).

Zakhartchouk, A. et al., Immunogenicity of a receptor-binding domain of SARS coronavirus spike protein in mice: implications for a subunit vaccine, Vaccine, 25(1):136-43 (2007).

Zeng, C. et al., Leveraging mRNAs sequences to express SARS-CoV-2 antigens in vivo, bioRxiv, 16 pages (2020), Retrieved from the Internet: URL:https://www.biorxiv.org/content/10.1101/2020.04.01.019877v1.full.pdf.

Zeng, C. et al., Leveraging mRNAs sequences to express SARS-CoV-2 antigens in vivo, Supplementary Information, bioRxiv, 13 pages (2020).

Zhang, J. et al., Progress and Prospects on Vaccine Developement against SARS-CoV-2, Vaccines, 8(153):1-12 (2020).

Zhang, N. et al., A Thermostable mRNA Vaccine against COVID-19, Cell, 182(5):1271-1283 (2020).

Zhang, Y. et al., Wuhan seafood market pneumonia virus isolate Wuhan-Hu-1, complete genome, Database EMBL, Database Accession No. MN908947 (Jan. 15, 2020).

Zhao, L. et al., Nanoparticle vaccines, Vaccine, 32(3):327-37 (2014).

Zhou, M. et al., Coronavirus disease 2019 (COVID-19): a clinical update, Front Med., 14(2):126-135 (2020).

Zhou, P. et al., A pneumonia outbreak associated with a new coronavirus of probable bat origin, Nature, vol. 579, online publication: Feb. 3, 2020.

Zhou, Y. et al., Enhancement versus neutralization by SARS-CoV-2 antibodies from a convalescent donor associates with distinct epitopes on the RBD, Cell Repo., 34(108699):1-23 (2021).

Zhu, F. et al., Safety, tolerability, and immunogenicity of a recombinant adenovirus type-5 vectored COVID-19 vaccine: a dose-escalation, open-label, non-randomised, first-in-human trial, Lancet, 395(10240):1845-1854 (2020).

Zhu, N. et al., A Novel Coronavirus from Patients with Pneumonia in China, 2019, N Engl J Med., 382(8):727-733 (2020).

Zhu, X. et al., Receptor-binding domain as a target for developing SARS vaccines, J Thorac Dis., 5 Suppl 2(Suppl 2):S142-8 (2013).

Zimmer, Katarina, A Guide to Emerging SARS-CoV-2 Variants, retrieved from the Internet: https://www.the-scientist.com/news-opinion/a-guide-to-emerging-sars-cov-2-variants-68387, 7 pages (May 31, 2021).

Zivanov, J. et al., New tools for automated high-resolution cryo-EM structure determination in RELION-3, Elife, 7:e42166, 22 pages (2018).

Zost, S. et al.,Rapid isolation and profiling of a diverse panel of human monoclonal antibodies targeting the SARS-CoV-2 spike protein, Nat Med., 26(9):1422-1427 (2020).

Zou, J. et al., Improved Neutralization of Omicron BA. 4/5, BA. 4.6, BA. 2.75. 2, BQ. 1.1, and XBB. 1 with Bivalent BA. 4/5 Vaccine. BioRxiv (2022).

Zou, L. et al., Sars-CoV-2 Viral Load in Upper Respiratory Specimens of Infected Patients, N Engl J Med., 382(12):1177-1179 (2020).

| 4th Dose Vaccine | Wuhan | BA.1 | BA.2 | BA.2.75.2 | BA.4/BA.5 | BF.7 | BN.1 | CH.1.1 | BQ.1.1 | XBB.1.5 | XBB.1.16 |
|---|---|---|---|---|---|---|---|---|---|---|---|
| | | | | | | Omicron | | | | | |
| BNT162b2 BA.4/5 | 54379 | 10793 | 20741 | 2963 | 71457 | 63209 | 3745 | 1589 | 21297 | 1120 | 1831 |
| BNT162b2 WT + BA.4/5 | 71748 | 5374 | 16799 | 2448 | 40689 | 28425 | 2100 | 835 | 10138 | 444 | 733 |
| BNT162b2 XBB.1.5 | 100108 | 10685 | 22796 | 2832 | 41055 | 28248 | 3692 | 2480 | 9243 | 1800 | 3766 |
| BNT162b2 BA.4/5 + XBB.1.5 | 74398 | 25025 | 20254 | 2288 | 54232 | 28420 | 2361 | 1036 | 9556 | 773 | 1523 |
| BNT162b2 BQ.1.1 | 42337 | 3600 | 29414 | 7452 | 159692 | 105315 | 3046 | 7742 | 49217 | 2042 | 1226* |
| BNT162b2 XBB.1.5 + BQ.1.1 | 77816 | 7437 | 34923 | 1817 | 125142 | 76331 | 6618 | 4611 | 40286 | 1817 | 4008 |
| BNT162b2 BA.4/5 + BQ.1.1 | 64623 | 9014 | 26229 | 7113 | 89562 | 112025 | 4151 | 5549 | 30654 | 2511 | 3990 |

| 4th Dose Vaccine | Wuhan | Omicron | | | |
|---|---|---|---|---|---|
| | | BA.4/BA.5 | CH.1.1 | BQ.1.1 | XBB.1.5 |
| BNT162b2 BA.4/5 | 0.8 | 9.7 | 16.8 | 11.1 | 11.8 |
| BNT162b2 WT + BA.4/5 | 1.4 | 7.2 | 11.8 | 15.8 | 4.9 |
| BNT162b2 XBB.1.5 | 0.7 | 2.0 | 13.9 | 4.9 | 12.5 |
| BNT162b2 BA.4/5 + XBB.1.5 | 0.7 | 1.9 | 15.6 | 13.6 | 12.1 |
| BNT162b2 BQ.1.1 | 1.0 | 14.3 | 64.6 | 47.4 | 14.9 |
| BNT162b2 XBB.1.5 + BQ.1.1 | 0.9 | 10.2 | 27.7 | 20.4 | 16.1 |
| BNT162b2 BA.4/5 + BQ.1.1 | 0.8 | 8.5 | 30.0 | 20.2 | 17.0 |

SEQUENCE LISTING

```
Sequence total quantity: 177
SEQ ID NO: 1              moltype = AA   length = 1273
FEATURE                   Location/Qualifiers
REGION                    1..1273
                          note = S protein
source                    1..1273
                          mol_type = protein
                          organism = synthetic construct
SEQUENCE: 1
MFVFLVLLPL VSSQCVNLTT RTQLPPAYTN SFTRGVYYPD KVFRSSVLHS TQDLFLPFFS    60
NVTWFHAIHV SGTNGTKRFD NPVLPFNDGV YFASTEKSNI IRGWIFGTTL DSKTQSLLIV   120
NNATNVVIKV CEFQFCNDPF LGVYYHKNNK SWMESEFRVY SSANNCTFEY VSQPFLMDLE   180
GKQGNFKNLR EFVFKNIDGY FKIYSKHTPI NLVRDLPQGF SALEPLVDLP IGINITRFQT   240
LLALHRSYLT PGDSSSGWTA GAAAYYVGYL QPRTFLLKYN ENGTITDAVD CALDPLSETK   300
CTLKSFTVEK GIYQTSNFRV QPTESIVRFP NITNLCPFGE VFNATRFASV YAWNRKRISN   360
CVADYSVLYN SASFSTFKCY GVSPTKLNDL CFTNVYADSF VIRGDEVRQI APGQTGKIAD   420
YNYKLPDDFT GCVIAWNSNN LDSKVGGNYN YLYRLFRKSN LKPFERDIST EIYQAGSTPC   480
NGVEGFNCYF PLQSYGFQPT NGVGYQPYRV VVLSFELLHA PATVCGPKKS TNLVKNKCVN   540
FNFNGLTGTG VLTESNKKFL PFQQFGRDIA DTTDAVRDPQ TLEILDITPC SFGGVSVITP   600
GTNTSNQVAV LYQDVNCTEV PVAIHADQLT PTWRVYSTGS NVFQTRAGCL IGAEHVNNSY   660
ECDIPIGAGI CASYQTQTNS PRRARSVASQ SIIAYTMSLG AENSVAYSNN SIAIPTNFTI   720
SVTTEILPVS MTKTSVDCTM YICGDSTECS NLLLQYGSFC TQLNRALTGI AVEQDKNTQE   780
VFAQVKQIYK TPPIKDFGGF NFSQILPDPS KPSKRSFIED LLFNKVTLAD AGFIKQYGDC   840
LGDIAARDLI CAQKFNGLTV LPPLLTDEMI AQYTSALLAG TITSGWTFGA GAALQIPFAM   900
QMAYRFNGIG VTQNVLYENQ KLIANQFNSA IGKIQDSLSS TASALGKLQD VVNQNAQALN   960
TLVKQLSSNF GAISSVLNDI LSRLDKVEAE VQIDRLITGR LQSLQTYVTQ QLIRAAEIRA  1020
SANLAATKMS ECVLGQSKRV DFCGKGYHLM SFPQSAPHGV VFLHVTYVPA QEKNFTTAPA  1080
ICHDGKAHFP REGVFVSNGT HWFVTQRNFY EPQIITTDNT FVSGNCDVVI GIVNNTVYDP  1140
LQPELDSFKE ELDKYFKNHT SPDVDLGDIS GINASVVNIQ KEIDRLNEVA KNLNESLIDL  1200
QELGKYEQYI KWPWYIWLGF IAGLIAIVMV TIMLCCMTSC CSCLKGCCSC GSCCKFDEDD  1260
SEPVLKGVKL HYT                                                   1273
```

```
SEQ ID NO: 2            moltype = RNA  length = 3819
FEATURE                 Location/Qualifiers
misc_feature            1..3819
                        note = Coding Sequence
source                  1..3819
                        mol_type = other RNA
                        organism = synthetic construct
SEQUENCE: 2
atgtttgtgt tcttgtgct gctgcctctt gtgtcttctc agtgtgtgaa tttgacaaca    60
agaacacagc tgccaccagc ttatacaaat tcttttacca gaggagtgta ttatcctgat   120
aaagtgttta gatcttctgt gctgcacagc acacaggacc tgtttctgcc atttttagc    180
aatgtgacat ggtttcatgc aattcatgtg tctggaacaa atggaacaaa aagatttgat   240
aatcctgtgc tgccttttaa tgatggagtg tattttgctt caacagaaaa gtcaaatatt   300
attagaggat ggatttttgg aacaacactg gattctaaaa cacagtctct gctgattgtg   360
aataatgcaa caaatgtggt gattaaagtg tgtgaattt c agttttgtaa tgatcctttt   420
ctgggagtgt attatcacaa aaataataaa tcttggatgg aatctgaatt tagagtgtat   480
tcctctgcaa ataattgtac atttgaatat tgtctcagc cttttctgat ggatctggaa    540
ggaaaacagg gcaattttaa aaatctgaga gaatttgtgt taaaaatat tgatggatat    600
tttaaaattt attctaaaca cacaccaatt aatttagtga gagatctgcc tcagggattt   660
tctgctctgg aacctctggt ggatctgcca attggcatta atattacaag atttcagaca   720
ctgctgctc tgcacagatc ttatctgaca cctggagatt cttcttctgg atggacagcc    780
ggagctgcag cttattatgt gggctatctg cagccaagaa catttctgct gaaatataat   840
gaaaatggaa caattacaga tgctgtggat tgtgctctgg atcctctgtc tgaaacaaaa   900
tgtacattaa aatcttttac agtggaaaaa ggcatttatc agacatctaa ttttagagtg   960
cagccaacag aatctattgt gagatttcca aatattacaa atctgtgtcc atttggagaa  1020
gtgtttaatg caacaagatt tgcatctgtg tatgcatgaa atagaaaaag aatttctaat  1080
tgtgtggctg attattctgt gctgtataat agtgcttctt tttccacatt taaatgttat  1140
ggagtgtctc aacaaaaatt aaatgattta tgttttacaa atgtgtatgc tgattctttt  1200
gtgatcagag gtgatgaagt gagacagatt gccccggac agacaggaaa aattgctgat  1260
tacaattaca aactgcctga tgattttaca ggatgtgtga ttgcttggaa ttctaataat  1320
ttagattcta aagtggggagg aaattacaat tatctgtaca gactgtttag aaaatcaaat  1380
ctgaaacctt ttgaaagaga tatttcaaca gaaatttatc aggctggatc aacaccttgt  1440
aatggagtgg aaggatttaa ttgttattt ccattacaga gctatgagtt tcagccaacc  1500
aatggtgtgg gatatcagcc atatagagtg gtggtgctgt cttttgaact gctgcatgca  1560
cctgcaacag tgtgtggacc taaaaaatct acaatttag tgaaaaataa atgtgtgaat  1620
tttaatttta tggattaac aggaacagga gtgctgacag aatctaataa aaaatttctg  1680
ccttttcagc agtttggcag agatattgca gataccacag atgcagtgag agatcctcag  1740
acattagaaa ttctggatat tacaccttgt tctttggagg gtgtgtctgt gattacacct  1800
ggaacaaata catctaatca ggtggctgtg ctgtatcagg atgtgaattg tacagaagtg  1860
ccagtggcaa tcatgcaga tcagctgaca ccaacatgga gagtgtattc tacaggatct  1920
aatgtgtttc agacaagagc aggatgtctg attggagcag aacatgtgaa taattcttat  1980
gaatgtgata ttccaattgg agcaggcatt tgtgcatctt atcagacaca gacaaattcc  2040
ccaaggagag caagatctgt ggcatctcag tctattattg catacaccat gtctctggga  2100
gcagaaaatt ctgtggcata ttcaataat tctattgcta ttccaacaaa ttttaccatt  2160
tctgtgacaa cagaaatttt acctgtgtct atgcaaaaaa catctgtgga ttgtaccatg  2220
tacatttgtg gagattctac agaatgtttc atctgctgc tgcagtatgg atcttttttgt  2280
acacagctga atagagcttt aacaggaatt gctgtgaac aggataaaaa tacacaggaa  2340
gtgtttgctc aggtgaaaca gatttacaaa acaccaccaa ttaaagattt tggaggattt  2400
aatttttagcc agattctgcc tgatccttct aaaccttcta aagatctttt tattgaagat  2460
ctgctgttta taaagtgac actggcagat gcaggattta ttaaacagta tggagattgc  2520
ctgggtgata ttgctgcaag agatctgatt tgtgctcaga aatttaatgg actgacagtg  2580
ctgcctcctc tgctgacaga tgaaatgatt gctcagtaca catctgcttt actggctgga  2640
acaattacaa gcggatggac atttggagct ggagctgctc tgcagattcc ttttgcaatg  2700
cagatggctt acagatttaa tggaattgga gtgacacaga tgtgttata tgaaaatcag  2760
aaactgattg caaatcagtt taattctgca attggcaaaa ttcaggattc tctgtcttct  2820
acagcttctg ctctgggaaa actgcaggat gtggtgaatc agaatgcaca ggcactgaat  2880
actctggtga acagctgtc tagcaatttt ggggcaattt cttctgtgct gaatgatatt  2940
ctgtctagac tggataaagt ggaagctgaa gtgcagattg atagactgat cacaggaaga  3000
ctgcagtctc tgcagactta tgtgacacag cagctgatta gagctgctga attagagct   3060
tctgctaatc tggctgctac aaaaatgtct gaatgtgtgc tgggacagtc aaaaagagtg  3120
gattttgtg gaaaggata tcatctgatg tcttttccac atctgcgtcc acatggagtg  3180
gtgttttac atgtgacata tgtgccagca caggaaaaga tttaccacc agcaccagca  3240
atttgtcatg atggaaagc acattttcca agagaaggag tgtttgtgtc aatggaaca   3300
cattggtttg tgacacagag aaatttttat gaacctcaga ttattacaac agataataca  3360
tttgtgtcag gaaattgtga tgtggtgatt ggaattgtga ataatacagt gtatgatcca  3420
ctgcagccag aactggatc ttttaaagaa gaactggata aatattttaa aaatcacaca  3480
tctcctgatg tggatttagg agatattct ggaatcaatg catctgtggt gaatattcag  3540
aaagaaattg atagactgaa tgaagtggcc aaaaatctga atgaatctct gattgatctg  3600
caggaacttg gaaatatga acagtacatt aaatggcctt ggtacatttg cttgggatt t  3660
attgcaggat taattgcaat tgtgatggtg acaattatgt tatgttgtat gacatcatgt  3720
tgttcttgtt taaaggatg ttgtcttgt ggaagctgtt gtaaatttga tgaagatgat  3780
tctgaacctg tgttaaaagg agtgaaattg cattacaca                         3819

SEQ ID NO: 3            moltype = AA  length = 218
FEATURE                 Location/Qualifiers
REGION                  1..218
                        note = S Protein RBD Fusion
```

-continued

```
source                  1..218
                        mol_type = protein
                        organism = synthetic construct
SEQUENCE: 3
MFVFLVLLPL VSSQCVVRFP NITNLCPFGE VFNATRFASV YAWNRKRISN CVADYSVLYN  60
SASFSTFKCY GVSPTKLNDL CFTNVYADSF VIRGDEVRQI APGQTGKIAD YNYKLPDDFT  120
GCVIAWNSNN LDSKVGGNYN YLYRLFRKSN LKPFERDIST EIYQAGSTPC NGVEGFNCYF  180
PLQSYGFQPT NGVGYQPYRV VVLSFELLHA PATVCGPK                        218

SEQ ID NO: 4            moltype = RNA  length = 654
FEATURE                 Location/Qualifiers
misc_feature            1..654
                        note = Coding Sequence
source                  1..654
                        mol_type = other RNA
                        organism = synthetic construct
SEQUENCE: 4
atgtttgtgt ttcttgtgct gctgcctctt gtgtcttctc agtgtgtggt gagatttcca  60
aatattacaa atctgtgtcc atttggagaa gtgtttaatg caacaagatt tgcatctgtg  120
tatgcatgga atagaaaaag aatttctaat tgtgtggctg attattctgt gctgtataat  180
agtgcttctt tttccacatt taaatgttat ggagtgtctc caacaaaatt aaatgattta  240
tgttttacaa atgtgtatgc tgattctttt gtgatcagag gtgatgaagt gagacagatt  300
gcccccggac agacaggaaa aattgctgat tacaattaca aactgcctga tgattttaca  360
ggatgtgtga ttgcttggaa ttctaataat ttagattcta aagtgggagg aaattacaat  420
tatctgtaca gactgtttag aaaatcaaat ctgaaacctt ttgaaagaga tatttcaaca  480
gaaatttatc aggctggatc aacaccttgt aatggagtgg aaggatttaa ttgttatttt  540
ccattacaga gctatggatt tcagccaacc aatggtgtgg gatatcagcc atatagagtg  600
gtggtgctgt cttttgaact gctgcatgca cctgcaacag tgtgtggacc taaa        654

SEQ ID NO: 5            moltype = AA  length = 266
FEATURE                 Location/Qualifiers
REGION                  1..266
                        note = S Protein RBD Fusion
source                  1..266
                        mol_type = protein
                        organism = synthetic construct
SEQUENCE: 5
MFVFLVLLPL VSSQCVVRFP NITNLCPFGE VFNATRFASV YAWNRKRISN CVADYSVLYN  60
SASFSTFKCY GVSPTKLNDL CFTNVYADSF VIRGDEVRQI APGQTGKIAD YNYKLPDDFT  120
GCVIAWNSNN LDSKVGGNYN YLYRLFRKSN LKPFERDIST EIYQAGSTPC NGVEGFNCYF  180
PLQSYGFQPT NGVGYQPYRV VVLSFELLHA PATVCGPKGS PGSGSGSGYI PEAPRDGQAY  240
VRKDGEWVLL STFLGRSLEV LFQGPG                                     266

SEQ ID NO: 6            moltype = RNA  length = 798
FEATURE                 Location/Qualifiers
misc_feature            1..798
                        note = Coding Sequence
source                  1..798
                        mol_type = other RNA
                        organism = synthetic construct
SEQUENCE: 6
atgtttgtgt ttcttgtgct gctgcctctt gtgtcttctc agtgtgtggt gagatttcca  60
aatattacaa atctgtgtcc atttggagaa gtgtttaatg caacaagatt tgcatctgtg  120
tatgcatgga atagaaaaag aatttctaat tgtgtggctg attattctgt gctgtataat  180
agtgcttctt tttccacatt taaatgttat ggagtgtctc caacaaaatt aaatgattta  240
tgttttacaa atgtgtatgc tgattctttt gtgatcagag gtgatgaagt gagacagatt  300
gcccccggac agacaggaaa aattgctgat tacaattaca aactgcctga tgattttaca  360
ggatgtgtga ttgcttggaa ttctaataat ttagattcta aagtgggagg aaattacaat  420
tatctgtaca gactgtttag aaaatcaaat ctgaaacctt ttgaaagaga tatttcaaca  480
gaaatttatc aggctggatc aacaccttgt aatggagtgg aaggatttaa ttgttatttt  540
ccattacaga gctatggatt tcagccaacc aatggtgtgg gatatcagcc atatagagtg  600
gtggtgctgt cttttgaact gctgcatgca cctgcaacag tgtgtggacc taaaggctcc  660
cccggctccg gctccggatc tggttatatt cctgaagctc caagagatgg gcaagcttac  720
gttcgtaaag atggcgaatg ggtattactt tctacctttt taggccggtc cctggaggtg  780
ctgttccagg gccccggc                                                798

SEQ ID NO: 7            moltype = AA  length = 1273
FEATURE                 Location/Qualifiers
REGION                  1..1273
                        note = S Protein Variant
source                  1..1273
                        mol_type = protein
                        organism = synthetic construct
SEQUENCE: 7
MFVFLVLLPL VSSQCVNLTT RTQLPPAYTN SFTRGVYYPD KVFRSSVLHS TQDLFLPFFS  60
NVTWFHAIHV SGTNGTKRFD NPVLPFNDGV YFASTEKSNI IRGWIFGTTL DSKTQSLLIV  120
NNATNVVIKV CEFQFCNDPF LGVYYHKNNK SWMESEFRVY SSANNCTFEY VSQPFLMDLE  180
GKQGNFKNLR EFVFKNIDGY FKIYSKHTPI NLVRDLPQGF SALEPLVDLP IGINITRFQT  240
LLALHRSYLT PGDSSSGWTA GAAAYYVGYL QPRTFLLKYN ENGTITDAVD CALDPLSETK  300

```
CTLKSFTVEK GIYQTSNFRV QPTESIVRFP NITNLCPFGE VFNATRFASV YAWNRKRISN    360
CVADYSVLYN SASFSTFKCY GVSPTKLNDL CFTNVYADSF VIRGDEVRQI APGQTGKIAD    420
YNYKLPDDFT GCVIAWNSNN LDSKVGGNYN YLYRLFRKSN LKPFERDIST EIYQAGSTPC    480
NGVEGFNCYF PLQSYGFQPT NGVGYQPYRV VVLSFELLHA PATVCGPKKS TNLVKNKCVN    540
FNFNGLTGTG VLTESNKKFL PFQQFGRDIA DTTDAVRDPQ TLEILDITPC SFGGVSVITP    600
GTNTSNQVAV LYQDVNCTEV PVAIHADQLT PTWRVYSTGS NVFQTRAGCL IGAEHVNNSY    660
ECDIPIGAGI CASYQTQTNS PRRARSVASQ SIIAYTMSLG AENSVAYSNN SIAIPTNFTI    720
SVTTEILPVS MTKTSVDCTM YICGDSTECS NLLLQYGSFC TQLNRALTGI AVEQDKNTQE    780
VFAQVKQIYK TPPIKDFGGF NFSQILPDPS KPSKRSFIED LLFNKVTLAD AGFIKQYGDC    840
LGDIAARDLI CAQKFNGLTV LPPLLTDEMI AQYTSALLAG TITSGWTFGA GAALQIPFAM    900
QMAYRFNGIG VTQNVLYENQ KLIANQFNSA IGKIQDSLSS TASALGKLQD VVNQNAQALN    960
TLVKQLSSNF GAISSVLNDI LSRLDPPEAE VQIDRLITGR LQSLQTYVTQ QLIRAAEIRA   1020
SANLAATKMS ECVLGQSKRV DFCGKGYHLM SFPQSAPHGV VFLHVTYVPA QEKNFTTAPA   1080
ICHDGKAHFP REGVFVSNGT HWFVTQRNFY EPQIITTDNT FVSGNCDVVI GIVNNTVYDP   1140
LQPELDSFKE ELDKYFKNHT SPDVDLGDIS GINASVVNIQ KEIDRLNEVA KNLNESLIDL   1200
QELGKYEQYI KWPWYIWLGF IAGLIAIVMV TIMLCCMTSC CSCLKGCCSC GSCCKFDEDD   1260
SEPVLKGVKL HYT                                                     1273

SEQ ID NO: 8           moltype = RNA  length = 3819
FEATURE                Location/Qualifiers
misc_feature           1..3819
                       note = Coding Sequence
source                 1..3819
                       mol_type = other RNA
                       organism = synthetic construct
SEQUENCE: 8
atgtttgtgt tcttgtgct gctgcctctt gtgtcttctc agtgtgtgaa tttgacaaca      60
agaacacagc tgccaccagc ttatacaaat tcttttacca gaggagtgta ttatcctgat    120
aaagtgttta gatcttctgt gctgcacagc acacaggacc tgtttctgcc atttttttagc   180
aatgtgacat ggtttcatgc aattcatgtg tctggaacaa atggaacaaa aagatttgat    240
aatcctgtgc tgcctttaa tgatggagtg tatttgctt caacagaaaa gtcaaatatt     300
attagaggat ggattttttgg aacaacactg gattctaaaa cacagtctct gctgattgtg    360
aataatgcaa caaatgtggt gattaaagtg tgtgaatttc agttttgtaa tgatcctttt    420
ctgggagtgt attatcacaa aaataataaa tcttggatga aatctgaatt tagagtgtat    480
tcctctgcaa ataattgtac atttgaatat tgtgtctcag ccttttctgat ggatctggaa    540
ggaaaacagg gcaattttaa aaatctgaga gaatttgtgt taaaaaatat tgatggatat    600
tttaaaattt attctaaaca cacaccaatt aatttagtga gagatctgcc tcagggatgt    660
tctgctctgg aacctctggt ggatctgcca attggcatta atattacaag atttcagaca    720
ctgctggctc tgcacagatc ttatctgaca cctggagatt cttcttctgg atggacagtg    780
ggagctgcag cttattatgt gggctatctg cagccaagaa catttctgct gaaatataat    840
gaaaatggaa caattacaga tgctgtggat tgtgctctgg atcctctgtc tgaaacaaaa    900
tgtacattaa atcttttac agtggaaaaa ggcatttatc agacatctaa ttttagagtg    960
cagccaacag aatctattgt gagatttcca aatattacaa atctgtgtcc atttggaaaa   1020
gtgtttaatg caacaagatt tgcatctgtg tatgcatgga atagaaaaag aatttctaat   1080
tgtgtggctg attattctgt gctgtataat agtgcttctt ttccacattt aaatgttat    1140
ggagtgtctc caacaaaatt aaatgattta tgttttacaa atgtgtatgc tgattctttt   1200
gtgatcagag gtgatgaagt gagacagatt gccccccgga agacaggaaa aattgctgat   1260
tacaattaca aactgcctga tgatttttaca ggatgtgtga ttgcttggaa ttctaataat   1320
ttagattcta aagtgggagg aaattacaat tatctgtaca gactgtttag aaaatcaaat   1380
ctgaaacctt ttgaaagaga tatttcaaca gaaatttatc aggctggatc aacaccttgt   1440
aatggagtgg aaggatttaa ttgttatttt ccattacaga gctatggatt tcagccaacc   1500
aatggtgtgg gatatcagcc atatagagtg gtggtgctgt cttttgaact gctgcatgca   1560
cctgcaacag tgtgtggacc taaaaaatct acaaatttag tgaaaaataa atgtgtgaat   1620
tttaatttta tggattaaac aggaacagga gtgctgacag aatctaataa aaaatttctg   1680
ccttttcagc agtttggcag agatattgca gataccacag atgcagtgag agatcctcag   1740
acattagaaa ttctggatat tacacccttg tcttttgggg gtgtgtctgt gattacacct   1800
ggaacaaata catctaatca ggtggctgtg ctgtatcagg atgtgaattg tacagaagtg   1860
ccagtggcaa ttcatgcaga tcagctgaca ccaacatgga gtgtattc tacaggatct    1920
aatgtgtttc agacaagagc aggatgtctg attggagcag aacatgtgaa taattcttat   1980
gaatgtgata ttccaattgg agcaggcatt tgtgcatctt atcagacaca gacaaattcc   2040
ccaaggagag caagatctgt ggcatctcag tctattattg catacaccat gtctctggga   2100
gcagaaaatt ctgtggcata ttctaataat tctattgcta ttccaacaaa ttttaccatt   2160
tctgtgacaa cagaaatttt acctgtgtct atgacaaaaa catctgtgga ttgtaccatg   2220
tacatttgtg gagattctac agaatgttct aatctgttgt tgcagtatgg atcttttgt    2280
acacagctga atagagcttt aacaggaatt gctgtggaac aggataaaaa tacacaggaa   2340
gtgtttgctc aggtgaaaca gatttacaaa acaccaccaa ttaaagattt tggaggattt   2400
aattttagcc agattctgcc tgatccttct aaaccttcta aagatcttt tattgaagat   2460
ctgctgttta taaagtgac actggcagat gcaggattta taacagta tggagattgt   2520
ctgggtgata ttgctgcaag agatctgatt tgtgctcaga aatttaatgg actgacagtg   2580
ctgcctcctc tgctgacaga tgaaatgatt gctcagtaca catctgcttt actggctgga   2640
acaattacaa gcggatggac atttggagct ggagctgctc tgcagattcc ttttgcaatg   2700
cagatggctt acagatttaa tggaattgga gtgacacaga tgtgttata tgaaaatcag   2760
aaactgattg caaatcagtt taattctgca attggcaaaa ttcaggattc tctgtcttct   2820
acagcttctg ctctgggaaa actgcaggat gtggtgaatc aaaatgcaca ggcactgaat   2880
actctggtga aacagctgtc tagcaatttt ggggcaattt cttctgtgct gaatgatatt   2940
ctgtctagac tggatcctcc tgaagctgaa gtgcagattg atagactgat cacaggaaga   3000
ctgcagtctc tgcagactta tgtgacacag cagctgatta gagctgctga aattagagct   3060
tctgctaatc tggctgctac aaaaatgtct gaatgtgtgc tgggacagtc aaaaagagtg   3120
gattttttgtg gaaaaggata tcatctgatg tcttttccac agtctgctcc acatggagtg   3180
```

```
gtgttttac atgtgacata tgtgccagca caggaaaaga attttaccac agcaccagca   3240
atttgtcatg atggaaaagc acattttcca agagaaggag tgtttgtgtc taatggaaca   3300
cattggtttg tgacacagag aaatttttat gaacctcaga ttattacaac agataataca   3360
tttgtgtcag gaaattgtga tgtggtgatt ggaattgtga ataatacagt gtatgatcca   3420
ctgcagccag aactggattc tttttaaagaa gaactggata aatattttaa aaatcacaca   3480
tctcctgatg tggatttagg agatatttct ggaatcaatg catctgtggt gaatattcag   3540
aaagaaattg atagactgaa tgaagtggcc aaaaatctga atgaatctct gattgatctg   3600
caggaacttg gaaaatatga acagtacatt aaatggcctt ggtacatttg gcttggatt   3660
attgcaggat taattgcaat tgtgatggtg acaattatgt tatgttgtat gacatcatgt   3720
tgttcttgtt taaaaggatg ttgttcttgt ggaagctgtt gtaaatttga tgaagatgat   3780
tctgaacctg tgttaaaagg agtgaaattg cattacaca               3819
```

| SEQ ID NO: 9 | moltype = RNA  length = 3819 |
|---|---|
| FEATURE | Location/Qualifiers |
| misc_feature | 1..3819 |
| | note = Coding Sequence |
| source | 1..3819 |
| | mol_type = other RNA |
| | organism = synthetic construct |

SEQUENCE: 9

```
atgttcgtgt tcctggtgct gctgcctctg gtgtccagcc agtgtgtgaa cctgaccacc    60
agaacacagc tgcctccagc ctacaccaac agctttacca gaggcgttca ctaccccgac   120
aaggtgttca gatccagcgt gctgcactct acccaggacc tgttcctgcc tttcttcagc   180
aacgtgacct ggtccacgc catccacgtg tccggcacca tggaccaa gagattcgac   240
aaccccgtgc tgcccttcaa cgacggggtg tactttgcca gcaccgagaa gtccaacatc   300
atcagagcag ggatcttcgg caccacactg gacagcaaga cccagagcct gctgatcgtg   360
aacaacgcca ccaacgtggt catcaaagtg tgcgagttcc agttctgcaa cgaccccttc   420
ctgggcgtct actaccacaa gaacaacaag agctggatgg aaagcgagtt ccggggtgtac   480
agcagcgcca acaactgcac cttcgagtac gtgtcccagc ctttcctgat ggacctggaa   540
ggcaagcagg gcaacttcaa gaacctgcgc gagttcgtgt ttaagaacat cgacggctac   600
ttcaagatct acagcaagca caccccatc aacctcgtgc gggatctgcc tcagggcttc   660
tctgctctgg aaccctggt ggatctgccc atcggcatca acatcacccg gtttcagaca   720
ctgctggccc tgcacagaag ctacctgaca cctggcgata gcagcagcgg atggacagct   780
ggtgccgcgc ttactatgt gggctacctg cagcctagaa ccttcctgct gaagtacaac   840
gagaacgca ccatcaccga cgccgtggat tgtgctctgg atcctctgag cgagacaaag   900
tgcaccctga gtccttcac cgtggaaaag ggcatctacc agaccagcaa cttccgggtg   960
cagcccaccg aatccatcgt gcggttcccc aatatcacca atctgtgccc cttcggcgag  1020
gtgttcaatg ccaccagatt cgcctctgtg tacgcctgga accggaagcg gatcagcaat  1080
tgcgtggccg actactccgt gctgtacaac tccgccactc tcagcacctt caagtgctac  1140
ggcgtgtccc ctaccaagct gaacgacctg tgcttcacaa acgtgtacgc cgacagcttc  1200
gtgatccggg gagatgaagt gcggcagatt gcccctggac agacaggcaa gatcgccgac  1260
tacaactaca agctgcccga cgacttcacc ggctgtgtga ttgcctggaa cagcaacaac  1320
ctggactcca aagtcggcgg caactacaat taccgtaccg gctgttccg gaagtccaat  1380
ctgaagccct tcgagcggga catctccacc gagatctatc aggccggcag caccccttgt  1440
aacggcgtgg aaggcttcaa ctgctacttc ccactgcagt cctacggctt tcagcccaca  1500
aatggcgtgg gctatcagcc ctacagagtg gtggtgctga gcttcgaact gctgcatgcc  1560
cctgccacag tgtgcggccc taagaaaagc accaatctcg tgaagaacaa atgcgtgaac  1620
ttcaacttca acggcctgac cggcaccggc gtgctgacag agagcaacaa gaagttcctg  1680
ccattccagc agtttggccg ggatatcgcc gataccacag acgccgttag agatcccag  1740
acactggaaa tcctggacat cacccccttgc agcttcggcg gagtgtctgt gatcaccct  1800
ggcaccaaca ccagcaatca ggtggcagtg ctgtaccagg acgtgaactg taccgaagtg  1860
cccgtggcca ttcacgccga tcagctgaca cctacatggc gggtgtactc caccggcagc  1920
aatgtgtttc agaccagagc cggcctgtct atcggagccg agcacgtgaa caatagctac  1980
gagtgcgaca tccccatcgg cgctggaatc tgcgccagct accagacaca gacaaacagc  2040
cctcggagag ccagaagcgt ggccagccag agcatcattg cctacacaat gtctctgggc  2100
gccgagaaca gcgtggccta tccaacacaa tctatcgcta tccccaccaa cttcaccatc  2160
agcgtgacca cagagatcct gcctgtgtcc atgaccaaga ccagcgtgga ctgcaccatg  2220
tacatctgcg gcgattccac cgagtgctcc aacctgctgc tgcagtacgg cagcttctgc  2280
acccagctga atagagccct gacagggatc gccgtggaac aggacaagaa cacccaaagg  2340
gtgttcgccc aagtgaagca gatctacaag accccctcct caaggactt cggcggcttc  2400
aatttcagcc agattctgcc cgatcctagc aagcccagca gcggagctt catcgaggac  2460
ctgctgttca acaaagtgac actggccgac gccggcttca tcaagcagta tggcgattgt  2520
ctgggcgaca ttgccgccag ggatctgatt tgcgcccaga gtttaacgg actgacagtg  2580
ctgcctcctc tgctgaccga tgagatgatc gcccagtaca tctgcct ggccgcgg  2640
acaatcacaa gcggctggac atttggagca ggcgccgctc tgcagatccc ctttgctatg  2700
cagatggcct accggttcaa cggcatcgga gtgacccaga atgtgctgta cgagaaccag  2760
aagctgatcg ccaaccagtt caacagcgcc atcggcaaga tccaggacag cctgagcagc  2820
acagcaaagcg ccctgggaaa gctgcaggac gtggtcaacc agaatgccca ggcactgaac  2880
accctggtca gcagcctgtc ctccaacttc ggcgctccaa gctctgtgct gaacgatatc  2940
ctgagcagac tggaccctcc tgaggccgag gtgcagatcg acagactgat cacaggcaga  3000
ctgcagagcc tccagacata cgtgacccag cagctgatca gaccgccga gattagagcc  3060
tctgccaatc tggccgccac caagatgtct gagtgtgtgc tgggcagag caagagagtg  3120
gactttttgcg gcaagggcta ccacctgatg agcttccctc agtctgcccc tcacggcgtg  3180
gtgttccacg gacgtgacata tttgcccgct caagagaaga attccaccac cgctccagca  3240
atctgccacg acggcaaagc ccactttcct agagaaggcg tgttcgtgtc caacggcacc  3300
cattggtttcg tgacacagcg gaacttctac gagcccagga tcatccacac cgacaacacc  3360
ttcgtgtctg gcaactgcga cgtcgtgatc ggcattgtga caataccgt gtacgaccct  3420
ctgcagcccg agctggacag cttcaaagag gaactggaca agtactttaa gaaccacaca  3480
agccccgacg tggacctggg cgatatcagc ggaatcaatg ccagcgtcgt gaacatccag  3540
```

```
                                     -continued
aaagagatcg accggctgaa cgaggtggcc aagaatctga acgagagcct gatcgacctg  3600
caagaactgg ggaagtacga gcagtacatc aagtggccct ggtacatctg gctgggcttt  3660
atcgccggac tgattgccat cgtgatggtc acaatcatgc tgtgttgcat gaccagctgc  3720
tgtagctgcc tgaagggctg ttgtagctgt ggcagctgct gcaagttcga cgaggacgat  3780
tctgagcccg tgctgaaggg cgtgaaactg cactacaca                         3819

SEQ ID NO: 10            moltype = AA   length = 41
FEATURE                  Location/Qualifiers
REGION                   1..41
                         note = Foldon Sequence
source                   1..41
                         mol_type = protein
                         organism = synthetic construct
SEQUENCE: 10
GSGYIPEAPR DGQAYVRKDG EWVLLSTFLG RSLEVLFQGP G                        41

SEQ ID NO: 11            moltype = RNA   length = 123
FEATURE                  Location/Qualifiers
misc_feature             1..123
                         note = Coding Sequence
source                   1..123
                         mol_type = other RNA
                         organism = synthetic construct
SEQUENCE: 11
ggatctggtt atattcctga agctccaaga gatgggcaag cttacgttcg taaagatggc   60
gaatgggtat tactttctac cttttttaggc cggtccctgg aggtgctgtt ccagggcccc  120
ggc                                                                 123

SEQ ID NO: 12            moltype = RNA   length = 47
FEATURE                  Location/Qualifiers
misc_feature             1..47
                         note = 5'-UTR
source                   1..47
                         mol_type = other RNA
                         organism = synthetic construct
SEQUENCE: 12
aactagtatt cttctggtcc ccacagactc agagagaacc cgccacc                  47

SEQ ID NO: 13            moltype = RNA   length = 278
FEATURE                  Location/Qualifiers
misc_feature             1..278
                         note = 3'-UTR
source                   1..278
                         mol_type = other RNA
                         organism = synthetic construct
SEQUENCE: 13
ctggtactgc atgcacgcaa tgctagctgc ccctttcccg tcctgggtac cccgagtctc   60
ccccgacctc gggtcccagg tatgctccca cctccacctg ccccactcac cacctctgct  120
agttccagac acctcccaag cacgcagcaa tgcagctcaa aacgcttagc ctagccacac  180
ccccacggga aacagcagtg attaaccttt agcaataaac gaaagtttaa ctaagctata  240
ctaacccag ggttggtcaa tttcgtgcca gccacacc                            278

SEQ ID NO: 14            moltype = RNA   length = 110
FEATURE                  Location/Qualifiers
misc_feature             1..110
                         note = A30L70
source                   1..110
                         mol_type = other RNA
                         organism = synthetic construct
SEQUENCE: 14
aaaaaaaaaa aaaaaaaaaa aaaaaaaaaa gcatatgact aaaaaaaaaa aaaaaaaaaa   60
aaaaaaaaaa aaaaaaaaaa aaaaaaaaaa aaaaaaaaaa aaaaaaaaaa              110

SEQ ID NO: 15            moltype = RNA   length = 4282
FEATURE                  Location/Qualifiers
misc_feature             1..4282
                         note = RBL063.1
source                   1..4282
                         mol_type = other RNA
                         organism = synthetic construct
SEQUENCE: 15
gggcgaacta gtattcttct ggtccccaca gactcagaga gaacccgcca ccatgtttgt   60
gtttcttgtg ctgctgcctc ttgtgtcttc tcagtgtgtg aatttgacaa caagaacaca  120
gctgccacca gcttatacaa attcttttac cagaggagtg tattatcctg ataaagtgtt  180
tagatcttct gtgctgcaca gcacacagga cctgtttctg ccatttttta gcaatgtgac  240
atggtttcat gcaattcatg tgtctggaac aaatggaaca aaaagatttg ataatcctgt  300
gctgccttt aatgatggag tgtatttgc ttcaacagaa aagtcaaata ttattagagg  360
atggatttt ggaacaacac tggattctaa aacacagtct ctgctgattg tgaataatgc  420
aacaaatgtg gtgattaaag tgtgtgaatt tcagtttttgt aatgatccttt tctggggagt  480
```

-continued

```
gtattatcac aaaaataata aatcttggat ggaatctgaa tttagagtgt attcctctgc    540
aaataattgt acatttgaat atgtgtctca gccttttctg atggatctgg aaggaaaaca    600
gggcaatttt aaaaatctga gagaatttgt gtttaaaaat attgatggat attttaaaat    660
ttattctaaa cacacaccaa ttaatttagt gagagatctg cctcaggat ttctgctct     720
ggaacctctg gtggatctgc caattggcat taatattaca agatttcaga cactgctggc    780
tctgcacaga tcttatctga cacctggaga ttcttcttct ggatggacag ccggagctgc    840
agcttattat gtgggctatc tgcagccaag aacatttctg ctgaaatata tgaaaatgg    900
aacaattaca gatgctgtgg attgtgctct ggatcctctg tctgaaacaa aatgtacatt    960
aaaatctttt acagtggaaa aaggcattta tcagacatct aattttagag tgcagccaac   1020
agaatctatt gtgagatttc caaatattac aaatctgtgt ccatttggag aagtgtttaa   1080
tgcaacaaga tttgcatctg tgtatgcatg gaatagaaaa agaatttcta attgtgtggc   1140
tgattattct gtgctgtata atagtgcttc ttttccaca tttaaatgtt atggagtgtc    1200
tccaacaaaa ttaaatgatt tatgtttac aaatgtgtat gctgattctt ttgtgatcag    1260
aggtgatgaa gtgagacaga ttgccccccgg acagacagga aaaattgctg attacaatta   1320
caaactgcct gatgatttta caggatgtgt gattgcttgg aattctaata atttagattc   1380
taaagtggga ggaaattaca attatctgta cagactgttt agaaaatcaa atctgaaacc   1440
ttttgaaaga gatatttcaa cagaaattta tcaggctgga tcaacaccttt gtaatggagt   1500
ggaaggattt aattgttatt ttccattaca gagctatgga tttcagccaa ccaatgctgt   1560
gggatatcag ccatatagag tggtggtgct gtcttttgaa ctgctgcatg cacctgcaac   1620
agtgtgtgga cctaaaaaat ctacaaattt agtgaaaaat aaatgtgtga atttaatttt   1680
taatggatta acaggaacag gagtgctgac agaatctaat aaaaaatttc tgccttttca   1740
gcagtttggc agagatattg cagataccac agatgcaggg agagatccc agacattaga   1800
aattctggat attacaccttt gttcttttg gggtgtgtct gtgattcac ctggaacaaa    1860
tacatctaat caggtggctg tgctgtatca ggatgtgaat tgtacagaag tgccagtggc   1920
aattcatgca gatcagctga caccaacatg gagagtgtat tctacaggat ctaatgtgtt   1980
tcagacaaga gcaggatgtc tgattggaag agaacatgtg aataattctt atgaatgtga   2040
tattccaatt ggagcaggca tttgtgcatc ttatcagaca cagacaaatt ccccaaggag   2100
agcaagatct gtgcatctc agtctattat tgcatacacc atgtctctgg agcagaaaa    2160
ttctgtggca tattctaata attctattgc tattccaaca aattttacca tttctgtgac   2220
aacagaaatt ttacctgtgt ctatgacaaa aacatcttgg gattgtacca tgtacatttg   2280
tggagattct acagaatgtt ctaatctgct gctgcagtat ggatcttttt gtacacagct   2340
gaatagagct ttaacaggaa ttgctgtgga acaggataaa aatacacagg aagtgtttgc   2400
tcaggtgaaa cagatttaca aaacaccacc aattaaagat tttggaggat ttaattttag   2460
ccagattctg cctgatcctt ctaaaccttc taaaagatct tttattgaag atctgctgtt   2520
taataaagtg acactggcag atgcaggatt tattaaacag tatggagatt gcctgggtga   2580
tattgctgca agagatctga tttgtgctca gaaatttaat ggactgacag tgctgcctcc   2640
tctgctgaca gatgaaatga ttgctcagta cacatctgct ttactggctg aacaattac    2700
aagcggatgg acatttggag ctggagctgc tctgcagatt cctttgcaa tgcagatggc   2760
ttacagattt aatgaaattg gagtgacaca gaatgtgtta tatgaaaatc agaaactgat   2820
tgcaaatcag tttaattctg caattggcaa aattcaggat tctctgtctt ctacagcttc   2880
tgctctggga aaactgcagg atgtggtgaa tcagaatgca caggcactga atactctggt   2940
gaaacagctg tctagcaatt ttgggcaat tcttctgtg ctgaatgata ttctgtctag    3000
actgatcct cctgaagctg aagtgcagat tgatagacta atcacaggaa gactgcagtc   3060
tctgcagact tatgtgacac agcagctgat tagagctgtc gaaattagag cttctgctaa   3120
tctggctgct acaaaaatgt ctgaatgtgt gctgggacag tcaaaagag tggattttg    3180
tggaaaagga tatcatctga tgtctttcc acagtctgct ccacatggag tggtgttttt   3240
acatgtgaca tatgtgccag cacaggaaaa gaatttacc acagcaccag caatttgtca   3300
tgatggaaaa gcacattttc caagagaagg agtgtttgtg tctaatgaa cacattggtt   3360
tgtgacacag agaattttt atgaacctca gattattaca acagataata catttgtgtc   3420
aggaaattgt gatgtggtga ttggaattgt gaataataca gtgtatgatc cactgcagcc   3480
agaactggat tcttttaaag aagaactgga taaatattt aaaaatcaca catctcctga   3540
tgtggattta ggagtatttt ctggaatcaa tgcatctgtg gtgaatattc agaaagaaat   3600
tgatagactg aatgaagtgg ccaaaaatct gaatgaatct ctgattgatc tgcaggaact   3660
tggaaaatat gaacagtaca ttaaatggcc ttggtacatt tggcttggat ttattgcagg   3720
attaattgca ttatgtatgg tgacaattat atgacatcat gttgttcttg    3780
tttaaaagga tgttgttctt gtggaagctg ttgtaaattt gatgaagatg attctgaacc   3840
tgtgttaaaa ggagtgaaat tgcattacac atgatgactc gagctggtac tgcatgcacg   3900
caatgctagc tgcccctttc ccgtcctggg tacccccgagt ctccccgac ctcgggtccc    3960
aggtatgctc ccacctccac ctgccccact caccacctct gctagttcca gacacctcc   4020
aagcacgcag caatgcagct caaaacgctt agcctagcca caccccacg ggaaacagca   4080
gtgattaacc tttagcaata aacgaaagtt taactaagct atactaaccc cagggttggt   4140
caattcgtg ccagccacac cctggagcta gcaaaaaaaa aaaaaaaaa aaaaaaaaa     4200
aagcatgatga ctaaaaaaaa aaaaaaaaa aaaaaaaaa aaaaaaaaa aaaaaaaaaa    4260
aaaaaaaaaa aaaaaaaaa aa                                             4282

SEQ ID NO: 16            moltype = RNA   length = 4282
FEATURE                  Location/Qualifiers
misc_feature             1..4282
                         note = RBL063.2
source                   1..4282
                         mol_type = other RNA
                         organism = synthetic construct
SEQUENCE: 16
gggcgaacta gtattcttct ggtccccaca gactcagaga gaacccgcca ccatgttcgt     60
gttcctggtg ctgctgcctc tggtgtccaa ccagtgtgtg aacctgacca ccagaacaca    120
gctgcctcca gcctacacca acagcttac cagaggcgtg tactaccccg acaaggtgtt    180
cagatccagc gtgctgcact ctacccagga cctgttcctg ccttctccta gcaacgtgac    240
ctggttccac gccatccacg tgtccggcac caatggcacc aagagattcg acaacccggt    300
gctgcccttc aacgacgggg tgtactttgc cagcaccgag aagtccaaca tcatcagagg    360
```

```
ctggatcttc ggcaccacac tggacagcaa gacccagagc ctgctgatcg tgaacaacgc    420
caccaacgtg gtcatcaaag tgtgcgagtt ccagttctgc aacgacccct tcctgggcgt    480
ctactaccac aagaacaaca agagctggat ggaaagcgag ttccgggtgt acagcagcgc    540
caacaactgc accttcgagt acgtgtccca gcctttcctg atggacctgg aaggcaagca    600
gggcaacttc aagaacctgc gcgagttcgt gtttaagaac atcgacggct acttcaagat    660
ctacagcaag cacaccccta tcaacctcgt gcgggatctg cctcagggct ctctgctct    720
ggaaccctg gtggatctgc ccatcggcat caacatcacc cggtttcaga cactgctggc    780
cctgcacaga agctacctga cacctggcga tagcagcagc ggatggacag ctggtgccgc    840
cgcttactat gtgggctacc tgcagcctag aaccttcctg ctgaagtaca acgagaacgg    900
caccatcacc gacgccgtgg attgtgctct ggatcctctg agcgagacaa agtgcaccct    960
gaagtccttc accgtggaaa agggcatcta ccagaccagc aacttccggg tgcagcccac   1020
cgaatccatc gtgcggttcc caatatcac caatctgtgc cccttcggcg aggtgttcaa   1080
tgccaccaga ttcgcctctg tgtacgcctg aaccggaag cggatcagca attcgtggc    1140
cgactactcc gtgctgtaca actccgcag cttcagcacc ttcaagtgct acggcgtgtc   1200
ccctaccaag ctgaacgacc tgtgcttcac aaacgtgtac gccgacagct cgtgatccg   1260
gggagatgaa gtgcggcaga ttgccccctgg acagacaggc aagatcgccg actacaacta   1320
caagctgccc gacgacttca ccggctgtgt gattgcctgg aacagcaaca acctggactc   1380
caaagtcggc ggcaactaca attacctgta ccggctgttc ggaagtcca atctgaagcc   1440
cttcgagcgg gacatctcca ccgagatcta tcaggccggc agcaccccctt gtaacgcgt   1500
ggaaggcttc aactgctact ccccactgca gtcctacggc tttcagccca caaatggcgt   1560
gggctatcag ccctacagag tggtggtgct gagcttcgaa ctgctgcatg ccctgccac   1620
agtgtgcggc cctaagaaaa gcaccaatct cgtgaagaac aaatgcgtga acttcaactt   1680
caacggcctg accggcaccg gcgtgctgac agagagcaac aagaagttcc tgccattcca   1740
gcagttttggc cgggatatcg ccgataccac agacgccgtt agagatcccc agacactgga   1800
aatcctggac atcaccccctt gcagcttcgg cggagtgtct gtgatcaccc ctggcaccaa   1860
caccagcaat caggtggcag tgctgtacca ggacgtgaac tgtaccgaag tgcccgtgga   1920
cattcacgcc gatcagctga cacctacatg gcgggtgtac tccaccggca gcaatgctgtt   1980
tcagaccaga gccggctgtc tgatcggagc cgagcacgtg aacaatagct acgagtgcga   2040
catccccatc ggcgctggaa tctgcgccag ctaccagaca cagacaaaca gccctcggag   2100
agccgaaagc gtgccagcc agagcatcat tgcctacaca atgtctctgg cgccgagaa   2160
cagcgtggcc tactccaaca actctatcgc tatccccacc aacttcacca tcagcgtgac   2220
cacagagatc ctgcctgtgt ccatgaccaa gaccagcgtg gactgcacca tgtacatctg   2280
cggcgattcc accgagtgct ccaacctgct gctgcagtac ggcagcttct gcacccagct   2340
gaatagacc ctgacaggga tcgccgtgga acaggacaag aacacccaag aggtgttcgc   2400
ccaagtgaag cagatctaca agaccctcc tatcaaggac ttcggcgggct tcaatttcag   2460
ccagattctg cccgatccta gcaagcccag caagcggagc ttcatcgagg acctgctgtt   2520
caacaaagtg acactggccg acgccggctt catcaagcag tatggcgatt gtctgggccga   2580
cattgccgcc agggatctga tttgcgccca gaagtttaac ggactgacag tgctgcctcc   2640
tctgctgacc gatgagatga tcgcccagta cacatctgcc ctgctggccg gcacaatcac   2700
aagcggctgg acattggag caggcgccgc tctgcagatc cccttttgcta tgcagatggc   2760
ctaccggttc aacggcatcg gagtgaccca gaatgtgctg tacgagaacc agaagctgat   2820
cgccaaccag ttcaacagcg ccatcggcaa gatccaggac agcctgagca gcacagcaag   2880
cgccctggga aagctgcagg acgtggtcaa ccagaatgcc caggcactga acacccctgg   2940
caagcagctg tcctccaact cggcgccat cagctctgtg ctgaacgata tcctgagcag   3000
actggacccct cctgaggccg aggtgcagat cgacagactg atcacaggca gactgcagag   3060
cctccagaca tacgtgaccc agcagctgat cagagccgcc gagattagag cctctgccaa   3120
tctgcccgcc accaagatgt ctgagtgtgt gctgggccag agcaagagag tggacttttg   3180
cggcaagggc taccacctga tgagcttccc tcagtctgcc cctcagcgcg tgggtgtttct   3240
gcacgtgaca tatgtgcccg ctcaagagaa gaatttcacc accgctccag ccatctgcca   3300
cgacggcaaa gcccactttc ctagagaagg cgtgttcgtg tccaacggca cccattggtt   3360
cgtgacacag cggaacttct acgagcccca gatcatcacc acggacaaca cctcgtgtc   3420
tgcaactgc gacgtcgtga tcggcattgt gaacaatacc gtgtacgacc ctctgcagcc   3480
cgagctggac agcttcaaag aggaactgga caagtacttt aagaaccaca aagcccccga   3540
cgtggacctg ggcgatatca gcgggaatcaa tgccagcgtc gtgaacatcc agaaagagat   3600
cgaccggctg aacgaggtgg ccaagaatct gaacgagagc ctgatcgacc tgcaagaact   3660
ggggaagtac gagcagtaca tcaagtggcc ctggtacatc tggctgggct ttatcgccgg   3720
actgattgcc atcgtgatgg tcacaatcat gctgtgttgc atgaccagct gctgtagctg   3780
cctgaagggc tgttgtagct gtggcagctg ctgcaagttc gacgaggacg attctgagcc   3840
cgtgctgaag ggcgtgaaac tgcactacac atgatgactc gagctggtac tgcatgcacg   3900
caatgctagc tgcccccttttc ccgtcctggg taccccgagt ctcccccgac ctcgggtccc   3960
aggtatgctc ccacctccac ctgccccact caccacctct gctagttcca gacacctccc   4020
aagcacgcag caatgcagct caaaacgctt agcctagcca caccccacg ggaaacagca   4080
gtgattaacc tttagcaata aacgaaagtt taactaagct atactaaccc cagggttggt   4140
caatttcgtg ccagccacac cctggagcta caaaaaaaa aaaaaaaaaa aaaaaaaaa    4200
aagcatatga ctaaaaaaaa aaaaaaaaaa aaaaaaaaaa aaaaaaaaaa aaaaaaaaaa   4260
aaaaaaaaaa aaaaaaaaaa aa                                            4282

SEQ ID NO: 17         moltype = RNA    length = 1261
FEATURE               Location/Qualifiers
misc_feature          1..1261
                      note = RBL063.3
source                1..1261
                      mol_type = other RNA
                      organism = synthetic construct
SEQUENCE: 17
gggcgaacta gtattcttct ggtccccaca gactcagaga gaaccgcca ccatgtttgt     60
gtttcttgtg ctgctgcctc ttgtgtcttc tcagtgtgtg gtgagatttc caaatattac    120
aaatctgtgt ccattggag aagtgtttaa tgcaacaaga tttgcatctg tgtatgcatg    180
gaatagaaaa agaatttcta attgtgtggc tgattattct gtgctgtata atagtgcttc    240
```

```
tttttccaca tttaaatgtt atggagtgtc tccaacaaaa ttaaatgatt tatgttttac    300
aaatgtgtat gctgattctt ttgtgatcag aggtgatgaa gtgagacaga ttgccccgg     360
acagacagga aaaattgctg attacaatta caaactgcct gatgatttta caggatgtgt   420
gattgcttgg aattctaata atttagattc taaagtggga ggaaattaca attatctgta   480
cagactgttt agaaaatcaa atctgaaacc ttttgaaaga gatatttcaa cagaaattta   540
tcaggctgga tcaacacctt gtaatggagt ggaaggattt aattgttatt ttccattaca   600
gagctatgga tttcagccaa ccaatggtgt gggatatcag ccatatagag tggtggtgct   660
gtcttttgaa ctgctgcatg cacctgcaac agtgtgtgga cctaaaggct cccccggctc   720
cggctccgga tctggttata ttcctgaagc tccaagagat gggcaagctc acgttcgtaa   780
agatggcgaa tgggtattac tttctacctt tttaggccgg tccctgggag tgctgttcca   840
gggccccggc tgatgactcg agctggtact gcatgcacgc aatgctagct gcccctttcc   900
cgtcctgggt accccgagtc tccccgacc tcgggtccca ggtatgctcc cacctccacc    960
tgccccactc accacctctg ctagttccag acacctccca agcacgcagc aatgcagcta  1020
aaaacgctta gcctagccac acccccacgg gaaacagcag tgattaacct ttagcaataa  1080
acgaaagttt aactaagcta tactaacccc agggttggtc aatttcgtgc cagccacacc  1140
ctggagctag caaaaaaaaa aaaaaaaaaa aaaaaaaaaa agcatatgac taaaaaaaaa  1200
aaaaaaaaa aaaaaaaaa aaaaaaaaa aaaaaaaaa aaaaaaaaa aaaaaaaaa        1260
a                                                                 1261

SEQ ID NO: 18           moltype = AA   length = 250
FEATURE                 Location/Qualifiers
REGION                  1..250
                        note = S Protein RBD Fusion
source                  1..250
                        mol_type = protein
                        organism = synthetic construct
SEQUENCE: 18
VRFPNITNLC PFGEVFNATR FASVYAWNRK RISNCVADYS VLYNSASFST FKCYGVSPTK    60
LNDLCFTNVY ADSFVIRGDE VRQIAPGQTG KIADYNYKLP DDFTGCVIAW NSNNLDSKVG   120
GNYNYLYRLF RKSNLKPFER DISTEIYQAG STPCNGVEGF NCYFPLQSYG FQPTNGVGYQ   180
PYRVVVLSFE LLHAPATVCG PKGSPGSGSG SGYIPEAPRD GQAYVRKDGE WVLLSTFLGR   240
SLEVLFQGPG                                                         250

SEQ ID NO: 19           moltype = RNA  length = 4283
FEATURE                 Location/Qualifiers
misc_feature            1..4283
                        note = RBP020.1
source                  1..4283
                        mol_type = other RNA
                        organism = synthetic construct
SEQUENCE: 19
agaataaact agtattcttc tggtccccac agactcagag agaacccgcc accatgtttg    60
tgtttcttgt gctgctgcct cttgtgtctt ctcagtgtga gaatttgaca acaagaacac   120
agctgccacc agcttataca aattctttta ccagaggagt gtattatcct gataaagtgt   180
ttagatcttc tgtgctgcac agcacacagg acctgtttct gccatttttt agcaatgtga   240
catgtgttca tgcaattcat gtgtctgaa caaatgaac aaaaagattt gataatcctg     300
tgctgccttt taatgatgga gtgtatttg cttcaacaga aagtcaaat attattagag     360
gatgattttt tggaacaaca ctggattcta aaacacagtc tctgctgatt gtgaataatg   420
caacaaatgt ggtgattaaa gtgtgtgaat ttcagttttg taatgatcct tttctgggag   480
tgtattatca caaaaataat aaatcttgga tggaatctga atttagagtg tattcctctg   540
caaataattg tacatttgaa tatgtgtctc agccttttct gatggatctg gaaggaaaac   600
agggcaattt taaaaatctg agagaatttg tgtttaaaaa tattgatgga tattttaaaa   660
tttattctaa acacacacca attaatttag tgagagatct gcctcaggga ttttctgctc   720
tggaacctct ggtggatctg ccaattgca ttaatattac aagatttcag acactgctgg    780
ctctgcacag atcttatctg acacctggag attcttctc tggatggaca gccggagctg    840
cagcttatta tgtgggctat ctgcagccaa gaacatttct gctgaaatat aatgaaaatg   900
gaacaattac agatgctgtg gattgtgctc tggatcctct gtctgaaaca aaatgtacat   960
taaaatcttt tacagtggaa aaaggcattt atcagacatc taattttaga gtgcagccaa  1020
cagaactat tgtgagattt ccaaatatta caaatctgtg tccatttgga gaagtgttta   1080
atgcaacaag atttgcatct gtgtatgcat ggaataaaag aatttct aattgtgtgg     1140
ctgattattc tgtgctgtat aatagtgctt cttttcccac atttaaatgt tatgagtgt    1200
ctccaacaaa attaaatgat ttatgtttta caatgtgta tgctgattct tttgtgatca    1260
gaggtgatga agtgagacag attgccccg gacagacagg aaaaattgct gattacaatt    1320
acaaactgcc tgatgatttt acaggatgtg tgattgcttg gaattctaat aatttagatt   1380
ctaaagtggg aggaaattac aattatctgt acagactgtt tagaaaatca atctgaaac    1440
cttttgaaag agatatttca acagaaattt atcaggctgg atcaacacct tgtaatggag   1500
tggaaggatt taattgttat tttccattac agagctatgg atttcagcca accaatggtg   1560
tgggatatca gccatataga gtggtggtgc tgtcttttga actgctgcat gcacctgcaa   1620
cagtgtgtgg acctaaaggc tcccccggct cggctccgga tctggttata ttcctgaagc   1680
tccaagagat gggcaagctc acgttcgtaa agatggcgaa tgggtattac tttctacctt   1740
tttaggccgg tccctgggag tgctgttcca gggccccggc tgatgactcg agctggtact   1800
gcatgcacgc aatgctagct gcccctttcc cgtcctgggt accccgagtc tccccgacct   1860
cgggtcccag gtatgctccc acctccacct gccccactca ccacctctgc tagttccaga   1920
cacctcccaa gcacgcagca atgcagctaa aaacgcttag cctagccaca cccccacggg   1980
aaacagcagt gattaacctt tagcaataaa cgaaagttta actaagctat actaacccca   2040
ggttggtcaa tttcgtgcca gccacaccct ggagctagca aaaaaaaaa aaaaaaaaaa    2100
gagcaagatc tgtggcatct cagtctatta ttgcatacac catgtctctg ggagcagaaa  2160
attctgtggc atattctaat aattctattg ctattccaac aaattttacc atttctgtga  2220
caacagaaat tttacctgtg tctatgacaa aaacatcgt ggattgtacc atgtacattt    2280
```

```
gtggagattc tacagaatgt tctaatctgc tgctgcagta tggatctttt tgtacacagc  2340
tgaatagagc tttaacagga attgctgtgg aacaggataa aaatacacag gaagtgtttg  2400
ctcaggtgaa acagatttac aaaacaccac caattaaaga ttttggagga tttaatttta  2460
gccagattct gcctgatcct tctaaaacctt ctaaaagatc ttttattgaa gatctgctgt  2520
ttaataaagt gacactggca gatgcaggat ttattaaaca gtatggagat tgcctgggtg  2580
atattgctgc aagagatctg atttgtgctc agaaatttaa tggactgaca gtgctgcctc  2640
ctctgctgac agatgaaatg attgctcagt acacatctgc tttactggct ggaacaatta  2700
caagcggatg gacatttgga gctggagctg ctctgcagat tccttttgca atgcagatgg  2760
cttacagatt taatggaatt ggagtgacac agaatgtgtt atatgaaaat cagaaactga  2820
ttgcaaatca gttttaattct gcaattggca aaattcagga ttctctgtct tctacagctt  2880
ctgctctggg aaaactgcag gatgtggtga atcagaatgc acaggcactg aatactctgg  2940
tgaaacagct gtctagcaat tttggggcaa tttcttctgt gctgaatgat attctgtcta  3000
gactggatcc tcctgaagct gaagtgcaga ttgatagact gatcacagga agactgcagt  3060
ctctgcagac ttatgtgaca cagcagctga ttagagctgc tgaaattaga gcttctgcta  3120
atctggctgc tacaaaaatg tctgaatgtg tgctgggaca gtcaaaaaga gtggattttt  3180
gtggaaaagg atatcatctg atgtcttttc cacagtctgc tccacatgga gtggtgtttt  3240
tacatgtgac atatgtgcca gcacaggaaa agaaattttac cacagcacca gcaatttgtc  3300
atgatggaaa agcacatttt ccaagagaag gagtgtttgt gtctaatgga acacattggt  3360
ttgtgacaca gagaaatttt tatgaacctc agattattac aacagataat acatttgtgt  3420
caggaaattg tgatgtggtg attggaattg tgaataatac agtgtatgat ccactgcagc  3480
cagaactgga ttcttttaaa gaagaactgg ataaatattt taaaaatcac acatctcctg  3540
atgtggattt aggagatatt tctggaatca atgcatctgt ggtgaatatt cagaaagaaa  3600
ttgatagact gaatgaagtg gccaaaaatc tgaatgaatc tctgattgat ctgcaggaac  3660
ttggaaaata tgaacagtac attaaatgc cttggtacat ttggcttgga tttattgcag  3720
gattaattgc aattgtgatg gtgacaatta tgttatgttg tatgacatca tgttgttctt  3780
gtttaaaagg atgttgttct tgtggaagct gttgtaaatt tgatgaagat gattctgaac  3840
ctgtgttaaa aggagtgaaa ttgcattaca catgatgact cgagctggta ctgcatgcac  3900
gcaatgctag ctgcccctttt cccgtcctgg gtaccccgag tctccccga cctcgggtcc  3960
caggtatgct cccacctcca cctgcccac tcaccacctc tgctagttcc agacacctcc  4020
caagcacgca gcaatgcagc tcaaaacgct tagcctagcc acaccccccac gggaaacagc  4080
agtgattaac ctttagcaat aaacgaaagt ttaactaagc tatactaacc ccagggttga  4140
tcaatttcgt gccagccaca ccctggagct agcaaaaaaa aaaaaaaaaa aaaaaaaaaa  4200
aaagcatatg actaaaaaaa aaaaaaaaaaa aaaaaaaaaa aaaaaaaaaa aaaaaaaaaa  4260
aaaaaaaaaa aaaaaaaaa aaa                                          4283

SEQ ID NO: 20           moltype = RNA  length = 4283
FEATURE                 Location/Qualifiers
misc_feature            1..4283
                        note = RBP020.2
source                  1..4283
                        mol_type = other RNA
                        organism = synthetic construct
SEQUENCE: 20
agaataaact agtattcttc tggtccccac agactcagag agaacccgcc accatgttcg  60
tgttcctggt gctgctgcct ctggtgtcca gccagtgtgt gaacctgacc accagaaaca  120
gctgcctcc agcctacacc aacagcttta ccagaggcgt gtactacccc gacaaggtgt  180
tcagatccag cgtgctgcac tctacccagg acctgttcct gcctttcttc agcaacgtga  240
cctggttcca cgccatccac gtgtccggca ccaatggcac caagagattc gacaaccccg  300
tgctgccctt caacgacggg gtgtactttg ccagcaccga aagtccaaac atcatcagag  360
gctggatctt cggcaccaca ctggacagca gacccagag cctgctgatc gtgaacaacg  420
ccaccaacgt ggtcatcaaa gtgtgcgagt tccagttcgt caacgacccc ttcctgggcg  480
tctactacca caagaacaac aagagctgga tggaaagcga gttccgggtg tacagcagcg  540
ccaacaactg caccttcgag tacgtgtccc agccttttcct gatggacctg gaaggcaagc  600
agggcaactt caagaacctg cgcgagttcg tgtttaagaa catcgacggc tacttcaaga  660
tctacagcaa gcacaccct atcaacctcg tgcgggatct gcctcagggc ttctctgtct  720
tggaaccccct ggtggatctg cccatcggca tcaacatcac ccggtttcag acactgctgg  780
ccctgcacag aagctacctg acacctggcg atagcagcag cggatggaca gctggtgccg  840
ccgcttacta tgtgggctac ctgcagccta gaaccttcct gctgaagtac aacgagaacg  900
gcaccatcac cgacgccgtg gattgtgctc tggatcctc gagcgagaca aagtgcaccc  960
tgaagtcctt caccgtggaa aagggcatct accagaccag caacttccgg gtgcagccca  1020
ccgaatccat cgtgcggttc cccaatatca ccaatctgtg ccccttcggc gaggtgttca  1080
atgccaccag attcgcctct gtgtacgcct ggaaccggaa gcggatcagc aattgcgtgg  1140
ccgactactc cgtgctgtac aactccgcca gcttcagcac cttcaagtgc tacggcgtgt  1200
cccctaccaa gctgaacgac ctgtgcttca caaacgtgta cgcagacagc ttcgtgatcc  1260
ggggagatga agtgcggcag attgccctg acagacaggg caagatcgcc gactacaact  1320
acaagctgcc cgacgacttc accggctgtg tgattgcctg aacagcaac aacctggact  1380
ccaaagtcgg cggcaactac aattacctgt accggctgtt ccggaagtcc aatctgaagc  1440
ccttcgagcg ggacatctcc accgagatct atcaggccgg cagcacccct tgtaacggcg  1500
tggaaggctt caactgctac ttcccactgc agtcctacgg ctttcagccc acaaatggcg  1560
tgggctatca gcctacaga gtggtggtgc tgagcttcga actgctgcat gcccctgcca  1620
cagtgtgcgg ccctaagaaa agcaccaatc tcgtgaagaa caaatgcgtg aacttcaact  1680
tcaacgccct gaccggcacc ggcgtgctga cagagagcaa caagaagttc tgccattcc  1740
agcagtttgg ccgggatatc gccgatacca cagacgccgt tagagatccc cagacactgg  1800
aaatcctgga catcacccct tgcagcttcg gcggagtgtc tgtgatcacc cctggcacca  1860
acaccagcaa tcaggtggca gtgctgtacc aggacgtgaa ctgtaccgaa gtgcccgtgg  1920
ccattcacgc cgatcagctg acacctacat ggcgggtgta ctccaccggc agcaatgtgt  1980
ttcagaccag agcggctgt ctgatcggag ccgagcacgt gaacaatagc tacgagtgcg  2040
acatccccat cggcgctgga atctgcgcca gctaccagac agacaaac agccctcgga  2100
gagccagaag cgtggccagc cagagcatca ttgcctacac aatgtctctg ggcgccgaga  2160
```

```
acagcgtggc ctactccaac aactctatcg ctatccccac caacttcacc atcagcgtga  2220
ccacagagat cctgcctgtg tccatgacca agaccagcgt ggactgcacc atgtacatct  2280
gcggcgattc caccgagtgc tccaacctgc tgctgcagta cggcagcttc tgcacccagc  2340
tgaatagagc cctgacaggg atcgccgtgg aacaggacaa gaacacccaa gaggtgttcg  2400
cccaagtgaa gcagatctac aagacccctc ctatcgcagg cttcggcggc ttcaatttca  2460
gccagattct gcccgatcct agcaagccca gcaagcggag cttcatcgag gacctgctgt  2520
tcaacaaagt gacactggcc gacgccggct tcatcaagga gtatggcgat tgtctgggcg  2580
acattgccgc cagggatctg atttgcgccc agaagtttaa cggactgaca gtgctgcctc  2640
ctctgctgac cgatgagatg atcgcccagt acacatctgc cctgctggcc ggcacaatca  2700
caagcggctg gacatttgga gcaggcgccg ctctgcagat ccccttttgct atgcagatgg  2760
cctaccggtt caacggcatc ggagtgaccc agaatgtgct gtacgagaac cagaagctga  2820
tcgccaacca gttcaacagc gccatcggca agatccagga cagcctgagc agcacagcaa  2880
gcgccctggg aaagctgcag gacgtggtca accagaatgc ccaggcactg aacccctgg   2940
tcaagcagct gtcctccaac ttcggcgcca tcagctctgt gctgaacgat atcctgagca  3000
gactggaccc tcctgaggcc gaggtgcaga tcgacagact gatcacaggc agactgcaga  3060
gcctccagac atacgtgacc cagcagctga tcagagccgc cgagattaga gcctctgcca  3120
atctggccgc caccaagatg tctgagtgtg tgctgggcca gagcaagaga gtggactttt  3180
gcggcaaggg ctaccacctg atgagcttcc ctcagtctgc ccctcacggc gtggtgttcc  3240
tgcacgtgac atatgtgccc gctcaagaga agaatttcac caccgctcca gccatctgcc  3300
acgacggcaa agcccacttt cctagagaag gcgtgttcgt gtccaacggc acccattggt  3360
tcgtgacaca gcggaacttc tacgagcccc agatcatcac caccgacaac accttcgtgt  3420
ctggcaactg cgacgtcgtg atcggcattg tgaacaatac cgtgtacgac cctctgcagc  3480
ccgagctgga cagcttcaaa gaggaactgg acaagtactt taagaaccac acaagccccg  3540
acgtggacct gggcgatatc agcggaatca atgccagcgt cgtgaacatc cagaaagaga  3600
tcgaccggct gaacgaggtg gccaagaatc tgaacgagag cctgatcgac ctgcaagaac  3660
tggggaagta cgagcagtac atcaagtggc cctggtacat ctggctgggc tttatcgccg  3720
gactgattgc catcgtgatg gtcacaatca tgctgtgttg catgaccagc tgctgtagct  3780
gcctgaaggg ctgttgtagc tgtggcagct gctgcaagtt cgacgaggac gattctgagc  3840
ccgtgctgaa gggcgtgaaa ctgcactaca atgatgact cgagctggta ctgcatgcac  3900
gcaatgctag ctgcccctt ccgtcctgg gtaccccga tctcccccga cctcgggtcc  3960
caggtatgct cccacctcca cctgccccac tcaccacctc tgctagttcc agacacctcc  4020
caagcacgca gcaatgcagc tcaaaacgct tagcctagcc acaccccac gggaaacagc  4080
agtgattaac ctttagcaat aaacgaaagt taactaagc tatactaacc cagggttgg  4140
tcaatttcgt gccagccaca ccctggagct agcaaaaaaa aaaaaaaaaaa aaaaaaaaaa  4200
aaagcatatg actaaaaaaa aaaaaaaaaaa aaaaaaaaa aaaaaaaaa aaaaaaaaaa  4260
aaaaaaaaaa aaaaaaaaaa aaa                                          4283

SEQ ID NO: 21           moltype = RNA   length = 1262
FEATURE                 Location/Qualifiers
misc_feature            1..1262
                        note = RBP020.3
source                  1..1262
                        mol_type = other RNA
                        organism = synthetic construct
SEQUENCE: 21
agaataaact agtattcttc tggtccccac agactcagag agaacccgcc accatgtttg   60
tgtttcttgt gctgctgcct cttgtgtctt ctcagtgtgt ggtgagattt ccaaatatta  120
caaatctgtg tccatttgga gaagtgttta atgcaacaag atttgcatct gtgtatgcat  180
ggaatagaaa aagatttct aattgtgtgg ctgattattc tgtgctgtat aatagtgctt   240
cttttttccac atttaaatgt tatggagtgt ctccaacaaa attaaatgat ttatgtttta  300
caaatgtgta tgctgattct tttgtgatca gaggtgatga agtagacag attgccccgg   360
gacagacagg aaaaattgct gattacaatt acaaactgcc tgatgatttt acaggatgtg  420
tgattgcttg gaattctaat aattagatt ctaaagtggg aggaaattac aattatctgt   480
acagactgtt tagaaaatca aatctgaaac ttttgaaag agatatttca acagaaattt   540
atcatgctgg atcaacacct tgtaatggag tggaaggatt taattgttat tttccattac  600
agagctatgg atttcagcca accaatggtg tgggatatca gccatataga gtggtgtgc   660
tgtctttga actgctgcat gcacctgcaa cagtgtgtgg acctaaaggc tcccccggct   720
ccggctccga atctggttat attcctgaag ctccaagaga tgggcaagct tacgttcgta   780
aagatggcga atgggtatta cttttctacc ttttaggccg gtccctggga gtgctgttca   840
agggccccgg ctgatgactc gagctggtac tgcatgcacg caatgctagc tgccccttc   900
ccgtcctggg taccccgagt ctcccccgac ctcgggtccc aggtatgctc ccacctccac  960
ctgccccact caccacctct gctagttcca gacacctccc aagcacgcag caatgcagct 1020
caaaacgctt agcctagcca caccccacg gaaacagca gtgattaacc tttagcaata  1080
aacgaaagtt taactaagct atactaaccc cagggttggt caatttcgtg ccagccacac  1140
cctggagcta gcaaaaaaaa aaaaaaaaaa aaaaaaaaaa aaagcatatga ctaaaaaaa  1200
aaaaaaaaaa aaaaaaaaaa aaaaaaaaaa aaaaaaaaaa aaaaaaaaaa aaaaaaaaaa 1260
aa                                                                1262

SEQ ID NO: 22           moltype = AA    length = 1879
FEATURE                 Location/Qualifiers
REGION                  1..1879
                        note = Viral Protein
source                  1..1879
                        mol_type = protein
                        organism = synthetic construct
SEQUENCE: 22
MEKVHVDIEE DSPFLRALQR SFPQFEVEAK QVTDNDHANA RAFSHLASKL IETEVDPSDT   60
ILDIGSAPAR RMYSKHKYHC ICPMRCAEDP DRLYKYATKL KKNCKEITDK ELDKKMKELA  120
AVMSDPDLET ETMCLHDDES CRYEGQVAVY QDVYAVDGPT SLYHQANKGV RVAYWIGFDT  180
```

```
TPFMFKNLAG AYPSYSTNWA DETVLTARNI GLCSSDVMER SRRGMSILRK KYLKPSNNVL    240
FSVGSTIYHE KRDLLRSWHL PSVFHLRGKQ NYTCRCETIV SCDGYVVKRI AISPGLYGKP    300
SGYAATMHRE GFLCCKVTDT LNGERVSFPV CTYVPATLCD QMTGILATDV SADDAQKLLV    360
GLNQRIVVNG RTQRNTNTMK NYLLPVVAQA FARWAKEYKE DQEDERPLGL RDRQLVMGCC    420
WAFRRHKITS IYKRPDTQTI IKVNSDFHSF VLPRIGSNTL EIGLRTRIRK MLEEHKEPSP    480
LITAEDVQEA KCAADEAKEV REAEELRAAL PPLAADVEEP TLEADVDLML QEAGAGSVET    540
PRGLIKVTSY AGEDKIGSYA VLSPQAVLKS EKLSCIHPLA EQVIVITHSG RKGRYAVEPY    600
HGKVVVPEGH AIPVQDFQAL SESATIVYNE REFVNRYLHH IATHGGALNT DEEYYKTVKP    660
SEHDGEYLYD IDRKQCVKKE LVTGLGLTGE LVDPPFHEPA YESLRTRPAA PYQVPTIGVY    720
GVPGSGKSGI IKSAVTKKDL VVSAKKENCA EIIRDVKKMK GLDVNARTVD SVLLNGCKHP    780
VETLYIDEAF ACHAGTLRAL IAIIRPKKAV LCGDPKQCGF FNMMCLKVHF NHEICTQVFH    840
KSISRRCTKS VTSVVSTLFY DKKMRTTNPK ETKIVIDTTG STKPKQDDLI LTCFRGWVKQ    900
LQIDYKGNEI MTAAASQGLT RKGVYAVRYK VNENPLYAPT SEHVNVLLTR TEDRIVWKTL    960
AGDPWIKTLT AKYPGNFTAT IEEWQAEHDA IMRHILERPD PTDVFQNKAN VCWAKALVPV   1020
LKTAGIDMTT EQWNTVDYFE TDKAHSAEIV LNQLCVRFFG LDLDSGLFSA PTVPLSIRNN   1080
HWDNSPSPNM YGLNKEVVRQ LSRRYPQLPR AVATGRVYDM NTGTLRNYDP RINLVPVNRR   1140
LPHALVLHHN EHPQSDFSSF VSKLKGRTVL VVGEKLSVPG KMVDWLSDRP EATFRARLDL   1200
GIPGDVPKYD IIFVNVRTPY KYHHYQQCED HAIKLSMLTK KACLHLNPGG TCVSIGYGYA   1260
DRASESIIGA IARQFKFSRV CKPKSSLEET EVLFVFIGYD RKARTHNPYK LSSTLTNIYT   1320
GSRLHEAGCA PSYHVVRGDI ATATEGVIIN AANSKGQPGG GVCGALYKKF PESFDLQPIE   1380
VGKARLVKGA AKHIIHAVGP NFNKVSEVEG DKQLAEAYES IAKIVNDNNY KSVAIPLLST   1440
GIFSGNKDRL TQSLNHLLTA LDTTDADVAI YCRDKKWEMT LKEAVARREA VEEICISDDS   1500
SVTEPDAELV RVHPKSSLAG RKGYSTSDGK TFSYLEGTKF HQAAKDIAEI NAMWPVATEA   1560
NEQVCMYILG ESMSSIRSKC PVEESEASTP PSTLPCLCIH AMTPERVQRL KASRPEQITV   1620
CSSFPLPKYR ITGVQKIQCS QPILFSPKVP AYIHPRKYLV ETPPVDETPE PSAENQSTEG   1680
TPEQPPLITE DETRTRTPEP IIIEEEEEDS ISLLSDGPTH QVLQVEADIH GPPSVSSSSW   1740
SIPHASDFDV DSLSILDTLE GASVTSGATS AETNSYFAKS MEFLARPVPA PRTVFRNPPH   1800
PAPRTRTPSL APSRACSRTS LVSTPPGVNR VITREELEAL TPSRTPSRSV SRTSLVSNPP   1860
GVNRVITREE FEAFVAQQQ                                                1879

SEQ ID NO: 23          moltype = AA  length = 613
FEATURE                Location/Qualifiers
REGION                 1..613
                       note = Viral Protein
source                 1..613
                       mol_type = protein
                       organism = synthetic construct
SEQUENCE: 23
RFDAGAYIFS SDTGQGHLQQ KSVRQTVLSE VVLERTELEI SYAPRLDQEK EELLRKKLQL     60
NPTPANRSRY QSRKVENMKA ITARRILQGL GHYLKAEGKV ECYRTLHPVP LYSSSVNRAF    120
SSPKVAVEAC NAMLKENFPT VASYCIIPEY DAYLDMVDGA SCCLDTASFC PAKLRSFPKK    180
HSYLEPTIRS AVPSAIQNTL QNVLAAATKR NCNVTQMREL PVLDSAAFNV ECFKKYACNN    240
EYWETFKENP IRLTEENVVN YITKLKGPKA AALFAKTHVI NMLQDIPMDR FVMDLKRDVK    300
VTPGTKHTEE RPKVQVIQAA DPLATAYLCG IHRELVRRLN AVLLPNIHTL FDMSAEDFDA    360
IIAEHFQPGD CVLETDIASF DKSEDDAMAL TALMILEDLG VDAELLTLIE AAFGEISSIH    420
LPTKTKFKFG AMMKSGMFLT LFVNTVINIV IASRVLRERL TGSPCAAFIG DDNIVKGVKS    480
DKLMADRCAT WLNMEVKIID AVVGEKAPYF CGGFILCDSV TGTACRVADP LKRLFKLGKP    540
LAADDEHDDD RRRALHEEST RWNRVGILSE LCKAVESRYE TVGTSIIVMA MTTLASSVKS    600
FSYLRGAPIT LYG                                                      613

SEQ ID NO: 24          moltype = RNA  length = 11917
FEATURE                Location/Qualifiers
misc_feature           1..11917
                       note = RBS004.1
source                 1..11917
                       mol_type = other RNA
                       organism = synthetic construct
SEQUENCE: 24
gatgggcggc gcatgagaga agcccagacc aattacctac ccaaaatgga gaaagttcac     60
gttgacatcg aggaagacag cccattcctc agagctttgc agcggagctt cccgcagttt    120
gaggtagaag ccaagcaggt cactgataat gaccatgcta atgccagagc gttttcgcat    180
ctggcttcaa aactgatcga aacggaggtg gacccatccg acacgatcct tgacattgga    240
agtgcgcccg cccgcagaat gtattctaag cacaagtatc attgtatctg tccgatgaga    300
tgtgcggaag atccggacag attgtataag atgcaacta agctgaagaa aaactgtaag    360
gaaataactg ataaggaatt ggacaagaaa atgaaggagc tcgccgccgt catgagcgac    420
cctgacctgg aaactgagac tatgtgcctc cacgacgacg agtcgtgtcg ctacgaaggg    480
caagtcgctg tttaccagga tgtatacgcg gttgacggac cgacaagtct ctatcaccaa    540
gccaataagg gagttagagt cgcctactgg ataggctttg acaccacccc tttttatatg    600
aagaacttgg ctggagcata tccatctac tctaccaact gggccgacga aaccgtgtta    660
acggctcgta acataggcct atgcagctct gacgttatgg agcggtcacg tagagggatg    720
tccattctta gaaagaagta tttgaaacca tccaacaatg ttctattctc tgttggctcg    780
accatctacc acgaaaagag ggacttactg aggagctggc acctgccgtc tgtatttcac    840
ttacgtggca agcaaaatta cacatgtcgg tgtgagacta gttagttg cgacgggtac    900
gtcgttaaaa gaatcgctat cagtccaggc ctgtatggga agccttcagg ctatgctgct    960
acgatgcacc gcgagggatt cttgtgctgc aaagtgacag acacattgaa cggggagagg   1020
gtctcttttc ccgtgtgcac gtatgtgcca gctacattgt gtgaccaaat gactggcata   1080
ctggcaacag atgtcagtgc ggacgacgcg caaaaactgc tggttgggct caaccagcgt   1140
atagtcgtca acggtcgcac ccagagaaac accaatacca tgaaaaatta cctttttgccc   1200
gtagtggccc aggcatttgc taggtgggca aaggaatata ggaagatca agaagatgaa   1260
```

```
aggccactag gactacgaga tagacagtta gtcatggggt gttgttgggc ttttagaagg    1320
cacaagataa catctattta taagcgcccg gataccccaaa ccatcatcaa agtgaacagc   1380
gatttccact cattcgtgct gcccaggata ggcagtaaca cattggagat cgggctgaga   1440
acaagaatca ggaaaatgtt agaggagcac aaggagccgt cacctctcat taccgccgag   1500
gacgtacaag aagctaagtg cgcagccgat gaggctaaga aggtgcgtga agccgaggag   1560
ttgcgcgcag ctctaccacc tttggcagct gatgttgagg agcccactct ggaagccgat   1620
gtcgacttga tgttacaaga ggctggggcc ggctcagtgg agacacctcg tggcttgata   1680
aaggttacca gctacgctgg cgaggacaag atcggctctt acgctgtgct ttctccgcag   1740
gctgtactca agagtgaaaa attatcttgc atccaccctc tcgctgaaca agtcatagtg   1800
ataacacact ctggccgaaa agggcgttat gccgtggaac cataccatgg taaagtagtg   1860
gtgccagagg gacatgcaat acccgtccag gactttcaag ctctgagtga aagtgccacc   1920
attgtgtaca acgaacgtga gttcgtaaac aggtacctgc accatattgc cacacatgga   1980
ggagcgctga acactgatga agaatattac aaaactgtca agcccagcga gcacgacggc   2040
gaatacctgt acgacatcga caggaaacag tgcgtcaaga aagagctagt cactgggcta   2100
gggctcacag gcgagctggt cgatcctccc ttccatgaat tcgcctacga gagtctgaga   2160
acacgaccag ccgctcctta ccaagtacca accatagggg tgtatggcgt gccaggatca   2220
ggcaagtctg gcatcattaa aagcgcagtc accaaaaaag atctagtggt gagcgccaag   2280
aaagaaaact gtgcagaaat tataagggac gtcaagaaaa tgaaagggct ggacgtcaat   2340
gccagaactg tggactcagt gctcttgaat ggatgcaaaa accccgtaga gaccctgtat   2400
attgacgagg cttttgcttg tcatgcaggt actctcagag cgctcatagc cattataaga   2460
cctaaaaagg cagtgctctg cggagatccc aaacagtgcg gttttttttaa catgatgtgc   2520
ctgaaagtgc attttaacca cgagatttgc acacaagttc tccacaaaag catctctcgg   2580
cgttgcacta aatctgtgac ttcggtcgtc tcaaccttgt tttacgacaa aaaaatgaga   2640
acgacgaatc cgaaagagac taagattgtg attgacacta ccggcagtac caaacctaag   2700
caggacgatc tcattctcac ttgtttcaga gggtgggtga agcagttgca aatagattac   2760
aaaggcaacg aaataatgac ggcagctgcc tctcaaggcc tgacccgtaa aggtgtgtat   2820
gccgttcggt acaaggtgaa tgaaaatcct ctgtacgcac ccacctcaga acatgtgaac   2880
gtcctactga cccgcacgga ggaccgcatc gtgtggaaaa cactagccgg cgacccatgg   2940
ataaaaacac tgactgccaa gtaccctggg aatttcactg ccacgataga ggagtggcaa   3000
gcagagcagtg atgccatcat gaggcacatc ttggagagac cggaccctac cgacgtcttc   3060
cagaataagg caaacgtgtg ttgggccaag cttagtgc cggtgctgaa gaccgctggc   3120
atagacatga ccactgaaca atggaacact gtggattatt ttgaaacgga caaagctcac   3180
tcagcagaga tagtattgaa ccaactatgc gtgaggttct ttggactcga tctggactcc   3240
ggtctatttt ctgcacccac tgttccgtta tccattagga taatcactg ggataactcc   3300
ccgtcgccta acatgtacgg gctgaataaa gaagtgtcc gtcagctctc tcgcaggtac   3360
ccacaactgc ctcgggcagt tgccactggt agagtctatg acatgaacac tggtacactg   3420
cgcaattatg atccgcgcat aaacctagta cctgtaaaca gaagactgcc tcatgcttta   3480
gtcctccacc ataatgaaca cccacagagt gacttttctt cattcgtcag caaattgaag   3540
ggcagaactg tcctggtggt cggggaaaag ttgtccgtcc caggcaaaat ggttgactgg   3600
ttgtcagacc ggcctgaggc taccttcaga gctcggctgg atttaggcat cccaggtgat   3660
gtgcccaaat atgacataat atttgttaat gtgaggaccc catataaata ccatcactat   3720
cagcagtgtg aagaccatgc cattaagcta agcatgttac caagaaagc atgtctgcat   3780
ctgaatcccg gcggaacctg tgtcagctaa ggttatgtt acgctgacag ggccagcgaa   3840
agcatcattg gtgctatagc gcggcagttc aagtttttcc gagtatgcaa accgaaatcc   3900
tcacttgagg agacggaagt tctgtttgta ttcattgggt acgatcgcaa ggcccgtacg   3960
cacaatcctt acaagctatc atcaaccttg accaacattt atacaggttc cagactccac   4020
gaagccggat gtgcaccctc atatcatgtg gtgcgagggg atattgccac ggccaccgaa   4080
ggagtgatta taaatgctgc taacagcaaa ggacaacctg gcggagggg tgcggagcg   4140
ctgtataaga aattcccgga aagttttgat ttacagccga tcgaagtagg aaaagcgcga   4200
ctggtcaaag gtgcagctaa acatatcatt catgccgtag gaccaaactt caacaaagtt   4260
tcggagggtg aaggtgacaa acagttggca gaggcttatg agtccatcgc taagattgtc   4320
aacgataaca attacaagtc agtagcgatt ccactgttgt ccaccggcat ctttcccggg   4380
aacaaagatc gactaaccca atcattgaac catttgctga cagctttaga caccactgat   4440
gcagatgtag ccatatactg cagggacaag aaatgggaaa tgactctcaa ggaagcagtg   4500
gctaggagag aagcagtgga ggagatatgc atatccgacg attcttcagt gacagaacct   4560
gatgcagagc tggtgaggt gcatcccaag agttctttgg ctggaaggaa gggctacagc   4620
acaagcgatg gcaaaacttt ctcatatttg aagggaccca agtttcacca ggcggccaag   4680
gatatagcag aaattaatgc catgtggccc gttgcaacgg aggccaatga gcaggtatgc   4740
atgtatatcc tcggagaaag catgacagct attaggtcga aatgccccgt cgaggagtcg   4800
gaagcctcca caccacctag cacgctgcct tgcttgtgca tccatgccat gactccagaa   4860
agagtacagc gcctaaaagc ctcacgtcca gaacaaatta ctgtgtgctc atcctttcca   4920
ttgccgaagt atagaatcac tggtgtgcag aagatccaat gctcccagcc tatattgttc   4980
tcaccgaaag tgcctgcgta tattcatcca aggaagtatc tcgtggaaac accaccggta   5040
gacgagctc cggagccatc ggcagagaac caatccacag aggggaccac tgaacaacca   5100
ccacttataa ccgaggatga gaccaggact agaacgcctg agccgatcat catcgaagaa   5160
gaagaagaag atagcataag tttgctgtca gatggcccga cccaccaggt gctgcaagtc   5220
gaggcagaca ttcacgggcc gcctctgta tctagctcat cctggtccat tcctcatgca   5280
tccgactttg atgtggacag tttatccata cttgacacca tggaggggca gctcgtgacc   5340
agcggggcaa cgtcagccga gactaactct tacttcgcaa aggatatgga gtttctgagt   5400
cgaccggtgc ctgcgcctcg aacagtattc aggaaccctc cacatcccgc tccgcgcaca   5460
agaacaccgt cacttgcacc cagcagggcc tgctccagaa ccagcctagt ttccaccccg   5520
ccaggcgtga atagggtgat cactagagag gagctcgaag cgcttaccc gtcacgcact   5580
cctagcaggt cggtctccag aaccagcctg tctccaacc cgcaggcgt aaataggtgt   5640
attacagag aggagtttga ggcgttcgta gcacaacaag atgcgtgtt tgatgcgggt   5700
gcatacatct tttcctccga caccggtcaa gggcatttac aacaaaaatc agtaaggcaa   5760
acggtgctat ccgaagtggt gttggagagg accgaattgg agatttcgta tgccccgcgc   5820
ctcgaccaag aaaaagaaga attactacgc aagaaattac agttaaatcc cacacctgct   5880
aacagaagca gataccagtc caggaaggtg gagaacatga aagccataac agctagacgt   5940
attctgcaag gcctagggca ttatttgaag gcagaaggaa aagtggagtg ctaccgaacc   6000
```

```
ctgcatcctg ttcctttgta ttcatctagt gtgaaccgtg ccttttcaag ccccaaggtc    6060
gcagtggaag cctgtaacgc catgttgaaa gagaactttc cgactgtggc ttcttactgt    6120
attattccag agtacgatgc ctatttggac atggttgacg gagcttcatg ctgcttagac    6180
actgccagtt tttgccctgc aaagctgcgc agctttccaa agaaacactc ctatttggaa    6240
cccacaatac gatcggcagt gccttcagcg atccagaaca cgctccagaa cgtcctggca    6300
gctgccacaa aaagaaattg caatgtcacg caaatgagag aattgcccgt attggattcg    6360
gcggccttta atgtgaatg cttcaagaaa tatgcgtgta ataatgaata ttgggaaacg    6420
tttaaagaaa accccatcag gcttactgaa gaaaacgtgg taaattacat taccaaatta    6480
aaaggaccaa aagctgctgc tcttttgcg aagacacata atttgaatat gttgcaggac    6540
ataccaatgg acaggtttgt aatggactta aagagagacg tgaaagtgac tccaggaaca    6600
aaacatactg aagaacggcc caaggtacag gtgatccagg ctgccgatcc gctagcaaca    6660
gcgtatctgt gcgaatcca ccgagagctg gttaggagat aaatgcggt cctgcttccg    6720
aacattcata cactgtttga tatgtcggct gaagactttg acgctattat agccgagcac    6780
ttccagcctg gggattgtgt tctggcagct gacatccgcat cgtttgataa aagtgaggac    6840
gacgccatgg ctctgaccgc gttaatgatt ctggaagact taggtgtgga cgcagagctg    6900
ttgacgctga ttgaggcggc tttcggcgaa atttcatcaa tacatttgcc cactaaaact    6960
aaatttaaat tcggagccat gatgaaatct ggaatgttcc tcacactgtt tgtgaacaca    7020
gtcattaaca ttgtaatcgc aagcagagtg ttgagagaac ggctaaccgg atcaccatgt    7080
gcagcattca ttggagatga caatatcgtg aaaggagtca atcggacaa attaatggca    7140
gacaggtgcg ccacctggtt gaatatgaaa gtcaagatta tagatgctgt ggtgggcgag    7200
aaagcgcctt atttctgtgg aggtttatt ttgtgtgact ccgtgaccgg cacagcgtgc    7260
cgtgtggcag accccctaaa aaggctgttt aagctaggca acctctgcc agacgactg    7320
gaacatgatg atgacaggag aagggcattg catgaggagt caacacgctg aaccgagtg    7380
ggtattcttt cagagctgtg caaggcagta gaatcaaggt atgaaaccgt aggaacttcc    7440
atcatagtta tggccatgac tactctagct agcagtgtta aatcattcag ctacctgaga    7500
ggggcccta taactctcta cggctaacct gaatgactca cgacatagtc tagtccgcca    7560
agactagtat gtttgtgttt cttgtgctgc tgcctcttgt gtcttctcag tgtgtgaatt    7620
tgacaacaag aacacagctg ccaccagctt atacaaattc ttttaccaga ggagtgtatt    7680
atcctgataa agtgtttaga tcttctgtgc tgcacagcac acaggacctg tttctgccat    7740
ttttagcaga tgtgacatgg tttcatgcaa ttcatgtgtc tggaacaaat ggaacaaaaa    7800
gatttgataa tcctgtgctg ccttttaatg atggagtgta ttttgcttca acagaaaagt    7860
caaatattat tagaggatgg attttggaa caacactgga ttctaaaaca cagtctctgc    7920
tgattgtgaa taatgcaaca aatgtggtga ttaaagtgtg tgaatttcag ttttgtaatg    7980
atccttttct gggagtgtat tatcacaaaa ataataaatc ttggatggaa tctgaattta    8040
gagtgtattc ctctgcaaat aattgtacat ttgaatatgt cagcgcct tttctgatgt    8100
atctggaagg aaaacaggc aattttaaaa atctgagaga atttgtgttt aaaaatattg    8160
atggatattt taaaatttat tctaaacaca caccaattaa tttagtgaga gatctgcctc    8220
agggattttc tgctctggaa cctctggtgg atctgccaat tggcattaat attcaagat    8280
ttcagacact gctggctctg cacagatctt atctgacacc tggagattct tcttctgcat    8340
ggacagccgg agctgcagct tattatgtgg gctatctgca gccaagaaca tttctgctga    8400
aatataatga aaatgaaca attacagatg ctgtggattg tgctctggat cctctgtctg    8460
aaacaaaatg tacattaaaa tctttacag tggaaaagg catttatcag acatctaatt    8520
ttagagtgca gccaacagaa tctattgtga gatttccaaa tattacaaat ctgtgtcaa    8580
ttggagaagt gtttaatgca acaagatttg catctgtgta tgcatggaat agaaaaagaa    8640
tttctaattg tgtggctgat tattctgtgc tgtataatag tgcttctttt tccacattta    8700
aatgttatgg agtgtctcca acaaaattaa atgatttatg ttttacaaat gtgtatgctg    8760
attctttttgt gatcagaggt gatgaagtga gacagattgc ccccgacag acaggaaaaa    8820
ttgctgatta caattacaaa ctgcctgatg attttacagg atgtgtgatt gcttggaatt    8880
ctaataattt agattctaaa gtgggaggaa attacaatta tctgtacaga ctgtttagaa    8940
aatcaaatct gaaaccttt gaaagagata tttcaacaga aatttatcag gctggatcaa    9000
caccttgtaa tggagtggaa ggattaatt gttattttcc attacagac tatggattc    9060
agccaaccaa tggtgtggga tatcagccat atagagtgg ggtgctgtct tttgaactgc    9120
tgcatgcacc tgcaacagtg tgtggaccta aaaaatctac aaatttagtg aaaaataat    9180
gtgtgaattt taattttaat ggattaacag gaacaggagt gctgacagaa tctaataaaa    9240
aatttctgcc tttttcagcag tttggcagag atattgcaga taccagat cagtgagag    9300
atcctcagac attagaaatt ctgatatta caccttgttc ttttggggt gtgtctgtga    9360
ttacacctgg aacaaataca tctaatcagg tggctgtgct gtatcaggat gtgaattgta    9420
cagaagtgcc agtggcaatt catgcagatc agctgacacc aacatggaga gtgtattcta    9480
caggatctaa tgtgtttcag acaagacaga gatgtctgat tggaacaga catgtgaata    9540
attcttatga atgtgatatt ccaattggag caggcattg tgcatcttat cagacacaga    9600
caaattcccc aaggagagca agatctgtgg catctcagtc tattattgca tacaccatgt    9660
ctctgggagc agaaaattct gtggcatatt ctaataattc tattgctatt ccaacaaatt    9720
ttaccatttc tgtgacaaca gaaattttac ctgtgtctat gacaaaaaca tctgtggatt    9780
gtaccatgta catttgtgga gattctacag aatgttctaa ttctgtctg cagtatgatt    9840
ctttttgtac acagctgaat agagctttaa caggaattgc tgtggaacag gataaaaata    9900
cacaggaagt gtttgctcag gtgaaacaga tttacaaaac accaccaatt aaagatttg    9960
gaggatttaa ttttagccag attctgcctg atccttctaa accttctaaa agatctttta    10020
ttgaagatct gctgtttaat aaagtgacac tggcagatgc aggatttatt aaacagtatg    10080
gagattgcct gggtgatatt gctgcaagag atctgatttg ttctcagaaa tttaatggac    10140
tgacagtgct gcctcctctg ctgacagatg aaatgattgc tcagtacaca tctgctttac    10200
tggctggaac aattacaagc ggatggacat ttggagctgg agctgctctg cagattcctt    10260
ttgcaatgca gatggcttac agatttaatg gaattggagt gacacagaat gtgttatatg    10320
aaaatcagaa actgattgca aatcagttta attctgcaat tggcaaaatt caggattctc    10380
tgtcttctac agcttctgct ctgggaaaac tgcaggatgt ggtgaatcag aatgcacagg    10440
cactgaatac tctggtgaaa cagctgtcta gcaattttgg ggcaatttct tctgtgctga    10500
atgatatttc gtctagactg gatcctcctg aagctgaagt gcagattgat agactgatca    10560
caggaagact gcagtctctg cagacttatg tgacacagca gctgattaga gctgctgaaa    10620
ttagagcttc tgctaatctg gctgctacaa aaatgtctga atgtgtgctg ggacagtcaa    10680
aaagagtgga ttttgtgga aaaggatatc atctgatgtc ttttccacag tctgctccac    10740
```

-continued

```
atggagtggt gttttacat gtgacatatg tgccagcaca ggaaaagaat tttaccacag    10800
caccagcaat ttgtcatgat ggaaaagcac attttccaag agaaggagtg tttgtgtcta    10860
atggaacaca ttggtttgtg acacagagaa attttatga acctcagatt attacaacag    10920
ataatacatt tgtgtcagga aattgtgatg tggtgattgg aattgtgaat aatacagtgt    10980
atgatccact gcagccagaa ctggattctt ttaaagaaga actggataaa tattttaaaa    11040
atcacacatc tcctgatgtg gatttaggag atatttctgg aatcaatgca tctgtggtga    11100
atattcagaa agaaattgat agactgaatg aagtggccaa aaatctgaat gaatctctga    11160
ttgatctgca ggaacttgga aaatatgaac agtacattaa atggccttgg tacatttggc    11220
ttggatttat tgcaggatta attgcaattg tgatgtgac aattatgtta tgttgtatga    11280
catcatgttg ttcttgttta aaaggatgtt gttcttgtgg aagctgttgt aaatttgatg    11340
aagatgattc tgaacctgtg ttaaaaggag tgaaattgca ttacacatga tgactcgagc    11400
tggtactgca tgcacgcaat gctagctgcc cctttcccgt cctgggtacc ccgagtctcc    11460
cccgacctcg ggtcccaggt atgctccac ctccacctgc cccactcacc acctgctcta    11520
gttccagaca cctcccaagc acgcagcaat gcagctcaaa acgcttagcc tagccacacc    11580
cccacgggaa acagcagtga ttaaccttta gcaataaacg aaagtttaac taagctatac    11640
taaccccagg gttggtcaat ttcgtgccag ccacaccgcg gccgcatgaa tacagcagca    11700
attggcaagc tgcttacata gaactcgcgg cgattggcat gccgccttaa aatttttatt    11760
ttattttttc ttttctttc cgaatcggat tttgttttta atatttcaaa aaaaaaaaaa    11820
aaaaaaaaaa aaaaaagca tatgactaaa aaaaaaaaaa aaaaaaaaaa aaaaaaaaaa    11880
aaaaaaaaaa aaaaaaaaaa aaaaaaaaaa aaaaaa                              11917

SEQ ID NO: 25         moltype = RNA   length = 11917
FEATURE               Location/Qualifiers
misc_feature          1..11917
                      note = RBS004.2
source                1..11917
                      mol_type = other RNA
                      organism = synthetic construct
SEQUENCE: 25
gatgggcggc gcatgagaga agcccagacc aattacctac ccaaaatgga gaaagttcac    60
gttgacatcg aggaagacag cccattcctc agagctttgc agcggagctt cccgcagttt    120
gaggtagaag ccaagcaggt cactgataat gaccatgcta atgccagagc gttttcgcat    180
ctggcttcaa aactgatcga acggagtg gacccatccg acacgatcct tgacattgga    240
agtgcgcccg cccgcagaat gtattctaag cacaagtatc attgtatctg tccgatgaga    300
tgtgcggaag atccggacag attgtataag tatgcaacta agctgaagaa aaactgtaag    360
gaaataactg ataaggaatt ggacaagaaa atgaaggagc tcgccgccgt catgagcgac    420
cctgacctgg aaactgagac tatgtgcctc cacgacgacg agtcgtgtcg ctacgaaggg    480
caagtcgctg tttaccagga tgtatacgcg gttgacggac cgacaagtct ctatcaccaa    540
gccaataagg gagttagagt cgcctactgg ataggctttg acaccacccc ttttatgttt    600
aagaacttgg ctggagcata tccatcatac tctaccaact gggccgacga aaccgtgtta    660
acggctcgta acataggcct atgcagctct gacgttatgg agcggtcacg tagagggatg    720
tccattctta gaaagaagta tttgaaacca tccaacaatg ttctattctc tgttggctcg    780
accatctacc acgaaaagag ggacttactg aggagctggc acctgccgtc tgtatttcac    840
ttacgtggca agcaaaatta cacatgtcgg tgtgagacta tagttagttg cgacgggtac    900
gtcgttaaaa gaatagctat cagtccaggc ctgtatggga agccttcagg ctatgctgct    960
acgatgcacc gcgagggatt cttgtgctgc aaagtgacga cacattgaa cggggagagg    1020
gtctcttttc ccgttgtgcac gtatgtgcca gctacattgt gtgaccaaat gactggcata    1080
ctggcaacag atgtcagtgc ggacgacgcg caaaaactgc tggttgggct caaccagcgt    1140
atagtcgtca acggtcgcac ccagagaaac accaatacca tgaaaaatta cctttttgccc    1200
gtagtggccc aggcatttgc taggtgggca aggaatata aggaagatca agaagatgaa    1260
aggccactag gactacgaga tagacagtta tcatggggt gttgttgggc ttttagaagg    1320
cacaagataa catctatttta taagcgcccg gataccaaa ccatcatcaa agtgaacagc    1380
gatttccact cattcgtgct gccaggata ggcagtaaca cattggagat cgggctgaga    1440
acaagaatca ggaaaatgtt agaggagcac aaggagccgt cacctctcat taccgccgag    1500
gacgtacaag aagctaagtg cgcagccgat gaggctaagg aggtcgtga agccgaggag    1560
ttgcgcgcag ctctaccacc tttggcagct gatgttgagg agcccactct ggaagccgat    1620
gtcgacttga tgttacaaga ggctgggcc ggctcagtgg agacacctcg tggcttgata    1680
aaggttacca gctacgctgg cgaggacaag atcggtcttc acgctgtgct ttctccgcag    1740
gctgtactca agtgaaaa attatcttgc atccaccctc tcgctgaaca agtcatagtg    1800
ataacacact ctggccgaaa agggcgttat gccgtggaac cataccatgt taagtagtg    1860
gtgcagagg gacatgcaat acccgtccga gactttcaag ctctgagtga aagtgccacc    1920
attgtgtaca cgaacgtga gtccgtaaac aggtacctgc accatattgc cacacatgga    1980
ggagcgctga acactgatga agaatattac aaaactgtca gcccagcga gcacgacggc    2040
gaatacctgt acgacatcga caggaaacag tgcgtcaaga aagagctagt cactgggcta    2100
gggctcacag gcgagctggt cgatcctccc ttccatgaat cgcctacga gagctctgaga    2160
acgaccag ccgctcctta ccaagtacca accatagggg tgtatggcgt gccaggatca    2220
ggcaagtctg cattcattaa aagcgcagtc accaaaaaag atctagtggt gagcgccaag    2280
aaagaaaact gtgcagaaat tataaggac gtcaagaaa tgaaagggct ggacgtcaat    2340
gccagaactg tggactcagt gctcttgaat ggatgcaaac accccgtaga gaccctgtat    2400
attgacgagg cttttgcttg tcatgcaggt actctcagag cgctcatagc cattataaga    2460
cctaaaaagg cagtgctctg cggagatccc aaacagtgcg gtttttttaa catgatgtgc    2520
ctgaaagtgc attttaacca cgagatttgc acacaagtct tccacaaaag catctctcgc    2580
cgttgcacta aatctgtgac ttcggtcgtc tcaaccttgt tttacgacaa aaaaatgaga    2640
acgacgaatc caaagagac taagattgtg attgacacta ccggcagtac caaacctaag    2700
caggacgatc tcattctcac ttgtttcaga gggtgggtga agcagttgca aatagattac    2760
aaaggcaacg aaataatgac ggcagctgcc tctcaagggc tgacccgtaa aggtgtgtat    2820
gccgttcggt acaaggtgaa tgaaaatcct ctgtacgcac ccacctcaga acatgtgaac    2880
gtcctactga cccgcacgga ggaccgcatc gtgtggaaaa cactagccgg cgacccatgg    2940
ataaaaaacac tgactgccaa gtaccctggg aatttcactg ccacgataga ggagtggcaa    3000
```

```
gcagagcatg atgccatcat gaggcacatc ttggagagac cggaccctac cgacgtcttc   3060
cagaataagg caaacgtgtg ttgggccaag gctttagtgc cggtgctgaa gaccgctggc   3120
atagacatga ccactgaaca atggaacact gtggattatt ttgaaacgga caaagctcac   3180
tcagcagaga tagtattgaa ccaactatgc gtgaggttct ttggactcga tctggactcc   3240
ggtctatttt ctgcacccac tgttccgtta tccattagga ataatcactg ggataactcc   3300
ccgtcgccta acatgtacgg gctgaataaa gaagtggtcc gtcagctctc tcgcaggtac   3360
ccacaactgc ctcgggcagt tgccactggt agagtctatg acatgaacac tggtacactg   3420
cgcaattatg atccgcgcat aaacctagta cctgtaaaca gaagactgcc tcatgcttta   3480
gtcctccacc ataatgaaca cccacagagt gacttttctt cattcgtcag caaattgaag   3540
ggcagaactg tcctggtggt cggggaaaag ttgtccgtcc caggcaaaat ggttgactgg   3600
ttgtcagacc ggcctgaggc taccttcaga gctcggctgg atttaggcat cccaggtgat   3660
gtgcccaaat atgacataat atttgttaat gtgaggaccc catataaata ccatcactat   3720
cagcagtgtg aagaccatgc cattaagcta agcatgttga ccaagaaagc atgtctgcat   3780
ctgaatcccg gcggaacctg tgtcagcata ggttatggtt acgctgacag ggccagcgaa   3840
agcatcattg gtgctatagc gcggcagttc aagttttccc gagtatgcaa accgaaatcc   3900
tcacttgagg agacggaagt tctgtttgta ttcattgggt acgatcgcaa ggcccgtacg   3960
cacaatcctt acaagctatc atcaaccttg accaacattt ataggttc cagactccac   4020
gaagccggat gtgcaccctc atatcatgtg gtgcgagggg atattgccac ggccaccgaa   4080
ggagtgatta taaatgctgc taacagcaaa ggacaacctg gcggagggt gtgcggagcg   4140
ctgtataaga aattcccgga aagtttcgat ttacagccga tcgaagtagg aaaagcgcga   4200
ctggtcaaag gtgcagctaa acatatcatt catgccgtag gaccaaactt caacaaagtt   4260
tcggaggttg aaggtgcaa acagttggca gaggcttatg agtccatcgc taagattgtc   4320
aacgataaca attacaagtc agtagcgatt ccactgttgt ccaccggcat cttttccggg   4380
aacaaagatc gactaaccca atcattgaac catttgctga cagctttaga caccactgat   4440
gcagatgtag ccatatactg cagggacaag aaatgggaaa tgactctcaa ggaagcagtg   4500
gctaggagag aagcagtgga ggagatatgc atatccgacg attcttcagt gacagaacct   4560
gatgcagagc tggtgagggt gcatcccaag agttctttgg ctggaaggaa gggctacagc   4620
acaagcgatg gcaaaacttt ctcatatttg gaagggacca gtttcacca ggcggccaag   4680
gatatagcag aaattaatgc catgtggccc gttgcaacgg aggccaatga gcaggtatgc   4740
atgtatatcc tcggagaaag catgagcagt attaggtcga aatgccccgt cgaggagtcg   4800
gaagcctcca caccacctag cacgctgcct tgcttgtgca tccatgccat gactccagaa   4860
agagtacagc gcctaaaagc ctcacgtcca aacaaattac tgtgtgctc atcctttcca   4920
ttgccgaagt atagaatcac tggtgtgcag aagatccaat gctcccagcc tatattgttc   4980
tcaccgaaag tgcctgcgta tattcatcca aggaagtatc tcgtggaaac accacgtga   5040
gacgagactc cggagccatc ggcagagaac caatccacag aggggacacc tgaacaacca   5100
ccacttataa ccgaggatga gaccaggact agaacgcctg agccgatcat catcgaagaa   5160
gaagaagaag atagcataag tttgctgtca gatggcccga cccaccaggt gctgcaagtc   5220
gaggcagaca ttcacgggcc gccctctgta tctagctcat cctggtccat tcctcatgca   5280
tccgactttg atgtggacag tttatccata cttgacaccc tggagggagc tagcgtgacc   5340
agcgggggcaa cgtcagccga gactaactct tacttcgcaa agagtatgga gtttctggcg   5400
cgaccggtgc ctgcgcctcg aacagtattc aggaaccctc cacatcccgc tccgcgcaca   5460
agaacaccgt cacttgcacc cagcagggcc tgctccagaa ccagcctagt ttccaccccg   5520
ccaggcgtga atagggtgat cactagagag gagctcgaag cgcttaccc gtcacgcact   5580
cctagcaggt cggtctccag aaccagcctg gtctccaacc cgccaggcgt aaataggtg   5640
attacaagag aggagtttga ggcgttcgta gcacaacaac aatgacggtt tgatgcgggt   5700
gcatacatct tttcctccga caccggtcaa gggcatttac aacaaaatc agtaaggcaa   5760
acggtgctat ccgaagtggt gttggagagg accgaattgg agatttcgta tgccccgcgc   5820
ctcgaccaag aaaaagaaga attactacgc aagaaattac agttaaatcc cacacctgct   5880
aacagaagca gataccagtc caggaaggtg gagaacatga agccataac agctagacgt   5940
attctgcaag gcctagggca ttatttgaag gcagaaggaa aagtggagtg ctaccgaacc   6000
ctgcatcctg ttcctttgta ttcatctagt gtgaaccgtg ccttttcaag ccccaaggtc   6060
gcagtggaag cctgtaacgc catgttgaaa gagaactttc cgactgtggc ttcttactgc   6120
attattccag agtacgatgc ctattttgac atggttgacg gagcttcatg ctgcttagac   6180
actgccagtt tttgccctgc aaagctgcgc agctttccaa agaaacactc ctatttggaa   6240
cccacaatac gatcggcagt gccttcagcg atccagaaca cgctccagaa cgtcctggca   6300
gctgccacaa aaagaaattg caatgtcacg caaatgagag aattgccgt attggattcc   6360
gcggccttta atgtgaatg cttcaagaaa tatgcgtgta ataatgaata ttgggaaacg   6420
tttaagaaa accccatcag gcttactgaa gaaacgtgg taattacat taccaaatta   6480
aaaggaccaa aagctgctgc tcttttttgcg aagacacata tttgaatat gttgcaggac   6540
ataccaatgg acaggtttgt aatggactta aagagagacg tgaaagtgac tccaggaaca   6600
aaacatactg aagaacggcc caaggtacag gtgatccagg ctgccgatcc gctagcaaca   6660
gcgtatctgt gcggaatcca ccgagagctg gttaggagat aaatgcggt cctgcttccg   6720
aacattcata cactgttttga tatgtcggct gaagactttg acgctattat agccgagcac   6780
ttccagcctg gggattgtgt tctggaaact gacatcgcgt cgtttgataa aagtgaggac   6840
gacgccatgg ctctgaccgc gttaatgatt ctggaagact taggtgtgga cgcagagctg   6900
ttgacgctga ttgaggcggc tttcggcgaa atttcatcaa tacatttgcc cactaaaact   6960
aaatttaaat tcggagccat gatgaaatct ggaatgttcc tcacactgtt tgtgaacaca   7020
gtcattaaca ttgtaatcgc aagcagagtg ttgagagaac ggctaaccgg atcaccatgt   7080
gcagcattca ttggagatga caatatcgtc aaaggagtca atcggacaa attaatgctg   7140
gacaggtgcg ccacctggtt gaatatgaa gtcaagatta tagatgctgt ggtgggcgag   7200
aaagcgcctt atttctgtgg agggtttatt ttgtgtgact ccgtgaccgg cacagcgtgc   7260
cgtgtggcag accccctaaa aaggctgttt aagctaggca aacctctggc agcagacgat   7320
gaacatgatg atgacaggag aagggcattg catgaggagt caacgctg gaaccgagtg   7380
gtgattcttt cagagctgtg caaggcagta gaataaccgt aggaacttcc   7440
atcatagtta tggccatgac tactctagct agcagtgtta aatcattcag ctacctgaga   7500
ggggccccta taactctcta cggctaacct gaatggacta cgacatgtc tagtccgcca   7560
agactagtat gttcgtgttc ctggtgctgc tgcctctggt gtccagcag tgtgtgaacc   7620
tgaccaccag aacacagctg cctccagcct acaccaacag ctttaccaga ggcgtgtact   7680
accccgacaa ggtgttcaga tccagcgtgc tgcactctac ccaggacctg ttcctgcctt   7740
```

```
tcttcagcaa cgtgacctgg ttccacgcca tccacgtgtc cggcaccaat ggcaccaaga  7800
gattcgacaa ccccgtgctg cccttcaacg acggggtgta ctttgccagc accgagaagt  7860
ccaacatcat cagaggctgg atcttcggca ccacactgga cagcaagacc cagagcctgc  7920
tgatcgtgaa caacgccacc aacgtggtca tcaaagtgtg cgagttccag ttctgcaacg  7980
accccttcct gggcgtctac taccacaaga acaacaagg ctggatggaa agcgagttcc  8040
gggtgtacag cagcgccaac aactgcacct tcgagtacgt gtcccagcct ttcctgatgg  8100
acctggaagg caagcagggc aacttcaaga acctgcgcga gttcgtgttt aagaacatcg  8160
acggctactt caagatctac agcaagcaca cccctatcaa cctcgtgcgg gatctgcctc  8220
agggcttctc tgctctggaa ccctggtgg atctgcccat cggcatcaac atcacccggt  8280
ttcagacact gctggccctg cacagaagct acctgacacc tggcgatagc agcagcggat  8340
ggacagctgg tgccgccgct tactatgtgg gctacctgca gcctagaacc ttcctgctga  8400
agtacaacga gaacggcacc atcaccgacg ccgtggattg tgctctggat cctctgagcg  8460
agacaaagtg caccctgaag tccttcaccg tggaaaaggg catctaccag accagcaact  8520
tccggtgca gcccaccgaa tccatcgtgc ggttcccaa tatccaccat ctgtgccct  8580
tcggcgaggt gttcaatgcc accagattcg cctctgtgta cgcctggaac cggaagcgga  8640
tcagcaattg cgtggccgac tactccgtgc tgtacaactc cgccagcttc agcaccttca  8700
agtgctacgg cgtgtcccct accaagctga acgacctgtg cttcacaaac gtgtacgccg  8760
acagcttcgt gatccgggga gatgaagtgc ggcagattgc ccctgacag acaggcaaga  8820
tcgccgacta caactacaag ctgcccgacg acttcaccgg ctgtgtgatt gcctggaaca  8880
gcaacaacct ggactccaaa gtcggcgca actacaatta cctgtaccgg ctgttccgga  8940
agtccaatct gaagcccttc gagcgggaca tctccaccga gatctatcag gccggcagca  9000
cccctgtaa cggcgtggaa ggcttcaact gctacttccc actgcagtcc tacggcttc  9060
agcccacaaa tggcgtgggc tatcagccct acagagtggt ggtgctgagc ttcgaactgc  9120
tgcatgcccc tgccacagtg tgcggcccta agaaaagcac caatctcgtg aagaacaaat  9180
gcgtgaactt caacttcaac ggcctgaccg gcaccggcgt gctgacagag agcaacaaga  9240
agttcctgcc attccagcag tttggccggg atatccgcag taccacagac gccgttagag  9300
atccccagac actggaaatc ctggacatca cccccttgcag cttcggcgga gtgtctgtga  9360
tcaccccctgg caccaacacc agcaatcagg tggcagtgct gtaccaggac gtgaactgta  9420
ccgaagtgcc cgtggccatt cacgccgatc agctgacacc tacatggcgg gtgtactcca  9480
ccggcagcaa tgtgtttcag accagagccg gctgtctgat cggagccgga cacgtgaaca  9540
atagctacga gtgcgacatc cccatcggcg ctggaatctg cgccagctac cagacacaga  9600
caaacagccc tcggagagcc agaagcgtgg ccagccagag catcattgcc tacacaatgt  9660
ctctgggcgc cgagaacagc gtggcctact ccaacaactc tatcgctatc cccaccaact  9720
tcaccatcag cgtgaccaca gagatcctgc ctgtgtccat gaccaagacc agcgtggact  9780
gcaccatgta catctgcggc gattccaccg agtgctccaa cctgctgctg cagtacgcca  9840
gcttctgcac ccagctgaat agagcctga cagggatcgc cgtggaacag gacaagaaca  9900
cccaagaggt gttcgcccaa gtgaagcaga tctacaagac ccctcctatc aaggacttcg  9960
gcggcttcaa tttcagccag attctgcccg atcctagcaa gcccagcaag cggagcttca  10020
tcgaggacct gctgttcaac aaagtgacac tggccgacgc cggcttcatc aagcagtatg  10080
gcgattgtct gggcgacatt gccgccaggg atctgatttg cgcccagaag tttaacggac  10140
tgacagtgct gcctcctctg ctgaccgatg agatgatcgc ccagtacaca tctgccctgc  10200
tggccggcac aatcacaagc ggctggacat ttggagcagg cgccgctctg cagatcccct  10260
ttgctatgca gatggcctac cggttcaacg gcatcggagt gacccagaat gtgctgtacg  10320
agaaccagaa gctgatcgcc aaccagttca acagcgccat cggcaagatc caggacagcc  10380
tgagcagcac agcaagcgcc ctgggaaagc tgcaggacgt ggtcaaccag aatgcccagg  10440
cactgaacac cctggtcaag cagctgtcct ccaacttcgg cgccatcagc tctgtgctga  10500
acgatatcct gagcagactg gaccctcctg aggccgaggt gcagatcgac agactgatca  10560
caggcagact gcagagcctc cagacatacg tgacccagca gctgatcaga gccgccgaga  10620
ttagagcctc tgccaatctg gccgccacca gatgtctga gtgtgtgctg ggccagagca  10680
agagagtgga cttttgcggc aagggctacc acctgatgag cttccctcag tctgcccctc  10740
acggcgtggt gtttctgcac gtgacatatg tgcccgctca agagaagaat ttcaccaccg  10800
ctccagccat ctgccacgac ggcaaagccc acttttccta agaaggcgtg ttcgtgtcca  10860
acggcaccca ttggttcgtg acacagcgga acttctacga gcccagatc atcaccaccg  10920
acaacacctt cgtgtctggc aactgcgacg tcgtgatcgg cattgtgaac aataccgtgt  10980
acgaccctct gcagcccgag ctggacagct tcaaagagga actggacaag tactttaaga  11040
accacacaag ccccgacgtg gacctggcg atatcagcgg aatcaatgcc agcgtcgtga  11100
acatccagaa agagatcgac cggctgaacg aggtggccaa gaatctgaac gagagccta  11160
tcgacctgca agaactgggg aagtacgagc agtacatcaa gtggccctgg tacatctggc  11220
tgggctttat cgccggactg attgccatcg tgatggtcac aatcatgctg tgttgcatga  11280
ccagctgctg tagctgcctg aagggctgtt gtagctgtgg cagctgctgc aagttcgacg  11340
aggacgattc tgagcccgtg ctgaagggcg tgaaactgca ctacacatga tgactcgagc  11400
tggtactgca tgcacgcaat gctagctgcc ccttccct cctgggtacc ccgagtctca  11460
cccgacctcg ggtcccaggt atgctcccac ctccacctgc ccactcacc acctctgcta  11520
gttccagaca cctcccaagc acgcagcaat gcagctcaaa acgcttagcc tagcacacc  11580
cccacgggaa acagcagtga ttaacctta gcaataaacg aaagtttaac taagctatac  11640
taaccccagg gttggtcaat ttcgtgccag ccacaccgcg gccgcatgaa tacagcagca  11700
attggcaagc tgcttacata gaactccgg cgattggcat gccgccttaa aattttatt  11760
ttatttttc ttttctttttc cgaatcggat tttgttttta atattttcaaa aaaaaaaaa  11820
aaaaaaaaaa aaaaaagca tatgactaaa aaaaaaaaaa aaaaaaaaaa aaaaaaaaaa  11880
aaaaaaaaaa aaaaaaaaaa aaaaaaaaaa aaaaaaa                            11917

SEQ ID NO: 26     moltype = RNA   length = 8896
FEATURE           Location/Qualifiers
misc_feature      1..8896
                  note = RBS004.3
source            1..8896
                  mol_type = other RNA
                  organism = synthetic construct
```

```
SEQUENCE: 26
gatgggcggc gcatgagaga agcccagacc aattacctac ccaaaatgga gaaagttcac   60
gttgacatcg aggaagacag cccattcctc agagctttgc agcggagctt cccgcagttt  120
gaggtagaag ccaagcaggt cactgataat gaccatgcta atgccagagc gttttcgcat  180
ctggcttcaa aactgatcga aacggaggtg gacccatccg acacgatcct tgacattgga  240
agtgcgcccg cccgcagaat gtattctaag cacaagtatc attgtatctg tccgatgaga  300
tgtgcggaag atccggacag attgtataag tatgcaacta agctgaagaa aaactgtaag  360
gaaataactg ataaggaatt ggacaagaaa atgaaggagc tcgccgccgt catgagcgac  420
cctgacctgg aaactgagac tatgtgcctc cacgacgacg agtcgtgtcg ctacgaaggg  480
caagtcgctg tttaccagga tgtatacgcg gttgacggac cgacaagtct ctatcaccaa  540
gccaataagg gagttagagt cgcctactgg ataggctttg acaccacccc ttttatgttt  600
aagaacttgg ctggagcata tccatcatac tctaccaact gggccgacga aaccgtgtta  660
acggctcgta acataggcct atgcagctct gacgttatgc agcggtcacg tagagggatg  720
tccattctta gaaagaagta tttgaaacca tccaacaatg ttctattctc tgttggctcg  780
accatctacc acgaaaagag ggacttactg aggagctggc acctgccgtc tgtatttcac  840
ttacgtggca agcaaaatta cacatgtcgg tgtgagacta tagttagttg cgacgggtac  900
gtcgttaaaa gaatagctat cagtccaggc ctgtatggga agccttcagg ctatgctgct  960
acgatgcacc gcgagggatt cttgtgctgc aaagtgacag acacattgaa cgggagagg  1020
gtctcttttc ccgtgtgcac gtatgtgcca gctacattgt gtgaccaaat gactggcata 1080
ctggcaacag atgtcagtgc ggacgacgcg caaaaactgc tggttgggct caaccagcgt 1140
atagtcgtca acggtcgcac ccagagaaac accaatacca tgaaaaatta cctttttgccc 1200
gtagtggccc aggcatttgc taggtgggca aaggaatata aggaagatca agaagatgaa 1260
aggccactag gactacgaga tagacagtta gtcatggggt gttgttgggc ttttagaagg 1320
cacaagataa catctattta taagcgcccg gatacccaaa ccatcatcaa agtgaacagc 1380
gatttccact cattcgtgct gcccaggata ggcagtaaca cattggagat cgggctgaga 1440
acaagaatca ggaaaatgtt agaggagcac aaggagcgct cacctctcat taccgccgag 1500
gacgtacaag aagctaagtg cgcagccgat gaggctaagg aggtgcgtga agccgaggag 1560
ttgcgcgcag ctctaccacc tttggcagct gatgttgagg agcccactct ggaagccgat 1620
gtcgacttga tgttacaaga ggctggggcc ggctcagtgg agacacctcg tggcttgata 1680
aaggttacca gctacgctgg cgaggacaag atcggctctt acgctgtgct ttctccgcag 1740
gctgtactca agagtgaaaa attatcttgc atccaccctc tcgctgaaca agtcatagtg 1800
ataacacact ctgccgaaaa agggcgttat gccgtggaac catccatgg taaagtagtg 1860
gtgccagagg gacatgcaat acccgtccag gactttcaag ctctgagtga aagtgccacc 1920
attgtgtaca acgaacgtga gttcgtaaac aggtactgc accatattgc cacacatgga 1980
ggagcgctga acactgatga agaatattac aaaaactgtca agcccagcga gcacgacggc 2040
gaatacctgt acgacatcga caggaaacag tgcgtcaaga aagagctagt cactgggcta 2100
gggctcacag gcgagctggt cgatcctccc ttccatgaat tcgcctacga gagtctgaga 2160
acacgaccag ccgctcctta ccaagtacca accataggg tgtatggcgt gccaggatca 2220
ggcaagtctg gcatcattaa aagcgcagtc accaaaaaag atctagtggt gagcgccaag 2280
aaagaaaact gtgcagaaat tataagggac gtcaagaaaa tgaaagggct ggacgtcaat 2340
gccagaactg tggactcagt gctccttgaat ggatgcaaac accccgtaga ccctgtat  2400
attgacgagg cttttgcttg tcatgcaggt actctcagag cgctcatagc cattataaga 2460
cctaaaaagg cagtgctctg cggagatccc aaacagtgcg gttttttttaa catgatgctg 2520
ctgaaagtgc attttaacca cgagatttgc acacaagtct tccacaaaag catctctcgc 2580
cgttgcacta aatctgtgac ttcggtcgtc tcaaccttgt tttacgacaa aaaaatgaga 2640
acgacgaatc cgaaagagac taagattgtg attgacacta ccggcagtac caaacctaag 2700
caggcagtca tcattctcac ttgttttcaga gggtgggtga agcagtttgca aatagattac 2760
aaaggcaacg aaataatgac ggcagctgcc tctcaagggc tgacccgtaa aggtgtgtat 2820
gccgttcggt acaaggtgaa tgaaaatcct ctgtacgcac ccacctcaga acatgtgaac 2880
gtcctactga cccgcacgga ggaccgcatc gtgtggaaaa cactagccgg cgacccatgg 2940
ataaaaacac tgactgccaa gtaccctggg aatttcactg ccacgataga gggatggcaa 3000
gcagagcatg atgccatcat gaggcacatc ttggagagac cggaccctac cgacgtcttc 3060
cagaataagg caaacgtgtg ttgggccaag gctttagtgc cggtgctgaa gaccgctggc 3120
atagacatga ccactgaaca atggaacact gtggattatt ttgaaacgga caaagctcac 3180
tcagcagaa tagtattgaa ccaactatgc gtgaggttct ttggactgga tctgactcg  3240
ggtctatttt ctgcacccac tgttccgtta tccattagga ataatcactg ggataactcc 3300
ccgtcgccta acatgtacgg gctgaataaa gaagtggtcc gtcagctctc tcgcaggtac 3360
ccacaactgc ctcgggcagt tgccactggt agagtctatg acatgaacac tggtacactg 3420
cgcaattatg atccgcgcat aaacctagta cctgtaaaca gaagactgcc tcatgcttta 3480
gtcctccacc ataatgaaca cccacagagt gacttttctt cattcgtcag caaattgaag 3540
ggcagaactg tcctggtggt cggggaaaag ttgtccgtcc aggcaaaat ggttgactgg 3600
ttgtcagacc ggcctgaggc taccttcaga gctcggctgg atttaggcat cccaggtgat 3660
gtgcccaaat atgacataat atttgttaat gtgaggaccc catataaata ccatcactat 3720
cagcagtgtg aagaccatgc cattaagcta agcatgttga ccaagaaagc atgtctgcat 3780
ctgaatcccg gcggaacctg tgtcagcata ggttatggtt acgctgacag ggccagcgaa 3840
agcatcattg tgctatagc gcggcagttc aagtttccc gagtatgcaa accgaaatcc 3900
tcacttgagg agacgaagt tctgtttgta ttcattgggt acgatcgcaa ggcccgtacg 3960
cacaatcctt acaagcattc atcaaccttg accaacttc atacaggttc cagactccac 4020
gaagccggat gtgcaccctc atatcatgtg gtgcgaggg atattgccac ggccaccgaa 4080
ggagtgatta taaatgctgc taacagcaaa ggacaacctg gcgagggggt gtgcggagcg 4140
ctgtataaga aattcccgga aagtttcgat ttacagccga tcgaagtagg aaaagcgcga 4200
ctggtcaaag gtgcagctaa acatatcatt catgccgtag accaaactt caacaaagtt 4260
tcggaggttg aaggtgacaa acagttgca gaggcttatg agtccatcgc taagattgtc 4320
aacgataaca attacaagtc agtagcgatt cccactgttgt ccaccggcat cttttcccggg 4380
aacaaagatc gactaacccca atcattgaac catttgctga cagctttaga caccactgat 4440
gcagatgtag cctatactg cagggacaag aaatgggaaa tgactctcaa ggaagcagtg 4500
gctaggagag aagcagtgga ggagatatgc atatccgacg attcttcagt gacagaacct 4560
gatgcagagc tggtgagggt gcatcccaag agttctttgg ctggaaggaa gggctacagc 4620
acaagcgatg gcaaaacttt ctcatatttg gaagggacca agtttcacca ggcggccaag 4680
```

```
gatatagcag aaattaatgc catgtggccc gttgcaacgg aggccaatga gcaggtatgc    4740
atgtatatcc tcggagaaag catgagcagt attaggtcga aatgcccgt cgaggagtcg     4800
gaagcctcca caccacctag cacgctgcct tgcttgtgca tccatgccat gactccagaa    4860
agagtacagc gcctaaaagc ctcacgtcca gaacaaatta ctgtgtgctc atcctttcca    4920
ttgccgaagt atagaatcac tggtgtgcag aagatccaat gctcccagcc tatattgttc    4980
tcaccgaaag tgcctgcgta tattcatcca aggaagtatc tcgtggaaac accaccggta    5040
gacgagactc cggagccatc ggcagagaac caatccacag aggggacacc tgaacaacca    5100
ccacttataa ccgaggatga gaccaggact agaacgcctg agccgatcat catcgaagaa    5160
gaagaagaag atagcataag tttgctgtca gatggcccga cccaccaggt gctgcaagtc    5220
gaggcagaca ttcacgggcc gccctctgta tctagctcat cctggtccat tcctcatgca    5280
tccgactttg atgtggacag tttatccata cttgacaccc tggagggagc tagcgtgacc    5340
agcgggcaa cgtcagccga gactaactct tacttcgcaa agagtatgga gtttctggcg      5400
cgaccggtgc ctgcgcctcg aacagtattc aggaaccctc cacatcccgc tccgcgcaca    5460
agaacaccgt cacttgcacc cagcagggcc tgctccagaa aagtggactg ttccacccg      5520
ccaggcgtga ataggtgat cactagagag gagctcgaag cgcttacccc gtcacgcact     5580
cctagcaggt cggtctccag aaccagcctg gtctccaacc cgccaggcgt aaataggtg      5640
attacaagag aggagtttga ggcgttcgta gcacaacaac aatgacggtt tgatgcgggt     5700
gcatacatct tttcctccga caccggtcaa gggcatttac aacaaaaatc agtaaggcaa     5760
acggtgctat ccgaagtggt gttggagagg accgaattgg agatttcgta tgccccgcgc     5820
ctcgaccaag aaaaagaaga attactacgc aagaaattac agttaaatcc cacacctgct     5880
aacagaagca gataccagtc caggaaggtg agaaacatga aagccataac agctagacgt     5940
attctgcaag gcctagggca ttatttgaag gcagaaggaa aagtggagtg ctaccgaacc     6000
ctgcatcctg ttcctttgta ttcatctagt gtgaaccgtg cctttcaag ccccaaggtc      6060
gcagtggaag cctgtaacgc catgttgaaa gagaactttc cgactgtggc ttcttactgt     6120
attattccag agtacgatgc ctatttggac atggttgacg gagcttcatg ctgcttagac     6180
actgccagtt tttgccctgc aaagctgcgc agctttccaa agaaacactc ctatttggaa     6240
cccacaatac gatcggcagt gccttcagcg atccagaaca cgctccgaaa cgtcctggca     6300
gctgccacaa aaagaaattg caatgtcacg caaatgagag aattgcccgt attggattcg     6360
gcggccttta atgtggaatg cttcaagaaa tatgcgtgta ataatgaata ttgggaaacg    6420
tttaaagaaa accccatcag gcttaaatga gaaaacgtgg taaattacat taccaaatta     6480
aaaggaccaa aagctgctgc tcttttttcg aagacacata atttgaatat gttgcaggac    6540
ataccaatgg acaggtttgt aatggactta aagagagacg tgaaagtgac tccaggaaca    6600
aaacatactg aagaacggcc caaggtacag gtgatccagg ctgccgatcc gctagcaaca    6660
gcgtatctgt gcggaatcca ccgagagctg gttaggagat taaatgcggt cctgcttccg    6720
aacattcata cactgtttga tatgtcggct gaagacttg acgctattat agcgcagcac    6780
ttccagcctg gggattgtgt tctgaaact gacatcgcgt cgtttgataa aagtgaggac     6840
gacgccatgg ctctgaccgc gttaatgatt ctggaagact taggtgtgga cgcagagctg    6900
ttgacgctga ttgaggcggc tttcggcgaa atttcatcaa tacatttgcc cactaaaact    6960
aaatttaaat tcggagccat gatgaaatct ggaatgtcc tccacactgtt tgtgaacaca    7020
gtcattaaca ttgtaatcgc aagcagagtg ttgagagaac ggctaaccgg atcaccatgt    7080
gcagcattca ttgagatgaa caatatcgtg aaaggagtca aatcggacaa attaatggca    7140
gacaggtgcg ccacctggtt gaatatgaa gtcaagatta tagatgctgt ggtgggcgag    7200
aaagccgctt atttctgtgg aggtttatt ttgtgtgact ccgtgaccgc cacagcgtgc    7260
cgtgtggcag accccctaaa aaggctgttt aagctaggca aacctctggc agcagacgat   7320
gaacatgatg atgacaggag aagggcattg catgaggagt caaacgctg gaaccgagtg   7380
ggtattcttt cagagctgtg caaggcagta gaatcaaggt atgaaaccgt aggaacttcc    7440
atcatagtta tggccatgac tactctagct agcagtgta aatcattcag ctacctgaga    7500
ggggccccta taactctcta cggctaacct gaatggacta cgacatagtc tagtccgcca    7560
agactagtat gtttgtgttt cttgtgctgc tgcctcttgt gtcttctcag tgtgtggtga    7620
gatttccaaa tattacaaat ctgtgtccat ttggagaagt gtttaatgca acaagatttg    7680
catctgtgta tgcatggaat agaaaaagaa tttctaattg tgtggctgat tattctgtgc    7740
tgtataatag tgcttctttt tccacattta aatgttatgg agtgtctcca acaaaattaa    7800
atgatttatg ttttacaaat gtgtatgctg attctttttgt gatcagaggt gatgaagtga    7860
gacagattgc ccccgacag acaggaaaaa ttgctgatta caattacaaa ctgcctgatg     7920
attttacagg atgtgtgatt gcttggaatt ctaataattt agattctaaa gtgggaggaa    7980
attacaatta tctgtacaga ctgtttagaa aatcaaatct gaaaccttt gaaagagata     8040
tttcaacaga aatttatcag gctggatcaa caccttgtaa tggagtggaa ggatttaatt    8100
gttatttttcc attacagagc tatggatttc agccaaccaa tggtgtggga tatcagccat    8160
atagagtggt ggtgctgtct tttgaactgc tgcatgcact tgcaacagtg tgtggaccta    8220
aaggctcccc cggctccggc tccggatctg gttatattcc tgaagctcca agagatgggc    8280
aagcttacgt tcgtaaagat ggcgaatggg tattactttc taccttttta ggccggtccc    8340
tggaggtgct gttccagggc cccggctgat gactcgagct ggtactgcat gcacgcaatg    8400
ctagctgccc ctttccccgtc ctgggtaccc cgagtctccc ccgacctcgg gtcccaggta    8460
tgctcccacc tccacctgcc ccactcacca cctctgctag ttccagacac ctccccaagca   8520
cgcagcaatg cagctcaaaa cgcttagcct agccacaccc cacgggaaa cagcagtgat     8580
taaccttag caataaacga aagtttaact aagctatact aaccccaggg ttggtcaatt     8640
tcgtgccagc cacaccgcgg ccgcatgaat acagcagcaa ttggcaagct gcttacatag    8700
aactcgcggc gattggcatg ccgccttaaa attttttattt tatttttttct tttcttttcc    8760
gaatcggatt ttgttttttaa tatttcaaaa aaaaaaaaaa aaaaaaaaaa aaaaaagcat     8820
atgactaaaa aaaaaaaaaa aaaaaaaaaa aaaaaaaaaa aaaaaaaaaa aaaaaaaaaa     8880
aaaaaaaaaa aaaaaa                                                     8896

SEQ ID NO: 27         moltype = RNA  length = 9079
FEATURE               Location/Qualifiers
misc_feature          1..9079
                      note = RBS004.4
source                1..9079
                      mol_type = other RNA
                      organism = synthetic construct
```

```
SEQUENCE: 27
gatgggcggc gcatgagaga agcccagacc aattacctac ccaaaatgga gaaagttcac    60
gttgacatcg aggaagacag cccattcctc agagctttgc agcggagctt cccgcagttt   120
gaggtagaag ccaagcaggt cactgataat gaccatgcta atgccagagc gttttcgcat   180
ctggcttcaa aactgatcga aacggaggtg gacccatccg cacagatcct tgacattgga   240
agtgcgcccg cccgcagaat gtattctaag cacaagtatc attgtatctg tccgatgaga   300
tgtgcggaag atccggacag attgtataag tatgcaacta agctgaagaa aaactgtaag   360
gaaataactg ataaggaatt ggacaagaaa atgaaggagc tcgccgccgt catgagcgac   420
cctgacctgg aaactgagac tatgtgcctc cacgacgacg agtcgtgtcg ctacgaaggg   480
caagtcgctg tttaccagga tgtatacgcg gttgacggac cgacaagtct ctatcaccaa   540
gccaataagg gagttagagt cgcctactgg ataggctttg acaccacccc ttttatgttt   600
aagaacttgg ctggagcata tccatcatac tctaccaact gggccgacga aaccgtgtta   660
acggctcgta acataggcct atgcagctct gacgttatgc agcggtcacg tagagggatg   720
tccattctta gaaagaagta tttgaaacca tccaacaatg ttctattctc tgttggctca   780
accatctacc acgaaaagag ggacttactg aggagctggc acctgccgtc tgtatttcac   840
ttacgtggca agcaaaatta cacatgtcgg tgtgagacta tagttagttg cgacgggtac   900
gtcgttaaaa gaatagctat cagtccaggc ctgtatggga agccttcagg ctatgctgct   960
acgatgcacc gcgagggatt cttgtgctgc aaagtgacag acacattgaa cggggagagg  1020
gtctcttttc ccgtgtgcac gtatgtgcca gctacattgt gtgaccaaat gactggcata  1080
ctggcaacag atgtcagtgc ggacgacgcg caaaaactgc tggttgggct caaccagcgt  1140
atagtcgtca acggtcgcac ccagagaaac accaatacca tgaaaaatta ccttttgccc  1200
gtagtgggcc aggcatttgc taggtgggca aaggaatata aggaagatca aggaagatgaa  1260
aggccactag gactacgaga tagacagtta gtcatggggt gttgttgggc ttttagaagg  1320
cacaagataa catctatttta taagcgcccg gatacccaaa ccatcatcaa agtgaacagc  1380
gatttccact cattcgtgct gcccaggata ggcagtaaca cattggagat cgggctgaga  1440
acaagaatca ggaaaatgtt agaggagcac aaggagcgct cacctctcat taccgccagg  1500
gacgtacaag aagctaagtg cgcagccgat gaggctaagg aggtgcgtga agccgaggag  1560
ttgcgcgcag ctctaccacc tttggcagct gatgttgagg agcccactct ggaagccgat  1620
gtcgacttga tgttacaaga ggctgggggcc ggctcagtgg agacacctcg tggcttgata  1680
aaggttacca gctacgctgg cgaggacaag atcggctctt acgctgtgct ttctccgcag  1740
gctgtactca agagtgaaaa attatcttgc atccaccctc tcgctgaaca agtcatagtg  1800
ataacacact ctgccgaaaa agggcgttat gccgtggaac catacatgg taaagtagtg  1860
gtgccagagg gacatgcaat acccgtccag gactttcaag ctctgagtga aagtgccacc  1920
attgtgtaca acgaactgga gttcgtaaac aggtacctgc accatattgc cacacatgga  1980
ggagcgctga acactgatga agaatattac aaaaactgtca agcccagcga gcacgacggc  2040
gaatacctgt acgacatcga caggaaacag tgcgtcaaga aagagctagt cactgggcta  2100
gggctcacag gcgagctggt cgatcctccc ttccatgaat cgcctacga gagtctgaga  2160
acacgaccag ccgctcctta ccaagtacca accataggg tgtatggcgt gccaggatca  2220
ggcaagtctg gcatcattaa aagcgcagtc accaaaaaag atctagtggt gagcgccaag  2280
aaagaaaact gtgcagaaat tataaggac gtcaagaaaa tgaaagggct ggacgtcaat  2340
gccagaactg tggactcagt gctcttgaat ggatgcaaac accccgtaga gaccctgtat  2400
attgacgagg cttttgcttg tcatgcaggt actctcagag cgctcatagc cattataaga  2460
cctaaaaagg cagtgctctg cggagatccc aaacagtgcg gttttttaa catgatgtgc  2520
ctgaaagtgc atttaacca cgagatttgc acacaagtct tccacaaaag catctctcgc  2580
cgttgcacta aatctgtgac ttcggtcgtc tcaaccttgt tttacgacaa aaaaatgaga  2640
acgacgaatc cgaagagac taagattgtg attgacacta ccggcagtac caaacctaag  2700
caggacgatc tcattctcac ttgtttcaga gggtgggtga agcagttgca aatagattac  2760
aaaggcaacg aaataatgac ggcagctgcc tctcaagggc tgaccccgtaa aggtgtgtat  2820
gccgttcggt acaaggtgaa tgaaaatcct ctgtacgcac ccacctcaga acatgtgaac  2880
gtcctactga cccgcacgga ggaccgcatc gtgtggaaaa cactagccgg cgacccatgg  2940
ataaaaacac tgactgccaa gtaccctggg aatttcactg ccacgataga ggagtggcaa  3000
gcagagcatg atgccatcat gaggcacatc ttggagagac cggaccctac cgacgtcttc  3060
cagaataagg caaacgtgtg ttgggccaag gctttagtgc cggtgctgaa gaccgctggc  3120
atagacatga ccactgaaca atggaacact gtggatattt ttgaaacgga caaagctcac  3180
tcagcagaa tagtattgaa ccaactatgc gtgaggttcc ttggactgga tctggactcc  3240
ggtctatttt ctgcacccac tgttccgtta tccattagga taatcactg ggataactcc  3300
ccgtcgccta acatgtacgg gctgaataaa gaagtggtcc gtcagctctc tcgcaggtac  3360
ccacaactgc ctcgggcagt tgccactggt agagtctatg acatgaacac tggtacactg  3420
cgcaattatg atccgcgcat aaacctagta cctgtaaaca gaagactgcc tcatgcttta  3480
gtcctccacc ataatgaaca cccacagagt gactttttctt cattcgtcag caaattgaag  3540
ggcagaactg tcctggtggt cggggaaaag ttgtccgtcc caggcaaaat ggttgactgg  3600
ttgtcagacc ggcctgaggc taccttcaga gctcggctgg atttaggcat cccaggtgat  3660
gtgcccaaat atgacataat atttgttaat gtgaggaccc catataaata ccatcactat  3720
cagcagtgtg aagaccatgc cattaagcta atgcatgtga ccaagaaagc atgtctgcat  3780
ctgaatcccg gcggaacctg tgtcagcata ggttatggtt acgctgacag ggccagcgaa  3840
agcatcattg tgctatagc gcggcagttc aagtttcccc gagtatgcaa accgaaatcc  3900
tcacttgagg agacggaagt tctgtttgta ttcattgggt acgatcgcaa ggcccgtacg  3960
cacaatccct acaagcattc atcaaccttg accaacattt atacaggttc cagactccac  4020
gaagccggat gtgcaccctc atatcatgtg gtgcgaggg atattgccac ggccaccgaa  4080
ggagtgatta taaatgctgc taacagcaaa ggacaacctg gcggaggggt gtgcggagcg  4140
ctgtataaga aattcccgga aagtttcgat ttacagccga tcgaagtagg aaaagcgcga  4200
ctggtcaaag gtgcagctaa acatatcatt catgccgtag accaaactt caacaaagtt  4260
tcggaggttg aaggtgacaa acagttggca gaggcttatg agtccatcgc taagattgtc  4320
aacgataaca acaaagtgg ccactgtttgt ccaccgcat cttttccggg  4380
aacaaagatc gactaaccca atcattgaac catttgctga cagctttaga caccactgat  4440
gcagatgtag ccatatactg cagggacaag aaatgggaaa tgactctcaa ggaagcagtg  4500
gctaggagag aagcagtgga ggagatagcc atatccgacg attcttcagt gacagaacct  4560
gatgcagagc tggtgagggt gcatcccaag agttcttttgg ctggaaggaa gggctacagc  4620
acaagcgatg gcaaaacttt ctcatatttg gaagggacca gtttcaccaa ggcggccaag  4680
```

```
gatatagcag aaattaatgc catgtggccc gttgcaacgg aggccaatga gcaggtatgc   4740
atgtatatcc tcggagaaag catgagcagt attaggtcga aatgcccgt cgaggagtcg    4800
gaagcctcca caccacctag cacgctgcct tgcttgtgca tccatgccat gactccagaa   4860
agagtacagc gcctaaaagc ctcacgtcca gaacaaatta ctgtgtgctc atcctttcca   4920
ttgccgaagt atagaatcac tggtgtgcag aagatccaat gctcccagcc tatattgttc   4980
tcaccgaaag tgcctgcgta tattcatcca aggaagtatc tcgtggaaac accaccggta   5040
gacgagactc cggagccatc ggcagagaac caatccacag aggggacacc tgaacaacca   5100
ccacttataa ccgaggatga gaccaggact agaacgcctg agccgatcat catcgaagaa   5160
gaagaagaag atagcataag tttgctgtca gatggcccga cccaccaggt gctgcaagtc   5220
gaggcagaca ttcacgggcc gccctctgta tctagctcat cctggtccat tcctcatgca   5280
tccgactttg atgtggacag tttatccata cttgacaccc tggagggagc tagcgtgacc   5340
agcgggcaa cgtcagccga gactaactct tacttcgcaa agagtatgga gtttctggcg    5400
cgaccggtgc ctgcgcctcg aacagtattc aggaaccctc cacatcccgc tccgcgcaca   5460
agaacaccgt cacttgcacc cagcagggcc tgctccagaa ccagcctagt ttccaccccg   5520
ccaggcgtga ataggttgat cactagagag gagctcgaag cgcttacccc gtcacgcact   5580
cctagcaggt cggtctccag aaccagcctg tctccaacc cgccaggcgt aaataggtg     5640
attacaagag aggagtttga ggcgttcgta gcacaacaac aatgacgtt tgatgcgggt    5700
gcatacatct tttcctccga caccggtcaa gggcatttaa aacaaaaatc agtaaggcaa   5760
acggtgctat ccgaagtggt gttggagagg accgaattgg agatttcgta tgccccgcgc   5820
ctcgaccaag aaaaagaaga attactacgc aagaaattac agttaaatcc cacacctgct   5880
aacagaagca gataccagtc caggaaggtg gagaacatga agccataac agctagacgt    5940
attctgcaag gcctagggca ttatttgaag gcagaaggaa aagtggagtg ctaccgaacc   6000
ctgcatcctg ttcctttgta ttcatctagt gtgaaccgtg cctttcaag ccccaaggtc    6060
gcagtggaag cctgtaacgc catgttgaaa gagaactttc cgactgtggc ttcttactgt   6120
attattccag agtacgatgc ctatttggac atggttgacg gagcttcatg ctgcttagac   6180
actgccagtt tttgccctgc aaagctgcgc agctttccaa gaaaacactc ctatttggaa   6240
cccacaatac gatcggcagt gccttcagcg atccagaaca cgctccagaa cgtcctggca   6300
gctgccacaa aaagaaattg caatgtcacg caaatgagag aattgcccgt attggattcg   6360
gcggcctttta atgtggaatg cttcaagaaa tatgcgtgta taatgaata ttgggaaacg   6420
tttaaagaaa accccatcag gcttaacgaa gaaaacgtgg taaattacat taccaaatta   6480
aaaggaccaa aagctgctgc tcttttttgcg aagacacata atttgaatat gttgcaggac   6540
ataccaatgg acaggtttgt aatggactta aagagagacg tgaaagtgac tccaggaaca   6600
aaacatactg aagaacggcc caaggtacag gtgatccagg ctgccgatcc gctagcaaca   6660
gcgtatctgt gcggaatcca ccgagagctg gttaggagat taaatgcggt cctgcttccg   6720
aacattcata cactgtttga tatgtcggct gaagactttg acgctattat gccgagcac    6780
ttccagcctg gggattgtgt tctgaaact gacatcgcgt cgtttgataa aagtgaggac    6840
gacgccatgg ctctgaccgc gttaatgatt ctggaagact taggtgtgga cgcagagctg   6900
ttgacgctga ttgaggcggc tttcggcgaa atttcatcaa tacatttgcc cactaaaact   6960
aaatttaaat tcggagccat gatgaaatct tggaatgtcc tcacactgtt tgtgaacaca   7020
gtcattaaca ttgtaatcgc aagcagagtt gagagaac ggctaaccgg atcaccatgt    7080
gcagcattca ttggagatga caatatcgtg aaaggagtca aatcggacaa attaatggca   7140
gacaggtgcg ccacctggtt gaatatgaa gtcaagatta tagatgctgt ggtgggcgag   7200
aaagcgcctt atttctgtgg aggtttatt ttgtgtgact ccgtgaccgg cacagcgtgc   7260
cgtgtggcag accccctaaa aaggctgttt aagctaggca aacctctggc agcagacgat   7320
gaacatgatg atgacaggag aagggcattg catgaggagt caaacgctg gaaccgagtg   7380
ggtattcttt cagagctgtg caaggcagta gaatcaaggt atgaaaccgt aggaacttcc   7440
atcatagtta tggccatgac tactctagct agcagtgttt aatcattcag ctacctgaga   7500
ggggcccta taactctcta cggctaacct gaatggacta cgacatagtc tagtccgcca   7560
agactagtat gtttgtgttt cttgtgctgc tgcctcttgt gtcttctcag tgtgtggtga   7620
gatttccaaa tattacaaat ctgtgtccat ttggagaagt gtttaatgca acaagatttg   7680
catctgtgta tgcatggaat agaaaaagaa ttttaattg tgtggctgat tattctgtgc   7740
tgtataatag tgcttctttt tccacatta aatgttatgt agtgtctcca acaaaattaa   7800
atgatttatg ttttacaaat gtgtatgctg attcttttgt gatcagaggt gatgaagtga   7860
gacagattgc ccccggacag acaggaaaaa ttgctgatta caattacaaa ctgcctgatg   7920
attttacagg atgtgtgatt gcttggaatt ctaataattt agattctaaa gtgggaggaa   7980
attacaatta tctgtacaga ctgtttagaa aatcaaatct gaaacctttt gaaagagata   8040
tttcaacaga aatttatcag gctggatcaa caccttgtaa tggagtggaa ggatttaatt   8100
gttattttcc attacagagc tatggatttc agccaaccaa tggtgtggga tatcagccat   8160
atagagtggt ggtgctgtct tttgaactgc tgcatgcact tgcaacagtg tgtggaccta   8220
aaggctcccc cggctccggc tccggatctg gttatattcc tgaagctcca agagatgggc   8280
aagcttacgt tcgtaaagat ggcgaatggg tattactttc tacctttta ggaagcggca   8340
gcggatctga acagtacatt aaatggcctt ggtacatttg gcttggattt attgcaggat   8400
taattgcaat tgtgatggtg acaattatgt tatgttgtat gacatcatgt tgttcttgtt   8460
taaaaggatg ttgttcttgt ggaagctgtt gtaaatttga aagatgtttg cgtaactgcc   8520
tgttaaaagg agtgaaattg cattacacat gatgactcga gctggtactg catgcacgca   8580
atgctagctg cccctttccc gtcctgggta ccccgagtct ccccgacct cgggtcccag    8640
gtatgctccc acctccacct gccccactca ccacctctgc tagttccaga cacctcccaa   8700
gcacgcagca atgcagctca aaacgcttag cctagcacca ccccacggg aaacagcagt    8760
gattaacctt tagcaataaa cgaaagttta actaagctat actaacccca gggttgtca   8820
atttcgtgcc agccacaccg cggccgcatg aatacagcag caattggcaa gctgcttaca   8880
tagaactcgc ggcgattggc atgccgcctt aaaattttta tttatttt tcttttcttt    8940
tccgaatcgg attttgttt taatatttca aaaaaaaaaa aaaaaaaaa aaaaaaaag    9000
catatgacta aaaaaaaaa aaaaaaaaa aaaaaaaaaa aaaaaaaaaa aaaaaaaaaa     9060
aaaaaaaaaa aaaaaaaaa                                                9079

SEQ ID NO: 28         moltype = AA   length = 327
FEATURE               Location/Qualifiers
REGION                1..327
                      note = Vaccine Antigen
```

```
source                    1..327
                          mol_type = protein
                          organism = synthetic construct
SEQUENCE: 28
MFVFLVLLPL VSSQCVVRFP NITNLCPFGE VFNATRFASV YAWNRKRISN CVADYSVLYN    60
SASFSTFKCY GVSPTKLNDL CFTNVYADSF VIRGDEVRQI APGQTGKIAD YNYKLPDDFT   120
GCVIAWNSNN LDSKVGGNYN YLYRLFRKSN LKPFERDIST EIYQAGSTPC NGVEGFNCYF   180
PLQSYGFQPT NGVGYQPYRV VVLSFELLHA PATVCGPKGS PGSGSGSGYI PEAPRDGQAY   240
VRKDGEWVLL STFLGSGSGS EQYIKWPWYI WLGFIAGLIA IVMVTIMLCC MTSCCSCLKG   300
CCSCGSCCKF DEDDSEPVLK GVKLHYT                                      327

SEQ ID NO: 29             moltype = AA   length = 311
FEATURE                   Location/Qualifiers
REGION                    1..311
                          note = BNT162b3c
source                    1..311
                          mol_type = protein
                          organism = synthetic construct
SEQUENCE: 29
MFVFLVLLPL VSSQCVNLTV RFPNITNLCP FGEVFNATRF ASVYAWNRKR ISNCVADYSV    60
LYNSASFSTF KCYGVSPTKL NDLCFTNVYA DSFVIRGDEV RQIAPGQTGK IADYNYKLPD   120
DFTGCVIAWN SNNLDSKVGG NYNYLYRLFR KSNLKPFERD ISTEIYQAGS TPCNGVEGFN   180
CYFPLQSYGF QPTNGVGYQP YRVVVLSFEL LHAPATVCGP KGSPGSGSGS GYIPEAPRDG   240
QAYVRKDGEW VLLSTFLGSG SGSEQYIKWP WYIWLGFIAG LIAIVMVTIM LCCMTSCCSC   300
LKGCCSCGSC C                                                       311

SEQ ID NO: 30             moltype = RNA   length = 1397
FEATURE                   Location/Qualifiers
misc_feature              1..1397
                          note = BNT162b3c
source                    1..1397
                          mol_type = other RNA
                          organism = synthetic construct
SEQUENCE: 30
agaataaact agtattcttc tggtccccac agactcagag agaacccgcc accatgtttg    60
tgttcttgt gctgctgcct cttgtgtctt ctcagtgtgt gaatttgaca gtgagatttc   120
caaatattac aaatctgtgt ccatttggag aagtgtttaa tgcaacaaga tttgcatctg   180
tgtatgcatg gaatagaaaa agaatttcta attgtgtggc tgattattct gtgctgtata   240
atagtgttc ttttccaca tttaaatgtt atggagtgtc tccaacaaaa ttaaatgatt   300
tatgttttac aaatgtgtat gctgattctt ttgtgatcag aggtgatgaa gtgagacaga   360
ttgcccccgg acagacagga aaaattctg attacaatta caaactgcct gatgatttta   420
caggatgtgt gattgcttgg aattctaata ttttagattc taaagtggga ggaaattaca   480
attatctgta cagactgttt agaaaatcaa atctgaaacc ttttgaaaga gatatttcaa   540
cagaaattta tcaggctgga tcaacacctt gtaatgagt ggaaggattt aattgttatt   600
ttccattaca gagctatgga tttcagccaa ccaatggtgt gggatatcag ccatatagag   660
tggtggtgct gtcttttgaa ctgctgcatg cacctgcaac agtgtgtgga cctaaaggct   720
ccccggctc cggctccgga tctggttata tcctgaagcc tccaagagat gggcaagctc   780
acgttcgtaa agatgcgaa tgggtattac tttctacctt tttaggaagc ggcagcggat   840
ctgaacagta cattaaatgg ccttggtaca tttggcttgg atttattgca ggattaattg   900
caattgtgat ggtgacaatt atgttatgtt gtatgacatc atgttgtct tgtttaaaag   960
gatgttgttc ttgtgggaagc tgttgttgat gactcgagct ggtactgcat gcacgcaatg  1020
ctagctgccc ctttccccgtc ctgggtaccc cgagtcctcc ccgacctcgg gtcccaggta  1080
tgctcccacc tccacctgcc ccactcacca cctctgctag ttccagacac ctcccaagca  1140
cgcagcaatg cagctcaaaa cgcttagcct agccacaccc cacgggaaa cagcagtgat  1200
taaccttag caataaacga agtttaact aagctatact aaccccaggg ttggtcaatt  1260
tcgtgccagc cacaccctgg agctagcaaa aaaaaaaaaa aaaaaaaaaa aaaaaagca  1320
tatgactaaa aaaaaaaaaa aaaaaaaaaa aaaaaaaaaa aaaaaaaaaa aaaaaaaaaa  1380
aaaaaaaaaa aaaaaaa                                                1397

SEQ ID NO: 31             moltype = AA   length = 314
FEATURE                   Location/Qualifiers
REGION                    1..314
                          note = BNT162b3d
source                    1..314
                          mol_type = protein
                          organism = synthetic construct
SEQUENCE: 31
MDWIWRILFL VGAATGAHSQ MQVRFPNITN LCPFGEVFNA TRFASVYAWN RKRISNCVAD    60
YSVLYNSASF STFKCYGVSP TKLNDLCFTN VYADSFVIRG DEVRQIAPGQ TGKIADYNYK   120
LPDDFTGCVI AWNSNNLDSK VGGNYNYLYR LFRKSNLKPF ERDISTEIYQ AGSTPCNGVE   180
GFNCYFPLQS YGFQPTNGVG YQPYRVVVLS FELLHAPATV CGPKGSPGSG SGSGYIPEAP   240
RDGQAYVRKD GEWVLLSTFL GSGSGSEQYI KWPWYIWLGF IAGLIAIVMV TIMLCCMTSC   300
CSCLKGCCSC GSCC                                                    314

SEQ ID NO: 32             moltype = RNA   length = 1406
FEATURE                   Location/Qualifiers
misc_feature              1..1406
                          note = BNT162b3d
```

```
source                  1..1406
                        mol_type = other RNA
                        organism = synthetic construct
SEQUENCE: 32
agaataaact agtattcttc tggtccccac agactcagag agaacccgcc accatggatt    60
ggatttggag aatcctgttc ctcgtgggag ccgctacagg agcccactcc cagatgcagg   120
tgagatttcc aaatattaca aatctgtgtc catttggaga agtgtttaat gcaacaagat   180
ttgcatctgt gtatgcatgg aatagaaaaa gaatttctaa ttgtgtggct gattattctg   240
tgctgtataa tagtgcttct ttttccacat ttaaatgtta tggagtgtct ccaacaaaat   300
taaatgattt atgttttaca aatgtgtatg ctgattcttt tgtgatcaga ggtgatgaag   360
tgagacagat tgcccccgga cagacaggaa aaattgctga ttacaattac aaactgcctg   420
atgattttac aggatgtgtg attgcttgga attctaataa tttagattct aaagtgggag   480
gaaattacaa ttatctgtac agactgttta gaaaatcaaa tctgaaacct tttgaaagag   540
atatttcaac agaaatttat caggctggat caacacctg taatggagtg gaaggattta    600
attgttattt tccattacag agctatggat ttcagccaac caatggtgtg ggatatcagc   660
catatagagt ggtggtgctg tcttttgaac tgctgcatgc acctgcaaca gtgtgtggac   720
ctaaaggctc ccccggctcc ggctccggat ctggttatat tcctgaagct ccaagagatg   780
ggcaagctca cgttcgtaaa gatggcgaat gggtattact ttctaccttt ttaggaagcc   840
gcagcggatc tgaacagtac attaaatggc cttggtacat ttggcttgga ttattgcag    900
gattaattgc aattgtgatg gtgacaatta tgttatgttg tatgacatca tgttgttctt   960
gtttaaaagg atgttgttct tgtggaagct gttgtgatg actcgagctg gtactgcatg   1020
cacgcaatgc tagctgcccc tttcccgtcc tgggtaccgc gagtctcccc cgacctcggg  1080
tcccaggtat gctcccacct ccacctgccc cactcaccac ctctgctagt tccagacacc  1140
tcccaagcac gcagcaatgc agctcaaaac gcttagccta gccacacccc cacgggaaac  1200
agcagtgatt aaccttagc aataaacgaa agtttaacta gctatacta accccagggt   1260
tggtcaattt cgtgccagcc acccctgga gctagcaaaa aaaaaaaaaa aaaaaaaaa   1320
aaaaaagcat atgactaaaa aaaaaaaaaa aaaaaaaaaa aaaaaaaaaa aaaaaaaaaa  1380
aaaaaaaaaa aaaaaaaaaa aaaaaa                                     1406

SEQ ID NO: 33           moltype = AA   length = 9
FEATURE                 Location/Qualifiers
REGION                  1..9
                        note = Linker
source                  1..9
                        mol_type = protein
                        organism = synthetic construct
SEQUENCE: 33
GSPGSGSGS                                                             9

SEQ ID NO: 34           moltype = AA   length = 6
FEATURE                 Location/Qualifiers
REGION                  1..6
                        note = Linker
source                  1..6
                        mol_type = protein
                        organism = synthetic construct
SEQUENCE: 34
GSGSGS                                                                6

SEQ ID NO: 35           moltype = AA   length = 9
FEATURE                 Location/Qualifiers
REGION                  1..9
                        note = Epitope
source                  1..9
                        mol_type = protein
                        organism = synthetic construct
SEQUENCE: 35
YLQPRTFLL                                                             9

SEQ ID NO: 36           moltype = AA   length = 9
FEATURE                 Location/Qualifiers
REGION                  1..9
                        note = Epitope
source                  1..9
                        mol_type = protein
                        organism = synthetic construct
SEQUENCE: 36
RLQSLQTYV                                                             9

SEQ ID NO: 37           moltype = AA   length = 9
FEATURE                 Location/Qualifiers
REGION                  1..9
                        note = Epitope
source                  1..9
                        mol_type = protein
                        organism = synthetic construct
SEQUENCE: 37
QYIKWPWYI                                                             9
```

```
SEQ ID NO: 38           moltype = AA   length = 9
FEATURE                 Location/Qualifiers
REGION                  1..9
                        note = Epitope
source                  1..9
                        mol_type = protein
                        organism = synthetic construct
SEQUENCE: 38
NYNYLYRLF                                                              9

SEQ ID NO: 39           moltype = AA   length = 10
FEATURE                 Location/Qualifiers
REGION                  1..10
                        note = Epitope
source                  1..10
                        mol_type = protein
                        organism = synthetic construct
SEQUENCE: 39
KWPWYIWLGF                                                            10

SEQ ID NO: 40           moltype = AA   length = 9
FEATURE                 Location/Qualifiers
REGION                  1..9
                        note = Epitope
source                  1..9
                        mol_type = protein
                        organism = synthetic construct
SEQUENCE: 40
QPTESIVRF                                                              9

SEQ ID NO: 41           moltype = AA   length = 9
FEATURE                 Location/Qualifiers
REGION                  1..9
                        note = Epitope
source                  1..9
                        mol_type = protein
                        organism = synthetic construct
SEQUENCE: 41
IPFAMQMAY                                                              9

SEQ ID NO: 42           moltype = AA   length = 9
FEATURE                 Location/Qualifiers
REGION                  1..9
                        note = Epitope
source                  1..9
                        mol_type = protein
                        organism = synthetic construct
SEQUENCE: 42
LPFNDGVYF                                                              9

SEQ ID NO: 43           moltype = AA   length = 9
FEATURE                 Location/Qualifiers
REGION                  1..9
                        note = Epitope
source                  1..9
                        mol_type = protein
                        organism = synthetic construct
SEQUENCE: 43
GVYFASTEK                                                              9

SEQ ID NO: 44           moltype = AA   length = 9
FEATURE                 Location/Qualifiers
REGION                  1..9
                        note = Epitope
source                  1..9
                        mol_type = protein
                        organism = synthetic construct
SEQUENCE: 44
CVADYSVLY                                                              9

SEQ ID NO: 45           moltype = AA   length = 9
FEATURE                 Location/Qualifiers
REGION                  1..9
                        note = Epitope
source                  1..9
                        mol_type = protein
                        organism = synthetic construct
SEQUENCE: 45
KCYGVSPTK                                                              9
```

```
SEQ ID NO: 46            moltype = AA   length = 9
FEATURE                  Location/Qualifiers
REGION                   1..9
                         note = Epitope
source                   1..9
                         mol_type = protein
                         organism = synthetic construct
SEQUENCE: 46
FQPTNGVGY                                                                 9

SEQ ID NO: 47            moltype = AA   length = 9
FEATURE                  Location/Qualifiers
REGION                   1..9
                         note = Epitope
source                   1..9
                         mol_type = protein
                         organism = synthetic construct
SEQUENCE: 47
GTHWFVTQR                                                                 9

SEQ ID NO: 48            moltype = AA   length = 9
FEATURE                  Location/Qualifiers
REGION                   1..9
                         note = Epitope
source                   1..9
                         mol_type = protein
                         organism = synthetic construct
SEQUENCE: 48
VYDPLQPEL                                                                 9

SEQ ID NO: 49            moltype = AA   length = 1270
FEATURE                  Location/Qualifiers
REGION                   1..1270
                         note = Vaccine sequence
source                   1..1270
                         mol_type = protein
                         organism = synthetic construct
SEQUENCE: 49
MFVFLVLLPL VSSQCVNLTT RTQLPPAYTN SFTRGVYYPD KVFRSSVLHS TQDLFLPFFS    60
NVTWFHVISG TNGTKRFDNP VLPFNDGVYF ASIEKSNIIR GWIFGTTLDS KTQSLLIVNN   120
ATNVVIKVCE FQFCNDPFLD HKNNKSWMES EFRVYSSANN CTFEYVSQPF LMDLEGKQGN   180
FKNLREFVFK NIDGYFKIYS KHTPIIVREP EDLPQGFSAL EPLVDLPIGI NITRFQTLLA   240
LHRSYLTPGD SSSGWTAGAA AYYVGYLQPR TFLLKYNENG TITDAVDCAL DPLSETKCTL   300
KSFTVEKGIY QTSNFRVQPT ESIVRFPNIT NLCPFDEVFN ATRFASVYAW NRKRISNCVA   360
DYSVLYNLAP FFTFKCYGVS PTKLNDLCFT NVYADSFVIR GDEVRQIAPG QTGNIADYNY   420
KLPDDFTGCV IAWNSNKLDS KVSGNYNYLY RLFRKSNLKP FERDISTEIY QAGNKPCNGV   480
AGFNCYFPLR SYSFRPTYGV GHQPYRVVVL SFELLHAPAT VCGPKKSTNL VKNKCVNFNF   540
NGLKGTGVLT ESNKKFLPFQ QFGRDIADTT DAVRDPQTLE ILDITPCSFG GVSVITPGTN   600
TSNQVAVLYQ GVNCTEVPVA IHADQLTPTW RVYSTGSNVF QTRAGCLIGA EYVNNSYECD   660
IPIGAGICAS YQTQTKSHRR ARSVASQSII AYTMSLGAEN SVAYSNNSIA IPTNFTISVT   720
TEILPVSMTK TSVDCTMYIC GDSTECSNLL LQYGSFCTQL KRALTGIAVE QDKNTQEVFA   780
QVKQIYKTPP IKYFGGFNFS QILPDPSKPS KRSFIEDLLF NKVTLADAGF IKQYGDCLGD   840
IAARDLICAQ KFKGLTVLPP LLTDEMIAQY TSALLAGTIT SGWTFGAGAA LQIPFAMQMA   900
YRFNGIGVTQ NVLYENQKLI ANQFNSAIGK IQDSLSSTAS ALGKLQDVVN HNAQALNTLV   960
KQLSSKFGAI SSVLNDIFSR LDPPEAEVQI DRLITGRLQS LQTYVTQQLI RAAEIRASAN  1020
LAATKMSECV LGQSKRVDFC GKGYHLMSFP QSAPHGVVFL HVTYVPAQEK NFTTAPAICH  1080
DGKAHFPREG VFVSNGTHWF VTQRNFYEPQ IITTDNTFVS GNCDVVIGIV NNTVYDPLQP  1140
ELDSFKEELD KYFKNHTSPD VDLGDISGIN ASVVNIQKEI DRLNEVAKNL NESLIDLQEL  1200
GKYEQYIKWP WYIWLGFIAG LIAIVMVTIM LCCMTSCCSL KGCCSCGSC CKFDEDDSEP  1260
VLKGVKLHYT                                                        1270

SEQ ID NO: 50            moltype = RNA   length = 3816
FEATURE                  Location/Qualifiers
misc_feature             1..3816
                         note = Coding sequence
source                   1..3816
                         mol_type = other RNA
                         organism = synthetic construct
SEQUENCE: 50
atgttcgtgt tcctggtgct gctgcctctg gtgtccagcc agtgtgtgaa cctgaccacc    60
agaacacagc tgcctccagc ctacaccaac agctttacca gaggcgtgta ctaccccgac   120
aaggtgttca gatccagcgt gctgcactct acccaggacc tgttcctgcc tttcttcagc   180
aacgtgacct ggttccacgt gatctccggc accaatggca caaagagatt cgacaacccc   240
gtgctgccct tcaacgacgg ggtgtacttt gccagcatcg agaagtccaa catcatcaga   300
ggctggatct tcggcaccac actggacagc aagacccaga gcctgctgat cgtgaacaac   360
gccaccaacg tggtcatcaa agtgtgcgag ttccagttct gcaacgaccc cttcctggac   420
cacaagaaca acaagagctg gatggaaagc gagttccggg tgtacagcag cgccaacaac   480
tgcaccttcg agtacgtgtc ccagcctttc ctgatggacc tggaaggcaa gcagggcaac   540
```

```
ttcaagaacc tgcgcgagtt cgtgtttaag aacatcgacg gctacttcaa gatctacagc   600
aagcacaccc ctatcatcgt gagagagccc gaggatctgc ctcagggctt ctctgctctg   660
gaaccctgg tggatctgcc catcggcatc aacatcaccc ggtttcagac actgctggcc   720
ctgcacagaa gctacctgac acctggcgat agcagcagcg gatggacagc tggtgccgcc   780
gcttactatg tgggctacct gcagcctaga accttcctgc tgaagtacaa cgagaacgtg   840
accatcaccg acgccgtgga ttgtgctctg gatcctctga gcgagacaaa gtgcaccctg   900
aagtccttca ccgtggaaaa gggcatctac cagaccagca acttccgggt gcagcccacc   960
gaatccatcg tgcggttccc caatatcacc aatctgtgcc ccttcgacga ggtgttcaat  1020
gccaccagat tcgcctctgt gtacgcctgg aaccggaagc ggatcagcaa ttgcgtggcc  1080
gactactccg tgctgtacaa cctggccccc ttcttcacct tcaagtgcta cggcgtgtcc  1140
cctaccaagc tgaacgacct gtgcttcaca aacgtgtacg ccgacagctt cgtgatccgg  1200
ggagatgaag tgcggcagat tgcccctgga cagacaggca acatcgccga ctacaactac  1260
aagctgcccg acgacttcac cggctgtgtg attgcctgga acagcaacaa gctggactcc  1320
aaagtcagcg gcaactacaa ttacctgtac cggctgttcc ggaagtccaa tctgaagccc  1380
ttcgagcggg acatctccac cgagatctat caggccggca acaagccttg taacggcgtg  1440
gccggcttca actgctactt cccactgcgg tcctacagct ttaggcccac atacggcgtg  1500
ggccaccagc cctacagagt ggtggtgctg agcttcgaac tgctgcatgc ccctgccaca  1560
gtgtgcggcc ctaagaaaag caccaatctc gtgaagaaca aatgcgtgaa cttcaacttc  1620
aacggcctga agggcaccgg cgtgctgaca gagagcaaca agaagttcct gccattccag  1680
cagtttggcc gggatatcgc cgataccaca acgccgttaa gagatcccca gacactggaa  1740
atcctggaca tcacccctg cagcttcggc ggagtgtctg tgatcacccc tggcaccaac  1800
accagcaatc aggtggcagt gctgtaccag gcgtgaagt gcccgtggcc  1860
attcacgccg atcagctgac acctacatgg cgggtgtact ccaccggcag caatgtgttt  1920
cagaccagag ccggctgtct gatcggagcc gagtacgtga acaatagcta cgagtgcgac  1980
atccccatcg gcgctggaat ctgcgccagc taccagacac agacaaagag ccaccggaga  2040
gccagaagcg tggccagcca gagcatcatt gcctacacaa tgtctctgg cgccgagaac  2100
agcgtggcct actccaacaa ctctatcgct atccccacca acttcaccat cagcgtgacc  2160
acagagatcc tgcctgtgtc catgaccaag accagcgtgg actgcaccat gtacatctgc  2220
ggcgattcca ccgagtgctc caacctgctg ctgcagtacg gcagcttctg cacccagctg  2280
aaaagagccc tgacagggat cgccgtggaa caggacaaga acacccaaga ggtgttcgcc  2340
caagtgaagc agatctacaa gacccctcct atcaagtact tcggcggctt caatttcagc  2400
cagattctgc ccgatcctag caagcccagc aagcggagct catcgagga cctgctgttc  2460
aacaaagtga cactggccga cgccggcttc atcaagcagt atggcgattg tctgggcgac  2520
attgccgcca gggatctgat ttgcgccagg aagtttaagg gactgacagt gctgcctcct  2580
ctgctgaccg atgagatgat cgcccagtac acatctgccc tgctggccgg cacaatcaca  2640
agcggctgga catttggagc aggcgccgct ctgcagatcc cctttgctat gcagatggcc  2700
taccggttca acggcatcgg agtgacccag aatgtgctgt acgagaacca gaagctgatc  2760
gccaaccagt tcaacagcgc catcggcaag atccaggaca gcctgagcag cacagcaagc  2820
gccctggaa agctgcagga cgtggtcaac caaatgccaa aggcactgaa caccctggtc  2880
aagcagctgt cctccaagtt cggcgccatc agctctgtgc tgaacgatat cttcagcaga  2940
ctggaccctc tgaggccga ggtgcagatc gacagactga tcacaggcag actgcagagc  3000
ctccagacat acgtgaccca gcagctgatc agagccgccg agattagagc ctctgccaat  3060
ctggccgcca ccaagatgtc tgagtgtgtg ctgggccaga gcaagagagt ggactttgc  3120
ggcaagggct accaccctga tgagcttcct cagtctgccc ctcacggcgt ggtgtttctg  3180
cacgtgacat atgtgcccgc tcaagagaag aatttcacca ccgctccagc catctgccac  3240
gacggcaaag cccactttcc tagagaaggc gtgttcgtgt ccaacggcac ccattggttc  3300
gtgacacagc ggaacttcta cgagccccag atcatcacca cgacaacac cttcgtgtct  3360
ggcaactgcg acgtcgtgat cggcattgtg aacaataccg tgtacgaccc tctgcagccc  3420
gagctggaca gcttcaaaga ggaactggac aagtacttta gaaccacac aagcccgac  3480
gtggacctgg cgatatcag cggaatcaat gccagcgtcg tgaacatcca gaaagagatc  3540
gaccggctga acgaggtggc caagaatctg aacgagagcc tgatcgacct gcaagaactg  3600
gggaagtacg agcagtacat caagtggccc tggtacatct ggctgggctt tatcgccgga  3660
ctgattgcca tcgtgatggt cacaatcatg ctgtgttgca tgaccagctg ctgtagctgc  3720
ctgaagggct gttgtagctg tggcagctgc tgcaagttcg acgaggacga ttctgagccc  3780
gtgctgaagg gcgtgaaact gcactacaca tgatga                            3816

SEQ ID NO: 51          moltype = RNA   length = 4274
FEATURE                Location/Qualifiers
misc_feature           1..4274
                       note = Vaccine RNA
source                 1..4274
                       mol_type = other RNA
                       organism = synthetic construct
SEQUENCE: 51
agaataaact agtattcttc tggtccccac agactcagag agaacccgcc accatgttcg   60
tgttcctggt gctgctgcct ctggtgtcca gccagtgtgt gaacctgacc accagaaaac  120
agctgcctcc agcctacacc aacagctta ccagaggcgt gtactacccc gacaaggtgt  180
tcagatccag cgtgctgcac tctacccagg acctgttcct gccttcttc agcaacgtga  240
cctggttcca cgtgatctcc ggcaccaatg gcaccaagag attcgacaac cccgtgctgc  300
ccttcaacga cggggtgtac tttgccagca tcgagaagtc caacatcatc agaggctgga  360
tcttcggcac cacactggac agcaagaccc agagcctgct gatcgtgaac aacgccacca  420
acgtggtcat caaagtgtgc gagttccagt tctgcaacga ccccttcctg gaccacaaga  480
acaacaagag ctggatggaa agcgagttcc gggtgtacag cagcgccaac aactgcacct  540
tcgagtacgt gtcccagcct ttcctgatgg acctggaagg caagcagggc aacttcaaga  600
acctgcgcga gttcgtgttt aagaacatcg acggctactt caagatctac agcaagcaca  660
ccctatcat cgtgagagag cccgaggatc tgcctcaggg cttctctgct ctggaacccc  720
tggtggatct gcccatcggc atcaacatca cccggtttca gacactgctg gcctgcaca  780
gaagctacct gacacctggc gatagcagca gcggatggac agctggtgcc gccgcttact  840
atgtgggcta cctgcagcct agaaccttcc tgctgaagta caacgagaac ggcaccatca  900
```

-continued

```
ccgacgccgt ggattgtgct ctggatcctc tgagcgagac aaagtgcacc ctgaagtcct    960
tcaccgtgga aaagggcatc taccagacca gcaacttccg ggtgcagccc accgaatcca   1020
tcgtgcggtt ccccaatatc accaatctgt gcccccttcga cgaggtgttc aatgccacca   1080
gattcgcctc tgtgtacgcc tggaaccgga agcggatcag caattgcgtg ccgactact    1140
ccgtgctgta caacctggcc cccttcttca ccttcaagtg ctacgcgtg tccccctacca   1200
agctgaacga cctgtgcttc acaaacgtgt acgccgacag cttcgtgatc cggggagatg   1260
aagtgcggca gattgcccct ggacagacag gcaacatcgc cgactacaac tacaagctgc   1320
ccgacgactt caccggctgt gtgattgcct ggaacagcaa caagctggac tccaaagtca   1380
gcggcaacta caattacctg taccggttcc tcccggaagtc caatctgaag cccttcgagc   1440
gggacatctc caccgagatc tatcaggccg gcaacaagcc ttgtaacggc gtggccggct   1500
tcaactgcta cttcccactg cggtcctaca gctttaggcc cacatacggc gtgggccacc   1560
agccctacag agtggtggtg ctgagcttcg aactgctgca tgcccctgcc acagtgtgcg   1620
gccctaagaa aagcaccaat ctcgtgaaga caaaatgcgt gaacttcaac ttcaacggcc   1680
tgaagggcac cggcgtgctg acagaagca acaagaagt cctgccattc cagcagtttg   1740
gccgggatat cgccgatacc acagacgccg ttagagatcc ccagacactg gaaatcctgg   1800
acatcacccc ttgcagcttc ggcggagtgt ctgtgatcac ccctggcacc aacaccagca   1860
atcaggtggc agtgctgtac cagggcgtga actgtaccga agtgcccgtg gccattcacg   1920
ccgatcagct gacacctaca tggcggtgt actccaccag cagcaatgtg tttcagacca   1980
gagccggctg tctgatcgga gccgagtacg tgaacaatag ctacgagtgc gacatcccca   2040
tcggcgctgg aatctgcgcc agctaccaga cacagacaaa gagccaccgg agagccagaa   2100
gcgtggccag ccagagcatc attgcctaca atgtctct gggcgccgag aacagcgtgg   2160
cctactccaa caactctatc gctatccca ccaacttcac catcagcgtg accacagaga   2220
tcctgcctgt gtccatgacc aagaccagcg tggactgcca catgtacatc tgcggcgatt   2280
ccaccgagtg ctcaacctg ctgctgcagt acggcagctt ctgcacccag ctgaaaagag   2340
ccctgacagg gatcggcgtg aacaggaca agaacaccca gaggtgttc gcccaagtga   2400
agcagatcta caagaccct cctatcaagt acttcggcgg cttcaatttc agccagattc   2460
tgcccgatcc tagcaagccc agcaagcgga gcttcatcga ggacctgctg ttcaacaaag   2520
tgacactggc cgacgccggc ttcatcaagc agtatgcga ttgtctgggc gacattgccg   2580
ccagggatct gatttgcgcc cagaagttta agggactgac agtgctgcct cctctgctga   2640
ccgatgagat gatcgcccag tacacatctg ccctgctggc cggcacaatc acaagcggct   2700
ggacatttgg agcaggcgcc gctctgcaga tccccttgc tatgcagatg gcctaccggt   2760
tcaacggcat cggagtgacc cagaatgtgc tgtacgagaa ccagaagctg atcgccaacc   2820
agttcaacag cgccatcggc aagatccagg acagcctgag cagcacagca gcgccctgg   2880
gaaagctgca ggacgtggtc aaccacaatg cccaggcact gaacaccctg gtcaagcagc   2940
tgtcctccaa gttcggcgcc atcagctctg tgctgaacga tatcttcagc agactgatga   3000
ctcctgaggc cgaggtgcag atcgacagac tgatcacagg cagactgcag agcctccaga   3060
catacgtgac ccagcagctg atcagagccg ccgagattag agcctctgcc aatctggccg   3120
ccaccaagat gtctgagtgt gtgctgggcc agagcaagag agtggacttt tgcggcaagg   3180
gctaccacct gatgagcttc cctcagtctg ccctccacgg ctggtgttt ctgcacgtga   3240
catatgtgcc cgctcaagag aagaatttca ccaccgctcc agcatctgc cacgacggca   3300
aagcccactt tcctagagaa ggcgtgttcg tgtccaacgg cacccattgg ttcgtgacac   3360
agcggaactt ctacgagccc cagatcatca ccaccgacaa caccttcgtg tctggcaact   3420
gcgacgtcgt gatcggcatt gtgaacaata cgtgtacga ccctcgtgca cccgagctgg   3480
acagcttcaa agaggaactg gacaagtact ttaagaacca cacaagcccc gacgtggacc   3540
tgggcgatat cagcggaatc aatgccagct cgtgaacat ccagaaagag atcgaccggc   3600
tgaacgaggt ggccaagaat ctgaacgaga gcctgatcga cctgcaagaa ctggggaagt   3660
acgagcagta catcaagtgg ccctggtaca tctggctggg cttttatcgcc ggactgattg   3720
ccatcgtgat ggtcacaatc atgctgtgtt gcatgaccag ctgctgtagc tgcctgaagg   3780
gctgttgtag ctgtggcagc tgctgcaagt tcgacgagga cgattctgag cccgtgctga   3840
agggcgtgaa actgcactac acatgatgac tcgagctgg actgcatgca cgcaatgcta   3900
gctgcccctt tcccgtcctg ggtaccccga gtctccccg acctcgggtc ccaggtatgc   3960
tcccacctcc acctgcccca ctcaccacct ctgctagttc cagacacctc ccaagcacgc   4020
agcaatgcag ctcaaaacgc ttagcctagc cacaccccca cgggaaacag cagtgattaa   4080
cctttagcaa taaacgaaag tttaactaag ctatactaac cccagggttg gtcaatttcg   4140
tgccagccac accctggagc tagcaaaaaa aaaaaaaaaa aaaaaaaaaa aaagcatat    4200
gactaaaaaa aaaaaaaaaa aaaaaaaaaa aaaaaaaaaa aaaaaaaaaa aaaaaaaaaa   4260
aaaaaaaaaa aaaa                                                    4274

SEQ ID NO: 52          moltype = AA   length = 1270
FEATURE                Location/Qualifiers
REGION                 1..1270
                       note = Vaccine sequence
source                 1..1270
                       mol_type = protein
                       organism = synthetic construct
SEQUENCE: 52
MFVFLVLLPL VSSQCVNLTT RTQLPPAYTN SFTRGVYYPD KVFRSSVLHS TQDLFLPFFS    60
NVTWFHVISG TNGTKRFDNP VLPFNDGVYF ASIEKSNIIR GWIFGTTLDS KTQSLLIVNN   120
ATNVVIKVCE FQFCNDPFLD HKNNKSWMES EFRVYSSANN CTFEYVSQPF LMDLEGKQGN   180
FKNLREFVFK NIDGYFKIYS KHTPIIVREP EDLPQGFSAL EPLVDLPIGI NITRFQTLLA   240
LHRSYLTPGD SSSGWTAGAA AYYVGYLQPR TFLLKYNENG TITDAVDCAL DPLSETKCTL   300
KSFTVEKGIY QTSNFRVQPT ESIVRFPNIT NLCPFDEVFN ATRFASVYAW NRKRISNCVA   360
DYSVLYNLAP FFTFKCYGVS PTKLNDLCFT NVYADSFVIR GDEVRQIAPG QTGKIADYNY   420
KLPDDFTGCV IAWNSNNLDS KVGGNYNYLY RLFRKSNLKP FERDISTEIY QAGNKPCNGV   480
AGFNCYFPLR SYSFRPTYGV GHQPYRVVVL SFELLHAPAT VCGPKKSTNL VKNKCVNFNF   540
NGLKGTGVLT ESNKKFLPFQ QFGRDIADTT DAVRDPQTLE ILDITPCSFG GVSVITPGTN   600
TSNQVAVLYQ GVNCTEVPVA IHADQLTPTW RVYSTGSNVF QTRAGCLIGA EYVNNSYECD   660
IPIGAGICAS YQTQTKSHRR ARSVASQSII AYTMSLGAEN SVAYSNNSIA IPTNFTISVT   720
TEILPVSMTK TSVDCTMYIC GDSTECSNLL LQYGSFCTQL KRALTGIAVE QDKNTQEVFA   780
```

```
QVKQIYKTPP IKYFGGFNFS QILPDPSKPS KRSFIEDLLF NKVTLADAGF IKQYGDCLGD    840
IAARDLICAQ KFKGLTVLPP LLTDEMIAQY TSALLAGTIT SGWTFGAGAA LQIPFAMQMA    900
YRFNGIGVTQ NVLYENQKLI ANQFNSAIGK IQDSLSSTAS ALGKLQDVVN HNAQALNTLV    960
KQLSSKFGAI SSVLNDIFSR LDPPEAEVQI DRLITGRLQS LQTYVTQQLI RAAEIRASAN   1020
LAATKMSECV LGQSKRVDFC GKGYHLMSFP QSAPHGVVFL HVTYVPAQEK NFTTAPAICH   1080
DGKAHFPREG VFVSNGTHWF VTQRNFYEPQ IITTDNTFVS GNCDVVIGIV NNTVYDPLQP   1140
ELDSFKEELD KYFKNHTSPD VDLGDISGIN ASVVNIQKEI DRLNEVAKNL NESLIDLQEL   1200
GKYEQYIKWP WYIWLGFIAG LIAIVMVTIM LCCMTSCCSC LKGCCSCGSC CKFDEDDSEP   1260
VLKGVKLHYT                                                         1270

SEQ ID NO: 53           moltype = RNA   length = 3816
FEATURE                 Location/Qualifiers
misc_feature            1..3816
                        note = Coding sequence
source                  1..3816
                        mol_type = other RNA
                        organism = synthetic construct
SEQUENCE: 53
atgttcgtgt tcctggtgct gctgcctctg gtgtccagcc agtgtgtgaa cctgaccacc     60
agaacacagc tgcctccagc ctacaccaac agctttacca gaggcgtgta ctaccccgac    120
aaggtgttca gatccagcgt gctgcactct acccaggacc tgttcctgcc tttcttcagc    180
aacgtgacct ggttccacgt gatctccggc accaatgcca ccagagatt cgacaaccgt    240
gtgctgccct tcaacgacgg ggtgtacttt gccagcatcg agaagtccaa catcatcaga    300
ggctggatct ccggcaccac actggacagc aagacccaga gcctgctgat cgtgaacaac    360
gccaccaacg tggtcatcaa agtgtgcgag ttccagttct gcaacgaccc cttcctggac    420
cacaagaaca acaagagctg gatggaaagc gagttccggg tgtacagcag cgccaacaac    480
tgcaccttcg agtacgtgtc ccagcctttc ctgatggacc tggaaggcaa gcagggcaac    540
ttcaagaacc tgcgcgagtt cgtgtttaag aacatcgacg gctacttcaa gatctacagc    600
aagcacaccc ctatcatcgt gagagagccc gaggatctgc ctcagggctt ctctgctctg    660
gaaccctgg tggatctgcc catcggcatc aacatcacgg ggtttcagac actgctggcc    720
ctgcacagaa gctacctgac acctggcgat agcagcagcg gatggacagc tggtgccgcc    780
gcttactatg tgggctacct gcagcctaga accttcctgc tgaagtacaa cgagaacggc    840
accatcaccg acgccgtgga ttgtgctctg gatcctctga cgagacaaa gtgcaccctg    900
aagtccttca ccgtggaaaa gggcatctac cagaccagca attcccgggt gcagcccacc    960
gaatccatcg tgcggttccc caatatcacc aatctgtgcc ccttccgacg gggtgttcaat   1020
gccaccagat tcgcctctgt gtacgcctgg aaccggaagc ggatcagcaa ttgcgtggcc   1080
gactactccg tgctgtacaa cctggccccc ttcttccacc tcaagtgcta cggcgtgtcc   1140
cctaccaagc tgaacgacct gtgcttcaca aacgtgtacg ccgacagctt cgtgatccgg   1200
ggagatgaag tgcggcagat tgcccctgga cagacaggca gcgatcgga ctacaactac   1260
aagctgcccg acgacttcac cggctgtgtg attgccctgga acagcaacaa cctggactcc   1320
aaagtcggcg gcaactacaa ttacctgtac cggctgttcc ggaagtccaa tctgaagccc   1380
ttcgagcggg acatctccac cgagatctat caggccggca caagcccttg taacggcgtg   1440
gccggcttca actgctactt cccactgcgg tcctacagct ttaggcccac atacggctgg   1500
ggccaccagc cctacagagt ggtggtgctg agcttcgaac tgctgcatgc ccctgccaca   1560
gtgtgcggcc ctaagaaaag caccaatctc tgaagaacaa aatgcgtgaa cttcaacttc   1620
aacggcctga agggcaccgg cgtgctgaca gagagcaaca gaagttcct gccattccag   1680
cagtttggcc gggatatcgc cgataccaca gacgccgtta gagatcccca gacactggaa   1740
atcctggaca tcacccccttg cagcttcggc ggagtgtctg tgatcacccc tggcaccaac   1800
accagcaatc aggtggcagt gctgtaccag ggcgtgaact gtaccgaagt gcccgtggcc   1860
attcacgccg atcagctgac acctatatgg cgggtgtact ccaccggcag caatgtgttt   1920
cagaccagag ccggctgtct gatcggagcc gagtacgtga acatagcta cgagtgcgac   1980
atccccatcg gcgctggaat ctgcgccagc taccagacac agacaaagag ccaccggaga   2040
gccagaagcg tggccagcca gagcatcatt gcctacacaa tgtctctggg cgccgagaac   2100
agcgtggcct actccaacaa ctctatcgct atccccacca acttcaccat cagcgtgacc   2160
acagagatcc tgcctgtgtc catgaccaag accagcgtgg actgcaccat gtacatctgc   2220
ggcgattcca ccgagtgctc caacctgctg ctgcagtacg gcagcttctg cacccagctg   2280
aaaagagccc tgacagggat cgccgtggaa caggacaaga acacccaaga ggtgttcgcc   2340
caagtgaagc agatctacaa gaccccctcc atcaagtact cggcggcttc aattttcagc   2400
cagattctgc ccgatcctag caagcccagc aagcggagct tcatcgagga cctgctgttc   2460
aacaaagtga cactggccga cgccggcttc atcaagcagt atggcgattg tctgggcgac   2520
attgccgcca gggatctgat tgcgcccag aagtttaagg gactgacagt gctgcctcct   2580
ctgctgaccg atgagatgat cgcccagtac acatctgccc tgctggccgg cacaatcaca   2640
agcggctgga catttggagc aggcgccgct ctgcagatcc cctttgctat gcagatggcc   2700
taccggttca acggcatcgg agtgacccag aatgtgctct acgagaacca agctgaa   2760
gccaaccagt tcaacagcgc catcggcaag atccaggaca gcctgagcag cacagcaagc   2820
gccctgggaa agctgcagga cgtggtcaac cacaatgccc aggcactgaa caccctggtc   2880
aagcagctgt cctccaagtt cggcgccatc agctctgtgc tgaacgatat cttcagcaga   2940
ctggacccct ctgaggccga ggtgcagatc gacagactga tcacaggcag actgcagagc   3000
ctccagacat acgtgaccca gcagctgatc agagccgcg agattagaac tctgccaat   3060
ctggccgcca ccaagatgtc tgagtgtgtg ctgggccaga gcaagagagt ggactttgc   3120
ggcaagggct accacctgat gagcttccct cagtctgccc ctcacggcgt ggtgtttctg   3180
cacgtgcat atgtgcccgc tcaagagaag aatttcacca ccgctccagc catctgccac   3240
gacggcaaag cccactttcc tagagaaggc gtgttcgtgt ccaacggcac ccattggttc   3300
gtgacacagc ggaacttcta cgagcccag atcatcacca ccgacaacac cttcgtgtct   3360
ggcaactgcg acgtcgtgat cggcattgtg aacaataccg tgtacgaccc tctgcagccc   3420
gagctggaca gcttcaaaga ggaactggac aagtactta agaaccacac aagccccgac   3480
gtggacctgg gcgatatcag cggaatcaat gccagcgtcg tgaacatcca gaaagagatc   3540
gaccgcctga acgaggtggc caagaatctg aacgagagcc tgatcgacct gcaagaactg   3600
gggaagtacg agcagtacat caagtggccc tggtacatct ggctgggctt tatcgccgga   3660
```

```
ctgattgcca tcgtgatggt cacaatcatg ctgtgttgca tgaccagctg ctgtagctgc   3720
ctgaagggct gttgtagctg tggcagctgc tgcaagttcg acgaggacga ttctgagccc   3780
gtgctgaagg gcgtgaaact gcactacaca tgatga                             3816

SEQ ID NO: 54           moltype = RNA   length = 4274
FEATURE                 Location/Qualifiers
misc_feature            1..4274
                        note = Vaccine RNA
source                  1..4274
                        mol_type = other RNA
                        organism = synthetic construct
SEQUENCE: 54
agaataaact agtattcttc tggtccccac agactcagag agaacccgcc accatgttcg     60
tgttcctggt gctgctgcct ctggtgtcca gccagtgtgt gaacctgacc accagaaacac   120
agctgcctcc agcctacacc aacagcttta ccagaggcgt gtactacccc gacaaggtgt   180
tcagatccag cgtgctgcac tctacccagg acctgttcct gcctttcttc agcaacgtga   240
cctggttcca cgtgatctcc ggcaccaatg caccaagag attcgacaac cccgtgctgc   300
ccttcaacga cggggtgtac tttgccagca tcgagaagtc caacatcatc agaggctgga   360
tcttcggcac cacactggac agcaagaccc agagcctgct gatcgtgaac aacgccacca   420
acgtggtcat caaagtgtgc gagttccagt tctgcaacga ccccttcctg gaccacaaga   480
acaacaagag ctggatggaa agcgagttcc gggtgtacag cagcgccaac aactgcacct   540
tcgagtacgt gtcccagcct ttcctgatgg acctggaagg caagcagggc aacttcaaga   600
acctgcgcga gttcgtgttt aagaacatcg acggctactt caagatctac agcaagcaca   660
cccctatcat cgtgagagag cccgaggatc tgcctcaggg cttctctgct ctggaacccc   720
tggtggatct gcccatcggc atcaacatca cccggtttca gacactgctg gccctgcaca   780
gaagctacct gacacctggc gatagcagca cggatggac agctggtgcc gccgcttact   840
atgtgggcta cctgcagcct agaaccttcc tgctgaagta caacgagaac ggcaccatca   900
ccgacgccgt ggattgtgct ctggatcctc tgagcgagac aaagtgcacc ctgaagtcct   960
tcaccgtgga aaagggcatc taccagacca gcaacttccg ggtgcagccc accgaatcca  1020
tcgtcgggtt cccaaatatc accaatctgt gcccccttcg cggggtgttc aatgccacca  1080
gattcgcctc tgtgtacgcc tggaaccgga gcggatcag caattgcgtg gccgactact  1140
ccgtgctgta caacctggcc cccttcttca cctttcaagtg ctacggcgtg tccctacca  1200
agctgaacga ccctgtgctt cacaaacgtgt acgccgacag cttcgtgatc cggggagatg  1260
aagtgcggca gattgcccct ggacagacag gcaagctcgc cgactacaac tacaagctga  1320
ccgacgactt caccggctgt gtgattgcct ggaacagcaa caacctggac tccaaagtcg  1380
gcggcaacta caattacctg taccggctgt tccggaagtc caatctgaag cccttcgagc  1440
gggacatctc caccgagatc tatcaggccg gcaacaagcc ttgtaacggc gtggccggct  1500
tcaactgcta cttcccactg cggtcctaca gctttaggcc cacatacggc gtgggccacc  1560
agccctacag agtggtggtg ctgagcttcg aactgctgca tgccctgccc acagtgtgcg  1620
gccctaagaa aagcaccaat ctcgtgaaga caaatgcgt gaacttcaac ttcaacggcc  1680
tgaagggcac cggcgtgctg acagagagca caagaagtt cctgccattc agcagtttg   1740
gccgggatat cgccgatacc acagacgccg ttagagatcc ccagacactg gaaatcctgg  1800
acatcacccc ttgcagcttc ggcggagtgt ctgtgatcac ccctggcacc aacaccagca  1860
atcaggtggc agtgctgtac caggggcgtga actgtaccga agtgcccgtg gccattcacg  1920
ccgatcagct gacacctaca tggcgggtgt actccaccgg cagcaatgtg tttcagacca  1980
gagcggctg tctgatcgga gccgagtacg tgaacaatag ctacgagtgc gacatcccca  2040
tcggcgctgg aatctgcgcc agctaccaga cacagacaaa gagccacggg agagccagaa  2100
gcgtggccag ccagagcatc attgcctaca atgtctct gggcgccgag aacagcgtgg  2160
cctactccaa caactctatc gctatcccca ccaacttcac catcagcgtg accacagaga  2220
tcctgcctgt gtccatgacc aagaccagcg tggactgcac catgtacatc tgcggcgatt  2280
ccaccagtg ctccaacctg ctgctgcagt acggcagctt ctgcacccag ctgaaaagag  2340
ccctgacagg gatcgccgtg gaacaggaca agaacaccca agaggtgttc gcccaagtga  2400
agcagatcta caagaccccct cctatcaagt acttcggcgg cttcaatttc agccagattc  2460
tgcccgatcc tagcaagccc agcaagcgga gcttcatcga ggacctgctg ttcaacaaag  2520
tgacactggc cgacgccggc ttcatcaagc agtatggcga ttgtctgggc gacattgccg  2580
ccagggatct gatttgcgcc cagaagttta aggggactga cagtgctgcct cctctgctga  2640
ccgatgagat gatcgcccag tacacatctg ccctgctggc cggcacaatc acaagcgggt  2700
ggacatttgg agcaggcgcc gctctgcaga tccccttttgc tatgcagatg gcctaccggt  2760
tcaacggcat cggagtgacc cagaatgtgc tgtacgagaa ccagaagctg atcgccaacc  2820
agttcaacag cgccatcggc aagatccagg acagcctgag cagcacagca agcgccctgg  2880
gaaagctgca ggacgtggtc aaccacaatg cccaggcact gaacaccctg gtcaagcagc  2940
tgtcctccaa gttcggcgcc atcagctctg tgctgaacga tatcttcagc agactggacc  3000
ctcctgaggc cgaggtgcag atcgacagac tgatcacagg cagactgcag agcctccaga  3060
catacgtgac ccagcagctg atcagagccg ccgagattag ggcctctgcc aatctggccg  3120
ccaccaagat gtctgagtgt gtgctgggcc agagcaagag agtggacttt tgcggcaagg  3180
gctaccacct gatgagcttc cctcagtctg ccctcacggg cgtggtgttt ctgcacgtga  3240
catatgtgcc cgctcaagag aagaatttca ccaccgctcc agccatctgc cacgacggca  3300
aagcccactt tcctagagaa ggcgtgttcg tgtccaacgg cacccattgg ttcgtgacac  3360
agcggaactt ctacgagccc cagatcatca ccaccgacaa caccttcgtg tctggcaact  3420
gcgacgtcgt gatcggcatt gtgaacaata ccgtgtacga ccctctgcag cccgagctgg  3480
acagcttcaa agaggaactg gacaagtact ttaagaacca cacaagcccc gacgtggacc  3540
tgggcgatat cagcggaatc aatgccagcg tcgtgaacat ccagaaagag atcgaccggc  3600
tgaacgaggt ggccaagaat ctgaacgaga gcctgatcga cctgcaagaa ctggggaagt  3660
acgagcagta catcaagtgg ccctggtaca tctggctggg ctttatcgcc ggactgattg  3720
ccatcgtgat ggtcacaatc atgctgtgtt gcatgaccag ctgctgtagc tgcctgaagg  3780
gctgttgtag ctgtggcagc tgctgcaagt cgacgagga cgattctgag cccgtgctga  3840
agggcgtgaa actgcactac acatgatgac tcgagctggt actgcatgca cgcaatgcta  3900
gctgcccctt tcccgtcctg ggtaccccga gtctcccccg acctcgggtc ccaggtatgc  3960
tcccacctcc acctgcccca ctcaccacct gctagttca cagacacctc ccaagcacgc  4020
```

```
agcaatgcag ctcaaaacgc ttagcctagc cacaccccca cgggaaacag cagtgattaa    4080
cctttagcaa taaacgaaag tttaactaag ctatactaac cccagggttg gtcaatttcg    4140
tgccagccac accctggagc tagcaaaaaa aaaaaaaaaa aaaaaaaaaa aaaagcatat    4200
gactaaaaaa aaaaaaaaaa aaaaaaaaaa aaaaaaaaaa aaaaaaaaaa aaaaaaaaaa    4260
aaaaaaaaaa aaaa                                                      4274

SEQ ID NO: 55          moltype = AA  length = 1270
FEATURE                Location/Qualifiers
source                 1..1270
                       mol_type = protein
                       organism = synthetic construct
SEQUENCE: 55
MFVFLVLLPL VSSQCVNFTT RTQLPPAYTN SFTRGVYYPD KVFRSSVLHS TQDLFLPFFS     60
NVTWFHAIHV SGTNGTKRFA NPVLPFNDGV YFASTEKSNI IRGWIFGTTL DSKTQSLLIV    120
NNATNVVIKV CEFQFCNDPF LGVYYHKNNK SWMESEFRVY SSANNCTFEY VSQPFLMDLE    180
GKQGNFKNLR EFVFKNIDGY FKIYSKHTPI NLVRGLPQGF SALEPLVDLP IGINITRFQT    240
LHISYLTPGD SSSGWTAGAA AYYVGYLQPR TFLLKYNENG TITDAVDCAL DPLSETKCTL    300
KSFTVEKGIY QTSNFRVQPT ESIVRFPNIT NLCPFGEVFN ATRFASVYAW NRKRISNCVA    360
DYSVLYNSAS FSTFKCYGVS PTKLNDLCFT NVYADSFVIR GDEVRQIAPG QTGNIADYNY    420
KLPDDFTGCV IAWNSNNLDS KVGGNYNYLY RLFRKSNLKP FERDISTEIY QAGSTPCNGV    480
KGFNCYFPLQ SYGFQPTYGV GYQPYRVVVL SFELLHAPAT VCGPKKSTNL VKNKCVNFNF    540
NGLTGTGVLT ESNKKFLPFQ QFGRDIADTT DAVRDPQTLE ILDITPCSFG GVSVITPGTN    600
TSNQVAVLYQ GVNCTEVPVA IHADQLTPTW RVYSTGSNVF QTRAGCLIGA EHVNNSYECD    660
IPIGAGICAS YQTQTNSPRR ARSVASQSII AYTMSLGVEN SVAYSNNSIA IPTNFTISVT    720
TEILPVSMTK TSVDCTMYIC GDSTECSNLL LQYGSFCTQL NRALTGIAVE QDKNTQEVFA    780
QVKQIYKTPP IKDFGGFNFS QILPDPSKPS KRSFIEDLLF NKVTLADAGF IKQYGDCLGD    840
IAARDLICAQ KFNGLTVLPP LLTDEMIAQY TSALLAGTIT SGWTFGAGAA LQIPFAMQMA    900
YRFNGIGVTQ NVLYENQKLI ANQFNSAIGK IQDSLSSTAS ALGKLQDVVN QNAQALNTLV    960
KQLSSNFGAI SSVLNDILSR LDPPEAEVQI DRLITGRLQS LQTYVTQQLI RAAEIRASAN   1020
LAATKMSECV LGQSKRVDFC GKGYHLMSFP QSAPHGVVFL HVTYVPAQEK NFTTAPAICH   1080
DGKAHFPREG VFVSNGTHWF VTQRNFYEPQ IITTDNTFVS GNCDVVIGIV NNTVYDPLQP   1140
ELDSFKEELD KYFKNHTSPD VDLGDISGIN ASVVNIQKEI DRLNEVAKNL NESLIDLQEL   1200
GKYEQYIKWP WYIWLGFIAG LIAIVMVTIM LCCMTSCCSC LKGCCSCGSC CKFDEDDSEP   1260
VLKGVKLHYT                                                          1270

SEQ ID NO: 56          moltype = RNA  length = 3817
FEATURE                Location/Qualifiers
source                 1..3817
                       mol_type = other RNA
                       organism = synthetic construct
SEQUENCE: 56
atgttcgtgt tcctggtgct gctgcctctg gtgtccagcc agtgtgtgaa cttcaccacc     60
agaacacagc tgcctccagc ctacaccaac agctttaccc gaggcgtgta ctaccccgac    120
aaggtgttca gatccagcgt gctgcactct acccaggacc tgttcctgcc tttcttcagc    180
aacgtgacct ggttccacgc catccacgtg tccggcacca atggcaccaa gagattcgcc    240
aaccccgtgc tgcccttcaa cgacggggtg tactttgcca gcaccgagaa gtccaacatc    300
atcagaggct ggatcttcgg caccacactg gacagcaaga cccagagcct gctgatcgtg    360
aacaacgcca ccaacgtggt catcaaagtg tgcgagttcc agttctgcaa cgaccccttc    420
ctgggcgtct actaccacaa gaacaacaag agctggatgg aaagcgagtt ccgggtgtac    480
agcagcgcca acaactgcac cttcgagtac gtgtcccagc cttttctgat ggacctggaa    540
ggcaagcagg gcaacttcaa gaacctgcgc gagttcgtgt ttaagaacat cgacggctac    600
ttcaagatct acagcaagca cacccctatc aacctcgtgc ggggcctgcc tcagggcttc    660
tctgctctgg aaccctggt ggatctgccc atcggcatca acatcacccg gtttcagaca    720
ctgcacatca gctacctgac acctggcgat agcagcagcg gatggacagc tggtgccgcc    780
gcttactatg tgggctacct gcagcctaga accttcctgc tgaagtacaa cgagaacggc    840
accatcaccg acgccgtgga ttgtgctctg gatcctctga gcgagacaaa gtgcaccctg    900
aagtccttca ccgtggaaaa gggcatctac cagaccagca acttccgggt gcagcccacc    960
gaatccatcg tgcggttccc caatatcacc aatctgtgcc cctttcggga ggtgttcaat   1020
gccaccagat tcgcctctgt gtacgcctgg aaccggaagc ggatcagcaa ttgcgtggcc   1080
gactactccg tgctgtacaa ctccgccagc ttcagcacct tcaagtgcta cggcgtgtcc   1140
cctaccaagc tgaacgacct gtgcttcaca aacgtgtacg ccgacagctt cgtgatccgg   1200
ggagatgaag tgcggcagat tgccctggga cagacaggca atatcgccga ctacaactac   1260
aagctgcccg acgacttcac cggctgtgtg attgcctgga acagcaacaa cctggactcc   1320
aaagtcggcg gcaactacaa ttacctgtac cggctgttcc ggaagttcaa tctgaagccc   1380
ttcgagcggg acatctccac cgagatctat caggccggca gcaccccttg taacggcgtg   1440
aagggcttca actgctactt cccactgcag tcctacggct tcagcccaca tacggcgtg   1500
ggctatcagc cctacagagt ggtggtgctg agcttcgaac tgctgcatgc ccctgccaca   1560
gtgtgcggcc ctaagaaaag caccaatctc gtgaagaaca aatgcgtgaa cttcaacttc   1620
aacggcctga ccggcaccgg cgtgctgaca gagagcaaca agaagtttct gccattccag   1680
cagtttggcc gggatatcgc cgataccaca gacgccgtta gagatcccca gacactggaa   1740
atcctggaca tcacccctg cagcttcggc ggagtgtctg tgatcacccc tggcaccaac   1800
accagcaatc aggtggcagt gctgtaccag ggcgtgaact gtaccgaagt gcccgtggcc   1860
attacgccg atcagctgac acctacatgg cgggtgtact ccaccggcag caatgtgttt   1920
cagaccaggg ccggctgtct gatcggagcc gagcactgga acaatagcta cgagtgcgac   1980
atccccatcg gcgctggaat ctgcgccagc taccagacac agacaaacag ccctcggaga   2040
gccagaagcg tggccagcca gagcatcatt gcctacacaa tgtctctggg cgtcgagaac   2100
agcgtggcct actccaacaa ctctatcgct atccccacca acttcaccat cagcgtgacc   2160
acagagatcc tgcctgtgtc catgaccaag accagcgtgg actgcaccat gtacatctgc   2220
ggcgattcca ccgagtgctc caacctgctg ctgcagtacg gcagcttctg cacccagctg   2280
```

```
aatagagccc tgacagggat cgccgtggaa caggacaaga acacccaaga ggtgttcgcc   2340
caagtgaagc agatctacaa gacccctcct atcaaggact tcggcggctt caatttcagc   2400
cagattctgc ccgatcctag caagcccagc aagcggagct tcatcgagga cctgctgttc   2460
aacaaagtga cactggccga cgccggcttc atcaagcagt atggcgattg tctgggcgac   2520
attgccgcca gggatctgat ttgcgcccag aagtttaacg gactgacagt gctgcctcct   2580
ctgctgaccg atgagatgat cgcccagtac acatctgccc tgctggccgg cacaatcaca   2640
agcggctgga catttggagc aggcgccgct ctgcagatcc cctttgctat gcagatggcc   2700
taccggttca acggcatcgg agtgacccag aatgtgctgt acgagaacca gaagctgatc   2760
gccaaccagt tcaacagcgc catcggcaag atccaggaca gcctgagcag cacagcaagc   2820
gccctgggaa agctgcagga cgtggtcaac cagaatgccc aggcactgaa cacccctggtc   2880
aagcagctgt cctccaactt cggcgccatc agctctgtgc tgaacgatat cctgagcaga   2940
ctggaccctc ctgaggccga ggtgcagatc gacagactga tcacaggcag actgcagagc   3000
ctccagacat acgtgaccca gcagctgatc agagccgccg agattagagc ctctgccaat   3060
ctggccgcca ccaagatgtc tgagtgtgtg ctgggccaga gcaagagagt ggacttttgc   3120
ggcaagggct accacctgat gagcttccct cagtctgccc ctcacggcgt ggtgtttctg   3180
cacgtgacat atgtgcccgc tcaagagaag aatttcacca ccgctccagc catctgccac   3240
gacggcaaag cccactttcc tagagaaggc gtgttcgtgt ccaacggcac ccattggttc   3300
gtgacacagc ggaacttcca cgagcccag atcatccaca ccgacaacac cttcgtgtct   3360
ggcaactgcg acgtcgtgat cggcattgtg aacaataccg tgtacgaccc tctgcagccc   3420
gagctggaca gcttcaaaga ggaactggac aagtacttta agaaccacac aagcccccgac   3480
gtggacctgg cgatatcag cggaatcaat gccagcgtcg tgaacatcca gaaagagatc   3540
gaccggctga acgaggtggc caagaatctg aacgagagcc tgatcgacct gcaagaactg   3600
gggaagtacg agcagtacat caagtggccc tggtacatct ggctgggctt tatcgccgga   3660
ctgattgcca tcgtgatggt cacaatcatg ctgtgttgca tgaccagctg ctgtagctgc   3720
ctgaagggct gttgtagctg tggcagctgc tgcaagttcg acgaggacga ttctgagccc   3780
gtgctgaagg gcgtgaaact gcactacaca tgatgac                            3817

SEQ ID NO: 57          moltype = RNA   length = 4274
FEATURE                Location/Qualifiers
source                 1..4274
                       mol_type = other RNA
                       organism = synthetic construct
SEQUENCE: 57
agaataaact agtattcttc tggtccccac agactcagag agaacccgcc accatgttcg     60
tgttcctggt gctgctgcct ctggtgtcca gccagtgtgt gaacttcacc accagaacac    120
agctgcctcc agcctacacc aacagcttta ccagaggcgt gtactacccc gacaaggtgt    180
tcagatccag cgtgctgcac tctacccagg acctgttcct gcctttcttc agcaacgtga    240
cctggttcca cgccatccac gtgtccggca ccaatgcac aagagattc gccaacccg      300
tgctgcctt caacgacggg gtgtactttg ccagcaccga gaagttccaac atcatcagag    360
ctggatcttt cggcaccaca ctggacagca gacccagag cctgctgatc gtgaacaacg    420
ccaccaacgt ggtcatcaaa gtgtgcgagt tccagttctg caacgacccc ttcctgggcg    480
tctactacca caagaacaac aagagctgga tggaaagcga gttccgggtg tacagcagcg    540
ccaacaactg caccttcgag tacgtgtccc agccttctct gatggacctg gaaggcaagc    600
agggcaactt caagaacctg cgcgagttcg tgtttaagaa catcgacggc tacttcaaga    660
tctacagcaa gcacaccct atcaacctcg tgcgggcct gctcagggc ttctctgctc      720
tggaaccct ggtggatctg cccatcgca tcaacatcac ccgttcag acactgcaca       780
tcagctacct gacacctggc gatagcagca gcggatggaa agctggtgcc gccgcttact    840
atgtgggcta cctgcagcct agaaccttcc tgctgaagta caacgagaac ggcaccatca    900
ccgacgccgt ggattgtgct ctggatcctc tgagcgagac aaagtgcacc ctgaagtcct    960
tcaccgtgga aaagggcatc taccagacca gcaacttccg ggtgcagccc accgaatcca   1020
tcgtgcggtt ccccaatatc accaatctgt gcccttccg cgaggtgttc aatgccaca    1080
gattcgcctc tgtgtacgcc tggaaccgga gcggatcag caattgcgtg gccgactact   1140
ccgtgctgta caactccgcc agcttcagca ccttcaagtg ctacggcgtg tcccctacca   1200
agctgaacga cctgtgcttc acaaacgtgt acgccgacag cttcgtgatc cggggagatg   1260
aagtgcggca gattgccct ggacacagag gcaacatgc cgactacaac tacaagctga    1320
ccgacgactt caccggctgt gtgattgcct ggaacagcaa caacctggac tccaaagtgc   1380
gcggcaacta caattacctg taccggctgt tccggaagtc caatctgaag cccttcgagc   1440
gggacatctc caccgagatc tatcaggccg gcagcacccc ttgtaacggc gtgaagggct   1500
tcaactgcta cttcccactg cagtcctacg gcttcagcc cacatcagtg gtggctatc    1560
agccctacag agtggtggtg ctgagcttcg aactgctgca tgcccctgcc acagtgtgcg   1620
gccctaagaa aagcaccaat ctcgtgaaga caaatgcgt gaacttcaac ttcaacggcc    1680
tgaccggcac cggcgtgctg acagagagca acaagaagtt cctgccattc cagcagtttg   1740
gccgggatat cgccgatacc acagacgccg ttagagatcc ccagacactg gaaatcctgg   1800
acatcacccc ttgcagcttc ggcggagtgt ctgtgatcac cctggcac aaccaccaga    1860
atcaggtggc agtgctgtac cagggcgtga actgtaccga agtgcccgtg gccattcacg   1920
ccgatcagct gacacctaca tggcgggtgt actccaccgg cagcaatgtg tttcagacca   1980
gagcggctg tctgatcgga gccgagcacg tgaacaatag ctacgagtgc gacatcccca   2040
tcggcgctgg aatctgcgcc agctaccaga cacagacaaa cagccctcgg agagccagaa   2100
gcgtggccag ccagagcatc attgcctaca atgtctct gccgtcgag aacagctgtg    2160
cctactccaa caactctatc gctatccca ccaacttcac catcagcgtg accacagaga   2220
tcctgcctgt gtccatgacc aagaccagcg tggactgcac catgtacatc tgcggcgatt   2280
ccaccgagtg ctccaacctg ctgctgcagt acggcagctt ctgcacccag ctgaatagag   2340
ccctgacagg gatcgccgtg aacaggaca agaacaccca gaggtgttc gcccaagtga    2400
agcagatcta caagacccct cctatctaagg acttcggcg cttcaatttc agccagattc    2460
tgcccgatcc tagcaagccc agcaagcgga gcttcatcga ggacctgctg ttcaacaaag   2520
tgacactggc cgacgccggc ttcatcaagc agtatgcga ttgtctgggc gacattgccg    2580
ccagggatct gatttgcgcc cagaagttta acggactgac agtgctgcct cctctgctga   2640
ccgatgagat gatcgcccag tacacatctg ccctgctggc cggcacaatc acaagcggct   2700
ggacatttgg agcaggcgcc gctctgcaga tcccctttgc tatgcagatg gcctaccggt   2760
```

-continued

```
tcaacggcat cggagtgacc cagaatgtgc tgtacgagaa ccagaagctg atcgccaacc    2820
agttcaacag cgccatcggc aagatccagg acagcctgag cagcacagca agcgccctgg    2880
gaaagctgca ggacgtggtc aaccagaatg cccaggcact gaacaccctg gtcaagcagc    2940
tgtcctccaa cttcggcgcc atcagctctg tgctgaacga tatcctgagc agactggacc    3000
ctcctgaggc cgaggtgcag atcgacagac tgatcacagg cagactgcag agcctccaga    3060
catacgtgac ccagcagctg atcagagccg ccgagattag agcctctgcc aatctggccg    3120
ccaccaagat gtctgagtgt gtgctgggcc agagcaagag agtggacttt tgcggcaagg    3180
gctaccacct gatgagcttc cctcagtctg cccctcacgg cgtggtgttt ctgcacgtga    3240
catatgtgcc cgctcaagag aagaatttca ccaccgctcc agccatctgc cacgacggca    3300
aagcccactt tcctagagaa ggcgtgttcg tgtccaacgg cacccattgg ttcgtgacac    3360
agcggaactt ctacgagccc cagatcatca ccaccgacaa caccttcgtg tctggcaact    3420
gcgacgtcgt gatcggcatt gtgaacaata ccgtgtacga ccctctgcag cccgagctgg    3480
acagcttcaa agaggaactg acaagtact ttaagaacca caagcccc gacgtggacc    3540
tgggcgatat cagcggaatc aatgccagcg tcgtgaacat ccagaaagag atcgaccggc    3600
tgaacgaggt ggccaagaat ctgaacgaga gcctgatcga cctgcaagaa ctggggaagt    3660
acgagcagta catcaagtgg ccctggtaca tctggctggg ctttatcgcc ggactgattg    3720
ccatcgtgat ggtcacaatc atgctgtgtt gcatgaccag ctgctgtagc tgcctgaagg    3780
gctgtttgtag ctgtggcagc tgctgcaagt tcgacgagga cgattctgag cccgtgctga    3840
agggcgtgaa actgcactac acatgatgac tcgagctggt actgcatgca cgcaatgcta    3900
gctgcccctt tcccgtcctg gtaccccga gtctccccg acctcgggtc ccaggtatgc    3960
tcccacctcc acctgcccca ctcaccacct ctgctagttc cagacacctc ccaagcacgc    4020
agcaatgcag ctcaaaacgc ttagcctagc cacaccccca cgggaaacag cagtgattaa    4080
cctttagcaa taaacgaaag tttaactaag ctatactaac cccagggttg gtcaatttcg    4140
tgccagccac ccctggagc tagcaaaaaa aaaaaaaaaa aaaaaaaaaa aaaagcatat    4200
gactaaaaaa aaaaaaaaaa aaaaaaaaaa aaaaaaaaaa aaaaaaaaaa aaaaaaaaaa    4260
aaaaaaaaaa aaaa                                                      4274

SEQ ID NO: 58          moltype = AA   length = 1270
FEATURE                Location/Qualifiers
source                 1..1270
                       mol_type = protein
                       organism = synthetic construct
SEQUENCE: 58
MFVFLVLLPL VSSQCVNLTT RTQLPPAYTN SFTRGVYYPD KVFRSSVLHS TQDLFLPFFS     60
NVTWFHAISG TNGTKRFDNP VLPFNDGVYF ASTEKSNIIR GWIFGTTLDS KTQSLLIVNN    120
ATNVVIKVCE FQFCNDPFLG VYHKNNKSWM ESEFRVYSSA NNCTFEYVSQ PFLMDLEGKQ    180
GNFKNLREFV FKNIDGYFKI YSKHTPINLV RDLPQGFSAL EPLVDLPIGI NITRFQTLLA    240
LHRSYLTPGD SSSGWTAGAA AYYVGYLQPR TFLLKYNENG TITDAVDCAL DPLSETKCTL    300
KSFTVEKGIY QTSNFRVQPT ESIVRFPNIT NLCPFGEVFN ATRFASVYAW NRKRISNCVA    360
DYSVLYNSAS FSTFKCYGVS PTKLNDLCFT NVYADSFVIR GDEVRQIAPG QTGKIADYNY    420
KLPDDFTGCV IAWNSNNLDS KVGGNYNYLY RLFRKSNLKP FERDISTEIY QAGSTPCNGV    480
EGFNCYFPLQ SYGFQPTYGV GYQPYRVVVL SFELLHAPAT VCGPKKSTNL VKNKCVNFNF    540
NGLTGTGVLT ESNKKFLPFQ QFGRDIDDTT DAVRDPQTLE ILDITPCSFG GVSVITPGTN    600
TSNQVAVLYQ GVNCTEVPVA IHADQLTPTW RVYSTGSNVF QTRAGCLIGA EHVNNSYECD    660
IPIGAGICAS YQTQTNSHRR ARSVASQSII AYTMSLGAEN SVAYSNNSIA IPINFTISVT    720
TEILPVSMTK TSVDCTMYIC GDSTECSNLL LQYGSFCTQL NRALTGIAVE QDKNTQEVFA    780
QVKQIYKTPP IKDFGGFNFS QILPDPSKPS KRSFIEDLLF NKVTLADAGF IKQYGDCLGD    840
IAARDLICAQ KFNGLTVLPP LLTDEMIAQY TSALLAGTIT SGWTFGAGAA LQIPFAMQMA    900
YRFNGIGVTQ NVLYENQKLI ANQFNSAIGK IQDSLSSTAS ALGKLQDVVN QNAQALNTLV    960
KQLSSNFGAI SSVLNDILAR LDPPEAEVQI DRLITGRLQS LQTYVTQQLI RAAEIRASAN   1020
LAATKMSECV LGQSKRVDFC GKGYHLMSFP QSAPHGVVFL HVTYVPAQEK NFTTAPAICH   1080
DGKAHFPREG VFVSNGTHWF VTQRNFYEPQ IITTHNTFVS GNCDVVIGIV NNTVYDPLQP   1140
ELDSFKEELD KYFKNHTSPD VDLGDISGIN ASVVNIQKEI DRLNEVAKNL NESLIDLQEL   1200
GKYEQYIKWP WYIWLGFIAG LIAIVMVTIM LCCMTSCCSC LKGCCSCGSC CKFDEDDSEP   1260
VLKGVKLHYT                                                          1270

SEQ ID NO: 59          moltype = RNA   length = 3816
FEATURE                Location/Qualifiers
source                 1..3816
                       mol_type = other RNA
                       organism = synthetic construct
SEQUENCE: 59
atgttcgtgt tcctggtgct gctgcctctg gtgtccagcc agtgtgtgaa cctgaccacc     60
agaacacagc tgcctccagc ctacaccaac agctttacca gaggcgtgta ctacccgac    120
aaggtgttca gatccagcgt gctgcactct acccaggacc tgttcctgcc tttcttcagc    180
aacgtgacct ggttccacgc catctccggc accaatggca ccaagagatt cgacaacccc    240
gtgctgccct tcaacgacgg ggtgtacttt gccagcaccg agaagtccaa catcatcaga    300
ggctggatct tcggcaccac actggacagc aagacccaga gcctgctgat cgtgaacaac    360
gccaccaacg tggtcatcaa agtgtgcgag ttccagttct gcaacgaccc cttcctgggc    420
gtctaccaca agaacaacaa gagctggatg gaaagcgagt tccgggtgta cagcagcgcc    480
aacaactgca ccttcgagta cgtgtcccag cctttcctga tggacctgga aggcaagcag    540
ggcaacttca agaacctgcg cgagttcgtg tttaagaaca tcgacggcta cttcaagatc    600
tacagcaagc acacccctat caacctcgtg cgggatctgc ctcagggctt ctctgctctg    660
gaacccctgg tggatctgcc catcggcatc aacatccgct ttcagac actgctgctc    720
ctgcacagaa gctacctgac acctggcgat agcagcagcg gatggacagc tggtgccgcc    780
gcttactatg tgggctacct gcagcctaga accttcctgc tgaagtacaa cgagaacggc    840
accatcaccg acgccgtgga ttgtgctctg gatcctctga gcgagacaaa gtgcacctg    900
aagtccttca ccgtggaaaa gggcatctac cagaccagca cttccgggt gcagccacc    960
gaatccatcg tgcggttccc caatatcacc aatctgtgcc ccttcggcga ggtgttcaat   1020
```

```
gccaccagat tcgcctctgt gtacgcctgg aaccggaagc ggatcagcaa ttgcgtggcc    1080
gactactccg tgctgtacaa ctccgccagc ttcagcacct tcaagtgcta cggcgtgtcc    1140
cctaccaagc tgaacgacct gtgcttcaca aacgtgtacg ccgacagctt cgtgatccgg    1200
ggagatgaag tgcggcagat tgcccctgga cagacaggca agatcgccga ctacaactac    1260
aagctgcccg acgacttcac cggctgtgtg attgcctgga acagcaacaa cctggactcc    1320
aaagtcggcg gcaactacaa ttacctgtac cggctgttcc ggaagtccaa tctgaagccc    1380
ttcgagcggg acatctccac cgagatctat caggccggca gcaccccttg taacggcgtg    1440
gaaggcttca actgctactt cccactgcag tcctacggct tcagcccac atacggcgtg     1500
ggctatcagc cctacagagt ggtggtgctg agcttcgaac tgctgcatgc ccctgccaca    1560
gtgtcggcc ctaagaaaag caccaatctc gtgaagaaca aatgcgtgaa cttcaacttc     1620
aacggcctga ccggcaccgg cgtgctgaca gagagcaaca agaagttcct gccattccag    1680
cagtttggcc gggatatcga cgataccaca gacgccgtta gagatcccca gacactggaa    1740
atcctggaca tcacccccttg cagcttcggc ggagtgtctg tgatcacccc tggcaccaac    1800
accagcaatc aggtggcagt gctgtaccag ggcgtgaact gccgtgaagt gcccgtggcc    1860
attcacgccg atcagctgac acctacatgg cgggtgtact ccaccggcag caatgtgttt    1920
cagaccagag ccggctgtct gatcggagcc gagcacgtga caatagcta cgagtgcgac     1980
atccccatcg gcgctggaat ctgcgccagc taccagacac agacaaacag ccaccggaga    2040
gccagaagcg tggccagcca gagcatcatt gcctacacaa tgtctctggg cgccgagaac    2100
agcgtggcct actccaacaa ctctatcgct atccccatca acttcaccat cagcgtgacc    2160
acagagatcc tgcctgtgtc catgaccaag accagcgtgg actgcaccat gtacatctgc    2220
ggcgattcca ccgagtgctc caacctgctg ctgcagtacg gcagcttctg cacccagctg    2280
aatagagccc tgacagggat cgccgtgaa caggacaaga acacccaaga ggtgttcgcc     2340
caagtgaagc agatctacaa gacccctcct atcaaggact tcggcggctt caatttcagc    2400
cagattctgc ccgatcctag caagcccagc aagcggagct tcatcgagga cctgctgttc    2460
aacaaagtga cactggccga cgccggcttc atcaagcagt atggcgattg ctgggcgac     2520
attgccgcca gggatctgat ttgcgccaag aagtttaacg gactgacagt gctgcctcct    2580
ctgctgaccg atgagatgat cgcccagtac acatctgccc tgctggccgg cacaatcaca    2640
agcggctgga catttggagc aggcgccgct ctgcagatcc cctttgctat gcagatggcc    2700
taccggttca acggcatcgg agtgacccag aatgtgctgt acgagaacca gaagctgatc    2760
gccaaccagt tcaacagcgc catcggcaag atccaggacg cctacagccg cacagcaagc    2820
gccctgggaa agctgcagga cgtggtcaac cagaatgccc aggcactgaa caccctggtc    2880
aagcagctgt cctccaactt cggcgccatc agctctgtgc tgaacgatat cctgccaga     2940
ctggaccctc ctgaggccga ggtgcagatc gacagactga tcacaggcag actgcagagc    3000
ctccagacat acgtgaccca gcagctgatc agagccgccg agattagacc ctctgccaat    3060
ctggccgcca ccaagatgtc tgagtgtgtg ctgggccaga gcaagagagt ggactttgc    3120
ggcaagggct accacctgat gagcttccct cagtctgccc ctcacggcgt ggtgtttctg    3180
cacgtgacat atgtgcccgc tcaagagaag aatttcacca ccgctccagc catctgccac    3240
gacggcaaag cccactttcc tagagaaggc gtgttcgtgt ccaacggcac ccattggttc    3300
gtgacacagc ggaacttcta cgagcccag atcatcacca ccacaacac cttcgtgtct      3360
ggcaactgcg acgtcgtgat cggcattgtg aacaataccg tgtacgaccc tctgcagccc    3420
gagctggaca gcttcaaaga ggaactggac aagtacttta gaaccacac aagcccgac     3480
gtggacctgg gcgatatcag cggaatcaat gccagcgtcg tgaacatcca gaagagatc    3540
gaccggctga acgaggtggc caagaatctg aacgagagcc tgatcgacct gcaagaactg    3600
gggaagtacg agcagtacat caagtggccc tggtacatct ggctgggctt tatcgccgga    3660
ctgattgcca tcgtgatggt cacaatcatg ctgtgttgca tgaccagctg ctgtagctgc    3720
ctgaagggct gttgtagctg tggcagctgc tgcaagttcg acgaggacga ttctgagccc    3780
gtgctgaagg gcgtgaaact gcactacaca tgatga                               3816
```

```
SEQ ID NO: 60          moltype = RNA   length = 4274
FEATURE                Location/Qualifiers
source                 1..4274
                       mol_type = other RNA
                       organism = synthetic construct
SEQUENCE: 60
agaataaact agtattcttc tggtccccac agactcagag agaacccgcc accatgttcg    60
tgttcctggt gctgctgcct ctggtgtcca gccagtgtgt gaacctgacc accagaacac    120
agctgcctcc agcctacacc aacagcttta ccagaggcgt gtactacccc gacaaggtgt    180
tcagatccag cgtgctgcac tctacccagg acctgttcct gcctttcttc agcaacgtga    240
cctggttcca cgccatctcc ggcaccaatg gcaccaagga attcgacaac cccgtgctgc    300
ccttcaacga cggggtgtac tttgccagca ccgagaagtc caacatcatc agaggctgga    360
tcttcggcac cacactggac agcaagaccc agagcctgct gatcgtgaac aacgccacca    420
acgtggtcat caaagtgtgc gagttccagt tctgcaacga ccccttcctg ggcgtctacc    480
acaagaacaa caagagctgg atggaaagcg agttccgggt gtacagcagc gccaacaact    540
gcacccttga gtacgtgtcc cagccttttc tgatgaccct ggaaggcaag cagggcaact    600
tcaagaacct gcgcgagttc gtgtttaaga acatcgacgg ctacttcaag atctacagca    660
agcacacccc tatcaacctc gtgcgggatc tgcctcaggg cttctctgct ctggaaccc    720
tggtggatct gcccatcggc atcaacatca cccgatttca gacactctg ccctgcaca     780
gaagctacct gacaccggc gatagcagca cgggatgga gctggtgc cgcgttact         840
atgtgggcta cctgcagcc tgctgaagta caacgagaac ggccaccatca             900
ccgacgccgt ggattgtgct ctggatcctc tgagcgagac aaagtgcacc ctgaagtcct   960
tcaccgtgga aaagggcatc taccagacca gcaacttccg ggtgcagccc accgaatcca   1020
tcgtgcggtt cccccaatatc accaatctgt gccccttcgg cgaggtgttc aatgccacca    1080
gattcgcctc tgtgtacgcc tggaaccgga gcggatcag caattgcgtg gccgactact    1140
ccgtgctgta caactccgcc agcttcagca ccttcaagtg ctacggcgtg tcccctacca   1200
agctgaacga cctgtgcttc acaaacgtgt acgccgacag cttcgtgatc ggggagatg    1260
aagtgcggca gattgcccct ggacagacag gcaagatcgc cgactacaac tacaagctgc    1320
ccgacgactt caccggctgt gtgattgcct ggaacagcaa caacctggac tccaaagtcg    1380
gcggcaacta caattacctg taccggctgt tccggaagtc caatctgaag cccttcgagc    1440
gggacatctc caccgagatc tatcaggccg gcagcacccc ttgtaacggc gtggaaggct    1500
```

```
tcaactgcta cttcccactg cagtcctacg gctttcagcc cacatacggc gtgggctatc 1560
agccctacag agtggtggtg ctgagcttcg aactgctgca tgcccctgcc acagtgtgcg 1620
gccctaagaa aagcaccaat ctcgtgaaga acaaatgcgt gaacttcaac ttcaacggcc 1680
tgaccggcac cggcgtgctg acagagagca acaagaagtt cctgccattc agcagtttg 1740
gccgggatat cgacgatacc acagacgccg ttagagatcc ccagacactg gaaatcctgg 1800
acatcacccc ttgcagcttc ggcggagtgt ctgtgatcac ccctggcacc aacaccagca 1860
atcaggtggc agtgctgtac cagggcgtga actgtaccga agtcccgtg gccattcacg 1920
ccgatcagct gacacctaca tggcgggtgt actccaccgg cagcaatgtg tttcagacca 1980
gagccggctg tctgatcgga gccgagcacg tgaacaatag ctacgagtgc gacatcccca 2040
tcggcgctgg aatctgcgcc agctaccaga cacagacaaa cagccaccgg agagccagaa 2100
gcgtggccag ccagagcatc attgcctaca atgtctct gggcgccgag aacagcgtgg 2160
cctactccaa caactctatc gctatcccca tcaacttcac catcagcgtg accacagaga 2220
tcctgcctgt gtccatgacc aagaccagcg tggactgcac catgtacatc tgcggcgatt 2280
ccaccgagtg ctccaacctg ctgctgcagt acggcagctt ctgcacccag ctgaatagag 2340
ccctgacagg gatcgccgtg aacaggaca agaacccca agaggtgttc gcccaagtga 2400
agcagatcta caagacccct cctatcaagg acttcggcgg cttcaatttc agccagattc 2460
tgcccgatcc tagcaagccc agcaagcgga gcttcatcga ggacctgctg ttcaacaaag 2520
tgcactggc cgacgccggc ttcatcaagc agtatggcga ttgtctgggc gacattgcg 2580
ccagggatct gatttgcgcc cagaagttta acggactgac agtgctgcct cctctgctga 2640
ccgatgagat gatcgcccag tacacatctg ccctgctggc cggcacaatc acaagcggct 2700
ggacatttgg agcaggcgcc gctctgcaga tcccctttgc tatgcagatg gcctaccggt 2760
tcaacggcat cggagtgacc cagaatgtgc tgtacgagaa ccagaagctg atcgccaacc 2820
agttcaacag cgccatcggc aagatccagg acagcctgag cagcacagca agcgccctgg 2880
gaaagctgca ggacgtggtc aaccagaatg cccaggcact gaacaccctg gtcaagcagc 2940
tgtcctccaa cttcggcgcc atcagctctg tgctgaacga tatcctggcc agactggacc 3000
ctcctgaggc cgaggtgcag atcgacagac tgatcacagg cagactgcag agcctccagc 3060
atacgtgac ccagcagctg atcagagccg ccgagattag agcctctgcc aatctggccg 3120
ccaccaagat gtctgagtgt gtgctgggcc agagcaagag agtggacttt tgcggcaagg 3180
gctaccacct gatgagcttc cctcagtctg cccctcacgg cgtggtgttt ctgcacgtga 3240
catatgtgcc cgctcaagag aagaatttca ccaccgctcc agccatctgc cacgacgtga 3300
aagcccactt tcctagagaa ggcgtgttcg tgtccaacgg cacccattgg ttcgtgacac 3360
agcggaactt ctacgagccc cagatcatca ccacccacaa caccttcgtg tctggcaact 3420
gcgacgtcgt gatcggcatt gtgaacaata ccgtgtacga ccctctgcag cccgagctgg 3480
acagcttcaa agaggaactg gacaagtact ttaagaacca cacaagcccc gacgtggacc 3540
tgggcgatat cagcggaatc aatgccagcg tcgtgaacat ccagaaagag atcgaccggc 3600
tgaacgaggt ggccaagaat ctgaacgaga gcctgatcga cctgcaagaa ctggggaagt 3660
acgagcagta catcaagtgg ccctggtaca tctggctggg cttatcgcc ggactgattg 3720
ccatcgtgat ggtcacaatc atgctgtgtt gcatgaccag ctgctgtagc tgcctgaagg 3780
gctgttgtag ctgtggcagc tgctgcaagt tcgacgagga cgattctgag ccgtgctga 3840
agggcgtgaa actgcactac acatgatgag atctgctggt actgcatgca cgcaatgcta 3900
gctgcccctt tccgtcctg ggtaccccga gtctccccg acctcgggtc ccaggtatgc 3960
tcccacctcc acctgcccca ctcaccacct ctgctagttc cagacacctc ccaagcacgc 4020
agcaatgcag ctcaaaacgc ttagcctagc cacacccca cggaaacag cagtgattaa 4080
cctttagcaa taaacgaaag tttaactaag ctatactaac cccagggttg gtcaatttcg 4140
tgccagccac accctggagc tagcaaaaaa aaaaaaaaa aaaaaaaa aaaagcatat 4200
gactaaaaaa aaaaaaaa aaaaaaaaa aaaaaaaa aaaaaaaaa aaaaaaaaaa 4260
aaaaaaaaaa aaaa                                                  4274
```

SEQ ID NO: 61        moltype = AA  length = 1271
FEATURE              Location/Qualifiers
source               1..1271
                        mol_type = protein
                        organism = synthetic construct

```
SEQUENCE: 61
MFVFLVLLPL VSSQCVNLRT RTQLPPAYTN SFTRGVYYPD KVFRSSVLHS TQDLFLPFFS   60
NVTWFHAIHV SGTNGTKRFD NPVLPFNDGV YFASTEKSNI IRGWIFGTTL DSKTQSLLIV  120
NNATNVVIKV CEFQFCNDPF LDVYYHKNNK SWMESGVYSS ANNCTFEYVS QPFLMDLEGK  180
QGNFKNLREF VFKNIDGYFK IYSKHTPINL VRDLPQGFSA LEPLVDLPIG INITRFQTLL  240
ALHRSYLTPG DSSSGWTAGA AAYYVGYLQP RTFLLKYNEN GTITDAVDCA LDPLSETKCT  300
LKSFTVEKGI YQTSNFRVQP TESIVRFPNI TNLCPFGEVF NATRFASVYA WNRKRISNCV  360
ADYSVLYNSA SFSTFKCYGV SPTKLNDLCF TNVYADSFVI RGDEVRQIAP GQTGKIADYN  420
YKLPDDFTGC VIAWNSNNLD SKVGGNYNYR YRLFRKSNLK PFERDISTEI YQAGSKPCNG  480
VEGFNCYFPL QSYGFQPTNG VGYQPYRVVV LSFELLHAPA TVCGPKKSTN LVKNKCVNFN  540
FNGLTGTGVL TESNKKFLPF QQFGRDIADT TDAVRDPQTL EILDITPCSF GGVSVITPGT  600
NTSNQVAVLY QGVNCTEVPV AIHADQLTPT WRVYSTGSNV FQTRAGCLIG AEHVNNSYEC  660
DIPIGAGICA SYQTQTNSRR RARSVASQSI IAYTMSLGAE NSVAYSNNSI AIPTNFTISV  720
TTEILPVSMT KTSVDCTMYI CGDSTECSNL LLQYGSFCTQ LNRALTGIAV EQDKNTQEVF  780
AQVKQIYKTP PIKDFGGFNF SQILPDPSKP SKRSFIEDLL FNKVTLADAG FIKQYGDCLG  840
DIAARDLICA QKFNGLTVLP PLLTDEMIAQ YTSALLAGTI TSGWTFGAGA ALQIPFAMQM  900
AYRFNGIGVT QNVLYENQKL IANQFNSAIG KIQDSLSSTA SALGKLQNVV NQNAQALNTL  960
VKQLSSNFGA ISSVLNDILS RLDPPEAEVQ IDRLITGRLQ SLQTYVTQQL IRAAEIRASA 1020
NLAATKMSEC VLGQSKRVDF CGKGYHLMSF PQSAPHGVVF LHVTYVPAQE KNFTTAPAIC 1080
HDGKAHFPRE GVFVSNGTHW FVTQRNFYEP QIITTDNTFV SGNCDVVIGI VNNTVYDPLQ 1140
PELDSFKEEL DKYFKNHTSP DVDLGDISGI NASVVNIQKE IDRLNEVAKN LNESLIDLQE 1200
LGKYEQYIKW PWYIWLGFIA GLIAIVMVTI MLCCMTSCCS CLKGCCSCGS CCKFDEDDSE 1260
PVLKGVKLHY T                                                     1271
```

SEQ ID NO: 62        moltype = DNA  length = 3819
FEATURE              Location/Qualifiers

| | | |
|---|---|---|
| source | 1..3819 | |
| | mol_type = other DNA | |
| | organism = synthetic construct | |

SEQUENCE: 62

```
atgttcgtgt tcctggtgct gctgcctctg gtgtccagcc agtgtgtgaa cctgagaacc    60
agaacacagc tgcctccagc ctacaccaac agctttacca gaggcgtgta ctaccccgac   120
aaggtgttca gatccagcgt gctgcactct acccaggacc tgttcctgcc tttcttcagc   180
aacgtgacct ggttccacgc catccacgtg tccggcacca atggcaccaa gagattcgac   240
aaccccgtgc tgcccttcaa cgacggggtg tactttgcca gcaccgagaa gtccaacatc   300
atcagagact ggatcttcgg caccacactg gacagcaaga cccagagcct gctgatcgtg   360
aacaacgcca ccaacgtggt catcaaagtg tgcgagttcc agttctgcaa cgaccccttc   420
ctggacgtct actaccacaa gaacaacaag agctggatgg aaagcggcgt gtacagcagc   480
gccaacaact gcaccttcga gtacgtgtcc cagccttttc ctgatggacct ggaaggcaag   540
cagggcaact tcaagaacct gcgcgagttc gtgtttaaga acatcgacgg ctacttcaag   600
atctacagca agcacacccc tatcaactcc gtgcgggatc tgcctcaggg cttctctgct   660
ctggaacccc tggtggatct gcccatcggc atcaacatca cccggtttca gacactgctg   720
gccctgcaca gaagctacct gacacctggc gatagcagca gcggatggac agctggtgcc   780
gccgcttact atgtgggcta cctgcagcct agaaccttcc tgctgaagta caacgagaac   840
ggcaccatca ccgacgccgt ggattgtgct ctggatcctc tgagcgagac aaagtgcacc   900
ctgaagtcct tcaccgtgga aagggcatc taccagacca gcaacttccg ggtgcagccc   960
accgaatcca tcgtgcggtt ccccaatatc accaatctgt gcccccttcgg cgaggtgttc  1020
aatgccacca gattcgcctc tgtgtacgcc tggaaccgga agcggatcag caattgcgtg  1080
gccgactact ccgtgctgta caactccgcc agcttcagca ccttcaagtg ctacggcgtg  1140
tcccctacca agctgaacga cctgtgcttc acaaacgtgt acgccgacag cttcgtgatc  1200
cggggagatg aagtgcggca gattgcccct ggacagacag gcaagatcgc cgactacaac  1260
tacaagctgc ccgacgactt caccggctgt gtgattgcct ggaacagcaa caacctggac  1320
tccaaagtcg gcggcaacta caattacagg taccggctgt tccggaagtc caatctgaag  1380
cccttcgagc gggacatctc caccgagatc tatcaggccg gcagcaagcc ttgtaacggc  1440
gtggaaggct tcaactgcta cttccccactg cagtcctacg gctttcagcc cacaaatggc  1500
gtgggctatc agccctacag agtggtggtg ctgagcttcg aactgctgca tgcccctgcc  1560
acagtgtgcg gccctaagaa aagcaccaat ctcgtgaaga caaatgcgt gaacttcaac  1620
ttcaacggcc tgaccggcac cggcgtgctg acagagagca caagaagtt cctgccattc  1680
cagcagtttg gccgggatat cgccgatacc acagacgccg ttagatacc ccagacactg  1740
gaaatcctgg acatcacccc ttgcagcttc ggcgagtgc tgtgatcac ccctggcacc  1800
aacaccagca atcaggtggc agtgctgtac cagggcgtga actgtaccga agtgcccgtg  1860
gccattcacg ccgatcagct gacacctaca tggcgggtgt actccaccgg cagcaatgtg  1920
tttcagacca gagccggctg tctgatcgga gccgagcacg tgaacaatag ctacgagtgc  1980
gacatcccca tcggcgctgg aatctgcgcc agctaccaga cacagacaaa cagcaggcgg  2040
agagccagaa gcgtggccag ccagagcatc attgcctaca caatgtctct gggcgccgaa  2100
aacagcgtgg cctactccaa caactctatc gctatcccca ccaacttcac catcagcgtg  2160
accacagaga tcctgcctgt gtccatgacc aagaccagcg tggactgcac catgtacatc  2220
tgcggcgatt ccaccgagtg ctccaacctg ctgctgcagt acggcagctt ctgcacccag  2280
ctgaatagag ccctgacagg gatcgccgtg gaacaggaca agaacccca gaggtgttc  2340
gcccaagtga agcagatcta caagaccct cctatcaagg acttcggcgg cttcaatttc  2400
agccagattc tgcccgatcc tagcaagccc agcaagcgga gcttcatcga ggacctgctg  2460
ttcaacaaag tgacactggc cgacgccggc ttcatcaagc agtatggcga ttgtctgggc  2520
gacattgccg ccagggatct gatttgcgcc cagaagttta aggactgac agtgctgcct  2580
cctctgctga ccgatgagat gatcgcccag tacacatctg ccctgctggc cggcacaatc  2640
acaagcggct ggacatttgg agcaggcgcc gctctgcaga tccccttttgc tatgcagatg  2700
gcctaccggt tcaacggcat cggagtgacc cagaatgtgc tgtacgagaa ccagaagctg  2760
atcgccaacc agttcaacag cgccatcggc aagatccagg acagcctgag cacacagca  2820
agcgccctgg gaaagctgca gaacgtggtc aaccagaatg cccaggcact gaacaccctg  2880
gtcaagcagc tgtcctccaa cttcggcgcc atcagctctg tgctgaacga tatcctgagc  2940
agactggacc ctcctgaggc cgaggtgcag atcgacagac tgatcacagg cagactgcag  3000
agcctccaga catcgtgac cagcagctg atcagagccg ccgagattag agcctctgcc  3060
aatctggccg ccaccaagat gtctgagtgt gtgctgggcc agagcaagag agtggacttt  3120
tgcggcaagg gctaccacct gatgagcttc cctcagtctg cccctcacgg cgtggtgttt  3180
ctgcacgtga catatgtgcc cgctcaagag aagaatttca ccaccgctcc agccatctgc  3240
cacgacgca aagccactt tcctagagaa ggcgtgttcg tgtccaacgg cacccattgg  3300
ttcgtgacac agcggaactt ctacgagccc cagatcatca ccaccgacaa caccttcgtg  3360
tctggcaact cgacgtcgt gatcggcatt gtgaacaata ccgtgtacga ccctctgcag  3420
cccgagctgg acagcttcaa agaggaactg gacaagtact taagaacca cacaagccc  3480
gacgtggacc tgggcgatat cagcggaatc aatgccagcg tcgtgaacat ccagaaagag  3540
atcgaccggc tgaacgaggt ggccaagaat ctgaacgaga agctgatcga cctgcaagaa  3600
ctggggaagt acgagcagta catcaagtgg ccctggtaca tctggctggg ctttatcgcc  3660
ggactgattg ccatcgtgat ggtcacaatc atgctgtgtt gcatgaccag ctgctgtagc  3720
tgcctgaagg gctgttgtag ctgtggcagc tgctgcaagt cgacgagga cgattctgag  3780
cccgtgctga agggcgtgaa actgcactac acatgatga                          3819
```

| | | |
|---|---|---|
| SEQ ID NO: 63 | moltype = DNA length = 4277 | |
| FEATURE | Location/Qualifiers | |
| source | 1..4277 | |
| | mol_type = other DNA | |
| | organism = synthetic construct | |

SEQUENCE: 63

```
agaataaact agtattcttc tggtccccac agactcagag agaacccgcc accatgttcg    60
tgttcctggt gctgctgcct ctggtgtcca gccagtgtgt gaacctgaga accagaacac   120
agctgcctca gcctacacc aacagcttta ccagaggcgt gtactacccc gacaaggtgt   180
tcagatccag cgtgctgcac tctacccagg acctgttcct gcctttcttc agcaacgtga   240
```

```
cctggttcca cgccatccac gtgtccggca ccaatggcac caagagattc gacaaccccg    300
tgctgccctt caacgacggg gtgtactttg ccagcaccga gaagtccaac atcatcagag    360
gctggatctt cggcaccaca ctggacagca agacccagag cctgctgatc gtgaacaacg    420
ccaccaacgt ggtcatcaaa gtgtgcgagt tccagttctg caacgacccc ttcctggacg    480
tctactacca caagaacaac aagagctgga tggaaagcga cgtgtacagc agcgccaaca    540
actgcacctt cgagtacgtg tcccagcctt cctgatgga cctggaaggc aagcagggca    600
acttcaagaa cctgcgcgag ttcgtgttta agaacatcga cggctacttc aagatctaca    660
gcaagcacac ccctatcaac ctcgtgcggg atctgcctca gggcttctct gctctggaac    720
ccctggtgga tctgcccatc ggcatcaaca tcacccggtt tcagacactg ctggccctgc    780
acagaagcta cctgacacct ggcgatagca gcagcggatg gacagctggt gccgccgctt    840
actatgtggg ctacctgcag cctagaacct tcctgctgaa gtacaacgag aacggcacca    900
tcaccgacgc cgtggattgt gctctggatc ctctgagcga gacaaagtgc accctgaagt    960
ccttcaccgt ggaaaagggc atctaccaga ccagcaactt ccgggtgcag cccaccgaat   1020
ccatcgtgcg gttccccaat atcaccaatc tgtgccctt cggcgaggtg ttcaatgcca   1080
ccagattcgc ctctgtgtac gcctggaacc ggaagcggaa cagcaattgc gtggccgact   1140
actccgtgct gtacaactcc gccagcttca gcaccttcaa gtgctacggc gtgtccccta   1200
ccaagctgaa cgacctgtgc ttcacaaacg tgtacgccga cagcttcgtg atccgggag   1260
atgaagtgcg gcagattgcc cctgcagca caggcaagat cgccgactac aactacaagc   1320
tgcccgacga cttcaccggc tgtgtgattg cctggaacag caacaacctg gactccaaag   1380
tcggcggcaa ctacaattac aggtaccggc tgttccggaa gtccaatctg aagcccttcg   1440
agcgggacat ctccaccgag atctatcagg ccggcagcaa gccttgtaac ggcgtggaag   1500
gcttcaactg ctacttccca ctgcagtcct acggctttca gcccacaaat ggcgtgggct   1560
atcagcccta cagagtggtg gtgctgagct cgaactgct gcatgcccct gccacagtgt   1620
gcggccctaa gaaaagcacc aatctcgtga agaacaaatg cgtgaacttc aacttcaacg   1680
gcctgaccgg caccggcgtg ctgacagaga gcaacaagaa gttcctgcca ttccagcagt   1740
ttggccggga tatcgccgat accacagacg ccgttagaga tccccagaca ctggaaatcc   1800
tggacatcac cccttgcagc ttcggcgagg tgtctgtgat caccctggc accaacacca   1860
gcaatcaggt ggcagtgctg taccagggcg tgaactgtac cgaagtgccc gtggccattc   1920
acgccgatca gctgacacct acatggcggg tgtactccac cggcagcaat gtgtttcaga   1980
ccagagcgg ctgtctgatc ggagccgagc acgtgaacaa tagctacgag tgcgacatcc   2040
ccatcggcgc tggaatctgc gccagctacc agacacagac aaacagcagg cggagagcca   2100
gaagcgtggc cagccagagc atcattgcct acacaatgtc tctgggcgcc gagaacagcg   2160
tggcctactc caacaactct atcgctatcc ccaccaactt caccatcagc gtgaccacag   2220
agatcctgcc tgtgtccatg accaagacca gcgtggactg caccatgtac atctgcggcg   2280
attccaccga gtgctccaac ctgctgctgc agtacggcag cttctgcacc cagctgaata   2340
gagccctgac agggatcgcc gtggaacagg acaagaacac ccaagaggtg ttcgcccaag   2400
tgaagcagat ctacaagacc cctcctatca aggacttcgg cggcttcaat ttcagccaga   2460
ttctgcccga tcctagcaag cccagcaagc ggagcttcat cgaggacctg ctgttcaaca   2520
aagtgacact ggccgacgcc ggcttcatca gcagtatgc cgattgtctg ggcgacattg   2580
ccgccaggga tctgatttgc gcccagaagt ttaacggact gacagtgctg cctcctctgc   2640
tgaccgatga gatgatcgcc cagtacacat ctgcccgct ggccggcaca atcacaagcg   2700
gctggacatt tggagcaggc gccgctctgc agatccccctt tgctatgcag atggcctacc   2760
ggttcaacgg catcggagtg acccagaatg tgctgtacga gaaccagaag ctgatcgcca   2820
accagttcaa cagcgccatc ggcaagatcc aggacagcct gagcagcaca gcaagcgccc   2880
tgggaaagct gcagaacgtg gtcaaccaga atgcccaggc actgaacacc ctggtcaagc   2940
agctgtcctc caacttcggc gccatcagct ctgtgctgaa cgatatcctg agcagactgg   3000
accctcctga ggccgaggtg cagatcgaca ggctgatcac aggcagactg cagagcctcc   3060
agacatacgt gacccagcag ctgatcagag ccgccgagat tagagcctct gccaatctgg   3120
ccgccaccaa gatgtctgag tgtgtgctgg ccagagcaa gagagtggac ttttgcggca   3180
agggctacca ccctgatgagc ttccctcagt ctgcccctca cggcgtggtg tttctgcacg   3240
tgacatatgt gcccgctcaa gagaagaatt tcaccaccgc tccagccatc tgccacgacg   3300
gcaaagccca ctttcctaga gaaggcgtgt tcgtgtccaa cggcacccat tggttcgtga   3360
cacagcggaa cttctacgag ccccagatca tcaccaccga caacacctc gtgtctggca   3420
actgcgacgt cgtgatcggc attgtgaaca ataccgtgta cgaccctctg cagcccgagc   3480
tggacagctt caaagaggaa ctggacaagt actttaagaa ccacacaagc cccgacgtgg   3540
acctgggcga tatcagcgga atcaatgcca gcgtcgtgaa catccagaaa gagatcgacc   3600
ggctgaacga ggtggccaag aatctgaacg agagcctgat cgacctgcaa gaactcggga   3660
agtacgagca gtacatcaag tggcccctgg acatctggct gggctttatc gccggactga   3720
ttgccatcgt gatggtcaca atcatgctgt gttgcatgac cagctgctgt agctgcctga   3780
agggctgttg tagctgtggc agctgctgca gttcgacga ggacgattct gagcccgtgc   3840
tgaagggcgt gaaactgcac tacacatgat gatttcacct ggtactgcat gcacgcaatg   3900
ctagctgccc ctttccgtc ctgggtaccc gagtctcc ccgacctcgg gtcccaggta   3960
tgctcccacc tccacctgcc ccactcacca cctctgctag ttccagacac ctcccaagca   4020
cgcagcaatg cagctcaaaa cgcttagcct agccacaccc cacgggaaa cagcagtgat   4080
taacctttag caataaacga aagtttaact aagctatcct aaccccaggg ttggtcaatt   4140
tcgtgccagc cacaccctgg agctagcaaa aaaaaaaaaa aaaaaaaaaa aaaaaagca   4200
tatgactaaa aaaaaaaaaa aaaaaaaaa aaaaaaaaa aaaaaaaaa aaaaaaaaaa   4260
aaaaaaaaaa aaaaaaa                                                4277

SEQ ID NO: 64         moltype = AA  length = 1270
FEATURE               Location/Qualifiers
source                1..1270
                      mol_type = protein
                      organism = synthetic construct
SEQUENCE: 64
MFVFLVLLPL VSSQCVNLIT RTQSYTNSFT RGVYYPDKVF RSSVLHSTQD LFLPFFSNVT    60
WFHAIHVSGT NGTKRFDNPV LPFNDGVYFA STEKSNIIRG WIFGTTLDSK TQSLLIVNNA   120
TNVVIKVCEF QFCNDPFLDV YYHKNNKSWM ESEFRVYSSA NNCTFEYVSQ PFLMDLEGKQ   180
GNFKNLREFV FKNIDGYFKI YSKHTPINLG RDLPQGFSAL EPLVDLPIGI NITRFQTLLA   240
```

```
LHRSYLTPGD SSSGWTAGAA AYYVGYLQPR TFLLKYNENG TITDAVDCAL DPLSETKCTL    300
KSFTVEKGIY QTSNFRVQPT ESIVRFPNIT NLCPFDEVFN ATRFASVYAW NRKRISNCVA    360
DYSVLYNFAP FFAFKCYGVS PTKLNDLCFT NVYADSFVIR GNEVSQIAPG QTGNIADYNY    420
KLPDDFTGCV IAWNSNKLDS KVGGNYNYLY RLFRKSNLKP FERDISTEIY QAGNKPCNGV    480
AGFNCYFPLR SYGFRPTYGV GHQPYRVVVL SFELLHAPAT VCGPKKSTNL VKNKCVNFNF    540
NGLTGTGVLT ESNKKFLPFQ QFGRDIADTT DAVRDPQTLE ILDITPCSFG GVSVITPGTN    600
TSNQVAVLYQ GVNCTEVPVA IHADQLTPTW RVYSTGSNVF QTRAGCLIGA EYVNNSYECD    660
IPIGAGICAS YQTQTKSHRR ARSVASQSII AYTMSLGAEN SVAYSNNSIA IPTNFTISVT    720
TEILPVSMTK TSVDCTMYIC GDSTECSNLL LQYGSFCTQL KRALTGIAVE QDKNTQEVFA    780
QVKQIYKTPP IKYFGGFNFS QILPDPSKPS KRSFIEDLLF NKVTLADAGF IKQYGDCLGD    840
IAARDLICAQ KFNGLTVLPP LLTDEMIAQY TSALLAGTIT SGWTFGAGAA LQIPFAMQMA    900
YRFNGIGVTQ NVLYENQKLI ANQFNSAIGK IQDSLSSTAS ALGKLQDVVN HNAQALNTLV    960
KQLSSKFGAI SSVLNDILSR LDPPEAEVQI DRLITGRLQS LQTYVTQQLI RAAEIRASAN   1020
LAATKMSECV LGQSKRVDFC GKGYHLMSFP QSAPHGVVFL HVTYVPAQEK NFTTAPAICH   1080
DGKAHFPREG VFVSNGTHWF VTQRNFYEPQ IITTDNTFVS GNCDVVIGIV NNTVYDPLQP   1140
ELDSFKEELD KYFKNHTSPD VDLGDISGIN ASVVNIQKEI DRLNEVAKNL NESLIDLQEL   1200
GKYEQYIKWP WYIWLGFIAG LIAIVMVTIM LCCMTSCCSC LKGCCSCGSC CKFDEDDSEP   1260
VLKGVKLHYT                                                         1270

SEQ ID NO: 65           moltype = RNA   length = 3816
FEATURE                 Location/Qualifiers
source                  1..3816
                        mol_type = other RNA
                        organism = synthetic construct
SEQUENCE: 65
atgttcgtgt tcctggtgct gctgcctctg gtgtccagcc agtgtgtgaa cctgatcacc     60
agaacacagt catacaccaa cagctttacc agaggcgtgt actacccga caaggtgttc    120
agatccagcg tgctgcactc tacccaggac tgttcctgc cttcttcag caacgtgacc     180
tggttccacg ccatccacgt gtccggcacc aatggcacca agagattcga caaccccgtg    240
ctgcccttca acgacggggt gtactttgcc agcaccgaga gtccaacat catcagaggc     300
tggatcttcg gcaccacact ggacagcaag acccagagcc tgctgatcgt gaacaacgcc    360
accaacgtgg tcatcaaagt gtgcgagttc cagttctgca acgacccctt cctggacgtc    420
tactaccaca gaacaacaa gagctggatg gaaagcgagt ccgggtgta cagcagcgcc     480
aacaactgca cctttgagta cgtgtcccag ccttttcctga tggacctgga aggcaagcag    540
ggcaacttca agaacctgcg cgagttcgtg tttaagaaca tcgacggcta cttcaagatc    600
tacagcaagc acacccctat caacctcggc cgggatctgc ctcagggctt ctctgctctg    660
gaaccctgg tggatctgcc catcggcatc aacatcaccc ggtttcagac actgctggcc     720
ctgcacagaa gctacctgac acctggcgat agcagcagcg gatggacagc tggtgccgcc    780
gcttactatg tgggctacct gcagcctaga accttcctgc tgaagtacaa cgagaacggc    840
accatcaccg acgccgtgga ttgtgctctg gatcctctga gcgagacaaa gtgcaccctg    900
aagtccttca ccgtggaaaa gggcatctac cagaccagca acttccgggt gcagcccacc    960
gaatccatcg tgcggttccc caatatcacc aatctgtgcc ccttcgacga ggtgttcaat   1020
gccaccagat tcgcctctgt gtacgcctgg aaccggaagc ggatcagcaa ttgcgtggcc   1080
gactactccg tgctgtacaa cttcgccccc ttcttcgcat tcaagtgcta cggcgtgtcc   1140
cctaccaagc tgaacgacct gtgcttcaca aacgtgtacg ccgacagctt cgtgatccgg   1200
ggaaacgaag tgtcacagat tgcccctgga cagacaggca acatcgccga ctacaactac   1260
aagctgcccg acgacttcac cggctgtgtg attgcctgga acagcaacaa gctggactcc   1320
aaagtcggcg gcaactacaa ttacctgtac cggctgttcc ggaagtccaa tctgaagccc   1380
ttcgagcggg acatctccac cgagatctat caggccggca caagccttg taacggcgtg   1440
gcaggcttca actgctactt cccactgagg tcctacggct ttaggcccac atacggcgtg   1500
ggccaccagc cctacagagt ggtggtgctg agcttcgaac tgctgcatgc ccctgccaca   1560
gtgtgcggcc ctaagaaaag caccaatctc gtgaagaaca aatgcgtgaa cttcaacttc   1620
aacggcctga ccggcaccgg cgtgctgaca gagagcaaca agaagttcct gccattccag   1680
cagtttggcc gggatatcgc cgataccaca gacgccgtta gagatcccca gacactggaa   1740
atcctggaca tcaccccttg cagcttcggc ggagtgtctg tgatcacccc tggcaccaac   1800
accagcaatc aggtggcagt gctgtaccag ggcgtgaact gtaccgaagt gcccgtggcc   1860
attcacgccg atcagctgac acctacatgg cgggtgtact ccaccggcag caatgtgttt   1920
cagaccagag ccgctgtct gatcggagcc gagtacgtga acaatagcta cgagtgcgac   1980
atcccatcg gcgctggaat ctgcgctagc taccagacac agacaaagag caccggaaca   2040
gccagaagcg tggccagcca gagcatcatt gcctacacaa tgtctctggg cgccgagaac   2100
agcgtggcct actccaacaa ctctatcgct atccccacca acttcaccat cagcgtgacc   2160
acagagatcc tgcctgtgtc catgaccaag accagcgtgg actgcaccat gtacatctgc   2220
ggcgattcca ccgagtgctc caacctgctg ctgcagtacg gcagcttctg cacccagctg   2280
aaaagagcc tgacagggat cgccgtggaa caggacaaga acacccaaga ggtgttcgcc   2340
caagtgaagc agatctacaa gacccctcct atcaagtact tcggcggctt caatttcagc   2400
cagattctgc ccgatcctag caagcccagc aagcggagct tcatcgagga cctgctgttc   2460
aacaaagtga cactggccga cgccggcttc atcaagcagt atggcgattg tctgggcgac   2520
attgccgcca gggatctgat ttgcgcccag aagtttaacg gactgacagt gctgcctcct   2580
ctgctgaccg atgagatgat cgcccagtac acatctgccg ctgccggg cacaatcaca   2640
agcggctgga catttggagc aggcgccgct ctgcagatcc cctttgctat gcagatggcc   2700
taccggttca acggcatcgg agtgacccag aatgtgctgt acgagaacca gaagctgatc   2760
gccaaccagt tcaacagcgc catcggcaag atccaggaca gcctgagcag cacagcaagc   2820
gccctgggaa agctgcagga cgtggtcaac cacaatgccc aggcactgaa caccctggtc   2880
aagcagctgt cctccaagtt tggcgccatc agctctgtgc tgaacgatat cctgagcaga   2940
ctggacccta tgagggccga ggtgcagatc gacagactga tcacaggcag actgcagagc   3000
ctccagacat acgtgaccca gcagctgatc agagccgccg agattagagc ctctgccaat   3060
ctggccgcca ccaagatgtc tgagtgtgtg ctgggccaga gcaagagagt ggactttgc   3120
ggcaagggct accacctgat gagcttccct cagtctgccc ctcacggcgt ggtgtttctg   3180
cacgtgacat atgtgcccgc tcaagagaag aatttccacca ccgctccagc catctgccac   3240
```

```
gacggcaaag cccactttcc tagagaaggc gtgttcgtgt ccaacggcac ccattggttc 3300
gtgacacagc ggaacttcta cgagcccag  atcatcacca ccgacaacac cttcgtgtct 3360
ggcaactgcg acgtcgtgat cggcattgtg aacaataccg tgtacgaccc tctgcagccc 3420
gagctggaca gcttcaaaga ggaactggac aagtacttta agaaccacac aagccccgac 3480
gtggacctgg gcgatatcag cggaatcaat gccagcgtcg tgaacatcca gaaagagatc 3540
gaccggctga acgaggtggc caagaatctg aacgagagcc tgatcgacct gcaagaactg 3600
gggaagtacg agcagtacat caagtggccc tggtacatct ggctgggctt tatcgccgga 3660
ctgattgcca tcgtgatggt cacaatcatg ctgtgttgca tgaccagctg ctgtagctgc 3720
ctgaagggct gttgtagctg tggcagctgc tgcaagttcg acgaggacga ttctgagccc 3780
gtgctgaagg gcgtgaaact gcactacaca tgatga                           3816
```

SEQ ID NO: 66           moltype = DNA   length = 3816
FEATURE                 Location/Qualifiers
source                  1..3816
                        mol_type = other DNA
                        organism = synthetic construct
SEQUENCE: 66

```
atgttcgtgt tcctggtgct gctgcctctg gtgtccagcc agtgtgtgaa cctgatcacc 60
agaacacagt catacaccaa cagctttacc agaggcgtgt actacccga  caaggtgttc 120
agatccagcg tgctgcactc tacccaggac tgttcctgc  cttcttcag  caacgtgacc 180
tggttccacg ccatccacgt gtccggcacc aatggcacca agagattcga caaccccgtg 240
ctgcccttca acgacgggt  gtactttgcc agcaccgaga agtccaacat catcagagc  300
tggatcttcg gcaccacact ggacagcaag acccagagcc tgctgatcgt gaacaacgcc 360
accaacgtgg tcatcaaagt gtgcgagttc agttctgca  acgaccctt  cctgacgtc  420
tactaccaca agaacaacaa gagctggatg gaaagcgagt tccgggtgta cagcagcgcc 480
aacaactgca ccttcgagta cgtgtcccag ccttcctga  tggacctga  aggcaagcag 540
ggcaacttca gaacctgcg  cgagttcgtg tttaagaaca tcgacggcta cttcaagatc 600
tacagcaagc acacccctat caacctcggc cgggatctgc ctcagggctt ctctgctctg 660
gaaccctg   tggatctgcc catcggcatc aacatcaccc ggtttcagac actgctggcc 720
ctgcacagaa gctacctgac acctggcgat agcagcagcg gatggacagc tggtgccgcc 780
gcttactatg tgggctacct gcagcctaga accttcctgc tgaagtacaa cgagaacggc 840
accatcaccg acgccgtgga ttgtgctctg gatcctctga gcgagacaaa gtgcaccctg 900
aagtccttca ccgtggaaaa gggcatctac cagaccagca cttccgggt  gcagcccacc 960
gaatcctcca tgcggttccc caatatcacc aatctgtgcc ccttcgacga ggtgttcaat 1020
gccaccagat tcgcctctgt tacgcctgg  aaccggaagc ggatcagcaa ttgcgtggcc 1080
gactactccg tgctgtacaa cttcgccccc ttcttcgcat tcaagtgcta cggcgtgtcc 1140
cctaccaagc tgaacgacct gtgcttcaca acgtgtacg  ccgacagctt cgtgatccgg 1200
ggaaacgaag tgtcacagat tgcccctgga cagacaggca acatgccga  ctacaactac 1260
aagctgcccg acgacttcac cggctgtgtg attgcctgga acagcaacaa gctggactcc 1320
aaagtcggcg gcaactacaa ttacctgtac cggctgttcc ggaagtccaa tctgaagccc 1380
ttcgagcggg acatctccac cgagatctat caggccggca acaagccttg taacggcgtg 1440
gcaggcttca actgctactt cccactgagg tcctacggct taggccac  atacggcgtg 1500
ggccaccagc cctacagagt ggtggtgctg agcttcgaac tgctgcatgc ccctgccaca 1560
gtgtgcggcc ctaagaaaag caccaatctc gtgaagaaca aatgcgtgaa cttcaacttc 1620
aacgcctga  ccggcaccgg cgtgctgaca gagagcaaca gaagttcct  gccattccag 1680
cagtttggcc gggatatcgc cgataccaca gacgccgtta gagatcccca gacactggaa 1740
atcctggaca tcacccctg  cagcttcggc ggagtgctg  tgatcaccc  tggcaccaac 1800
accagcaatc aggtggcagt gctgtaccag ggcgtgaact gtaccgaagt gcccgtggcc 1860
attcacgccg atcagctgac acctacatgg cgggtgtact ccaccggcag caatgtgttt 1920
cagaccagag ccggctgtct gatcggagcc gagtacgtga caatagcta  cgagtgcgac 1980
atccccatcg gcgctggaat ctgcgccagc taccagacac agacaaagag ccaccggaca 2040
gccagaagcg tggccagcca gagcatcatt gcctacacaa tgtctctggg cgccgagaac 2100
agcgtggcct actccaacaa ctctatcgct atccccacca acttcaccat cagcgtgacc 2160
acagagatcc tgcctgtgtc catgaccaag accagcgtgg actgcaccat gtacatctgc 2220
ggcgattcca ccgagtgctc caacctgctg ctgcagtacg gcagcttctg cacccagctg 2280
aaaagagccc tgacagggat cgccgtggaa caggacaaga acacccaaga ggtgttcgcc 2340
caagtgaagc agatctacaa gacccctcct atcaagtact cggcggctt  caatttcagc 2400
cagattctgc ccgatcctag caagcccagc aagcggagct catcgagga  cctgctgttc 2460
aacaaagtga cactggccga cgccggcttc atcaagcagt atggcgattg tctgggcgac 2520
attgccgcca gggatctgat ttgcgcccag aagtttaacg gactgacagt gctgcctcct 2580
ctgctgaccg atgagatgat cgcccagtac acatctgccc tgctggccgg cacaatcaca 2640
agcggctgga catttggagc aggcgccgct ctgcagatcc cctttgctat gcagatggcc 2700
taccggttca acggcatcgg agtgacccag aatgtgctgt acgagaacca gaagctgatc 2760
gccaaccagt tcaacagcgc catcggcaag atccaggacg ctgagcag   cacagcaagc 2820
gccctgggaa agctgcagga cgtggtcaac cacaatgccc aggcactgaa cacccctggtc 2880
aagcagctgt cctccaagtt cggcgccatc agctctgtgc tgaacgatat cctgagcaga 2940
ctggaccctc ctgaggccga ggtgcagatc gacagactga tcacaggcag actgcagagc 3000
ctccagacat acgtgaccca gcagctgatc agagccgccg agattagagc ctctgccaat 3060
ctggccgcca ccaagatgtc tgagtgtgtg ctgggccaga gcaagagagt ggacttttg  3120
ggcaagggct accacctgat gagcttccct cagtctgccc ctcacggcgt ggtgtttctg 3180
cacgtgacat atgtgcccgc tcaagagaag aatttcacca ccgctccagc catctgccac 3240
gacggcaaag cccactttcc tagagaaggc gtgttcgtgt ccaacggcac ccattggttc 3300
gtgacacagc ggaacttcta cgagcccag  atcatcacca ccgacaacac cttcgtgtct 3360
ggcaactgcg acgtcgtgat cggcattgtg aacaataccg tgtacgaccc tctgcagccc 3420
gagctggaca gcttcaaaga ggaactggac aagtacttta agaaccacac aagccccgac 3480
gtggacctgg gcgatatcag cggaatcaat gccagcgtcg tgaacatcca gaaagagatc 3540
gaccggctga acgaggtggc caagaatctg aacgagagcc tgatcgacct gcaagaactg 3600
gggaagtacg agcagtacat caagtggccc tggtacatct ggctgggctt tatcgccgga 3660
ctgattgcca tcgtgatggt cacaatcatg ctgtgttgca tgaccagctg ctgtagctgc 3720
```

```
ctgaagggct gttgtagctg tggcagctgc tgcaagttcg acgaggacga ttctgagccc  3780
gtgctgaagg gcgtgaaact gcactacaca tgatga                            3816
```

| SEQ ID NO: 67 | moltype = RNA  length = 4274 |
|---|---|
| FEATURE | Location/Qualifiers |
| source | 1..4274 |
| | mol_type = other RNA |
| | organism = synthetic construct |

SEQUENCE: 67
```
agaataaact agtattcttc tggtccccac agactcagag agaacccgcc accatgttcg  60
tgttcctggt gctgctgcct ctggtgtcca gccagtgtgt gaacctgatc accagaaacac 120
agtcatacac caacagcttt accagaggcg tgtactaccc cgacaaggtg ttcagatcca  180
gcgtgctgca ctctacccag gacctgttcc tgcctttctt cagcaacgtg acctggttcc  240
acgccatcca cgtgtccggc accaatggca ccaagagatt cgacaacccc gtgctgccct  300
tcaacgacgg ggtgtacttt gccagccacg agaagtccaa catcatcaga ggctggatct  360
tcggcaccac actggacagc aagacccaga gcctgctgat cgtgaacaac gccaccaacg  420
tggtcatcaa agtgtgcgag ttccagttct gcaacgaccc cttcctggac gtctactacc  480
acaagaacaa caagagctgg atggaaagcg agttccggat gtacagcagc gccaacaact  540
gcaccttcga gtacgtgtcc cagcctttcc tgatggacct ggaaggcaag cagggcaact  600
tcaagaacct gcgcgagttc gtgtttaaga acatcgacgg ctacttcaag atctacagca  660
agcacacccc tatcaacctc ggcccgggatc tgcctcaggg cttctctgct ctggaacccc  720
tggtggatct gcccatcggc atcaacatca cccggtttca gacactgctg gccctgcaca  780
gaagctacct gacacctggc gatagcagca gcggatggac agctggtgcc gccgcttact  840
atgtgggcta cctgcagcct agaaccttcc tgctgaagta caacgagaac ggcaccatca  900
ccgacgccgt ggattgtgct ctggatcctc tgagcgagac aaagtgcacc ctgaagtcct  960
tcaccgtgga aaagggcatc taccagacca gcaacttcag ggtgcagccc accgaatcca  1020
tcgtgcggtt ccccaatatc accaatctgt gccccttcga cgaggtgttc aatgccacca  1080
gattcgcctc tgtgtacgcc tggaaccgga gcggatcag caattgcgtg gccgactact  1140
ccgtgctgta caactctgcc cccttcttcg cattcaagtg ctacggcgtg tcccctacca  1200
agctgaacga cctgtgcttc acaaacgtgt acgccgacag cttcgtgatc cggggaaacg  1260
aagtgtcaca gattgccct ggacagacag gcaacatcgc cgactacaac tacaagctgc  1320
ccgacgactt caccggctgt gtgattgcct ggaacagcaa caagctggac tccaaagtcg  1380
gcggcaacta caattacctg taccggctgt tccggaagtc caatctgaag cccttcgagc  1440
gggacatctc caccgagatc tatcaggccg gcaacaagcc ttgtaacggc gtggcaggct  1500
tcaactgcta cttcccactg aggtcctacg gctttaggcc cacatacggc gtgggccacc  1560
agccctacag agtggtggtg ctgagcttcg aactgctgca tgcccctgcc acagtgtgcg  1620
gccctaagaa aagcaccaat ctcgtgaaga acaaatgcgt gaacttcaac ttcaacggcc  1680
tgaccggcac cggcgtgctg acagagagca acaagaagtt cctgccattc cagcagtttg  1740
gccgggatat cgccgatacc acagacgccg ttagagatcc ccagacactg gaaatcctgg  1800
acatcacccc ttgcagcttc ggcggagtgt ctgtgatcac ccctggcacc aacaccagca  1860
atcaggtggc agtgctgtac cagggcgtga actgtaccga agtgcccgtg gccattcacg  1920
ccgatcagct gacacctaca tggcgggtgt actccaccgg cagcaatgtg tttcagacca  1980
gagcggctg tctgatcgga gccgagtacg tgaacaatag ctacgagtgc gacatcccca  2040
tcggcgctgg aatctgcgcc agctaccaga cacagacaaa gagccaccgg agagccagaa  2100
gcgtggccag ccagagcatc attgcctaca atgtctct gggcgccgag aacagcgtgg  2160
cctactccaa caactctatc gctatcccca ccaacttcac catcagcgtg accacagaga  2220
tcctgcctgt gtccatgacc aagaccagcg tggactgcac catgtacatc tgcggcgatt  2280
ccaccgagtg ctccaacctg ctgctgcagt acggcagctt ctgcacccag ctgaaaagag  2340
ccctgacagg gatcgccgtg gaacaggaca gaaacccca gaggtgttc gcccaagtga  2400
agcagatcta caagacccct cctatcaagt acttcggcgg cttcaatttc agccagattc  2460
tgcccgatcc tagcaagccc agcaagcgga gcttcatcga ggacctgctg ttcaacaaga  2520
tgacactggc cgacgccggc ttcatcaagc agtatggcga ttgtctgggc gacattgccg  2580
ccagggatct gatttgcgcc cagaagttta acggactgac agtgctgcct cctctgctga  2640
ccgatgagat gatcgcccag tacacatctg ccctgctggc cggcacaatc acaagcggct  2700
ggacatttgg agcaggcgcc gctctgcaga tccccttcgc gatggccacc gcc  2760
tcaacggcat cggagtgacc cagaatgtgc tgtacgagaa ccagaagctg atcgccaacc  2820
agttcaacag cgccatcggc aagatccagg acagcctgag cagcacagca agcgccctgg  2880
gaaagctgca ggacgtggtc aaccacaatg cccaggcact gaacaccctg gtcaagcagc  2940
tgtcctccaa gttcggcgcc atcagctctg tgctgaacga tatcctgagc agactggacc  3000
ctcctgaggc cgaggtgcag atcgacagac tgatcacagg cagactgcag agcctccaga  3060
catacgtgac ccagcagctg atcagagccg ccgagattag agcctctgcc aatctggccg  3120
ccaccaagat gtctgagtgt gtgctggccc agagcaagag agtggacttt tgcggcaagg  3180
gctaccacct gatgagcttc cctcagtctg cccctcacgg cgtggtgttt ctgcacgtga  3240
catatgtgcc cgctcaagag aagaatttca caccgctc agccatctgc cacgacggca  3300
aagcccactt tcctagagaa ggcgtgttcg tgtccaacgg cacccattgg ttcgtgacac  3360
agcggaactt ctacgagccc cagatcatca ccaccgacaa caccttcgtg tctggcaact  3420
gcgacgtcgt gatcggcatt gtgaacaata ccgtgtacga ccctctgcag cccgagctgg  3480
acagcttcaa agaggaactg gacaagtact ttaagaacca cacaagcccc gacgtggacc  3540
tgggcgatat cagcggaatc aatgccagcg tcgtgaacat ccagaaagag atcgaccggc  3600
tgaacgaggt ggccaagaat ctgaacgaga gcctgatcga cctgcaagaa ctggggaagt  3660
acgagcagta catcaagtgg ccctggtaca tctggctggg cttatcgcc ggactgattg  3720
ccatcgtgat ggtcacaatc atgctgtgtt gcatgaccag ctgctgtagc tgcctgaagg  3780
gctgttgtag ctgtggcagc tgctgcaagt tcgacgagga cgattctgag cccgtgctga  3840
agggcgtgaa actgcactac acatgatgac tcgactgact actgcatga cgaatgcta  3900
gctgcccctt tcccgtcctg ggtacccga gtcccccg acctcgggtc ccaggtatgc  3960
tcccacctcc acctgcccca ctcaccacct ctgctagttc cagacacctc ccaagcacgc  4020
agcaatgcag ctcaaaacgc ttagcctagc cacaccccca cggaaacag cagtgattaa  4080
cctttagcaa taaacgaaag tttaactaag ctatactaac cccaggggttg gtcaatttcg  4140
tgccagccac accctggagc tagcaaaaaa aaaaaaaaaa aaaaaaaaaa aaagcatat  4200
```

```
gactaaaaaa aaaaaaaaaa aaaaaaaaaa aaaaaaaaaa aaaaaaaaaa aaaaaaaaaa   4260
aaaaaaaaaa aaaa                                                     4274

SEQ ID NO: 68         moltype = DNA   length = 4274
FEATURE               Location/Qualifiers
source                1..4274
                      mol_type = other DNA
                      organism = synthetic construct
SEQUENCE: 68
agaataaact agtattcttc tggtccccac agactcagag agaacccgcc accatgttcg     60
tgttcctggt gctgctgcct ctggtgtcca gccagtgtgt gaacctgatc accagaaacac   120
agtcatacac caacagcttt accagaggcg tgtactaccc cgacaaggtg ttcagatcca   180
gcgtgctgca ctctacccag gacctgttcc tgcctttctt cagcaacgtg acctggttcc   240
acgccatcca cgtgtccggc accaatggca ccaagagatt cgacaacccc gtgctgccct   300
tcaacgacgg ggtgtacttt gccagcaccg agaagtccaa catcatcaga ggctggatct   360
tcggcaccac actggacagc aagacccaga gcctgctgat cgtgaacaac gccaccaacg   420
tggtcatcaa agtgtgcgag ttccagttct gcaacgaccc cttcctggac gtctactacc   480
acaagaacaa caagagctgg atggaaagcg agttccgggt gtacagcagc gccaacaact   540
gcaccttcga gtacgtgtcc cagcctttcc tgatggacct ggaaggcaag cagggcaact   600
tcaagaacct gcgcgagttc gtgtttaaga acatcgacgg ctacttcaag atctacagca   660
agcacacccc tatcaacctc ggccgggatc tgcctcaggg ctttctgctc tggaacccca   720
tggtggatct gcccatcggc atcaacatca cccggtttca gactctgctg gcctgcaca   780
gaagctacct gacacctggc gatagcagca gcggatggac agctggtgcc gccgcttact   840
atgtgggcta cctgcagcct agaaccttcc tgctgaagta caacgagaac ggcaccatca   900
ccgacgccgt ggattgtgct ctggatcctc tgagcgagac aaagtgcacc ctgaagtcct   960
tcaccgtgga aaagggcatc taccagacca gcaacttccg ggtgcagccc accgaatcca  1020
tcgtgcggtt ccccaatatc accaatctgt gccccttcga cgaggtgttc aatgccacca  1080
gattcgcctc tgtgtacgcc tggaaccgga gcggatcag caattgcgtg gccgactact  1140
ccgtgctgta caacttcgcc cccttcttcg cattcaagtg ctacggcgtg tccctacca   1200
agctgaacga cctgtgcttc acaaacgtgt acgccgacag cttcgtgatc cggggaaacg  1260
aagtgtcaca gattgccct ggacagacag gcaacatcgc cgactacaac tacaagctgc   1320
ccgacgactt caccggctgt gtgattgcct ggaacagcaa caagctggac tccaaagtcg   1380
gcggcaacta caattacctg taccggctgt tccggaagtc caatctgaag cccttcgagc   1440
gggacatctc caccgagatc tatcaggccg gcaacaagcc ttgtaacggc gtggcaggct   1500
tcaactgcta cttcccactg gaggtcctac gctttaggcc cacatacgg gtgggccacc   1560
agccctacag agtggtggtg ctgagcttcg aactgctgca tgccctgcc acagtgtgcg   1620
gccctaagaa aagcaccaat ctcgtgaaga caaatgcgt gaacttcaac ttcaacggcc   1680
tgaccggcac cggcgtgctg acagagagca caagaagtt cctgccattc cagcagtttg   1740
gccgggatat cgccgatacc acagacgccg ttagagatcc ccagacactg gaaatcctg   1800
acatcacccc ttgcagcttc ggcggagtgt ctgtgatcac ccctggcacc aacaccagca   1860
atcaggtggc agtgctgtac cagggcgtga actgtaccga agtgcccgtg gccattcacg   1920
ccgatcagct gacacctaca tggcgggtgt actccaccgg cagcaatgtg tttcagacca   1980
gagccggctg tctgatcgga gccgagtacg tgaacaatag ctacgagtgc gacatcccca   2040
tcggcgctgg aatctgcgcc agctaccaga cacagacaaa gagccaccgg agagccagaa   2100
gcgtggccag ccagagcatc attgcctaca atgtctct gggcgccgag aacagcgtgg   2160
cctactccaa caactctatc gctatccca ccaacttcac catcagcgtg accacagaga   2220
tcctgcctgt gtccatgacc aagaccagcg tggactgcac catgtacatc tgcggcgatt   2280
ccaccgagtg ctccaacctg ctgctgcagt acggcagctt ctgcacccag ctgaaaagag   2340
ccctgacagg gatcgccgtg gaacaggaca gaaacccca gaggtgttc gcccaagtga   2400
agcagatcta caagaccct cctatcaagt acttcggcgg cttcaatttc agccagattc   2460
tgcccgatcc tagcaagccc agcaagcgga gcttcatcga ggacctgctg ttcaacaaag   2520
tgacactggc cgacgccggc ttcatcaagc agtatggcga ttgtctgggc gacattgccg   2580
ccagggatct gatttgcgcc cagaagttta cggactgac agtgctgcct cctctgctga   2640
ccgatgagat gatcgcccag tacacatctg ccctgctggc cggcacaatc acaagcggct   2700
ggacatttgg agcaggcgcc gctctgcaga tccccttcgc tatgcagatg gcctaccgt   2760
tcaacggcat cggagtgacc cagaatgtgc tgtacgagaa ccagaagctg atcgccaacc   2820
agttcaacag cgccatcggc aagatccagg acagcctgag cagcacagca agcgccctgg   2880
gaaagctgca ggacgtggtc aaccacaatg cccaggcact gaacacctg gtcaagcagc   2940
tgtcctccaa gttcggcgcc atcagctctg tgctgaacga tatcctgagc agactggacc   3000
ctcctgaggc cgaggtgcag atcgacagac tgatcacagg cagactgcag agcctccaga   3060
catacgtgac ccagcagctg atcagagccg ccgagattag gcctctgccc aatctggccg   3120
ccaccaagat gtctgagtgt gtgctggccc agagcaagag agtggacttt tgcggcaagg   3180
gctaccacct gatgagcttc cctcagtctg ccctcacgg cgtggtgttt ctgcacgtga   3240
catatgtgcc cgctcaagag aagaatttca caccgctcc agcacctcgc cacgacggca   3300
aagcccactt tcctagagaa ggcgtgttcg tgtccaacgg cacccattgg ttcgtgacac   3360
agcggaactt ctacgagccc cagatcatca ccaccgacaa caccttcgtg tctggcaact   3420
gcgacgtcgt gatcggcatt gtgaacaata ccgtgtacga ccctctgcag cccgagctgg   3480
acagcttcaa agaggaactg gacaagtact ttaagaacca cacagccccc gacgtggacc   3540
tgggcgatat cagcggaatc aatgccagcg tcgtgaacat ccagaaagag atcgaccggc   3600
tgaacgaggt ggccaagaat ctgaacgaga gcctgatcga cctgcaagaa ctggggaagt   3660
acgagcagta catcaagtgg ccctggtaca tctggctggg ctttatcgcc ggactgattg   3720
ccatcgtgat ggtcacaatc atgctgtgtt gcatgaccag ctgctgtagc tgcctgaagg   3780
gctgttgtag ctgtggcagc tgctgcaagt tcgacgagga cgattctgag cccgtgctga   3840
agggcgtgaa actgcactac acatgtgac tcgagctgga tactgatgca ccaatgcta   3900
gctgcccctt tccgtcctg ggtacccga gtcccccg acctcgggtc ccaggtatgc   3960
tcccacctcc acctgcccca ctcaccacct ctgctagttc agacaccctc caagcacgc   4020
agcaatgcag ctcaaaacgc ttagcctagc cacacccca cgggaaacag cagtgattaa   4080
cctttagcaa taaacgaaag tttaactaag ctatactaac cccaggggttg gtcaatttcg   4140
tgccagccac accctggagc tagcaaaaaa aaaaaaaaaa aaaaaaaaaa aaagcatat   4200
```

```
                                                     -continued
gactaaaaaa aaaaaaaaaa aaaaaaaaaa aaaaaaaaaa aaaaaaaaaa aaaaaaaaaa  4260
aaaaaaaaaa aaaa                                                   4274

SEQ ID NO: 69          moltype = AA  length = 1268
FEATURE                Location/Qualifiers
source                 1..1268
                       mol_type = protein
                       organism = synthetic construct
SEQUENCE: 69
MFVFLVLLPL VSSQCVNLIT RTQSYTNSFT RGVYYPDKVF RSSVLHSTQD LFLPFFSNVT   60
WFHAISGTNG TKRFDNPVLP FNDGVYFAST EKSNIIRGWI FGTTLDSKTQ SLLIVNNATN  120
VVIKVCEFQF CNDPFLDVYY HKNNKSWMES EFRVYSSANN CTFEYVSQPF LMDLEGKQGN  180
FKNLREFVFK NIDGYFKIYS KHTPINLGRD LPQGFSALEP LVDLPIGINI TRFQTLLALH  240
RSYLTPGDSS SGWTAGAAAY YVGYLQPRTF LLKYNENGTI TDAVDCALDP LSETKCTLKS  300
FTVEKGIYQT SNFRVQPTES IVRFPNITNL CPFDEVFNAT RFASVYAWNR KRISNCVADY  360
SVLYNFAPFF AFKCYGVSPT KLNDLCFTNV YADSFVIRGN EVRQIAPGQT GNIADYNYKL  420
PDDFTGCVIA WNSNKLDSKV GGNYNYRYRL FRKSNLKPFE RDISTEIYQA GNKPCNGVAG  480
VNCYFPLQSY GFRPTYGVGH QPYRVVVLSF ELLHAPATVC GPKKSTNLVK NKCVNFNFNG  540
LTGTGVLTES NKKFLPFQQF GRDIADTTDA VRDPQTLEIL DITPCSFGGV SVITPGTNTS  600
NQVAVLYQGV NCTEVPVAIH ADQLTPTWRV YSTGSNVFQT RAGCLIGAEY VNNSYECDIP  660
IGAGICASYQ TQTKSHRRAR SVASQSIIAY TMSLGAENSV AYSNNSIAIP TNFTISVTTE  720
ILPVSMTKTS VDCTMYICGD STECSNLLLQ YGSFCTQLKR ALTGIAVEQD KNTQEVFAQV  780
KQIYKTPPIK YFGGFNFSQI LPDPSKPSKR SFIEDLLFNK VTLADAGFIK QYGDCLGDIA  840
ARDLICAQKF NGLTVLPPLL TDEMIAQYTS ALLAGTITSG WTFGAGAALQ IPFAMQMAYR  900
FNGIGVTQNV LYENQKLIAN QFNSAIGKIQ DSLSSTASAL GKLQDVVNHN AQALNTLVKQ  960
LSSKFGAISS VLNDILSRLD PPEAEVQIDR LITGRLQSLQ TYVTQQLIRA AEIRASANLA 1020
ATKMSECVLG QSKRVDFCGK GYHLMSFPQS APHGVVFLHV TYVPAQEKNF TTAPAICHDG 1080
KAHFPREGVF VSNGTHWFVT QRNFYEPQII TTDNTFVSGN CDVVIGIVNN TVYDPLQPEL 1140
DSFKEELDKY FKNHTSPDVD LGDISGINAS VVNIQKEIDR LNEVAKNLNE SLIDLQELGK 1200
YEQYIKWPWY IWLGFIAGLI AIVMVTIMLC CMTSCCSCLK GCCSCGSCCK FDEDDSEPVL 1260
KGVKLHYT                                                         1268

SEQ ID NO: 70          moltype = RNA  length = 3810
FEATURE                Location/Qualifiers
source                 1..3810
                       mol_type = other RNA
                       organism = synthetic construct
SEQUENCE: 70
atgttcgtgt tcctggtgct gctgcctctg gtgtccagcc agtgtgtgaa cctgatcacc   60
agaacacagt catacaccaa cagctttacc agaggcgtgt actacccga caaggtgttc  120
agatccagcg tgctgcactc tacccaggac ctgttcctgc ctttcttcag caacgtgacc  180
tggttccacg ccatctccgg caccaatggc accaagagat cgacaaccc cgtgctgccc  240
ttcaacgacg gggtgtactt tgccagcacc gagaagtcca acatcatcag aggctggatc  300
ttcggcacca cactgacag caagacccag agcctgctga tcgtgaacaa cgccaccaac  360
gtggtcatca agtgtgcga gttccagttc tgcaacgacc ccttcctgga cgtctactac  420
cacaagaaca acaagagctg gatggaaagc gagttccggg tgtacagcag cgccaacaac  480
tgcaccttcg agtacgtgtc ccagcctttc ctgatgaacc tggaaggcaa gcagggcaac  540
ttcaagaacc tgcgcgagtt cgtgtttaag aacatcgacg gctacttcaa gatctacagc  600
aagcacaccc ctatcaacct cggccgggat ctgcctcagg gcttctctgc tctgaaccc  660
ctggtggatc tgcccatcgg catcaacatc acccggtttc agacactgct ggccctgcac  720
agaagctacc tgacacctgg cgatagcagc agcggatgga gctggtgc cgccgcttca  780
tatgtgggct acctgcagcc tagaaccttc ctgctgaagt acaacgagaa cggcaccatc  840
accgacgccg tggattgtgc tctgatcct ctgagcgaga caaagtgcac cctgaagtcc  900
ttcaccgtgg aaaagggcat ctaccagacc agcaacttcc gggtgcagcc caccgaatcc  960
atcgtgcggt tccccaatat caccaatctg tgcccttcg acgaggtgtt caatgccacc 1020
agattcgcct ctgtgtacgc ctggaaccg aagcggatca gcaattgcgt ggccgactac 1080
tccgtgctgt acaacttcgc cccttcttc gcattcaagt gctacggcgt gtcccctacc 1140
aagctgaacg acctgtgctt cacaaacgtg tacgccgaca gcttcgtgat ccggggaaac 1200
gaagtgcggc agattgcccc tggacagaca ggcaacatcg ccgactacaa ctacaagctg 1260
cccgacgact tcaccggctg tgtgattgcc tggaacagca acaagctgga ctccaaagtc 1320
ggcggcaact acaattacag gtaccggctg ttccggaagt ccaatctgaa gcccttcgag 1380
cgggacatct ccaccgagat ctatcaggcc ggcaacaagc cttgtaacgg cgtggcaggc 1440
gtgaactgct acttccccact gcagtcctac ggctttagc ccacatacgg cgtgggccac 1500
cagccctaca gagtggtggt gctgagcttc gaactgctgc acgccccctgc cacagtgtgt 1560
ggccctaaga aaagcaccaa tctcgtgaag aacaaatgcg tgaacttcaa cttcaacggc 1620
ctgaccggca ccggcgtgct gacagagagc aacaagaagt tcctgccatt ccagcagttt 1680
ggccgggata tcgccgatac cacagacgcc gttagagatc cccagacact ggaaatcctg 1740
gacatcaccc cttgcagctt cggcgagtg tctgtgatca cccctggcac caacaccagc 1800
aatcaggtgg cagtgctgta ccagggcgtg aactgcaccg aagtgcccgt ggccattcac 1860
gccgatcagc tgacacctac atggcgggtg tactccaccg gcagcaatgt gtttcagacc 1920
agagccggct gtctgatcgg agccgagtac gtgaacaata gctacgagtg cgacatcccc 1980
atcggcgctg aatcgcgc cagctaccag acacagacaa agccaccg gagagccaga 2040
agcgtggcca gccagagcat cattgcctac acaatgtctc tgggcgccga aaacagcgtg 2100
gcctactcca caactctat cgctatcccc accaacttca ccatcagcgt gaccacagag 2160
atcctgcctg tgtccatgac caagaccagc gtggactgca ccatgtacat ctgcggcgat 2220
tccaccgagt gctccaacct gctgctgcag tacggcagct tctgcaccca gctgaaaaga 2280
gccctgacag gatccgccgt ggaacaggac aagaacaccc aagaggtgtt cgcccaagtg 2340
aagcagatct acaagacccc tcctatcaag tacttcggcg gcttcaattt cagccagatt 2400
ctgcccgatc ctagcaagcc cagcaagcgg agcttcatcg aggacctgct gttcaacaaa 2460
```

```
gtgacactgg ccgacgccgg cttcatcaag cagtatggcg attgtctggg cgacattgcc    2520
gccagggatc tgatttgcgc ccagaagttt aacggactga cagtgctgcc tcctctgctg    2580
accgatgaga tgatcgccca gtacacatct gccctgctgg ccggcacaat cacaagcggc    2640
tggacatttg gagcaggcgc cgctctgcag atccccttttg ctatgcagat ggcctaccgg    2700
ttcaacggca tcggagtgac ccagaatgtg ctgtacgaga accagaagct gatcgccaac    2760
cagttcaaca cgccatcgg caagatccag gacagcctga gcagcacagc aagcgccctg    2820
ggaaagctgc aggacgtggt caaccacaat gcccaggcac tgaacaccct ggtcaagcag    2880
ctgtcctcca agttcggcgc catcagctct gtgctgaacg atatcctgag cagactggac    2940
cctcctgagg ccgaggtgca gatcgacaga ctgatcacag gcagactgca gagcctccag    3000
acatacgtga cccagcagct gatcagagcc gccgagatta gagcctctgc caatctggcc    3060
gccaccaaga tgtctgagtg tgtgctgggc cagagcaaga gagtggactt ttgcggcaag    3120
ggctaccacc tgatgagctt ccctcagtct gcccctcacg cgtggtgtt tctgcacgtg    3180
acatatgtgc ccgctcaaga aagaatttc accaccgctc cagccatctg ccacgacggc    3240
aaagcccact ttcctagaga aggcgtgttc gtgtccaaca gcacccattg gttcgtgaca    3300
cagcggaact tctacgagcc ccagatcatc accaccgaca cacccttcgt gtctggcaac    3360
tgcgacgtcg tgatcggcat tgtgaacaat accgtgtacg accctctgca gcccgagctg    3420
gacagcttca aagaggaact ggacaagtac tttaagaacc acacaagccc cgacgtggac    3480
ctgggcgata tcagcggaat caatgccagc gtcgtgaaca tccagaaaga gatcgaccgg    3540
ctgaacgagg tggccaagaa tctgaacgag agcctgatcg acctgcaaga actggggaag    3600
tacgagcagt acatcaagtg gcccctggtac atctggctgg gctttatcgc cggactgatt    3660
gccatcgtga tggtcacaat catgctgtgt tgcatgacca gctgctgtag ctgcctgaag    3720
ggctgttgta gctgtggcag ctgctgcaag ttcgacgagg acgattctga gcccgtgctg    3780
aagggcgtga aactgcacta cacatgatga                                     3810

SEQ ID NO: 71         moltype = DNA   length = 3810
FEATURE               Location/Qualifiers
source                1..3810
                      mol_type = other DNA
                      organism = synthetic construct
SEQUENCE: 71
atgttcgtgt tcctggtgct gctgcctctg gtgccagcc agtgtgtgaa cctgatcacc    60
agaacacagt catacaccaa cagctttacc agaggcgtgt actacccga caaggtgttc    120
agatccagcg tgctgcactc tacccaggac ctgttcctgc cttttcttcag caacgtgacc    180
tggttccacg ccatctccgg caccaatggc accaagagat tcgacaaccc cgtgctgccc    240
ttcaacgacg gggtgtactt tgccagcacc gagaagtcca acatcatcag aggctggatc    300
ttcggcacca cactggacag caagacccag agcctgctga tcgtgaacaa cgccaccaac    360
gtggtcatca aagtgtgcga gttccagttc tgcaacgacc ccttcctgga cgtctactac    420
cacaagaaca acaagagctg gatggaaagc gagttccggg tgtacagcag cgccaacaac    480
tgcacctttg agtacgtgtc ccagcctttc ctgatgaacc tggaaggcaa gcagggcaac    540
ttcaagaacc tgcgcgagtt cgtgtttaag aacatcgacg gctacttcaa gatctacagc    600
aagcacaccc ctatcaacct cggccgggat ctgcctcagg gcttctctgc tctggaaccc    660
ctggtggatc tgcccatcgg catcaacatc acccggtttc agacactgct ggccctgcac    720
agaagctacc tgacacctgg cgatagcagc agcggatgga cagcctggtc cgccgcttac    780
tatgtgggct acctgcagcc tagaaccttc ctgctgaagt acaacgagaa cggcaccatc    840
accgacgccg tggattgtgc tctgatcct ctgagcgaga caaagtgcac cctgaagtcc    900
ttcaccgtga aaagggcat ctaccagacc agcaacttcc gggtgcagcc caccgaatcc    960
atcgtgcggt tccccaatat caccaatctg tgcccctcg acgaggtgtt caatgccacc    1020
agattcgcct ctgtgtacgc ctggaaccgg aagcggatca gcaattgcgt ggccgactac    1080
tccgtgctgt acaacttcgc cccctttcttc gcattcaagt gctacggcgt gtccctacc    1140
aagctgaacg acctgtgctt cacaaacgtg tacgccgaca gcttcgtgat ccggggaaac    1200
gaagtgcgac agattgcccc tggacagaca ggcaacatcg ccgactacaa ctacaagctg    1260
cccgacgact tcaccggctg tgtgattgcc tggaacagca caagctgga ctccaaagtg    1320
ggcggcaact acaattacag gtaccggctg ttccggaagt ccaatctgaa gcccttcgag    1380
cgggacatct ccaccgagat ctatcaggcc ggcaacaagc cttgtaacgg cgtggcaggc    1440
gtgaactgct acttcccact gcagtcctac ggctttaggc ccacatacgg cgtgggccac    1500
cagcccttaca gagtggtggtg gctgagcttc gaactgctgc atgcccctgc cacagtgtgc    1560
ggccctaaga aaagcaccaa tctcgtgaag aacaaatgcg tgaacttcaa cttcaacggc    1620
ctgaccggca ccggcgtgct gacagagagc aacaagaagt tcctgccatt ccagcagttt    1680
ggcagggata tcgccgatac cacagacgcc gttagagatc cccagacact ggaaatcctg    1740
gacatcaccc cttgcagctt cggcggagtg tctgtgatca cccctggcac caacaccagc    1800
aatcaggtgg cagtgctgta ccagggcgtg aactgtaccg aagtgccgt ggccattcac    1860
gccgatcagc tgacacctac atggcgggtg tactccaccg gcagcaatgt gtttcagacc    1920
agagccggct gtctgatcgg agccgagtac gtgaacaata gctacgagtg cgacatcccc    1980
atcggcgctg gaatctgcgc cagctaccag acacagaca agagccaccg gagagccgaa    2040
agcgtggcca gccagagcat cattgcctac acaatgtctc tgggcgccga gaacagcgtg    2100
gcctactcca caaactctat cgctatcccc accaacttca ccatcagcgt gaccacagag    2160
atcctgcctg tgtccatgac caagaccagc gtggactgca atgtacat ctgcggcgat    2220
tccaccgagt gctccaacct gctgctgcag tacggcagct tctgcacaca gctgaaaaga    2280
gccctgacag ggatcgccgt ggaacaggac aagaacacc aagaggtgtt cgcccaagtg    2340
aagcagatct acaagacccc tcctatcaag tacttcggcg gcttcaattt cagccagatt    2400
ctgcccgatc ctagcaagcc cagcaagcgg agcttcatcg aggacctgct gttcaacaaa    2460
gtgacactgg ccgacgccgg cttcatcaag cagtatggcg attgtctggg cgacattgcc    2520
gccagggatc tgatttgcgc ccagaagttt aacggactga cagtgctgcc tcctctgctg    2580
accgatgaga tgatcgccca gtacacatct gccctgctgg ccggcacaat cacaagcggc    2640
tggacatttg gagcaggcgc cgctctgcag atccccttttg ctatgcagat ggcctaccgg    2700
ttcaacggca tcggagtgac ccagaatgtg ctgtacgaga accagaagct gatcgccaac    2760
cagttcaaca cgccatcgg caagatccag gacagcctga gcagcacagc aagcgccctg    2820
ggaaagctgc aggacgtggt caaccacaat gcccaggcac tgaacaccct ggtcaagcag    2880
ctgtcctcca agttcggcgc catcagctct gtgctgaacg atatcctgag cagactggac    2940
```

```
cctcctgagg ccgaggtgca gatcgacaga ctgatcacag gcagactgca gagcctccag   3000
acatacgtga cccagcagct gatcagagcc gccgagatta gagcctctgc caatctggcc   3060
gccaccaaga tgtctgagtg tgtgctgggc cagagcaaga gagtggactt ttgcggcaag   3120
ggctaccacc tgatgagctt ccctcagtct gcccctcacg gcgtggtgtt tctgcacgtg   3180
acatatgtgc ccgctcaaga gaagaatttc accaccgctc cagccatctg ccacgacggc   3240
aaagcccact ttcctagaga aggcgtgttc gtgtccaacg gcaccccatt ggttcgtgaca   3300
cagcggaact tctacgagcc ccagatcatc accaccgaca acaccttcgt gtctggcaac   3360
tgcgacgtcg tgatcggcat tgtgaacaat accgtgtacg accctctgca gcccgagctg   3420
gacagcttca aagaggaact ggacaagtac tttaagaacc acacaagccc cgacgtggac   3480
ctgggcgata tcagcggaat caatgccagc gtcgtgaaca tccagaaaga gatcgaccgg   3540
ctgaacgagg tggccaagaa tctgaacgag agcctgatcg acctgcaaga actggggaag   3600
tacgagcagt acatcaagtg gcccctggtac atctggctgg gctttatcgc cggactgatt   3660
gccatcgtga tggtcacaat catgctgtgt tgcatgacca gctgctgtag ctgcctgaag   3720
ggctgttgta gctgtggcag ctgctgcaag ttcgacgagg acgattctga gcccgtgctg   3780
aagggcgtga aactgcacta cacatgatga                                    3810

SEQ ID NO: 72        molttype = RNA  length = 4268
FEATURE              Location/Qualifiers
source               1..4268
                     mol_type = other RNA
                     organism = synthetic construct
SEQUENCE: 72
agaataaact agtattcttc tggtccccac agactcagag agaacccgcc accatgttcg   60
tgttcctggt gctgctgcct ctggtgtcca gccagtgtgt gaacctgatc accagaaacac  120
agtcatacac caacagcttt accagaggcg tgtactaccc cgacaaggtg ttcagatcca  180
gcgtgctgca ctctacccag gacctgttcc tgcctttctt cagcaacgtg acctggttcc  240
acgccatctc cggcaccaat ggcaccaaga gattcgacaa ccccgtgctg ccctcaacg   300
acggggtgta ctttgccagc accgagaagt ccaacatcat cagaggctgg atcttcggca  360
ccacactgga cagcaagacc cagagcctgc tgatcgtgaa caacgccacc aacgtggtca  420
tcaaagtgtg cgagttccag ttctgcaacg acccctccgg cagcgtctac taccacaaga  480
acaacaagag ctggatggaa agcgagttcc gggtgtacag cagcgccaac aactgcacct  540
tcgagtacgt gtcccagcct ttcctgatgg acctggaagg caagcagggc aacttcaaga  600
acctgcgcga gttcgtgttt aagaacatcg acggctactt caagatctac agcaagcaca  660
cccctatcaa cctcgtgcgg gatctgcctc agggcttctc tgctctggaa cccctggtgg  720
atctgcccat cggcatcaac atcacccggt tcagacact gctggcccctg cacagaagct  780
acctgacacc tggcgatagc agcagcggat ggacagctgg tgccgccgct actatgtgg   840
gctacctgca gcctagaacc ttcctgctga gtacaacga gaacggcacc atcaccgacg  900
ccgtggattg tgctctggat cctctgagcg agacaaagtg caccctgaag tccttcaccg  960
tggaaaaggg catctaccag accagcaact tccgggtgac gccaccgaa tccatcgtg  1020
ggttccccaa tatcaccaat ctgtgcccct tcgacgaggt gttcaatgcc accagattcg  1080
cctctgtgta cgcctggaac cggaagcgga tcagcaattg cgtggccgac tactccgtgc  1140
tgtacaactt cgccccttc ttcgcattca agtgctacgg cgtgtcccct accaagctga  1200
acgacctgtg cttcacaaac gtgtacgccg acagcttcgt gatcggggga acgaagtgc  1260
ggcagattgc ccctggacag acaggcaaca tcgccgacta caactacaag ctgcccgacg  1320
acttcaccgg ctgtgtgatt gcctggaaca gcaacaagct ggactccaaa gtcggcggca  1380
actacaatta caggtaccgg ctgttccgga gtccaatct gaagcccttc gagcgggaca  1440
tctccaccga gatctatcag gccggcaaca gccttgtaa cggcgtggca ggcgtgaact  1500
gctacttccc actgcagtcc tacgctttta ggcccacata cggcgtgggc caccagccct  1560
acagagtggt ggtgctgagc ttcgaactgc tgcatgcccc tgccacagtg tgcggcccta  1620
agaaaagcac caatctcgtg aagaacaaat gcgtgaactt caacttcaac ggcctgaccg  1680
gcaccggcgt gctgacagag agcaacaaga gttcctgcac attccagcag tttggccgga  1740
atatcgccga taccacgac gccgttagag atccccagac actggaaatc ctggacatca  1800
ccccttgcag cttcggcgga gtgtctgtga tcacccctgg caccaacacc agcaatcagg  1860
tggcagtgct gtaccagggc gtgaactgta ccgaagtgcc cgtggccatt cacgccgatc  1920
agctgacacc tacatggcgg gtgtactcca ccggcagcaa tgtgtttcag accagagcg   1980
gctgtctgat cggagccgag tacgtgaaca atagctacga gtgcgacatc cccatcggcg  2040
ctggaatctg cgccagctac cagacacaga caaagagcca ccggagagcc agaagcgtgg  2100
ccagccagag catcattgcc tacacaatgt ctctgggcgc cgagaacagc gtggcctact  2160
ccaacaactc tatcgctatc cccaccaact tcaccatcag cgtgaccaca gagatctgac  2220
ctgtgtccat gaccaagacc agcgtggact gcaccatga catctgcggc gattccaccg  2280
agtgctccaa cctgctgctg cagtacggca gcttctgcac ccagctgaaa agagccctga  2340
cagggatcgc cgtggaacag gacaagaaca cccaagaggt gttcgcccaa gtgaagcaga  2400
tctacaagac ccctcctatc aagtacttcg gcggcttcaa tttcagccag attctgcccg  2460
atcctagcaa gcccagcaag cggagcttca tcgaggacct gctgttcaac aaagtgacac  2520
tggccgacgc cggcttcatc aagcagtatg cgcattgtc gggcgacatt gccgccaggg  2580
atctgatttg cgcccagaag tttaacggac tgacagtgct gcctcctctg ctgaccgatg  2640
agatgatcgc ccagtacaca tctgccctgc tggccggcac aatcacaagc ggctggacat  2700
ttggagcagg cgccgctctg cagatcccct tgctatgca gatggcctac cggttcaacg  2760
gcatcggagt gacccagaat gtgctgtacg agaaccagaa gctgatcgcc aaccagttca  2820
acagcgccat cggcaagatc caggacagcc tgagcagcac agcaagcgcc ctgggaaagc  2880
tgcaggacgt ggtcaaccac aatgcccagg cactgaacac cctggtcaag cagctgtcct  2940
ccaagttcgg cgccatcagc tctgtgctga acgatatcct gagcagactg gaccctcctg  3000
aggccgaggt gcagatcgac agactgatca ggcagactg gcagagcctc cagacatacg  3060
tgacccgcag cgtgatcaga gccgcgaga ttagagcctc tgcaatctgg ccgccacca   3120
agatgtctga gtgtgtgctg ggccagagca agagagtgga cttttgcggc aagggctacc  3180
acctgatgag cttccctcag tctgcccctc acggcgtggt gtttctgcac gtgacatatg  3240
tgcccgctca agagaagaat ttcaccaccg ctccagccat ctgccacgac ggcaaagccc  3300
actttcctag agaaggcgtg ttcgtgtcca acggcaccca ttggttcgtg acacagcgga  3360
acttctacga gccccagatc atcaccaccg acaacacctt cgtgtctggc aactgcgacg  3420
```

```
tcgtgatcgg cattgtgaac aataccgtgt acgaccctct gcagcccgag ctgacagct   3480
tcaaagagga actggacaag tactttaaga accacacaag ccccgacgtg gacctgggcg   3540
atatcagcgg aatcaatgcc agcgtcgtga acatccagaa agagatcgac cggctgaacg   3600
aggtggccaa gaatctgaac gagagcctga tcgacctgca agaactgggg aagtacgagc   3660
agtacatcaa gtggccctgg tacatctggc tgggctttat cgccgactg attgccatcg   3720
tgatggtcac aatcatgctg tgttgcatga ccagctgctg tagctgcctg aagggctgtt   3780
gtagctgtgg cagctgctgc aagttcgacg aggacgattc tgagcccgtg ctgaagggcg   3840
tgaaactgca ctacacatga tgactcgagc tggtactgca tgcacgcaat gctagctgcc   3900
cctttcccgt cctgggtacc ccgagtctcc cccgacctcg ggtcccaggt atgctcccac   3960
ctccacctgc cccactcacc acctctgcta gttccagaca cctcccaagc acgcagcaat   4020
gcagctcaaa acgcttagcc tagccacacc cccacgggaa acagcagtga ttaacctta   4080
gcaataaacg aaagtttaac taagctatac taaccccagg gttggtcaat ttcgtgccaa   4140
ccacaccctg gagctagcaa aaaaaaaaaa aaaaaaaaaa aaaaaaagc atatgactaa   4200
aaaaaaaaaa aaaaaaaaaa aaaaaaaaaa aaaaaaaaaa aaaaaaaaaa aaaaaaaaaa   4260
aaaaaaaa                                                            4268

SEQ ID NO: 73           moltype = DNA  length = 4268
FEATURE                 Location/Qualifiers
source                  1..4268
                        mol_type = other DNA
                        organism = synthetic construct
SEQUENCE: 73
agaataaact agtattcttc tggtccccac agactcagag agaacccgcc accatgttcg   60
tgttcctggt gctgctgcct ctggtgtcca gccagtgtgt gaacctgatc accagaaacac  120
agtcatacac caacagcttt accagaggcg tgtactaccc cgacaaggtg ttcagatcca  180
gcgtgctgca ctctacccag gacctgttcc tgcctttctt cagcaacgtg acctggttcc  240
acgccatctc cggcaccaat ggcaccaaga gattcgacaa ccccgtgctg ccctttcaac  300
acgggggtgta ctttgccagc accgagaagt ccaacatcat cagaggctgg atcttcggca  360
ccacactgga cagcaagacc cagagcctgc tgatcgtgaa caacgccacc aacgtggtca  420
tcaaagtgtg cgagttccag ttctgcaacg acccctccgg acgtctac taccacaaga  480
acaacaagag ctggatggaa agcgagttcc gggtgtacag cagcgccaac aactgcacct  540
tcgagtacgt gtcccagcct ttcctgatgg acctggaagg caagcagggc aacttcaaga  600
acctgcgcga gttcgtgttt aagaacatcg acggctactt caagatctac agcaagcaca  660
cccctatcaa cctcggccgg gatctgcctc agggcttctc tgctctggaa cccctggtgg  720
atctgcccat cggcatcaac atcacccggt tcagacact gctggcctg cacagaagct  780
acctgacacc tggcgatagc agcagcggat ggacagctgg tgccgccgct actatgtgg   840
gctacctgca gcctagaacc ttcctgctga gtacaacga gaacggcacc atcaccgacg  900
ccgtggattg tgctctggat cctctgagcg agacaaagtg caccctgaag tccttcaccg  960
tggaaaaggg catctaccag accagcaact tccgggtgca gcccaccgaa tccatcgtg   1020
ggttccccaa tatcaccaat ctgtgccccct tcgacgaggt gttcaatgcc accagattcg  1080
cctctgtgta cgcctggaac cggaagcgga tcagcaatg cgtggccgac tactccgtgc  1140
tgtacaactt cgcccccctc ttcgcattca agtgctacg cgtgtcccct accaagctga  1200
acgacctgtg cttcacaaac gtgtacgccg acagcttcgt gatccgggga acgaagtgc  1260
ggcagattgc ccctggacag acaggcaaca tcgccgacta caactacaag ctgcccgacg  1320
acttcaccgg ctgtgtgatt gcctggaaca gcaacaagct ggactccaaa gtcggcggca  1380
actacaatta caggtaccgg ctgttccgga gtccaatct gaagcccttc gagcgggaca  1440
tctccaccga gatctatcag gccggcaaca gccttgtaa tgccgtggca gcgtgaact  1500
gctacttccc actgcagtcc tacgctttta ggcccacata cggcgtgggc caccagccct  1560
acagagtggt ggtgctgagc ttcgaactgc tgcatgcccc tgccacagtg tgcggcccta  1620
agaaaagcac caatctcgtg aagaacaaat gcgtgaactt caacttcaac ggcctgaccg  1680
gcaccggcgt gctgacagag agcaacaaga gttcctgca attccagcag tttggccggg  1740
atatcgccga taccacagac gccgttagag atccccagac actggaaatc ctggacatca  1800
ccccttgcag cttcggcgga gtgtctgtga caccctgg caccaacacc agcaatcagg  1860
tggcagtgct gtaccagggc gtgaactgta ccgaagtgcc cgtggccatt cacgccgatc  1920
agctgacacc tacatggcgg gtgtactcca ccggcagcaa tgtgtttcag accagagcg   1980
gctgtctgat cggagccgag tacgtgaaca atagctacga gtgcgacatc cccatcggcg  2040
ctggaatctg cgccagctac cagacacaga aaagagcca ccggagagcc agaagcgtgg  2100
ccagccagag catcattgcc tacacaatgt ctctgggcgc cgagaacagc gtggcctact  2160
ccaacaactc tatcgctatc cccaccaact tcaccatcag cgtgaccaca gagatctgcc  2220
ctgtgtccat gaccaagacc agcgtggact gcaccatga catctgcggc gattccaccg  2280
agtgctccaa cctgctgctg cagtacggca gcttctgcac ccagctgaaa agagccctga  2340
cagggatcgc cgtggaacag gacaagaaca cccaagaggt gttcgcccaa gtgaagcaga  2400
tctacaagac ccctcctatc aagtacttcg gcggcttcaa tttcagccag attctgcccg  2460
atcctagcaa gcccagcaag cggagcttca tcgaggacct gctgttcaac aaagtgacac  2520
tggccgacgc cggcttcatc aagcagtatg cgcattgtc tgggcgacatt gccgccaggg  2580
atctgatttg cgcccagaag tttaacggac tgacagtgct gcctcctctg ctgaccgatg  2640
agatgatcgc ccagtacaca tctgccctgc tggccgcac aatcacaagc ggctggacat  2700
ttggagcagg cgccgctctg cagatcccct tgctatgca tgatgcctac cggttcaacg  2760
gcatcggagt gacccagaat gtgctgtacg agaaccagaa gcagatcgcc aaccagttca  2820
acagcgccat cggcaagatc caggacagct gagcagcac agcaagcgcc tgggaaagc   2880
tgcaggacgt ggtcaaccac aatgcccagg cactgaacac cctggtcaag cagctgtcct  2940
ccaagttcgg cgccatcagc tctgtgctga cgatatcct gagcagactg gaccctcctg  3000
aggccgaggt gcagatcgac agactgatca caggcagact gcagagcctc cagacatacg  3060
tgacccgaca gctgatcaga gccgccgaga ttagagcctg tgccaatctg gccgccacca  3120
agatgtctga gtgtgtgctg ggccagagca aagagtgga ctttgcggc aagggctacc  3180
acctgatgag cttccctcag tctgcccctc acggcgtggt gtttctgcac gtgacatatg  3240
tgcccgctca agaagaat ttcaccaccg ctccagccat ctgccacgac ggcaaagccc  3300
actttcctag agaaggcgtg ttcgtgtcca acggcaccca ttggttcgtg acacagcgga  3360
acttctacga gccccagatc atcaccaccg acaacacctt cgtgtctggc aactgcgacg  3420
```

```
tcgtgatcgg cattgtgaac ataccgtgt acgaccctct gcagcccgag ctgacagct    3480
tcaaagagga actggacaag tactttaaga accacacaag ccccgacgtg gacctgggcg    3540
atatcagcgg aatcaatgcc agcgtcgtga acatccagaa agagatcgac cggctgaacg    3600
aggtggccaa gaatctgaac gagagcctga tcgacctgca agaactgggg aagtacgagc    3660
agtacatcaa gtggccctgg tacatctggc tgggctttat cgccggactg attgccatcg    3720
tgatggtcac aatcatgctg tgttgcatga ccagctgctg tagctgcctg aagggctgtt    3780
gtagctgtgg cagctgctgc aagttcgacg aggacgattc tgagcccgtg ctgaagggcg    3840
tgaaactgca ctacacatga tgactcgagc tggtactgca tgcacgcaat gctagctgcc    3900
cctttcccgt cctgggtacc ccgagtctcc cccgacctcg ggtcccaggt atgctcccac    3960
ctccacctgc cccactcacc acctctgcta gttccagaca cctccaagc acgcagcaat    4020
gcagctcaaa acgcttagcc tagccacacc cccacgggaa acagcagtga ttaacctta    4080
gcaataaacg aaagtttaac taagctatac taaccccagg gttggtcaat ttcgtgccag    4140
ccacaccctg gagctagcaa aaaaaaaaaa aaaaaaaaaa aaaaaaagc atatgactaa    4200
aaaaaaaaaa aaaaaaaaaa aaaaaaaaaa aaaaaaaaaa aaaaaaaaaa aaaaaaaaaa    4260
aaaaaaaa                                                              4268

SEQ ID NO: 74          moltype = AA  length = 1268
FEATURE                Location/Qualifiers
source                 1..1268
                       mol_type = protein
                       organism = synthetic construct
SEQUENCE: 74
MFVFLVLLPL VSSQCVNLIT RTQSYTNSFT RGVYYPDKVF RSSVLHSTQD LFLPFFSNVT     60
WFHAISGTNG TKRFDNPVLP FNDGVYFAST EKSNIIRGWI FGTTLDSKTQ SLLIVNNATN    120
VVIKVCEFQF CNDPFLDVYY HKNNKSWMES ERVYSSANN CTFEYVSQPF LMDLEGKQGN    180
FKNLREFVFK NIDGYFKIYS KHTPINLGRD LPQGFSALEP LVDLPIGINI TRFQTLLALH    240
RSYLTPGDSS SGWTAGAAAY YVGYLQPRTF LLKYNENGTI TDAVDCALDP LSETKCTLKS    300
FTVEKGIYQT SNFRVQPTES IVRFPNITNL CPFDEVFNAT RFASVYAWNR KRISNCVADY    360
SVLYNFAPFF AFKCYGVSPT KLNDLCFTNV YADSFVIRGN EVSQIAPGQT GNIADYNYKL    420
PDDFTGCVIA WNSNKLDSKV GGNYNYRYRL FRKSNLKPFE RDISTEIYQA GNKPCNGVAG    480
VNCYFPLQSY GFRPTYGVGH QPYRVVVLSF ELLHAPATVC GPKKSTNLVK NKCVNFNFNG    540
LTGTGVLTES NKKFLPFQQF GRDIADTTDA VRDPQTLEIL DITPCSFGGV SVITPGTNTS    600
NQVAVLYQGV NCTEVPVAIH ADQLTPTWRV YSTGSNVFQT RAGCLIGAEY VNNSYECDIP    660
IGAGICASYQ TQTKSHRRAR SVASQSIIAY TMSLGAENSV AYSNNSIAIP TNFTISVTTE    720
ILPVSMTKTS VDCTMYICGD STECSNLLLQ YGSFCTQLKR ALTGIAVEQD KNTQEVFAQV    780
KQIYKTPPIK YFGGFNFSQI LPDPSKPSKR SFIEDLLFNK VTLADAGFIK QYGDCLGDIA    840
ARDLICAQKF NGLTVLPPLL TDEMIAQYTS ALLAGTITSG WTFGAGAALQ IPFAMQMAYR    900
FNGIGVTQNV LYENQKLIAN QFNSAIGKIQ DSLSSTASAL GKLQDVVNHN AQALNTLVKQ    960
LSSKFGAISS VLNDILSRLD PPEAEVQIDR LITGRLQSLQ TYVTQQLIRA AEIRASANLA   1020
ATKMSECVLG QSKRVDFCGK GYHLMSFPQS APHGVVFLHV TYVPAQEKNF TTAPAICHDG   1080
KAHFPREGVF VSNGTHWFVT QRNFYEPQII TTDNTFVSGN CDVVIGIVNN TVYDPLQPEL   1140
DSFKEELDKY FKNHTSPDVD LGDISGINAS VVNIQKEIDR LNEVAKNLNE SLIDLQELGK   1200
YEQYIKWPWY IWLGFIAGLI AIVMVTIMLC CMTSCCSCLK GCCSCGSCCK FDEDDSEPVL   1260
KGVKLHYT                                                            1268

SEQ ID NO: 75          moltype = RNA  length = 3810
FEATURE                Location/Qualifiers
source                 1..3810
                       mol_type = other RNA
                       organism = synthetic construct
SEQUENCE: 75
atgttcgtgt tcctggtgct gctgcctctg gtgtccagcc agtgtgtgaa cctgatcacc     60
agaacacaga gctacaccaa cagctttacc agaggcgtgt actacccga caaggtgttc    120
agatccagcg tgctgcactc tacccaggac ctgttcctgc cttttcttcag caacgtgacc    180
tggttccacg ccatctccgg caccaatggc accaagagat tcgacaaccc cgtgctgccc    240
ttcaacgacg gggtgtactt tgccagcacc gagaagtcca acatcatcag aggctggatc    300
ttcggcacca cactggacag caagacccag agcctgctga tcgtgaacaa cgccaccaac    360
gtggtcatca agtgtgcga gttccagttc tgcaacgacc ccttcctgga cgtgtactac    420
cacaagaaca acaagagctg gatggaaagc gagttccggg tgtacagcag cgccaacaac    480
tgcaccttcg agtacgtgtc ccagcctttc ctgatgaacc tggaaggcaa gcagggcaac    540
ttcaagaacc tgcgcgagtt cgtgtttaag aacatcgacg gctacttcaa gatctacagc    600
aagcacaccc ctatcaacct cggccgggat ctgcctcagg gcttctctgc tctggaaccc    660
ctggtggatc tgcccatcgg catcaacatc acccggtttc agacactgct ggccctgcac    720
agaagctacc tgacacctgg cgatagcagc agcggatgga cagctggtgc cgccgcttac    780
tatgtgggct acctgcagcc tagaaccttc ctgctgaagt acaacgagaa cggcaccatc    840
accgacgccg tggattgtgc tctggatcct ctgagcgaga caagtgcac cctgaagtcc    900
ttcaccgtgg aaaagggcat ctaccagacc agcaacttcc gggtgcagcc caccgaatcc    960
atcgtgcggt tccccaatat caccaatctg tgcccttcg acgaggtgtt caatgccatc   1020
agattcgcct ctgtgtacgc ctggaaccgg aagcggatca gcaattgcgt ggccgactac   1080
tccgtgctgt acaacttcgc ccccttcttc gccttcaagt gctacggcgt gtccctacc   1140
aagctgaacg acctgtgctt cacaaacgtg tacgccgaca gcttcgtgat ccggggaaac   1200
gaagtgagcc agattgcccc tggacagaca ggcaacatcg ccgactacaa ctacaagctg   1260
cccgacgact tcaccggctg tgtgattgcc tggaacagca acaagctgga ctccaaagtc   1320
ggcggcaact acaattacag gtaccgcctg ttccggaag ccaatctgaa gcccttcgag   1380
cgggacatcc ccaccgagat ctatcaggcc ggcaacaag cttgtaacgg cgtcggcggc   1440
gtgaactgct acttcccact gcagtcctac ggctttaggc ccacatatgg cgtgggccat   1500
cagcccctaca gagtggtggt gctgagcttc gaactgctgc atgcccctgc cacagtgtgc   1560
ggccctaaga aaagcaccaa tctcgtgaag aacaaatgcg tgaacttcaa cttcaacggc   1620
ctgaccggca ccggcgtgct gacagagagc aacaagaagt tcctgccatt ccagcagttt   1680
```

```
ggccgggata tcgccgatac cacagacgcc gttagagatc cccagacact ggaaatcctg  1740
gacatcaccc cttgcagctt cggcggagtg tctgtgatca cccctggcac caacaccagc  1800
aatcaggtgg cagtgctgta ccagggcgtg aactgtaccg aagtgcccgt ggccattcac  1860
gccgatcagc tgacacctac atggcgggtg tactccaccg gcagcaatgt gtttcagacc  1920
agagccggct gtctgatcgg agccgagtac gtgaacaata gctacgagtg cgacatcccc  1980
atcggcgctg gaatctgcgc cagctaccag acacagacaa agagccaccg gagagccaga  2040
agcgtggcca gccagagcat cattgcctac acaatgtctc tgggcgccga gaacagcgtg  2100
gcctactcca caaactctat cgctatcccc accaacttca ccatcagcgt gaccacagag  2160
atcctgcctg tgtccatgac caagaccagc gtggactgca ccatgtacat ctgcggcgat  2220
tccaccgagt gctccaacct gctgctgcag tacggcagct tctgcaccca gctgaagaga  2280
gccctgacag ggatcgccgt ggaacaggac aagaacaccc aagaggtgtt cgcccaagtg  2340
aagcagatct acaagacccc tcctatcaag tacttcggcg gcttcaattt cagccagatt  2400
ctgcccgatc ctagcaagcc cagcaagcgg agcttcatcg aggacctgct gttcaacaaa  2460
gtgacactgg ccgacgccgg cttcatcaag cagtatggcg attgtctggg cgacattgcc  2520
gccagggatc tgatttcgcg ccagaagttt aacggactga cagtgctgcc tcctctgctg  2580
accgatgaga tgatcgccca gtacacatct gccctgctgg ccggcacaat cacaagcggc  2640
tggacatttg agcaggcgc cgctctgcag atccccttg ctatgcagat ggcctaccgg  2700
ttcaacggca tcggagtgac ccagaatgtg ctgtacgaga accagaagct gatcgccaac  2760
cagttcaaca cgccatcgg caagatccag gacagcctga gcagcacagc aagcgccctg  2820
ggaaagctgc aggacgtggt caaccacaat gcccaggcac tgaacaccct ggtcaagcag  2880
ctgtcctcca agttcggcgc catcagctct gtgctgaacg atatcctgag cagactggac  2940
cctcctgagg ccgaggtgca gatcgacaga ctgatcacag gagactgca gagcctccag  3000
acatacgtga cccagcagct gatcagagcc gccgagatta gagcctctgc caatctggcc  3060
gccaccaaga tgtctgagtg tgtgctgggc cagagcaaga gagtggactt ttgcggcaag  3120
ggctaccacc tgatgagctt ccctcagtct gcccctcacg gcgtggtgtt tctgcacgtg  3180
acatatgtgc ccgctcaaga gaagaattc accaccgctc cagccatctg cacgtgga  3240
aaagccccact ttcctagaga aggcgtgttc gtgtccaacg gcaccccattg gttcgtgaca  3300
cagcggaact tctacgagcc ccagatcatc accaccgaca acaccttcgt gtctggcaac  3360
tgcgacgtcg tgatcggcat tgtgaacaat accgtgtacg accctctgca gcccgagctg  3420
gacagcttca agaggaact ggacaagtac tttaaagaac acacaagccc cgacgtggac  3480
ctgggcgata tcagcggaat caatgccagc gtcgtgaaca tccagaaaga gatcgaccgg  3540
ctgaacgagg tggccaagaa tctgaacgag agcctgatcg acctgcaaga actggggaag  3600
tacgagcagt acatcaagtg gcccctggtac atctggctgg gctttatcgc cggactgatt  3660
gccatcgtga tggtcacaat catgctgtgt tgcatgacca gctgctgtag ctgcctgaag  3720
ggctgttgta gctgtggcag ctgctgcaag ttcgacgagg acgattctga gcccgtgctg  3780
aagggcgtga aactgcacta cacatgatga                                    3810
```

SEQ ID NO: 76         moltype = DNA  length = 3810
FEATURE             Location/Qualifiers
source              1..3810
                     mol_type = other DNA
                     organism = synthetic construct

SEQUENCE: 76

```
atgttcgtgt tcctggtgct gctgcctctg gtgtccagcc agtgtgtgaa cctgatcacc   60
agaacacaga gctacaccaa cagctttacc agaggcgtgt actaccccga caagtgttc  120
agatccagcg tgctgcactc tacccaggac ctgttcctgc cttttcttcag caacgtgacc  180
tggttccacg ccatctccgg caccaatggc accaagagct tcgacaaccc cgtgctgccc  240
ttcaacgacg gggtgtactt tgccagcacc gagaagtcca acatcatcag aggctggatc  300
ttcggcacca cactggacag caagacccag agcctgctga tcgtgaacaa cgccaccaac  360
gtggtcatca agtgtgcga gttccagttc tgcaacgacc ccttcctgga cgtgtactac  420
cacaagagca acaagagctg gatggaaagc gagttccggg tgtacagcag cgccaacaac  480
tgcacctttg agtacgtgtc ccagcctttc ctgatggacc tggaaggcaa gcagggcaac  540
ttcaagaacc tgcgcgagtt cgtgtttaag aacatcgacg gctacttcaa gatctacagc  600
aagcacaccc ctatcaacct cggccgggat ctgcctcagg gcttctctgc tctggaaccc  660
ctggtggatc tgcccatcgg catcaacatc acccggttc agacactgct ggccctgcac  720
agaagctacc tgacacctgg cgatagcagc agcggatgga cagctggtgc cgccgcttac  780
tatgtgggct acctgcagcc tagaaccttc ctgctgaagt acaacgagaa cggcaccatc  840
accgacgccg tggattgtgc tctggatcct ctgagcgaga caagtgcac cctgaagtcc  900
ttcaccgtgg aaaagggcat ctaccagacc agcaacttcc gggtgcagcc caccgaatcc  960
atcgtgcggt tccccaatat caccaatctg tgcccttcg acgaggtgtt caatgccacc 1020
agattcgcct ctgtgtacgc ctggaaccgg aagcggatca gcaattgcgt ggccgactac 1080
tccgtgctgt acaacttcgc cccccttcttc gccttcaagt gctacggcgt gtcccctacc 1140
aagctgaacg acctgtgctt cacaaacgtg tacgccgaca gcttcgtgat ccggggaaac 1200
gaagtgagcc agattgcccc tggacagaca ggcaacatcc cgactacga ctacaagctg 1260
cccgacgact tcaccggctg tgtgattgcc tggaacagca caagctgga ctccaaagtc 1320
ggcggcaact acaattacag gtaccggctg ttccggaagt ccaatctgaa gcccttcgag 1380
cgggacatct ccaccgagat ctatcaggcc ggcaacaagc cttgtaacgg cgtggccggc 1440
gtgaactgct acttcccact gcagtcctac ggctttaggc ccacatatgg cgtgggccat 1500
cagccctaca gagtggtggt gctgagcttc gaactgctgc atgccctgc cacagtgtgc 1560
ggccctaaga aaagcaccaa tctcgtgaag aacaaatgcg tgaacttcaa cttcaacggc 1620
ctgaccggca ccggcgtgct gacagagagc aacaagaagt tcctgccatt ccagcagttt 1680
ggccgggata tcgccgatac cacagacgcc gttagagatc cccagacact ggaaatcctg 1740
gacatcaccc cttgcagctt cggcggagtg tctgtgatca cccctggcac caacaccagc 1800
aatcaggtgg cagtgctgta ccagggcgtg aactgtaccg aagtgcccgt ggccattcac 1860
gccgatcagc tgacacctac atggcgggtg tactccaccg gcagcaatgt gtttcagacc 1920
agagccggct gtctgatcgg agccgagtac gtgaacaata gctacgagtg cgacatcccc 1980
atcggcgctg gaatctgcgc cagctaccag acacagacaa agagccaccg gagagccaga 2040
agcgtggcca gccagagcat cattgcctac acaatgtctc tgggcgccga gaacagcgtg 2100
gcctactcca caaactctat cgctatcccc accaacttca ccatcagcgt gaccacagag 2160
```

```
atcctgcctg tgtccatgac caagaccagc gtggactgca ccatgtacat ctgcggcgat 2220
tccaccgagt gctccaacct gctgctgcag tacggcagct tctgcaccca gctgaagaga 2280
gccctgacag ggatcgccgt ggaacaggac aagaacaccc aagaggtgtt cgcccaagtg 2340
aagcagatct acaagacccc tcctatcaag tacttcggcg gcttcaattt cagccagatt 2400
ctgccggatc ctagcaagcc cagcaagcgg gcttcatcg aggacctgct gttcaacaaa 2460
gtgacactgg ccgacgccgg cttcatcaag cagtatggcg attgtctggg cgacattgcc 2520
gccagggatc tgatttgcgc ccagaagttt aacggactga cagtgctgcc tcctctgctg 2580
accgatgaga tgatcgccca gtacacatct gccctgctgg ccggcacaat cacaagcggc 2640
tggacatttg gagcaggcgc cgctctgcag atcccctttg ctatgcagat ggcctaccgg 2700
ttcaacggca tcggagtgac ccagaatgtg ctgtacgaga accagaagct gatcgccaac 2760
cagttcaaca cgccatcgg caagatccag gacagcctga gcagcacagc aagcgccctg 2820
ggaaagctgc aggacgtggt caaccacaat gcccaggcac tgaacaccct ggtcaagcag 2880
ctgtcctcca agttcggcgc catcagctct gtgctgaacg atatcctgag cagactggac 2940
cctcctgagg ccgaggtgca gatcgacaga gcagactgca gagcctccaa 3000
acatacgtga cccagcagct gatcagagcc gccgagatta gagcctctgc caatctggcc 3060
gccaccaaga tgtctgagtg tgtgctgggc cagagcaaga gagtggactt tgcggcaag 3120
ggctaccacc tgatgagctt ccctcagtct gcccctcacg gcgtggtgtt tctgcacgtg 3180
acatatgtgc ccgctcaaga gaagaatttc accaccgctc cagccatctg ccacgacggc 3240
aaagcccact tcctagagaa ggcgtgttc gtgtccaacg gcacccattg gttcgtgaca 3300
cagcggaact tctacgagcc ccagatcatc accaccgaca acaccttcgt gtctggcaac 3360
tgcgacgtcg tgatcggcat tgtgaacaat accgtgtacg accctctgca gcccgagctg 3420
gacagcttca agaggaact ggacaagtac tttaagaacc acacaagccc cgacgtggac 3480
ctgggcgata tcagcggaat caatgccagc gtcgtgaaca tccagaaaga gatcgaccgg 3540
ctgaacgagg tggccaagaa tctgaacgag agcctgatcg acctgcaaga actggggaag 3600
tacgagcagt acatcaagtg gccctggtac atctggctgg gctttatcgc cggactgatt 3660
gccatcgtga tggtcacaat catgctgtgt tgcatgacca gctgctgtag ctgcctgaag 3720
ggctgttgta gctgtggcag ctgctgcaag ttcgacgagg acgattctga gcccgtgctg 3780
aagggcgtga aactgcacta cacatgatga 3810
```

SEQ ID NO: 77    moltype = AA   length = 1268
FEATURE          Location/Qualifiers
source           1..1268
                 mol_type = protein
                 organism = synthetic construct
SEQUENCE: 77
```
MFVFLVLLPL VSSQCVNLIT RTQSYTNSFT RGVYYPDKVF RSSVLHSTQD LFLPFFSNVT   60
WFHAISGTNG TKRFDNPVLP FNDGVYFAST EKSNIIRGWI FGTTLDSKTQ SLLIVNNATN  120
VVIKVCEFQF CNDPFLDVYY HKNNKSWMES EFRVYSSANN CTFEYVSQPF LMDLEGKQGN  180
FKNLREFVFK NIDGYFKIYS KHTPINLGRD LPQGFSALEP LVDLPIGINI TRFQTLLALH  240
RSYLTPGDSS SGWTAGAAAY YVGYLQPRTF LLKYNENGTI TDAVDCALDP LSETKCTLKS  300
FTVEKGIYQT SNFRVQPTES IVRFPNITNL CPFDEVFNAT RFASVYAWNR KRISNCVADY  360
SVLYNFAPFF AFKCYGVSPT KLNDLCFTNV YADSFVIRGN EVRQIAPGQT GNIADYNYKL  420
PDDFTGCVIA WNSNKLDSKV GGNYNYRYRL FRKSNLKPFE RDISTEIYQA GNKPCNGVAG  480
VNCYFPLQSY GFRPTYGVGH QPYRVVVLSF ELLHAPATVC GPKKSTNLVK NKCVNFNFNG  540
LTGTGVLTES NKKFLPFQQF GRDIADTTDA VRDPQTLEIL DITPCSFGGV SVITPGTNTS  600
NQVAVLYQGV NCTEVPVAIH ADQLTPTWRV YSTGSNVFQT RAGCLIGAEY VNNSYECDIP  660
IGAGICASYQ TQTKSHRRAR SVASQSIIAY TMSLGAENSV AYSNNSIAIP TNFTISVTTE  720
ILPVSMTKTS VDCTMYICGD STECSNLLLQ YGSFCTQLKR ALTGIAVEQD KNTQEVFAQV  780
KQIYKTPPIK YFGGFNFSQI LPDPSKPSKR SFIEDLLFNK VTLADAGFIK QYGDCLGDIA  840
ARDLICAQKF NGLTVLPPLL TDEMIAQYTS ALLAGTITSG WTFGAGAALQ IPFAMQMAYR  900
FNGIGVTQNV LYENQKLIAN QFNSAIGKIQ DSLSSTASAL GKLQDVVNHN AQALNTLVKQ  960
LSSKFGAISS VLNDILSRLD PPEAEVQIDR LITGRLQSLQ TYVTQQLIRA AEIRASANLA 1020
ATKMSECVLG QSKRVDFCGK GYHLMSFPQS APHGVVFLHV TYVPAQEKNF TTAPAICHDG 1080
KAHFPREGVF VSNGTHWFVT QRNFYEPQII TTDNTFVSGN CDVVIGIVNN TVYDPLQPEL 1140
DSFKEELDKY FKNHTSPDVD LGDISGINAS VVNIQKEIDR LNEVAKNLNE SLIDLQELGK 1200
YEQYIKWPWY IWLGFIAGLI AIVMVTIMLC CMTSCCSCLK GCCSCGSCCK FDEDDSEPVL 1260
KGVKLHYT                                                        1268
```

SEQ ID NO: 78    moltype = RNA  length = 3810
FEATURE          Location/Qualifiers
source           1..3810
                 mol_type = other RNA
                 organism = synthetic construct
SEQUENCE: 78
```
atgttcgtgt tcctggtgct gctgcctctg gtgtccagcc agtgtgtgaa cctgatcacc   60
agaacacagt catacaccaa cagctttacc agaggcgtgt actacccga caaggtgttc  120
agatccagcg tgctgcactc tacccaggac ctgttcctgc ctttcttcag caacgtgacc  180
tggttccacg ccatctccgg caccaatggc accaagagat tcgacaaccc cgtgctgccc  240
ttcaacgacg gggtgtactt tgccagcacc gagaagtcca acatcatcag aggctggatc  300
ttcggcacca cactgacag caagacccag agcctgctga tcgtgaacaa cgccaccaac  360
gtggtcatca aagtgtgcga gttccagttc tgcaacgacc ccttcctgga cgtctactac  420
cacaagaaca caagagctg atggaaagc gagttccggg tgtacagcag cgccaacaac  480
tgcacctttg agtacgtgtc ccagcctttc ctgatgacc tggaaggcaa gcagggcaac  540
ttcaagaacc tgcgcgagtt cgtgtttaag aacatcgagg acttcaa gatctacagc  600
aagcacaccc ctatcaacct cggcggat ctgcctcagg gcttctctgc tctggaaccc  660
ctggtggatc tgcccatcgg catcaacatc acccggtttc agacactgct ggccctgcac  720
agaagctacc tgacacctgg cgatagcagc agcggatgga cagctggtgc cgccgcttac  780
tatgtgggct acctgcagcc tagaaccttc ctgctgaagt acaacgagaa cggcaccatc  840
accgacgccg tggattgtgc tctggatcct ctgagcgaga caaagtgcac cctgaagtcc  900
```

```
ttcaccgtgg aaaagggcat ctaccagacc agcaacttcc gggtgcagcc caccgaatcc   960
atcgtgcggt tccccaatat caccaatctg tgccccttcg acgaggtgtt caatgccacc  1020
agattcgcct ctgtgtacgc ctggaaccgg aagcggatca gcaattgcgt ggccgactac  1080
tccgtgctgt acaacttcgc ccccttcttc gcattcaagt gctacggcgt gtcccctacc  1140
aagctgaacg acctgtgctt cacaaacgtg tacgccgaca gcttcgtgat ccggggaaac  1200
gaagtgcggc agattgcccc tggacagaca ggcaacatcg ccgactacaa ctacaagctg  1260
cccgacgact tcaccggctg tgtgattgcc tggaacagca acaagctgga ctccaaagtc  1320
ggcggcaact acaattacag gtaccggctg ttccggaagt ccaatctgaa gcccttcgag  1380
cgggacatct ccaccgagat ctatcaggcc ggcaacagc cttgtaacgg cgtggcaggc   1440
gtgaactgct acttcccact gcagtcctac ggctttaggc ccacatacgg cgtgggccac  1500
cagccctaca gagtggtggt gctgagcttc gaactgctgc atgccctgc cacagtgtgc   1560
ggccctaaga aaagcaccaa tctcgtgaag aacaaatgcg tgaacttcaa cttcaacggc  1620
ctgaccggca ccggcgtgct gacagagagc aacaagaagt tcctgccatt ccagcagttt  1680
ggccggata tcgccgatac cacagacgcc gttagagatc cccagacact ggaaatcctg  1740
gacatcaccc cttgcagctt cggcggagtg tctgtgatca cccctggcac caacaccagc  1800
aatcaggtgg cagtgctgta ccagggcgtg aactgtaccg aagtgcccgt ggccattcac  1860
gccgatcagc tgacacctac atggcgggtg tactccaccg gcagcaatgt gtttcagacc  1920
agagccggct gtctgatcgg agccgagtac gtgaacaata gctacgagtg cgacatcccc  1980
atcggcgctg gaatctgcgc cagctaccag acacagacaa agagccaccg gagagccaga  2040
agcgtggcca gccagagcat cattgcctac acaatgtctc tgggcgccga aacagcgtg   2100
gcctactcca acaactctat cgctatcccc accaacttca ccatcagcgt gaccacagag  2160
atcctgcctg tgtccatgac caagaccagc gtggactgac ccatgtacat ctgcggcgat  2220
tccaccgagt gctccaacct gctgctgcag tacggcagct tctgcaccca gctgaaaaga  2280
gccctgacag gatcgccgt ggaacaggac aagaacaccc aagaggtgtt cgcccaagtg   2340
aagcagatct acaagacccc tcctatcaag tacttcggcg gcttcaattt cagccagatt  2400
ctgcccgatc ctagcaagcc cagcaagcgg agcttcatcg aggacctgct gttcaacaaa  2460
gtgacactgg ccgacgccgg cttcatcaag cagtatggcg attgtctggg cgacattgcc  2520
gccagggatc tgatttgcgc ccagaagttt aacggactga cagtgctgcc tcctctgctg  2580
accgatgaga tgatcgccca gtacacatct gccctgctgg ccggcacaat cacaagcggc  2640
tggacatttg gagcaggcgc cgctctgcag atcccctttg ctatgcagat ggcctaccgg  2700
ttcaacggca tcggagtgac ccagaatgtg ctgtacgaga accagaagct gatcgccaac  2760
cagttcaaca cgccatcgg caagatccag gacagcctga gcagcacagc aagcgccctg  2820
ggaaagctgc aggacgtggt caaccacaat gcccaggcac tgaacaccct ggtcaagcag  2880
ctgtcctcca gttcggcgc catcagttct gtgctgaacg atatcctgag cagactggac  2940
cctcctgagg ccgaggtgca gatcgacaga ctgatcacag gcagactgca gagcctccag  3000
acatacgtga cccagcagct gatcagagcc gccgagatta gagcctctgc caatctggcc  3060
gccaccaaga tgtctgagtg tgtgctgggc cagagcaaga gagtggactt tgcggcaag   3120
ggctaccacc tgatgagctt ccctcagtct gcccctcacg gcgtggtgtt tctgcacgtg  3180
acatatgtgc ccgctcaaga gaaatttc accaccgctc cagccatctg ccacgacggc  3240
aaagcccact ttcctagaga aggcgtgttc gtgtccaacg gcacccattg gttcgtgaca  3300
cagcggaact tctacgagcc ccagatcatc accaccgaca acaccttcgt gtctggcaac  3360
tgcgacgtcg tgatcggcat tgtgaacaat accgtgtacg accctctgca gcccgagctg  3420
gacagcttca aagaggaact ggacaagtac tttaagaacc acacaagccc cgacgtggac  3480
ctgggcgata tcagcggaat caatgccagc gtcgtgaaca tccagaaaga gatcgaccgg  3540
ctgaacgagg tggccaagaa tctgaacgag agcctgatcg acctgcaaga actggggaag  3600
tacgagcagt acatcaagtg gccctggtac atctggctgg ctttatcgc cggactgatt  3660
gccatcgtga tggtcacaat catgctgtgt tgcatgacca gctgctgtag ctgcctgaag  3720
ggctgttgta gctgtggcag ctgctgcaag ttcgacgagg acgattctga gcccgtgctg  3780
aagggcgtga aactgcacta cacatgatga                                   3810

SEQ ID NO: 79         moltype = DNA  length = 3810
FEATURE               Location/Qualifiers
source                1..3810
                      mol_type = other DNA
                      organism = synthetic construct
SEQUENCE: 79
atgttcgtgt tcctggtgct gctgcctctg gtgtccagcc agtgtgtgaa cctgatcacc    60
agaacacagt catacaccaa cagctttacc agaggcgtgt actacccga caaggtgttc   120
agatccagcg tgctgcactc tacccaggac ctgttcctga ctttcttcag caacgtgacc  180
tggttccacg ccatctccgg caccaatggc accaagagat tcgacaaccc cgtgctgccc  240
ttcaacgacg gggtgtactt tgccagcacc gagaagtcca acatcatcag aggctggatc  300
ttcggcacca cactggacag caagacccag agcctgctga tcgtgaacaa cgccaccaac  360
gtggtcatca aagtgtgcga gttccagttc tgcaacgacc ccttcctgga cgtctactac  420
cacaagaaca acaagagctg gatggaaagc gagttccggg tgtacagcag cgccaacaac  480
tgcaccttcg agtacgtgtc ccagcctttc ctgatgcac tggaaggcaa gcagggcaac   540
ttcaagaacc tgcgcgagtt cgtgtttaag aacatcgacg gctacttcaa gatctacagc  600
aagcacaccc ctatcaacct cggccgggat ctgcctcagg gcttctctgc tctggaaccc  660
ctggtggatc tgcccatcgg catcaacatc acccggtttc agacactgct ggccctgcac  720
agaagctacc tgacacctgg cgatagcagc agcggatggg cagctggtgc cgccgcttac  780
tatgtgggct acctgcagcc tagaaccttc ctgctgaagt acaacgagaa cggcaccatc  840
accgacgccg tggattgtgc tctgatcct ctgagcgaga caagtgcac cctgaagtcc   900
ttcaccgtgg aaaagggcat ctaccagacc agcaacttcc gggtgcagcc caccgaatcc  960
atcgtgcggt tccccaatat caccaatctg tgccccttcg acgaggtgtt caatgccacc  1020
agattcgcct ctgtgtacgc ctggaaccgg aagcggatca gcaattgcgt ggccgactac  1080
tccgtgctgt acaacttcgc ccccttcttc gcattcaagt gctacggcgt gtcccctacc  1140
aagctgaacg acctgtgctt cacaaacgtg tacgccgaca gcttcgtgat ccggggaaac  1200
gaagtgcggc agattgcccc tggacagaca ggcaacatcg ccgactacaa ctacaagctg  1260
cccgacgact tcaccggctg tgtgattgcc tggaacagca acaagctgga ctccaaagtc  1320
ggcggcaact acaattacag gtaccggctg ttccggaagt ccaatctgaa gcccttcgag  1380
```

```
cgggacatct ccaccgagat ctatcaggcc ggcaacaagc cttgtaacgg cgtggcaggc   1440
gtgaactgct acttcccact gcagtcctac ggctttaggc ccacatacgg cgtgggccac   1500
cagcccaca gagtggtggt gctgagcttc gaactgctgc atgcccctgc acagtgtgc    1560
ggccctaaga aaagcaccaa tctcgtgaag aacaaatgcg tgaacttcaa cttcaacggc   1620
ctgaccggca ccggcgtgct gacagagagc aacaagaagt tcctgccatt ccagcagttt   1680
ggccgggata tcgccgatac cacagacgcc gttagagatc cccagacact ggaaatcctg   1740
gacatcaccc cttgcagctt cggcggagtg tctgtgatca cccctggcac caacaccagc   1800
aatcaggtgg cagtgctgta ccagggcgtg aactgtaccg aagtgccgt ggccattcac    1860
gccgatcagc tgacacctac atggcgggtg tactccaccg gcagcaatgt gtttcagacc   1920
agagccggct gtctgatcgg agccgagtac gtgaacaata gctacgagtg cgacatcccc   1980
atcggcgctg gaatctgcgc cagctaccag acacagacaa agagccaccg gagagccaga   2040
agcgtggcca gccagagcat cattgcctac aatgtctc tgggcgccga aacagcgtg     2100
gcctactcca acaactctat cgctatcccc accaacttca ccatcagcgt gaccacagag   2160
atcctgcctg tgtccatgac caagaccagc tgggactgca ccatgtacat ctgcggcgat   2220
tccaccgagt gctccaacct gctgctgcag tacggcagct tctgcaccca gctgaaaaga   2280
gccctgacag gatcgccgt ggaacaggac aagaacaccc aagaggtgtt cgcccaagtg    2340
aagcagatct acaagacccc tcctatcaag tacttcggcg gcttcaattt cagccagatt   2400
ctgccgatc ctagcaagcc cagcaagcgg agcttcatcg aggacctgc gttcaacaaa    2460
gtgacactgg ccgacgccgg cttcatcaag cagtatggcg attgtctggg cgacattgcc   2520
gccagggatc tgatttgcgc ccagaagttt aacggactga cagtgctgcc tcctctgctg   2580
accgatgaga tgatcgccca gtacacatct gccctgctgg ccggcacaat cacaagcggc   2640
tggacatttg gagcaggcgc cgctctgcag atccccttg ctatgcagat ggcctaccgg    2700
ttcaacggca tcggagtgac ccagaatgtg ctgtacgaga accagaagct gatcgccaac   2760
cagttcaaca gcgccatcgg caagatccag gacagcctga gcagcacagc aagcgccctg   2820
ggaaagctgc aggacgtggt caaccacaat gcccaggcac tgaacaccct ggtcaagcag   2880
ctgtcctcca agttcggcgc catcagctct gtgctgaacg atatcctgag cagactggac   2940
cctcctgagg ccgaggtgca gatcgacaga ctgatcacag gcagactgca gagcctccag   3000
acatacgtga cccagcagct gatcagagcc gccgagatta gcctctgc caatctggcc    3060
gccaccaaga tgtctgagtg tgtgctgggc cagagcaaga gagtggactt tgcggcaag   3120
ggctaccacc tgatgagctt ccctcagtct gcccctcacg gcgtggtgtt tctgcacgtg   3180
acatatgtgc ccgctcaaga aaagaattc accaccgctc cagccatctg ccacgacggc   3240
aaagcccact ttcctagaga aggcgtgttc gtgtccaacg gcacccattg gttcgtgaca   3300
cagcggaact tctacgagcc ccagatcatc accaccgaca cacccttcgt gtctggcaac   3360
tgcgacgtcg tgatcggcat tgtgaacaat accgtgtacg accctctgca gcccgagctg   3420
gacagcttca agaggaact ggacaagtac tttaagaacc acacaagcc cgacgtggac    3480
ctgggcgata tcagcggaat caatgccagc gtcgtgaaca tccagaaaga gatcgaccgg   3540
ctgaacgagg tggccaagaa tctgaacgag agcctgatcg acctgcaaga actggggaag   3600
tacgagcagt acatcaagtg gcctggtac atctggctgg gctttatcgc cggactgatt    3660
gccatcgtga tggtcacaat catgctgtgt tgcatgacca gctgctgtag ctgcctgaag   3720
ggctgtttgta gctgtggcag ctgctgcaag ttcgacgagg acgattctga gcccgtgctg   3780
aagggcgtga aactgcacta cacatgatga                                    3810

SEQ ID NO: 80            moltype = AA   length = 1270
FEATURE                  Location/Qualifiers
source                   1..1270
                         mol_type = protein
                         organism = synthetic construct
SEQUENCE: 80
MFVFLVLLPL VSSQCVNLIT RTQSYTNSFT RGVYYPDKVF RSSVLHSTQD LFLPFFSNVT    60
WFHAIHVSGT NGTKRFDNPV LPFNDGVYFA STEKSNIIRG WIFGTTLDSK TQSLLIVNNA   120
TNVVIKVCEF QFCNDPFLDV YYHENNKSRM ESELRVYSSA NNCTFEYVSQ PFLMDLEGKQ   180
GNFKNLREFV FKNIDGYFKI YSKHTPVNLG RDLPQGFSAL EPLVDLPIGI NITRFQTLLA   240
LHRSYLTPGD SSSSWTAGAA AYYVGYLQPR TFLLKYNENG TITDAVDCAL DPLSETKCTL   300
KSFTVEKGIY QTSNFRVQPT ESIVRFPNIT NLCPFHEVFN ATRFASVYAW NRKRISNCVA   360
DYSVLYNFAP FFAFKCYGVS PTKLNDLCFT NVYADSFVIR GNEVSQIAPG QTGNIADYNY   420
KLPDDFTGCV IAWNSNKLDS KVSGNYNYLY RLFRKSKLKP FERDISTEIY QAGNKPCNGV   480
AGFNCYFPLQ SYGFRPTYGV GHQPYRVVVL SFELLHAPAT VCGPKKSTNL VKNKCVNFNF   540
NGLTGTGVLT ESNKKFLPFQ QFGRDIADTT DAVRDPQTLE ILDITPCSFG GVSVITPGTN   600
TSNQVAVLYQ GVNCTEVPVA IHADQLTPTW RVYSTGSNVF QTRAGCLIGA EYVNNSYECD   660
IPIGAGICAS YQTQTKSHRR ARSVASQSII AYTMSLGAEN SVAYSNNSIA IPTNFTISVT   720
TEILPVSMTK TSVDCTMYIC GDSTECSNLL LQYGSFCTQL KRALTGIAVE QDKNTQEVFA   780
QVKQIYKTPP IKYFGGFNFS QILPDPSKPS KRSFIEDLLF NKVTLADAGF IKQYGDCLGD   840
IAARDLICAQ KFNGLTVLPP LLTDEMIAQY TSALLAGTIT SGWTFGAGAA LQIPFAMQMA   900
YRFNGIGVTQ NVLYENQKLI ANQFNSAIGK IQDSLSSTAS ALGKLQDVVN HNAQALNTLV   960
KQLSSKFGAI SSVLNDILSR LDPPEAEVQI DRLITGRLQS LQTYVTQQLI RAAEIRASAN  1020
LAATKMSECV LGQSKRVDFC GKGYHLMSFP QSAPHGVVFL HVTYVPAQEK NFTTAPAICH  1080
DGKAHFPREG VFVSNGTHWF VTQRNFYEPQ IITTDNTFVS GNCDVVIGIV NNTVYDPLQP  1140
ELDSFKEELD KYFKNHTSPD VDLGDISGIN ASVVNIQKEI DRLNEVAKNL NESLIDLQEL  1200
GKYEQYIKWP WYIWLGFIAG LIAIVMVTIM LCCMTSCCSC LKGCCSCGSC CKFDEDDSEP  1260
VLKGVKLHYT                                                        1270

SEQ ID NO: 81            moltype = RNA   length = 3816
FEATURE                  Location/Qualifiers
source                   1..3816
                         mol_type = other RNA
                         organism = synthetic construct
SEQUENCE: 81
atgttcgtgt tcctggtgct gctgcctctg gtgtccagcc agtgtgtgaa cctgatcacc     60
agaacacagt catacaccaa cagctttacc agaggcgtgt actaccccga caaggtgttc    120
```

```
agatccagcg tgctgcactc tacccaggac ctgttcctgc ctttcttcag caacgtgacc   180
tggttccacg ccatccacgt gtccggcacc aatggcacca agagattcga caaccccgtg   240
ctgcccttca acgacggggt gtactttgcc agcaccgaga agtccaacat catcagaggc   300
tggatcttcg gcaccacact ggacagcaag acccagagcc tgctgatcgt gaacaacgcc   360
accaacgtgg tcatcaaagt gtgcgagttc cagttctgca acgacccctt cctggacgtc   420
tactaccacg agaacaacaa gagcaggatg gaaagcgagc tccgggtgta cagcagcgcc   480
aacaactgca ccttcgagta cgtgtcccag cctttcctga tggacctgga aggcaagcag   540
ggcaacttca agaacctgcg cgagttcgtg tttaagaaca tcgacggcta cttcaagatc   600
tacagcaagc acaccctgt gaacctcggc cgggatctgc ctcagggctt ctctgctctg   660
gaaccctgg tggatctgcc catcggcatc aacatcaccc ggtttcagac actgctggcc   720
ctgcacagaa gctacctgac acctggcgat agcagcagca gctggacagc tggtgccgcc   780
gcttactatg tgggctacct gcagcctaga accttcctgc tgaagtacaa cgagaacggc   840
accatcaccg acgccgtgga ttgtgctctg gatcctctga gcgagacaaa gtgcaccctg   900
aagtccttca ccgtggaaaa gggcatctac cagaccagca cttccggt gcagcccacc   960
gaatccatcg tgcggttccc caatatcacc aatctgtgcc ccttccacga ggtgttcaat  1020
gccaccagat tcgcctctgt gtacgcctgg aaccggaagc ggatcagcaa ttgcgtggcc  1080
gactactccg tgctgtacaa cttcgccccc ttcttcgcat tcaagtgcta cggcgtgtcc  1140
cctaccaagc tgaacgacct gtgcttcaca aacgtgtacg ccgacagctt cgtgatccgg  1200
ggaaacgaag tgtcacagat tgcccctgga cagacaggca acatcgccga ctacaactac  1260
aagctgcccg acgacttcac cggctgtgtg attgcctgga acagcaacaa gctggactcc  1320
aaagtcagcg gcaactacaa ttacctgtac cggctgttcc ggaagtccaa gctgaagccc  1380
ttcgagcggg acatctccac cgagatctat caggccgagc acaagcccttg taacggctgg  1440
gcaggcttca actgctactt ccccactgca gtcctacggct ttaggccac atacggcgtg  1500
ggccaccagc cctacagagt ggtggtgctg agcttcgaac tgctgcatgc ccctgccaca  1560
gtgtgcggcc ctaagaaaag caccaatctc gtgaagaaca aatgcgtgaa cttcaacttc  1620
aacggcctga ccggcaccgg cgtgctgaca gagagcaaca agaagttcct gccattccag  1680
cagtttggcc gggatatcgc cgataccaca gacgccgtta gagatcccca gacactggaa  1740
atcctggaca tcacccttg cagcttcggc ggagtgtctg tgatcacccc tggcaccaac  1800
accagcaatc aggtggcagt gctgtaccag ggcgtgaact gtaccgaagt gcccgtggcc  1860
attcacgccg atcagctgac acctacatgg cgggtgtact ccaccggcac caatgtgttt  1920
cagaccagag ccggctgtct gatcggagcc gagtacgtga acaatagcta cgagtgcgac  1980
atccccatcg gcgctggaat ctgcgccagc taccagacac agacaaagag ccaccggaga  2040
gccagaagcg tggccagcca gagcatcatt gcctacacaa tgtctctggg cgccgagaac  2100
agcgtggcct actccaacaa ctctatcgct atccccacca acttcaccat cagcgtgacc  2160
acagagatcc tgcctgtgtc catgaccaag accagcgtgg actgcaccat gtacatctgc  2220
ggcgattcca ccgagtgctc caacctgctg ctgcagtacg gcagcttctg cacccagctg  2280
aaaagagccc tgacagggat cgccgtggaa caggacaaga cacccaagat ggtgttcgcc  2340
caagtgaagc agatctacaa gaccccctcct atcaagtact cggcggcttc aatttcagc  2400
cagattctgc ccgatcctag caagcccagc aagcggagct tcatcgagga cctgctgttc  2460
aacaaagtga cactgccga cgccggcttc atcaagcagt atggcgattg tctgggcgac  2520
attgccgcca gggatctgat ttgcgcccag aagtttaacg gactgacagt gctgcctcct  2580
ctgctgaccg atgagatgat cgcccagtac acatctgccc tgctggccgg cacaatcaca  2640
agcggctgga catttggagc agggcccgct cctgcagatc cctttgctat cgagatgcct  2700
taccggttca acggcatcgg agtgacccag aatgtgctgt acgagaacca gaagctgatc  2760
gccaaccagt tcaacagcgc catcggcaag atccaggaca gcctgagcag cacagcaagc  2820
gccctgggaa agctgcagga cgtggtcaac cacaatgccc aggcactgaa caccctggtc  2880
aagcagctgt cctccaagtt cggcgccatc agctctgtgc tgaacgatat cctgagcaga  2940
ctggacccctc ctgaggccga ggtgcagatc gacagactga tcacaggcag actgcagagc  3000
ctccagacat acgtgaccca gcagctgatc agagccgccg agattagagc ctctgccaat  3060
ctggccgcca ccaagatgtc tgagtgtgtg ctgggccaga gcaagagagt ggactttttgc  3120
ggcaagggct accacctgat gagcttccct cagtctgccc ctcacggacg ggtgtttcca  3180
cacgtgacat atgtgcccgc tcaagagaag aatttcacca ccgctccagc catctgccac  3240
gacggcaaag cccactttcc tagagaaggc gtgttcgtgt ccaacggcac ccattggttc  3300
gtgacacagc ggaacttcta cgagcccag atcatcacca ccgacaacac cttcgtgtct  3360
ggcaactgcg atgtcgtgat cggcattgtg aacaataccg tgtacgaccc tctgcagccc  3420
gagctggaca gcttcaaaga ggaactggac aagtactttta agaaccacac aagccccgac  3480
gtggacctgg gcgatatcag cggaatcaat gccagcgtcg tgaacatcca gaaagagatc  3540
gaccggctga acgaggtggc caagaatctg aacgagagcc tgatcgacct gcaagaactg  3600
gggaagtacg agcagtacat caagtggccc tggtacatct ggctgggctt tatcgccgga  3660
ctgattgcca tcgtgatggt cacaatcatg ctgtgttgca tgaccagctg ctgtagctgc  3720
ctgaagggct gttgtagctg tggcagctgc tgcaagttcg acgaggacga ttctgagccc  3780
gtgctgaagg gcgtgaaact gcactacaca tgatga                             3816
```

SEQ ID NO: 82        moltype = DNA  length = 3816
FEATURE             Location/Qualifiers
source              1..3816
                       mol_type = other DNA
                       organism = synthetic construct
SEQUENCE: 82

```
atgttcgtgt tcctggtgct gctgcctctg gtgtccagcc agtgtgtgaa cctgatcacc    60
agaacacagt catacaccaa cagctttacc agaggcgtgt actacccgga caaggtgttc   120
agatccagcg tgctgcactc tacccaggac ctgttcctgc ctttcttcag caacgtgacc   180
tggttccacg ccatccacgt gtccggcacc aatggcacca agagattcga caaccccgtg   240
ctgcccttca acgacggggt gtactttgcc agcaccgaga agtccaacat catcagaggc   300
tggatcttcg gcaccacact ggacagcaag acccagagcc tgctgatcgt gaacaacgcc   360
accaacgtgg tcatcaaagt gtgcgagttc cagttctgca acgacccctt cctggacgtc   420
tactaccacg agaacaacaa gagcaggatg gaaagcgagc tccgggtgta cagcagcgcc   480
aacaactgca ccttcgagta cgtgtcccag cctttcctga tggacctgga aggcaagcag   540
ggcaacttca agaacctgcg cgagttcgtg tttaagaaca tcgacggcta cttcaagatc   600
```

-continued

```
tacagcaagc acacccctgt gaacctcggc cgggatctgc ctcagggctt ctctgctctg    660
gaacccctgg tggatctgcc catcggcatc aacatcaccc ggtttcagac actgctggcc    720
ctgcacagaa gctacctgac acctggcgat agcagcagca gctggacagc tggtgccgcc    780
gcttactatg tgggctacct gcagcctaga accttcctgc tgaagtacaa cgagaacggc    840
accatcaccg acgccgtgga ttgtgctctg gatcctctga gcgagacaac gtgcaccctg    900
aagtccttca ccgtgaaaaa gggcatctac cagaccagca acttccgggt gcagcccacc    960
gaatccatcg tgcggttccc caatatcacc aatctgtgcc ccttcacga ggtgttcaat    1020
gccaccagat tcgcctctgt gtacgcctgg aaccggaagc ggatcagcaa ttgcgtggcc    1080
gactactccg tgctgtacaa cttcgccccc ttcttcgcat tcaagtgcta cggcgtgtcc    1140
cctaccaagc tgaacgacct gtgcttcaca aacgtgtacg ccgacagctt cgtgatccgg    1200
ggaaacgaag tgtcacagat tgccctggaa cagacaggca acatcgccga ctacaactac    1260
aagctgcccg acgacttcac cggctgtgtg attgctggaa cagcaacaa gctggactcc    1320
aaagtcagcg gcaactacaa ttacctgtac cggctgttcc ggaagtccaa gctgaagccc    1380
ttcgagcggg acatctccac cgagatctat caggccgca acaagccttg taacggcgtg    1440
gcaggcttca actgctactt cccactgcag tcctacggct ttaggcccac atacggcgtg    1500
ggccaccagc cctacagagt ggtggtgctg agcttcgaac tgctgcatgc ccctgccaca    1560
gtgtgcggcc ctaagaaaag caccaatctc gtgaagaaca atgcgtgaa cttcaacttc    1620
aacggcctga ccggcaccgg cgtgctgaca gagagcaaca agaagttcct gccattccag    1680
cagtttggcc gggatatcgc cgataccaca gacgccgtta gagatcccca gacactggaa    1740
atcctggaca tcaccccttg cagcttcggc ggagtgtctg tgatcacccc tggcaccaac    1800
accagcaatc aggtggcagt gctgtaccag ggcgtgaact gtaccgaagt gcccgtggcc    1860
attcacgccg atcagctgac acctacatgg cgggtgtact ccaccggcac caatgtgttt    1920
cagaccagag ccggctgtct gatcggagcc gagtacgtga acaatagcta cgagtgcgac    1980
atccccatcg cgctggaat ctgcgccagc taccagacac agacaaagag ccaccggaga    2040
gccagaagcg tggccagcca gagcatcatt gcctacacaa tgtctctggg cgccgagaac    2100
agcgtggcct actccaacaa ctctatcgct atcccccaca acttcaccat cagcgtgacc    2160
acagagatcc tgcctgtgtc catgaccaag accagcgtgg actgcaccat gtacatctgc    2220
ggcgattcca ccgagtgctc caacctgctg ctgcagtacg gcagcttctg cacccagctg    2280
aaaagagccc tgacagggat cgccgtggaa caggacaaga cacccaaga ggtgttcgcc    2340
caagtgaagc agatctacaa gacccctcct atcaagtact tcggcggctt caatttcagc    2400
cagattctgc ccgatcctag caagcccagc aagcggagct catccgagga cctgctgttc    2460
aacaaagtga cactggccga cgccggcttc atcaagcagt atggcgattg tctgggcgac    2520
attgccgcca gggatctgat tgcgcccag aagtttaacg gactgacagt gctgcctcct    2580
ctgctgaccg atgagatgat cgcccagtac acatctgccc tgctggccgg cacaatcaca    2640
agcgctggaa catttggagc aggcgccgct ctgcagatcc cctttgctat gcagatggcc    2700
taccggttca acggcatcgg agtgacccag aatgtgctgt acgagaacca gaagctgatc    2760
gccaaccagt tcaacagcgc catcggcaag atccaggaca gcctgagcag cacagcaagc    2820
gccctgggaa agctgcagga cgtggtcaac cacaatgccc aggcactgaa caccctggtc    2880
aagcagctgt cctccaagtt cggcgccatc agctctgtgc tgaacgatat cctgagcaga    2940
ctggaccctc ctgaggccga ggtgcagatc gacagactga tcacaggcag actgcagagc    3000
ctccagacat acgtgaccca gcagctgatc agagccgccg agattagagc ctctgccaat    3060
ctggccgcca ccaagatgtc tgagtgtgtg ctgggccaga gcaagagagt ggacttttgc    3120
ggcaagggct accacctgat gagcttccct cagtctgccc ctcacggcgt ggtgtttctg    3180
cacgtgacat atgtgccgc tcaagagaag aatttccaca ccgctccagc catctgccac    3240
gacggcaaag cccactttcc tagagaaggc gtgttcgtgt ccaacggcac ccattggttc    3300
gtgacacagc ggaacttcta cgagcccag atcatcacca ccgacaacac cttcgtgtct    3360
ggcaactgcg acgtcgtgat cggcattgtg aacaataccg tgtacgaccc tctgcagccc    3420
gagctggaca gcttcaaaga ggaactggac aagtacttta agaaccacac aagccccgac    3480
gtggacctgg cgatatcag cggaatcaat gccagcgtcg tgaacatcca gaaagagatc    3540
gaccggctga acgaggtggc caagaatctg aacgagagcc tgatcgacct gcaagaactg    3600
gggaagtacg agcagtacat caagtggccc tggtacatct ggctgggctt tatcgccgga    3660
ctgattgcca tcgtgatggt cacaatcatg ctgtgttgca tgaccagctg ctgtagctgc    3720
ctgaagggct gttgtagctg tggcagctgc tgcaagttcg acgaggacga ttctgagccc    3780
gtgctgaagg gcgtgaaact gcactacaca tgatga                               3816
```

SEQ ID NO: 83           moltype = RNA    length = 4273
FEATURE                 Location/Qualifiers
source                  1..4273
                        mol_type = other RNA
                        organism = synthetic construct
SEQUENCE: 83
```
agaataaact agtattcttc tggtccccac agactcagag agaacccgcc accatgttcg    60
tgttcctggt gctgctgcct ctggtgtcca gccagtgtgt gaacctgatc accagaacac    120
agtcatacac caacagcttt accagaggcg tgtactacca gacaaggtg ttcagatcca    180
gcgtgctgca ctctacccag gacctgttcc tgcctttctt cagcaacgat aacctggttca    240
acgccatcca cgtgtccggc accaatggca ccaagagatt cgacaacccc gtgctgccct    300
tcaacgacgg ggtgtacttt gccagcaccg agaagtccaa catcatcaga ggctggatct    360
tcggcaccac actggacagc aagacccaga gcctgctgat cgtgaacaac gccaccaacg    420
tggtcatcaa agtgtgcgag ttccagttct gcaacgaccc cttcctggac gtctactaca    480
acgagaacaa caagagcagg atggaaagcg agctccgggt gtacagcagc gccaacaact    540
gcaccttcga gtacgtgtcc cagcctttcc tgatggacct ggaaggcaag cagggcaact    600
tcaagaacct gcgcgagttc gtgtttaaga acatcgacgg ctacttcaag atctacagca    660
agcacacccc tgtgaacctc ggccgggatc tgcctcaggg ctttctgtct ctggaaccc    720
tggtgatcac ccagggcttc ccggtggcct tctggaaggg cacactctgg    780
gaagctacct gacacctggc gatagcagca gcagctggac agctggtgcc ccgcttact    840
atgtgggcta cctgcagcct agaaccttcc tgctgaagta caacgagaac ggcaccatca    900
ccgacgccgt ggattgtgct ctggatcctc tgagcgagac aaaagtgcacc ctgaagtcct    960
tcaccgtgga aaagggcatc taccagacca gcaacttccg ggtgcagccc accgaatcca    1020
tcgtgcggtt ccccaatatc accaatctgt gccccttcca cgaggtgttc aatgccacca    1080
```

```
gattcgcctc tgtgtacgcc tggaaccgga agcggatcag caattgcgtg gccgactact    1140
ccgtgctgta caacttcgcc cccttcttcg cattcaagtg ctacggcgtg tcccctacca    1200
agctgaacga cctgtgcttc acaaacgtgt acgccgacag cttcgtgatc cggggaaacg    1260
aagtgtcaca gattgcccct ggacagacag gcaacatcgc cgactacaac tacaagctgc    1320
ccgacgactt caccggctgt gtgattgcct ggaacagcaa caagctggac tccaaagtca    1380
gcggcaacta caattacctg taccggctgt tccggaagtc caagctgaag cccttcgagc    1440
gggacatctc caccgagatc tatcaggccg gcaacaagcc ttgtaacggc gtggcaggct    1500
tcaactgcta cttcccactg cagtcctacg gctttaggcc cacatacggc gtgggccacc    1560
agccctacag agtggtggtg ctgagcttcg aactgctgca tgcccctgcc acagtgtgcg    1620
gccctaagaa aagcaccaat ctcgtgaaga caaaatgcgt gaacttcaac ttcaacggcc    1680
tgaccggcac cggcgtgctg acagagagca acaagaagtt cctgccattc cagcagtttg    1740
gccgggatat cgccgatacc acagacgccg ttagagatcc ccagacactg gaaatcctgg    1800
acatcacccc ttgcagcttc ggcggagtgt ctgtgatcac ccctggcacc aacaccagca    1860
atcaggtggc agtgctgtac cagggcgtga actgtaccga agtgcccgtg gccattcagc    1920
ccgatcagct gacacctaca tggcgggtgt actccaccgg cagcaatgtg tttcagacca    1980
gagccggctg tctgatcgga gccgagtacg tgaacaatag ctacgagtgc gacatcccca    2040
tcggcgctgg aatctgcgcc agctaccaga cacagacaaa gagccaccgg agagccgaaa    2100
gcgtggccag ccagagcatc attgctacaa caatgtctct gggcgccgga aacagcgtcg    2160
cctactccaa caactctatc gctatcccca ccaacttcac catcagcgtg accacagaga    2220
tcctgcctgt gtccatgacc aagaccagcg tggactgcac catgtacatc tgcggcgatt    2280
ccaccgagtg ctccaacctg ctgctgcagt acggcagctt ctgcacccag ctgaaaagag    2340
ccctgacagg gatcgccgtg gaacaggaca gaaacaccag agaggtgttc gcccaagtga    2400
agcagatcta caagaccccc ctatcaagt acttcggcgg cttcaatttc agccagattc    2460
tgcccgatcc tagcaagccc agcaagcgga gcttcatcga ggacctgctg ttcaacaaag    2520
tgacactggc cgacgccggc ttcatcaagc agtatgcga ttgtctgggc gacattgccg    2580
ccagggatct gatttgcgcc cagaagttta acggactgac agtgctgcct cctctgctga    2640
ccgatgagat gatcgcccag tacacatctg ccctgctggc cggcacaatc acaagcggct    2700
ggacatttgg agcaggcgcc gctctgcaga tccccttttgc tatgcagatg gcctaccggt    2760
tcaacggcat cggagtgacc cagaatgtgc tgtacgagaa ccagaagctg atcgccaacc    2820
agttcaacag cgccatcggc aagatccagg acagcctgag cagcacagca agcgccctgg    2880
gaaagctgca ggacgtggtc aaccacaatg cccaggcact gaacaccctg gtcaagcagc    2940
tgtcctccaa gttcggcgcc atcagctctg tgctgaacga tatcctgagc agactggacc    3000
ctcctgaggc cgaggtgcag atcgacagac tgatcacagg cagactgcag agcctccaga    3060
catacgtgac ccagcagctg atcagagccg ccgagattag agcctctgcc aatctggccg    3120
ccaccaagat gtctgagtgt gtgctgggcc agagcaagag agtggactt tgcggcaagg    3180
gctaccacct gatgagcttc cctcagtctg cccctcacgg cgtggtgttt ctgcacgtga    3240
catatgtgcc cgctcaagag aagaatttca ccaccgctcc agcatctgcc cacgacggca    3300
aagcccactt tcctagagaa ggcgtgttcg tgtccaacgg cacccattgg ttcgtgacac    3360
agcggaattt ctacgagccc cagatcatca ccaccgacaa cacctttgtg tctggcaact    3420
gcgacgtcgt gatcggcatt gtgaacaata ccgtgtacga ccctctgcag cccgagctgg    3480
acagcttcaa agaggaactg gacaagtact taagaacca caagccccc gacgtggacc    3540
tgggcgatat cagcggaatc aatgccgcg tcgtgaacat ccagaaagag atcgaccggc    3600
tgaacgaggt ggccaagaat ctgaacgaga gcctgatcga cctgcaagaa ctggggaagt    3660
acgagcagta catcaagtgg ccctggtaca tctggctggg ctttatcgcc ggactgattg    3720
ccatcgtgat ggtcacaatc atgctgtgtt gcatgaccag ctgctgtagc tgcctgaagg    3780
gctgttgtag ctgtggcagc tgctgcaagt tcgacgagga cgattctgag cccgtgctga    3840
agggcgtgaa actgcactac acatgatgac tcgagctgat actgcatgca gcaatgcta    3900
gctgcccctt tcccgtcctg ggtacccga gtctccccg acctcgggtc ccaggtatgc    3960
tcccacctcc acctgcccca ctcaccacct ctgctagttc cagacacctc ccaagcacgc    4020
agcaatgcag ctcaaaacgc ttagcctagc cacaccccca cggaaacag cagtgattaa    4080
cctttagcaa taaacgaaag tttaactaag ctatactaac cccagggttg gtcaatttca    4140
tgccagccac accctggagc tagcaaaaaa aaaaaaaaa aaaaaaaaaa aaaagcatat    4200
gactaaaaaa aaaaaaaaaa aaaaaaaaa aaaaaaaaaa aaaaaaaaaa aaaaaaaaaa    4260
aaaaaaaaaa aaa                                                      4273

SEQ ID NO: 84          moltype = DNA   length = 4273
FEATURE                Location/Qualifiers
source                 1..4273
                       mol_type = other DNA
                       organism = synthetic construct
SEQUENCE: 84
agaataaact agtattcttc tggtccccac agactcagag agaacccgcc accatgttcg      60
tgttcctggt gctgctgcct ctggtgtcca gccagtgtgt gaacctgatc accagaacac     120
agtcatacac caacagcttt accagaggcg tgtactaccc tgacaaggtg ttcagatcca     180
gcgtgctgca ctctacccag gacctgttcc tgccttttct cagcaacgtc acctggttcc     240
acgccatcca cgtgtccggc accaatggca ccaagagatt cgacaacccc gtgctgccct     300
tcaacgacgg ggtgtacttt gccagcaccg agaagtccaa catcatcaga ggctggatct     360
tcggcaccac actggacagc aagacccaga gcctgctgat cgtgaacaac gccaccaacg     420
tggtcatcaa agtgtgcgag ttccagttct gcaacgaccc cttcctggac gtctactaca     480
acgagaacaa caagagcagg atggaaagcg agctccgggt gtacagcagc gccaacaact     540
gcaccttcga gtacgtgtcc cagccttttcc tgatggacct ggaaggcaag cagggcaact     600
tcaagaacct gcgcgagttc gtgtttaaga acatcgacgg ctacttcaag atctacagca     660
agcacacccc tgtgaacctc ggccgggatc tgcctcaggg cttctctgct ctggaacccc     720
tggtggatca gccatcgtga atcaacatca cccggtttca tgactgctg gcgcacacgt     780
gaagctacct gacacctggc gatagcagca gcagctggaa agctggtgcc ccgcttact     840
atgtgggcta cctgcagcct agaaccttcc tgctgaagta caacgagaac ggcaccatca     900
ccgacgccgt ggattgtgct ctggatcctc tgagcgagac aaagtgcacc ctgaagtcct     960
tcaccgtgga aaagggcatc taccagacca gcaacttccg ggtgcagccc accgaatcca    1020
tcgtgcggtt ccccaatatc accaatctgt gccccttcca cgaggtgttc aatgccacca    1080
```

```
gattcgcctc tgtgtacgcc tggaaccgga agcggatcag caattgcgtg gccgactact    1140
ccgtgctgta caacttcgcc cccttcttcg cattcaagtg ctacggcgtg tccctacca     1200
agctgaacga cctgtgcttc acaaacgtgt acgccgacag cttcgtgatc cggggaaacg    1260
aagtgtcaca gattgcccct ggacagacag gcaacatcgc cgactacaac tacaagctgc    1320
ccgacgactt caccggctgt gtgattgcct ggaacagcaa caagctggac tccaaagtca    1380
gcggcaacta caattacctg taccggctgt tccggaagtc caagctgaag cccttcgagc    1440
gggacatctc caccgagatc tatcaggccg gcaacaagcc ttgtaacggc gtggcaggct    1500
tcaactgcta cttcccactg cagtcctacg gctttaggcc cacatacggc gtgggccacc    1560
agcccttacag agtggtggtg ctgagcttcg aactgctgca tgcccctgcc acagtgtgcg    1620
gccctaagaa aagcaccaat ctcgtgaaga caaatgcgt gaacttcaac ttcaacggcc    1680
tgaccggcac cggcgtgctg acagagagca caagaagtt cctgccattc agcagtttg     1740
gccgggatat cgccgatacc acagacgccg ttagagatcc ccagacactg gaaatcctgg    1800
acatcacccc ttgcagcttc ggcggagtgt ctgtgatcac ccctggcacc aacaccagca    1860
atcaggtggc agtgctgtac cagggcgtga actgtaccga agtgccgtcg gccattcacg    1920
ccgatcagct gacacctaca tggcgggtgt actccaccgg cagcaatgtg tttcagacca    1980
gagccggctg tctgatcgga gccgagtacg tgaacaatag ctacgagtgc gacatcccca    2040
tcggcgctgg aatctgcgcc agctaccaga cacagacaaa gagccaccgg agagccgaaa    2100
gcgtggccag ccagagcatc attgcctaca atgtctct gggcgccgga aacagctgcg    2160
cctactccaa caactctatc gctatcccca ccaacttcac catcagcgtg accacagaga    2220
tcctgcctgt gtccatgacc aagaccagcg tggactgcac catgtacatc tgcggcgatt    2280
ccaccgagtg ctccaacctg ctgctgcagt acggcagctt ctgcacccag ctgaaaagag    2340
ccctgacagg gatcgccgtg gaacaggaca gaaacccca agaggtgttc gcccaagtga    2400
agcagatcta caagacccct cctatcaagt acttcggcgg cttcaatttc agccagattc    2460
tgcccgatcc tagcaagccc agcaagcgga gcttcatcga ggacctgctg ttcaacaaag    2520
tgacactggc cgacgccggc ttcatcaagc agtatgcga ttgtctgggc gacattgccg    2580
ccagggatct gatttgcgct cagaagttta acggactgac agtgctgcct cctctgctga    2640
ccgatgagat gatcgcccag tacacatctg ccctgctggc cggcacaatc acaagcggct    2700
ggacatttgg agcaggcgcc gctctgcaga tccctttgc tatgcagatg gcctaccggt    2760
tcaacggcat cggagtgacc cagaatgtgc tgtacgagaa ccagaagctg atcgccaacc    2820
agttcaacag cgccatcggc aagatccagg acagcctgag ctcacagca agcgccctgg    2880
gaaagctgca ggacgtggtc aaccacaatg cccaggcact gaacaccctg gtcaagcagc    2940
tgtcctccaa gttcggcgcc atcagctctg tgctgaacga tatcctgagc agactggacc    3000
ctcctgaggc cgaggtgcag atcgacagac tgatcacagg cagactgcag agcctccaga    3060
catacgtgac ccagcagctg atcagagccg ccgagattag agcctctgcc aatctggccg    3120
ccaccaagat gtctgagtgt gtgctgggcc agagcaagag agtggacttt tgcggcaagg    3180
gctaccacct gatgagcttc cctcagtctg cccctcacgg cgtggtgttt ctgcacgtga    3240
catatgtgcc cgctcaagag aagaatttca ccaccgctcc agccatcgc cacgacggca    3300
aagcccactt tcctagagaa ggcgtgttcg tgtccaacgg cacccattgg ttcgtgacac    3360
agcggaactt ctacgagccc cagatcatca ccaccgacaa caccttcgtg tctggcaact    3420
gcgacgtcgt gatcggcatt gtgaacaata ccgtgtacga ccctctgcag cccgagctgg    3480
acagcttcaa agaggaactg gacaagtact ttaagaacca cacaagcccc gacgtggacc    3540
tgggcgatat cagcggaatc aatgccagcg tcgtgaacat ccagaaagag atcgaccggc    3600
tgaacgaggt ggccaagaat ctgaacgaga gcctgatcga cctgcaagaa tgtggagaagt    3660
acgagcagta catcaagtgg cccctggtaca tctggctggg ctttatcgcc ggactgattg    3720
ccatcgtgat ggtcacaatc atgctgtgtt gcatgaccag ctgctgtagc tgcctgaagg    3780
gctgttgtag ctgtggcagc tgctgcaagt tcgacgagga cgattctgag cccgtgctga    3840
agggcgtgaa actgcactac acatgatgac tcgagctgtg actgcatgca atgcatgcta    3900
gctgccccttt tcccgtcctg ggtacccga gtccccccg acctcgggtc ccaggtatgc    3960
tcccacctcc acctgcccca ctcaccacct ctgctagttc cagacacctc ccaagcacgc    4020
agcaatgcag ctcaaaacgc ttagcctagc cacacccccca cgggaaacag cagtgattaa    4080
cctttagcaa taaacgaaag tttaactaag ctatactaac cccagggttg gtcaatttcg    4140
tgccagccac accctggagc tagcaaaaaa aaaaaaaaaa aaaaaaaaaa aaaagcatat    4200
gactaaaaaa aaaaaaaaaa aaaaaaaaaa aaaaaaaaaa aaaaaaaaaa aaaaaaaaaa    4260
aaaaaaaaaa aaa                                                      4273
SEQ ID NO: 85        moltype = AA   length = 1270
FEATURE              Location/Qualifiers
source               1..1270
                     mol_type = protein
                     organism = synthetic construct
SEQUENCE: 85
MFVFLVLLPL VSSQCVNLIT RTQSYTNSFT RGVYYPDKVF RSSVLHSTQD LFLPFFSNVT     60
WFHAIHVSGT NGTKRFDNPV LPFNDGVYFA STEKSNIIRG WIFGTTLDSK TQSLLIVNNA   120
TNVVIKVCEF QFCNDPFLDV YYHENNKSRM ESELRVYSSA NNCTFEYVSQ PFLMDLEGKQ   180
GNFKNLREFV FKNIDGYFKI YSKHTPVNLG RDLPQGFSAL EPLVDLPIGI NITRFQTLLA   240
LHRSYLTPGD SSSSWTAGAA AYYVGYLQPR TFLLKYNENG TITDAVDCAL DPLSETKCTL   300
KSFTVEKGIY QTSNFRVQPT ESIVRFPNIT NLCPFHEVFN ATTFASVYAW NRKRISNCVA   360
DYSVLYNFAP FFAFKCYGVS PTKLNDLCFT NVYADSFVIR GNEVSQIAPG QTGNIADYNY   420
KLPDDFTGCV IAWNSNKLDS KVSGNYNYLY RLFRKSKLKP FERDISTEIY QAGNKPCNGV   480
AGSNCYFPLQ SYGFRPTYGV GHQPYRVVVL SFELLHAPAT VCGPKKSTNL VKNKCVNFNF   540
NGLTGTGVLT ESNKKFLPFQ QFGRDIADTT DAVRDPQTLE ILDITPCSFG GVSVITPGTN   600
TSNQVAVLYQ GVNCTEVPVA IHADQLTPTW RVYSTGSNVF QTRAGCLIGA EYVNNSYECD   660
IPIGAGICAS YQTQTKSHRR ARSVASQSII AYTMSLGAEN SVAYSNNSIA IPTNFTISVT   720
TEILPVSMTK TSVDCTMYIC GDSTECSNLL LQYGSFCTQL KRALTGIAVE QDKNTQEVFA   780
QVKQIYKTPP IKYFGGFNFS QILPDPSKPS KRSFIEDLLF NKVTLADAGF IKQYGDCLGD   840
IAARDLICAQ KFNGLTVLPP LLTDEMIAQY TSALLAGTIT SGWTFGAGAA LQIPFAMQMA   900
YRFNGIGVTQ NVLYENQKLI ANQFNSAIGK IQDSLSSTAS ALGKLQDVVN HNAQALNTLV   960
KQLSSKFGAI SSVLNDILSR LDPPEAEVQI DRLITGRLQS LQTYVTQQLI RAAEIRASAN  1020
LAATKMSECV LGQSKRVDFC GKGYHLMSFP QSAPHGVVFL HVTYVPAQEK NFTTAPAICH  1080
```

```
DGKAHFPREG VFVSNGTHWF VTQRNFYEPQ IITTDNTFVS GNCDVVIGIV NNTVYDPLQP    1140
ELDSFKEELD KYFKNHTSPD VDLGDISGIN ASVVNIQKEI DRLNEVAKNL NESLINLQEL    1200
GKYEQYIKWP WYIWLGFIAG LIAIVMVTIM LCCMTSCCSC LKGCCSCGSC CKFDEDDSEP    1260
VLKGVKLHYT                                                          1270

SEQ ID NO: 86           moltype = RNA  length = 3816
FEATURE                 Location/Qualifiers
source                  1..3816
                        mol_type = other RNA
                        organism = synthetic construct
SEQUENCE: 86
atgttcgtgt tcctggtgct gctgcctctg gtgtccagcc agtgtgtgaa cctgatcacc      60
agaacacagt catacaccaa cagctttacc agaggcgtgt actacccga caaggtgttc     120
agatccagcg tgctgcactc tacccaggac ctgttcctgc cttcttcag caacgtgacc     180
tggttccacg ccatccacgt gtccggcacc aatggcacca agagattcga caaccccgtg     240
ctgcccttca cgacggggt gtactttgcc agcaccgaga agtccaacat catcagaggc     300
tggatcttcg gcaccacact ggacagcaag acccagagcc tgctgatcgt gaacaacgcc     360
accaacgtgg tcatcaaagt gtgcgagttc cagttctgca acgacccctt cctggacgtc     420
tactaccacg agaacaacaa gagcaggatg gaaagcgagc tccgggtgta cagcagcgcc     480
aacaactgca ccttcgagta cgtgtcccag ccttcctga tggacctgga aggcaagcag     540
ggcaacttca gaacctgcg cgagttcgtg tttaagaaca tcgacggcta cttcaagatc     600
tacagcaagc acaccctgt gaacctggc cgggatctgc ctcagggctt ctctgctctg     660
gaaccctgg tggatctgcc catcggcatc aacatcaccc ggtttcagac actgctggac     720
ctgcacagaa gctacctgac acctggcgat agcagcagca gctggacagc tggtgccgcc     780
gcttactatg tgggctacct gcagcctaga accttcctgc tgaagtacaa cgagaacggc     840
accatcaccg acgccgtgga ttgtgctctg gatcctctga gcgagacaaa gtgcaccctg     900
aagtccttca cccgtggaaa gggcatctac cagaccgcca gctctgcggt agcccatcc     960
gaatccatcg tgcggttccc caatatcacc aatctgtgcc ccttccacga ggtgttcaat    1020
gccaccacct tcgcctctgt gtacgcctgg aaccggaagc ggatcagcaa ttgcgtggcc    1080
gactactccg tgctgtacaa cttcgccccc ttcttcgcat tcaagtgcta cggcgtgtcc    1140
cctaccaagc tgaacgacct gtgcttcaca aacgtgtacg ccgacagctt cgtgatccgg    1200
ggaaacgaag tgtcacagat tgcccctgga cagacaggca acatcgccga ctacaactac    1260
aagctgcccg acgacttcac cggctgtgtg attgcctgga acagcaacaa gctggactcc    1320
aaagtcagcg gcaactacaa ttacctgtac cggctgttcc ggaagtccaa gctgaagccc    1380
ttcgagcggg acatctccac cgagatctat caggccggca acaagccttg taacggcgtg    1440
gcaggcagca actgctactt cccactgcag tcctacggct taggcccac atacggcgtg    1500
ggccaccagc cctacagagt ggtggtgctg agcttcgaac tgctgcatgc ccctgccaca    1560
gtgtgcggcc ctaagaaaag caccaatctc gtgaagaaca aatgcgtgaa cttcaacttc    1620
aacggcctga ccggcaccgg cgtgctgaca gagagcaaca gaagttcct gccattccag    1680
cagtttggcc gggatatcgc cgataccaca acgccgtta gagatcccca cactggaa    1740
atcctggaca tcacccttg cagcttcggc ggagtgtctg tgatcacccc tggcaccaac    1800
accagcaatc aggtggcagt gctgtaccag ggcgtgaact gtaccgaagt gcccgtggcc    1860
attcacgccg atcagctgac acctacatgg cgggtgtact caatgtgttt cagaccagag    1920
ccggctgtct gatcggagcc gagtacgtga acaatagcta cgagtgcgca atccccatcg    1980
cgctggaat ctgcgccagc taccagacac agacaaagag ccaccggaga                 2040
gccagaagcg tggccagcca gagcatcatt gcctacacaa tgtctctggg cgccgagaac    2100
agcgtggcct actccaacaa ctctatcgct atccccacca acttcaccat cagcgtgacc    2160
acagagatcc tgcctgtgtc catgaccaag accagcgtgg actgccacat gtacatctgt    2220
ggcgattcca ccgagtgctc caacctgctg ctgcagtacg gcagcttctg cacccagctg    2280
aaaagagccc tgacagggat cgccgtggaa caggacaaga acacccaaga ggtgttcgcc    2340
caagtgaagc agatctacaa gaccctcct atcaagtact cggcggctt caattcagc     2400
cagattctgc ccgatcctag caagcccagc aagcggagct catcgagga cctgctgttc    2460
aacaaagtga cactggccga cgccggcttc atcaagcagt atggcgattg tctgggcgac    2520
attgccgcca gggatctgat ttgcgcccag aagtttaacg gactgacagt gctgcctcct    2580
ctgctgaccg atgagatgat cgcccagtac acatctgccc tgctggccgg cacaatcaca    2640
agcggctgga catttggagc aggcgccgct ctgcagatcc cctttgctat gcagatggcc    2700
taccggttca acggcatcgg agtgacccag aatgtgctgt acgagaacca gaagctgatc    2760
gccaaccagt tcaacagcgc catcggcaag atccaggaca gcctgagcag cacagcaagc    2820
gccctgggaa agctgcagga cgtggtcaac cacaatgcca ggcactgaa caccctggtc    2880
aagcagctgt cctccaagtt cggcgccatc agctctgtgc tgaacgatat cctgagcaga    2940
ctggaccctc tgaggccga ggtgcagatc gacagactga tcacaggcag actgcagagc    3000
ctccagacat acgtgaccca gcagctgatc agagccgccg agattagagc ctctgccaat    3060
ctggccgcca ccaagatgtc tgagtgtgtg ctgggccaga gcaagagagt ggacttttgc    3120
ggcaagggct accacctgat gagctcccct cagtctgccc ctcacggctg ggtgttcctg    3180
cacgtggaca tgtgcccgc tcaagagaag aatttccca ccgctccagc catctgccac    3240
gacggcaaag cccactttcc tagagaaggc gtgttcgtgt ccaacggcac ccattggttc    3300
gtgacacagc ggaacttcta cgagcccag atcatcacca ccgacaacac cttcgtgtct    3360
ggcaactgcg acgtcgtgat cggcattgtg aacaataccg tgtacgaccc tctgcagccc    3420
gagctggaca gcttcaaaga ggaactgaca aagtacttta agaaccacac aagccccgac    3480
gtggacctgg gcgatatcag cggaatcaat gccagcgtcg tgaacatcca gaaagatc    3540
gaccggctga acgaggtggc caagaatctg aacgagagcc tgatcaacct gcaagaactg    3600
gggaagtacg agcagtacat caagtggccc tggtacatct ggctgggctt tatcgccgga    3660
ctgattgcca tcgtgatggt cacaatcatg ctgtgttgca tgaccagctg ctgtagctgc    3720
ctgaagggct gttgtagctg tggcagctgc tgcaagttcg acgaggacga ttctgagccc    3780
gtgctgaagg gcgtgaaact gcactacaca tgatga                              3816
```

```
SEQ ID NO: 87           moltype = DNA  length = 3816
FEATURE                 Location/Qualifiers
source                  1..3816
                        mol_type = other DNA
                        organism = synthetic construct
SEQUENCE: 87
atgttcgtgt tcctggtgct gctgcctctg gtgtccagcc agtgtgtgaa cctgatcacc    60
agaacacagt catacaccaa cagctttacc agaggcgtgt actacccga caaggtgttc   120
agatccagcg tgctgcactc tacccaggac ctgttcctgc ctttcttcag caacgtgacc   180
tggttccacg ccatccacgt gtccggcacc aatggcacca agagattcga caaccccgtg   240
ctgcccttca acgacggggt gtactttgcc agcaccgaga agtccaacat catcagaggc   300
tggatcttcg gcaccacact ggacagcaag acccagagcc tgctgatcgt gaacaacgcc   360
accaacgtgg tcatcaaagt gtgcgagttc cagttcgtgc acgaccccct cctggacgtc   420
tactaccacg agaacaacaa gagcaggatg gaaagcgagc tccgggtgta cagcagcgcc   480
aacaactgca ccttcgagta cgtgtcccag cctttcctga tggacctgga aggcaagcag   540
ggcaacttca agaacctgcg cgagttcgtg tttaagaaca tcgacggcta cttcaagatc   600
tacagcaagc acacccctgt gaacctcggc cgggatctgc ctcagggctt ctctgctctg   660
gaaccccctgg tggatctgcc catcggcatc aacatcaccc ggtttcagac actgctggcc   720
ctgcacagaa gctacctgac acctggcgat agcagcagca gctggacagc tggtgccgcc   780
gcttactatg tgggctacct gcagcctaga accttcctgc tgaagtacaa cgagaacggc   840
accatcaccg acgccgtgga ttgtgctctg gatcctctga gcgagacaaa gtgcacccgg   900
aagtccttca ccgtggaaaa gggcatctac cagaccagca acttccgggt gcagcccacc   960
gaatccatcg tgcggttccc caatatcacc aatctgtgcc ccttccacga ggtgttcaat  1020
gccaccacct tcgcctctgt gtacgcctgg aaccggaagc ggatcagcaa ttgcgtggcc  1080
gactactccg tgctgctacaa cttcgccccc ttcttcgcat tcaagtgcta cggcgtgtcc  1140
cctaccaagc tgaacgacct gtgcttcaca aacgtgtacg ccgacagctt cgtgatccgg  1200
ggaaacgaag tgtcacagat tgcccctgga cagacaggca acatcgccga ctacaactac  1260
aagctgcccg acgacttcac cggctgtgtg attgcctgga acagcaacaa gctggactcc  1320
aaagtcagcg gcaactacaa ttacctgtac cggctgttca ggaagtccaa gctgaagccc  1380
ttcgagcggg acatctccac cgagatctat caggccggca acaagccttg taacggcgtg  1440
gcaggcagca actgctactt cccactgcag tcctacggct ttaggcccac atacggcgtg  1500
ggccaccagc cctacagagt ggtggtgctg agcttcgaac tgctgcatgc ccctgccaca  1560
gtgtgcggcc ctaagaaaag caccaatctc gtgaagaaca atgcgtgaa cttcaacttc  1620
aacggcctga ccggcaccgg cgtgctgaca gagagcaaca agaagttcct gccattccag  1680
cagtttggcc gggatatcgc cgataccaca gacgccgtta gagatcccca gacactggaa  1740
atcctggaca tcacccccttg cagcttcggc ggagtgtctg tgatcacccc tggcaccaac  1800
accagcaatc aggtggcagt gctgtaccag ggcgtgaact gtaccgaagt gcccgtggcc  1860
attcacgccg atcagctgac acctacatgg cgggtgtact ccaccggcag caatgtgttt  1920
cagaccagag ccggctgtct gatcggagcc gagtacgtga acaatagcta cgagtgcgac  1980
atccccatcg gcgctggaat ctgcgccagc taccagacac agacaaagag ccaccggaga  2040
gccagaagcg tggccagcca gagcatcatt gcctacacaa tgtctctggg cgccgagaac  2100
agcgtggcct actccaacaa ctctatcgct atccccacca acttcaccat cagcgtgacc  2160
acagagatcc tgcctgtgtc catgaccaag accagcgtgg actgcaccat gtacatctgc  2220
ggcgattcca ccgagtgctc caacctgctg ctgcagtacg gcagcttctg cacccagctg  2280
aaaagagccc tgacagggat cgccgtggaa caggacaaga cacccaaga ggtgttcgcc  2340
caagtgaagc agatctacaa gacccctcct atcaagtact cggcggcttc aatttcagc  2400
cagattctgc ccgatcctag caagcccagc aagcggagct catcgagga cctgctgttc  2460
aacaaagtga cactggccga cgccggcttc atcaagcagt atggcgattg tctgggcgac  2520
attgccgcca gggatctgat tgcgcccag aagtttaacg gactgacagt gctgcctcct  2580
ctgctgaccg atgagatgat cgcccagtac acatctgtgct tgctgccgg cacaatcaca  2640
agcggctgga catttggagc aggcgccgct ctgcagatcc cctttgctat gcagatggcc  2700
taccggttca acggcatcgg agtgacccag aatgtgctgt acgagaacca gaagctgatc  2760
gccaaccagt tcaacagcgc catcggcaag atccaggaca gcctgagcag cacagcaagc  2820
gccctgggaa agctgcagga cgtggtcaac cacaatgccc aggcactgaa cacccctggtc  2880
aagcagctgt cctccaagtt cggcgccatc agctctgtgc tgaacgatat cctgagcaga  2940
ctggacctc tgaggccga ggtgcagatc gacagactga tcacaggcag actgcagagc  3000
ctccagacat acgtgaccca gcagctgatc agagccgccg agattagagc ctctgccaat  3060
ctggccgcca ccaagatgtc tgagtgtgtg ctggccaga gcaagagagt ggactttgc  3120
ggcaagggct accacctgat gagcttccct cagtctgccc ctcacggcgt ggtgtttctg  3180
cacgtgacat atgtgccgc tcaagagaag aatttcacca ccgctccacg catctgccga  3240
gacggcaaag cccactttcc tagagaaggc gtgttcgtgt ccaaccggcac ccattggttc  3300
gtgacacagc ggaacttcta cgagcccag atcatcacca ccgacaacac cttcgtgtct  3360
ggcaactgcg acgtcgtgat cggcattgtg aacaataccg tgtacgaccc tctgcagccc  3420
gagctggaca gcttcaaaga ggaactggac aagtacttta agaaccacac aagccccgac  3480
gtggacctgg gcgatatcag cggaatcaat gccagcgtcg tgaacatcca gaaagagatc  3540
gaccggctga acgaggtggc caagaatctg aacgagagcc tgatcaacct gcaagaactg  3600
gggaagtacg agcagtacat caagtggccc tggtacatct ggctgggctt tatcgccgga  3660
ctgattgcca tcgtgatggt cacaatcatg ctgtgttgca tgaccagctg ctgtagctgc  3720
ctgaagggct gttgtagctg tggcagctgc tgcaagttcg acgaggacga ttctgagccc  3780
gtgctgaagg gcgtgaaact gcactacaca tgatga                            3816

SEQ ID NO: 88           moltype = RNA  length = 4273
FEATURE                 Location/Qualifiers
source                  1..4273
                        mol_type = other RNA
                        organism = synthetic construct
```

```
SEQUENCE: 88
agaataaact agtattcttc tggtccccac agactcagag agaacccgcc accatgttcg   60
tgttcctggt gctgctgcct ctggtgtcca gccagtgtgt gaacctgatc accagaacac  120
agtcatacac caacagcttt accagaggcg tgtactaccc cgacaaggtg ttcagatcca  180
gcgtgctgca ctctacccag gacctgttcc tgcctttctt cagcaacgtg acctggttcc  240
acgccatcca cgtgtccggc accaatggca ccaagagatt cgacaaccc gtgctgccct  300
tcaacgacgg ggtgtacttt gccagcaccg agaagtccaa catcatcaga ggctggatct  360
tcggcaccac actggacagc aagacccaga gcctgctgat cgtgaacaac gccaccaacg  420
tggtcatcaa agtgtgcgag ttccagttct gcaacgaccc cttcctggac gtctactacc  480
acgagaacaa caagagcagg atggaaagcg agctccgggt gtacagcagc gccaacaact  540
gcaccttcga gtacgtgtcc cagcctttcc tgatggacct ggaaggcaag cagggcaact  600
tcaagaacct cgcgcgagttc gtgtttaaga acatcgacgg ctacttcaag atctacagca  660
agcacacccc tgtgaacctc ggccgggatc tgcctcaggg cttctctgct ctggaacccc  720
tggtggatct gcccatcggc atcaacatca cccggtttca gacactgctg gccctgcaca  780
gaagctacct gacacctggc gatagcagca gcagctggac agctggtgcc ccgcttact  840
atgtgggcta cctgcagcct agaaccttcc tgctgaagta caacgagaac ggcaccatca  900
ccgacgccgt ggattgtgct ctggatcctc tgagcgagac aaagtgcacc ctgaagtcct  960
tcaccgtgga aaagggcatc taccagacca gcaacttccg ggtgcagccc accgaatcca 1020
tcgtgcggtt ccccaatatc accaatctgt gccccttcca cgaggtgttc aatgccacca 1080
ccttcgcctc tgtgtacgcc tggaaccgga agcggatcag caattgcgtg gccgactact 1140
ccgtgctgta caacttcgcc cccttcttcg cattcaagtg ctacgcgtg tcccctacca 1200
agctgaacga cctgtgcttc acaaacgtgt acgccgacga cttcgtgatc cggggaaacg 1260
aagtgtcaca gattgcccct ggacagacag gcaacatcgc cgactacaac tacaagctgc 1320
ccgacgactt caccggctgt gtgattgcct ggaacagcaa caagctggac tccaaagtca 1380
gcggcaacta caattacctg taccggctgt tccgaagtc caagctgaag cccttcgagc 1440
gggacatctc caccggagatc tatcaggccg gcaacaagcc ttgtaacggc gtggcaggca 1500
gcaactgcta cttccactg cagtcctacg gctttaggcc cacatacggc gtgggcacc 1560
agccctacag agtggtggtg ctgagcttcg aactgctgca tgcccctgcc acagtgtgcg 1620
gccctaagaa aagcaccaat ctcgtgaaga acaaatgcgt gaacttcaac ttcaacggcc 1680
tgaccggcac cggcgtgctg acagagagca acaagaagtt cctgccattc cagcagttcg 1740
gccgggatat cgccgatacc acagacgcc ttagagatcc ccagacactg gaaatcctga 1800
acatcacccc ttgcagcttc ggcggagtgt ctgtgatcac ccctggcacc aacaccagca 1860
atcaggtggc agtgctgtac cagggcgtga actgtaccga agtgcccgtg gccattcacg 1920
ccgatcagct gacacctaca tggcgggtgt actccaccgg cagcaatgtg tttcagacca 1980
gagccggctg tctgatcgga gccgagtacg tgaacaatag ctacgagtgc gacatccca 2040
tcggcgctgg aatctgcgcc agctaccaga cacagacaaa gagccaccgg agagccagaa 2100
gcgtggccag ccagagcatc attgcctaca caatgtctct gggcgccgag aacagcgtgg 2160
cctactccaa caactctatc gctatcccca ccaacttcac catcagcgtg accacagaga 2220
tcctgcctgt gtccatgacc aagaccagcg tggactgcac catgtacatc tgcggcgatt 2280
ccaccgagtg ctccaacctg ctgctgcagt acggcagctt ctgcacccag ctgaaaagag 2340
ccctgacagg gatcgccgtg gaacaggaca gaaaccca agaggtgttc gcccaagtga 2400
agcagatcta caagaccct cctatcaagt acttcggcgg cttcaatttc agccagattc 2460
tgcccgatcc tagcaagcc agcaagcgga gcttcatcga ggacctgctg ttcaacaag 2520
tgacactggc cgacgccggc ttcatcaagc agtatggcga ttgtctgggc gacattgccg 2580
ccagggatct gatttgcgcc cagaagttta acggactgac agtgctgcct cctctgctga 2640
ccgatgagat gatcgcccag tacacatctg ccctgctggc cggcacaatc acaagcggct 2700
ggacatttgg agcaggcgcc gctctgcaga tccccttttcg tatgcagatg gcctaccggt 2760
tcaacggcat cggagtgacc cagaatgtgc tgtacgagaa ccagaagcg atcgccaacc 2820
agttcaacag cgccatcggc aagatccagg acagcctgag cagcacagca agcgccctgg 2880
gaaagctgca ggacgtggtc aaccacatg cccaggcact gaacaccctg gtcaagcagc 2940
tgtcctccaa gttcggcgcc atcagctctg tgctgaacga tatcctgagc agactggacc 3000
ctcctgaggc cgaggtgcag atcgacagac tgatcacagg cagactgcag agcctccaga 3060
catacgtgac ccagcagctg atcagagccg ccgagattag agcctctgcc aatctggccg 3120
ccaccaagat gtctgagtgt gtgctgggcc agagcaagag agtggacttt tgcggcaagg 3180
gctaccacct gatgagcttc cctcagtctg cccctcacgg cgtggtgttt ctgcacgtga 3240
catatgtgcc cgctcaagag aagaatttca ccaccgctcc agccatctgc cacgacggca 3300
aagcccactt tcctagagaa ggcgtgttcg tgtccaacgg cacccattgg ttcgtgacac 3360
agcggaactt ctacgagccc cagatcatca ccaccgacaa caccttcgtg tctggcaact 3420
gcgacgtcgt gatcggcatt gtgaacaata ccgtgtacga ccctctgcag cccgagctgg 3480
acagcttcaa agaggaactg gacaagtact ttaagaacca cacaagcccc gacgtggacc 3540
tgggcgatat cagcggaatc aatgccagct ccgtgaacat ccagaaagag atcgaccggc 3600
tgaacgaggt ggccaagaat ctgaacgaga gcctgatcaa cctgcaagaa ctgggaagt 3660
acgagcagta catcaagtgg ccctggtaca tctggctggg ctttatcgcc ggactgattg 3720
ccatcgtgat ggtcacaatc atgctgtgtt gcatgacca ctgctgtagc tgcctgaaag 3780
gctgttgtag ctgtggcagc tgctgcaagt tcgacgagga cgattctgag cccgtgctga 3840
agggcgtgaa actgcactac acatgatgac tcgagctggt actgcatgca cgcaatgcta 3900
gctgcccctt tcccgtcctg ggtaccccga gtctccccg acctcgggtc ccaggtatgc 3960
tcccacctcc acctgcccca ctcaccacct ctgctagttc cagacacctc ccaagcacgc 4020
agcaatgcag ctcaaaacgc ttagcctagc cacaccccca cgggaaacag cagtgattaa 4080
cctttagcaa taaacgaaag tttaactaag ctatactaac cccagggttg gtcaatttcg 4140
tgccagccac accctggagc tagcaaaaaa aaaaaaaaa aaaaaaaaa aaaagcatat 4200
gactaaaaaa aaaaaaaaaa aaaaaaaaaa aaaaaaaaa aaaaaaaaa aaaaaaaaaa 4260
aaaaaaaaaa aaa                                                   4273

SEQ ID NO: 89        moltype = DNA   length = 4273
FEATURE              Location/Qualifiers
source               1..4273
                     mol_type = other DNA
                     organism = synthetic construct
```

```
SEQUENCE: 89
agaataaact agtattcttc tggtccccac agactcagag agaacccgcc accatgttcg    60
tgttcctggt gctgctgcct ctggtgtcca gccagtgtgt gaacctgatc accagaacac   120
agtcatacac caacagcttt accagaggcg tgtactaccc cgacaaggtg ttcagatcca   180
gcgtgctgca ctctacccag gacctgttcc tgcctttctt cagcaacgtg acctggttcc   240
acgccatcca cgtgtccggc accaatggca ccaagagatt cgacaacccc gtgctgccct   300
tcaacgacgg ggtgtacttt gccagcaccg agaagtccaa catcatcaga ggctggatct   360
tcggcaccac actggacagc aagacccaga gcctgctgat cgtgaacaac gccaccaacg   420
tggtcatcaa agtgtgcgag ttccagttct gcaacgaccc cttcctggac gtctactacc   480
acgagaacaa caagagcagg atggaaagcg agctccgggt gtacagcagc gccaacaact   540
gcaccttcga gtacgtgtcc cagcctttcc tgatggacct ggaaggcaag cagggcaact   600
tcaagaacct cgcgcgagttc gtgtttaaga acatcgacgg ctacttcaag atctacagca   660
agcacacccc tgtgaacctc ggccgggatc tgcctcaggg cttctctgct ctggaacccc   720
tggtggatct gcccatcggc atcaacatca cccggtttca gacactgctg gccctgcaca   780
gaagctacct gacacctggc gatagcagca gcagctggac agctggtgcc ccgcttact   840
atgtgggcta cctgcagcct agaaccttcc tgctgaagta caacgagaac ggcaccatca   900
ccgacgccgt ggattgtgct ctggatcctc tgagcgagac aaagtgcacc ctgaagtcct   960
tcaccgtgga aaagggcatc taccagacca gcaacttccg ggtgcagccc accgaatcca  1020
tcgtgcggtt ccccaatatc accaatctgt gcccccttcca cgaggtgttc aatgccacca  1080
ccttcgcctc tgtgtacgcc tggaaccgga agccggatcag caattgcgtg gccgactact  1140
ccgtgctgta caacttcgcc cccttcttcg cattcaagtg ctacgcgtg tcccctacca  1200
agctgaacga cctgtgcttc acaaacgtgt acgccgacga cttcgtgatc cggggaaacg  1260
aagtgtcaca gattgcccct ggacagacag gcaacatcgc cgactacaac tacaagctgc  1320
ccgacgactt caccggctgt gtgattgcct ggaacagcaa caagctggac tccaaagtca  1380
gcggcaacta caattacctg taccggctgt tccgaagtc caagctgaag cccttcgagc  1440
gggacatctc caccggagatc tatcaggccg gcaacaagtc ttgtaacggc tggcaggca  1500
gcaactgcta cttccactg cagtcctacg gctttaggcc cacatacggc gtgggcacc  1560
agccctacag agtggtggtg ctgagcttcg aactgctgca tgcccctgcc acagtgtgcg  1620
gccctaagaa aagcaccaat ctcgtgaaga acaaatgcgt gaacttcaac ttcaacggcc  1680
tgaccggcac cggcgtgctg acagagagca acaagaagtt cctgccattc cagcagttcg  1740
gccgggatat cgccgatacc acagacgccg ttagagatcc ccagacactg gaaatcctgg  1800
acatcacccc ttgcagcttc ggcggagtgt ctgtgatcac ccctggcacc aacaccagca  1860
atcaggtggc agtgctgtac cagggcgtga actgtaccga agtgcccgtg gccattcacg  1920
ccgatcagct gacacctaca tggcgggtgt actccaccag cagcaatgtg tttcagacca  1980
gagccggctg tctgatcgga gccgagtacg tgaacaatag ctacgagtgc gacatcccca  2040
tcggcgctgg aatctgcgcc agctaccaga cacagacaaa gagccaccgg agagccagaa  2100
gcgtggccag ccagagcatc attgcctaca atgtctct gggcgccgag aacagcgtgg  2160
cctactccaa caactctatc gctatcccca ccaacttcac catcagcgtg accacagaga  2220
tcctgcctgt gtccatgacc aagacccagc tggactgac catgtacatc tgcgggcgatt  2280
ccaccgagtg ctccaacctg ctgctgcagt acggcagctt ctgcacccag ctgaaaagag  2340
ccctgacagg gatcgccgtg gaacaggaca gaaacccca agaggtgttc gcccaagtga  2400
agcagatcta caagacccct cctatcaagt acttcggcgg cttcaatttc agccagattc  2460
tgcccgatcc tagcaagccc agcaagcgga gcttcatcga ggacctgctg ttcaacaag  2520
tgacactggc cgacgccggc ttcatcaagc agtatggcga ttgtctgggc gacattgccg  2580
ccagggatct gatttgcgcc cagaagttta acggactgac agtgctgcct cctctgctga  2640
ccgatgagat gatcgcccag tacacatctg ccctgctggc cggcacaatc acaagcggct  2700
ggacatttgg agcaggcgcc gctctgcaga tccccttcg tatgcagatg gcctaccggt  2760
tcaacggcat cggagtgacc cagaatgtgc tgtacgagaa ccagaagcag atcgccaacc  2820
agttcaacag cgccatcggc aagatccagg acagcctgag cagcacagca agcgccctgg  2880
gaaagctgca ggacgtggtc aaccacatg cccaggcact gaacaccctg gtcaagcagc  2940
tgtcctccaa gttcggcgcc atcagctctg tgctgaacga tatcctgagc agactggac  3000
ctccctgaggc cgaggtgcag atcgacagac tgatcacagg cagactgcag agcctccaga  3060
catacgtgac ccagcagctg atcagagccg ccgagattag agcctctgcc aatctggccg  3120
ccaccaagat gtctgagtgt gtgctgggcc agagcaagag agtggactt tgcggcaagg  3180
gctaccacct gatgagcttc cctcagtctg cccctcacgg cgtggtgttt ctgcacgtga  3240
catatgtgcc cgctcaagag aagaatttca ccaccgctcc agccatctgc cacgacggca  3300
aagcccactt tcctagagaa ggcgtgttcg tgtccaacgg cacccattgg ttcgtgacac  3360
agcggaactt ctacgagccc cagatcatca ccaccgacaa caccttcgtg tctggcaact  3420
gcgacgtcgt gatcggcatt gtgaacaata ccgtgtacga ccctctgcag cccgagctgg  3480
acagcttcaa agaggaactg gacaagtact ttaagaacca cacaagcccc gacgtggacc  3540
tgggcgatat cagcggaatc aatgccagct cgtgaacat ccagaaagag atcgaccggc  3600
tgaacgaggt ggccaagaat ctgaacgaga gcctgatcaa cctgcaagaa ctggggaagt  3660
acgagcagta catcaagtgg ccctggtaca tctggctggg ctttatcgcc ggactgattg  3720
ccatcgtgat ggtcacaatc atgctgtgtt gcatgaccag ctgctgtagc tgcctgaagg  3780
gctgttgtag ctgtggcagc tgctgcaagt tcgacgagga cgattctgag cccgtgctga  3840
agggcgtgaa actgcactac acatgatgac tcgagctggt actgcatgca cgcaatgcta  3900
gctgccccctt tcccgtcctg ggtaccccga gtctccccg acctcgggtc ccaggtatgc  3960
tcccacctcc acctgcccca ctcaccacct ctgctagttc cagacacctc ccaagcacgc  4020
agcaatgcag ctcaaaacgc ttagcctagc cacaccccca cgggaaacag cagtgattaa  4080
cctttagcaa taaacgaaag tttaactaag ctatactaac cccagggttg gtcaatttcg  4140
tgccagccac accctggagc tagcaaaaaa aaaaaaaaa aaaaaaaaaa aaagcatat  4200
gactaaaaaa aaaaaaaaaa aaaaaaaaa aaaaaaaaa aaaaaaaaa aaaaaaaaa  4260
aaaaaaaaaa aaa                                                      4273

SEQ ID NO: 90        moltype = AA  length = 1268
FEATURE              Location/Qualifiers
source               1..1268
                     mol_type = protein
                     organism = synthetic construct
```

```
SEQUENCE: 90
MFVFLVLLPL VSSQCVNLIT RTQSYTNSFT RGVYYPDKVF RSSVLHSTQD LFLPFFSNVT    60
WFPHAISGTNG TKRFDNPVLP FNDGVYFAST EKSNIIRGWI FGTTLDSKTQ SLLIVNNATN  120
VVIKVCEFQF CNDPFLDVYY HKNNKSWMES EFRVYSSANN CTFEYVSQPF LMDLEGKQGN  180
FKNLREFVFK NIDGYFKIYS KHTPINLGRD LPQGFSALEP LVDLPIGINI TRFQTLLALH  240
RSYLTPGDSS SGWTAGAAAY YVGYLQPRTF LLKYNENGTI TDAVDCALDP LSETKCTLKS  300
FTVEKGIYQT SNFRVQPTES IVRFPNITNL CPFDEVFNAT TFASVYAWNR KRISNCVADY  360
SVLYNFAPFF AFKCYGVSPT KLNDLCFTNV YADSFVIRGN EVRQIAPGQT GNIADYNYKL  420
PDDFTGCVIA WNSNKLDSKV GGNYNYRYRL FRKSNLKPFE RDISTEIYQA GNKPCNGVAG  480
VNCYFPLQSY GFRPTYGVGH QPYRVVVLSF ELLHAPATVC GPKKSTNLVK NKCVNFNFNG  540
LTGTGVLTES NKKFLPFQQF GRDIADTTDA VRDPQTLEIL DITPCSFGGV SVITPGTNTS  600
NQVAVLYQGV NCTEVPVAIH ADQLTPTWRV YSTGSNVFQT RAGCLIGAEY VNNSYECDIP  660
IGAGICASYQ TQTKSHRRAR SVASQSIIAY TMSLGAENSV AYSNNSIAIP TNFTISVTTE  720
ILPVSMTKTS VDCTMYICGD STECSNLLLQ YGSFCTQLKR ALTGIAVEQD KNTQEVFAQV  780
KQIYKTPPIK YFGGFNFSQI LPDPSKPSKR SFIEDLLFNK VTLADAGFIK QYGDCLGDIA  840
ARDLICAQKF NGLTVLPPLL TDEMIAQYTS ALLAGTITSG WTFGAGAALQ IPFAMQMAYR  900
FNGIGVTQNV LYENQKLIAN QFNSAIGKIQ DSLSSTASAL GKLQDVVHN AQALNTLVKQ  960
LSSKFGAISS VLNDILSRLD PPEAEVQIDR LITGRLQSLQ TYVTQQLIRA AEIRASANLA 1020
ATKMSECVLG QSKRVDFCGK GYHLMSFPQS APHGVVFLHV TYVPAQEKNF TTAPAICHDG 1080
KAHFPREGVF VSNGTHWFVT QRNFYEPQII TTDNTFVSGN CDVVIGIVNN TVYDPLQPEL 1140
DSFKEELDKY FKNHTSPDVD LGDISGINAS VVNIQKEIDR LNEVAKNLNE SLIDLQELGK 1200
YEQYIKWPWY IWLGFIAGLI AIVMVTIMLC CMTSCCSCLK GCCSCGSCCK FDEDDSEPVL 1260
KGVKLHYT                                                          1268

SEQ ID NO: 91           moltype = RNA  length = 3810
FEATURE                 Location/Qualifiers
source                  1..3810
                        mol_type = other RNA
                        organism = synthetic construct
SEQUENCE: 91
atgttcgtgt tcctggtgct gctgcctctg gtgtccagcc agtgtgtgaa cctgatcacc   60
agaacacagt catacaccaa cagctttacc agaggcgtgt actacccga caaggtgttc  120
agatccagcg tgctgcactc tacccaggac ctgttcctgc ctttcttcag caacgtgacc  180
tggttccacg ccatctccgg caccaatggc accaagagat tcgacaaccc cgtgctgccc  240
ttcaacgacg gggtgtactt tgccagcacc gagaagtcca acatcatcag aggctggatc  300
ttcggcacca cactggacag caagacccag agcctgctga tcgtgaacaa cgccaccaac  360
gtggtcatca aagtgtgcga gttccagttc tgcaacgacc ccttcctgga cgtctactac  420
cacaagaaca acaagagctg gatggaaagc gagttccggg tgtacagcag cgccaacaac  480
tgcaccttcg agtacgtgtc ccagcctttc ctgatgaacc tggaaggcaa gcagggcaac  540
ttcaagaacc tgcgcgagtt cgtgtttaag aacatcgacg gctacttcaa gatctacagc  600
aagcacaccc ctatcaacct cggccgggat ctgcctcagg gcttctctgc tctggaaccc  660
ctggtggatc tgcccatcgg catcaacatc acccggtttc agacactgct ggccctgcac  720
agaagctacc tgacacctgg cgatagcagc agcggatgga cagctggtgc cgccgcttac  780
tatgtgggct acctgcagcc tagaaccttc ctgctgaagt acaacgagaa cggcaccatc  840
accgacgccg tggattgtgc tctggatcct ctgagcgaga caaagtgcac cctgaagtcc  900
ttcaccgtgg aaaagggcat ctaccagacc agcaacttcc gggtgcagcc caccgaatcc  960
atcgtgcggt tccccaatat caccaatctg tgccccttcg acgaggtgtt caatgccacc 1020
accttcgcct ctgtgtacgc ctggaaccgg aagcggatca gcaattgcgt ggccgactac 1080
tccgtgctgt acaacttcgc cccctccttc gcattcaagt gctacggcgt gtcccctacc 1140
aagctgaacg acctgtgctt cacaaacgtg tacgccgaca gcttcgtgat ccggggaaac 1200
gaagtgcgcc agattgcccc tggacagaca ggcaacatcg ccgactacaa ctacaagctg 1260
cccgacgact tcaccggctg tgtgattgcc tggaacagca acaagctgga ctccaaagtc 1320
ggcggcaact acaattacag gtaccggctg ttccggaagt ccaatctgaa gcccttcgag 1380
cgggacatct ccaccgagat ctatcaggcc ggcaacaagc cttgtaacgg cgtggcaggc 1440
gtgaactgct acttcccact gcagtcctac ggctttgagc ccacataccg cgtgggccac 1500
cagccctaca gagtggtggt gctgagcttc gaactgctgc atgcccctgc cacagtgtgc 1560
ggccctaaga aaagcaccaa tctcgtgaag aacaaatgcg tgaacttcaa cttcaacggc 1620
ctgaccggca ccgcgtgct gacagagagc aacaagagt tcctgccatt ccagcagttt 1680
ggccgggata tcgccgatac cacagacgcc gttagagatc cccagacact ggaaatcctg 1740
gacatcaccc cttgcagctt cggcggagtg tctgtgatca ccctggcac caacaccagc 1800
aatcaggtgg cagtgctgta ccagggcgtg aactgtaccg aagtgccgt ggccattcac 1860
gccgatcagc tgacacctac atggcgggtg tactccaccg gcagcaatgt gtttcagacc 1920
agagccggct gtctgatcgg agccgagtac gtgaacaata gctacgagtg cgacatcccc 1980
atcggcgctg gaatctgcgc cagctaccag acacagacaa agagccaccg gagagccaga 2040
agcgtggcca gccagagcat cattgcctac acaatgtctc tgggcgccga aaacagcgtg 2100
gcctactcca caaactctat cgctatcccc accaacttca ccatcagcgt gaccacagag 2160
atcctgcctg tgtccatgac caagaccagc gtggactgca ccatgtacat ctgcggcgat 2220
tccaccgagt gctccaacct gctgctgcag tacggcagct tctgcaccca gctgaaaaga 2280
gccctgacag gagatcgccgt ggaactggac aagaacctgt cctgccatt ccagcagttt 2340
aagcagatct acaagacccc tcctatcaag tacttcggcg gcttcaattt cagccagatt 2400
ctgcccgatc ctagcaagcc cagcaagcgg agcttcatcg aggacctgct gttcaacaaa 2460
gtgacactgg ccgacgccgg cttcatcaag cagtatggcg attgtctggg cgacattgcc 2520
gccagggatc tgatttgcgc ccagaagttt aacggactga cagtgctgcc tcctctgctg 2580
accgatgaga tgatccccga tacacatct gcctgcctgg gcacaat caccaagcga 2640
tggacatttg gagcaggcgc cgctctgcag atcccctttg ctatgcagat ggcctaccgg 2700
ttcaacggca tcggagtgac ccagaatgtg ctgtacgaga accagaagct gatcgccaac 2760
cagttcaaca gcgccatcgg caagatccag gacagcctga gcagcacagc aagcgccctg 2820
ggaaagctgc aggacgtggt caaccacaat gcccaggcac tgaacaccct ggtcaagcag 2880
ctgtcctcca agttcggcgc catcagctct gtgctgaacg atatcctgag cagactggac 2940
```

```
cctcctgagg ccgaggtgca gatcgacaga ctgatcacag gcagactgca gagcctccag 3000
acatacgtga cccagcagct gatcagagcc gccgagatta gagcctctgc caatctggcc 3060
gccaccaaga tgtctgagtg tgtgctgggc cagagcaaga gagtggactt ttgcggcaag 3120
ggctaccacc tgatgagctt ccctcagtct gcccctcacg cgtggtgtt tctgcacgtg 3180
acatatgtgc ccgctcaaga gaagaatttc accaccgctc cagccatctg ccacgacggc 3240
aaagcccact ttcctagaga aggcgtgttc gtgtccaacg gcacccattg gttcgtgaca 3300
cagcggaact tctacgagcc ccagatcatc accaccgaca acaccttcgt gtctggcaac 3360
tgcgacgtcg tgatcggcat tgtgaacaat accgtgtacg accctctgca gcccgagctg 3420
gacagcttca aagaggaact ggacaagtac tttaagaacc acacaagccc cgacgtggac 3480
ctgggcgata tcagcggaat caatgccagc gtcgtgaaca tccagaaaga gatcgaccgg 3540
ctgaacgagg tggccaagaa tctgaacgag agcctgatcg acctgcaaga actggggaag 3600
tacgagcagt acatcaagtg gccctggtac atctggctgg gctttatcgc cggactgatt 3660
gccatcgtga tggtcacaat catgctgtgt tgcatgacca gctgctgtag ctgcctgaag 3720
ggctgttgta gctgtggcag ctgctgcaag ttcgacgagg acgattctga gcccgtgctg 3780
aagggcgtga aactgcacta cacatgatga              3810

SEQ ID NO: 92           moltype = DNA  length = 3810
FEATURE                 Location/Qualifiers
source                  1..3810
                        mol_type = other DNA
                        organism = synthetic construct
SEQUENCE: 92
atgttcgtgt tcctggtgct gctgcctctg gtgtccagcc agtgtgtgaa cctgatcacc  60
agaacacagt catacaccaa cagctttacc agaggcgtgt actacccga caaggtgttc 120
agatccagcg tgctgcactc tacccaggac ctgttcctgc ctttcttcag caacgtgacc 180
tggttccacg ccatctccgg caccaatggc accaagagat cgacaaccac cgtgctgccc 240
ttcaacgacg gggtgtactt tgccagcacc gagaagtcca acatcatcag aggctggatc 300
ttcggcacca cactggacag caagacccag agcctgctga tcgtaacaa cgccaccaac 360
gtggtcatca aagtgtgcga gttccagttc tgcaacgacc ccttcctgga cgtctactac 420
cacaagaaca acaagagctg gatggaaagc gagttccggg tgtacagcag cgccaacaac 480
tgcaccttcg agtacgtgtc ccagcctttc ctgatggacc tggaaggcaa gcagggcaac 540
ttcaagaacc tgcgcgagtt cgtgtttaag aacatcgacg gctacttcaa gatctacagc 600
aagcacaccc tatcaacct cggccgggat ctgcctcagg gcttctctgc tctggaaccc 660
ctggtggatc tgccatcgg catcaacatc cccggtttc agacactgct ggccctgcac 720
agaagctacc tgacacctgg cgatagcagc agcggatggc agctggtgc cgccgcttac 780
tatgtgggct acctgcagcc tagaaccttc ctgctgaagt acaacgagaa cggcaccatc 840
accgacgccg tggattgtgc tctggatcct ctgagcgaga caaagtgcac cctgaagtcc 900
ttcaccgtgg aaaagggcat ctaccagacc agcaacttcc gggtgcagcc caccgaatcc 960
atcgtgcggt tccccaatat caccaatctg tgcccctccg acgaggtgtt caatgccacc 1020
accttcgcct ctgtgtacgc ctggaaccgg aagcggatca gcaattgcgt ggccgactac 1080
tccgtgctgt acaacttcgc cccttcttc gcattcaagt gctacggcgt gtcccctacc 1140
aagctgaacg acctgtgctt cacaaacgtg tacgccgaca gcttcgtgat ccggggaaac 1200
gaagtgcggc agattgcccc tggacagaca ggcaacatcg ccgactacaa ctacaagctg 1260
cccgacgact tcaccggctg tgtgattgcc tggaacagca caagctgga ctccaaagtc 1320
ggcggcaact acaattacag gtaccggctg ttccggaagt ccaatctgaa gcccttcgag 1380
cgggacatct ccaccgagat ctatcaggcc ggcaacaagc cttgtaacgg cgtggcaggc 1440
gtgaactgct acttcccact gcagtcctac ggctttgagc ccacatacgg tgggccac 1500
cagcccctaca gagtggtgg gctgagcttc gaactgctgc atgcccctgc cacagtgtgc 1560
ggccctaaga aaagcaccaa tctcgtgaag aacaaatgcg tgaacttcaa cttcaacggc 1620
ctgaccggca ccggcgtgct gacagagagc aacaagaagt tcctgccatt ccagcagttt 1680
ggccgggata tcgccgatac cacagacgcc gttagagatc cccagacact ggaaatcctg 1740
gacatcaccc cttgcagctt cggcggagtg tctgtgatca ccctggcac aacaccagc 1800
aatcaggtgg cagtgctgta ccagggcgtg aactgtaccg aagtgccgt ggccattcac 1860
gccgatcagc tgacacctac atggcgggtg tactccaccg gcagcaatgt gtttcagacc 1920
agagccggct gtctgatcgg agccgagtac gtgaacaata gctacgagtg cgacatcccc 1980
atcggcgctg gaatctgcgc cagctaccag acacagacaa agagccaccg gagagccaga 2040
agcgtggcca gccagagcat cattgcctac acaatgtctc tgggcgccga aacagcgtg 2100
gcctactcca caaactctat cgctatcccc accaacttca ccatcagcgt gaccacagag 2160
atcctgcctg tgtccatgac caagaccagc gtggactgca ccatgtacat ctgcggcgat 2220
tccaccgagt gctccaacct gctgctgcag tacggctcag tctgcaccca gctgaaaaga 2280
gccctgacag gatcgccgt ggaacaggac aagaacaccc aagaggtgtt cgcccaagtg 2340
aagcagatct acaagacccc tcctatcaag tacttcggcg gcttcaattt cagccagatt 2400
ctgcccgatc ctagcaagcc cagcaagcgg agcttcatcg aggacctgct gttcaacaaa 2460
gtgacactgg ccgacgccgg cttcatcaag cagtatggcg attgtctggg cgacattgtg 2520
gccagggatc tgatttgcgc ccagaagttt aacggactga cagtgctgcc tcctctgctg 2580
accgatgaga tgatcgccca gtacacatct gccctgctgg ccggcacaat cacaagcggc 2640
tggacatttg gagcaggcgc cgctctgcag atcccctttg ctatgcagat ggcctaccgg 2700
ttcaacggca tcggagtgac ccagaatgtg ctgtacgaga accagaagct gatcgccaac 2760
cagttcaaca gcgccatcgg caagatccag gacagcctga gcagcacagc aagcgccctg 2820
ggaaagctgc aggacgtggt caaccacaat gcccaggcac tgaacaccct ggtcaagcag 2880
ctgtcctcca gttcggcgc catcagctct gtgctgaacg atatcctgag cagactggac 2940
cctcctgagg ccgaggtgca gatcgacaga ctgatcacag gcagactgca gagcctccag 3000
acatacgtga cccagcagct gatcagagcc gccgagatta gagcctctgc caatctggcc 3060
gccaccaaga tgtctgagtg tgtgctgggc cagagcaaga gagtggactt ttgcggcaag 3120
ggctaccacc tgatgagctt ccctcagtct gcccctcacg cgtggtgtt tctgcacgtg 3180
acatatgtgc ccgctcaaga gaagaatttc accaccgctc cagccatctg ccacgacggc 3240
aaagcccact ttcctagaga aggcgtgttc gtgtccaacg gcacccattg gttcgtgaca 3300
cagcggaact tctacgagcc ccagatcatc accaccgaca acaccttcgt gtctggcaac 3360
tgcgacgtcg tgatcggcat tgtgaacaat accgtgtacg accctctgca gcccgagctg 3420
```

```
gacagcttca aagaggaact ggacaagtac tttaagaacc acacaagccc cgacgtggac   3480
ctgggcgata tcagcggaat caatgccagc gtcgtgaaca tccagaaaga gatcgaccgg   3540
ctgaacgagg tggccaagaa tctgaacgag agcctgatcg acctgcaaga actggggaag   3600
tacgagcagt acatcaagtg gccctggtac atctggctgg gctttatcgc cggactgatt   3660
gccatcgtga tggtcacaat catgctgtgt tgcatgacca gctgctgtag ctgcctgaag   3720
ggctgttgta gctgtggcag ctgctgcaag ttcgacgagg acgattctga gcccgtgctg   3780
aagggcgtga aactgcacta cacatgatga                                    3810

SEQ ID NO: 93         moltype = RNA  length = 4267
FEATURE               Location/Qualifiers
source                1..4267
                      mol_type = other RNA
                      organism = synthetic construct
SEQUENCE: 93
agaataaact agtattcttc tggtccccac agactcagag agaacccgcc accatgttcg   60
tgttcctggt gctgctgcct ctggtgtcca gccagtgtgt gaacctgatc accagaacac   120
agtcatacac caacagcttt accagaggcg tgtactaccc cgacaaggtg ttcagatcca   180
gcgtgctgca ctctacccag gacctgttcc tgcctttctt cagcaacgtg acctggttcc   240
acgccatctc cggcaccaat ggcaccaaga gattcgacaa ccccgtgctg cccttcaacg   300
acgggggtgta ctttgccagc accgagaagt ccaacatcat cagaggctgg atcttcggca   360
ccacactgga cagcaagacc cagagcctgc tgatcgtgaa caacgccacc aacgtggtca   420
tcaaagtgtg cgagttccag ttctgcaacg acccctttcct ggacgtctac taccacaaga   480
acaacaagag ctggatggaa agcgagttcc gggtgtacag cagcgccaac aactgcacct   540
tcgagtacgt gtcccagcct ttcctgatgg acctggaagg caagcagggc aacttcaaga   600
acctgcgcga gttcgtgttt aagaacatcg acggctactt caagatctac agcaagcaca   660
cccctatcaa cctcggccgg gatctgcctc agggcttctc tgctctggaa cccctggtgg   720
atctgcccat cggcatcaac atcccccggt tcagacact gctggccctg cacagaagct    780
acctgacacc tggcgatagc agcagcggat ggacagctgg tgccgccgct tactatgtgg   840
gctacctgca gcctagaacc ttcctgctga gtacaacga aacggcacc atcaccgacg     900
ccgtggattg tgctctggat cctctgagcg agacaaagtg caccctgaag tccttcaccg   960
tggaaaaggg catctaccag accagcaact tccgggtgca gcccaccgaa tccatcgtgc   1020
ggttccccaa tatcaccaat ctgtgcccct tcgacgaggt gttcaatgcc accaccttcg   1080
cctctgtgta cgcctggaac cggaagcgga tcagcaattg cgtggccgac tactccgtgc   1140
tgtacaactt cgcccccttc ttcgcattca agtgctacgg cgtgtccccct accaagctga   1200
acgacctgtg cttcacaaac gtgtacgccg acagcttcgt gatccgggga aacgaagtgc   1260
ggcagattgc ccctggacag acaggcaaca tcgccgacta caactacaag ctgcccgacg   1320
acttcaccgg ctgtgtgatt gcctggaaca gcaacaagct ggactccaaa gtcggcggca   1380
actacaatta caggtaccgg ctgttccgga agtccaatct gaagcccttc gagcgggaca   1440
tctccaccga gatctatcag gccggcaaca agccttgtaa cggcgtggca ggcgtgaact   1500
gctacttccc actgcagtcc tacggcttta ggcccacata cggcgtgggc caccagccct   1560
acagagtggt ggtgctgagc ttcgaactgc tgcatgcccc tgccacagtg tgcggcccta   1620
agaaaagcac caatctcgtg aagaacaaat gcgtgaactt caacttcaac ggcctgaccg   1680
gcaccggcgt gctgacagag agcaacaaga gttcctgcc attccagcag tttggccggg    1740
atatcgccga taccacagac gccgttagag atccccagac actggaaatc ctggacatca   1800
cccccttgca cttcggcgga gtgtctgtga tcacccctgg caccaacacc agcaatcagg   1860
tggcagtgct gtaccagggc gtgaactgta ccgaagtgcc cgtggccatt cacgccgatc   1920
agctgacacc tacatggcgg gtgtactcca ccggcagcaa tgtgtttcag accagagccg   1980
gctgtctgat cggagccgag tacgtgaaca atagctacga gtgcgacatc cccatcggcg   2040
ctggaatctg cgccagctac cagacacaga aaagagcca ccggagagcc agaagcgtgg    2100
ccagccagag catcattgcc tacacaatgt ctctgggcgc cgagaacagc gtggcctact   2160
ccaacaactc tatcgctatc cccaccaact tcaccatcag cgtgaccaca gagatcctgc   2220
ctgtgtccat gaccaagacc agcgtggact gcaccatgta catctgcggc gattccaccg   2280
agtgctccaa cctgctgctg cagtacggca gcttctgcac ccagctgaaa agagccctga   2340
cagggatcgc cgtggaacag gacaagaaca cccaagaggt gttcgcccaa gtgaagcaga   2400
tctacaagac ccctcctatc aagtacttcg gcggcttcaa tttcagccag attctgcccg   2460
atcctagcaa gcccagcaag cggagcttca tcgaggacct gctgttcaac aaagtgacac   2520
tggccgacgc cggcttcatc aagcagtatg gcgattgtct gggcgacatt gccgccaggg   2580
atctgatttg cgcccagaag tttaacggac tgacagtgct gcctcctctg ctgaccgatg   2640
agatgatcgc ccagtacaca tctgccctgc tggccggac aatcacaagc ggctggacat   2700
ttggagcagg cgccgctctg cagatccctt ttgctatgca gatggcctac cggttcaacg   2760
gcatcggagt gacccagaat gtgctgtacg agaaccagaa gctgatcgcc aaccagttca   2820
acagcgccat cggcaagatc caggacagcc tgagcagcac agcaagcgcc ctgggaaagc   2880
tgcaggacgt ggtcaaccac aatgcccagg cactgaacac cctggtcaag cagctgtcct   2940
ccaagttcgg cgccatcagc tctgtgctga cgatatccag cagcgactg gaccctcctg    3000
aggccgaggt gcagatcgac agactgatca caggcagact gcagagcctc cagacatacg   3060
tgacccagca gctgatcaga gccgccgaga ttagagcctc tgccaatctg gccgccacca   3120
agatgtctga gtgtgtgctg ggccagagca agagagtgga cttttgcggc aagggctacc   3180
acctgatgag cttcccctca gtctgccccac acggcgtggt gtttctgcac gtgacatatg   3240
tgcccgctca agagaagaat ttcaccaccg ctccagccat ctgccacgac ggcaaagccc   3300
actttcctag agaaggcgtg ttcgtgtcca acggcaccca ttggttcgtg acacagcgga   3360
acttctacga gccccagatc atcaccaccg acaacacctt cgtgtctggc aactgcgacg   3420
tcgtgatcgg cattgtgaac aataccgtgt acgaccctct gcagcccgag ctggacagct   3480
tcaaagagga actggacaag tactttaaga accacacaag ccccgacgtg gacctgggcg   3540
atatcagcgg aatcaatgcc agcgtcgtga atccagaaa gagatcgacg               3600
aggtggccaa gaatctgaac gagagcctga tcgacctgca agaactgggg aagtacgagc   3660
agtacatcaa gtgccctgg tacatctggc tgggctttat cgccgactg attgccatcg    3720
tgatggtcac aatcatgctg tgttgcatga ccagctgctg tagctgcctg aagggctgtt   3780
gtagctgtgg cagctgctgc aagttcgacg aggacgatt tgagcccgtg ctgaagggcg   3840
tgaaactgca ctacacatga tgactcgagc tggtactgca tgcacgcaat gctagctgcc   3900
```

```
cctttcccgt cctgggtacc ccgagtctcc cccgacctcg ggtcccaggt atgctcccac    3960
ctccacctgc cccactcacc acctctgcta gttccagaca cctcccaagc acgcagcaat    4020
gcagctcaaa acgcttagcc tagccacacc cccacgggaa acagcagtga ttaacccttta   4080
gcaataaacg aaagtttaac taagctatac taaccccagg gttggtcaat ttcgtgccag    4140
ccacaccctg gagctagcaa aaaaaaaaaa aaaaaaaaa aaaaaaaagc atatgactaa    4200
aaaaaaaaaa aaaaaaaaaa aaaaaaaaaa aaaaaaaaaa aaaaaaaaaa aaaaaaaaaa    4260
aaaaaaa                                                              4267

SEQ ID NO: 94           moltype = DNA  length = 4267
FEATURE                 Location/Qualifiers
source                  1..4267
                        mol_type = other DNA
                        organism = synthetic construct
SEQUENCE: 94
agaataaact agtattcttc tggtccccac agactcagag agaacccgcc accatgttcg     60
tgttcctggt gctgctgcct ctggtgtcca gccagtgtgt gaacctgatc accagaacac    120
agtcatacac caacagcttt accagaggcg tgtactaccc cgacaaggtg ttcagatcca    180
gcgtgctgca ctctacccag gacctgttcc tgcctttctt cagcaacgtg acctggttcc    240
acgccatctc cggcaccaat ggcaccaaga gattcgacaa ccccgtgctg cccttcaacg    300
acgggtgta ctttgccagc accgagaagt ccaacatcat cagaggctgg atcttcggca    360
ccacactgga cagcaagacc cagagcctgc tgatcgtgaa aacgccacc aacgtggtca    420
tcaaagtgtg cgagttccag ttctgcaacg accccttcct gacgtctac taccacaaga    480
acaacaagag ctgatggaa agcgagttcc gggtgtacag cagcgccaac aactgcacct    540
tcgagtacgt gtcccagcct ttcctgatgg acctggaagg caagcagggc aacttcaaga    600
acctgcgcga gttcgtgttt aagaacatcg acggctactt caagatctac agcaagcaca    660
cccctatcaa cctcggccgg gatctgcctc agggcttctc tgctctggaa cccctggtgg    720
atctgcccat cggcatcaac atcccggt ttcagacact gctggccctg cacagaagct    780
acctgacacc tggcgatagc agcagcggat ggacagctgg tgccgccgct tactatgtgg    840
gctacctgca gcctagaacc ttcctgctga agtacaacga gaacggcacc atcaccgacg    900
ccgtggattg tgctctggat cctctgagcg agacaaagtg caccctgaag tccttcaccg    960
tggaaaaggg catctaccag accagcaact tccgggtgca gcccaccgaa tccatcgtgc   1020
ggttccccaa tatcaccaat ctgtgcccct tcgacgaggt gttcaatgcc accaccttcg   1080
cctctgtgta cgcctggaac cggaagcgga tcagcaattg cgtggccgac tactccgtgc   1140
tgtacaactt cgccccttc ttcgcattca agtgctacgg cgtgtcccct accaagctga   1200
acgacctgtg cttcaccaac gtgtacgccg acagcttcgt gatccgggga aacgaagtgc   1260
ggcagattgc ccctggacag acaggcaaca tcgccgacta caactacaag ctgcccgacg   1320
acttcaccgg ctgtgtgatt gcctggaaca gcaacaagct ggactccaaa gtcggcggca   1380
actacaatta caggtaccgg ctgttccgga agtccaatct gaagcccttc gagcgggaca   1440
tctccaccga gatctatcag accggcaaca gccttgtaa cggcgtggca ggcgtgaact   1500
gctacttccc actgcagtcc tacggcttta ggcccacata cggcgtgggc caccagccct   1560
acagagtggt ggtgctgagc ttcgaactgc tgcatgcccc tgccacagtg tgcggcccta   1620
agaaaagcac caatctcgtg aagaacaaat gcgtgaactt caacttcaac ggcctgaccg   1680
gcaccggctg gacagag agcaacaaga gttcctgcc attccagcag tttggccggg   1740
atatcgccga taccagagac gccgttagag atccccagac actggaaatc ctggacatca   1800
ccccttgcag cttcggcgga gtgtctgtga tcacccctgg caccaacacc agcaatcagg   1860
tggcagtgct gtaccagggc gtgaactgta ccgaagtgcc cgtggccatt cacgccgatc   1920
agctgacacc tacatggcgg gtgtactcca ccggcagcaa tgtgtttcag accagagccg   1980
gctgtctgat cggagccgag tacgtgaaca atagctacga gtgcgacatc cccatcggcg   2040
ctggaatctg cgccagctac cagacacaga aaagagcca ccggagagcc agaagcgtgg   2100
ccagccagag catcattgcc tacacaatgt ctctgggcgc cgagaacagc gtggcctact   2160
ccaacaactc tatcgctatc cccaccaact tcaccatcag cgtgaccaca gagatctgcc   2220
ctgtgtccat gaccaagacc agcgtggact gcaccatgta catctgcggc gattccaccg   2280
agtgctccaa cctgctgctg cagtacggca gcttctgcac ccagctgaaa agagccctga   2340
cagggatcgc cgtggaacag gacaagaaca cccaagaggt gttcgcccaa gtgaagcaga   2400
tctacaagac ccctcctatc aagtacttcg gcggcttcaa tttcagccag attctgcccg   2460
atcctagcaa gcccagcaag cggagcttca tcgaggacct gctgttcaac aaagtgacac   2520
tggccgacgc cggcttcatc aagcagtatg cgcattgtct gggcgacatt gccgccaggg   2580
atctgatttg cgcccagaag tttaacggac tgacagtgct gcctcctctg ctgaccgatg   2640
agatgatcgc ccagtacaca tctgccctgc tggccggac aatcacaagc ggctggacat   2700
ttggagcagg cgccgctctg cagatcccct ttgctatgca gatggcctac cggttcaacg   2760
gcatcggagt gacccagaat gtgctgtacg agaaccagaa gctgatcgcc aaccagttca   2820
acagcgccat cggcaagatc caggacagcc tgagcagcac agcaagcgcc ctgggaaagc   2880
tgcaggacgt ggtcaaccac aatgcccagg cactgaacac cctggtcaag cagctgtcct   2940
ccaagttcgg cgccatcagc tctgtgctga acgatatcct gagcagactg gaccctcctg   3000
aggccgaggt gcagatcgac agactgatca caggcagact gcagagcctc cagacatacg   3060
tgacccagca gctgatcaga gccgccgaga ttagagcctc tgccaatctg gccgccacca   3120
agatgtctga gtgtgtgctg ggccagagca agagagtgga cttttgcggc aagggctacc   3180
acctgatgag cttccctcag tctgcccctc acggcgtggt gtttctgcac gtgacatatg   3240
tgcccgctca agagaagaat ttcaccaccg ctccagccat ctgccacgac ggcaaagcc   3300
actttcctag agaaggcgtg ttcgtgtcca acggcacccc ttggttcgtg acacagcgga   3360
acttctacga gccccagatc atcaccaccg acaacacctt cgtgtctggc aactgcgacg   3420
tcgtgatcgg cattgtgaac aataccgtgt acgaccctct gcagcccgag ctggacagct   3480
tcaaagagga actggacaag tactttaaga accacacaag ccccgacgtg gacctgggcg   3540
atatcagcgg aatcaatgcc agcgtcgtga atatccagaa agagattgac cggctgaacg   3600
aggtggccaa gaatctgaac gagagcctga tcgacctgca agaactgggg aagtacgagc   3660
agtacatcaa gtggccctgg tacatctggc tgggctttat cgccggactg attgccatcg   3720
tgatggtcac aatcatgctg tgttgcatga ccagctgctg tagctgcctg aagggctgtt   3780
gtagctgtgg cagctgctgc aagttcgacg aggacgattc tgagcccgtg ctgaagggcg   3840
tgaaactgca ctacacatga tgactcgagc tggtactgca tgcacgcaat gctagctgcc   3900
```

```
cctttcccgt cctgggtacc ccgagtctcc cccgacctcg ggtcccaggt atgctcccac   3960
ctccacctgc cccactcacc acctctgcta gttccagaca cctcccaagc acgcagcaat   4020
gcagctcaaa acgcttagcc tagccacacc cccacgggaa acagcagtga ttaacctta    4080
gcaataaacg aaagtttaac taagctatac taaccccagg gttggtcaat ttcgtgccag   4140
ccacaccctg gagctagcaa aaaaaaaaaa aaaaaaaaa aaaaaaaagc atatgactaa    4200
aaaaaaaaaa aaaaaaaaaa aaaaaaaaaa aaaaaaaaaa aaaaaaaaaa aaaaaaaaaa   4260
aaaaaaa                                                             4267

SEQ ID NO: 95          moltype = AA   length = 1269
FEATURE                Location/Qualifiers
source                 1..1269
                       mol_type = protein
                       organism = synthetic construct
SEQUENCE: 95
MFVFLVLLPL VSSQCVNLIT RTQSYTNSFT RGVYYPDKVF RSSVLHSTQD LFLPFFSNVT    60
WFHAIHVSGT NGTKRFDNPA LPFNDGVYFA STEKSNIIRG WIFGTTLDSK TQSLLIVNNA   120
TNVVIKVCEF QFCNDPFLDV YQKNNKSWME SEFRVYSSAN NCTFEYVSQP FLMDLEGKEG   180
NFKNLREFVF KNIDGYFKIY SKHTPINLER DLPQGFSALE PLVDLPIGIN ITRFQTLLAL   240
HRSYLTPGDS SSGWTAGAAA YYVGYLQPRT FLLKYNENGT ITDAVDCALD PLSETKCTLK   300
SFTVEKGIYQ TSNFRVQPTE SIVRFPNITN LCPFHEVFNA TTFASVYAWN RKRISNCVAD   360
YSVIYNFAPF FAFKCYGVSP TKLNDLCFTN VYADSFVIRG NEVSQIAPGQ TGNIADYNYK   420
LPDDFTGCVI AWNSNKLDSK PSGNYNYLYR LFRKSKLKPF ERDISTEIYQ AGNKPCNGVA   480
GSNCYSPLQS YGFRPTYGVG HQPYRVVVLS FELLHAPATV CGPKKSTNLV KNKCVNFNFN   540
GLTGTGVLTE SNKKFLPFQQ FGRDIADTTD AVRDPQTLEI LDITPCSFGG VSVITPGTNT   600
SNQVAVLYQG VNCTEVPVAI HADQLTPTWR VYSTGSNVFQ TRAGCLIGAE YVNNSYECDI   660
PIGAGICASY QTQTKSHRRA RSVASQSIIA YTMSLGAENS VAYSNNSIAI PTNFTISVTT   720
EILPVSMTKT SVDCTMYICG DSTECSNLLL QYGSFCTQLK RALTGIAVEQ DKNTQEVFAQ   780
VKQIYKTPPI KYFGGFNFSQ ILPDPSKPSK RSFIEDLLFN KVTLADAGFI KQYGDCLGDI   840
AARDLICAQK FNGLTVLPPL LTDEMIAQYT SALLAGTITS GWTFGAGAAL QIPFAMQMAY   900
RFNGIGVTQN VLYENQKLIA NQFNSAIGKI QDSLSSTASA LGKLQDVVNH NAQALNTLVK   960
QLSSKFGAIS SVLNDILSRL DPPEAEVQID RLITGRLQSL QTYVTQQLIR AAEIRASANL  1020
AATKMSECVL GQSKRVDFCG KGYHLMSFPQ SAPHGVVFLH VTYVPAQEKN FTTAPAICHD  1080
GKAHFPREGV FVSNGTHWFV TQRNFYEPQI ITTDNTFVSG NCDVVIGIVN NTVYDPLQPE  1140
LDSFKEELDK YFKNHTSPDV DLGDISGINA SVVNIQKEID RLNEVAKNLN ESLIDLQELG  1200
KYEQYIKWPW YIWLGFIAGL IAIVMVTIML CCMTSCCSCL KGCCSCGSCC KFDEDDSEPV  1260
LKGVKLHYT                                                         1269

SEQ ID NO: 96          moltype = RNA  length = 3813
FEATURE                Location/Qualifiers
source                 1..3813
                       mol_type = other RNA
                       organism = synthetic construct
SEQUENCE: 96
atgttcgtgt tcctggtgct gctgcctctg gtgtccagcc agtgtgtgaa cctgatcacc    60
agaacacagt catacaccaa cagctttacc agaggcgtgt actacccga caaggtgttc    120
agatccagcg tgctgcactc tacccaggac ctgttcctgc ctttcttcag caacgtgacc    180
tggttccacg ccatccacgt gtccggcacc aatggcaccaa agagattga caaccccgac    240
ctgcccttca cgacggggt gtactttgcc agcaccgaga gtccaacat catcagaggc    300
tggatcttcg gcaccacact ggacagcaag acccagagcc tgctgatcgt gaacaacgcc   360
accaacgtgg tcatcaaagt gtgcgagttc cagttctgca cgacccctt cctggacgtc    420
taccagaaga acaacaagag ctggatgaa agcgagttc gggtgtacag cagcgccaac    480
aactgcacct tcgagtacgt gtcccagcct ttcctgatgg acctggaagg caaggagggc   540
aacttcaaga acctgcgcga gttcgtgttt aagaacatcg acggctactt caagatctac    600
agcaagcaca cccctatcaa cctcgagcgg gatctgcctc agggcttctc tgctctggaa    660
cccctggtg atctgcccat cggcatcaac atcaccggt ttcagacact gctggcctg    720
cacagaagct acctgacacc tggcgatagc agcagcggat ggacagctgg tgccgccgct   780
tactatgtgg gctacctgca gcctagaacc ttcctgctga gtacaacga gaacggcacc    840
atcaccgacg ccgtggattg tgctctggat cctctgagcg agacaaagtg caccctgaag    900
tccttcaccg tggaaaaggg catctaccag accagcaact tccgggtgca gcccaccgaa   960
tccatcgtgc ggttccccaa tatcaccaat ctgtgcccct tccacgaggt gttcaatgac   1020
accaccttcg cctctgtgta cgcctggaac cggaagcgga tcagcaattg cgtggccgac   1080
tactccgtga tctacaactt cgcccccttc ttcgcattca gtgctacgg cgtgtcccct   1140
accaagctga acgacctgtg cttcacaaac gtgtacgccg acagcttcgt gatccgggga   1200
aacgaagtgt cacagattgc ccctggacag acaggcaaca tcgccgacta caactacaag   1260
ctgcccgacg acttcaccgg ctgtgtgatt gcctggaaca gcaacaagct ggactcaaa    1320
cccagcggca actacaatta cctgtaccgg ctgttccgga gtccaagct gaagcccttc    1380
gagcgggaca ctctccacga gatctatcag gccggcaaca agcttgtaa cggcgtggca   1440
ggcagcaact gctacagccc actgcagtcc tacggcttta ggcccacata cggcgtgggc    1500
caccagcct acagagtggt ggtgctgagc ttcgaactgc tgcatgcccc tgccacagtg    1560
tgcggcccta agaaaagcac caatctcgtg aagaacaaat gcgtgaactt caacttcaac    1620
ggcctgaccg gcaccggcgt gctgacagag agcaacaaga agttcctgcc attccagcag   1680
tttggccggg atatcgccga taccacagac gccgttagaa tccccagac actggaaatc    1740
ctggacatca ccccttgcag cttcggcgga gtgtctgtga tcaccctgg caccaacacc    1800
agcaatcagg tggcagtgct gtaccagggc gtgaactgca ccgaagtgcc agtggccatt   1860
cacgccgatc agctgacacc tacatgcgcg gtgtactcca ccggcagcaa tgtgtttcag   1920
accagagccg gctgtctgat cggagccgag tacgtgaaca atagctacga gtgcgacatc   1980
cccatcggcg ctggaatctg cgccagctac cagacacaga caaagagcca ccggagagcc   2040
agaagcgtgg ccagccagag catcattgcc tacacaatgt ctctgggcgc cgagaacagc   2100
gtggcctact ccaacaactc tatcgctatc cccaccaact tcaccatcag cgtgaccaca   2160
```

```
gagatcctgc ctgtgtccat gaccaagacc agcgtggact gcaccatgta catctgcggc  2220
gattccaccg agtgctccaa cctgctgctg cagtacggca gcttctgcac ccagctgaaa  2280
agagccctga cagggatcgc cgtggaacag gacaagaaca cccaagaggt gttcgcccaa  2340
gtgaagcaga tctacaagac ccctcctatc aagtacttcg gcggcttcaa tttcagccag  2400
attctgcccg atcctagcaa gcccagcaag cggagcttca tcgaggacct gctgttcaac  2460
aaagtgacac tggccgacgc cggcttcatc aagcagtatg gcgattgtct gggcgacatt  2520
gccgccaggg atctgatttg cgcccagaag tttaacggac tgacagtgct gcctcctctg  2580
ctgaccgatg agatgatcgc ccagtacaca tctgccctgc tggccggcac aatcacaagc  2640
ggctggacat ttggagcagg cgccgctctg cagatcccct ttgctatgca gatggcctac  2700
cggttcaacg gcatcggagt gacccagaat gtgctgtacg agaaccagaa gctgatcgcc  2760
aaccagttca acagcgccat cggcaagatc caggacagcc tgagcagcac agcaagcgcc  2820
ctgggaaagc tgcaggacgt ggtcaaccac aatgcccagg cactgaacac cctggtcaag  2880
cagctgtcct ccaagttcgg cgccatcagc tctgtgctga acgatatcct gagcagactg  2940
gaccctcctg aggccgaggt gcagatcgac agactgatca caggcagact gcagagcctc  3000
cagacatacg tgacccagca gctgatcaga gccgccgaga ttagagcctc tgccaatctg  3060
gccgccacca agatgtctga gtgtgtgctg ggcagagca agagagtgga cttttgcggc  3120
aagggctacc acctgatgag cttccctcag tctgcccctc acggcgtggt gtttctgcac  3180
gtgacatatg tgcccgctca agagaagaat ttcaccaccg ctccagccat ctgccacgac  3240
ggcaaagccc actttcctag agaaggcgtg ttcgtgtcca acggcaccca ttggttcgtg  3300
acacagcgga acttctacga gccccagatc atcaccaccg acaaccctt cgtgtctggc  3360
aactgcgacg tcgtgatcgg cattgtgaac aataccgtgt acgaccctct gcagcccgag  3420
ctggacagct tcaaagagga actggacaag tactttaaga accacacaga cccccgacgtg  3480
gacctgggcg atatcagcgg aatcaatgcc agcgtcgtga acatccagaa agagatcgac  3540
cggctgaacg aaggtggcca agaatctgaac gagagcctga tcgacctgca agaactgggg  3600
aagtacgagc agtacatcaa gtggcccctgg tacatctggc tgggctttat cgccggactg  3660
attgccatcg tgatggtcac aaatcatgctg tgttgcatga ccagctgctg tagctgcctg  3720
aagggctgtt gtagctgtgg cagctgctgc aagttcgacg aggacgattc tgagcccgtg  3780
ctgaagggcg tgaaactgca ctacacatga tga                                  3813

SEQ ID NO: 97         moltype = DNA   length = 3813
FEATURE               Location/Qualifiers
source                1..3813
                      mol_type = other DNA
                      organism = synthetic construct
SEQUENCE: 97
atgttcgtgt tcctggtgct gctgcctctg gtgtccagcc agtgtgtgaa cctgatcacc  60
agaacacagt catacaccaa cagctttacc agaggcgtgt actacccccga caaggtgttc  120
agatccagcg tgctgcactc tacccaggac ctgttcctgc cttcttcag caacgtgacc  180
tggttccacg ccatccacgt gtccggcacc aatggcaccaa agagattcga caacccgac  240
ctgcccttca cgacggggt gtactttgcc agcaccgaga gtccaacat catcagaggc  300
tggatcttcg gcaccacact ggacagcaag acccagagcc tgctgatcgt gaacaacgcc  360
accaacgtgg tcatcaaagt gtgcgagttc agttctgca cgaccccctt cctggacgtc  420
taccagaaga acaacaagag ctggatgaaa agcgagttcc gggtgtacag cagcgccaac  480
aactgcaccct tcgagtacgt gtcccagcct ttcctgatgg acctggaagg caaggagggc  540
aacttcaaga acctgcgcga gttcgtgttt aagaacatcg acggcatctt caagatctac  600
agcaagcaca cccctatcaa cctcgagcgg atctgcctc agggcttctc tgctctggaa  660
cccctgtgg atctgcccat cggcatcaac atcacccgt ttcagacact gctggccctg  720
cacagaagct acctgacacc tggcgatagc agcagcggat ggacagctgg tgccgccgct  780
tactatgtgg gctacctgca gcctagaacc ttcctgctga gtacaacga gaacggcacc  840
atcaccgacg ccgtggattg tgctctggat cctctgagcg agacaaagtg caccctgaag  900
tccttcaccg tggaaaagg catctaccag accagcaact tccgggtgca gccaccgaa  960
tccatcgtgc ggttccccaa tatcaccaat ctgtgcccct tccacgaggt gttcaatgcc  1020
accaccttcg cctctgtgta cgcctggaac cggaagcgga tcagcaattg cgtggccgac  1080
tactccgtga tctacaactt cgcccccttc ttcgcattca gtgctacgg cgtgtcccct  1140
accaagctga acgacctgtg cttcacaaac gtgtacgccg acagcttcgt gatccgggga  1200
aacgaagtgt cacagattgc ccctggacag acaggcaaca tcgccgacta caactacaag  1260
ctgcccgacg acttcaccgg ctgtgtgatt gcctggaaca gcaacaagct ggactccaaa  1320
cccagcggca actacaatta cctgtaccgg ctgttccgga gtccaagct gaagcccttc  1380
gagcgggaca tctccaccga gatctatcag gccggcaaca agccttgtaa cggcgtggca  1440
ggcagcaact gctacagccc actgcagtcc tacggctta ggcccacata cggcgtgggc  1500
caccagccct acagagtggt ggtgctgagc ttcgaactgc tgcatgcccc tgccacagtg  1560
tgcggcccta gaaaagcac caatctcgtg aagaacaaat gcgtgaactt caacttcaac  1620
ggcctgaccg gcaccggcgt gctgacagag agcaacaaga gttcctgcc attccagcag  1680
tttggccggg atatcgcga taccacagac gccgttagga atccccagac actgaaaatc  1740
ctggacatca ccccttgcag cttcggcgga gtgtctgtga tcaccccctgg caccaacacc  1800
agcaatcagg tggcagtgct gtaccagggc gtgaactgta ccgaagtgcc cgtggccatt  1860
cacgccgatc agctgacacc tacatggcgg gtgtactcca ccggcagcaa tgtgtttcag  1920
accagagccg gctgtctgat cggagccgag tacgtgaaca tagctacga gtgcgacatc  1980
cccatcggcg ctggaatctg cgccagctac cagacagaca caaagagcca ccggagagcc  2040
agaagcgtgg ccagcagag catcattgcc tacacaatgt ctctgggcgc cgagaacagc  2100
gtggcctact ccaacaactc tatcgctatc cccaccaact tcaccatcag cgtgaccaca  2160
gagatcctgc ctgtgtccat gaccaagacc agcgtggact gcaccatgta catctgcggc  2220
gattccaccg agtgctccaa cctgctgctg cagtacggca gcttctgcac ccagctgaaa  2280
agagccctga cagggatcgc cgtggaacag gacaagaaca cccaagaggt gttcgcccaa  2340
gtgaagcaga tctacaagac ccctcctatc aagtacttcg gcggcttcaa tttcagccag  2400
attctgcccg atcctagcaa gcccagcaag cggagcttca tcgaggacct gctgttcaac  2460
aaagtgacac tggccgacgc cggcttcatc aagcagtatg gcgattgtct gggcgacatt  2520
gccgccaggg atctgatttg cgcccagaag tttaacggac tgacagtgct gcctcctctg  2580
ctgaccgatg agatgatcgc ccagtacaca tctgccctgc tggccggcac aatcacaagc  2640
```

```
ggctggacat ttggagcagg cgccgctctg cagatcccct ttgctatgca gatggcctac  2700
cggttcaacg gcatcggagt gacccagaat gtgctgtacg agaaccagaa gctgatcgcc  2760
aaccagttca acagcgccat cggcaagatc caggacagcc tgagcagcac agcaagcgcc  2820
ctgggaaagc tgcaggacgt ggtcaaccac aatgcccagg cactgaacac cctggtcaag  2880
cagctgtcct ccaagttcgg cgccatcagc tctgtgctga acgatatcgt gagcagactg  2940
gaccctcctg aggccgaggt gcagatcgac agactgatca caggcagact gcagagcctc  3000
cagacatacg tgacccagca gctgatcaga gccgccgaga ttagagcctc tgccaatctg  3060
gccgccacca agatgtctga gtgtgtgctg ggccagagca agagtgga cttttgcggc  3120
aagggctacc acctgatgag cttccctcag tctgcccctc acggcgtggt gtttctgcac  3180
gtgacatatg tgcccgctca agagaagaat ttcaccaccg ctccagccat ctgccacgac  3240
ggcaaagccc actttcctag agaaggcgtg ttcgtgtcca acggcaccca ttggttcgtg  3300
acacagcgga acttctacga gccccagatc atcaccaccg caacaccttc gtgtctggc  3360
aactgcgacg tcgtgatcgg cattgtgaac aataccgtgt acgaccctct gcagcccgag  3420
ctggacagct tcaaagagga actggacaag tactttaaga accacaagc ccccgacgtg  3480
gacctgggcg atatcagcgg aatcaatgcc agcgtcgtga acatccagaa agagatcgac  3540
cggctgaacg aggtggccaa gaatctgaac gagagcctga tcgacctgca gaactgggg  3600
aagtacgagc agtacatcaa gtggccctgg tacatctggc tgggctttat cgccggactg  3660
attgccatcg tgatggtcac aatcatgctg tgttgcatga ccagctgctg tagctgcctg  3720
aagggctgtt gtagctgtgg cagctgctgc aagttcgacg aggacgattc tgagcccgtg  3780
ctgaagggcg tgaaactgca ctacacatga tga                                3813

SEQ ID NO: 98         moltype = RNA  length = 4270
FEATURE               Location/Qualifiers
source                1..4270
                      mol_type = other RNA
                      organism = synthetic construct
SEQUENCE: 98
agaataaact agtattcttc tggtccccac agactcagag agaacccgcc accatgttcg  60
tgttcctggt gctgctgcct ctggtgtcca gccagtgtgt gaacctgatc accagaacac  120
agtcatacac caacagcttt accagaggcg tgtactaccc cgacaaggtg ttcagatcca  180
gcgtgctgca ctctacccag gacctgttcc tgccttttct cagcaacgtg acctggttcc  240
acgccatcca cgtgtccggc accaatggca ccaagagatt cgacaacccc gccctgccct  300
tcaacgacgg ggtgtacttt gccagcaccg agaagtccaa catcatcaga ggctggatct  360
tcggcaccac actggacagc aagacccaga gcctgctgat cgtgaacaac gccaccaacg  420
tggtcatcaa agtgtgcgag ttccagttct gcaacgaccc cttcctggac gtctaccaga  480
agaacaacaa gagctggatg gaaagcgagt tcagggtgt acagcagcgcc aacaactgca  540
ccttcgagta cgtgtcccag cctttcctga tggacctgga aggcaaggag ggcaacttca  600
agaacctgcg cgagttcgtg tttaagaaca tcgacggcta cttcaagatc tacagcaagc  660
acacccctat caacctcgag cgggatctgc ctcagggtct ctctgctctg gaacccctgg  720
tggatctgcc catcggcatc aacatcaccc ggtttcagac actgctggcc ctgcacagaa  780
gctacctgac acctggcgat agcagcagcg gatggacagc tggtgccgcc gcttactatg  840
tgggctacct gcagcctaga accttcctgc tgaagtacaa cgagaacggc accatcaccg  900
acgccgtgga ttgtgctctg gatcctctga gcgagacaaa gtgcaccctg aagtccttca  960
ccgtggaaaa gggcatctac cagaccagca acttccgggt gcagcccacc gaatccatcg  1020
tgcggttccc caatatcacc aatctgtgcc ccttccacga ggtgttcaat gccaccacct  1080
tcgcctctgt gtacgcctgg aaccggaagc ggatcagcaa ttgcgtggcc gactactccg  1140
tgatctacaa cttcgccccc ttcttcgcat tcaagtgcta cggcgtgtcc cctaccaagc  1200
tgaacgacct gtgcttcaca aacgtgtacg ccgacagctt cgtgatcggg ggaaacgaag  1260
tgtcacagat tgcccctgga cagacaggca acatcgccga ctacaactac aagctgcccg  1320
acgacttcac cggctgtgtg attgcctgga acagcaacaa gctggactcc aaacccagcg  1380
gcaactacaa ttacctgtac cggctgttcc ggaagtccaa gctgaagccc ttcgagcggg  1440
acatctccac cgagatctat caggccggca caaagcttg taacggcgtg gcaggcagca  1500
actgctacag cccactgcag tcctacggct ttaggcccac atacgcgtg ggccaccagc  1560
cctacagagt ggtggtgctg agcttcgaac tgctgcatgc ccctgccaca gtgtgcggcc  1620
ctaagaaaag caccaatctc gtgaagaaca aatgcgtgaa cttcaacttc aacggcctga  1680
ccggcaccgg cgtgctgaca gagagcaaca agaagttcct gccattccag cagtttggcc  1740
gggatatcgc cgataccaca gacgccgtta gagatcccca gactggaa atcctggaca  1800
tcacccttg cagcttcggc ggagtgtctg tgatcacccc tggcaccaac accagcaatc  1860
aggtggcagt gctgtaccag ggcgtgaact gtaccgaagt gcccgtggcc attcacgccg  1920
atcagctgac acctacatgg cgggtgtact ccaccggcag caatgtgttt cagaccagag  1980
ccggctgtct gatcggagcc gagtacgtga acatagcta cgagtgcgac atccccatcg  2040
gcgctggaat ctgcgccagc taccagacac agacaaagag ccaccggaga gccagaagcg  2100
tggccagcca gagcatcatt gcctacaaa tgtctctggg cgccgagaac agcgtggcct  2160
actccaacaa ctctatcgct atcccacca acttcaccat cagcgtgacc acagagatcc  2220
tgcctgtgtc catgaccaag accagctgg actgcaccat gtacatctgc ggcgattcca  2280
ccgagtgctc caacctgctg ctgcagtacg gcagcttctg cacccagctg aaaagagccc  2340
tgacaggat cgccgtggaa caggacaaga acacccaaga ggtgttcgcc caagtgaagc  2400
agatctacaa gacccctcct atcaagtact tcggcggctt caatttcagc cagattctgc  2460
ccgatcctag caagcccagc aagcggagct tcatcgagga cctgctgttc aacaaagtga  2520
cactggccga cgccggcttc atcaagcagt atggcgattg tctgggcgac attgccgcca  2580
gggatctgat ttgcgcccag aagtttaacg gactgacagt gctgcctcct ctgctgaccg  2640
atgagatgat cgcccagtac acatctgccc tgctggccgg cacaatcaca agcggctgga  2700
catttggagc aggcgccgct ctgcagatcc cctttgctat gcagatggcc taccggttca  2760
acggcatcgg agtgacccag aatgtgctgt acgagaaccag gccaacagt  2820
tcaacagcgc catcggcaag atccaggaca gcctgagcag cacagcaagc gccctgggaa  2880
agctgcagga cgtggtcaac cacaatgccc aggcactgaa cacctgtc aagcagctgt  2940
cctccaagtt cggcgccatc agctctgtgc tgaacgatat cctgagcaga ctggaccctc  3000
ctgaggccga ggtgcagatc gacagactga tcacaggcag actgcagagc tccagacat  3060
acgtgaccca gcagctgatc agagccgccg agattagagc tctgccaat ctggccgcca  3120
```

```
ccaagatgtc tgagtgtgtg ctgggccaga gcaagagagt ggactttgc ggcaagggct   3180
accacctgat gagcttccct cagtctgccc ctcacggcgt ggtgtttctg cacgtgacat   3240
atgtgcccgc tcaagagaag aatttcacca ccgctccagc catctgccac gacggcaaag   3300
cccactttcc tagagaaggc gtgttcgtgt ccaacggcac ccattggttc gtgacacagc   3360
ggaacttcta cgagcccag atcatcacca ccgacaacc cttcgtgtct ggcaactgca   3420
acgtcgtgat cggcattgtg aacaataccg tgtacgaccc tctgcagccc gagctggaca   3480
gcttcaaaga ggaactggac aagtacttta agaaccacac aagccccgac gtggacctgg   3540
gcgatatcag cggaatcaat gccagcgtcg tgaacatcca gaaagagatc gaccggctga   3600
acgaggtggc caagaatctg aacgagagcc tgatcgacct gcaagaactg gggaagtacg   3660
agcagtacat caagtggccc tggtacatct ggctgggctt tatcgccgga ctgattgcca   3720
tcgtgatggt cacaatcatg ctgtgttgca tgaccagctg ctgtagctgc ctgaagggct   3780
gttgtagctg tggcagctgc tgcaagttcg acgaggacga ttctgagccc gtgctgaagg   3840
gcgtgaaact gcactacaca tgatgactcg agctggtact gcatgcacgc aatgctagct   3900
gcccctttcc cgtcctgggt acccgagtc tccccgacc tcgggtccca ggtatgctcc   3960
cacctccacc tgcccactc accacctctg ctagttccag acacctccca agcacgcagc   4020
aatgcagctc aaaacgctta gcctagccac accccacgg gaaacagcag tgattaacct   4080
ttagcaataa acgaaagttt aactaagcta tactaacccc agggttggtc aatttcgtgc   4140
cagccacacc ctggagctag caaaaaaaaa aaaaaaaaa aaaaaaaaaa agcatatgac   4200
taaaaaaaaa aaaaaaaaa aaaaaaaaa aaaaaaaaa aaaaaaaaa aaaaaaaaaa   4260
aaaaaaaaaa                                                          4270

SEQ ID NO: 99         moltype = DNA   length = 4270
FEATURE               Location/Qualifiers
source                1..4270
                      mol_type = other DNA
                      organism = synthetic construct
SEQUENCE: 99
agaataaact agtattcttc tggtccccac agactcagag agaacccgcc accatgttcg   60
tgttcctggt gctgctgcct ctggtgtcca gccagtgtgt gaacctgatc accagaacac   120
agtcatacac caacagcttt accagaggcg tgtactaccc tcacaaggtg ttcagatcca   180
gcgtgctgca ctctacccag gacctgttcc tgccttttct cagcaacgta acctggttcc   240
acgccatcca cgtgtccggc accaatggca ccaagagatt cgacaacccc gccctgccct   300
tcaacgacgg ggtgtacttt gccagcaccg agaagtccaa catcatcaga ggctggatct   360
tcggcaccac actggacagc aagacccaga gcctgctgat cgtgaacaac gccaccaacg   420
tggtcatcaa agtgtgcgag ttccagttct gcaacgaccc cttcctggac gtctaccaga   480
agaacaacaa gagctggatg gaaagcgagt ccgggtgta cagcagcgcc aacaactgca   540
ccttcgagta cgtgtcccag cctttcctga tggacctgga aggcaaggag ggcaacttca   600
agaacctgcg cgagttcgtg tttaagaaca tcgacggcta cttcaagatc tacagcaagc   660
acacccctat caacctcgag cgggatctgc ctcagggctt ctctgctctg gaaccctcg   720
tggatctgcc catcggcatc aacatcaccc ggtttcagac actgctggcc ctgcacagaa   780
gctacctgac acctggcgat agcagcagcg gatggacagc tggtgccgcc gcttactatg   840
tgggctacct gcagcctaga accttcctgc tgaagtacaa cgagaacggc accatcaccg   900
acgccgtgga ttgtgctctg gatcctctga gcgagacaaa gtgcaccctg aagtccttca   960
ccgtggaaaa gggcatctac cagaccagca acttccgggt gcagcccacc gaatccatcg   1020
tgcggttccc caatatcacc aatctgtgcc ccttccacga ggtgttcaat gccaccacct   1080
tcgcctctgt gtacgcctgg aaccggaagc ggatcagcaa ttgcgtggcc gactactccg   1140
tgatctacaa cttcgccccc ttcttcgcat tcaagtgcta cggcgtgtcc cctaccaagc   1200
tgaacgacct gtgcttcaca aacgtgtacg ccgacagctt cgtgatccgg ggaaacgaag   1260
tgtcacagat tgcccctgga cagacaggca acatcgccga ctacaactac aagctgcccg   1320
acgacttcac cggctgtgtg attgcctgga acagcaacaa gctggactcc aaacccagcg   1380
gcaactacaa ttacctgtac cggctgttcc ggaagtccaa gctgaagccc ttcgagcggg   1440
acatctccac cgagatctat caggccggca caagccttg taacggcgtg gcaggcagca   1500
actgctacag cccactgcag tcctacggct taggcccac atacgcgtg ggccaccagc   1560
cctacagagt ggtggtgctg agcttcgaac tgctgcatgc ccctgccaca gtgtgcggcc   1620
ctaagaaaag caccaatctc gtgaagaaca aatgcgtgaa cttcaacttc aacggcctga   1680
ccggcaccgg cgtgctgaca gagagcaaca agaagttcct gccattccag cagtttggcc   1740
gggatatcgc cgataccaca gacgccgtta gagatcccca gacactggaa atcctggaca   1800
tcaccccttg cagcttcggc ggagtgtctg tgatcacccc tggcaccaac accagcaatc   1860
aggtggcagt gctgtaccag ggcgtgaact gtaccgaagt gcccgtggcc attcacgccg   1920
atcagctgac acctacatgg cgggtgtact ccaccggcag caatgtgttt cagaccagag   1980
ccggctgtct gatcggagcc gagtacgtga caaatagcta cgagtgcgac atccccatcg   2040
gcgctggaat ctgcgccagc taccagacac agacaaagag ccaccggaga gccagaagcg   2100
tggccagcca gagcatcatt gcctacacaa tgtctctggg cgccgagaac agcgtggcct   2160
actccaacaa ctctatcgct atcccacca acttcaccat ccagatgct acagagatcc   2220
tgcctgtgtc catgaccaag accagcgtgg actgcaccat gtacatctgc ggcgattcca   2280
ccgagtgctc caacctgctg ctgcagtacg gcagcttctg cacccagctg aaaagagccc   2340
tgacaggat cgccgtggaa caggacaaga caccccaaga ggtgttcgcc caagtgaagc   2400
agatctacaa gaccccctct atcaagtact tcggcggctt caatttcagc cagattctgc   2460
ccgatcctag caagcccagc aagcggagct tcatcgagga cctgctgttc aacaaagtga   2520
cactggccga cgccggcttc atcaagcagt atggcgattg tctgggcgac attgccgcca   2580
gggatcgat tgcgcccag aagtttaacg gactgacagt gctgcctcct ctgctgaccg   2640
atgagatgat cgcccagtac acatctgccc tgctggccgg cacaatcaca agcggctgga   2700
catttggagc aggcgccgct ctgcagatcc cttttgctat gcagatggcc taccggttca   2760
acggcatcgg agtgacccag aatgtgctgt acgagaaccc agctgccctg aacaaccagt   2820
tcaacgcgc catcggcaag atccaggaca gctgagcag cacagcaagc gcctggaa   2880
agctgcagga cgtggtcaac cacaatgccc aggcactgaa cacccctgtc aagcagctgt   2940
cctccaagtt cggcgccatc agctctgtgc tgaacgatat cctgagcaga ctggaccctc   3000
ctgaggccga ggtgcagatc gacagactga tcacaggcag actgcagagc ctccagacat   3060
acgtgaccca gcagctgatc agagccgccg agattagagc ctctgccaat ctggccgcca   3120
```

```
ccaagatgtc tgagtgtgtg ctgggccaga gcaagagagt ggacttttgc ggcaagggct   3180
accacctgat gagcttccct cagtctgccc ctcacggcgt ggtgtttctg cacgtgacat   3240
atgtgcccgc tcaagagaag aatttcacca ccgctccagc catctgccac gacggcaaag   3300
cccactttcc tagagaaggc gtgttcgtgt ccaacggcac ccattggttc gtgacacagc   3360
ggaacttcta cgagcccaag atcatcacca ccgacaacac cttcgtgtct ggcaactgcg   3420
acgtcgtgat cggcattgtg aacaataccg tgtacgaccc tctgcagccc gagctggaca   3480
gcttcaaaga ggaactggac aagtacttta agaaccacac aagccccgac gtggacctgg   3540
gcgatatcag cggaatcaat gccagcgtcg tgaacatcca gaaagagatc gaccggctga   3600
acgaggtggc caagaatctg aacgagagcc tgatcgacct gcaagaactg gggaagtacg   3660
agcagtacat caagtggccc tggtacatct ggctgggctt tatcgccgga ctgattgcca   3720
tcgtgatggt cacaatcatg ctgtgttgca tgaccagctg ctgtagctgc ctgaagggct   3780
gttgtagctg tggcagctgc tgcaagttcg acgaggacga ttctgagccc gtgctgaagg   3840
gcgtgaaact gcactacaca tgatgactcg agctggtact gcatgcacgc aatgctagct   3900
gcccctttcc cgtcctgggt acccgagtc tccccgacc tcgggtccca ggtatgctcc   3960
cacctccacc tgcccactc accacctctg ctagttccag acacctccca agcacgcagc   4020
aatgcagctc aaaacgctta gcctagccac accccacgg gaaacagcag tgattaacct   4080
ttagcaataa acgaaagttt aactaagcta tactaacccc agggttggtc aatttcgtgc   4140
cagccacacc ctggagctag caaaaaaaaa aaaaaaaaa aaaaaaaaaa agcatatgac   4200
taaaaaaaaa aaaaaaaaaa aaaaaaaaa aaaaaaaaa aaaaaaaaaa aaaaaaaaaa   4260
aaaaaaaaaa                                                         4270

SEQ ID NO: 100        moltype = AA   length = 1268
FEATURE               Location/Qualifiers
source                1..1268
                      mol_type = protein
                      organism = synthetic construct
SEQUENCE: 100
MFVFLVLLPL VSSQCVNLIT RTQSYTNSFT RGVYYPDKVF RSSVLHSTQD LFLPFFSNVT    60
WFHAISGTNG TKRFDNPVLP FNDGVYFAST EKSNIIRGWI FGTTLDSKTQ SLLIVNNATN   120
VVIKVCEFQF CNDPFLDVYY HKNNKSWMES EFRVYSSANN CTFEYVSQPF LMDLEGKQGN   180
FKNLREFVFK NIDGYFKIYS KHTPINLGRD LPQGFSALEP LVDLPIGINI TRFQTLLALH   240
RSYLTPGDSS SGWTAGAAAY YVGYLQPRTF LLKYNENGTI TDAVDCALDP LSETKCTLKS   300
FTVEKGIYQT SNFRVQPTES IVRFPNITNL CPFDEVFNAT TFASVYAWNR KRISNCVADY   360
SVLYNFAPFF AFKCYGVSPT KLNDLCFTNV YADSFVIRGN EVSQIAPGQT GNIADYNYKL   420
PDDFTGCVIA WNSNKLDSTV GGNYNYRYRL FRKSKLKPFE RDISTEIYQA GNKPCNGVAG   480
VNCYFPLQSY GFRPTYGVGH QPYRVVVLSF ELLHAPATVC GPKKSTNLVK NKCVNFNFNG   540
LTGTGVLTES NKKFLPFQQF GRDIADTTDA VRDPQTLEIL DITPCSFGGV SVITPGTNTS   600
NQVAVLYQGV NCTEVPVAIH ADQLTPTWRV YSTGSNVFQT RAGCLIGAEY VNNSYECDIP   660
IGAGICASYQ TQTKSHRRAR SVASQSIIAY TMSLGAENSV AYSNNSIAIP TNFTISVTTE   720
ILPVSMTKTS VDCTMYICGD STECSNLLLQ YGSFCTQLKR ALTGIAVEQD KNTQEVFAQV   780
KQIYKTPPIK YFGGFNFSQI LPDPSKPSKR SFIEDLLFNK VTLADAGFIK QYGDCLGDIA   840
ARDLICAQKF NGLTVLPPLL TDEMIAQYTS ALLAGTITSG WTFGAGAALQ IPFAMQMAYR   900
FNGIGVTQNV LYENQKLIAN QFNSAIGKIQ DSLSSTASAL GKLQDVVNHN AQALNTLVKQ   960
LSSKFGAISS VLNDILSRLD PPEAEVQIDR LITGRLQSLQ TYVTQQLIRA AEIRASANLA  1020
ATKMSECVLG QSKRVDFCGK GYHLMSFPQS APHGVVFLHV TYVPAQEKNF TTAPAICHDG  1080
KAHFPREGVF VSNGTHWFVT QRNFYEPQII TTDNTFVSGN CDVVIGIVNN TVYDPLQPEL  1140
DSFKEELDKY FKNHTSPDVD LGDISGINAS VVNIQKEIDR LNEVAKNLNE SLIDLQELGK  1200
YEQYIKWPWY IWLGFIAGLI AIVMVTIMLC CMTSCCSCLK GCCSCGSCCK FDEDDSEPVL  1260
KGVKLHYT                                                           1268

SEQ ID NO: 101        moltype = RNA   length = 3810
FEATURE               Location/Qualifiers
source                1..3810
                      mol_type = other RNA
                      organism = synthetic construct
SEQUENCE: 101
atgttcgtgt tcctggtgct gctgcctctg gtgtccagcc agtgtgtgaa cctgatcacc    60
agaacacagt catacaccaa cagctttacc agaggcgtgt actacccga caaggtgttc   120
agatccagcg tgctgcactc tacccaggac ctgttcctgc cttttcttag caacgtgacc   180
tggttccacg ccatctccgg caccaatggc accaagagat tcgacaaccc cgtgctgccc   240
ttcaacgacg gggtgtactt tgccagcacc gagaagtcca acatcatcag aggctggatc   300
ttcggcacca cactggacag caagacccag agcctgctga tcgtgaacaa cgccaccaac   360
gtggtcatca aagtgtgcga gttccagttc tgcaacgacc ccttcctgga cgtctactac   420
cacaagaaca caagagctg gatggaaagc gagttccggg tgtacagcag cgccaacaac   480
tgcaccttcg agtacgtgtc ccagcctttc ctgatgacc tggaaggcaa gcagggcaac   540
ttcaagaacc tgcgcgagtt cgtgtttaag aacatcgacg gctacttcaa gatctacagc   600
aagcacaccc ctatcaacct cggccgggat ctgcctcagg gcttctctgc tctggaaccc   660
ctggtggatc tgcccatcgg catcaacatc accggtttc agacactgct ggccctgcac   720
agaagctacc tgacacctgg cgatagcagc agcggatgga cagctggtgc cgccgcttac   780
tatgtgggct acctgcagcc tagaaccttc ctgctgaagt acaacgagaa cggcaccatc   840
accgacgccg tggattgtgc tctggatcct ctgagcgaga caagtgcac cctgaagtcc   900
ttcaccgtgg aaaagggcat ctaccagacc agcaacttcc gggtgcagcc caccgaatcc   960
atcgtgcggt tccccaatat caccaatctg tgccccttcg acgaggtgtt caatgccacc  1020
accttcgcct ctgtgtacgc ctggaaccgg aagcgatca ccaatgcgac tactactac  1080
tccgtgctgt acaacttcgc ccccttcttc gcattcaagt gctacggcgt gtccctcacc  1140
aagctgaacg acctgtgctt cacaaacgtg tacgccgaca gcttcgtgat ccggggaaac  1200
gaagtgtcac agattgcccc tggacagaca ggcaacatcg ccgactacaa ctacaagctg  1260
cccgacgact tcaccggctg tgtgattgcc tggaacagca acaagctgga ctccaccgtc  1320
ggcggcaact acaattacag gtaccggctg ttccggaagt ccaagctgaa gcccttcgag  1380
```

```
cgggacatct ccaccgagat ctatcaggcc ggcaacaagc cttgtaacgg cgtggcaggc     1440
gtgaactgct acttcccact gcagtcctac ggctttaggc ccacatacgg cgtgggccac     1500
cagcctaca gagtggtggt gctgagcttc gaactgctgc atgccctgc cacagtgtgc       1560
ggccctaaga aaagcaccaa tctcgtgaag aacaaatgcg tgaacttcaa cttcaacggc     1620
ctgaccggca ccggcgtgct gacagagagc aacaagaagt tcctgccatt ccagcagttt     1680
ggccgggata tcgccgatac cacagacgcc gttagagatc cccagacact ggaaatcctg     1740
gacatcaccc cttgcagctt cggcggagtg tctgtgatca cccctggcac caacaccagc    1800
aatcaggtgg cagtgctgta ccagggcgtg aactgtaccg aagtgcccgt ggccattcac     1860
gccgatcagc tgacacctac atggcgggtg tactccacga gcagcaatgt gtttcagacc    1920
agagccggct gtctgatcgg agccgagtac gtgaacaata gctacgagtg cgacatcccc    1980
atcggcgctg gaatctgcgc cagctaccag acacagacaa agagccaccg gagagccaga    2040
agcgtggcca gccagagcat cattgcctac acaatgtctc tgggcgccga gaacagcgtg    2100
gcctactcca acaactctat cgctatcccc accaacttca ccatcagcgt gaccacagag    2160
atcctgcctg tgtccatgac caagaccagc gtggactgca ccatgtacat ctgcggcgat    2220
tccaccgagt gctccaacct gctgctgcag tacggcagct tctgcaccca gctgaaaaga    2280
gccctgacag ggatcgccgt ggaacaggac aagaacaccc aagaggtgtt cgcccaagtg    2340
aagcagatct acaagacccc tcctatcaag tacttcggcg gcttcaattt cagccagatt    2400
ctgcccgatc ctagcaagcc cagcaagcgg agcttcatcg aggacctgct gttcaacaaa    2460
gtgacactgg ccgacgccgg cttcatcaag cagtatggcg attgtctggg cgacattgcc    2520
gccagggatc tgatttgcgc ccagaagttt aacggactga cagtgctgcc tcctctgctg    2580
accgatgaga tgatcgccca gtacacatct gccctgctgg ccggcacaat cacaagcggc    2640
tggacatttg gagcaggcgc cgctctgcag atcccctttg ctatgcagat ggcctaccgg    2700
ttcaacggca tcggagtgac ccagaatgtg ctgtacgaga accagaagct gatcgccaac    2760
cagttcaaca cgccatcgg caagatccag gacagcctga gcagcacagc aagcgccctg    2820
ggaaagctgc aggacgtggt caaccacaat gcccaggcac tgaacaccct ggtcaagcag    2880
ctgtcctcca agttcggcgc catgtctctc gtgctgaacg atatcctgag cagactggac    2940
cctcctgagg ccgaggtgca gatcgacaga ctgatcacag gcagactgca gagcctccag    3000
acatacgtga cccagcagct gatcagagcc gccgagatta gcctctgc caatctggcc      3060
gccaccaaga tgtctgagtg tgtgctgggc cagagcaaga gagtggactt ttgcggcaag    3120
ggctaccacc tgatgagctt ccctcagtct gcccctcacg gcgtggtgtt tctgcacgtg    3180
acatatgtgc ccgctcaaga gaagaatttc accaccgctc cagccatctg ccacgacggc    3240
aaagcccact ttcctagaga aggcgtgttc gtgtccaacg gcacccattg gttcgtgaca    3300
cagcggaact tctacgagcc ccagatcatc accaccgaca acaccttcgt gtctggcaac    3360
tgcgacgtcg tgatcggcat tgtgaacaat accgtgtacg accctctgca gcccgagctg    3420
gacagcttca aagaggaact ggacaagtac tttaagaacc acacaagccc cgacgtggac    3480
ctgggcgata tcagcggaat caatgccagc gtcgtgaaca tccagaaaga gatcgaccgg    3540
ctgaacgagg tggccaagaa tctgaacgag agcctgatcg acctgcaaga actggggaag    3600
tacgagcagt acatcaagtg gccctggtac atctggctgg gctttatcgc cggactgatt    3660
gccatcgtga tggtcacaat catgctgtgt tgcatgacca gctgctgtag ctgcctgaag    3720
ggctgtttgta gctgtggcag ctgctgcaag ttcgacgagg acgattctga gcccgtgctg    3780
aagggcgtga aactgcacta cacatgatga                                     3810
SEQ ID NO: 102         moltype = DNA  length = 3810
FEATURE                Location/Qualifiers
source                 1..3810
                       mol_type = other DNA
                       organism = synthetic construct
SEQUENCE: 102
atgttcgtgt tcctggtgct gctgcctctg gtgtccagcc agtgtgtgaa cctgatcacc      60
agaacacagt catacaccaa cagctttacc agaggcgtgt actaccccga caaggtgttc    120
agatccgacg tgctgcactc tacccaggac ctgttcctgc cttctcttcag caacgtgacc   180
tggttccacg ccatctccgg caccaatggc accaagagat tcgacaaccc cgtgctgccc   240
ttcaacgacg gggtgtactt tgccagcacc gagaagtcca acatcatcag aggctggatc    300
ttcggcacca cactggacag caagacccag agcctgctga tcgtgaacaa cgccaccaac    360
gtggtcatca agtgtgcga gttccagttc tgcaacgacc ccttcctggc cgtctactac    420
cacaagaaca acaagagctg gatggaaagc gagttccggg tgtacagcag cgccaacaac    480
tgcaccttcg agtacgtgtc ccagcctttc ctgatggacc tggaaggcaa gcagggcaac    540
ttcaagaacc tgcgcgagtt cgtgtttaag aacatcgacg gctacttcaa gatctacagc    600
aagcacaccc ctatcaacct cggccgggat ctgcctcagg gcttctctgc tctgaaaccc    660
ctggtggatc tgcccatcgg catcaacatc acccggttc agacactgct ggccctgcac    720
agaagctacc tgacacctgg cgatagcagc agcggatgga cagctggtgc cgccgcttac    780
tatgtgggct acctgcagcc tagaaccttc ctgctgaagt acaacgagaa cggcaccatc    840
accgacgccg tggattgtgc tctggatcct ctgagcgaga caaagtgcac cctgaagtcc    900
ttcaccgtgg aaaagggcat ctaccagacc agcaacttcc gggtgcagcc caccgaatcc    960
atcgtgcggt tccccaatat caccaatctg tgccccttcg acgaggtgtt caatgccacc   1020
accttcgcct ctgtgtacgc ctggaacc ggaagcggatca gcaattgcgt ggccgactac   1080
tccgtgctgt acaacttcgc cccccttcttc gcattcaagt gctacggcgt gtcccctacc    1140
aagctgaacg acctgtgctt cacaaacgtg tacgccgaca gcttcgtgat ccggggaaac    1200
gaagtgtcac agattgcccc tggacagaca ggcaagatcg ccgactacaa ctacaagctg    1260
cccgacgact tcaccggctg tgtgattgcc tggaacagca acaagctgga ctccaccgtc    1320
ggcgcaact acaattacag gtaccggctg ttccggaagt ccaagctgaa gcccttcgag    1380
cgggacatct ccaccgagat ctatcaggcc ggcaacaagc cttgtaacgg cgtggcaggc    1440
gtgaactgct acttcccact gcagtcctac ggctttaggc ccacatacgg cgtgggccac    1500
cagcctaca gagtggtggt gctgagcttc gaactgctgc atgccctgc cacagtgtgc      1560
ggccctaaga aaagcaccaa tctcgtgaag aacaaatgcg tgaacttcaa cttcaacggc    1620
ctgaccggca ccggcgtgct gacagagagc aacaagaagt tcctgccatt ccagcagttt    1680
ggccgggata tcgccgatac cacagacgcc gttagagatc cccagacact ggaaatcctg    1740
gacatcaccc cttgcagctt cggcggagtg tctgtgatca cccctggcac caacaccagc    1800
aatcaggtgg cagtgctgta ccagggcgtg aactgtaccg aagtgcccgt ggccattcac    1860
```

```
gccgatcagc tgacacctac atggcgggtg tactccaccg gcagcaatgt gtttcagacc 1920
agagccggct gtctgatcgg agccgagtac gtgaacaata gctacgagtg cgacatcccc 1980
atcggcgctg gaatctgcgc cagctaccag acacagacaa agagccaccg gagagccaga 2040
agcgtggcca gccagagcat cattgcctac acaatgtctc tgggcgccga gaacagcgtg 2100
gcctactcca acaactctat cgctatcccc accaacttca ccatcagcgt gaccacagag 2160
atcctgcctg tgtccatgac caagaccagc gtggactgca ccatgtacat ctgcggcgat 2220
tccaccgagt gctccaacct gctgctgcag tacggcagct tctgcaccca gctgaaaaga 2280
gccctgacag ggatcgccgt ggaacaggac aagaacaccc aagaggtgtt cgcccaagtg 2340
aagcagatct acaagacccc tcctatcaag tacttcggcg gcttcaattt cagccagatt 2400
ctgcccgatc ctagcaagcc cagcaagcgg agcttcatcg aggacctgct gttcaacaaa 2460
gtgacactgg ccgacgccgg cttcatcaag cagtatggcg attgtctggg cgacattgcc 2520
gccagggatc tgatttgcgc ccagaagttt aacggactga cagtgctgcc tcctctgctg 2580
accgatgaga tgatcgccca gtacacatct gcctgctgg ccggcacaat cacaagcggc 2640
tggacatttg gagcaggcgc cgctctgcag atcccctttg ctatgcagat ggcctaccgg 2700
ttcaacggca tcggagtgac ccagaatgtg ctgtacgaga accagaagct gatcgccaac 2760
cagttcaaca gcgccatcgg caagatccag gacagcctga gcagcacagc aagcgccctg 2820
ggaaagctgc aggacgtggt caaccacaat gcccaggcac tgaacaccct ggtcaagcag 2880
ctgtcctcca agttcggcgc catcgctctc tgtctgaacg atatcctgag cagactggac 2940
cctcctgagg ccgaggtgca gatcgacaga ctgatcacag gcagactgca gagcctccag 3000
acatacgtga cccagcagct gatcagagcc gccgagatta gagcctctgc caatctggcc 3060
gccaccaaga tgtctgagtg tgtgctgggc cagagcaaga gagtggactt tgcggcaaag 3120
ggctaccacc tgatgagctt ccctcagtct gccctcacg gcgtggtgtt tctgcacgtg 3180
acatatgtgc ccgctcaaga gaagaatttc accaccgctc cagccatctg ccacgacggc 3240
aaagcccact ttcctagaga aggcgtgttc gtgtccaacg gcaccccattg gttcgtgaca 3300
cagcggaact tctacgagcc ccagatcatc accaccgaca acaccttcgt gtctggcaac 3360
tgcgacgtcg tgatcggcat tgtgaacaat accgtgtacg accctctgca gcccgagctg 3420
gacagcttca agaggaact ggacaagtac tttaagaacc acacaagccc cgacgtggac 3480
ctgggcgata tcagcggaat caatgccagc gtcgtgaaca tccagaaaga gatcgaccgg 3540
ctgaacgagg tggccaagaa tctgaacgag agcctgatcg acctgcaaga actggggaag 3600
tacgagcagt acatcaagtg gccctggtac atctggctgg gctttatcgc cggactgatt 3660
gccatcgtga tggtcacaat catgctgtgt tgcatgacca gctgctgtag ctgcctgaag 3720
ggctgttgta gctgtggcag ctgctgcaag ttcgacgagg acgattctga gcccgtgctg 3780
aagggcgtga aactgcacta cacatgatga           3810

SEQ ID NO: 103         moltype = RNA   length = 4267
FEATURE                Location/Qualifiers
source                 1..4267
                       mol_type = other RNA
                       organism = synthetic construct
SEQUENCE: 103
agaataaact agtattcttc tggtccccac agactcagag agaacccgcc accatgttcg 60
tgttcctggt gctgctgcct ctggtgtcca gccagtgtgt gaacctgatc accagaacac 120
agtcatacac caacagcttt accagaggcg tgtactaccc cgacaaggtg ttcagatcca 180
gcgtgctgca ctctacccag gacctgttcc tgccttttct cagcaacgtg acctggttcc 240
acgccatctc cggcaccaat ggcaccaaga gattcgacaa ccccgtgctg ccctttaacg 300
acggggtgta ctttgccagc accgagaagt ccaacatcat cagaggctgg atcttcggca 360
ccacactgga cagcaagacc cagagcctgc tgatcgtgaa caacgccacc aacgtggtca 420
tcaaagtgtg cgagttccag ttctgcaacg accctttcct ggacgtctac taccacaaga 480
acaacaagag ctggatggaa agcgagttcc gggtgtacag cagcgccaac aactgcacct 540
tcgagtacgt gtcccagcct ttcctgatgg acctggaagg caagcagggc aacttcaaga 600
acctgcgcga gttcgtgttt aagaacatcg acggctactt caagatctac agcaagcaca 660
cccctatcaa cctcggccgg gatctgcctc agggcttctc tgctctggaa cccctggtg 720
atctgcccat cggcatcaac atcacccggt tcagacactg ctggccctg cacagaagct 780
acctgacacc tggcgatagc agcagcggat ggacagctgg tgccgccgct tactatgtgg 840
gctacctgca gcctagaacc ttcctgctga gtacaacga agcggccatc accgacg 900
ccgtggattg tgctctggat cctctgagcg agacaaagtg caccctgaag tccttcaccg 960
tggaaaaggg catctaccag accagcaact tccgggtgca gcccaccgaa tccatcgtgc 1020
ggttccccaa tatcaccaat ctgtgcccct tcgacgaggt gttcaatgcc accaccttcg 1080
cctctgtgta cgcctggaac cggaagcgga tcagcaattg cgtggccgac tactccgtgc 1140
tgtacaactt cgccccccttc ttcgcattca gtgctacgg cgtgtccct accaagctga 1200
acgacctgtg cttcacaaac gtgtacgccg acagcttcgt gatccgggga acgaagtgt 1260
cacagattgc ccctggacag acaggcaaca tcgccgacta caactacaag ctgcccgacg 1320
acttcaccgg ctgtgtgatt gcctggaaca gcaacaagct ggactccacc gtcggcggca 1380
actacaatta caggtaccgg ctgttccgga gtccaagct gagcgggaca 1440
tctccaccga gatctatcag gccggcaaca agcttgtaa cggcgtggca ggcgtgaact 1500
gctacttccc actgcagtcc tacggcttta ggccacata cggcgtgggc caccagccct 1560
acagagtggt ggtgctgagc ttcgaactgc tgcatgcccc tgccacagtg tgcggcccta 1620
agaaaagcac caatctcgtg aagaacaaat gcgtgaactt caacttcaac ggcctgaccg 1680
gcaccggcgt gctgacagag agcaacaaga agttcctgcc attccagcag tttggccggg 1740
atatcgccga taccacagac gccgttagag atccccagac actggaaatc ctggacatca 1800
ccccttgcag cttcggcgga gtgtctgtga tcacccctgg caccaacacc agcaatcagg 1860
tggcagtgct gtaccagggc gtgaactgta ccgaagtgcc cgtggccatt cacgccgatc 1920
agctgacacc tacatggcgg gtgtactcca ccggcagcaa tgtgtttcag accagagccg 1980
gctgtctgat cggagccgag tacgtgaaca atagctacga gtgcgacatc cccatcggcg 2040
ctggaatctg cgccagctac cagacacaga caaagagcca ccggagagcc agaagcgtgg 2100
ccagccagag catcattgcc tacacaatgt ctctgggcgc cgagaacagc gtggcctact 2160
ccaacaactc tatcgctatc cccaccaact tcaccatcag cgtgaccaca gagatcctgc 2220
ctgtgtccat gaccaagacc agcgtggact gcaccatgta catctgcggc gattccaccg 2280
agtgctccaa cctgctgctg cagtacggca gcttctgcac ccagctgaaa agagccctga 2340
```

```
caggga tcgc cgtggaacag gacaagaaca cccaagaggt gttcgcccaa gtgaagcaga    2400
tctacaagac ccctcctatc aagtacttcg gcggcttcaa tttcagccag attctgcccg    2460
atcctagcaa gcccagcaag cggagcttca tcgaggacct gctgttcaac aaagtgacac    2520
tggccgacgt cggcttcatc aagcagtatg gcgattgtct gggcgacatt gccgccaggg    2580
atctgatttg cgcccagaag tttaacggac tgacagtgct gcctcctctg ctgaccgatg    2640
agatgatcgc ccagtacaca tctgccctgc tggccggcac aatcacaagc ggctggacat    2700
ttggagcagg cgccgctctg cagatcccct ttgctatgca gatggcctac cggttcaacg    2760
gcatcggagt gacccagaat gtgctgtacg agaaccagaa gctgatcgcc aaccagttca    2820
acagcgccat cggcaagatc caggacagcc tgagcagcaa agcaagcgcc ctgggaaagc    2880
tgcaggacgt ggtcaaccac aatgcccagg cactgaacac cctggtcaag cagctgtcct    2940
ccaagttcgg cgccatcagc tctgtgctga acgatatcct gagcagactg gaccctcctg    3000
aggccgaggt gcagatcgac agactgatca caggcagact gcagagcctc cagacatacg    3060
tgacccagca gctgatcaga gccgccgaga ttagagcctc tgccaatctg gccgccacca    3120
agatgtctga gtgtgtgctg ggccagagca agagggtgga cttttgcggc aagggctaca    3180
acctgatgag cttccctcag tctgcccctc acggcgtggt gtttctgcac gtgacatatg    3240
tgcccgctca agagaagaat ttcaccaccg ctccagccat ctgccacgac ggcaaagccc    3300
actttcctag agaaggcgtg ttcgtgtcca acggcaccca ttggttcgtg acacagcgga    3360
acttctacga gccccagatc atcaccaccg acaaacacctt cgtgtctggc aactgcgacg    3420
tcgtgatcgg cattgtgaac aataccgtgt acgaccctct gcagcccgag ctggacagct    3480
tcaaagagga actggacaag tactttaaga ccacacaag cccgacgtg gacctgggcg    3540
atatcagcgg aatcaatgcc agcgtcgtga acatccagaa agatcgac cggctgaacg    3600
aggtggccaa gaatctgaac gagagcctga tcgacctgca gaactgggga agtacgagc    3660
agtacatcaa gtggccctgg tacatctggc tgggctttat cgccggactg attgccatcg    3720
tgatggtcac aatcatgctg tgttgcatga ccagctgctg tagctgcctg aagggctgtt    3780
gtagctgtgg cagctgctgc aagttcgacg aggacgattc tgagcccgtg ctgaagggcg    3840
tgaaactgca ctacacatga tgactcgagc tggtactgca tgcacgcaat gctagctgcc    3900
cctttcccgt cctgggtacc ccgagtctcc cccgacctcg ggtcccaggt atgctcccac    3960
ctccacctgc cccactcacc acctctgcta gttccagaca cctcccaagc acgcagcaat    4020
gcagctcaaa acgcttagcc tagccacacc cccacgggaa acagcagtga ttaacctta    4080
gcaataaacg aaagtttaac taagctatac taaccccagg gttggtcaat ttcgtgccag    4140
ccacaccctg gagctagcaa aaaaaaaaaa aaaaaaaaa aaaaaaagc atatgactaa    4200
aaaaaaaaaa aaaaaaaaaa aaaaaaaaaa aaaaaaaaa aaaaaaaaa aaaaaaaaaa    4260
aaaaaaa                                                                4267

SEQ ID NO: 104          moltype = DNA    length = 4267
FEATURE                 Location/Qualifiers
source                  1..4267
                        mol_type = other DNA
                        organism = synthetic construct
SEQUENCE: 104
agaataaact agtattcttc tggtccccac agactcagag agaacccgcc accatgttcg      60
tgttcctggt gctgctgcct ctggtgtcca gccagtgtgt gaacctgatc accagaacac     120
agtcatacac caacagcttt accagaggcg tgtactaccc cgacaaggtg ttcagatcca     180
gcgtgctgca ctctacccag gacctgttcc tgcctttctt cagcaacagc aacctggttcc    240
acgccatctc cggcaccaat ggcaccaaga gattcgacaa ccccgtgctg ccctttcaacg    300
acggggtgta ctttgccagc accgagaagt ccaaacatcat cagaggctgg atcttcggca    360
ccacactgga cagcaagacc cagagcctgc tgatcgtgaa caacgccacc aacgtggtca    420
tcaaagtgtg cgagttccag ttctgcaacg accccttcct ggacgtctac taccacaaga    480
acaacaagag ctggatggaa agcgagttcc gggtgtacag cagcgccaac aactgcaccct    540
tcgagtacgt gtccagcct ttcctgatgg acctggaagg caagcagggc aacttcaaga     600
acctgcgcga gttcgtgttt aagaacatcg acggctactt caagatctac agcaagcaca     660
cccctatcaa cctcggccgg gatctgcctc agggcttctc tgctctggaa ccccgtggtg     720
atctgcccat cggcatcaac atcacccggt tcagacact gctggccctg cacagaagct     780
acctgacacc tggcgatagc agcagcggat ggacagctgg tgccgccgct actatgtgg     840
gctacctgca gcctagaacc ttcctgctga agtacaacga gaatggcacc atcaccgacg     900
ccgtggattg tgctctggat cctctgagcg agacaaagtg caccctgaag tccttcaccg     960
tggaaaaggg catctaccag accagcaact tccgggtgca gcccaccgaa tccatcgtgc    1020
ggttccccaa tatcaccaat ctgtgcccct tcgacgaggt gttcaatgcc accaccttcg    1080
cctctgtgta cgcctggaac cggaagcgga tcagcaattg cgtggccgac tactccgtgc    1140
tgtacaactt cgcccccttc ttcgcattca gtgctacgg cgtgtcccct accaagctga    1200
acgacctgtg cttcacaaac gtgtacgccg acagcttcgt gatccgggga acgaagtgt    1260
cacagattgc ccctggacag acaggcaaca tcgccgacta caactacaag ctgcccgacg    1320
acttcaccgg ctgtgtgatt gcctggaaca gcaacaagct ggactccacc gtcggcgcca    1380
actacaatta caggtaccgg ctgttccgga gtccaagct gagcgggaca ggcgggaca    1440
tctccaccgg gatctatcag gccggcaaca gccttgtaa cggcgtggca ggcgtgaact    1500
gctacttccc actgcagtcc tacggcttta ggccacata cggcgtggc caccagccct    1560
acagagtggt ggtgctgagc ttcgaactgc tgcatgcccc tgccacagt tgcggcccta    1620
agaaaagcac caatctcgtg aagaacaaat gcgtgaactt caacttcaac ggcctgaccg    1680
gcaccggcgt gctgacagag agcaacaaga agttcctgcc attccagcag tttggccggg    1740
atatcgccga taccagagac gccgttagag atccccagac actggaaatc ctggacatca    1800
ccccttgcag cttcggcgga gtgtctgtga tcaccctgg caccaacacc agcaatcagg    1860
tggcagtgct gtaccagggc gtgaactgta ccgaagtgcc cgtggccatt cacgccgatc    1920
agctgacacc tacatggcgg gtgtactcca cggcagcaa tgtgtttcag accagagccg    1980
gcgtctgat cggagcgag tacgtgaaca atagctacga gtgcgacatc ccatccgtgg    2040
ctggaatctg cgccagctac cagacacaga caaagagcca ccggagagcc agaagctgtgg   2100
ccagccagag catcattgcc tacacaatgt ctctgggcgc cgagaacagc gtggcctact   2160
ccaacaactc tatcgctatc cccaccaact tcaccatcag cgtgaccaca gagatcctgc    2220
ctgtgtccta gaccaagacc agcgtggact gcaccatgta catctgcggc gattccaccg    2280
agtgctccaa cctgctgctg cagtacggca gcttctgcac ccagctgaaa agagcccctga   2340
```

-continued

```
cagggatcgc cgtggaacag gacaagaaca cccaagaggt gttcgcccaa gtgaagcaga   2400
tctacaagac ccctcctatc aagtacttcg gcggcttcaa tttcagccag attctgcccg   2460
atcctagcaa gcccagcaag cggagcttca tcgaggacct gctgttcaac aaagtgacac   2520
tggccgacgt cggcttcatc aagcagtatg gcgattgtct gggcgacatt gccgccaggg   2580
atctgatttg cgcccagaag tttaacggac tgacagtgct gcctcctctg ctgaccgatg   2640
agatgatcgc ccagtacaca tctgccctgc tggccggcac aatcacaagc ggctggacat   2700
ttggagcagg cgccgctctg cagatccct ttgctatgca gatggcctac cggttcaacg    2760
gcatcggagt gacccagaat gtgctgtacg agaaccagaa gctgatcgcc aaccagttca   2820
acagcgccat cggcaagatc caggacagcc tgagcagcag cagcaagcgc ctgggaaagc   2880
tgcaggacgt ggtcaaccac aatgcccagg cactgaacac cctggtcaag cagctgtcct   2940
ccaagttcgg cgccatcagc tctgtgctga cgatatcct gagcagactg gaccctcctg    3000
aggccgaggt gcagatcgac agactgatca caggcagact gcagagcctc cagacatacg   3060
tgacccagca gctgatcaga gccgccgaga ttagagcctc tgccaatctg gccgccacca   3120
agatgtctga gtgtgtgctg ggccagagca agagagtgga cttttgcggc aagggctacc   3180
acctgatgag cttccctcag tctgcccctc acggcgtggg gtttctgcac gtgacatatg   3240
tgcccgctca agagaagaat ttcaccaccg ctccagccat ctgccacgac ggcaaagccc   3300
actttcctag agaaggcgtg ttcgtgtcca acggcaccca ttggttcgtg acacagcgga   3360
acttctacga gccccagatc atcaccaccg acaacaccct cgtgtctggc aactgcgacg   3420
tcgtgatcgg cattgtgaac aataccgtgt cgaccctct gcagcccgag ctggacagct    3480
tcaaagagga actggacaag tactttaaga accacacaag ccccgacgtg gacctgggcg   3540
atatcagcgg aatcaatgcc agcgtcgtga acatccagaa agagatcgac cggctgaacg   3600
aggtggccaa gaatctgaac gagagcctga tcgacctgca gaactggggg aagtacgagc   3660
agtacatcaa gtggccctgg tacatctggc tgggctttat cgccggactg attgccatcg   3720
tgatggtcac aatcatgctg tgttgcatga ccagctgctg tagctgcctg aagggctgtt   3780
gtagctgtgg cagctgctgc aagttcgacg gaacgattc tgagcccgtg ctgaagggcg    3840
tgaaactgca ctacacatga tgactcgaca tggtactgca tcacgcaat gctagctgcc    3900
cctttcccgt cctgggtacc ccgagtctcc cccgacctcg ggtcccaggt atgctcccac   3960
ctccacctgc cccactcacc acctctgcta gttccagaca cctcccaagc acgcagcaat   4020
gcagctcaaa acgcttagcc tagccacacc cccacgggaa acagcagtga ttaacctta    4080
gcaataaacg aaagtttaac taagctatac taaccccagg gttggtcaat ttcgtgccaa   4140
ccacaccctg gagctagcaa aaaaaaaaaa aaaaaaaaa aaaaaaaagc atatgactaa    4200
aaaaaaaaaa aaaaaaaaaa aaaaaaaaaa aaaaaaaaaa aaaaaaaaaa aaaaaaaaaa   4260
aaaaaaa                                                             4267
```

```
SEQ ID NO: 105          moltype = AA    length = 27
FEATURE                 Location/Qualifiers
source                  1..27
                        mol_type = protein
                        organism = synthetic construct
SEQUENCE: 105
MGGAAARLGA VILFVVIVGL HGVRSKY                                       27

SEQ ID NO: 106          moltype = AA    length = 25
FEATURE                 Location/Qualifiers
source                  1..25
                        mol_type = protein
                        organism = synthetic construct
SEQUENCE: 106
MGRLTSGVGT AALLVVAVGL RVVCA                                         25

SEQ ID NO: 107          moltype = AA    length = 28
FEATURE                 Location/Qualifiers
source                  1..28
                        mol_type = protein
                        organism = synthetic construct
SEQUENCE: 107
MGRLTSGVGT AALLVVAVGL RVVCAKYA                                      28

SEQ ID NO: 108          moltype = AA    length = 19
FEATURE                 Location/Qualifiers
source                  1..19
                        mol_type = protein
                        organism = synthetic construct
SEQUENCE: 108
MFVFLVLLPL VSSQCVNLT                                                19

SEQ ID NO: 109          moltype = AA    length = 21
FEATURE                 Location/Qualifiers
source                  1..21
                        mol_type = protein
                        organism = synthetic construct
SEQUENCE: 109
MDWIWRILFL VGAATGAHSQ M                                             21

SEQ ID NO: 110          moltype = AA    length = 20
FEATURE                 Location/Qualifiers
source                  1..20
                        mol_type = protein
                        organism = synthetic construct
```

```
SEQUENCE: 110
METPAQLLFL LLLWLPDTTG                                                      20

SEQ ID NO: 111         moltype = AA  length = 18
FEATURE                Location/Qualifiers
source                 1..18
                       mol_type = protein
                       organism = synthetic construct
SEQUENCE: 111
MDWTWILFLV AAATRVHS                                                        18

SEQ ID NO: 112         moltype = AA  length = 24
FEATURE                Location/Qualifiers
source                 1..24
                       mol_type = protein
                       organism = synthetic construct
SEQUENCE: 112
MLGSNSGQRV VFTILLLLVA PAYS                                                 24

SEQ ID NO: 113         moltype = AA  length = 17
FEATURE                Location/Qualifiers
source                 1..17
                       mol_type = protein
                       organism = synthetic construct
SEQUENCE: 113
MKCLLYLAFL FIGVNCA                                                         17

SEQ ID NO: 114         moltype = AA  length = 18
FEATURE                Location/Qualifiers
source                 1..18
                       mol_type = protein
                       organism = synthetic construct
SEQUENCE: 114
MDWTWILFLV AAATRVHS                                                        18

SEQ ID NO: 115         moltype = AA  length = 19
FEATURE                Location/Qualifiers
source                 1..19
                       mol_type = protein
                       organism = synthetic construct
SEQUENCE: 115
ETPAQLLFLL LLWLPDTTG                                                       19

SEQ ID NO: 116         moltype = AA  length = 24
FEATURE                Location/Qualifiers
source                 1..24
                       mol_type = protein
                       organism = synthetic construct
SEQUENCE: 116
MLGSNSGQRV VFTILLLLVA PAYS                                                 24

SEQ ID NO: 117         moltype = AA  length = 17
FEATURE                Location/Qualifiers
source                 1..17
                       mol_type = protein
                       organism = synthetic construct
SEQUENCE: 117
MKCLLYLAFL FIGVNCA                                                         17

SEQ ID NO: 118         moltype = AA  length = 15
FEATURE                Location/Qualifiers
source                 1..15
                       mol_type = protein
                       organism = synthetic construct
SEQUENCE: 118
MWLVSLAIVT ACAGA                                                           15

SEQ ID NO: 119         moltype = AA  length = 15
FEATURE                Location/Qualifiers
source                 1..15
                       mol_type = protein
                       organism = synthetic construct
SEQUENCE: 119
MFVFLVLLPL VSSQC                                                           15
```

```
SEQ ID NO: 120         moltype = DNA   length = 81
FEATURE                Location/Qualifiers
source                 1..81
                       mol_type = other DNA
                       organism = synthetic construct
SEQUENCE: 120
atggggggg ctgccgccag gttgggggcc gtgattttgt ttgtcgtcat agtgggcctc    60
catggggtcc gcagcaaata t                                             81

SEQ ID NO: 121         moltype = DNA   length = 81
FEATURE                Location/Qualifiers
source                 1..81
                       mol_type = other DNA
                       organism = synthetic construct
SEQUENCE: 121
atgggaggag ccgccgccag actgggagcc gtgatcctgt tcgtggtgat cgtgggactg    60
catggagtga gaagcaagta c                                             81

SEQ ID NO: 122         moltype = DNA   length = 57
FEATURE                Location/Qualifiers
source                 1..57
                       mol_type = other DNA
                       organism = synthetic construct
SEQUENCE: 122
atgtttgtgt tcttgtgct gctgcctctt gtgtcttctc agtgtgtgaa tttgaca        57

SEQ ID NO: 123         moltype = DNA   length = 63
FEATURE                Location/Qualifiers
source                 1..63
                       mol_type = other DNA
                       organism = synthetic construct
SEQUENCE: 123
atggattgga tttggagaat cctgttcctc gtgggagccg ctacaggagc ccactcccag    60
atg                                                                 63

SEQ ID NO: 124         moltype = AA   length = 5
FEATURE                Location/Qualifiers
source                 1..5
                       mol_type = protein
                       organism = synthetic construct
SEQUENCE: 124
YLYRL                                                               5

SEQ ID NO: 125         moltype = AA   length = 5
FEATURE                Location/Qualifiers
source                 1..5
                       mol_type = protein
                       organism = synthetic construct
SEQUENCE: 125
YRYRL                                                               5

SEQ ID NO: 126         moltype = AA   length = 5
FEATURE                Location/Qualifiers
source                 1..5
                       mol_type = protein
                       organism = synthetic construct
SEQUENCE: 126
AGSTP                                                               5

SEQ ID NO: 127         moltype = AA   length = 5
FEATURE                Location/Qualifiers
source                 1..5
                       mol_type = protein
                       organism = synthetic construct
SEQUENCE: 127
AGSKP                                                               5

SEQ ID NO: 128         moltype = AA   length = 5
FEATURE                Location/Qualifiers
source                 1..5
                       mol_type = protein
                       organism = synthetic construct
SEQUENCE: 128
AGNKP                                                               5
```

```
SEQ ID NO: 129          moltype = AA   length = 250
FEATURE                 Location/Qualifiers
source                  1..250
                        mol_type = protein
                        organism = synthetic construct
SEQUENCE: 129
CTLKSFTVEK GIYQTSNFRV QPTESIVRFP NITNLCPFGE VFNATRFASV YAWNRKRISN    60
CVADYSVLYN SASFSTFKCY GVSPTKLNDL CFTNVYADSF VIRGDEVRQI APGQTGKIAD   120
YNYKLPDDFT GCVIAWNSNN LDSKVGGNYN YLYRLFRKSN LKPFERDIST EIYQAGSTPC   180
NGVEGFNCYF PLQSYGFQPT NGVGYQPYRV VVLSFELLHA PATVCGPKKS TNLVKNKCVN   240
FNFNGLTGTG                                                          250

SEQ ID NO: 130          moltype = AA   length = 250
FEATURE                 Location/Qualifiers
source                  1..250
                        mol_type = protein
                        organism = synthetic construct
SEQUENCE: 130
CTLKSFTVEK GIYQTSNFRV QPTESIVRFP NITNLCPFGE VFNATRFASV YAWNRKRISN    60
CVADYSVLYN SASFSTFKCY GVSPTKLNDL CFTNVYADSF VIRGDEVRQI APGQTGKIAD   120
YNYKLPDDFT GCVIAWNSNN LDSKVGGNYN YLYRLFRKSN LKPFERDIST EIYQAGSTPC   180
NGVEGFNCYF PLQSYGFQPT YGVGYQPYRV VVLSFELLHA PATVCGPKKS TNLVKNKCVN   240
FNFNGLTGTG                                                          250

SEQ ID NO: 131          moltype = AA   length = 250
FEATURE                 Location/Qualifiers
source                  1..250
                        mol_type = protein
                        organism = synthetic construct
SEQUENCE: 131
CTLKSFTVEK GIYQTSNFRV QPTESIVRFP NITNLCPFGE VFNATRFASV YAWNRKRISN    60
CVADYSVLYN SASFSTFKCY GVSPTKLNDL CFTNVYADSF VIRGDEVRQI APGQTGKIAD   120
YNYKLPDDFT GCVIAWNSNN LDSKVGGNYN YRYRLFRKSN LKPFERDIST EIYQAGSKPC   180
NGVEGFNCYF PLQSYGFQPT NGVGYQPYRV VVLSFELLHA PATVCGPKKS TNLVKNKCVN   240
FNFNGLTGTG                                                          250

SEQ ID NO: 132          moltype = AA   length = 250
FEATURE                 Location/Qualifiers
source                  1..250
                        mol_type = protein
                        organism = synthetic construct
SEQUENCE: 132
CTLKSFTVEK GIYQTSNFRV QPTESIVRFP NITNLCPFDE VFNATRFASV YAWNRKRISN    60
CVADYSVLYN LAPFFTFKCY GVSPTKLNDL CFTNVYADSF VIRGDEVRQI APGQTGNIAD   120
YNYKLPDDFT GCVIAWNSNK LDSKVSGNYN YLYRLFRKSN LKPFERDIST EIYQAGNKPC   180
NGVAGFNCYF PLRSYSFRPT YGVGHQPYRV VVLSFELLHA PATVCGPKKS TNLVKNKCVN   240
FNFNGLKGTG                                                          250

SEQ ID NO: 133          moltype = AA   length = 250
FEATURE                 Location/Qualifiers
source                  1..250
                        mol_type = protein
                        organism = synthetic construct
SEQUENCE: 133
CTLKSFTVEK GIYQTSNFRV QPTESIVRFP NITNLCPFDE VFNATRFASV YAWNRKRISN    60
CVADYSVLYN FAPFFAFKCY GVSPTKLNDL CFTNVYADSF VIRGNEVSQI APGQTGNIAD   120
YNYKLPDDFT GCVIAWNSNK LDSKVGGNYN YRYRLFRKSN LKPFERDIST EIYQAGNKPC   180
NGVAGVNCYF PLQSYGFRPT YGVGHQPYRV VVLSFELLHA PATVCGPKKS TNLVKNKCVN   240
FNFNGLTGTG                                                          250

SEQ ID NO: 134          moltype = AA   length = 9
FEATURE                 Location/Qualifiers
source                  1..9
                        mol_type = protein
                        organism = synthetic construct
SEQUENCE: 134
GSPGSGSGS                                                             9

SEQ ID NO: 135          moltype = AA   length = 6
FEATURE                 Location/Qualifiers
source                  1..6
                        mol_type = protein
                        organism = synthetic construct
SEQUENCE: 135
GSGSGS                                                                6

SEQ ID NO: 136          moltype = AA   length = 4
FEATURE                 Location/Qualifiers
```

```
source                         1..4
                               mol_type = protein
                               organism = synthetic construct
SEQUENCE: 136
RRAR                                                                         4

SEQ ID NO: 137                 moltype = AA   length = 12
FEATURE                        Location/Qualifiers
source                         1..12
                               mol_type = protein
                               organism = synthetic construct
SEQUENCE: 137
CGGAGAGCCA GA                                                                12

SEQ ID NO: 138                 moltype = AA   length = 9
FEATURE                        Location/Qualifiers
source                         1..9
                               mol_type = protein
                               organism = synthetic construct
SEQUENCE: 138
YLQPRTFLL                                                                    9

SEQ ID NO: 139                 moltype = AA   length = 9
FEATURE                        Location/Qualifiers
source                         1..9
                               mol_type = protein
                               organism = synthetic construct
SEQUENCE: 139
RLQSLQTYV                                                                    9

SEQ ID NO: 140                 moltype = AA   length = 9
FEATURE                        Location/Qualifiers
source                         1..9
                               mol_type = protein
                               organism = synthetic construct
SEQUENCE: 140
QYIKWPWYI                                                                    9

SEQ ID NO: 141                 moltype = AA   length = 9
FEATURE                        Location/Qualifiers
source                         1..9
                               mol_type = protein
                               organism = synthetic construct
SEQUENCE: 141
NYNYLYRLF                                                                    9

SEQ ID NO: 142                 moltype = AA   length = 10
FEATURE                        Location/Qualifiers
source                         1..10
                               mol_type = protein
                               organism = synthetic construct
SEQUENCE: 142
KWPWYIWLGF                                                                   10

SEQ ID NO: 143                 moltype = AA   length = 9
FEATURE                        Location/Qualifiers
source                         1..9
                               mol_type = protein
                               organism = synthetic construct
SEQUENCE: 143
QPTESIVRF                                                                    9

SEQ ID NO: 144                 moltype = AA   length = 9
FEATURE                        Location/Qualifiers
source                         1..9
                               mol_type = protein
                               organism = synthetic construct
SEQUENCE: 144
IPFAMQMAY                                                                    9

SEQ ID NO: 145                 moltype = AA   length = 9
FEATURE                        Location/Qualifiers
source                         1..9
                               mol_type = protein
                               organism = synthetic construct
SEQUENCE: 145
LPFNDGVYF                                                                    9
```

| SEQ ID NO: 146 | moltype = AA length = 9 |
| --- | --- |
| FEATURE | Location/Qualifiers |
| source | 1..9 |
| | mol_type = protein |
| | organism = synthetic construct |

SEQUENCE: 146
GVYFASTEK 9

| SEQ ID NO: 147 | moltype = AA length = 9 |
| --- | --- |
| FEATURE | Location/Qualifiers |
| source | 1..9 |
| | mol_type = protein |
| | organism = synthetic construct |

SEQUENCE: 147
CVADYSVLY 9

| SEQ ID NO: 148 | moltype = AA length = 9 |
| --- | --- |
| FEATURE | Location/Qualifiers |
| source | 1..9 |
| | mol_type = protein |
| | organism = synthetic construct |

SEQUENCE: 148
FQPTNGVGY 9

| SEQ ID NO: 149 | moltype = AA length = 9 |
| --- | --- |
| FEATURE | Location/Qualifiers |
| source | 1..9 |
| | mol_type = protein |
| | organism = synthetic construct |

SEQUENCE: 149
GTHWFVTQR 9

| SEQ ID NO: 150 | moltype = AA length = 9 |
| --- | --- |
| FEATURE | Location/Qualifiers |
| source | 1..9 |
| | mol_type = protein |
| | organism = synthetic construct |

SEQUENCE: 150
VYDPLQPEL 9

| SEQ ID NO: 151 | moltype = AA length = 9 |
| --- | --- |
| FEATURE | Location/Qualifiers |
| source | 1..9 |
| | mol_type = protein |
| | organism = synthetic construct |

SEQUENCE: 151
KCYGVSPTK 9

| SEQ ID NO: 152 | moltype = DNA length = 3817 |
| --- | --- |
| FEATURE | Location/Qualifiers |
| source | 1..3817 |
| | mol_type = other DNA |
| | organism = synthetic construct |

SEQUENCE: 152
```
atgttcgtgt tcctggtgct gctgcctctg gtgtccagcc agtgtgtgaa cttcaccacc    60
agaacacagc tgcctccagc ctacaccaac agctttacca gaggcgtgta ctaccccgac   120
aaggtgttca gatccagcgt gctgcactct acccaggacc tgttcctgcc tttcttcagc   180
aacgtgacct ggttccacgc catccacgtg tccggcacca atggcaccaa gagattcgcc   240
aaccccgtgc tgcccttcaa cgacggggtg tactttgcca gcaccgagaa gtccaacatc   300
atcagaggct ggatcttcgg caccacactg acagcaagaa cccagagcct gctgatcgtg   360
aacaacgcca ccaacgtggt catcaaagtg tgcgagttcc agttctgcaa cgaccccttc   420
ctgggcgtct actaccacaa gaacaacaag agctggatgg aaagcgagtt ccgggtgtac   480
agcagcgcca acaactgcac cttcgagtac gtgtcccagc ctttcctgat ggacctggaa   540
ggcaagcagg gcaacttcaa gaacctgcgc gagttcgtgt ttaagaacat cgacggctac   600
ttcaagatct acagcaagca cacccctatc aacctcgtgc ggggcctgcc tcagggcttc   660
tctgctctgg aaccctggt ggatctgccc atcggcatca acatcacccg gtttcagaca   720
ctgcacatca gctacctgac acctggcgat agcagcagcg gatggacagc tggtgccgcc   780
gcttactatg tgggctacct gcagcctaga accttcctgc tgaagtacaa cgagaacggc   840
accatcaccg acgccgtgga ttgtgctctg gatcctctga gcgagacaaa gtgcaccctg   900
aagtccttca ccgtgaaaa gggcatctac cagaccagca cttccgggt gcagcccacc   960
gaatccatcg tgcggttccc caatatcacc aatctgtgcc cttcggcga ggtgttcaat  1020
gccaccagat tcgcctctgt gtacgcctgg aaccggaagc ggatcagcaa ttgcgtggcc  1080
gactactccg tgctgtacaa ctccgccagc ttcagcacct tcaagtgcta cggcgtgtcc  1140
cctaccaagc tgaacgacct gtgcttcaca aacgtgtacg ccgacagctt cgtgatccgg  1200
ggagatgaag tgcggcagat tgccctggga cagacaggca acatgcccga ctacaactac  1260
aagctgcccg acgacttcac cggcgtgtgt attgcctgga caacaacaa cctggactcc  1320
aaagtcggcg gcaactacaa ttacctgtac cggctgttcc ggaagtccaa tctgaagccc  1380
ttcgagcggg acatctccac cgagatctat caggccggca gcacccctg taacggcgtg  1440
```

```
aagggcttca actgctactt cccactgcag tcctacggct ttcagcccac atacggcgtg    1500
ggctatcagc cctacagagt ggtggtgctg agcttcgaac tgctgcatgc ccctgccaca    1560
gtgtgcggcc ctaagaaaag caccaatctc gtgaagaaca aatgcgtgaa cttcaacttc    1620
aacgcctga ccggcaccgg cgtgctgaca gagagcaaca agaagttcct gccattccag     1680
cagtttggcc gggatatcgc cgataccaca gacgccgtta gagatcccca gacactggaa    1740
atcctggaca tcaccccttg cagcttcggc ggagtgtctg tgatcacccc tggcaccaac    1800
accagcaatc aggtggcagt gctgtaccag ggcgtgaact gtaccgaagt gcccgtggcc    1860
attcacgccg atcagctgac acctacatgg cgggtgtact ccaccggcag caatgtgttt    1920
cagaccagag ccggctgtct gatcggagcc gagcacgtga acaatagcta cgatgcgaga    1980
atccccatcg cgcgctggaat ctgcgccagc taccagacac agacaaacag ccctcggaga   2040
gccagaagcg tggccagcca gagcatcatt gcctacacaa tgtctctggg cgtcgagaac    2100
agcgtggcct actccaacaa ctctatcgct atccccacca acttcaccat cagcgtgacc    2160
acagagatcc tgcctgtgtc catgaccaag accagcgtgg actgcaccat gtacatctgc    2220
ggcgattcca ccgagtgctc caacctgctg ctgcagtacg gcagcttctg cacccagctg    2280
aatagagccc tgacagggat cgccgtggaa caggacaaga acacccaaga ggtgttcgcc    2340
caagtgaagc agatctacaa gacccctcct atcaaggact tcggcggctt caatttcagc    2400
cagattctgc ccgatcctag caagcccagc aagcggagct catcgagga cctgctgttc     2460
aacaaagtga cactggccga cgccggcttc atcaagcagt atggcgattg tctgggcgac    2520
attgccgcca gggatctgat tgcgcccag aagtttaacg gactgacagt gctgcctcct     2580
ctgctgaccg atgagatgat cgcccagtac acatctgccc tgctggccgg cacaatcaca    2640
agcggctgga catttggagc aggcgccgct ctgcagatcc cctttgctat gcagatggcc    2700
taccggttca acggcatcgg agtgacccag aatgtgctgt acgagaacca gaagctgatc    2760
gccaaccagt tcaacagcgc catcggcaag atccaggaca gcctgagcag cacagcaagc    2820
gccctgggaa agctgcagga cgtggtcaac cagaatgccc aggcactgaa cacccctggtc   2880
aagcagctgt cctccaactt cggcgccatc agctctgtgc tgaacgatat cctgagcaga    2940
ctggaccctc ctgaggccga ggtgcagatc gacagactga tcacaggcag actgcagagc    3000
ctccagacat acgtgaccca gcagctgatc agagccgccg agattagagc ctctgccaat    3060
ctggccgcca ccaagatgtc tgagtgtgtg ctgggccaga gcaagagagt ggacttttgc    3120
ggcaagggct accacctgat gagcttccct cagtctgccc ctcacggcgt ggtgtttctg    3180
cacgtgacat atgtgcccgc tcaagagaag aatttcacca ccgtccagc catctgccac     3240
gacggcaaag cccactttcc tagagaaggc gtgttcgtgt ccaacggcac ccattggttc    3300
gtgacacagc ggaacttcta cgagcccag atcatcacca ccgacaacac cttcgtgtct     3360
ggcaactgcg acgtcgtgat cggcattgtg aacaataccg tgtacgaccc tctgcagccc    3420
gagctggaca gcttcaaaga ggaactggac aagtacttta gaaccacac aagcccgac     3480
gtggacctgg gcgatatcag cggaatcaat gccagcgtcg tgaacatcca gaaagatc     3540
gaccggctga acgaggtggc caagaatctg aacgagagcc tgatcgacct gcaagaactg    3600
gggaagtacg agcagtacat caagtggccc tggtacatct ggctgggctt tatcgccgga    3660
ctgattgcca tcgtgatggt cacaatcatg ctgtgttgca tgaccagctg ctgtagctgc    3720
ctgaagggct gttgtagctg tggcagctgc tgcaagttcg acgaggacga ttctgagccc    3780
gtgctgaagg gcgtgaaact gcactacaca tgatgac                             3817
SEQ ID NO: 153           moltype = DNA  length = 4274
FEATURE                  Location/Qualifiers
source                   1..4274
                         mol_type = other DNA
                         organism = synthetic construct
SEQUENCE: 153
agaataaact agtattcttc tggtccccac agactcagag agaacccgcc accatgttcg      60
tgttcctggt gctgctgcct ctggtgtcca gccagtgtgt gaacttcacc accagaaacac    120
agctgcctcc agcctacacc aacagcttta ccagaggcgt gtactacccc gacaaggtgt    180
tcagatccag cgtgctgcac tctacccagg acctgttcct gccttctctc agcaacgtga    240
cctggttcca cgccatccac gtgtccggca ccaatggcac caagagattc gccaaccccg    300
tgctgccctt caacgacggg gtgtactttg ccagcaccga agtccaac atcatcagag       360
gctggatctt cggcaccaca ctggacagca agacccagag cctgctgatc gtgaacaacg    420
ccaccaacgt ggtcatcaaa gtgtgcgagt tccagttcgt caacgacccc ttcctgggcg    480
tctactacca caagaacaac aagagctgga tggaaagcga gttccgggtg tacagcagcg    540
ccaacaactg caccttcgag tacgtgtccc agccttccct gatggacctg gaaggcaagc    600
agggcaactt caagaacctg cgcgagttcg tgtttaagaa catcgacggc tacttcaaga    660
tctacagcaa gcacacccct atcaacctcg tgcgggggct gcctcagggc ttctctgctc    720
tggaaccct ggtggatctg cccatcggca tcaacatcac ccggtttcag acactgcaca     780
tcagctacct gacacctggc gatagcagca gcggatggac agctggtgcc gccgcttact    840
atgtgggcta cctgcagcct agaaccttcc tgctgaagta caacgagaac ggcaccatca    900
ccgacgcgt ggattgtgct ctggatcctc tgagcgagac aaagtgcacc ctgaagtcct     960
tcaccgtgga aaagggcatc taccagacca gcaacttccg ggtgcagccc accgaatcca   1020
tcgtgcggtt ccccaatatc accaatctgt gcccccttcg cgaggtgttc aatgccacca   1080
gattcgcctc tgtgtacgcc tggaaccgga gcggatcag caattgcgtg gccgactact    1140
ccgtgctgta caactccgcc agcttcagca ccttcaagtg ctacggcgtg tccctacca    1200
agctgaacga cctgtgcttc acaaaacgtgt acgccgacac cttcgtgatc cggggagatg    1260
aagtgcggca gattgccct ggacagacag gcaacatcgc tgactacaa tacaagctgc       1320
ccgacgactt caccggctgt gtgattgcct ggaacagcaa caacctggac tccaaagtcg    1380
gcggcaacta caattacctg tacggctgt tccggaagtc caatctgaag cccttcgagc     1440
gggacatctc caccgagatc tatcaggccg gcagcacccc ttgtaacggc gtgaagggct   1500
tcaactgcta cttcccactg cagtcctacg gtttcagcc cacatacggc gtgggctatc    1560
agccctcacag agtggtggtg ctgagcttcg aactgctgca tgcccctgcc acagtgtgcg   1620
gccctaagaa aagcaccaat ctcgtgaaga acaatgcgt gaacttcaac ttcaacggcc     1680
tgaccggcac cggcgtgctg acagagagca acaagaagtt cctgccattc cagcagtttg    1740
ccgggatat cgccgatacc acagacgccg ttagagatcc ccagacactg gaaatcctgg     1800
acatcacccc ttgcagcttc ggcggagtgt ctgtgatcac ccctggcacc aacaccagca    1860
atcaggtggc agtgctgtac cagggcgtga actgtaccga agtgcccgtg gccattcacg    1920
```

```
ccgatcagct gacacctaca tggcgggtgt actccaccgg cagcaatgtg tttcagacca    1980
gagccggctg tctgatcgga gccgagcacg tgaacaatag ctacgagtgc gacatcccca    2040
tcggcgctgg aatctgcgcc agctaccaga cacagacaaa cagccctcgg agagccagaa    2100
gcgtggccaa ccagagcatc attgcctaca caatgtctct gggcgtcgag aacagcgtgg    2160
cctactccaa caactctatc gctatcccca ccaacttcac catcagcgtg accacagaga    2220
tcctgcctgt gtccatgacc aagaccagcg tggactgcac catgtacatc tgcggcgatt    2280
ccaccgagtg ctccaacctg ctgctgcagt acggcagctt ctgcacccag ctgaatagag    2340
ccctgacagg gatcgccgtg aacaggaca agaaacccca agaggtgttc gcccaagtga    2400
agcagatcta caagaccct cctatcaagg acttcggcgg cttcaatttc agccagattc    2460
tgcccgatcc tagcaagccc agcaagcgga gcttcatcga ggacctgctg ttcaacaaag    2520
tgacactggc cgacgccggc ttcatcaagc agtatggcga ttgtctgggc gacattgccg    2580
ccagggatct gatttgcgcc cagaagttta acggactgac agtgctgcct cctctgctga    2640
ccgatgagat gatcgcccag tacacatctg ccctgctggc cggcacaatc acaagcggct    2700
ggacatttgg agcaggcgcc gctctgcaga tccccttttgc tatgcagatg gcctaccggt    2760
tcaacggcat cggagtgacc cagaatgtgc tgtacgagaa ccagaagctg atcgccaacc    2820
agttcaacag cgccatcggc aagatccagg acagcctgag cagcacagca agcgccctgg    2880
gaaagctgca ggacgtggtc aaccagaatg cccaggcact gaacaccctg gtcaagcagc    2940
tgtcctccaa cttcggcgcc atcagctctg tgctgaacga tatcctgagc agactggacc    3000
ctccctgaggc cgaggtgcag atcgacagac tgatcacaga cagactgcag agcctccaga    3060
catacgtgac ccagcagctg atcagagccg ccgagattag agcctctgcc aatctggccg    3120
ccaccaagat gtctgagtgt gtgctgggcc agagcaagag agtggacttt tgcggcaagg    3180
gctaccacct gatgagcttc cctcagtctg cccctcagtg cgtggtgttt ctgcacgtga    3240
catatgtgcc cgctcaagag aagaatttca ccaccgctcc agccatcgc cacgacggca    3300
aagcccactt tcctagagaa ggcgtgttcg tgtccaacgg cacccattgg ttcgtgacac    3360
agcggaactt ctacgagccc cagatcatca ccaccgacaa caccttcgtg tctggcaact    3420
gcgacgtcgt gatcggcatt gtgaacaata ccgtgtacga ccctctgcag cccgagctgg    3480
acagcttcaa agaggaactg gacaagtact ttaagaacca cacaagcccc gacgtggacc    3540
tgggcgatat cagcggaatc aatgccagcg tcgtgaacat ccagaaagag atcgaccggc    3600
tgaacgaggt ggccaagaat ctgaacgaga gcctgatcga cctgcaagaa ctggggaagt    3660
acgagcagta catcaagtgg ccctgtaca tctggctgg ctttatcgcc ggactgattg    3720
ccatcgtgat ggtcacaatc atgctgtgtt gcatgaccag ctgctgtagc tgcctgaagg    3780
gctgttgtag ctgtggcagc tgctgcaagt cgacgagga cgattctgag cccgtgctga    3840
agggcgtgaa actgcactac acatgatgac tcgagctggt actgcatgca cgcaatgcta    3900
gctgcccctt tcccgtcctg ggtaccccga gtctccccg acctcggtc ccaggtatgc    3960
tcccacctcc acctgcccca ctcaccacct ctgctagttc cagacacctc ccaagcacgc    4020
agcaatgcag ctcaaaacgc ttagcctagc cacacccca cgggaaacag cagtgattaa    4080
cctttagcaa taaacgaaag tttaactaag ctatactaac cccagggttg gtcaatttcg    4140
tgccagccac accctggagc tagcaaaaaa aaaaaaaaaa aaaagcatat    4200
gactaaaaaa aaaaaaaaaa aaaaaaaaaa aaaaaaaaaa aaaaaaaaaa aaaaaaaaaa    4260
aaaaaaaaaa aaaa                                                      4274
```

```
SEQ ID NO: 154          moltype = DNA  length = 3816
FEATURE                 Location/Qualifiers
source                  1..3816
                        mol_type = other DNA
                        organism = synthetic construct
SEQUENCE: 154
atgttcgtgt tcctggtgct gctgcctctg gtgccagcc agtgtgtgaa cctgaccacc     60
agaacacagc tgcctccagc ctacaccaac agctttacca gagcgtgta ctaccccgac    120
aaggtgttca gatccagcgt gctgcactct acccaggacc tgttcctgcc tttcttcagc    180
aacgtgacct ggttccacgc catctccggc accaatggca ccaagagatt cgacaactgc    240
gtgctgccct tcaacgacgg ggtgtacttt gccagcaccg agaagtccaa catcatcaga    300
ggctggatct tcggcaccac actggacagc aagacccaga gcctgctgat cgtgaacaac    360
gccaccaacg tggtcatcaa agtgtgcgag ttccagttct gcaacgaccc cttcctgggc    420
gtctaccaca agaacaacaa gagctggatg gaaagcgagt tccgggtgta cagcagcgcc    480
aacaactgca ccttcgagta cgtgtcccga ccttcctga tggacctgga aggcaagcag    540
ggcaacttca agaacctgcg cgagttcgtg tttaagaaca tcgacggcta cttcaagatc    600
tacagcaagc acacccctat caacctcgtg cgggatctgc ctcagggctt ctctgctctg    660
gaaccctcg tggatctgcc catcggcatc aacatcaccc ggtttcagac actgctggcc    720
ctgcacagaa gctacctgac acctggcgat agcagcagcg gatgcagc tggtgccgcc    780
gcttactatg tgggctacct gcagcctaga accttcctgc tgaagtacaa cgagaacggc    840
accatcaccg acgccgtgga ttgtgctctg gatcctctga cgagacaaa gtgcaccctg    900
aagtccttca cggtggaaaa gggcatctac cagaccagca cttccgggt gcagcccacc    960
gaatccatcg tgcggttccc caatatcacc aatctgtgcc ccttcggcga ggtgttcaat   1020
gccaccagat tcgcctctgt gtacgcctgg aaccggaagc ggatcagcaa ttgcgtggcc   1080
gactactccg tgctgtacaa ctccgccagc ttcagcacct tcaagtgcta cggcgtgtcc   1140
cctaccaagc tgaacgacct gtgcttcaca aacgtgtacg ccgacagctt cgtgatccgg   1200
ggagatgaag tgcggcagat tgcccctgga cagacaggca gatgccgga ctacaactac   1260
aagctgcccg acgacttcac cggctgtgtg attgctggaa acagcaacaa cctggactcc   1320
aaagtcggcg gcaactacaa ttacctgtac cggctgttcc ggaagtccaa tctgaagccc   1380
ttcgagcggg acatctccac cgagatctat caggccggca gcacccttg taacggcgtg   1440
gaaggcttca actgctactt cccactgcag tcctacggct tcagcccac atacggcgtg   1500
ggctatcagc cctacagagt ggtggtgctg agcttcgaac tgctgcatgc cctgccaca   1560
gtgtgcggc ctaagaaaag caccaatctc gtgaagaaca atgcgtgaa cttcaacttc   1620
aacggcctga ccggcaccgg cgtgctgaca gagagcaaca agaagttcct gccattccag   1680
cagtttggcc gggatatcga cgataccaca gacgccgtta gagatcccca gacactggaa   1740
atcctggaca tcaccccttg cagcttcggc ggagtgtctg tgatcacccc tggcaccaac   1800
accagcaatc aggtggcagt gctgtaccag ggcgtgaact ataccgaagt gcccgtggcc   1860
attcacgccg atcagctgac acctacatgg cgggtgtact ccaccggcag caatgtgttt   1920
```

```
cagaccagag ccggctgtct gatcggagcc gagcacgtga acaatagcta cgagtgcgac 1980
atccccatcg gcgctggaat ctgcgccagc taccagacac agacaaacag ccaccggaga 2040
gccagaagcg tggccagcca gagcatcatt gcctacacaa tgtctctggg cgccgagaac 2100
agcgtggcct actccaacaa ctctatcgct atccccatca acttcaccat cagcgtgacc 2160
acagagatcc tgcctgtgtc catgaccaag accagcgtga actgcaccat gtacatctgc 2220
ggcgattcca ccgagtgctc caacctgctg ctgcagtacg gcagcttctg cacccagctg 2280
aatagagccc tgacagggat cgccgtggaa caggacaaga acacccaaga ggtgttcgcc 2340
caagtgaagc agatctacaa gacccctcct atcaaggact tcggcggctt caatttcagc 2400
cagattctgc ccgatcctag caagcccagc aagcggagct tcatcgagga cctgctgttc 2460
aacaaagtga cactggccga cgccggcttc atcaagcagt atggcgattg tctgggcgac 2520
attgccgcca gggatctgat ttgcgcccag aagtttaacg gactgacagt gctgcctcct 2580
ctgctgaccg atgagatgat cgcccagtac acatctgccc tgctggccgg cacaatcaca 2640
agcggctgga catttggagc aggcgccgct ctgcagatcc cctttgctat gcagatggcc 2700
taccggttca acggcatcgg agtgacccag aatgtgctgt acgagaacca gaagctgatc 2760
gccaaccagt tcaacagcgc catcggcaag atccaggaca gcctgagcag cacagcaagc 2820
gccctgggaa agctgcagga cgtggtcaac cagaatgccc aggcactgaa caccctggtc 2880
aagcagctgt cctccaactt cggcgccatc agctctgtgc tgaacgatat cctggccaga 2940
ctggaccctc ctgaggccga ggtgcagatc gacagactga tcacaggcag actgcagagc 3000
ctccagacat acgtgaccca gcagctgatc agagccgccg agattagagc ctctgccaat 3060
ctggccgcca ccaagatgtc tgagtgtgtg ctgggccaga gcaagagagt ggactttgc 3120
ggcaagggct accacctgat gagcttccct cagtctgccc tcacggcgt ggtgtttctg 3180
cacgtgacat atgtgcccgc tcaagagaag aatttcacca ccgctccagc catctgccac 3240
gacggcaaag cccactttcc tagagaaggc gtgttcgtgt ccaacggcac ccattggttc 3300
gtgacacagc ggaacttcta cgagcccag atcatcacca cccacaacac cttcgtgtct 3360
ggcaactgcg acgtcgtgat cggcattgtg aacaataccg tgtacgaccc tctgcagccc 3420
gagctggaca gcttcaaaga ggaactgcga aagtacttta gaaccacac aagccccgac 3480
gtggacctgg gcgatatcag cggaatcaat gccagcgtcg tgaacatcca gaaagagatc 3540
gaccggctga cgaggtggc caagaatctg aacgagagcc tgatcgacct gcaagaactg 3600
gggaagtacg agcagtacat caagtggccc tggtacatct ggctgggctt tatcgccgga 3660
ctgattgcca tcgtgatggt cacaatcatg ctgtgttgca tgaccagctg ctgtagctgc 3720
ctgaagggct gttgtagctg tggcagctgc tgcaagttcg acgaggacga ttctgagccc 3780
gtgctgaagg gcgtgaaact gcactacaca tgatga                            3816
```

SEQ ID NO: 155　　　　moltype = DNA　length = 4274  
FEATURE　　　　　　Location/Qualifiers  
source　　　　　　　1..4274  
　　　　　　　　　　mol_type = other DNA  
　　　　　　　　　　organism = synthetic construct  
SEQUENCE: 155

```
agaataaact agtattcttc tggtccccac agactcagag agaacccgcc accatgttcg  60
tgttcctggt gctgctgcct ctggtgtcca gccagtgtgt gaacctgacc accagaacac 120
agctgcctcc agcctacacc aacagcttta ccagaggcgt gtactacccc gacaaggtgt 180
tcagatccag cgtgctgcac tctacccagg acctgttcct gccttcttc agcaacgtga 240
cctggttcca cgccatctcc ggcaccaatg gcaccaagag attcgacaac cccgtgctgc 300
ccttcaacga cggggtgtac tttgccagca ccgagaagtc caacatcatc agaggctgga 360
tcttcggcac cacactggac agcaagaccc agagcctgct gatcgtgaac aacgccacca 420
acgtgtcat caaagtgtgc gagttccagt tctgcaacga cccccttctg ggcgtctacc 480
acaagaacaa caagagctgg atggaaagcg agttccgggt gtacagcagc gccaacaact 540
gcaccttcga gtacgtgtcc cagcctttcc tgatggacct ggaaggcaag cagggcaact 600
tcaagaacct gcgcgagttc gtgtttaaga acatcgacgg ctacttcaag atctacagca 660
agcacacccc tatcaacctc gtgcgggatc tgcctcaagc cttctctgct ctggaaccc 720
tggtggatct gcccatcggc atcaacatca cccggtttca gacactgctg gccctgcaca 780
gaagctacct gacacctggc gatagcagca gcggatggac agctggtgcc gccgcttact 840
atgtgggcta cctgcagcct agaaccttcc tgctgaagta caacgagaac ggcaccatca 900
ccgacgccgt ggattgtgct ctggatcctc tgagcgagac aaagtgcacc ctgaagtcct 960
tcaccgtgga aaagggcatc taccagacca gcaacttccg ggtgcagccc accgaatcca 1020
tcgtgcggtt ccccaatatc accaatcgt gcccccttcgg cgaggtgttc aatgccacca 1080
gattcgcctc tgtgtacgcc tggaaccgga agcggatcag caattgcgtg gccgactact 1140
ccgtgctgta caactccgcc agcttcagca ccttcaagtg ctacggcgtg tcccctacca 1200
agctgaacga cctgtgcttc acaaacgtgt acgccgacag cttcgtgatc cgggagatg 1260
aagtgcggca gattgcccct ggacagacag gcaagatcgc cgactacaac tacaagctgc 1320
ccgacgactt caccggctgt gtgattgcct ggaacagcaa caacctggac tccaaagtcg 1380
gcggcaacta caattacctg taccggctgt tccggaagtc caatctgaag ccttcgagc 1440
gggacatctc caccgagatc tatcaggccg gcagcaccc ttgtaacggc gtggaaggct 1500
tcaactgcta cttccactg cagtcctacg gctttcagcc cacatacggc gtgggctatc 1560
agccctacag agtggtggtg ctgagcttcg aactgctgca tgcccctgcc acagtgtgcg 1620
gccctaagaa aagcaccaat ctcgtgaaga caaatgcgt gaacttcaac ttcaacggcc 1680
tgaccggcac cggcgtgctg acagagagca acaagaagt cctgccattc cagcagtttg 1740
gccggatat cgacgatacc acagacgccg ttagagacactg gaaatcctgg 1800
acatcaccc ttgcagcttc ggcggagtgt ctgtgatcac ccctggcacc aacaccagca 1860
atcaggtggc agtgctgtac caggcgtga actgtaccga agtgcccgtg gccattcacg 1920
ccgatcagct gacacctaca tggcgggtgt actccaccgg cagcaatgtg tttcagacca 1980
gagccggctg tctgatcgga gccgagcacg tgaacaatag ctacgagtgc gacatcccca 2040
tcggccgtg aatctgcgcc agctaccaga cacagacaaa cagccaccgg agagccagaa 2100
gcgtggccca ccagagcatc attgcctaca atgtctctct gggcgccgag aacagcgtgg 2160
cctactccaa caactctatc gctatcccca tcaacttcac catcagcgtg accacagaga 2220
tcctgcctgt gtccatgacc aagaccagcg tggactgcac catgtacatc tgcggcgatt 2280
ccaccgagtg ctccaacctg ctgctgcagt acggcagctt ctgcacccag ctgaatagag 2340
ccctgacagg gatcgccgtg gaacaggaca agaacaccca gaggtgttc gcccaagtga 2400
```

```
agcagatcta caagacccct cctatcaagg acttcggcgg cttcaatttc agccagattc   2460
tgcccgatcc tagcaagccc agcaagcgga gcttcatcga ggacctgctg ttcaacaaag   2520
tgacactggc cgacgccggc ttcatcaagc agtatgcgca ttgtctgggc gacattgccg   2580
ccagggatct gatttgcgcc cagaagttta acggactgac agtgctgcct cctctgctga   2640
ccgatgagat gatcgcccag tacacatctg ccctgctggc cggcacaatc acaagcggct   2700
ggacatttgg agcaggcgcc gctctgcaga tcccctttgc tatgcagatg gcctaccggt   2760
tcaacggcat cggagtgacc cagaatgtgc tgtacgagaa ccagaagctg atcgccaacc   2820
agttcaacag cgccatcggc aagatccagg acagcctgag cagcacagca agcgccctgg   2880
gaaagctgca ggacgtggtc aaccagaatg cccaggcact gaacaccctg gtcaagcagc   2940
tgtcctccaa cttcggcgcc atcagctctg tgctgaacga tatcctggcc agactggacc   3000
ctcctgaggc cgaggtgcag atcgacagac tgatcacagg cagactgcag agcctccaga   3060
catacgtgac ccagcagctg atcagagccg ccgagattag agcctctgcc aatctggccg   3120
ccaccaagat gtctgagtgt gtgctgggcc agagcaagag agtggacttt tgcggcaagg   3180
gctaccacct gatgagcttc cctcagtctg ccctcacgg gctggtgttt ctgcacgtgg   3240
catatgtgcc cgctcaagag aagaatttca ccaccgctcc agccatctgc cacgacggca   3300
aagcccactt tcctagagaa ggcgtgttcg tgtccaacgg cacccattgg ttcgtgacac   3360
agcggaactt ctacgagccc cagatcatca ccacccacaa caccttcgtg tctggcaact   3420
gcgacgtcgt gatcggcatt gtgaacaata ccgtgtacga ccctctgcag cccgagctgg   3480
acagcttcaa agaggaactg gacaagtact ttaagaacca cacaagcccc gacgtggacc   3540
tgggcgatat cagcggaatc aatgccagcg tcgtgaacat ccagaaagag atcgaccggc   3600
tgaacgaggt ggccaagaat ctgaacgaga gcctgatcga cctgcaagaa ctggggaagt   3660
acgagcagta catcaagtgg ccctggtaca tctggctggg ctttatcgcc ggactgattg   3720
ccatcgtgat ggtcacaatc atgctgtgtt gcatgaccag ctgctgtagc tgcctgaagg   3780
gctgttgtag ctgtggcagc tgctgcaagt tcgacgagga cgattctgag cccgtgctga   3840
agggcgtgaa actgcactac acatgatgag atctgctggt actgcatgca cgcaatgcta   3900
gctgcccctt tcccgtcctg ggtacccga gtctccccg acctcgggtc ccaggtatgc   3960
tcccacctcc acctgcccca ctcaccacct ctgctagttc cagacaccct ccaagcacgc   4020
agcaatgcag ctcaaaacgc ttagcctagc cacacccca cgggaaacag cagtgattaa   4080
cctttagcaa taaacgaaag tttaactaag ctatactaac cccaggggttg gtcaatttcg   4140
tgccagccac accctggagc tagcaaaaaa aaaaaaaaaa aaaaaaaaaa aaaagcatat   4200
gactaaaaaa aaaaaaaaaa aaaaaaaaaa aaaaaaaaaa aaaaaaaaaa aaaaaaaaaa   4260
aaaaaaaaaa aaaa                                                    4274

SEQ ID NO: 156          moltype = RNA   length = 3819
FEATURE                 Location/Qualifiers
source                  1..3819
                        mol_type = other RNA
                        organism = synthetic construct
SEQUENCE: 156
atgttcgtgt tcctggtgct gctgcctctg gtgtccagcc agtgtgtgaa cctgagaacc     60
agaacacagc tgcctccagc ctacaccaac agctttacca gaggcgtgta ctaccccgac    120
aaggtgttca gatccagcgt gctgcactct acccaggacc tgttcctgcc tttcttcagc    180
aacgtgacct ggttccacgc catccacgtg tccggcacca atggcaccaa gagattcgac    240
aaccccgtgc tgcccttcaa cgacggggtg tactttgcca gcaccgagaa gtccaacatc    300
atcagaggct ggatcttcgg caccacactg gacagcaaga cccagagcct gctgatcgtg    360
aacaacgcca ccaacgtggt catcaaagtg tgcgagttcc agttctgcaa cgaccccttc    420
ctggacgtct actaccacaa gaacaacaag agctggatgg aaagcggcgt gtacagcagc    480
gccaacaact gcaccttcga gtacgtgtcc cagcctttcc tgatggacct ggaaggcaag    540
cagggcaact tcaagaacct gcgcgagttc gtgtttaaga catcgacgg ctacttcaag    600
atctacagca agcacacccc tatcaacctc gtgcgggatc tgcctcaggg cttctctgct    660
ctggaacccc tggtggatct gcccatcggc atcaacatca cccggtttca gacactgctg    720
gccctgcaca gaagctacct gacacctggc gatagcagca gcggatggac agctggtgcc    780
gccgcttact atgtgggcta cctgcagcct agaaccttcc tgctgaagta caacgagaac    840
ggcaccatca ccgacgccgt ggattgtgct ctggatcctc tgagcgagac aaagtgcacc    900
ctgaagtcct tcaccgtgga aaagggcatc taccagacca gcaacttccg ggtgcagccc    960
accgaatcca tcgtgcggtt ccccaatatc accaatctgt gccccttcgg cgaggtgttc   1020
aatgccacca gattcgcctc tgtgtacgcc tggaaccgga gcggatcag caattgcgtg   1080
gccgactact ccgtgctgta caactccgcc agcttcagca ccttcaagtg ctacggcgtg   1140
tccccctacca agctgaacga cctgtgcttc acaaacgtgt acgccgacag cttcgtgatc   1200
cggggagatg aagtgcggca gattgccccc ggacagacag gcaagatcgc cgactacaac   1260
tacaagctgc ccgacgactt caccggctgt gtgattgcct ggaacagcaa caacctggac   1320
tccaaagtcg gcggcaacta caattacagg taccggctgt tccggaagtc caatctgaag   1380
cccttcgagc gggacatctc caccgagatc tatcaggccg gcagcaagcc ttgtaacggc   1440
gtggaaggct tcaactgcta cttcccactg cagtcctacg gctttcaacc cacaaatggc   1500
gtgggctatc agcccctacag agtggtggtg ctgagcttcg aactgctgca tgccccctgcc  1560
acagtgtgcg gccctaagaa aagcaccaat tcgtgaaga caaatgcgt gaacttcaac    1620
ttcaacggcc tgaccggcac cggcgtgctg acagagagca caagaagtt cctgccattc    1680
cagcagtttg gccgggatat cgccgatacc acagacgccg ttagagatcc ccagacactg    1740
gaaatcctgg acatcacccc ttgcagcttc ggcggagtgt ctgtgatcac ccctggcacc    1800
aacaccagca atcaggtggc agtgctgtac cagggcgtga actgtaccga agtgccccgtg    1860
gccattcacg ccgatcagct gacacctaca tggcggggtgt actccaccgg cagcaatgtg    1920
tttcagacca gagccggctg tctgatcgga gccgagcacg tgaacaatag ctacgagtgc    1980
gacatcccca tcggcgctgg aatctgcgcc agctaccaga cacagacaaa cagcaggcgg    2040
agagccagaa gcgtggccag cagtggccag attgcctaca atgtctct gggcgccgga    2100
aacagcgtgg cctactccaa caactctatc gctatcccca ccaacttcac catcagcgtg    2160
accacagaga tcctgcctgt gtccatgacc aagaccagcg tggactgcac catgtacatc    2220
tgcggcgatt ccaccgagtg ctccaacctg ctgctgcagt acggcagctt ctgcacccag    2280
ctgaatagag ccctgacagg gatcgccgtg gaacaggaca agaaccccca agaggtgttc    2340
gcccaagtga agcagatcta caagacccct cctatcaagg acttcggcgg cttcaatttc    2400
```

-continued

```
agccagattc tgcccgatcc tagcaagccc agcaagcgga gcttcatcga ggacctgctg  2460
ttcaacaaag tgacactggc cgacgccggc ttcatcaagc agtatggcga ttgtctgggc  2520
gacattgccg ccagggatct gatttgcgcc cagaagttta acggactgac agtgctgcct  2580
cctctgctga ccgatgagat gatcgcccag tacacatctg ccctgctggc cggcacaatc  2640
acaagcggct ggacatttgg agcaggcgcc gctctgcaga tccccttttgc tatgcagatg  2700
gcctaccggt tcaacggcat cggagtgacc cagaatgtgc tgtacgagaa ccagaagctg  2760
atcgccaacc agttcaacag cgccatcggc aagatccagg acagcctgag cagcacagca  2820
agcgccctgg gaaagctgca gaacgtggtc aaccagaatg cccaggcact gaacaccctg  2880
gtcaagcagc tgtcctccaa cttcggcgcc atcagctctg tgctgaacga tatcctgagc  2940
agactggacc ctcctgaggc cgaggtgcag atcgacagac tgatcacagg cagactgcag  3000
agcctccaga catacgtgac ccagcagctg atcagagccg ccgagattag agcctctgcc  3060
aatctggccg ccaccaagat gtctgagtgt gtgctgggcc agagcaagag agtggacttt  3120
tgcggcaagg gctaccacct gatgagcttc cctcagtctg cccctcacgg cgtggtgttt  3180
ctgcacgtga catatgtgcc cgctcaagag aagaatttca ccaccgctcc agccatctgc  3240
cacgacggca aagcccactt tcctagagaa ggcgtgttcg tgtccaacgg cacccattgg  3300
ttcgtgacac agcggaactt ctacgagccc cagatcatca ccaccgacaa caccttcgtg  3360
tctggcaact gcgacgtcgt gatcggcatt gtgaacaata ccgtgtacga ccctctgcag  3420
cccgagctgg acagcttcaa agaggaactg gacaagtact ttaagaacca cacaagcccc  3480
gacgtggacc tgggcgatat cagcggaatc aatgccagcg tcgtgaacat ccagaaaagg  3540
atcgaccggc tgaacgaggt ggccaagaat ctgaacgaga gcctgatcga cctgcaagaa  3600
ctggggaagt acgagcagta catcaagtgg cccctggtaca tctggctggg ctttatcgcc  3660
ggactgattg ccatcgtgat ggtcacaatc atgctgtgtt gcatgaccag ctgctgtagc  3720
tgcctgaagg gctgttgtag ctgtggcagc tgctgcaagt tcgacgagga cgattctgag  3780
cccgtgctga agggcgtgaa actgcactac acatgatga                          3819

SEQ ID NO: 157        moltype = RNA   length = 4277
FEATURE               Location/Qualifiers
source                1..4277
                      mol_type = other RNA
                      organism = synthetic construct
SEQUENCE: 157
agaataaact agtattcttc tggtccccac agactcagag agaacccgcc accatgttcg   60
tgttcctggt gctgctgcct ctggtgtcca gccagtgtgt gaacctgaga accagaacac   120
agctgctcc agcctacacc aacagcttta ccagaggcgt gtactacccc gacaaggtgt   180
tcagatccag cgtgctgcac tctacccagg acctgttcct gcctttcttc agcaacgtga   240
cctggttcca cgccatccac gtgtccggca ccaatggcac caagagattc gacaaccccg   300
tgctgccctt caacgacggg gtgtactttg ccagcaccga agtccaac atcatcagag    360
gctggatctt cggcaccaca ctggacagca gacccagag cctgctgatc gtgaacaacg   420
ccaccaacgt ggtcatcaaa gtgtgcgagt tccagttctg caacgacccc ttcctggacg   480
tctactacca caagaacaac aagagctgga tggaaagcgg cgtgtacagc agcgccaaca   540
actgcacctt cgagtacgtg tcccagccct tcctgatgga cctggaaggc aagcagggca   600
acttcaagaa cctgcgcgag ttcgtgtttta agaacatcga cggctacttc aagatctaca   660
gcaagcacac ccctatcaac ctcgtgcggg atctgcctca gggcttctct gctctgtaac   720
ccctggtgga tctgcccatc ggcatcaaca tcacccggtt tcagacactg ctggccctgc   780
acagaagcta cctgacacct ggcgatagca gcagcggatg gacagctggt gccgccgctt   840
actatgtggg ctacctgcag cctagaacct tcctgctgaa gtacaacgag aacggcacca   900
tcaccgacgc cgtggattgt gctctggatc tctgagcg gacaaagtgc accctgaagt   960
ccttcaccgt ggaaaagggc atctaccaga ccagcaactt ccgggtgcag cccaccgaat  1020
ccatcgtgcg gttccccaat atcaccaatc tgtgcccctt cggcgaggtg ttcaatgcca  1080
ccagattcgc ctctgtgtac gcctggaacc ggaagcggat cagcaattgc gtggccgact  1140
actccgtgct gtacaactcc gccagcttca gcaccttcaa gtgctacggc gtgtccctca  1200
ccaagctgaa cgacctgtgc ttcacaaacg tgtacgccga cagcttcgtg atccggggag  1260
atgaagtgcg gcagattgcc cctggacaga caggcaagat cgccgactac aactacaagc  1320
tgcccgacga cttcaccggc tgtgtgattg cctggaacag caacaacctg gactccaaag  1380
tcggcggcaa ctacaattac aggtaccggc tgttccggaa gtccaatctg aagccctcg   1440
agcgggacat ctccaccgag atctatcagg ccggcagcaa gccttgtaac ggcgtggaag  1500
gcttcaactg ctacttccca ctgcagtcct acggctttca gcccacaaat ggcgtgggct  1560
atcagcccta cagagtggtg gtgctgagct tcgaactgct gcatgcccct gccacagtgt  1620
gcggccctaa gaaaagcacc aatctcgtga agaacaaatg cgtgaacttc aacttcaacg  1680
gcctgaccgg caccggcgtg ctgacagaga gcaacaagaa gttcctgcca ttccagcagt  1740
ttggccggga tatcgccgat accacagacg ccgttagaga tccccagaca ctggaaatcc  1800
tggacatcac cccttgcagc ttcggcgag tgtctgtgat caccctggc accaacacca   1860
gcaatcaggt ggcagtgctg taccaggcgc tgaactgtac cgaagtgccc gtggccattc  1920
acgccgatca gctgacacct acatgccggg tgtactccac cggcagcaat gtgtttcaga  1980
ccagagccgg ctgtctgatc ggagccgagc acgtgaacaa tagctacgag tgcgacatcc  2040
ccatcggcgc tggaatctgc gccagctacc agacacagac aaacagcagg cggagagcca  2100
gaagcgtggc cagccagagc atcattgcct acacaatgtc tctgggcgcc gagaacagcg  2160
tggcctactc caacaactct atcgctatcc ccaccaactt caccatcagc gtgaccacag  2220
agatcctgcc tgtgtccatg accaagacca gcgtggactg caccatgtac atctgcggcg  2280
attccaccga gtgctccaac ctgctgctgc agtacggcag cttctgcacc cagctgaata  2340
gagccctgac agggatcgcc gtgaacagg acaagaacac caagaggtg ttcgcccaag   2400
tgaagcagat ctacaagacc cctcctatca aggacttcgg cggcttcaat ttcagccaga  2460
ttctgcccga tcctagcaag cccagcaagc ggagcttcat cgaggacctg ctgttcaaca  2520
aagtgacact ggccgacgcc ggcttcatca agcagtatgg cgattgtctg ggcgacattg  2580
ccgcagggga tctgatttgc gcccagaagt taacggact gacagtgctg cctcctctgc   2640
tgaccgatga gatgatcgcc cagtacacat ctgcccctgct ggccggcaca atcacaagcg  2700
gctggacatt tggagcaggc gccgctctgc agatcccctt tgctatgcag atggcctacc  2760
ggttcaacgg catcggagtg acccagaatg tgctgtacga gaaccagaag ctgatcgcca  2820
accagttcaa cagcgccatc ggcaagatcc aggacagcct gagcagcaca gcaagcgccc  2880
```

```
tgggaaagct gcagaacgtg gtcaaccaga atgcccaggc actgaacacc ctggtcaagc  2940
agctgtcctc caacttcggc gccatcagct ctgtgctgaa cgatatcctg agcagactgg  3000
accctcctga ggccgaggtg cagatcgaca gactgatcac aggcagactg cagagcctcc  3060
agacatacgt gacccagcag ctgatcagag ccgccgagat tagagcctct gccaatctgg  3120
ccgccaccaa gatgtctgag tgtgtgctgg gccagagcaa gagagtggac ttttgcggca  3180
agggctacca cctgatgagc ttccctcagt ctgcccctca cggcgtggtg tttctgcacg  3240
tgacatatgt gcccgctcaa gagaagaatt tcaccaccgc tccagccatc tgccacgacg  3300
gcaaagccca ctttcctaga gaaggcgtgt tcgtgtccaa cggcacccat ggttcgtgaa  3360
cacagcggaa cttctacgag ccccagatca tcaccaccgc caacaccttc gtgtctggca  3420
actgcgacgt cgtgatcggc attgtgaaca ataccgtgta cgaccctctg cagcccgtgg  3480
tggacagctt caaagaggaa ctggacaagt actttaagaa ccacacaagc cccgacgtgg  3540
acctgggcga tatcagcgga atcaatgcca gcgtcgtgaa catccagaaa gagatcgacc  3600
ggctgaacga ggtggccaag aatctgaacg agagcctgat cgacctgcaa gaactgggga  3660
agtacgagca gtacatcaag tggccctggt acatctgggt gggctttatc gccggactga  3720
ttgccatcgt gatggtcaca atcatgctgt gttgcatgac cagctgctgt agctgcctga  3780
agggctgttg tagctgtggc agctgctgca agttcgacga ggacgattct gagcccgtgc  3840
tgaagggcgt gaaactgcac tacacatgat gatttcacct ggtactgcat gcacgcaatg  3900
ctagctgccc ctttccccgtc ctgggtaccc cgagtcctcc ccgacctcgg gtccaggta  3960
tgctcccacc tccacctgcc ccactcacca cctctgctag ttccagacac ctcccaagca  4020
cgcagcaatg cagctcaaaa cgcttagcct agccacaccc cacgggaaa cagcagtgat  4080
taaccttag caataaacga aagtttaact aagctatact aaccccaggg ttggtcaatt  4140
tcgtgccagc cacaccctgg agctagcaaa aaaaaaaaaa aaaaaaaaaa aaaaaagca  4200
tatgactaaa aaaaaaaaaa aaaaaaaaaa aaaaaaaaaa aaaaaaaaaa aaaaaaaaaa  4260
aaaaaaaaaa aaaaaaa                                                 4277
```

SEQ ID NO: 158          moltype = AA   length = 1269
FEATURE                 Location/Qualifiers
source                  1..1269
                        mol_type = protein
                        organism = synthetic construct
SEQUENCE: 158
MFVFLVLLPL VSSQCVNLIT RTQSYTNSFT RGVYYPDKVF RSSVLHSTQD LFLPFFSNVT    60
WFHAIHVSGT NGTKRFDNPA LPFNDGVYFA STEKSNIIRG WIFGTTLDSK TQSLLIVNNA   120
TNVVIKVCEF QFCNDPFLDV YQKNNKSWME SEFRVYSSAN NCTFEYVSQP FLMDLEGKEG   180
NFKNLREFVF KNIDGYFKIY SKHTPINLER DLPQGFSALE PLVDLPIGIN ITRFQTLLAL   240
HRSYLTPVDS SSGWTAGAAA YYVGYLQPRT FLLKYNENGT ITDAVDCALD PLSETKCTLK   300
SFTVEKGIYQ TSNFRVQPTE SIVRFPNITN LCPFHEVFNA TTFASVYAWN RKRISNCVAD   360
YSVIYNFAPF FAFKCYGVSP TKLNDLCFTN VYADSFVIRG NEVSQIAPGQ TGNIADYNYK   420
LPDDFTGCVI AWNSNKLDSK PSGNYNYLYR LFRKSKLKPF ERDISTEIYQ AGNKPCNGVA   480
GPNCYSPLQS YGFRPTYGVG HQPYRVVVLS FELLHAPATV CGPKKSTNLV KNKCVNFNFN   540
GLTGTGVLTE SNKKFLPFQQ FGRDIADTTD AVRDPQTLEI LDITPCSFGG VSVITPGTNT   600
SNQVAVLYQG VNCTEVPVAI HADQLTPTWR VYSTGSNVFQ TRAGCLIGAE YVNNSYECDI   660
PIGAGICASY QTQTKSHRRA RSVASQSIIA YTMSLGAENS VAYSNNSIAI PTNFTISVTT   720
EILPVSMTKT SVDCTMYICG DSTECSNLLL QYGSFCTQLK RALTGIAVEQ DKNTQEVFAQ   780
VKQIYKTPPI KYFGGFNFSQ ILPDPSKPSK RSFIEDLLFN KVTLADAGFI KQYGDCLGDI   840
AARDLICAQK FNGLTVLPPL LTDEMIAQYT SALLAGTITS GWTFGAGAAL QIPFAMQMAY   900
RFNGIGVTQN VLYENQKLIA NQFNSAIGKI QDSLSSTASA LGKLQDVVNH NAQALNTLVK   960
QLSSKFGAIS SVLNDILSRL DPPEAEVQID RLITGRLQSL QTYVTQQLIR AAEIRASANL  1020
AATKMSECVL GQSKRVDFCG KGYHLMSFPQ SAPHGVVFLH VTYVPAQEKN FTTAPAICHD  1080
GKAHFPREGV FVSNGTHWFV TQRNFYEPQI ITTDNTFVSG NCDVVIGIVN NTVYDPLQPE  1140
LDSFKEELDK YFKNHTSPDV DLGDISGINA SVVNIQKEID RLNEVAKNLN ESLIDLQELG  1200
KYEQYIKWPW YIWLGFIAGL IAIVMVTIML CCMTSCCSCL KGCCSCGSCC KFDEDDSEPV  1260
LKGVKLHYT                                                          1269

SEQ ID NO: 159          moltype = RNA   length = 3813
FEATURE                 Location/Qualifiers
source                  1..3813
                        mol_type = other RNA
                        organism = synthetic construct
SEQUENCE: 159
atgttcgtgt tcctggtgct gctgcctctg gtgtccagcc agtgtgtgaa cctgatcacc    60
agaacacagt catacaccaa cagctttacc agaggcgtgt actacccccga caaggtgttc   120
agatccagcg tgctgcactc tacccaggac ctgttcctgc cttttcttcag caacgtgacc   180
tggttccacg ccatccacgt gtccggcacc aatggcaccca agagattcga caacccccgc   240
ctgcccttca cgacggggt gtactttgcc agcaccgaga gtccaacat catcagaggc   300
tggatcttcg gcaccacact ggacagcaag acccagagcc tgctgatcgt gaacaacgcc   360
accaacgtgt catcaaagt gtgcgagttc cagttctgca cgacccctt cctggacgtc   420
taccagaaga caacaagag ctggatgaa agcgagttcc gggtgtacag cagcgccaac   480
aactgcacct tcgagtacgt gtcccagcct ttcctggaagg caaggagggc   540
aacttcaaga acctgcgcga gttcgtgttt aagaacatcg acggctactt caagatctac   600
agcaagcaca cccctatcaa cctcgagcgg gatctgcctc agggcttctc tgctctggaa   660
cccctggtgg atctgcccat cggcatcaac atcacccggt tcagacact gctggccctg   720
cacagaagct acctgacacc tgtggatagc agcagcggat ggacagctgg tgccgccgct   780
tactatgtgg gctacctgca gcctagaacc ttcctgctga agtacaacga gaacggcacc   840
atcaccgacg ccgtggattg tgctctggat cctctgagcg agacaaagtg cacccctgaag   900
tccttcaccg tggaaaaggg catctaccag accagcaact ccggtgtgca gcccaccgaa   960
tccatcgtgc ggttccccaa tatcaccaat ctgtgcccct tccacgaggt gttcaatgcc  1020
accaccttcg cctctgtgta cgcctggaac cggaagcgga tcagcaattg cgtggccgac  1080
tactccgtga tctacaactt cgcccccttc ttcgcattca gtgctacgg cgtgtcccct  1140
```

```
accaagctga acgacctgtg cttcacaaac gtgtacgccg acagcttcgt gatccgggga 1200
aacgaagtgt cacagattgc ccctggacag acaggcaaca tcgccgacta caactacaag 1260
ctgcccgacg acttcaccgg ctgtgtgatt gcctggaaca gcaacaagct ggactccaaa 1320
cccagcggca actacaatta cctgtaccgg ctgttccgga agtccaagct gaagcccttc 1380
gagcgggaca tctccaccga gatctatcag gccggcaaca agccttgtaa cggcgtggca 1440
ggccccaact gctacagccc actgcagtcc tacggcttta ggcccacata cggcgtgggc 1500
caccagccct acagagtggt ggtgctgagc ttcgaactgc tgcatgcccc tgccacagtg 1560
tgcgccccta agaaaagcac caatctcgtg aagaacaaat gcgtgaactt caacttcaac 1620
ggcctgaccg gcaccggcgt gctgacagag agcaacaaga agttcctgcc attccagcag 1680
tttggccggg atatcgccga taccacagac gccgttagag atccccagac actggaaatc 1740
ctggacatca cccccttgcag cttcggcgga gtgtctgtga tcacccctgg caccaacacc 1800
agcaatcagg tggcagtgct gtaccagggc gtgaactgta ccgaagtgcc cgtggccatt 1860
cacgccgatc agctgacacc tacatggcgg gtgtactcca ccggcagcaa tgtgtttcag 1920
accagagccg gctgtctgat cggagccgag tacgtgaaca atagctacga gtgcgacatc 1980
cccatcggcg ctggaatctg cgccagctac cagacacaga caaagagcca ccggagagcc 2040
agaagcgtgg ccagccagag catcattgcc tacacaatgt ctctgggcgc cgagaacagc 2100
gtggcctact ccaacaactc tatcgctatc ccaccaactt tcaccatcag cgtgaccaca 2160
gagatcctgc ctgtgtccat gaccaagacc agcgtggact gcaccatgta catctgcggc 2220
gattccaccg agtgctccaa cctgctgctg cagtacggcc gcttctgcac ccagctgaaa 2280
agagccctga cagggatcgc cgtggaacag gacaagaaca cccaagaggt gttcgcccaa 2340
gtgaagcaga tctacaagac ccctcctatc aagtacttcg gcggcttcaa tttcagccag 2400
attctgcccg atcctagcaa gcccaccaag cggagcttca tcgaggacct gctgttcaac 2460
aaagtgacac tggccgacgc cggcttcatc aagcagtatg gcgattgtct gggcgacatt 2520
gccgccaggt atctgatttg cgcccagaag tttaacggac tgacagtgct gcctcctctg 2580
ctgaccgatg agatgatcgc ccagtacaca tctgccctgc tggccggcac aatcacaagc 2640
ggctggacat ttggagcagg cgccgctctg cagatccctt tgctatgaga tgaggcctac 2700
cggttcaacg gcatcggagt gacccagaat gtgctgtacg agaaccagaa gctgatcgca 2760
aaccagttca acagcgccat cggcaagatc caggacagcc tgagcagcac agcaagcgcc 2820
ctgggaaagc tgcaggacgt ggtcaaccac aatgcccagg cactgaacac cctggtcaag 2880
cagctgtcct ccaagttcgg cgccatcagc tctgtgctga acgatatcct gagcagactg 2940
gaccctcctg aggccgaggt gcagatcgac agactgatca caggcagact gcagagcctc 3000
cagacatacg tgacccagca gctgatcaga gccgccgaga ttagagcctc tgccaatctg 3060
gccgccacca gatgtctgaa gtgtgtgctg ggccagagca agagagtgga cttttgcggc 3120
aagggctacc acctgatgag cttccctcag tctccccctc acggcgtggt gtttctgcac 3180
gtgacatatg tgcccgctca agagaagaat ttcaccaccg ctccagccat ctgccacgac 3240
ggcaaagccc actttcctag agaaggcgtg ttcgtgtcca acggcaccca ttggttcgtg 3300
acacagcgga acttctacga gccccagatc atcaccaccg acaacacctt cgtgtctggc 3360
aactgcgacg tcgtgatcgg cattgtgaac aataccgtgt acgaccctct gcagcccgag 3420
ctggacagct tcaaagagga actggacaag tactttaaga accacacaag ccccgacgtg 3480
gacctgggcg atatcagcgg aatcaatgcc agcgtcgtga acatccagaa agatatcgac 3540
cggctgaacg aggtggccaa gaatctgaac gagagcctga tcgacctgca agaactgggg 3600
aagtacgagc agtacatcaa gtggccctgg tacatctggc tgggctttat cgccggactg 3660
attgccatcg tgatggtcac aatcatgctg tgttgcatga ccagctgctg tagctgcctg 3720
aagggctgtt gtagctgtgg cagctgctgc aagttcgacg aggacgattc tgagcccgtg 3780
ctgaagggcg tgaaactgca ctacacatga tga                                3813
SEQ ID NO: 160         moltype = DNA  length = 3813
FEATURE                Location/Qualifiers
source                 1..3813
                       mol_type = other DNA
                       organism = synthetic construct
SEQUENCE: 160
atgttcgtgt tcctggtgct gctgcctctg gtgccagcc agtgtgtgaa cctgatcacc 60
agaacacagt catacaccaa cagctttacc agaggcgtgt actacccga caaggtgttc 120
agatccagcg tgctgcactc tacccaggac ctgttcctgc ctttcttcag caacgtgacc 180
tggttccacg ccatccacgt gtccggcacc aatggcacca agagattcga caaccccgcc 240
ctgcccttca cgacggggt gtactttgcc agcaccgaga gtccaacat catcagaggc 300
tggatcttcg gcaccacact ggacagcaag acccagagcc tgctgatcgt gaacaacgcc 360
accaacgtgg tcatcaaagt gtgcgagttc cagttctgca acgaccccct cctggacgtc 420
taccagaaga acaacaagag ctggatggaa agcgagttcc gggtgtacag cagcgccaac 480
aactgcacct tcgagtacgt gtcccagcct ttcctgatgg acctggaagg caaggagggc 540
aacttcaaga acctgcgcga gttcgtgttt aagaacatcg acggctactt caagatctac 600
agcaagcaca cccctatcaa cctcgagcgg gatctgcctc agggcttctc tgctctggaa 660
cccctgtggg atctgcccat cggcatcaac atcacccggt ttcagacact gctggccctg 720
cacagaagct acctgacacc tgtggatagc agcagcggat ggacagctgg tgccgccgct 780
tactatgtgg gctacctgca gcctagaacc ttcctgctga gtacaacga gaacggcacc 840
atcaccgacg ccgtggattg tgctctggat cctctgagcg agacaaagtg caccctgaag 900
tccttcaccg tggaaaaggg catctaccag accagcaact tccgggtgca gcccaccgaa 960
tccatcgtgc ggttccccaa tatcaccaat ctgtgcccct tccacgaggt gttcaatgcc 1020
accaccttcg cctctgtgta cgcctggaac cggaagcgga tcagcaattg cgtggccgac 1080
tactccgtga tctacaactt cgcccccttc ttcgcattca gtgctacgg cgtgtcccct 1140
accaagctga acgacctgtg cttcacaaac gtgtacgccg acagcttcgt gatccgggga 1200
aacgaagtgt cacagattgc ccctggacag acaggcaaca tcgccgacta caactacaag 1260
ctgcccgacg acttcaccgg ctgtgtgatt gcctggaaca gcaacaagct ggactccaaa 1320
cccagcggca actacaatta cctgtaccgg ctgttccgga agtccaagct gaagcccttc 1380
gagcgggaca tctccaccga gatctatcag gccggcaaca agccttgtaa cggcgtggca 1440
ggccccaact gctacagccc actgcagtcc tacggcttta ggcccacata cggcgtgggc 1500
caccagccct acagagtggt ggtgctgagc ttcgaactgc tgcatgcccc tgccacagtg 1560
tgcgccccta agaaaagcac caatctcgtg aagaacaaat gcgtgaactt caacttcaac 1620
```

```
ggcctgaccg gcaccggcgt gctgacagag agcaacaaga agttcctgcc attccagcag   1680
tttggccggg atatcgccga taccacagac gccgttagag atccccagac actggaaatc   1740
ctggacatca cccccttgcag cttcggcgga gtgtctgtga tcacccctgg caccaacacc   1800
agcaatcagg tggcagtgct gtaccagggc gtgaactgta ccgaagtgcc cgtggccatt   1860
cacgccgatc agctgacacc tacatgccgg gtgtactcca ccggcagcaa tgtgtttcag   1920
accagagccg gctgtctgat cggagccgga tacgtgaaca atagctacga gtgcgacatc   1980
cccatcggcg ctggaatctg cgccagctac cagacacaga caaagagcca ccggagagcc   2040
agaagcgtgg ccagccagag catcattgcc tacacaatgt ctctgggcgc cgagaacagc   2100
gtggcctact ccaacaactc tatcgctatc cccaccaact tcaccatcag cgtgaccaca   2160
gagatcctgc ctgtgtccat gaccaagacc agcgtggact gcaccatgta catctgcggc   2220
gattccaccg agtgctccaa cctgctgctg cagtacggca gcttctgcac ccagctgaaa   2280
agagccctga cagggatcgc cgtggaacag gacaagaaca cccaagaggt gttcgcccaa   2340
gtgaagcaga tctacaagac ccctcctatc aagtacttcg gcggcttcaa tttcagccag   2400
attctgcccg atcctagcaa gcccagcaag cggagcttca tcgaggacct gctgttcaac   2460
aaagtgacac tggccgacgc cggcttcatc aagcagtatg gcgattgtct gggcgacatt   2520
gccgccaggg atctgatttg cgcccagaag tttaacggac tgacagtgct gcctcctctg   2580
ctgaccgatg agatgatcgc ccagtacaca tctgccctgc tggccggcac aatcacaagc   2640
ggctggacat ttggagcagg cgccgctctg cagatccct ttgctatgca gatggcctac   2700
cggttcaacg gcatcggagt gacccagaat gtgctgtacg agaaccagaa gctgatcgcc   2760
aaccagttca acagcgccat cggcaagatc caggacagcc tgagcagcac agcaagcgcc   2820
ctgggaaagc tgcaggacgt ggtcaaccac aatgcccagg cactgaacac cctggtcaag   2880
cagctgtcct ccaagttcgg cgccatcagc tctgtgctga acgatatcct gagcagactg   2940
gaccctcctg aggccgaggt gcagatcgac agactgatca caggcagact gcagagcctc   3000
cagacatacg tgacccagca gctgatcaga ccgccgaga ttagagcctc tgccaatctg   3060
gccgccacca agatgtctga gtgtgtgctg ggccagagca agagagtgga cttttgcggc   3120
aagggctacc acctgatgag cttccctcag tctgccccctc acggcgtggt gtttctgcac   3180
gtgacatatg tgcccgctca agagaagaat ttcaccaccg ctccagccat ctgccacgac   3240
ggcaaagccc actttcctag agaaggcgtg ttcgtgtcca acggcaccca ttggttcgtg   3300
acacagcgga acttctacga gccccagatc atcaccaccg acaaccctt cgtgtctggc   3360
aactgcgacg tcgtgatcgg cattgtgaac aataccgtgt cgaccctct gcagcccgag   3420
ctggacagct tcaaagagga actggacaag tactttaaga accacacaag ccccgacgtg   3480
gacctggggcg atatcagcgg aatcaatgcc agcgtcgtga acatccagaa agagatcgac   3540
cggctgaacg aggtggccaa gaatctgaac gagagcctga tcgacctgca gaactgggg   3600
aagtacgagc agtacatcaa gtggccctgg tacatctggc tgggctttat cgccggactg   3660
attgccatcg tgatggtcac aatcatgctg tgttgcatga ccagctgctg tagctgcctg   3720
aagggctgtt gtagctgtgg cagctgctgc aagttcgacg aggacgattc tgagcccgtg   3780
ctgaagggcg tgaaactgca ctacacatga tga                                3813

SEQ ID NO: 161           moltype = RNA   length = 4270
FEATURE                  Location/Qualifiers
source                   1..4270
                         mol_type = other RNA
                         organism = synthetic construct
SEQUENCE: 161
agaataaact agtattcttc tggtccccac agactcagag agaacccgcc accatgttcg     60
tgttcctggt gctgctgcct ctggtgtcca gccagtgtgt gaacctgatc accagaacac    120
agtcatacac caacagcttt accagaggcg tgtactaccc cgacaaggtg ttcagatcca    180
gcgtgctgca ctctacccag gacctgttcc tgccttttct cagcaacgtg acctggttcc    240
acgccatcca cgtgtccggc accaatggca ccaagagatt cgacaacccc gccctgccct    300
tcaacgacgg ggtgtacttt gccagcaccg agaagtccaa catcatcaga ggctggatct    360
tcggcaccac actggacagc aagacccaga gcctgctgat cgtgaacaac gccaccaacg    420
tggtcatcaa agtgtgcgag ttccagttct gcaacgaccc cttcctggac gtctaccaga    480
gaacaacaa gagctggatg gaaagcgagt tcgggtgta cagcagcgcc aacaactgca    540
ccttcgagta cgtgtcccag ccttttctga tggacctgga aggcaaggag ggcaacttca    600
agaacctgcg cgagttcgtg tttaagaaca tcgacggcta cttcaagata tacagcaagc    660
acaccccctat caacctcgag cgggatctgc ctcagggctt ctctgctctg gaaccctgg    720
tggatctgcc catcggcatc aacatcaccc ggtttcagac actgctggcc ctgcacagaa    780
gctacctgac acctgtggat agcagcagcg gatggacagc tggtgccgcc gcttactatg    840
tgggctacct gcagcctaga accttcctgc tgaagtacaa cgagaacggc accatcaccg    900
acgccgtgga ttgtgctctg gatcctctga gcgagacaaa gtgcaccctg aagtccttca    960
ccgtggaaaa gggcatctac cagaccagca acttccgggt gcagcccacc gaatccatcg   1020
tgcggttccc caatatcacc aatctgtgcc ccttccgga ggtgttcaat gccaccacct   1080
tcgcctctgt gtacgcctgg aaccggaagc ggatcagcaa ttgcgtggcc gactactccg   1140
tgatctacaa cttcgccccc ttcttcgcat tcaagtgcta cggcgtgtcc cctaccaagc   1200
tgaacgacct gtgcttcaca aacgtatacg ccgacagctt cgtgatccgg ggaaacgaag   1260
tgtcacagat tgcccctgga cagacaggca acatcgccga ctacaactac aagctgcccg   1320
acgacttcac cggctgtgtg attgcctgga acagcaacaa gctggactcc aaacccagcg   1380
gcaactacaa ttacctgtac cggctgttcc ggaagtccaa gctgaagccc ttcgagcggg   1440
acatctccac cgagatctat caggccggca acaagccttg taacggcgtg gcaggcccca   1500
actgctacag cccccactgc agtcctacggct ttaggcccac atacggcgtg ggccaccagc   1560
cctacagagt ggtggtgctg agcttcgaac tgctgcatgc cctgccaca gtgtgcggcc   1620
ctaagaaaag caccaatctc gtgaagaaca atgcgtgaa cttcaacttc aacggcctga   1680
ccggcaccgg cgtgctgaca gagagcaaca gaagttcct gccattccag cagtttggcc   1740
gggatatcgc cgataccaca gacgccgtta gagatcccca gcactgtgaa atcctggaca   1800
tcacccccttg cagcttcggc ggagtgtctg tgatcacccc tggcaccaac cagagcaatc   1860
aggtggcagt gctgtaccag ggcgtgaact gtaccgaagt gcccgtggcc attcacgccg   1920
atcagctgac acctacatgg cgggtgtact ccaccggcag caatgtgttt cagaccagag   1980
ccggctgtct gatcggagcc gagtacgtga acaatagcta cgagtgcgac atcccccatcg   2040
gcgctggaat ctgcgccagc taccagacac agacaaagag ccaccggaga gccagaagcg   2100
```

```
tggccagcca gagcatcatt gcctacacaa tgtctctggg cgccgagaac agcgtggcct   2160
actccaacaa ctctatcgct atccccacca acttcaccat cagcgtgacc acagagatcc   2220
tgcctgtgtc catgaccaag accagcgtgg actgcaccat gtacatctgc ggcgattcca   2280
ccgagtgctc caacctgctg ctgcagtacg gcagcttctg cacccagctg aaaagagccc   2340
tgacagggat cgccgtggaa caggacaaga cacccaaga ggtgttccgc caagtgaagc    2400
agatctacaa gaccccctcct atcaagtact tcggcggctt caatttcagc cagattctgc   2460
ccgatcctag caagcccagc aagcggagct tcatcgagga cctgctgttc aacaaagtga   2520
cactggccga cgccggcttc atcaagcagt atggcgattg tctgggcgac attgccgcca   2580
gggatctgat ttgcgcccag aagtttaacg gactgacagt gctgcctcct ctgctgaccg   2640
atgagatgat cgcccagtac acatctgccc tgctggccgg cacaatcaca agcggctgga   2700
catttggagc aggcgccgct ctgcagatcc cctttgctat gcagatggcc taccggttca   2760
acggcatcgg agtgacccag aatgtgctgt acgagaacca gaagctgatc gccaaccagt   2820
tcaacagcgc catcggcaag atccaggaca gcctgagcga cacacaagc gccctgggaa    2880
agctgcagga cgtggtcaac cacaatgccc aggcactgaa caccctggtc aagcagctgt   2940
cctccaagtt cggcgccatc agctctgtgc tgaacgatat cctgagcaga ctggaccctc   3000
ctgaggccga ggtgcagatc gacagactga tcacaggcag actgcagagc tccagacat    3060
acgtgaccca gcagctgatc agagccgccg agattagaga ctctgccaat ctggccgcca   3120
ccaagatgtc tgagtgtgtg ctgggccaga gcaagagagt ggacttttgc ggcaagggct   3180
accacctgat gagcttccct cagtctgccc ctcacgcgt ggtgtttctg cacgtcgacat    3240
atgtgcccgc tcaagagaag aatttcacca ccgctccagc catctgccac gacggcaaag   3300
cccacttttcc tagagaaggc gtgttcgtgt ccaacgcac ccattggttc gtgacacagc    3360
ggaacttcta cgagccccca atcatccaca ccgacaacac cttcgtgtct ggcaactgcg   3420
acgtcgtgat cggcattgtg aacaataccg tgtacgaccc tctgcagccc gagctggaca   3480
gcttcaaaga ggaactggac aagtacttta gaaccacac aagccccgac gtggacctgg    3540
gcgatatcag cggaatcaat gccagcgtcg tgaacatcca gaaagagatc gaccggctga   3600
acgaggtggc caagaatctg aacgagagcc tgatcgacct gcaagaactg gggaagtacg   3660
agcagtacat caagtggccc tggtacatct ggctgggctt tatcgccgga ctgattgcca   3720
tcgtgatggt cacaatcatg ctgtgttgca tgaccagctg ctgtagctgc ctgaagggct   3780
gttgtagctg tggcagctgc tgcaagttcg acgaggacga ttctgagccc gtgctgaagg   3840
gcgtgaaact gcactacaca tgatgactcg agctagtact gcatgacc aatgctagct     3900
gcccctttcc cgtcctgggt acccgagtc tccccgacc tgggtccca ggtatgctcc      3960
cacctccacc tgccccactc accacctg ctagttccag acacctccca agcacgcagc     4020
aatgcagctc aaaacgctta gcctagcac acccccacgg gaaacagcag tgattaacct    4080
ttagcaataa acgaaagttt aactaagcta tactaaccca aggttggtc aatttcgtgc    4140
cagccacacc ctggagctag caaaaaaaaa aaaaaaaaa aaaaaaaaaa agcatatgac    4200
taaaaaaaaa aaaaaaaaaa aaaaaaaaaa aaaaaaaaaa aaaaaaaaaa aaaaaaaaaa   4260
aaaaaaaaaa                                                         4270

SEQ ID NO: 162          moltype = DNA  length = 4270
FEATURE                 Location/Qualifiers
source                  1..4270
                        mol_type = other DNA
                        organism = synthetic construct
SEQUENCE: 162
agaataaact agtattcttc tggtccccac agactcagag agaacccgcc accatgttcg      60
tgttcctggt gctgctgcct ctggtgtcca gccagtgtgt gaacctgatc accagaacac     120
agtcatacac caacagcttt accagaggcg tgtactaccc cagcaaggtg ttcagatcca     180
gcgtgctgca ctctacccag gacctgttcc tgcctttctt cagcaacgtg acctggttca     240
acgccatcca cgtgtccggc accaatggca ccaagagatt cgacaacccc gccctgccct     300
tcaacgacgg ggtgtacttt gccagcaccg agaagtccaa catcatcaga ggctggatct     360
tcggccacca ctggacagga aagcccaga gcctgctgat cgtgaacaac accaccaacg       420
tggtcatcaa agtgtgcgag ttccagttct gcaacgaccc cttcctggac gtctaccaga     480
agaacaacaa gagctggatg gaaagcgagt tccgggtgta cagcagcgcc aacaactgca     540
ccttcgagta cgtgtcccag ccttttcctga tggacctgga aggcaaggag ggcaacttca   600
agaacctgcg cgagttcgtg tttaagaaca tcgacggcta cttcaagata tacagcaagc     660
acaccctat caacctcgag cgggatctgc ctcagggctt ctctgctctg gaaccctgg       720
tggatctgcc catcggcatc aacatcaccc ggtttcagac actgctggcc ctgcacagaa     780
gctacctgac acctgtggat agcagcagcg gatggacagc tggtgccgcc gcttactatg     840
tgggctacct gcagcctaga accttcctgc tgaagtacaa cgagaaccgc accatcaccg     900
acgccgtgga ttgtgctctg gatcctctga gcgagacaaa gtgcaccctg aagtccttca     960
ccgtggaaaa gggcatctac cagaccagca cttccgggt gcagcccacc gaatccatcg     1020
tgcggttccc caatatcacc aatctgtgcc ccttccacga ggtgttcaat gccaccacct    1080
tcgcctctgt gtacgcctgg aaccggaagc ggatcagcaa ttgcgtggcc gactactccg   1140
tgatctacaa cttcgccccc ttcttcgcat tcaaggtcta cctaccaagc cctaccaagc   1200
tgaacgacct gtgcttcaca aacgtgtacg ccgacagctt cgtgatccgg ggaaacgaag   1260
tgtcacagat tgcccctgga cagacaggca acatcgccga ctacaactac aagctgcccg   1320
acgacttcac cggctgtgtg attgcctgga acagcaacaa gctggactcc aaacccagcg   1380
gcaactacaa ttacctgtac cggctgttcc ggaagtccaa gctgaagccc ttcgagcggg   1440
acatctccac cgagatctat caggccggca acaagccttg taacggcgtg gcagcccca    1500
actgctacag cccactgcag tcctacggct taggcccac atacggcgtg ggccaccagc    1560
cctacagagt ggtggtgctg agcttcgaac tgctgcatgc cctgccaca gtgtgcggcc    1620
ctaagaaaag caccaatctc gtgaagaaca atgcgtgaa cttcaacttc aacggcctga     1680
ccggcaccgg cgtgctgaca gagagcaaca agaagttcct gccattccag cagtttggcc   1740
gggatatcgc cgataccaca gacgccgtta gagatcccca agtgcagatc cctgatcaca   1800
tcacccctt cagcttcggc ggagtgtctg tgatcacccc tggcaccaac cagagcaatc    1860
aggtggcagt gctgtaccag ggcgtgaact gtaccgaagt gcccgtggcc attcacgccg   1920
atcagctgac cctacatgg cgggtgtact ccaccggcag caatgtgttt cagaccgag     1980
ccggctgtct gatcggagcc gagtacgtga acaatagcta cgagtgcgac atcccccatcg   2040
gcgctggaat ctgcgccagc taccagacac agacaaagag ccaccggaga gccagaagcg   2100
```

```
tggccagcca gagcatcatt gcctacacaa tgtctctggg cgccgagaac agcgtggcct    2160
actccaacaa ctctatcgct atccccacca acttcaccat cagcgtgacc acagagatcc    2220
tgcctgtgtc catgaccaag accagcgtgg actgcaccat gtacatctgc ggcgattcca    2280
ccgagtgctc caacctgctg ctgcagtacg gcagcttctg cacccagctg aaaagagccc    2340
tgacagggat cgccgtggaa caggacaaga cacccaagg ggtgttcgcc caagtgaagc    2400
agatctacaa gaccccrcct atcaagtact cggcggctt caatttcagc cagattctgc    2460
ccgatcctag caagcccagc aagcggagct catcgagga cctgctgttc aacaaagtga    2520
cactggccga cgccggcttc atcaagcagt atggcgattg tctgggcgac attgccgcca    2580
gggatctgat ttgcgcccag aagtttaacg gactgacagt gctgcctcct ctgctgaccg    2640
atgagatgat cgcccagtac acatctgccc tgctggccgg cacaatcaca agcggctgga    2700
catttggagc aggcgccgct ctgcagatcc cctttgctat gcagatggcc taccggttca    2760
acggcatcgg agtgacccag aatgtgctgt acgagaacca gaagctgatc gccaaccagt    2820
tcaacagcgc catcggcaag atccaggaca gcctgagcag cacacaagc gccctgggaa    2880
agctgcagga cgtggtcaac cacaatgccc aggcactgaa caccctggtc aagcagctgt    2940
cctccaagtt cggcgccatc agctctgtgc tgaacgatat cctgagcaga ctggaccctc    3000
ctgaggccga ggtgcagatc gacagactga tcacaggcag actgcagagc tccagacat    3060
acgtgaccca gcagctgatc agagccgccg agattagagc ctctgccaat ctggccgcca    3120
ccaagatgtc tgagtgtgtg ctgggccaga gcaaagagt ggacttttgc ggcaagggcta    3180
accacctgat gagcttccct cagtctgccc tcacgcgct ggtgtttctg cacgtgacat    3240
atgtgcccgc tcaagagaag aatttcacca ccgtccagc catctgccac gacggcaaag    3300
cccacttttcc tagagaaggc gtgttcgtgt ccaacggcac ccattggttc gtgacacagc    3360
ggaacttcta cgagcccag atcatcacca ccgacaacact cttcgtgtct ggcaactgcg    3420
acgtcgtgat cggcattgtg aacaataccc tgtacgaccc tctgcagccc gagctggaca    3480
gcttcaaaga ggaactggac aagtactta agaaccacac aagccccgac gtggacctgg    3540
gcgatatcag cggaatcaat gccagcgtcg tgaacatcca gaaagagatc gaccggctga    3600
acgaggtggc caagaatctg aacgagagc tgatcgacct gcaagaactg gggaagtacg    3660
agcagtacat caagtggccc tggtacatct ggctgggctt tatcgccgga ctgattgcca    3720
tcgtgatggt cacaatcatg ctgtgttgca tgaccagctg ctgtagctgc ctgaagggct    3780
gttgtagctg tggcagctgc tgcaagttcg acgaggacga ttctgagccc gtgctgaagg    3840
gcgtgaaact gcactacaca tgatgactcg agctagtact cgagtcacgc aatgctagtc    3900
gccccttttcc cgtcctgggg accccgagtc tccccgacc tcgggtccca ggtatgctcc    3960
cacctccacc tgccccactc accacctctg ctagttccag acacctccca agcacgcagc    4020
aatgcagctc aaaacgctta gcctagccac accccacgg gaaacagcag tgattaacct    4080
ttagcaataa acgaaagttt aactaagcta tactaaccc aggggttggtc aatttcgtgc    4140
cagccacacc ctggagctag caaaaaaaaa aaaaaaaaaa aaaaaaaaaa agcatatgac    4200
taaaaaaaaa aaaaaaaaaa aaaaaaaaaa aaaaaaaaaa aaaaaaaaaa aaaaaaaaaa    4260
aaaaaaaaaa                                                          4270

SEQ ID NO: 163       moltype = AA   length = 1269
FEATURE              Location/Qualifiers
source               1..1269
                     mol_type = protein
                     organism = synthetic construct
SEQUENCE: 163
MFVFLVLLPL VSSQCVNLIT RTQSYTNSFT RGVYYPDKVF RSSVLHSTQD LFLPFFSNVT     60
WFHAIHVSGT NGTKRFDNPA LPFNDGVYFA STEKSNIIRG WIFGTTLDSK TQSLLIVNNA    120
TNVVIKVCEF QFCNDPFLDV YQKNNKSWME SEFRVYSSAN NCTFEYVSQP FLMDLVGKEG    180
NFKNLREFVF KNIDGYFKIY SKHTPINLER DLPQGFSALE PLVDLPIGIN ITRFQTLLAL    240
HRSYLTPVDS SSGWTAGAAA YYVGYLQPRT FLLKYNENGT ITDAVDCALD PLSETKCTLK    300
SFTVEKGIYQ TSNFRVQPTE SIVRFPNITN LCPFHEVFNA TTFASVYAWN RKRISNCVAD    360
YSVIYNFAPF FAFKCYGVSP TKLNDLCFTN VYADSFVIRG NEVSQIAPGQ TGNIADYNYK    420
LPDDFTGCVI AWNSNKLDSK PSGNYNYLYR LFRKSKLKPF ERDISTEIYQ AGNRPCNGVA    480
GPNCYSPLQS YGFRPTYGVG HQPYRVVVLS FELLHAPATV CGPKKSTNLV KNKCVNFNFN    540
GLTGTGVLTE SNKKFLPFQQ FGRDIADTTD AVRDPQTLEI LDITPCSFGG VSVITPGTNT    600
SNQVAVLYQG VNCTEVPVAI HADQLTPTWR VYSTGSNVFQ TRAGCLIGAE YVNNSYECDI    660
PIGAGICASY QTQTKSHRRA RSVASQSIIA YTMSLGAENS VAYSNNSIAI PTNFTISVTT    720
EILPVSMTKT SVDCTMYICG DSTECSNLLL QYGSFCTQLK RALTGIAVEQ DKNTQEVFAQ    780
VKQIYKTPPI KYFGGFNFSQ ILPDPSKPSK RSFIEDLLFN KVTLADAGFI KQYGDCLGDI    840
AARDLICAQK FNGLTVLPPL LTDEMIAQYT SALLAGTITS GWTFGAGAAL QIPFAMQMAY    900
RFNGIGVTQN VLYENQKLIA NQFNSAIGKI QDSLSSTASA LGKLQDVVNH NAQALNTLVK    960
QLSSKFGAIS SVLNDILSRL DPPEAEVQID RLITGRLQSL QTYVTQQLIR AAEIRASANL   1020
AATKMSECVL GQSKRVDFCG KGYHLMSFPQ SAPHGVVFLH VTYVPAQEKN FTTAPAICHD   1080
GKAHFPREGV FVSNGTHWFV TQRNFYEPQI ITTDNTFVSG NCDVVIGIVN NTVYDPLQPE   1140
LDSFKEELDK YFKNHTSPDV DLGDISGINA SVVNIQKEID RLNEVAKNLN ESLIDLQELG   1200
KYEQYIKWPW YIWLGFIAGL IAIVMVTIML CCMTSCCSCL KGCCSCGSCC KFDEDDSEPV   1260
LKGVKLHYT                                                          1269

SEQ ID NO: 164       moltype = RNA   length = 3813
FEATURE              Location/Qualifiers
source               1..3813
                     mol_type = other RNA
                     organism = synthetic construct
SEQUENCE: 164
atgttcgtgt tcctggtgct gctgcctctg gtgtccagcc agtgtgtgaa cctgatcacc     60
agaacacagt catacaccaa cagctttacc agaggcgtgt actacccga caaggtgttc    120
agatccagcg tgctgcactc tacccaggac ctgttcctgc cttttcttcag caacgtgacc    180
tggttccacg ccatccacgt gtccggcacc aatggcacca gagattcga caaccccgcc    240
ctgcccttca acgacggggt gtactttgcc agcaccgaga gtccaacat catcagaggc    300
tggatcttcg gcaccacact ggacagcaag acccagagct gctgatcgt gaacaacgcc    360
```

```
accaacgtgg tcatcaaagt gtgcgagttc cagttctgca acgacccctt cctggacgtc   420
taccagaaga acaacaagag ctggatggaa agcgagttcc gggtgtacag cagcgccaac   480
aactgcacct tcgagtacgt gtcccagcct ttcctgatgg acctggtggg caaggagggc   540
aacttcaaga acctgcgcga gttcgtgttt aagaacatcg acggctactt caagatctac   600
agcaagcaca cccctatcaa cctcgagcgg gatctgcctc agggcttctc tgctctggaa   660
cccctggtgg atctgcccat cggcatcaac atcacccggt ttcagacact gctggccctg   720
cacagaagct acctgacacc tgtggatagc agcagcggat ggacagctgg tgccgccgct   780
tactatgtgg gctacctgca gcctagaacc ttcctgctga agtacaacga gaacggcacc   840
atcaccgacg ccgtggattg tgctctggat cctctgagcg agacaaagtg caccctgaag   900
tccttcaccg tggaaaaggg catctaccag accagcaact tccgggtgca gcccaccgaa   960
tccatcgtgc ggttccccaa tatcaccaat ctgtgcccct ccacgaggt gttcaatgcc  1020
accaccttcg cctctgtgta cgcctggaac cggaagcgga tcagcaattg cgtggccgac  1080
tactccgtga tctacaactt cgccccttc ttcgcattca agtgctacgg cgtgtcccct  1140
accaagctga acgacctgtg cttcaacaac gtgtacgccg acagcttcgt gatccgggga  1200
aacgaagtgt cacagattgc ccctggacag acaggcaaca tcgccgacta caactacaag  1260
ctgcccgacg acttcaccgg ctgtgtgatt gcctggaaca gcaacaagct ggactccaaa  1320
cccagcggca actacaatta cctgtaccgg ctgttccgga agtccaagct gaagcccttc  1380
gagcgggaca tctccaccga gatctatcag gccggcaaca agccttgtaa cggcgtgggca  1440
ggccccaact gctacagccc actgcagtcc tacggcttta ggcccacata cggcgtgggc  1500
caccagccct acagagtggt ggtgctgagc ttcgaactgc tgcatgcccc tgccacagtg  1560
tgcggcccta agaaaagcac caatctcgtg aagaacaaat gcgtgaactt caacttcaac  1620
ggcctgaccg gcaccggcgt gctgacagag agcaacaaga agttcctgcc attccagcag  1680
tttggccggg atatcgccga taccacagac gccgttagag atccccagac actggaaatc  1740
ctggacatca ccccttgcag cttcggcgga gtgtctgtga tcaccctgg caccaacacc  1800
agcaatcagg tggcagtgct gtaccagggc gtgaactgta ccgaagtgcc cgtggccatt  1860
cacgccgatc agctgacacc tacatgcggg gtgtactcca ccggcagcaa tgtgtttcag  1920
accagagccg gctgtctgat cggagccgag tacgtgaaca atagctacga gtgcgacatc  1980
cccatcggcg ctggaatctg cgccagctac cagacacaga caaagagcca ccggagagcc  2040
agaagcgtgg ccagccagag catcattgcc tacacaatgt ctctgggcgc cgagaacagc  2100
gtggcctact ccaacaactc tatcgctatc cccaccaact tcaccatcag cgtgaccaca  2160
gagatcctgc ctgtgtccat gaccaagacc agcgtggact gcaccatgta catctgcggc  2220
gattccaccg agtgctccaa cctgctgctg cagtacggca gcttctgcac ccagctgaaa  2280
agagccctga cagggatcgc cgtggaacag gacaagaaca cccaagaggt gttcgcccaa  2340
gtgaagcaga tctacaagac ccctcctatc aagtacttcg gcggcttcaa tttcagccag  2400
attctgcccg atcctagcaa gcccagcaag cggagcttca tcgaggacct gctgttcaac  2460
aaagtgacac tggccgacgc cggcttcatc aagcagtatg gcgattgtct gggcgacatt  2520
gccgccaggg atctgatttg cgcccagaag tttaacggac tgacagtgct gcctcctctg  2580
ctgaccgatg agatgatcgc ccagtacaca tctgccctgc tggccggcac aatcacaagc  2640
ggctgacat ttggagcagg cgccgctctg cagatccctt ttgctatgca gatggcctac  2700
cggttcaacg gcatcggagt gacccagaat gtgctgtacg agaaccagaa gctgatcgcc  2760
aaccagttca acagcgccat cggcaagatc caggacagcc tgagcagcac agcaagcgcc  2820
ctgggaaagc tgcaggacgt ggtcaaccac aatgcccagg cactgaacac cctggtcaag  2880
cagctgtcct ccaagttcgg cgccatcagc tctgtgctga acgatatcct gagcagactg  2940
gaccctcctg aggccgaggt gcagatcgac agactgatca caggcagact gcagagcctc  3000
cagacatacg tgacccagca gctgatcaga gccgccgaga ttagagcctc tgccaatctg  3060
gccgccacca agatgtctga gtgtgtgctg ggccagagca agagagtgga cttttgcggc  3120
aagggctacc acctgatgag cttccctcag tctgccccctc acggcgtggt gtttctgcac  3180
gtgacatatg tgcccgctca agagaagaat ttcaccaccg ctccagccat ctgccacgac  3240
ggcaaagccc acttcctag agaaggcgtt ttcgtgtcca acggcaccca ttggttcgtg  3300
acacagcgga acttctacga gccccagatc atcaccaccg acaacacctt cgtgtctggc  3360
aactgcgacg tcgtgatcgg cattgtgaac aataccgtgt acgaccctct gcagcccgag  3420
ctggacagct tcaaagagga actggacaag tactttaaga accacacaag ccccgacgtg  3480
gacctgggcg atatcagcgg aatcaatgcc agcgtcgtga acatccagaa agagatcgac  3540
cggctgaacg aagtggccaa gaatctgaac gagagcctga tcgacctgca agaactgggg  3600
aagtacgagc agtacatcaa gtggccctgg tacatctggc tgggcttttat cgccggactg  3660
attgccatcg tgatggtcac aatcatgctg tgttgcatga ccagctgctg tagctgcctg  3720
aagggctgtt gtagctgtgg cagctgctgc aagttcgacg aggacgattc tgagcccgtg  3780
ctgaagggcg tgaaactgca ctacacatga tga                               3813
```

SEQ ID NO: 165        moltype = DNA   length = 3813
FEATURE                 Location/Qualifiers
source                  1..3813
                         mol_type = other DNA
                         organism = synthetic construct
SEQUENCE: 165

```
atgttcgtgt tcctggtgct gctgcctctg gtgtccagcc agtgtgtgaa cctgatcacc    60
agaacacagt catacaccaa cagctttacc agaggcgtgt actaccccga caaggtgttc   120
agatccagcg tgctgcactc tacccaggac ctgttcctgc ctttcttcag caacgtgacc   180
tggttccacg ccatccacgt gtccggcacc aatggcacca agagattcga caacccccgc   240
ctgcccttca acgacggggt gtactttgcc agcaccgaga gtccaacat catcagaggc   300
tggatcttcg gcaccacact ggacagcaag cccagagcc tgctgatcgt gaacaacgcc   360
accaacgtgg tcatcaaagt gtgcgagttc cagttctgca acgacccctt cctggacgtc   420
taccagaaga acaacaagag ctggatggaa agcgagttcc gggtgtacag cagcgccaac   480
aactgcacct tcgagtacgt gtcccagcct ttcctgatgg acctggtggg caaggagggc   540
aacttcaaga acctgcgcga gttcgtgttt aagaacatcg acggctactt caagatctac   600
agcaagcaca cccctatcaa cctcgagcgg gatctgcctc agggcttctc tgctctggaa   660
cccctggtgg atctgcccat cggcatcaac atcacccggt ttcagacact gctggccctg   720
cacagaagct acctgacacc tgtggatagc agcagcggat ggacagctgg tgccgccgct   780
tactatgtgg gctacctgca gcctagaacc ttcctgctga agtacaacga gaacggcacc   840
```

```
atcaccgacg ccgtggattg tgctctggat cctctgagcg agacaaagtg caccctgaag    900
tccttcaccg tggaaaaggg catctaccag accagcaact tccgggtgca gcccaccgaa    960
tccatcgtgc ggttccccaa tatcaccaat ctgtgccct  tccacgaggt gttcaatgcc   1020
accaccttcg cctctgtgta cgcctggaac cggaagcgga tcagcaattg cgtggccgac   1080
tactccgtga tctacaactt cgccccttc  ttcgcattca agtgctacgg cgtgtccct    1140
accaagctga acgacctgtg cttcacaaac gtgtacgccg acagcttcgt gatccgggga   1200
aacgaagtgt cacagattgc ccctggacag acaggcaaca tcgccgacta caactacaag   1260
ctgcccgacg acttcaccgg ctgtgtgatt gcctggaaca gcaacaagct ggactccaaa   1320
cccagcggca actacaatta cctgtaccgg ctgttccgga agtccaagct gaagcccttc   1380
gagcgggaca tctccaccga gatctatcag gccggcaaca ggccttgtaa cggcgtggca   1440
ggccccaact gctacagccc actgcagtcc tacggcttta ggcccacata cggcgtgggc   1500
caccagccct acagagtggt ggtgctgagc ttcgaactgc tgcatgcccc tgccacagtg   1560
tgcggcccta agaaaagcac caatctcgtg aagaacaaat gcgtgaactt caacttcaac   1620
ggcctgaccg gcaccggcgt gctgacagag agcaacaaga agttcctgcc attccagcag   1680
tttggccggg atatcgccga taccacagac gccgttagag atccccagac actggaaatc   1740
ctggacatca ccccttgcag cttcggcgga gtgtctgtga tcacccctgg caccaacacc   1800
agcaatcagg tggcagtgct gtaccagggc gtgaactgta ccgaagtgcc cgtggccatt   1860
cacgccgatc agctgacacc tacatgcggg gtgtactcca ccggcagcaa tgtgtttcag   1920
accagagccg gctgtctgat cggagccgag tacgtgaaca atagctacga gtgcgacatc   1980
cccatcggcg ctggaatctg cgccagctac cagacacaga caaagagcca ccggagagcc   2040
agaagcgtgg ccagccagag catcattgcc tacacaatgt ctctgggcgc cgagaacagc   2100
gtggcctact ccaacaactc tatcgctatc cccaccaact tcaccatcag cgtgaccaca   2160
gagatcctgc ctgtgtccat gaccaagacc agcgtggact gcaccatgta catctgcggc   2220
gattccaccg agtgctccaa cctgctgctg cagtacggca gcttctgcac ccagctgaaa   2280
agagccctga cagggatcgc cgtggaacag acaagaacac ccaagaggt  gttcgcccaa   2340
gtgaagcaga tctacaagac ccctcctatc aagtacttcg gcggcttcaa tttcagccag   2400
attctgcccg atcctagcaa gcccagcaag cggagcttca tcgaggacct gctgttcaac   2460
aaaagtgacac tggccgacgc cggcttcatc aagcagtatg gcgattgtct gggcgacatt   2520
gccgccaggg atctgatttg cgcccagaag tttaacggac tgacagtgct gcctcctctg   2580
ctgaccgatg agatgatcgc ccagtacaca tctgccctgc tggccggcac aatcacaagc   2640
ggctggacat ttggagcagg cgccgctctg cagatcccct tgctatgca  gatggcctac   2700
cggttcaacg gcatcggagt gacccagaat gtgctgtacg agaaccagaa gctgatcgcc   2760
aaccagttca acagcgccat cggcaagatc caggacagcc tgagcagcac agcaagcgcc   2820
ctgggaaagc tgcaggacgt ggtcaaccac aatgcccagg cactgaacac cctggtcaag   2880
cagctgtcct ccaagttcgg cgccatcagc tctgtgctga acgatatcct gagcagactg   2940
gaccctcctg aggccgaggt gcagatcgac agactgatca caggcagact gcagagcctc   3000
cagacatacg tgacccagca gctgatcaga ccgccgaga  ttagagcctc tgccaatctg   3060
gccgccacca agatgtctga gtgtgtgctg ggccagagca agagagtgga cttttgcggc   3120
aagggctacc acctgatgag cttccctcag tctgccccctc acggcgtggt gtttctgcac   3180
gtgacatatg tgcccgctca agagaagaat ttcaccaccg ctccagccat ctgccacgac   3240
ggcaaagccc acttcctag  agaaggcgtg ttcgtgtcca acggcaccca ttggttcgtg   3300
acacagcgga acttctacga gccccagatc atcaccaccg acaacacctt cgtgtctggc   3360
aactgctacg tcgtgatcgg cattgtgaac aataccgtgc acgaccctct gcagccccag   3420
ctggacagct tcaaagagga actggacaag tactttaaga accacacaag ccccgacgtg   3480
gacctggggc gatatcagcgg aatcaatgcc agcgtcgtga acatccagaa agagatcgac   3540
cggctgaacg aggtggccaa gaatctgaac gagagcctga tcgacctgca agaactgggg   3600
aagtacgagc agtacatcaa gtggccctgg tacatctggc tgggcttttat cgccggactg   3660
attgccatcg tgatggtcac aatcatgctg tgttgcatga ccagctgctg tagctgcctg   3720
aagggctgtt gtagctgtgg cagctgctgc aagttcgacg aggacgattc tgagcccgtg   3780
ctgaagggcg tgaaactgca ctacacatga tga                                3813
```

| | | |
|---|---|---|
| SEQ ID NO: 166 | moltype = RNA   length = 4270 | |
| FEATURE | Location/Qualifiers | |
| source | 1..4270 | |
| | mol_type = other RNA | |
| | organism = synthetic construct | |

SEQUENCE: 166
```
agaataaact agtattcttc tggtccccac agactcagag agaacccgcc accatgttcg     60
tgttcctggt gctgctgcct ctggtgtcca gccagtgtgt gaacctgatc accagaaacc    120
agtcatacac caacagcttt accagaggcg tgtactaccc cgacaaggtg ttcagatcca    180
gcgtgctgca ctctacccag gacctgttcc tgcctttctt cagcaacgtg acctggttcc    240
acgccatcca cgtgtccggc accaatggca ccaagagatt cgacaacccc gccctgccct    300
tcaacgacgg ggtgtacttt gccagcaccg agaagtccaa catcatcaga ggctggatct    360
tcggcaccac actggacagc aagacccaga gcctgctgat cgtgaacaac gccaccaacg    420
tggtcatcaa agtgtgcgag ttccagttct gcaacgaccc cttcctggac gtctaccaga    480
agaacaacaa gagctggatg gaaagcgagt tccgggtgta cagcagcgcc aacaactgca    540
ccttcgagta cgtgtcccag ccttccctga tggacctggt gggcaaggag ggcaacttca    600
agaacctgcg cgagttcgtg tttaagaaca tcgacggcta cttcaagatc tacagcaagc    660
acacccctat caacctcgag cgggatctgc ctcagggctt ctctgctctg gaaccctgga    720
tggatctgcc catcggcatc aacatcaccc ggtttcagac actgctggcc ctgcacagaa    780
gctacctgac acctgtggat agcagcagcg gatggacagc tggtgccgcc gcttactatg    840
tgggctacct gcagcctaga accttcctgc tgaagtacaa cgaaacggcc accatccaccg    900
acgccgtgga ttgtgctctg gatcctctga gcgagacaaa gtgcacccta agtccttca     960
ccgtggaaaa gggcatctac cagaccagca acttccgggt gcagcccac  gaatccatcg   1020
tgcggttccc caatatcacc aatctgtgcc ccttccacga ggtgttcaat gccacccct    1080
tcgcctctgt gtacgcctgg aaccggaagc ggatcagcaa ttgcgtggcc gactactccg   1140
tgatctacaa cttcgccccc cttcttcgcat tcaagtgcta cggcgtgtcc cctaccaagc   1200
tgaacgacct gtgcttcaca aacgtgtacg ccgacagctt cgtgatccgg ggaaacgaag   1260
tgtcacagat tgcccctgga cagacaggca acatcgccga ctacaactac aagctgcccg   1320
```

```
acgacttcac cggctgtgtg attgcctgga acagcaacaa gctggactcc aaacccagcg  1380
gcaactacaa ttacctgtac cggctgttcc ggaagtccaa gctgaagccc ttcgagcggg  1440
acatctccac cgagatctat caggccggca acaggccttg taacggcgtg gcaggcccca  1500
actgctacag cccactgcag tcctacggct ttaggcccac atacggcgtg ggccaccagc  1560
cctacagagt ggtggtgctg agcttcgaac tgctgcataa ccctgccaca gtgtgcggcc  1620
ctaagaaaag caccaatctc gtgaagaaca aatgcgtgaa cttcaacttc aacggcctga  1680
ccggcaccgg cgtgctgaca gagagcaaca agaagttcct gccattccag cagtttggcc  1740
gggatatcgc cgataccaca gacgccgtta gagatcccca gacactggaa atcctggaca  1800
tcaccccttg cagcttcggc ggagtgtctg tgatcacccc tggcaccaac accagcaatc  1860
aggtggcagt gctgtaccag ggcgtgaact gtaccgaagt gccccgtggc attcacgccg  1920
atcagctgac acctacatgg cgggtgtact ccaccggcag caatgtgttt cagaccagag  1980
ccggctgtct gatcggagcc gagtacgtga acaatagcta cgagtgcgac atccccatcg  2040
gcgctggaat ctgcgccagc taccagacac agacaaagag ccaccggaga gccagaagcg  2100
tggcagcca gagcatcatt gcctacacaa tgtctctgag gacgagaac agctggcct  2160
actccaacaa ctctatcgct atccccacca acttcaccat cagcgtgacc acagagatcc  2220
tgcctgtgtc catgaccaag accagcgtgg actgcaccat gtacatctgc ggcgattcca  2280
ccgagtgctc caacctgctg ctgcagtacg gcagcttctg cacccagctg aaaagagccc  2340
tgacagggat cgccgtggaa caggacaaga acacccaagg ggtgttcgcc caagtgaagc  2400
agatctacaa gaccccctcc atcaagtact tcggcggctt caatttcagc cagattctgc  2460
ccgatcctag caagcccagc aagcggagct tcatcgagga cctgctgttc aacaaagtga  2520
cactggccga cgccggcttc atcaagcagt atggcgattg tctgggcgac attgccgcca  2580
gggatctgat ttgcgcccag aagtttaacg gactgacagt gctgcctcct ctgctgaccg  2640
atgagatgat cgcccagtac acatctgccc tgctggccgg cacaatcaca agcggctgga  2700
catttggagc aggcgccgct ctgcagatcc cctttgctat gcagatggcc taccggttca  2760
acggcatcgg agtgacccag aatgtgctgt acgagaacca gaagctgatc gccaaccagt  2820
tcaacagcgc catcggcaag atccaggaca gcctgagcag cacagcaagc gccctgggaa  2880
agctgcagga cgtggtcaac cacaatgccc aggcactgaa cacccctggtc aagcagctgt  2940
cctccaagtt cggcgccatc agctctgtgc tgaacgatat cctgagcaga ctggaccctc  3000
ctgaggccga ggtgcagatc gacagactga tcacaggcag actgcagagc tccagacat  3060
acgtgaccca gcagctgatc agagccgcca agattagagc ctctgccaat ctggccgcca  3120
ccaagatgtc tgagtgtgtg ctgggccaga gcaagagagt ggacttttgc ggcaagggct  3180
accacctgat gagcttccct cagtctgccc tcacgcgcgt ggtgtttctg cacgtggacat  3240
atgtgcccgc tcaagagaag aatttcacca ccgctccagc catctgccac gacggcaaag  3300
cccactttcc tagagaaggc gtgttcgtgt ccaacggcac ccattggttc gtgacagcgg  3360
ggaacttcta cgagcccag atcatcacca ccgacaacac cttcgtgtct ggcaactgc  3420
acgtcgtgat cggcattgtg aacaataccg tgtacgaccc tctgcagccc gagctggaca  3480
gcttcaaaga ggaactggac aagtacttta gaaccacac aagccccgac gtggacctgg  3540
gcgatatcag cggaatcaat gccagcgtcg tgaacatcca gaaagagatc gaccggctga  3600
acgaggtggc caagaatctg aacgagagcc tgatcgacct gcaagaactg gggaagtaga  3660
agcagtacat caagtggccc tggtacatct ggctgggctt tatcgccgga ctgattgcca  3720
tcgtgatggt cacaatcatg ctgtgttgca tgaccagctg ctgtagctgc tgaagggct  3780
gttgtagctg tggcagctgc tgcaagttcg acgaggacga ttctgagccc gtgctgaagg  3840
gcgtgaaact gcactacaca tgatgactgg agctggtcag agctgcatgc aatgctagct  3900
gccccttttcc cgtcctgggt accccgagtc tcccccgacc tgggtccca ggtatgctcc  3960
cacctccacc tgcccactcc accacctctg ctagttccag acacctccca agcacgcagc  4020
aatgcagctc aaaacgctta gcctagccac accccacgg gaaacagcag tgattaacct  4080
ttagcaataa acgaaagttt aactaagcta tactaacccc agggttggtc aatttcgtgc  4140
cagccacacc ctggagctag caaaaaaaaa aaaaaaaaaa aaaaaaaaaa agcatatgac  4200
taaaaaaaaa aaaaaaaaaa aaaaaaaaa aaaaaaaaaa aaaaaaaaaa aaaaaaaaaa  4260
aaaaaaaaaa                                                         4270

SEQ ID NO: 167        moltype = DNA  length = 4270
FEATURE               Location/Qualifiers
source                1..4270
                      mol_type = other DNA
                      organism = synthetic construct
SEQUENCE: 167
agaataaact agtattcttc tggtccccac agactcagag agaacccgcc accatgttcg    60
tgttcctggt gctgctgcct ctggtgtcca gccagtgtgt gaacctgatc accagaaacac  120
agtcatacac caacagcttt accagaggcg tgtactaccc cgacaaggtg ttcagatcca  180
gcgtgctgca ctctacccag gacctgttcc tgccttcctt cagcaacgtg acctggttcc  240
acgccatcca cgtgtccggc accaatggca ccaagagatt cgacaacccc gccctgccct  300
tcaacgacgg ggtgtacttt gccagcaccg agaagtccaa catcatcaga ggctggatct  360
tcggcaccac actggacagc aagacccaga gcctgctga cgtgaacacg accaccagg  420
tggtcatcaa agtgtgcgag ttccagttct gcaacgaccc cttcctggac gtctaccaga  480
gaacaacaa gagctggatg gaaagcgagt tcgggtgta cagcagcgcc aacaactgca  540
ccttcgagta cgtgtcccag cctttcctga tggacctggt gggcaaggag ggcaacttca  600
agaacctgcg cgagttcgtg tttaagaaca tcgacggcta cttcaagatc tacagcaagc  660
acaccccaat caacctcgag cgggatctgc ctcagggctt ctctgctctg gaacccctga  720
tggatctgcc catcggcatc aacatcaccc ggtttcagac actgctggcc ctgcacagaa  780
gctacctgac acctggggat agcagcagcg gatggacagc tggtgccgcc gcttactatg  840
tgggctacct gcagcctaga accttcctgc tgaagtacaa cgaaacggc accatcaccg  900
acgccgtgga ttgtgctctg gatcctctga gcgagacaaa gtgcacactg aagtccttca  960
ccgtgaaaa gggcatctac cagaccagca acttccgggt gcagcccacc gaatccatcg  1020
tgcgttccc caatatcacc aatctgtgcc ccttcacgga ggtgttcaat gccaccccct  1080
tcgcctctgt gtacgcctgg aaccggaagc ggatcagcaa ttgcgtggcc gactactccg  1140
tgatctacaa cttcgccccc ttcttcgcat tcaagtgcta cggcgtgtcc cctaccaagc  1200
tgaacgacct gtgcttcaca aacgtgtacg ccgacagctt cgtgatccgg ggaaacgaag  1260
tgtcacagat tgcccctgga cagacaggca acatcgccga ctacaactac aagctgcccg  1320
```

```
acgacttcac cggctgtgtg attgcctgga acagcaacaa gctggactcc aaacccagcg    1380
gcaactacaa ttacctgtac cggctgttcc ggaagtccaa gctgaagccc ttcgagcggg    1440
acatctccac cgagatctat caggccggca acaggccttg taacggcgtg caggccccca    1500
actgctacag cccactgcag tcctacggct ttaggcccac atacggcgtg ggccaccagc    1560
cctacagagt ggtggtgctg agcttcgaac tgctgcatgc ccctgccaca cgtgtgcggc    1620
ctaagaaaag caccaatctc gtgaagaaca aatgcgtgaa cttcaacttc aacggcctga    1680
ccggcaccgg cgtgctgaca gagagcaaca agaagttcct gccattccag cagtttggcc    1740
gggatatcgc cgataccaca gacgccgtta gagatcccca gacactggaa atcctggaca    1800
tcaccccttg cagcttcggc ggagtgtctg tgatcacccc tggcaccaac accagcaatc    1860
aggtggcagt gctgtaccag ggcgtgaact gtaccgaagt gcccgtggcc attcacgccg    1920
atcagctgac acctacatgg cgggtgtact ccaccggcag caatgtgttt cagaccagag    1980
ccggctgtct gatcggagcc gagtacgtga acaatagcta cgagtgcgac atccccatcg    2040
gcgctggaat ctgcgccagc taccagacac agacaaagag ccaccggaga gccagaagcg    2100
tggcagcca gagcatcatt gcctacacaa tgtctctgga cgccggagaa agcgtggcct    2160
actccaacaa ctctatcgct atccccacca acttcaccat cagcgtgacc acagagatcc    2220
tgcctgtgtc catgaccaag accagcgtgg actgcaccat gtacatctgc ggcgattcca    2280
ccgagtgctc caacctgctg ctgcagtacg gcagcttctg cacccagctg aaaagagccc    2340
tgacagggat cgccgtggaa caggacaaga cacccagtg gtgttcgcc caagtgaagc    2400
agatctacaa gaccccttcct atcaagtact tcggcggctt caatttcagc cagattctgc    2460
ccgatcctag caagcccagc aagcggagct tcatcgagga cctgctgttc aacaaagtga    2520
cactggccga cgccggcttc atcaagcagt atggcgattg tctgggcgac attgccgcca    2580
gggatctgat ttgcgcccag aagtttaacg gactgacagt gctgcctcct ctgctgaccg    2640
atgagatgat cgcccagtac acatctgccc tgctggccgg cacaatcaca agcggctgga    2700
catttggagc aggcgccgct ctgcagatcc cctttgctat gcagatggcc taccggttca    2760
acggcatcgg agtgacccag aatgtgctgt acgagaacca gaagctgatc gccaaccagt    2820
tcaacagcgc catcggcaag atccaggaca gcctgagcag cacagcaagc gccctgggaa    2880
agctgcagga cgtggtcaac cacaatgccc aggcactgaa cacactggtc aagcagctgt    2940
cctccaagtt cggcgccatc agctctgtgc tgaacgatat cctgagcaga ctggaccctc    3000
tgaggccga ggtgcagatc gacagactga tcacaggcag actgcagagc tccagacat    3060
acgtgaccca gcagctgatc agagccgccg agattagagc ctctgccaat ctggccgcca    3120
ccaagatgtc tgagtgtgtg ctgggccaga gcaagagagt ggactttgtgc ggcaagggct    3180
accacctgat gagcttccct cagtctgccc tcacgcgcgt ggtgttctg cacgtggacat    3240
atgtgcccgc tcaagagaag aatttcacca ccgctccagc catctgccac gacggcaaag    3300
cccacttcc tagagaaggc gtgttcgtgt ccaacggcac ccattggttc gtgacacagc    3360
ggaacttcta cgagccccag atcatcacca ccgacaacac cttcgtgtct ggcaactgta    3420
acgtcgtgat cggcattgtg aacaataccg tgtacgaccc tctgcagccc gagctggaca    3480
gcttcaaaga ggaactggac aagtactta agaaccacac aagccccgac gtggacctgg    3540
gcgatatcag cggaatcaat gccagcgtcg tgaacatcca gaaagagatc gaccggctga    3600
acgaggtggc caagaatctg aacgagagcc tgatcgacct gcaagaactg ggggaagtga    3660
agcagtacat caagtggccc tggtacatct ggctgggctt tatcgccgga ctgattgcca    3720
tcgtgatggt cacaatcatg ctgtgttgca tgaccagctg ctgtagtgc ctgaagggct    3780
gttgtagctg tggcagctgc tgcaagttcg acgaggacga ttctgagccc gtgctgaagg    3840
gcgtgaaact gcactacaca tgatgactga agctggtact ggacgcacgc aatgctagct    3900
gccccttttcc cgtcctgggt accccgagtc tccccgacc tcgggtccca ggtatgctcc    3960
cacctccacc tgccccactc accacctctg ctagttccag acacctccca agcacgcagc    4020
aatgcagctc aaaacgctta gcctagccac accccacgg gaaacagcag tgattaacct    4080
ttagcaataa acgaaagttt aactaagcta tactaaccc aggggttggct aatttcgtgc    4140
cagccacacc ctggagctag caaaaaaaaa aaaaaaaaa aaaaaaaaa agcatatgac    4200
taaaaaaaaa aaaaaaaaaa aaaaaaaaaa aaaaaaaaa aaaaaaaaa aaaaaaaaaa    4260
aaaaaaaaaa                                                          4270

SEQ ID NO: 168        moltype = AA  length = 1269
FEATURE               Location/Qualifiers
source                1..1269
                      mol_type = protein
                      organism = synthetic construct
SEQUENCE: 168
MFVFLVLLPL VSSQCVNLIT RTQSYTNSFT RGVYYPDKVF RSSVLHSTQD LFLPFFSNVT     60
WFHAIHVSGT NGTKRFDNPA LPFNDGVYFA STEKSNIIRG WIFGTTLDSK TQSLLIVNNA    120
TNVVIKVCEF QFCNDPFLDV YQKNNKSWME SEFRVYSSAN NCTFEYVSQP FLMDLEGKEG    180
NFKNLREFVF KNIDGYFKIY SKHTPINLER DLPQGFSALE PLVDLPIGIN ITRFQTLLAL    240
HRSYLTPGGS SSGWTAGAAA YYVGYLQPRT FLLKYNENGT ITDAVDCALD PLSETKCTLK    300
SFTVEKGIYQ TSNFRVQPTE SIVRFPNITN LCPFHEVFNA TTFASVYAWN RKRISNCVAD    360
YSVIYNFAPF FAFKCYGVSP TKLNDLCFTN VYADSFVIRG NEVSQIAPGQ TGNIADYNYK    420
LPDDFTGCVI AWNSNKLDSK PSGNYNYLYR LFRKSKLKPF ERDISTEIYQ AGNKPCNGVA    480
GPNCYSPLQS YGFRPTYGVG HQPYRVVVLS FELLHASATV CGPKKSTNLV KNKCVNFNFN    540
GLTGTGVLTE SNKKFLPFQQ FGRDIADTTD AVRDPQTLEI LDITPCSFGG VSVITPGTNT    600
SNQVAVLYQG VNCTEVPVAI HADQLTPTWR VYSTGSNVFQ TRAGCLIGAE YVNNSYECDI    660
PIGAGICASY QTQTKSHRRA RSVASQSIIA YTMSLGAENS VAYSNNSIAI PTNFTISVTT    720
EILPVSMTKT SVDCTMYICG DSTECSNLLL QYGSFCTQLK RALTGIAVEQ DKNTQEVFAQ    780
VKQIYKTPPI KYFGGFNFSQ ILPDPSKPSK RSFIEDLLFN KVTLADAGFI KQYGDCLGDI    840
AARDLICAQK FNGLTVLPPL LTDEMIAQYT SALLAGTITS GWTFGAGAAL QIPFAMQMAY    900
RFNGIGVTQN VLYENQKLIA NQFNSAIGKI QDSLSSTASA LGKLQDVVNH NAQALNTLVK    960
QLSSKFGAIS SVLNDILSRL DPPEAEVQID RLITGRLQSL QTYVTQQLIR AAEIRASANL   1020
AATKMSECVL GQSKRVDFCG KGYHLMSFPQ SAPHGVVFLH VTYVPAQEKN FTTAPAICHD   1080
GKAHFPREGV FVSNGTHWFV TQRNFYEPQI ITTDNTFVSG NCDVVIGIVN NTVYDPLQPE   1140
LDSFKEELDK YFKNHTSPDV DLGDISGINA SVVNIQKEID RLNEVAKNLN ESLIDLQELG   1200
KYEQYIKWPW YIWLGFIAGL IAIVMVTIML CCMTSCCSCL KGCCSCGSCC KFDEDDSEPV   1260
LKGVKLHYT                                                          1269
```

| SEQ ID NO: 169 | moltype = RNA length = 3813 |
|---|---|
| FEATURE | Location/Qualifiers |
| source | 1..3813 |
| | mol_type = other RNA |
| | organism = synthetic construct |

SEQUENCE: 169

```
atgttcgtgt tcctggtgct gctgcctctg gtgtccagcc agtgtgtgaa cctgatcacc   60
agaacacagt catacaccaa cagctttacc agaggcgtgt actacccga caaggtgttc  120
agatccagcg tgctgcactc tacccaggac ctgttcctgc cttttcttcag caacgtgacc  180
tggttccacg ccatccacgt gtccggcacc aatggcacca agagattcga caaccccgcc  240
ctgcccttca cgacggggt gtactttgcc agcaccgaga gtccaacat catcagaggc  300
tggatcttcg gcaccacact ggacagcaag acccagagcc tgctgatcgt gaacaacgcc  360
accaacgtgg tcatcaaagt gtgcgagttc cagttctgca acgaccccectt cctggacgtc  420
taccagaaga caacaagag ctggatggaa agcgagttcc gggtgtacag cagcgccaac  480
aactgcacct tcgagtacgt gtcccagcct ttcctgatgg acctggaagg caaggagggc  540
aacttcaaga acctgcgcga gttcgtgttt aagaacatcg acggctactt caagatctac  600
agcaagcaca ccctatcaa cctcgaagcgg gatctgcctc agggcttctc tgctctgaa  660
ccctggtgg atctgcccat cggcatcaac atcacccggt tcagacact gctggccctg  720
cacagaagct acctgacacc tggcggcagc agcagcggat ggacagctgg tgccgccgct  780
tactatgtgg gctacctgca gcctagaacc ttcctgctga agtacaacga aacggcacc  840
atcaccgacg ccgtggattg tgctctggat cctctgaggg agacaaagtg caccctgaag  900
tccttcaccg tggaaaaggg catctaccag accagcaact tccgggtgca gcccaccgaa  960
tccatcgtgc ggttccccaa tatcaccaat ctgtgcccct tccacgaggt gttcaatgcc 1020
accaccttcc cctctgtgta cgcctggaac cggaagcgga tcagcaattg cgtggccgac 1080
tactccgtga tctacaactt cgcccccctt c ttcgcattca agtgctacgg cgtgtccccct 1140
accaagctga acgacctgtg cttcacaaac gtgtacgccg acagcttcgt gatccggga 1200
aacgaagtgt cacagattgc ccctggacag acaggcaaca tcgccgacta caactacaag 1260
ctgcccgacg acttcaccgg ctgtgtgatt gcctggaaca gcaacaagct ggactccaaa 1320
cccagcggca actacaatta cctgtgccgg ctgttccgga agtccaagct gaagcccttc 1380
gagcgggaca tctccaccga gatctatcag gccggcaaca agccttgtaa cggcgtggca 1440
ggccccaact gctacagccc actgcagtcc tacggcttta ggcccacata cggcgtgggc 1500
caccagcccct acagagtggt ggtgctgagc ttcgaactgc tgcatgcctc agccacagtg 1560
tgcggcccta agaaaagcac caatctcgtg aagaacaaat gcgtgaactt caacttcaac 1620
ggcctgaccg gcaccggctg gctgacagag agcaacaaga gttcctgcc attccagcag 1680
tttggccggg atatcgccga taccacagac gccgttagag atccccagac actggaaatc 1740
ctggacatca cccccttgca gttcggcgga gtgtctgtga tcaccccctgg caccaacacc 1800
agcaatcagg tggcagtgct gtaccagggc gtgaactgta ccgaagtgcc cgtggccatt 1860
cacgccgatc agctgacacc tacatggcgg gtgtactcca ccggcagcaa tgtgtttcag 1920
accagagccg gctgtctgat cggagccgag tacgtgaaca atagctacga gtgcgacatc 1980
cccatcggcg ctggaatctg cgccagctac cagacacaga caaagagcca ccggagagcc 2040
agaagcgtgg ccagcagag catcattgcc tacacaatgt ctctgggcgc cgagaacagc 2100
gtggcctact ccaacaactc tatcgctatc cccaccaact tcaccatcag cgtgaccaca 2160
gagatcctgc ctgtgtccat gaccaagacc agcgtggact gcaccatgta catctgcggc 2220
gattccaccg agtgctccaa cctgctgctg cagtacggca gcttctgcac ccagctgaaa 2280
agagccctga caggatccgc cgtggaacag gacaagaaca cccaagaggt gttcgcccaa 2340
gtgaagcaga tctacaagac ccctcctatc aagtacttcg gcggcttcaa tttcagccag 2400
attctgcccg atcctagcaa gcccagcaag cggagcttca tcgaggacct gctgttcaac 2460
aaagtgacac tggccgacgc cggcttcatc aagcagtatg gcgattgtct gggcgacatt 2520
gccgccaggg atctgatttg cgcccagaag tttaacggac tgacagtgct gcctcctctg 2580
ctgaccgatg agatgatcgc ccagtacaca tctgcccctgc tggccggcac aatcagcagc 2640
ggctggacat ttggagcagg cgccgctctg cagatcccct ttgctatgca gatggcctac 2700
cggttcaacg gcatcggagt gacccagaat gtgctgtacg agaaccagaa gctgatcgcc 2760
aaccagttca acagcgccat cggcaagatc caggacagcc tgagcagcac agcaagcgcc 2820
ctgggaaagc tgcaggacgt ggtcaaccac aatgcccagg cactgaacac cctggtcaag 2880
cagctgtcct ccaagttcgg cgccatcagc tctgtgctga acgatatcct gagcagactg 2940
gaccctcctg aggccgaggt gcagatcgac agactgatca caggcagact gcagagcctc 3000
cagacatacg tgacccagca gctgatcaga gccgccgaga ttagagcctc tgccaatctg 3060
gccgccacca gatgtctga gtgtgtgctg ggcagagca agagagtgga cttttgcggc 3120
aagggctacc acctgatgag cttccctcag tctgcccctc acgcgtggt gtttctgcac 3180
gtgacatatg tgcccgctca agagaagaat ttcaccaccg ctccagccat ctgccacgac 3240
ggcaaagccc actttcctag agaaggcgtg ttcgtgtcca acggcaccca ttggttcgtg 3300
acacagcgga acttctacga gccccagatc atcaccaccg acaacacctt cgtgtctggc 3360
aactgcgacg tcgtgatcgg cattgtgaac aataccgtgt acgaccctct gcagcccgag 3420
ctggacagct tcaaagagga actggacaag tactttaaga accacacaag ccccgacgtg 3480
gacctggcg atatcagcgg aatcaatgcc agcgtcgtga acatccagaa agatatcgac 3540
cggctgaacg aggtggccaa gaatctgaac gagagcctga tcgacctgca agaactggga 3600
aagtacgagc agtacatcaa gtggccctgg tacatctggc tggctttat cgccggactg 3660
attgccatcg tgatggtcac aatcatgctg tgttgcatga ccagctgctg tagctgcctg 3720
aagggctgtt gtagctgtgg cagctgctgc aagttcgacg aggacgattc tgagcccgtg 3780
ctgaagggcg tgaaactgca ctacacatga tga                              3813
```

| SEQ ID NO: 170 | moltype = DNA length = 3813 |
|---|---|
| FEATURE | Location/Qualifiers |
| source | 1..3813 |
| | mol_type = other DNA |
| | organism = synthetic construct |

SEQUENCE: 170
```
atgttcgtgt tcctggtgct gctgcctctg gtgtccagcc agtgtgtgaa cctgatcacc    60
agaacacagt catacaccaa cagctttacc agaggcgtgt actacccga caaggtgttc   120
agatccagcg tgctgcactc tacccaggac ctgttcctgc ctttcttcag caacgtgacc   180
tggttccacg ccatccacgt gtccggcacc aatggcacca agagattcga caaccccgcc   240
ctgcccttca acgacggggt gtactttgcc agcaccgaga gtccaacat catcagaggc    300
tggatcttcg gcaccacact ggacagcaag acccagagcc tgctgatcgt gaacaacgcc   360
accaacgtgg tcatcaaagt gtgcgagttc agttctgca acgaccctt cctggacgtc    420
taccagaaga caacaagag ctggatgaa agcgagttcc gggtgtacag cagcgccaac    480
aactgcacct tcgagtacgt gtcccagcct ttcctgatgg acctggaagg caaggaggc    540
aacttcaaga acctgcgcga gttcgtgttt aagaacatcg acggctactt caagatctac   600
agcaagcaca cccctatcaa cctcgagcgg gatctgcctc agggcttctc tgctctggaa    660
cccctggtgg atctgcccat cggcatcaac atcacccggt tcagacact gctggccctg    720
cacagaagct acctgacacc tggcgcagc agcagcggat ggacagctgg tgccgccgct    780
tactatgtgg gctacctgca gcctagaacc ttcctgctga agtacaacga gaacggcacc    840
atcaccgacg ccgtggattg tgctctggat cctctgagcg agacaaagtg caccctgaag    900
tccttcaccg tggaaaaggg catctaccag accagcaact tccgggtgca gcccaccgaa   960
tccatccgtg cggttcccaa tatcaccaat ctgtgcccct tccacgaggt gttcaatgcc   1020
accaccttcg cctctgtgta cgcctggaac cggaagcgga tcagcaattg cgtggccgac   1080
tactccgtga tctacaactt cgcccccttc ttcgcattca agtgctacgg cgtgtccct    1140
accaagctga acgacctgtg cttcacaaac gtgtacgccg acagcttcgt gatccgggga   1200
aacgaagtgt cacagattgc ccctggacag acaggcaaga tcgccgacta caactacaag   1260
ctgcccgacg acttcaccgg ctgtgtgatt gcctggaaca gcaacaagct ggactccaaa   1320
cccagcggca actacaatta cctgtaccgg ctgttccgga gtccaagct gaagcccttc   1380
gagcgggaca tctccaccga gatctatcag gccggcaaca agcttgtaa cggcgtggca    1440
ggccccaact gctacagccc actgcagtcc tacggcttta ggccacata cggcgtgggc    1500
caccagccct acagagtggt ggtgctgagc ttcgaactgc tgcatgcctc agccacagtg   1560
tgcggcccta agaaaagcac caatctcgtg aagaacaaat gcgtgaactt caacttcaac   1620
ggcctgaccg gcaccggcgt gctgacagag agcaacaaga agttcctgcc attccagcag   1680
tttggccggg atatcgccga taccacagac gccgttagag atccccagac actggaaatc   1740
ctggacatca ccccttgcag cttcggcgga gtgtctgtga tcaccctgg caccaacacc   1800
agcaatcagg tggcagtgct gtaccagggc gtgaactgta ccgaagtgcc cgtggccatt   1860
cacgccgatc agctgacacc tacatggcgg gtgtactcca ccggcagcaa tgtgtttcag   1920
accagagccg gctgtctgat cggagccgag tacgtgaaca atagctacga gtgcgacatc   1980
cccatccggc tggaatctg cgccagctac cagacacaga caaagagcca ccggagagcc   2040
agaagcgtgg ccagcagag catcattgcc tacacaatgt ctctgggcgc cgagaacagc   2100
gtggcctact ccaacaactc tatcgctatc cccaccaact tcaccatcag cgtgaccaca   2160
gagatcctgc ctgtgtccat gaccaagacc agcgtggact gcaccatgta catctgcggc   2220
gattccaccg agtgctccaa cctgctgctg cagtacgca gcttctgcac ccagctgaaa   2280
agagccctga cagggatcgc cgtggaacag gacaagaaca cccaagaggt gttcgcccaa   2340
gtgaagcaga tctacaagac ccctcctatc aagtacttcg gcggcttcaa tttcagccaa   2400
attctgcccg atcctagcaa gcccagcaag cggagcttca tcgaggacct gctgttcaac   2460
aaagtgacac tggccgagc cggcttcatc aagcagtatg gcgattgtct gggcgacatt   2520
gccgccaggg atctgatttg cgcccagaag tttaacggac tgacagtgct gcctcctctg   2580
ctgaccgatg agatgatcgc ccagtacaca tctgccctgc tggccggcac aatcacaagc   2640
ggctggacat ttgagcaggc gccgctctg cagatccct ttgctatgca gatggcctac   2700
cggttcaacg gcatcggagt gacccagaat gtgctgtacg agaaccagaa gctgatcgcc   2760
aaccagttca acagcgccat cggcaagatc caggacagcc tgagcagcac agcaagcgcc   2820
ctgggaaagc tgcaggacgt ggtcaaccac aatgcccagg cactgaacac cctggtcaag   2880
cagctgtcct ccaagttcgg cgccatcagc tctgtgctga cgatatcct gagcagactg   2940
gaccctcctg aggccgaggt gcagatcgac agactgatca ggcagact gcagagcctc   3000
cagacatacg tgacccagca gctgatcaga gccgccgaga ttagagcctc tgccaatctg   3060
gccgccacca agatgtctga gtgtgtgctg ggcagagca agagagtgga cttttgcggc   3120
aagggctacc acctgatgag cttccctcag tctgccctc acggcgtggt gtttctgcac   3180
gtgacatatg tgcccgctca agagaagaat ttcaccaccg ctccagccat ctgccacgac   3240
ggcaaagccc acttcctag agaaggcgtg ttcgtgtcca acggcaccca ttggttcgtg   3300
acacagcgga acttctacga gcccagatc atcaccaccg acaacacctt cgtgtctggc   3360
aactgcgacg tcgtgatcgg cattgtgaac aataccgtgt acgacctct gcagcccgag   3420
ctggacagct tcaaagagga actggacaag tactttaaga accacacaag ccccgacgtg   3480
gacctgggcg atatcagcgg aatcaatgcc agcgtcgtga acatccagaa agatgatcgac   3540
cggctgaacg aggtggccaa gaatctgaac gagagcctga tcgacctgca agaactgggg   3600
aagtacgagc agtacatcaa gtggccctgg tacatctggc tgggctttat cgccggactg   3660
attgccatcg tgatggtcac aatcatgctg tgttgcatga ccagctgctg tagctgcctg   3720
aagggctgtt gtagctgtgg cagctgctgc aagttcgacg aggacgattc tgagcccgtg   3780
ctgaagggcg tgaaactgca ctacacatga tga                                3813
```

| SEQ ID NO: 171 | moltype = RNA length = 4270 |
|---|---|
| FEATURE | Location/Qualifiers |
| source | 1..4270 |
| | mol_type = other RNA |
| | organism = synthetic construct |

SEQUENCE: 171
```
agaataaact agtattcttc tggtccccac agactcagag agaacccgcc accatgttcg    60
tgttcctggt gctgctgcct ctggtgtcca gccagtgtgt gaacctgatc accagaacac   120
agtcatacac caacagcttt accagaggcg tgtactaccc cgacaaggtg ttcagatcca   180
gcgtgctgca ctctacccag gacctgttcc tgcctttctt cagcaacgtg acctggttcc   240
acgccatcca cgtgtccggc accaatggca ccaagagatt cgacaacccc gccctgccct   300
tcaacgacgg ggtgtacttt gccagcaccg agaagtccaa catcatcaga ggctggatct   360
tcggcaccac actggacagc aagacccaga gcctgctgat cgtgaacaac gccaccaacg   420
```

```
tggtcatcaa agtgtgcgag ttccagttct gcaacgaccc cttcctggac gtctaccaga   480
agaacaacaa gagctggatg gaaagcgagt tccgggtgta cagcagcgcc aacaactgca   540
ccttcgagta cgtgtcccag cctttcctga tggacctgga aggcaaggag ggcaacttca   600
agaacctgcg cgagttcgtg tttaagaaca tcgacggcta cttcaagatc tacagcaagc   660
acaccctat caacctcgag cgggatctgc ctcagggcrt ctctgctctg gaaccctgg    720
tggatctgcc catcggcatc aacatcaccc ggtttcagac actgctggcc ctgcacagaa   780
gctacctgac acctggcggc agcagcagcg gatggacagc tggtgccgcc gcttactatg   840
tgggctacct gcagcctaga accttcctgc tgaagtacaa cgagaacggc accatcaccg   900
acgccgtgga ttgtgctctg gatcctctga gcgagacaaa gtgcaccctg aagtcctca   960
ccgtggaaaa gggcatctac cagaccagca acttccgggt gcagcccacc gaatccatcg  1020
tgcggttccc caatatcacc aatctgtgcc cttccacga ggtgttcaat gccaccacct  1080
tcgcctctgt gtacgcctgg aaccggaagc ggatcagcaa ttgcgtggcc gactactccg  1140
tgatctacaa cttcgccccc ttcttcgcat tcaagtgcta cggcgtgtcc cctaccaagc  1200
tgaacgacct gtgcttcaca aacgtgtacg ccgacgcctt cgtgatccgg ggaaacgaag  1260
tgtcacagat tgcccctgga cagacaggca acatcgccga ctacaactac aagctgcccg  1320
acgacttcac cggctgtgtg attgcctgga acagcaacaa gctggactcc aaacccagcg  1380
gcaactacaa ttacctgtac cggctgttcc ggaagtccaa gctgaagccc ttcgagcggg  1440
acatcctcca cgagatctat caggccggca acaagccttg taacggcgtg gcaggcccca  1500
actgctacag cccccactgcag tcctacggct ttaggcccac atacggcgtg gccaccagc  1560
cctacagagt ggtggtgctg agcttcgaac tgctgcatgc ctcagccaca gtgtgcggcc  1620
ctaagaaaag caccaatctc gtgaagaaca aatgcgtgaa cttcaacttc aacggcctga  1680
ccggcaccgg cgtgctgaca gagagcaaca agaagttcct gccattccag cagtttggcc  1740
gggatatcgc cgataccaca gacgccgtta gagatcccca cgacactgaa atcctggaca  1800
tcacccctttg cagcttcggc ggagtgtctg tgatcacccc tggcaccaac accagcaatc  1860
aggtggcagt gctgtaccag ggcgtgaact gtaccgaagt gcccgtggcc attcacgccg  1920
atcagctgac acctacatgg cgggtgtact ccaccgcgca caatgtgttt cagaccagag  1980
ccggctgtct gatcggagcc gagtacgtga acaatagcta cgagtgcgac atccccatcg  2040
gcgctggaat ctgcgccagc taccagacac agacaaagag ccaccggaga gccagaagcg  2100
tggccagcca gagcatcatt gcctacaaa tgtctctggg cgccgagaac agcgtggcct  2160
actccaacaa ctctatcgct atccccacca cttcaccat acagagatcc                2220
tgcctgtgtc catgaccaag accagctgtg actgcaccat gtacatctgc ggcgattcca  2280
ccgagtgctc caacctgctg ctgcagtacg gcagcttctg cacccagctg aaaagagccc  2340
tgacagggat cgccgtggaa caggacaaga acaccccaaga ggtgttcgcc caagtgaagc  2400
agatctacaa gaccccctcct tcaagtact tcggcggctt caatttcagc cagattctgc  2460
ccgatcctag caagcccagc aagcgtgagct tcatcgagga cctgctgttc aacaagtga  2520
cactggccga cgccggcttc atcaagcagt atggcgattg tctgggcgac attgccgcca  2580
gggatctgat ttgcgcccag aagtttaacg gactgacagt gctgcctcct ctgctgaccg  2640
atgagatgat cgcccagtac acatctgccc tgctggccgg cacaatcaca agcggctgga  2700
catttggagc aggcgccgct ctgcagatcc cctttgctat gcagatgccc taccggttca  2760
acggcatcgg agtgacccag aatgtgcgt cacgagaacca gaagctgatc gccaaccagt  2820
tcaacagcgc catcggcaag atccaggaca gcctgagcag cacagcaagc gccctgggaa  2880
agctgcagga cgtggtcaac cacaatgccc aggcactgaa caccctggtc aagcagctgt  2940
cctccaagtt cggcgccatc agctctgtgc tgaacgatat cctgagcaga ctggacccctc  3000
ctgaggccga ggtgcagatc gacagactga tcacaggcag actgcagagc ctccagacat  3060
acgtgaccca gcagctgatc agagccgcca gattagagc ctctgccaat ctggccgcca  3120
ccaagatgtc tgagtgtgtg ctgggccaga gcaagagagt ggacttttgc ggcaagggct  3180
accacctgat gagcttccct cagtctgccc ctcacggcgt ggtgttttctg cacgtgacat  3240
atgtgcccgc tcaagagaag aatttcacca ccgctccagc catctgccac gacggcaaag  3300
cccactttcc tagagaaggc gtgttcgtgt caacggcac ccattggttc gtgacacagc  3360
ggaacttcta cgagccccag atcatcacca ccgacaacac cttcgtgtct ggcaactgcg  3420
acgtcgtgat cggcattgtg aacaataccg tgtacgaccc tctgcagccc gagctggaca  3480
gcttcaaaga ggaactggac aagtactttc agaaccacac aagcccgac gtggacctgg  3540
gcgatatcag cggaatcaat gccagcgtcg tgaacatcca gaaagagatc gaccggctga  3600
acgaggtggc caagaatctg aacgagagcc tgatcgacct gcaagaactg gggaagtacg  3660
agcagtacat caagtgggcc tggtacatct ggctgggctt tatcgccgga ctgattgcca  3720
tcgtgatggt cacaatcatg ctgtgttgca tgaccagctg ctgtagctgc ctgaagggct  3780
gttgtagctg tggcagctgc tgcaagttcg acgaggacga ttctgagccc gtgctgaagg  3840
gcgtgaaact gcactacaca tgatgactcg agctggtact gcatgcacgc aatgctagct  3900
gcccctttcc cgtcctgggt acccctgagtc tccccccgacc tcgggtccca ggtatgctcc  3960
cacctccacc tgcccactcc accacctctg ctagttccag acacctccca agcacgcagc  4020
aatgcagctc aaaacgctta gcctagccac acccccacgg gaaacagcag tgattaacct  4080
ttagcaataa acgaaagttt aactaagcta tactaacccc agggttggtc aatttcgtgc  4140
cagccacacc ctggagctag caaaaaaaaa aaaaaaaaaa aaaaaaaaaa agcatatgac  4200
taaaaaaaaa aaaaaaaaaa aaaaaaaaaa aaaaaaaaaa aaaaaaaaaa aaaaaaaaaa  4260
aaaaaaaaaa                                                                                    4270
SEQ ID NO: 172         moltype = DNA   length = 4270
FEATURE                Location/Qualifiers
source                 1..4270
                       mol_type = other DNA
                       organism = synthetic construct
SEQUENCE: 172
agaataaact agtattcttc tggtccccac agactcagag agaacccgcc accatgttcg     60
tgttcctggt gctgctgcct ctggtgtcca gccagtgtgt gaacctgatc accagaaca   120
agtcatacac caaacagcttt accagaggcg tgtactaccc cgacaaggtg ttcagatcca   180
gcgtgctgca ctctacccag gacctgttcc tgccttttctt cagcaacgtg acctggttcc   240
acgccatcca cgtgtccggc accaatggca ccaagagatt cgacaacccc gccctgccct   300
tcaacgacgg ggtgtacttt gccagcaccg agaagtccaa catcatcaga ggctggatct   360
tcggcaccac actggacagc aagacccaga gcctgctgat cgtgaacaac gccaccaacg   420
```

```
tggtcatcaa agtgtgcgag ttccagttct gcaacgaccc cttcctggac gtctaccaga   480
agaacaacaa gagctggatg gaaagcgagt tccgggtgta cagcagcgcc aacaactgca   540
ccttcgagta cgtgtcccag cctttcctga tggacctgga aggcaaggag ggcaacttca   600
agaacctgcg cgagttcgtg tttaagaaca tcgacggcta cttcaagatc tacagcaagc   660
acaccctat caacctcgag cgggatctgc ctcagggctt ctctgctctg gaaccctgg    720
tggatctgcc catcggcatc aacatcaccc ggtttcagac actgctggcc ctgcacagaa   780
gctacctgac acctggcggc agcagcagcg gatggacagc tggtgccgcc gcttactatg   840
tgggctacct gcagcctaga accttcctgc tgaagtacaa cgagaacggc accatcaccg   900
acgccgtgga ttgtgctctg gatcctctga gcgagacaaa gtgcacccg aagtcctca   960
ccgtggaaaa gggcatctac cagaccagca acttccgggt gcagcccacc gaatccatcg  1020
tgcggttccc caatatcacc aatctgtgcc cttccacga ggtgttcaat gccaccacct  1080
tcgcctctgt gtacgcctgg aaccggaagc ggatcagcaa ttgcgtggcc gactactccg  1140
tgatctacaa cttcgccccc ttcttcgcat tcaagtgcta cggcgtgtcc cctaccaagc  1200
tgaacgacct gtgcttcaca aacgtgtacg ccgacagctt cgtgatccgg ggaacgaag   1260
tgtcacagat tgcccctgga cagacaggca acatcgccga ctacaactac aagctgcccg  1320
acgacttcac cggctgtgtg attgcctgga acagcaacaa gctggactcc aaacccagcg  1380
gcaactacaa ttacctgtac cggctgttcc ggaagtccaa gctgaagccc ttcgagcggg  1440
acatctccac cgagatctat caggccggca acaagccttg taacgcgtg gcaggcccca  1500
actgctacag cccactgcag tcctacggct taggcccac atacggcgtg ggccaccagc  1560
cctacagagt ggtggtgctg agcttcgaac tgctgcatgc ctcagccaca gtgtgcggcc  1620
ctaagaaaag caccaatctc gtgaagaaca atgcgtgaa cttcaacttc aacggcctga  1680
ccggcaccgg cgtgctgaca gagagcaaca agaagttcct gccattccag cagtttggcc  1740
gggatatcgc cgataccaca gacgccgtta gagatcccca gacactggaa atcctggaca  1800
tcacccttg cagcttcggc ggagtgtctg tgatcacccc tggcaccaac accagcaatc  1860
aggtggcagt gctgtaccag ggcgtgaact gtaccgaagt gcccgtggcc attcacgccg  1920
atcagctgac acctacatgg cgggtgtact ccaccgagca caatgtgttt cagaccagag  1980
ccggctgtct gatcggagcc gagtacgtga caatagcta cgagtgcgac atccccatcg  2040
gcgctggaat ctgcgccagc taccagacac agacaaagag ccaccggaga gccagaagcg  2100
tggccagcca gagcatcatt gcctacaaa tgtctctggg cgccgagaac agcgtggcct  2160
actccaacaa ctctatcgct atccccacca acttccaat gccgtgacc acagagatcc  2220
tgcctgtgtc catgaccaag accagctgg actgcaccat gtacatctgc ggcgattcca  2280
ccgagtgctc caacctgctg ctgcagtacg gcagcttctg cacccagctg aaaagagccc  2340
tgacagggat cgccgtggaa caggacaaga cacccaaga ggtgttcgcc caagtgaagc  2400
agatctacaa gacccctcct atcaagtact tcggcggctt caatttcagc cagattctgc  2460
ccgatcctag caagcccagc aagcggagct tcatcgagga cctgctgttc aacaaagtga  2520
cactggccga cgccggcttc atcaagcagt atggcgattg tctgggcgac attgccgcca  2580
gggatctgat ttgcgcccag aagtttaacg gactgacagt gctgcctcct ctgctgaccg  2640
atgagatgat cgcccagtac acatctgccc tgctggccgg cacaatcaca agcggctgga  2700
catttggagc aggcgccgct ctgcagatcc cctttgctat gcagatggcc taccggttca  2760
acggcatcgg agtgacccag aatgtgctgt acgagaacca gaagctgatc gccaaccagt  2820
tcaacagcgc catcggcaag atccaggaca ggctgagcag cacagcaagc gccctgggaa  2880
agctgcagga cgtggtcaac cacaatgccc aggcactgaa cacctggtc aagcagctgt  2940
cctccaagtt cggcgccatc agctctgtgc tgaacgatat cctgagcaga ctgacccctc  3000
ctgaggccga ggtgcagatc gacagactga tcaggcga actgcagagc tccagacat   3060
acgtgaccca gcagctgatc agagccgcg agattagagc ctctgccaat ctggccgcca  3120
ccaagatgtc tgagtgtgtg ctgggccaga gcaagagagt ggacttttgc ggcaagggct  3180
accacctgat gagcttccct cagtctgccc ctcacggcgt ggtgtttctg cacgtgacat  3240
atgtgccgc tcaagagaag aatttcacca ccgctccagc catctgccac gacggcaaag  3300
cccactttcc tagagaaggc gtgttcgtgt ccaacggcac ccattggttc gtgacacagc  3360
ggaacttcta cgagccccag atcatcacca ccgacaacac cttcgtgtct ggcaactgcg  3420
acgtcgtgat cggcattgtg aacaataccg tgtacgaccc tctgcagccc gagctggaca  3480
gcttcaaaga ggaactggac aagtacttta agaaccacac aagccccgac gtggacctgg  3540
gcgatatcag cggaatcaat gccagcgtcg tgaacatcca aaaagagatc gaccggctga  3600
acgaggtggc caagaatctg aacgagagcc tgatcgacct gcaagaactg gggaagtacg  3660
agcagtacat caagtggccc tggtacatct ggctgggctt tatcgccgga ctgattgcca  3720
tcgtgatggt cacaatcatg ctgtgttgca tgaccagctg ctgtagctgc ctgaagggct  3780
gttgtagctg tggcagctgc tgcaagttcg acgaggacga ttctgagccc gtgctgaagg  3840
gcgtgaaact gcactacaca tgatgactcg agctggtact gcatgcacgc aatgctagct  3900
gcccttcc cgtcctgggt accccgagtc tccccgacc tcgggtccca ggtatgctcc  3960
cacctccacc tgcccactc accacctctg ctagttccag acacctccca gcacgcagc  4020
aatgcagctc aaaacgctta gcctagccac accccacgg gaaacagcag tgattaacct  4080
ttagcaataa acgaaagttt aactaagcta tactaacccc aggggttggtc aatttcgtgc  4140
cagccacacc ctggagctag caaaaaaaaa aaaaaaaaa aaaaaaaaaa agcatatgac  4200
taaaaaaaaa aaaaaaaaaa aaaaaaaaaa aaaaaaaaaa aaaaaaaaaa aaaaaaaaaa  4260
aaaaaaaaa                                                         4270
SEQ ID NO: 173          moltype = AA   length = 1269
FEATURE                 Location/Qualifiers
source                  1..1269
                        mol_type = protein
                        organism = synthetic construct
SEQUENCE: 173
MFVFLVLLPL VSSQCVNLIT RTQSYTNSFT RGVYYPDKVF RSSVLHSTQD LFLPFFSNVT   60
WFHAIHVSGT NGTKRFDNPA LPFNDGVYFA STEKSNIIRG WIFGTTLDSK TQSLLIVNNA  120
TNVVIKVCEF QFCNDPFLDV YQKNNKSWME SEFRVYSSAN NCTFEYVSQP FLMDLEGKEV  180
NFKNLREFVF KNIDGYFKIY SKHTPINLER DLPQGFSALE PLVDLPIGIN ITRFQTLLAL  240
HRSYLTPGGS SSGWTAGAAA YYVGYLQPRT FLLKYNENGT ITDAVDCALD PLSETKCTLK  300
SFTVEKGIYQ TSNFRVQPTE SIVRFPNITN LCPFHEVFNA TTFASVYAWN RKRISNCVAD  360
YSVIYNFAPF FAFKCYGVSP TKLNDLCFTN VYADSFVIRG NEVSQIAPGQ TGNIADYNYK  420
```

```
LPDDFTGCVI AWNSNKLDSK PSGNYNYLYR LFRKSLKPF  ERDISTEIYQ AGNKPCNGVA   480
GPNCYSPLQS YGFRPTYGVG HQPYRVVVLS FELLHASATV CGPKKSTNLV KNKCVNFNFN   540
GLTGTGVLTE SNKKFLPFQQ FGRDIADTTD AVRDPQTLEI LDITPCSFGG VSVITPGTNT   600
SNQVAVLYQG VNCTEVPVAI HADQLTPTWR VYSTGSNVFQ TRAGCLIGAE YVNNSYECDI   660
PIGAGICASY QTQTKSHRRA RSVASQSIIA YTMSLGAENS VAYSNNSIAI PTNFTISVTT   720
EILPVSMTKT SVDCTMYICG DSTECSNLLL QYGSFCTQLK RALTGIAVEQ DKNTQEVFAQ   780
VKQIYKTPPI KYFGGFNFSQ ILPDPSKPSK RSFIEDLLFN KVTLADAGFI KQYGDCLGDI   840
AARDLICAQK FNGLTVLPPL LTDEMIAQYT SALLAGTITS GWTFGAGAAL QIPFAMQMAY   900
RFNGIGVTQN VLYENQKLIA NQFNSAIGKI QDSLSSTASA LGKLQDVVNH NAQALNTLVK   960
QLSSKFGAIS SVLNDILSRL DPPEAEVQID RLITGRLQSL QTYVTQQLIR AAEIRASANL  1020
AATKMSECVL GQSKRVDFCG KGYHLMSFPQ SAPHGVVFLH VTYVPAQEKN FTTAPAICHD  1080
GKAHFPREGV FVSNGTHWFV TQRNFYEPQI ITTDNTFVSG NCDVVIGIVN NTVYDPLQPE  1140
LDSFKEELDK YFKNHTSPDV DLGDISGINA SVVNIQKEID RLNEVAKNLN ESLIDLQELG  1200
KYEQYIKWPW YIWLGFIAGL IAIVMVTIML CCMTSCCSCL KGCCSCGSCC KFDEDDSEPV  1260
LKGVKLHYT                                                         1269

SEQ ID NO: 174         moltype = RNA  length = 3813
FEATURE                Location/Qualifiers
source                 1..3813
                       mol_type = other RNA
                       organism = synthetic construct
SEQUENCE: 174
atgttcgtgt tcctggtgct gctgcctctg gtgtccagcc agtgtgtgaa cctgatcacc    60
agaacacagt catacaccaa cagctttacc agaggcgtgt actacccga caaggtgttc   120
agatccagcg tgctgcactc tacccaggac ctgttcctgc cttcttcag caacgtgacc   180
tggttccacg ccatccacgt gtccggcacc aatggcaccaa agagattgca caaccccgac   240
ctgcccttca cgacggggt gtactttgcc agcaccgaga gtccaacat catcagaggc   300
tggatcttcg gcaccacact ggacagcaag acccagagcc tgctgatcgt gaacaacgcc   360
accaacgtgg tcatcaaagt gtgcgagttc agttctgca acgacccctt cctggacgtc   420
taccagagaa acaacaagag ctggatggaa agcgagttcc gggtgtacag cagcgccaac   480
aactgcaccct tcgagtacgt gtcccagcct ttcctgatgg acctggaagg caaggaggtg   540
aacttcaaga acctgcgcga gttcgtgttt aagaacatcg acggctactt caagatctac   600
agcaagcaca ccctatcaa cctcgagcgg gatctgcctc agggcttctc tgctctggaa   660
ccctggtgg atctgcccat cggcatcaac atcaccggt tcagacact gctgccctc   720
cacagaagct acctgacacc tggcggcagc agcagcggat ggacagctgg tgccgccgct   780
tactatgtgg gctacctgca gcctagaacc ttcctgctga gtacaacga gaacggcacc   840
atcaccgacg ccgtggattg tgctctggat cctctgagcg agacaaagtg cacccctgaag   900
tccttcaccg tggaaaaggg catctaccag accagcaact tccgggtgca gcccaccgaa   960
tccatccgtg ggttcccaa tatcaccaat ctgtgccct tccacgaggt gttcaatgca  1020
accaccttcg cctctgtgta cgcctggaac cggaagcgga tcagcaattg cgtggccgac  1080
tactccgtga tctacaactt cgcccccttc ttcgcattca agtgctacgg cgtgtccct  1140
accaagctga acgacctgtg cttcacaaac gtgtacgccg acagcttcgt gatccggga  1200
aacgaagtgt cacagattgc ccctggacag acaggcaaca tcgccgacta caactacaag  1260
ctgcccgacg acttcaccgg ctgtgtgatt gcctggaaca gcaacaagct ggactccaaa  1320
cccagcggca actacaatta cctgtaccgg ctgttccgga gtccaagct gaagcccttc  1380
gagcgggaca tctccaccga gatctatcag gccggcaaca agcttgtaa cggcgtggca  1440
ggcccaact gctcagccc actgcagtcc tacggcttta cccacacata cggcgtgggc  1500
caccagcct acagagtggt ggtgctgagc ttcgaactgc tgcatgcctc agccacagtg  1560
tgcggcccta gaaaagcac caatctcgtg aagaacaaat gcgtgaactt caacttcaac  1620
ggcctgaccg gcaccggcgt gctgacagag agcaacaaga agttcctgcc attccagcag  1680
tttggccggg atatcgccga taccacagac gccgttagg atcccagac actgaaatc  1740
ctggacatca cccctgcag cttcggcgga gtgtctgtga tcaccctgg caccaacacc  1800
agcaatcagg tggcagtgct gtaccagggc gtgaactgta ccgaagtgcc cgtggccatt  1860
cacgccgatc agctgacacc tacatggcgg gtgtactcca ccggcagcaa tgtgtttcag  1920
accagagccg gctgtctgat cggagccgag tacgtgaaca atagctacga gtgcgacatc  1980
cccatcggcg ctggaatctg cgccagctac cagacacaga caaagagcca ccggagagcc  2040
agaagcgtgg ccagccagag catcattgcc tacacaatgt ctctgggcgc cgagaacagc  2100
gtggcctact ccaacaactc tatcgctatc ccaccaact tcaccatcag cgtgaccaca  2160
gagatcctgc ctgtgtccat gaccaagacc agcgtggact gcaccatga catctgcggc  2220
gattccaccg agtgctccaa cctgctgctg cagtacggca gcttctgcac ccagctgaaa  2280
agagccctga cagggatcgc cgtggaacag gacaagaaca cccaagaggt gttcgcccaa  2340
gtgaagcaga tctacaagac ccctcctatc aagtacttcg gcggcttcaa ttccagccag  2400
attctgcccg atcctagcaa gcccagcaag cggagcttca tcgaggacct gctgttcaac  2460
aaagtgacac tggccgacgc cggcttcatc aagcagtatg gcgattgtct gggcgacatt  2520
gccgccaggg atctgatttg cgccagaag tttaacggac tgacagtgct gcctcctctg  2580
ctgaccgatg agatgatcgc ccagtacaca tctgccctgc tggccggcac aatcacaagc  2640
ggctggacat ttgagcaggg cgccgctctg cagatccct tgctatgca gatggcctac  2700
cggttcaacg gcatcggagt gacccagaat gtgctgtacg agaaccagaa gctgatcgcc  2760
aaccagttca acagcgccat cggcaagatc caggacagcc tgagcagcac agcaagcgcc  2820
ctggaaagc tgcaggacgt ggtcaaccac aatgccagg cactgaacac cctggtcaag  2880
cagctgtcct ccaagttcgg cgccatcagc tctgtgctga acgatatcct gagcagactg  2940
gaccctcctg aggccgaggt gcagatcgac agactgatca caggcagact gcagagcctc  3000
cagacatacg tgacccagca gctgatcaga gccgccgaga ttagagcctc tgccaatctg  3060
gccgccacaa agatgtctga gtgtgtgctg ggccagagca agagagtgga cttttgcggc  3120
aagggctacc acctgatgag cttccctcag tctgcccctc acggcgtggt gtttctgcac  3180
gtgacatatg tgcccgctca agagaagaat ttcaccaccg ctccagccat ctgccacgac  3240
ggcaaagccc acttcctag agaaggcgtg ttcgtgtcca acggcaccca ttggttcgtg  3300
acacagcgga acttctacga gccccagatc atcaccaccg acaacacctt cgtgtctggc  3360
aactgcgacg tcgtgatcgg cattgtgaac aataccgtgt acgaccctct gcagcccgag  3420
```

```
ctggacagct tcaaagagga actggacaag tactttaaga accacacaag ccccgacgtg   3480
gacctgggcg atatcagcgg aatcaatgcc agcgtcgtga acatccagaa agagatcgac   3540
cggctgaacg aggtggccaa gaatctgaac gagagcctga tcgacctgca agaactgggg   3600
aagtacgagc agtacatcaa gtgggcctgg tacatctggc tgggctttat cgccggactg   3660
attgccatcg tgatggtcac aatcatgctg tgttgcatga ccagctgctg tagctgcctg   3720
aagggctgtt gtagctgtgg cagctgctgc aagttcgacg aggacgattc tgagcccgtg   3780
ctgaagggcg tgaaactgca ctacacatga tga                                3813

SEQ ID NO: 175          moltype = DNA   length = 3813
FEATURE                 Location/Qualifiers
source                  1..3813
                        mol_type = other DNA
                        organism = synthetic construct
SEQUENCE: 175
atgttcgtgt tcctggtgct gctgcctctg gtgtccagcc agtgtgtgaa cctgatcacc    60
agaacacagt catacaccaa cagctttacc agaggcgtgt actacccccga caaggtgttc   120
agatccagcg tgctgcactc tacccaggac ctgttcctgc cttcttcag caacgtgacc    180
tggttccacg ccatccacgt gtccggcacc aatggcacca agagattcga caaccccgac   240
ctgccccttca acgacggggt gtactttgcc agcaccgaga agtccaacat catcagaggc   300
tggatcttcg gcaccacact ggacagcaag acccagagcc tgctgatcgt gaacaacgcc   360
accaacgtgg tcatcaaagt gtgcgagttc cagttctgca cgacccctt cctggacgtc   420
taccagaaga acaacaagag ctggatgaaa agcgagttcc gtgttacag cagcgccaac   480
aactgcaccct tcgagtacgt gtcccagcct ttcctgatgg acctggaagg caaggaggtg   540
aacttcaaga acctgcgcga gttcgtgttt aagaacatcg acggctactt caagatctac    600
agcaagcaca cccctatcaa cctcgagcgg gatctgcctc agggcttctc tgctctggaa   660
ccctggtgg atctgcccat cggcatcaac atcacccggt ttcagacact gctggccgtg   720
cacagaagct acctgacacc tggcggcagc agcagcggat ggacagctgg tgccgccgct   780
tactatgtgg gctacctgca gcctagaacc ttcctgctga gtacaacga aacggcacc   840
atcaccgacg ccgtggattg tgctctggat cctctgagcg acaaagtg caccctgaag   900
tccttcaccg tggaaagggg catctaccag accagcaact tccggggtgca gcccaccgaa   960
tccatcgtgc ggttcccaa tatcaccaat ctgtgcccct tccacgaggt gttcaatgcc   1020
accacctcg cctctgtgta cgcctggaac cggaagcgga tcagcaattg cgtggccgac   1080
tactccgtga tctacaactt cgcccccttc ttcgcattca agtgctacgg cgtgtcccct   1140
accaagctga acgacctgtg cttcacaaac gtgtacgccg acagcttcgt gatccgggga   1200
aacgaagtgt cacagattgc ccctggacag acaggcaaca tcgccgacta caactacaag   1260
ctgcccgacg acttcaccgg ctgtgtgatt gcctggaaca gcaacaagct ggactccaaa   1320
cccagcggca actacaatta cctgtaccgg ctgttccgga gtccaagct gaagcccttc   1380
gagcgggaca ctctccaccga gatctatcag gccggcaaca agcttgtaa cggcgtggca   1440
ggcccaact gctacagccc actgcagtcc tacggcttta ggccacata cggcgtgggc   1500
caccagcct acagagtggt ggtgctgagc ttcgaactgc tgcatgcctc agccacagtg   1560
tgcggcccta agaaaagcac caatctcgtg aagaacaaat gcgtgaactt caacttcaac   1620
ggcctgaccg gcaccggcgt gctgacagag agcaacaaga gttcctgcc attccagcag   1680
tttggccggg atatccgga taccacagac gccgttaagc atccccagac actgaaaatc   1740
ctggacatca cccccttgca gcttcggcgga gtgtctgtga tcaccctggg caccaacacc   1800
agcaatcagg tggcagtgct gtaccagggc gtgaactgta ccgaagtgcc cgtggccatt   1860
cacgccgatc agctgacacc tacatggcgg gtgtactcca ccggcagcaa tgtgtttcag   1920
accagagccg gctgtctgat cggagccgag tacgtgaaca tagctacga gtgcgacatc   1980
cccatcggcg ctggaatctg cgccagctac cagacacaga caaagagcca ccggagagcc   2040
agaagcgtgg ccagccagag catcattgcc tacacaatgt ctctgggcgc cgagaacagc   2100
gtggcctact ccaacaactc tatcgctatc cccaccaact tcaccatcag cgtgaccaca   2160
gagatcctgc ctgtgtccat gaccaagacc agcgtgagc gcaccatgta catctgccgg   2220
gattccaccg agtgctccaa cctgctgctg cagtacggca gcttctgcac ccagctgaaa   2280
agagccctga cagggatcgc cgtggaacag gacaagaaca cccaagaggt gttcgcccaa   2340
gtgaagcaga tctacaagac ccctcctatc aagtacttcg gcggcttcaa tttcagccag   2400
atcctgcccg atcctagcaa gcccagcaag cggacctctc tcgaggacct gctgttcaac   2460
aaagtgacac tggccgacgc cggcttcatc aagcagtatg gcgattgtct gggcgacatt   2520
gccgccaggg atctgatttg cgcccagaag tttaacggac tgacagtgct gcctcctctg   2580
ctgaccgatg agatgatcgc ccagtacaca tctgccctgc tggccggcac aatcacaagc   2640
ggctggacat ttggagcagg cgccgctctg cagatcccct ttgctatgca gatggcctac   2700
cggttcaacg gcatcggagt gacccagaat gtgctgtacg agaaccagaa gctgatcgcc   2760
aaccagttca acagcgccat cggcaagatc caggacagcc tgagcagcac agcaagcgcc   2820
ctgggaaagc tgcaggacgt ggtcaaccac aatgcccagg cactgaacac cctggtcaag   2880
cagctgtcct ccaagttcgg cgccatcagc tctgtgctga cgatatcct gagcagactg   2940
gaccctcctg aggccgaggt gcagatcgac agactgatca caggcagact gcagagcctc   3000
cagacatacg tgacccagca gctgatcaga gccgccgaga ttagagcctc tgccaatctg   3060
gccgccacca agatgtctga gtgtgtgctg ggcagagca agagtgga cttttgcggc   3120
aagggctacc acctgatgag cttccctcag tctgcccctc acggcgtggt gtttctgcac   3180
gtgacatatg tgcccgctca agagaagaat ttcaccaccg ctccagcca tgccacgtg   3240
ggcaaagccc acttcctag agaaggcgtg ttcgtgtca acggcaccca ttggttcgtg   3300
acacagcgga acttctacga gcccagatc atccaccacg acaacaccct cgtgtctggc   3360
aactgcgacg tcgtgatcgg cattgtgaac aataccgtgt acgaccctct gcagcccgag   3420
ctggacagct tcaaagagga actggacaag tactttaaga accacacaag ccccgacgtg   3480
gacctgggcg atatcagcgg aatcaatgcc agcgtcgtga acatccagaa agagatcgac   3540
cggctgaacg aggtggccaa gaatctgaac gagagcctga tcgacctgca agaactgggg   3600
aagtacgagc agtacatcaa gtgggcctgg tacatctggc tgggctttat cgccggactg   3660
attgccatcg tgatggtcac aatcatgctg tgttgcatga ccagctgctg tagctgcctg   3720
aagggctgtt gtagctgtgg cagctgctgc aagttcgacg aggacgattc tgagcccgtg   3780
ctgaagggcg tgaaactgca ctacacatga tga                                3813
```

SEQ ID NO: 176 moltype = RNA length = 4270
FEATURE Location/Qualifiers
source 1..4270
mol_type = other RNA
organism = synthetic construct
SEQUENCE: 176

```
agaataaact agtattcttc tggtcccac agactcagag agaacccgcc accatgttcg   60
tgttcctggt gctgctgcct ctggtgtcca gccagtgtgt gaacctgatc accagaacac  120
agtcatacac caacagcttt accagaggcg tgtactaccc cgacaaggtg ttcagatcca  180
gcgtgctgca ctctacccag gacctgttcc tgcctttctt cagcaacgtg acctggttcc  240
acgccatcca cgtgtccggc accaatggca ccaagagatt cgacaacccc gcctgccct   300
tcaacgacgg ggtgtacttt gccagcaccg agaagtccaa catcatcaga ggctggatct  360
tcggcaccac actggacagc aagacccaga gcctgctgat cgtgaacaac gccaccaacg  420
tggtcatcaa agtgtgcgag ttccagttct gcaacgaccc cttcctggac gtctaccaga  480
agaacaacaa gagctggatg gaaagcgagt tccgggtgta cagcagcgcc aacaactgca  540
ccttcgagta cgtgtcccag cctttcctga tggacctgga aggcaaggag gtgaacttca  600
agaacctgcg cgagttcgtg tttaagaaca tcgacggcta cttcaagatc tacagcaagc  660
acacccctat caacctcgag cgggatctgc ctcagggctt ctctgctctg gaaccctcg  720
tggatctgcc catcggcatc aacatcaccc ggtttcagac actgctggcc ctgcacagaa  780
gctacctgac acctggcggc agcagcagcg gatggacagc tggtgccgcc gcttactatg  840
tgggctacct gcagcctaga accttcctgc tgaagtacaa cgagaacggc accatcaccg  900
acgccgtgga ttgtgctctg gatcctctga gcgagacaaa gtgcaccctg aagtccttca  960
ccgtggaaaa gggcatctac cagaccagca acttccgggt gcagcccacc gaatccatcg 1020
tgcggttccc caatatcacc aatctgtgcc ccttccacga ggtgttcaat gccaccacct 1080
tcgcctctgt gtacgcctgg aaccggaagc ggatcagcaa ttgcgtggcc gactactccg 1140
tgatctacaa cttcgccccc ttcttcgcat tcaagtgcta cggcgtgtcc cctaccaagc 1200
tgaacgacct gtgcttcaca aacgtgtacg ccgacagctt cgtgatccgg ggaaacgaag 1260
tgtcacagat tgccctgga cagacaggca catcgccga ctacaactac aagctgcccg 1320
acgacttcac cggctgtgtg attgcctgga acagcaacaa gctggactcc aaacccagcg 1380
gcaactacaa ttacctgtac cggctgttcc ggaagtccaa gctgaagccc ttcgagcggg 1440
acatctccac cgagatctat caggccggca caaagcttg taacggcgtg caggccccca 1500
actgctacag cccactgcag tcctacggct taggcccac atacggcgtg gccaccagc  1560
cctacagagt ggtggtgctg agcttcgaac tgctgcatgc ctcagccaca gtgtgcggcc 1620
ctaagaaaag caccaatctc gtgaagaaca aatgcgtgaa cttcaacttc aacggcctgc 1680
ccggcaccgg cgtgctgaca gagagcaaca aagttcct gccattccag cagtttggcc  1740
gggatatcgc cgataccaca gacgccgtta gagatcccca gacactggaa atcctggaca 1800
tcaccccttg cagcttcggc ggagtgtctg tgatcacccc tggcaccaac accagcaatc 1860
aggtggcagt gctgtaccag ggcgtgaact gtaccgaagt gcccgtggcc attcacgccg 1920
atcagctgac acctacatgg cgggtgtact ccaccggcag caatgtgttt cagaccagag 1980
ccggctgtct gatcggagcc gagtacgtga acaatagcta cgagtgcgac atccccatcg 2040
gcgctggaat ctgcgccagc taccagacac agacaaagag ccaccggaga gccagaagcg 2100
tggccagcca gagcatcatt gcctacaaa tgtctctggg cgccgagaac agcgtggcct  2160
actccaacaa ctctatcgct atccccacca cacttcaccat accagagatcc 2220
tgcctgtgtc catgaccaag accagctggg actgcaccat gtacatctgc ggcgattcca 2280
ccgagtgctc caacctgctg ctgcagtacg gcagcttctg cacccagctg aaaagagccc 2340
tgacaggat cgccgtggaa caggacaaga cacccaaga ggtgttcgcc caagtgaagc  2400
agatctacaa gaccccctcc tcaagtact tcggcggctt caatttcagc cagattctgc 2460
ccgatcctag caagcccagc aagcggagct catccgagga cctgctgttc aacaaagtga 2520
cactggccga cgccggcttc atcaagcagt atggcgattg tctgggcgac attgccgcca 2580
gggatctgat ttgcgcccag aagtttaacg gactgacagt gctgcctcct ctgctgaccg 2640
atgagatgat cgcccagtac acatctgccc tgctggccag cacaatcaca agcggctgga 2700
catttggagc aggcgccgct ctgcagatcc cctttgctat gcagatggcc taccggttca 2760
acggcatcgg agtgacccag aatgtgctgt acgagaacca gaagctgatc gccaaccagt 2820
tcaacagcgc catcggcaag atccaggaca gcctgagcag cacagcaagc gccctgggaa 2880
agctgcagga cgtggtcaac cacaatgccc aggcactgaa caccctggtc aagcagctgt 2940
cctccaagtt cggcgccatc agctctgtgc tgaacgatat cctgagcaga ctggaccctc 3000
ctgaggccga ggtgcagatc gacagactga tcacaggcag actgcagagc ctccagacat 3060
acgtgaccca gcagctgatc agagccgccg agattagagc ctctgccaat ctggccgcca 3120
ccaagatgtc tgagtgtgtg ctgggccaga gcaagagagt ggacttttgc ggcaagggcc 3180
accacctgat gagcttccct cagtctgccc ctcacggcgt ggtgtttctg cacgtgacat 3240
atgtgcccgc tcaagagaag aatttcacca ccgctccagc catctgccac gacggcaaag 3300
cccactttcc tagagaaggc gtgttcgtgt ccaacggcac ccattggttc gtgacacagc 3360
ggaacttcta cgagccccag atcatcacca ccgacaacac cttcgtgtct ggcaactgcg 3420
acgtcgtgat cggcattgtg aacaataccg tgtacgaccc tctgcagccc gagctggaca 3480
gcttcaaaga ggaactggac aagtacttta agaaccacac aagccccgac gtggacctgg 3540
gcgatatcag cggaatcaat gccagcgtcg tgaacatcca gaaagagatc gaccggctga 3600
acgaggtggc caagaatctg aacgagagcc tgatcgacct gcaagaactg gggaagtacg 3660
agcagtacat caagtggccc tggtacatct ggctgggctt tatcgccgga ctgattgcca 3720
tcgtgatggt cacaatcatg ctgtgttgca tgaccagctg ctgtagctgc ctgaagggcg 3780
gttgtagctg tggcagctgc tgcaagttcg acgaggacga ttctgagccc gtgctgaagg 3840
gcgtgaaact gcactacaca tgatgactcg agctggtact gcatgcacgc aatgctagct 3900
gcccctttcc cgtcctgggt acccccgagtc tcccccgacc tcgggtccca ggtatgctcc 3960
cacctccacc tgcccactc accacctctg ctagttccag acacctccca agcacgcagc 4020
aatgcagctc aaaacgctta gcctagccac accccccacgg gaacaagcag tgattaacct 4080
ttagcaataa acgaaagttt aactaagcta tactaaccc agggttggtc aatttcgtgc 4140
cagccacacc ctgagctag caaaaaaaaa aaaaaaaaaa aaaaaaaaaa agcatatgac 4200
taaaaaaaaa aaaaaaaaaa aaaaaaaaaa aaaaaaaaaa aaaaaaaaaa aaaaaaaaaa 4260
aaaaaaaaaa                                                       4270
```

| SEQ ID NO: 177 | moltype = DNA length = 4270 |
|---|---|
| FEATURE | Location/Qualifiers |
| source | 1..4270 |
| | mol_type = other DNA |
| | organism = synthetic construct |

SEQUENCE: 177
```
agaataaact agtattcttc tggtccccac agactcagag agaacccgcc accatgttcg    60
tgttcctggt gctgctgcct ctggtgtcca gccagtgtgt gaacctgatc accagaacac   120
agtcatacac caacagcttt accagaggcg tgtactaccc cgacaaggtg ttcagatcca   180
gcgtgctgca ctctacccag gacctgttcc tgcctttctt cagcaacgtg acctggttcc   240
acgccatcca cgtgtccggc accaatggca ccaagagatt cgacaacccc gccctgccct   300
tcaacgacgg ggtgtacttt gccagcaccg agaagtccaa catcatcaga ggctggatct   360
tcggcaccac actggacagc aagacccaga gcctgctgat cgtgaacaac gccaccaacg   420
tggtcatcaa agtgtgcgag ttccagttct gcaacgaccc cttcctggac gtctaccaga   480
agaacaacaa gagctggatg gaaagcgagt tccgggtgta cagcagcgcc aacaactgca   540
ccttcgagta cgtgtcccag cctttcctga tggacctgga aggcaaggag gtgaacttca   600
agaacctgcg cgagttcgtg tttaagaaca tcgacggcta cttcaagatc tacagcaagc   660
acacccctat caacctcgag cgggatctgc ctcagggctt ctctgctctg gaaccctcgg   720
tggatctgcc catcggcatc aacatcaccc ggtttcagac actgctggcc ctgcacagaa   780
gctacctgac acctggcggc agcagcagcg gatggacagc tggtgccgcc gcttactatg   840
tgggctacct gcagcctaga accttcctgc tgaagtacaa cgagaacggc accatcaccg   900
acgccgtgga ttgtgctctg gatcctctga gcgagacaaa gtgcaccctg aagtccttca   960
ccgtggaaaa gggcatctac cagaccagca acttccgggt gcagcccacc gaatccatcg  1020
tgcggttccc caatatcacc aatctgtgcc ccttccacga ggtgttcaat gccaccacct  1080
tcgcctctgt gtacgcctgg aaccggaagc ggatcagcaa ttgcgtggcc gactactccg  1140
tgatctacaa cttcgcccc ttcttcgcat tcaagtgcta cggtgtcc cctaccaagc  1200
tgaacgacct gtgcttcaca aacgtgtacg ccgacagctt cgtgatccgg ggaaacgaag  1260
tgtcacagat tgcccctgga cagacaggca acatcgccga ctacaactac aagctgcccg  1320
acgacttcac cggctgtgtg attgcctgga acagcaacaa gctggactcc aaacccagcg  1380
gcaactacaa ttacctgtac cggctgttcc ggaagtccaa gctgaagccc ttcgagcggg  1440
acatctccac cgagatctat caggccggca caagccttg taacggcgtg gcaggcccca  1500
actgctacag cccactgcag tcctacggct taggcccac atacggcgtg ggccaccagc  1560
cctacagagt ggtggtgctg agcttcgaac tgctgcatgc ctcagccaca gtgtgcggcc  1620
ctaagaaaag caccaatctc gtgaagaaca aatgcgtgaa cttcaacttc aacggcctga  1680
ccggcaccgg cgtgctgaca gagagcaaca agaagttcct gccattccag cagtttggcc  1740
gggatatcgc cgataccaca gacgccgtta gagatcccca gacactgaa atcctggaca  1800
tcaccccttg cagcttcggc ggagtgtctg tgatcacccc tggcaccaac accagcaatc  1860
aggtggcagt gctgtaccag ggcgtgaact gtaccgaagt gcccgtggcc attcacgccg  1920
atcagctgac acctacatgg cgggtgtact ccaccgacgg caatgtgttt cagaccagag  1980
ccggctgtct gatcggagcc gagtacgtga acaatagcta cgagtgcgac atccccatcg  2040
gcgctggaat ctgcgccagc tacagacaca gacaaagag ccaccggaga gccagaagcg  2100
tggccagcca gagcatcatt gcctacaaa tgtctctggg cgccgagaac agcgtggcct  2160
actccaacaa ctctatcgct atccccacca acttcaccat cagcgtgacc acagagatca  2220
tgcctgtgtc catgaccaag accagcgtgg actgcaccat gtacatctgc ggcgattcca  2280
ccgagtgctc caacctgctg ctgcagtacg gcagcttctg cacccagctg aaaagagccc  2340
tgacaggat cgccgtggaa caggacaaga acacccaaga ggtgttcgcc caagtgaagc  2400
agatctacaa gaccccttct atcaagtact tcggcggctt caatttcagc cagattctgc  2460
ccgatcctag caagcccagc aagcggagct catcgagga cctgctgttc aacaaagtga  2520
cactggccga cgccggcttc atcaagcagt atggcgattg tctgggcgac attgccgcca  2580
gggatctgat ttgcgcccag aagtttaacg gactgacagt gctgcctcct ctgctgaccg  2640
atgagatgat cgcccagtac acatctgccc tgctggccag cacaatcaca agcggctgga  2700
catttggagc aggcgccgct ctgcagatcc cctttgctat gcagatggcc taccggttca  2760
acggcatcgg agtgacccag aatgtgctgt acgagaacca gaagctgatc gccaaccagt  2820
tcaacagcgc catcggcaag atccaggaca gcctgagcag cacagcaagc gccctgggaa  2880
agctgcagga cgtggtcaac cacaatgccc aggcactgaa caccctggtc aagcagctgt  2940
cctccaagtt cggcgccatc agctctgtgc tgaacgatat cctgagcaga ctggaccctc  3000
ctgaggccga ggtgcagatc gacagactga tcacaggcag actgcagagc ctccagacat  3060
acgtgaccca gcagctgatc agagccgccg agattagagc ctctgccaat ctggccgcca  3120
ccaagatgtc tgagtgtgtg ctgggccaga gcaagagagt ggacttttgc ggcaagggct  3180
accaccttgt gagcttccct cagtctgccc ctcacggcgt ggtgtttctg cacgtgacat  3240
atgtgcccgc tcaagagaag aatttcacca ccgctccagc catctgccac gacggcaaag  3300
cccactttcc tagagaaggc gtgttcgtgt ccaacggcac ccattggttc gtgacacagc  3360
ggaacttcta cgagccccag atcatcacca ccgacaacac cttcgtgtct ggcaactgcg  3420
acgtcgtgat cggcattgtg aacaataccg tgtacgaccc tctgcagccc gagctggaca  3480
gcttcaaaga ggaactggac aagtacttta agaaccacac aagccccgac gtggacctgg  3540
gcgatatcag cggaatcaat gccagcgtcg tgaacatcca gaaagagatc gaccggctga  3600
acgaggtggc caagaatctg aacgagagcc tgatcgacct gcaagaactg gggaagtacg  3660
agcagtacat caagtggccc tggtacatct ggctgggctt tatcgccgga ctgattgcca  3720
tcgtgatggt cacaatcatg ctgtgttgca tgaccagctg ctgtagctgc ctgaagggct  3780
gttgtagctg tggcagctgc tgcaagttcg acgaggacga ttctgagccc gtgctgaagg  3840
gcgtgaaact gcactacaca tgatgactcg agctggtact gcatgcacgc aatgctagct  3900
gcccctttcc cgtcctgggt acccccgagtc tccccgacc tcgggtccca ggtatgctcc  3960
cacctccacc tgcccactc accacctctg ctagttccag acacctccca agcacgcagc  4020
aatgcagctc aaaacgctta gcctagccac accccacgg tgattaacct  4080
ttagcaataa acgaaagttt aactaagcta tactaacccc agggttggtc aatttcgtgc  4140
cagccacacc ctgagctag caaaaaaaaa aaaaaaaaaa aaaaaaaaaa agcatatgac  4200
taaaaaaaa aaaaaaaaaa aaaaaaaaaa aaaaaaaaaa aaaaaaaaaa aaaaaaaaaa  4260
aaaaaaaaaa                                                         4270
```

CORONAVIRUS VACCINE

This application claims the benefit of priority under 35 U.S.C. § 120 to each of the following applications, the disclosure of each of which is hereby incorporated by reference in its entirety: U.S. Application No. 63/355,648, filed Jun. 26, 2022; U.S. Application No. 63/357,628 filed Jun. 30, 2022; U.S. Application No. 63/358,522, filed Jul. 5, 2022; U.S. Application No. 63/394,571, filed Aug. 2, 2022; U.S. Application No. 63/402,444, filed Aug. 30, 2022; U.S. Application No. 63/417,680, filed: Oct. 19, 2022; U.S. Application No. 63/422,404, filed Nov. 3, 2022; U.S. Application No. 63/425,290, filed Nov. 14, 2022; U.S. Application No. 63/486,953 filed: Feb. 24, 2023; U.S. Application No. 63/452,148 filed: Mar. 14, 2023; U.S. Application No. 63/465,521, filed: May 10, 2023; and U.S. Application No. 63/469,472, filed May 29, 2023. This application also claims the benefit of priority under 35 U.S.C. § 119 to international application no. PCT/EP2022/083740, filed Nov. 29, 2022, the contents of which is incorporated by reference herein in its entirety.

The instant application contains a Sequence Listing which has been submitted electronically in .xml format and is hereby incorporated by reference in its entirety. Said .xml file, created on Jun. 26, 2023, is identified as 2013237-0687_SL.xml and is 540,905 bytes in size.

This disclosure relates to the field of RNA to prevent or treat coronavirus infection. In particular, the present disclosure relates to methods and agents for vaccination against coronavirus infection and inducing effective coronavirus antigen-specific immune responses such as antibody and/or T cell responses. These methods and agents are, in particular, useful for the prevention or treatment of coronavirus infection. Administration of RNA disclosed herein to a subject can protect the subject against coronavirus infection. Specifically, in one embodiment, the present disclosure relates to methods comprising administering to a subject RNA encoding a peptide or protein comprising an epitope of SARS-CoV-2 spike protein (S protein) for inducing an immune response against coronavirus S protein, in particular S protein of SARS-CoV-2, in the subject, i.e., vaccine RNA encoding vaccine antigen. Administering to the subject RNA encoding vaccine antigen may provide (following expression of the RNA by appropriate target cells) vaccine antigen for inducing an immune response against vaccine antigen (and disease-associated antigen) in the subject.

SARS-CoV-2 infections and the resulting disease COVID-19 have spread globally, affecting a growing number of countries. On 11 Mar. 2020 the WHO characterized the COVID-19 outbreak as a pandemic. As of 1 Dec. 2020, there have been >63 million globally confirmed COVID-19 cases and >1.4 million deaths, with 191 countries/regions affected. The ongoing pandemic remains a significant challenge to public health and economic stability worldwide.

The present invention is directed to a composition comprising an RNA molecule having:
(a) a nucleotide sequence that is at least 99% identical to SEQ ID NO: 161;
(b) a nucleotide sequence that is at least 95% identical to SEQ ID NO: 161, and which encodes a SARS-CoV-2 S protein comprising the following mutations relative to SEQ ID NO: 1: T19I, Δ24-26, A27S, V83A, G142D, Δ145, H146Q, Q183E, V213E, G252V, G339H, R346T, L368I, S371F, S373P, S375F, T376A, D405N, R408S, K417N, N440K, V445P, G446S, N460K, S477N, T478K, E484A, F486P, F490S, Q498R, N501Y, Y505H, D614G, H655Y, N679K, P681H, N764K, D796Y, Q954H, N969K, K986P, and V987P; or
(c) a nucleotide sequence as set forth in SEQ ID NO: 161; and
wherein the RNA molecule comprises:
(i) a 5' cap; and
(ii) a modified uridine in place of each uridine.

The present invention is also directed to a composition of the invention for use in a method of inducing an immune response against coronavirus in a subject, said method comprising administering to a subject the composition.

In some embodiments, the modified uridine can be N1-methyl-pseudouridine.

In some embodiments, the 5' cap can comprise $m2^{7,3'\text{-}O}Gppp(m_1^{2'\text{-}O})ApG$.

In come embodiments, the RNA molecule can be encapsulated in a lipid nanoparticle (LNP), preferably wherein the LNP comprises molar ratios of 20-60% ionizable cationic lipid, 5-25% neutral lipid, 25-55% sterol, and 0.5-15% PEG-modified lipid.

In some embodiments, the composition can comprise one or more additional RNA molecules, each having a nucleotide sequence encoding an S protein of a SARS-CoV-2 strain or variant that is not XBB.1.5, preferably wherein the one or more additional RNA molecules comprise a sequence that is at least 95% identical to that set forth in SEQ ID NO: 20, 72, or 103.

In some embodiments, the RNA molecule comprises:
(i) N1-methyl-pseudouridine in place of each uridine; and
(ii) a 5' cap that comprises $m2^{7,3'\text{-}O}Gppp(m_1^{2'\text{-}O})ApG$;
wherein the RNA molecule is encapsulated in a lipid nanoparticle (LNP); and
wherein the LNP comprises molar ratios of 20-60% ionizable cationic lipid, 5-25% neutral lipid, 25-55% sterol, and 0.5-15% PEG-modified lipid.

In some embodiments, the composition can comprise about 10 mM Tris buffer and about 10% sucrose.

In some embodiments, the composition can comprise at least one unit dose of LNP-encapsulated RNA molecules, optionally wherein the unit dose comprises the RNA molecule in an amount of about 30 µg, or wherein the unit dose comprises the RNA molecule in an amount of about 10 µg, or wherein the unit dose comprises the RNA molecule in an amount of about 3 µg.

In some embodiments, the composition is formulated as a multi-dose formulation in a vial.

In some embodiments, the subject can be 12 years or older, and the composition can comprise 30 µg of the RNA molecule, or the subject can be 5 years to less than 12 years old, and the composition can comprise 10 µg of the RNA molecule, or the subject can be 6 months to less than 5 years old, and the composition can comprise 3 µg of the RNA molecule.

In some embodiments, the composition can be administered in a volume of about 200 µL to 300 µL.

In some embodiments, the subject was previously administered one or more doses of a SARS-CoV-2 vaccine, preferably wherein the subject was previously administered a complete dosing regimen of a SARS-CoV-2 vaccine.

In some embodiments, the subject was previously administered a first dose and a second dose of BNT162b2, wherein the first dose and the second dose were administered about 21 days apart, and/or wherein the subject was previously administered as a booster dose a bivalent vaccine that delivers (i) a SARS-CoV-2 S protein of an Omicron BA.4/5 variant and (ii) a SARS-CoV-2 S protein of a Wuhan strain.

In some embodiments, said method can further comprise administering one or more vaccines against a non-SARS-CoV-2 disease, preferably wherein the one or more vaccines comprises an RSV vaccine, an influenza vaccine, or a combination thereof.

In some embodiments, compositions disclosed herein (e.g., monovalent compositions comprising RNA encoding a SARS-CoV-2 S protein of an XBB.1.5 variant) can induce a strong immune response (e.g., high neutralization titers) against certain SARS-CoV-2 variants of concern (e.g., XBB variants of concern (including, e.g., an XBB.1.5 variant, an XBB.1.16 variant, an XBB.2.3 variant, and/or an XBB.2.3.2 variant)). In some embodiments, such compositions are monovalent compositions comprising RNA encoding a SARS-CoV-2 S protein of an XBB.1.5 variant. In some embodiments, such compositions are monovalent compositions comprising RNA encoding a SARS-CoV-2 S protein of an XBB.1.16 variant. In some embodiments, such compositions are monovalent compositions comprising RNA encoding a SARS-CoV-2 S protein of an XBB.2.3 variant. In some embodiments, such compositions are monovalent compositions comprising RNA encoding a SARS-CoV-2 S protein of an XBB.2.3.2 variant. As demonstrated herein, in some embodiments, such compositions can induce surprisingly high neutralization titers against certain XBB variants of concern (including, e.g., XBB.1.5, XBB.1.16, and XBB.2.3 variants of concern). Even more surprisingly, in some embodiments, such compositions can induce neutralization titers that are higher against a given variant than a variant-matched vaccine (e.g., in some embodiments, RNA described herein comprising a nucleotide sequence that encodes an XBB.1.5 S protein, can induce neutralization titers against a XBB.1.16 variant of concern that are higher than those induced by an XBB.1.16-adapted vaccine). In some embodiments, the strong immune response can be observed in vaccine-naïve subjects (e.g., young pediatric patients (e.g., patients 6 months to less than 5 years old). In some embodiments, the strong immune response can be observed in subjects without a previous or current coronavirus infection (e.g., a SARS-CoV-2 infection). In some embodiments, a strong immune response can be observed in subjects who previously received a SARS-CoV-2 vaccine (e.g., in some embodiments an RNA vaccine encoding a SARS-CoV-2 S protein, e.g., in some embodiments of a Wuhan strain) and/or who were previously infected with SARS-CoV-2. In some embodiments, such broader cross-neutralization can be observed in young pediatric subjects (e.g., subjects aged 6 months to less than 2 years, and/or 2 years to less than 5 years).

DEFINITIONS

Figure 1:
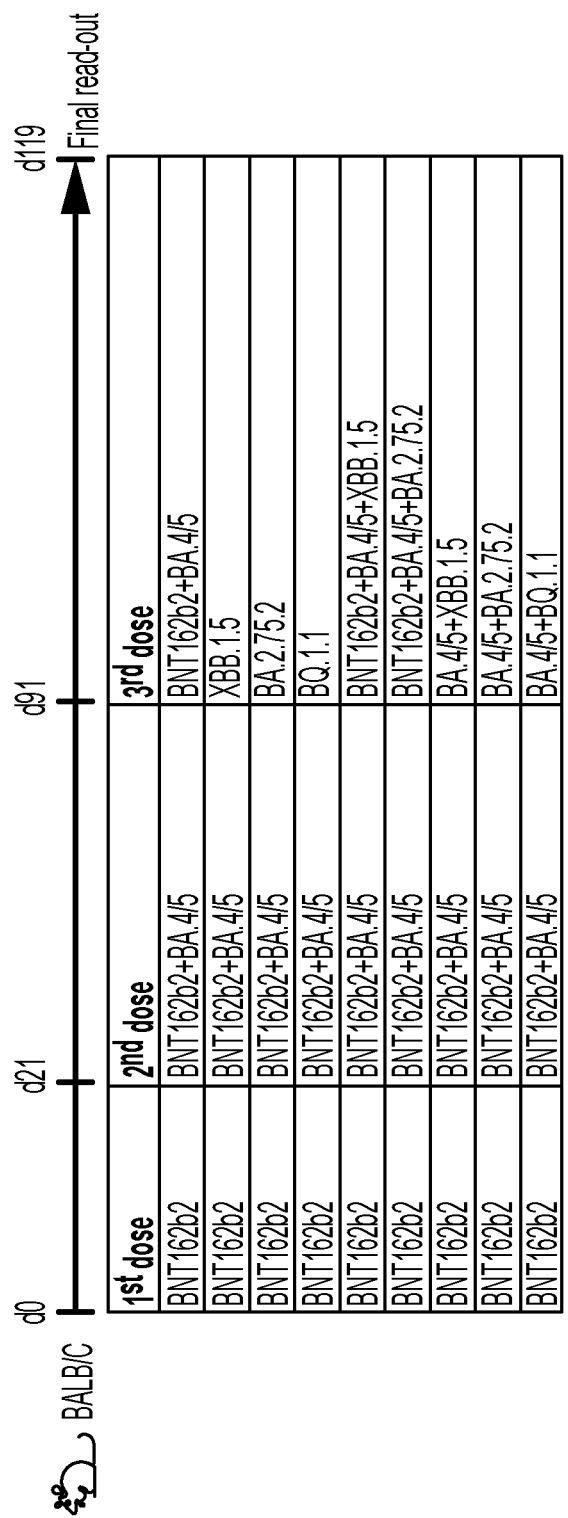
FIG. 1. Experimental design for a study to characterize immune responses induced by variant-adapted vaccines in SARS-CoV-2 vaccine-experienced mice. Mice are split into 9 groups, each of which is administered a first dose of an RNA encoding a SARS-CoV-2 S protein of a Wuhan strain (BNT162b2) and a second dose of a bivalent composition comprising a first RNA encoding a SARS-CoV-2 S protein of a Wuhan strain and a second RNA encoding a SARS-COV-2 S protein of an Omicron BA.4/5 variant (BNT162b2+BA.4/5). Following the second dose, mice are administered a composition comprising an RNA encoding a SARS-CoV-2 S protein of a strain or variant or combination of strains/variants, as indicated in the Figure. The first and second doses are administered 21 days apart, and the third dose is administered about 70 days after the third dose. 119 days after administering the first dose, mice are sacrificed and the experiment concluded.

The term "about" means approximately or nearly, and in the context of a numerical value or range set forth herein in one embodiment means±20%, ±10%, ±5%, or ±3% of the numerical value or range recited or claimed.

The terms "a" and "an" and "the" and similar reference used in the context of describing the present disclosure (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it was individually recited herein. All methods described herein can be performed in any suitable order unless otherwise indicated herein or otherwise clearly contradicted by context. The use of any and all examples, or exemplary language (e.g., "such as"), provided herein is intended merely to better illustrate the disclosure and does not pose a limitation on the scope of the claims. No language in the specification should be construed as indicating any non-claimed element essential to the practice of the disclosure.

RNA

In the present disclosure, the term "RNA" relates to a nucleic acid molecule which includes ribonucleotide residues. In preferred embodiments, the RNA contains all or a majority of ribonucleotide residues. As used herein, "ribonucleotide" refers to a nucleotide with a hydroxyl group at the 2'-position of a β-D-ribofuranosyl group. RNA encompasses without limitation, double stranded RNA, single stranded RNA, isolated RNA such as partially purified RNA, essentially pure RNA, synthetic RNA, recombinantly produced RNA, as well as modified RNA that differs from naturally occurring RNA by the addition, deletion, substitution and/or alteration of one or more nucleotides. Such alterations may refer to addition of non-nucleotide material to internal RNA nucleotides or to the end(s) of RNA. It is also contemplated herein that nucleotides in RNA may be non-standard nucleotides, such as chemically synthesized nucleotides or deoxynucleotides. For the present disclosure, these altered RNAs are considered analogs of naturally-occurring RNA.

In certain embodiments of the present disclosure, the RNA is messenger RNA (mRNA) that relates to a RNA transcript which encodes a peptide or protein. As established in the art, mRNA generally contains a 5' untranslated region (5'-UTR), a peptide coding region and a 3' untranslated region (3'-UTR). In some embodiments, the RNA is produced by in vitro transcription or chemical synthesis. In one embodiment, the mRNA is produced by in vitro transcription using a DNA template where DNA refers to a nucleic acid that contains deoxyribonucleotides.

In one embodiment, RNA described herein may have modified nucleosides. In some embodiments, RNA comprises a modified nucleoside in place of at least one (e.g., every) uridine. In some embodiments, one or more uridine in the RNA described herein is replaced by a modified nucleoside. In some embodiments, RNA comprises a modified nucleoside in place of each uridine. In some embodiments, the modified nucleoside is a modified uridine.

One exemplary modified nucleoside is N1-methyl-pseudouridine (m1Ψ), which has the structure:

In some embodiments, RNA according to the present disclosure comprises a 5'-cap. The term "5'-cap" refers to a structure found on the 5'-end of an mRNA molecule and generally consists of a guanosine nucleotide connected to the mRNA via a 5'- to 5'-triphosphate linkage. In one embodiment, this guanosine is methylated at the 7-position. Providing an RNA with a 5'-cap or 5'-cap analog may be achieved by in vitro transcription, in which the 5'-cap is co-transcriptionally expressed into the RNA strand, or may be attached to RNA post-transcriptionally using capping enzymes.

In some embodiments, the building block cap for RNA is $m_2^{7,3'-O}Gppp(m_1^{2'-O})ApG$ (also sometimes referred to as $m_2^{7,3'-O}G(5')ppp(5')m^{2'-O}ApG$), which has the following structure:

In one embodiment, the 5'-UTR sequence is derived from the human alpha-globin mRNA and optionally has an optimized 'Kozak sequence' to increase translational efficiency.

In one embodiment, RNA encoding an amino acid sequence comprising a SARS-CoV-2 S protein, an immunogenic variant thereof, or an immunogenic fragment of the SARS-CoV-2 S protein or the immunogenic variant thereof comprises a 5' UTR comprising the nucleotide sequence of SEQ ID NO: 12, or a nucleotide sequence having at least 99%, 98%, 97%, 96%, 95%, 90%, 85%, or 80% identity to the nucleotide sequence of SEQ ID NO: 12.

In one embodiment, a combination of two sequence elements (FI element) derived from the "amino terminal enhancer of split" (AES) mRNA (called F) and the mitochondrial encoded 12S ribosomal RNA (called I) are placed between the coding sequence and the poly(A) sequence to assure higher maximum protein levels and prolonged persistence of the RNA (e.g., mRNA). In one embodiment, two re-iterated 3'-UTRs derived from the human beta-globin mRNA are placed between the coding sequence and the poly(A) sequence to assure higher maximum protein levels and prolonged persistence of the RNA (e.g., mRNA).

In one embodiment, RNA encoding an amino acid sequence comprising a SARS-CoV-2 S protein, an immunogenic variant thereof, or an immunogenic fragment of the SARS-CoV-2 S protein or the immunogenic variant thereof comprises a 3' UTR comprising the nucleotide sequence of SEQ ID NO: 13, or a nucleotide sequence having at least 99%, 98%, 97%, 96%, 95%, 90%, 85%, or 80% identity to the nucleotide sequence of SEQ ID NO: 13.

In one embodiment, a poly(A) sequence measuring 110 nucleotides in length, consisting of a stretch of 30 adenosine residues, followed by a linker sequence (e.g., 10 nucleotide linker sequence) and another 70 adenosine residues is used. This poly(A) sequence was designed to enhance RNA stability and translational efficiency.

In one embodiment, the poly-A sequence comprises at least 100 nucleotides.

In one embodiment, the poly-A sequence comprises or consists of the nucleotide sequence of SEQ ID NO: 14.

RNA Encoding SARS-CoV-2 S Protein of an XBB.1.5 Variant

In some embodiments, RNA described herein encodes a SARS-CoV-2 S protein comprising one or more mutations characteristic of an Omicron XBB.1.5 variant. In some embodiments, the one or more mutations characteristic of an Omicron XBB.1.5 variant include F486P. In some embodiments, the one or more mutations characteristic of an Omicron XBB.1.5 variant include T19I, Δ24-26, A27S, V83A, G142D, Δ144, H146Q, Q183E, V213E, G252V, G339H, R346T, L368I, S371F, S373P, S375F, T376A, D405N, R408S, K417N, N440K, V445P, G446S, N460K, S477N, T478K, E484A, S486P, F490S, Q498R, N501Y, Y505H, D614G, H655Y, N679K, P681H, N764K, D796Y, Q954H, and N969K, or any combination thereof. In some embodiments, the one or more mutations characteristic of an Omicron XBB.1.5 variant include T19I, Δ24-26, A27S, V83A, G142D, Δ145, H146Q, Q183E, V213E, G252V, G339H, R346T, L368I, S371F, S373P, S375F, T376A, D405N, R408S, K417N, N440K, V445P, G446S, N460K, S477N, T478K, E484A, F486P, F490S, Q498R, N501Y, Y505H, D614G, H655Y, N679K, P681H, N764K, D796Y, Q954H, and N969K, or any combination thereof.

In some embodiments, RNA described herein encodes a SARS-CoV-2 S protein comprising one more mutations that stabilize a prefusion confirmation. In some embodiments, stabilization of a prefusion conformation of a SARS-CoV-2 S protein may be obtained by introducing two consecutive proline substitutions at residues 986 and 987 in the full length spike protein (positions shown relative to SEQ ID NO: 1; for variant adapted sequences, proline substitutions can be introduced at corresponding positions). Specifically, spike (S) protein stabilized protein variants can be obtained by exchanging the amino acid residue at position 986 to proline and the amino acid residue at position 987 to proline. In one embodiment, a SARS-CoV-2 S protein variant wherein the prototypical prefusion conformation is stabilized comprises the amino acid sequence shown in SEQ ID NO: 7. In one embodiment, the SARS-CoV-2 S protein can comprise the following mutations relative to SEQ ID NO: 7: T19I, Δ24-26, A27S, V83A, G142D, Δ145, H146Q, Q183E, V213E, G252V, G339H, R346T, L368I, S371F, S373P, S375F, T376A, D405N, R408S, K417N, N440K, V445P, G446S, N460K, S477N, T478K, E484A, F486P, F490S, Q498R, N501Y, Y505H, D614G, H655Y, N679K, P681H, N764K, D796Y, Q954H, and N969K.

In some embodiments, an RNA composition described herein comprises an RNA encoding a polypeptide as set forth in SEQ ID NO: 158 or an immunogenic fragment thereof, or a variant thereof (e.g., having at least 70% or more, including, e.g., at least 80%, at least 85%, at least 90%, at least 95%, at least 96%, at least 97%, at least 98%, or higher, identity to SEQ ID NO: 158). In some embodiments, an RNA composition comprises an RNA that includes the sequence of SEQ ID NO: 159 or a variant thereof (e.g., having at least 70% or more, including, e.g., at least 80%, at least 85%, at least 90%, at least 95%, at least 96%, at least 97%, at least 98%, or higher, identity to SEQ ID NO: 159). In some embodiments, an RNA composition comprises an RNA that includes the sequence of SEQ ID NO: 161 or a variant thereof (e.g., having at least 70% or more, including, e.g., at least 80%, at least 85%, at least 90%, at least 95%, at least 96%, at least 97%, at least 98%, or higher, identity to SEQ ID NO: 161).

In some embodiments, an RNA composition comprises an RNA comprising (a) a nucleotide sequence of SEQ ID NO: 161 or a sequence that is at least 70% identical to SEQ ID NO: 161 (e.g., at least 80%, at least 85%, at least 90%, at least 95%, at least 96%, at least 97%, at least 98%, at least 99% or higher, identity to SEQ ID NO: 161), and/or (b) a nucleotide sequence that encodes a SARS-CoV-2 S protein having an amino acid sequence of SEQ ID NO: 158, or an amino acid sequence that is at least 70% identical to SEQ ID NO: 158 (e.g., at least 80%, at least 85%, at least 90%, at least 95%, at least 96%, at least 97%, at least 98%, at least 99% or higher, identity to SEQ ID NO: 158), and (c) wherein the SARS-CoV-2 S protein optionally comprises one or more mutations that stabilize a prefusion confirmation (e.g., proline mutations at positions 982 and 983 of SEQ ID NO: 158). In some embodiments, such a composition comprises one or more additional RNAs, each encoding an S protein of a non-XBB.1.5 SARS-CoV strain or variant (e.g., a Wuhan strain, an Omicron BA.4/5 variant, and/or an Omicron BA.2.75.2 variant (e.g., such RNAs described herein)).

In some embodiments, an RNA composition comprises an RNA comprising a nucleotide sequence that encodes a SARS-CoV-2 S protein comprising one or more mutations characteristic of an Omicron XBB.1.5 variant and wherein:

a) the SARS-CoV-2 S protein comprises an amino acid sequence having at least 99%, 98%, 97%, 96%, 95%, 90%, 85%, or 80% identity to SEQ ID NO: 158, or an immunogenic fragment thereof, and/or b) the RNA molecule encoding the SARS-CoV-2 S protein comprises a nucleotide sequence having at least 99%, 98%, 97%, 96%, 95%, 90%, 85%, or 80% identity to SEQ ID NO: 159; and/or at least 99%, 98%, 97%, 96%, 95%, 90%, 85%, or 80% identity to SEQ ID NO: 161, and wherein c) the one or more mutations characteristic of an Omicron XBB.1.5 variant are optionally selected from: T19I, Δ24-26, A27S, V83A, G142D, Δ145, H146Q, Q183E, V213E, G252V, G339H, R346T, L368I, S371F, S373P, S375F, T376A, D405N, R408S, K417N, N440K, V445P, G446S, N460K, S477N, T478K, E484A, F486P, F490S, Q498R, N501Y, Y505H, D614G, H655Y, N679K, P681H, N764K, D796Y, Q954H, and N969K, or any combination thereof.

In some embodiments, a composition comprising an RNA that comprises a nucleotide sequence encoding a SARS-CoV-2 S protein comprising one or more mutations characteristic of an XBB.1.5 variant further comprises one or more additional RNAs, each having a nucleotide sequence encoding a SARS-CoV-2 S protein of a non-XBB.1.5 SARS-CoV-2 strain or variant or strain. In some embodiments, such non-XBB.1.5 strains or variants include a Wuhan strain, an Omicron BA.4/5 strain, and/or a BQ.1.1 variant. In some embodiments, the one or more additional RNA molecules comprise a sequence that is at least 70% identical (e.g., at least 80%, at least 85%, at least 90%, at least 95%, at least 96%, at least 97%, at least 98%, at least 99% or higher, identity to) SEQ ID NO: 20, 70, or 103, or wherein the one or more additional RNA molecules comprise a sequence SEQ ID NO: 20, 72, or 103.

TABLE 1

Sequence of one embodiment of an exemplary Omicron XBB.1.5-specific RNA vaccine

| SEQ ID NO. | Brief Description | Sequence |
|---|---|---|
| 158 | Amino acid sequence of RNA-encoded SARS-COV-2 S protein from an Omicron XBB.1.5 variant (with PRO mutations at positions corresponding to K986P and V987P of SEQ ID NO: 1; i.e., PRO mutations at positions 982 and 983 of SEQ ID NO: 158) | MFVFLVLLPLV TABLE 1-continued Sequence of one embodiment of an exemplary Omicron XBB.1.5-specific RNA vaccine

| SEQ ID NO. | Brief Description | Sequence |
|---|---|---|
| | | aggcccacauacggcugugggccaccagccacagagaggu TABLE 1-continued Sequence of one embodiment of an exemplary Omicron XBB.1.5-specific RNA vaccine

| SEQ ID NO. | Brief Description | Sequence |
|---|---|---

TABLE 1-continued

Sequence of one embodiment of an exemplary Omicron XBB.1.5-specific RNA vaccine

| SEQ ID NO. | Brief Description | Sequence |
|---|---|---|
| |

TABLE 1-continued

Sequence of one embodiment of an exemplary Omicron XBB.1.5-specific RNA vaccine

| SEQ ID NO. | Brief Description | Sequence |
|---|---|---|
| 162 | Full length DNA construct encoding a SARS-CoV-2 S protein from an Omicron XBB.1.5 variant | Agaataaactagtattct TABLE 1-continued Sequence of one embodiment of an exemplary Omicron XBB.1.5-specific RNA vaccine

| SEQ ID NO. | Brief Description | Sequence |
|---|---|---|
| | | gactgattgccatcgtgatggtcacaatcatgtgttgttgcatga

Lipid Nanoparticles (LNPs)

In one embodiment, nucleic acid such as RNA described herein is administered in the form of lipid nanoparticles (LNPs) (e.g., encapsulated within or associated with an LNP). The LNP may comprise any lipid capable of forming a particle to which the one or more nucleic acid molecules are attached, or in which the one or more nucleic acid molecules are encapsulated.

In one embodiment, LNP comprise a cationic lipid, a neutral lipid, a steroid, a polymer conjugated lipid; and RNA. In one embodiment, the cationic lipid is ALC-0315, the neutral lipid is DSPC, the steroid is cholesterol, and the polymer conjugated lipid is ALC-0159.

In one embodiment, the LNP comprises from 20 to 60 mol percent, 40 to 55 mol percent, from 40 to 50 mol percent, from 41 to 49 mol percent, from 41 to 48 mol percent, from 42 to 48 mol percent, from 43 to 48 mol percent, from 44 to 48 mol percent, from 45 to 48 mol percent, from 46 to 48 mol percent, from 47 to 48 mol percent, or from 47.2 to 47.8 mol percent of the cationic lipid. In one embodiment, the LNP comprises about 47.0, 47.1, 47.2, 47.3, 47.4, 47.5, 47.6, 47.7, 47.8, 47.9 or 48.0 mol percent of the cationic lipid.

In one embodiment, the neutral lipid is present in a concentration ranging from 5 to 25 mol percent, 5 to 15 mol percent, from 7 to 13 mol percent, or from 9 to 11 mol percent. In one embodiment, the neutral lipid is present in a concentration of about 9.5, 10 or 10.5 mol percent.

In one embodiment, the steroid is present in a concentration ranging from 25 to 55 mol percent, 30 to 50 mol percent, from 35 to 45 mol percent or from 38 to 43 mol percent. In one embodiment, the steroid is present in a concentration of about 40, 41, 42, 43, 44, 45 or 46 mol percent.

In some embodiments, an LNP comprises molar ratios of 20-60% ionizable cationic lipid, 5-25% neutral lipid, 25-55% sterol, and 0.5-15% PEG-modified lipid.

The preferred mode of administration is intramuscular administration, more preferably in aqueous cryoprotectant buffer for intramuscular administration. Drug product is a preferably a preservative-free, sterile dispersion of RNA formulated in lipid nanoparticles (LNP) in aqueous cryoprotectant buffer for intramuscular administration.

In different embodiments, drug product comprises the components shown below, e.g., at the proportions or concentrations shown below:

| Component | Function | Proportion (mol %) |
|---|---|---|
| ALC-0315 [1] | Functional lipid | 47.5 |
| ALC-0159 [2] | Functional lipid | 1.8 |
| DSPC [3] | Structural lipid | 10.0 |
| Cholesterol, synthetic | Structural lipid | 40.7 |

| Component | Function | Concentration (mg/mL) |
|---|---|---|
| Drug Substance | Active | 0.5 |
| ALC-0315 [1] | Functional lipid | 7.17 |
| ALC-0159 [2] | Functional lipid | 0.89 |
| DSPC [3] | Structural lipid | 1.56 |
| Cholesterol, synthetic | Structural lipid | 3.1 |
| Sucrose | Cryoprotectant | 102.69 |
| NaCl | Buffer | 6.0 |
| KCl | Buffer | 0.15 |
| Na$_2$HPO$_4$ | Buffer | 1.08 |
| KH$_2$PO$_4$ | Buffer | 0.18 |
| Water for injection | Solvent/Vehicle | q.s. |

| Component | Function | Concentration (mg/mL) |
|---|---|---|
| Drug Substance | Active | 1.0 |
| ALC-0315 [1] | Functional lipid | 13.56 |
| ALC-0159 [2] | Functional lipid | 1.77 |
| DSPC [3] | Structural lipid | 3.11 |
| Cholesterol, synthetic | Structural lipid | 6.20 |
| Sucrose | Cryoprotectant | 102.69 |
| NaCl | Buffer | 6.0 |
| KCl | Buffer | 0.15 |
| Na$_2$HPO$_4$ | Buffer | 1.08 |
| KH$_2$PO$_4$ | Buffer | 0.15 |
| Water for injection | Solvent/Vehicle | q.s. |

[1] ALC-0315=((4-hydroxybutyl)azanediyl)bis(hexane-6,1-diyl)bis(2-hexyldecanoate)/6-[N-6-(2-hexyldecanoyloxy)hexyl-N-(4-hydroxybutyl)amino]hexyl 2-hexyldecanoate

[2] ALC-0159=2-[(polyethylene glycol)-2000]-N,N-ditetradecylacetamide/2-[2-(co-methoxy (polyethyleneglycol2000) ethoxy]-N,N-ditetradecylacetamide

[3] DSPC=1,2-Distearoyl-sn-glycero-3-phosphocholine q.s.=quantum satis (as much as may suffice)

In some embodiments, particles disclosed herein are formulated in a solution comprising 10 mM Tris and 10% sucrose, and optionally having a pH of about 7.4. In some embodiments, particles disclosed herein are formulated in a solution comprising about 103 mg/ml sucrose, about 0.20 mg/ml tromethamine (Tris base), and about 1.32 mg/ml Tris.

In some embodiments, a composition comprises:
(a) about 0.1 mg/mL RNA comprising an open reading frame encoding a polypeptide that comprises a SARS-CoV-2 protein or an immunogenic fragment or variant thereof,
(b) about 1.43 mg/ml ALC-0315,
(c) about 0.18 mg/ml ALC-0159,
(d) about 0.31 mg/ml DSPC,
(e) about 0.62 mg/ml cholesterol,
(f) about 103 mg/ml sucrose,
(g) about 0.20 mg/ml tromethamine (Tris base),
(h) about 1.32 mg/ml Tris (hydroxymethyl) aminomethane hydrochloride (Tris HCl), and
(i) q.s. water.

In one embodiment, the ratio of RNA (e.g., mRNA) to total lipid (N/P) is between 6.0 and 6.5 such as about 6.0 or about 6.3.

In some embodiments, compositions provided herein are formulated as a multi-dose formulation, optionally in a vial.

Methods of Administering

Also described in the present disclosure, among other things, are methods that comprise administering a composition described herein. In some embodiments, methods described herein induce an immune response in a subject (e.g., an immune response against coronavirus).

In some embodiments, an amount of the RNA described herein of at least 0.25 µg, at least 0.5 µg, at least 1 µg, at least 2 µg, at least 3 µg, at least 4 µg, at least 5 µg, at least 10 µg, at least 15 µg, at least 20 µg, at least 25 µg, at least 30 µg, at least 40 µg, at least 50 µg, or at least 60 µg may be administered per dose (e.g., in a given dose). In some embodiments, an amount of the RNA described herein of at least 3 ug may be administered in at least one of given doses. In some embodiments, an amount of the RNA described herein of at least 10 ug may be administered in at least one of given doses. In some embodiments, an amount of the RNA described herein of at least 15 ug may be administered in at least one of given doses. In some embodiments, an amount of the RNA described herein of at least 20 ug may be administered in at least one of given doses. In some embodiments, an amount of the RNA described herein of at least 25 ug may be administered in at least one of given doses. In some embodiments, an amount of the RNA described herein of at least 30 ug may be administered in at least one of given doses. In some embodiments, combinations of aforementioned amounts may be administered in a regimen comprising two or more doses (e.g., a prior dose and a subsequent dose can be of different amounts as described herein). In some embodiments, combinations of aforementioned amounts may be administered in a primary regimen and a booster regimen (e.g., different doses can be given in a primary regimen and a booster regimen).

In some embodiments, a composition comprising an RNA described herein is administered as a first dose and/or as part of a priming vaccination regimen to a subject (e.g., a vaccine-naïve subject is administered (i) two doses of such a composition, approximately 21 days apart, or (ii) three doses of such a composition, where the first and the second doses are administered approximately 21 days apart and the second and the third dose are administered about 28 days apart).

In some embodiments, a composition that comprises an RNA described herein is administered to a subject who has previously been exposed to SARS-CoV-2 (e.g., a subject who has previously received at least one dose (e.g., a complete dosing regimen) of a SARS-CoV-2 vaccine and/or previously been infected one or more times with SARS-CoV-2). In some embodiments, a composition comprising an RNA described herein is administered as a booster dose. In some embodiments, a composition comprising an RNA described herein is administered as a booster dose to a subject who has previously received one or more doses (e.g., a complete primary dosing regimen and/or one or more booster doses) of a vaccine that delivers a SARS-CoV-2 S protein of a Wuhan strain (e.g., a composition comprising an RNA that comprises SEQ ID NO: 20, a commercially available vaccine (e.g., a commercially available vaccine described herein, (e.g., BNT162b2)) or any combination thereof).

Commercially available SARS-CoV-2 vaccines are known in the art, and include, e.g., an mRNA-1273 vaccine, an Ad26.CoV2.S vaccine, a ChAdxOx1 vaccine, an NVX-CoV2373 vaccine, a CvnCoV vaccine, a GAM-COVIDO-Vac vaccine, a CoronaVac vaccine, a BBIBP-CorV vaccine, an Ad5-nCoV vaccine, a zf2001 vaccine, a SCB-2019 vaccine, or other approved RNA (e.g., mRNA) or adenovector vaccines, etc.

In some embodiments, an RNA described herein is administered to a subject who has previously been administered at least two doses of BNT162b2 (e.g., two doses of BNT162b2 administered about 21 days apart). In some embodiments, an RNA described herein is administered to a subject who has previously been administered at least three doses of BNT162b2 embodiment, at least three doses are administered. In some embodiments, such third dose is administered a period of time after the second dose that is comparable to (e.g., the same as) the period of time between the first and second doses. For example, in some embodiments, a third dose may be administered about 21 days following administration of the second dose. In some embodiments, a third dose is administered after a longer period of time relative to the second dose than the second dose was relative to the first dose. In some embodiments, a three-dose regimen is administered to an immunocompromised patient, e.g., a cancer patient, an HIV patient, a patient who has received and/or is receiving immunosuppressant therapy (e.g., an organ transplant patient). In some embodiments, the length of time between the second and third dose (e.g., a second and third dose administered to an immunocompromised patient) is at least about 21 days (e.g., at least about 28 days).

In some embodiments, an RNA described herein is administered to a subject who has previously been administered a vaccine that delivers an antigen of a SARS-CoV-2 variant (e.g., an Omicron BA.4/5 variant). For example, in some embodiments, an RNA described herein is administered to a subject previously administered one or more doses of a SARS-CoV-2 vaccine that delivers a SARS-CoV-2 S protein of a Wuhan strain (e.g., BNT162b2), and one or more booster doses of a variant adapted vaccine (e.g., one or more doses of a bivalent vaccine that delivers a SARS-CoV-2 S protein of a Wuhan strain and a SARS-CoV-2 S protein of an Omicron BA.4/5 strain).

BNT162b2 (which comprises an RNA comprising SEQ ID NO: 20) is an mRNA vaccine for prevention of COVID-19 and demonstrated an efficacy of 95% or more at preventing COVID-19. The vaccine comprises a 5'capped mRNA encoding for the full-length SARS-CoV-2 spike glycoprotein (S) encapsulated in lipid nanoparticles (LNPs). The finished product is presented as a concentrate for dispersion for injection containing BNT162b2 as active substance. Other ingredients include: ALC-0315 (4-hydroxybutyl)azanediyl)bis(hexane-6,1-diyl)bis(2-hexyldecanoate), ALC-0159 (2-[(polyethylene glycol)-2000]-N,N-ditetradecylacetamide), 1,2-Distearoyl-sn-glycero-3-phosphocholine (DSPC), cholesterol, and, in some embodiments, potassium chloride, potassium dihydrogen phosphate, sodium chloride, disodium phosphate dihydrate, sucrose and water for injection.

In some embodiments, a composition comprising an RNA described herein is administered to a subject previously administered a priming dosing regimen of a composition (e.g., an RNA composition) that delivers a SARS-CoV-2 S protein of a Wuhan strain (e.g., a subject previously administered (i) two doses of an RNA vaccine that encodes a SARS-CoV-2 S protein of a Wuhan strain, where the first and the second doses were administered about 21 days apart, or (ii) three doses of an RNA vaccine that encodes a SARS-CoV-2 S protein of a Wuhan strain, where the first and the second dose were administered about 21 days apart and the third dose was administered about 28 days after the second dose).

In some embodiments, a composition comprising an RNA described herein was administered as a further booster dose to a subject previously administered a priming dosing regimen and one or more booster doses of a composition (e.g., an RNA composition) that delivers a SARS-CoV-2 S protein of a Wuhan strain (e.g., a subject previously administered (i) three doses of an RNA vaccine that encodes a SARS-CoV-2 S protein of a Wuhan strain, where the first and the second doses were administered about 21 days apart, and the third dose was administered at least about 2 months after the second dose, (ii) four doses of an RNA vaccine that encodes a SARS-CoV-2 S protein of a Wuhan strain, where the first and the second dose were administered about 21 days apart, the third dose was administered about 28 days after the second dose, and the fourth dose was administered at least about three months after the second dose, or (iii) four doses of an RNA vaccine that encodes a SARS-CoV-2 S protein of a Wuhan strain, where the first and the second dose were administered about 21 days apart, the third dose was administered at least about 2 months after the second dose, and the fourth dose was administered at least about two months after the second dose).

In some embodiments, a composition comprising an RNA described herein is administered to a subject previously administered one or more doses of a bivalent composition (e.g., an RNA composition) that delivers a SARS-CoV-2 S protein of a Wuhan strain and a SARS-CoV-2 S protein of an Omicron BA.4/5 variant. In some embodiments, a composition comprising an RNA described herein is administered as a booster dose to a subject previously administered a priming dosing regimen of a bivalent composition (e.g., an RNA composition) that delivers a SARS-CoV-2 S protein of a Wuhan strain and a SARS-CoV-2 S protein of an Omicron BA.4/5 variant (e.g., a subject previously administered (i) two doses of a bivalent RNA vaccine, where the first and the second doses were administered about 21 days apart, or (ii) three doses of a bivalent RNA vaccine, where the first and the second dose were administered about 21 days apart and the third dose was administered about 28 days after the second dose). In some embodiments, a composition comprising an RNA described herein is administered as a further booster dose to a subject previously administered a priming dosing regimen and one or more booster doses of a bivalent composition (e.g., an RNA composition) that delivers a SARS-CoV-2 S protein of a Wuhan strain and a SARS-CoV-2 S protein of an Omicron BA.4/5 variant (e.g., a subject previously administered (i) three doses of a bivalent RNA vaccine, where the first and the second doses were administered about 21 days apart, and the third dose was administered at least about 2 months after the second dose, (ii) four doses of a bivalent RNA vaccine, where the first and the second dose were administered about 21 days apart, the third dose was administered about 28 days after the second dose, and the fourth dose was administered at least about three months after the second dose, or (iii) four doses of a bivalent RNA vaccine, where the first and the second dose were administered about 21 days apart, the third dose was administered at least about 2 months after the second dose, and the fourth dose was administered at least about two months after the second dose).

In some embodiments, a composition comprising an RNA described herein is administered to a subject previously administered (i) one or more doses of a composition that delivers a SARS-CoV-2 S protein of a Wuhan strain and (ii) one or more doses of a bivalent composition (e.g., an RNA composition) that delivers a SARS-CoV-2 S protein of a Wuhan strain and a SARS-CoV-2 S protein of an Omicron BA.4/5 variant.

In some embodiments, a composition comprising an RNA described herein is administered to a subject previously administered:
(ii) two doses (administered about 21 days apart) of an RNA vaccine that delivers a SARS-CoV-2 S protein of a Wuhan strain, and a dose of a bivalent composition comprising a first RNA encoding a SARS-CoV-2 S protein of a Wuhan strain and a second RNA encoding a SARS-CoV-2 S protein of an Omicron BA.4/5 variant, where the bivalent composition was administered at least about two months after the most recent dose of a composition that delivers a SARS-CoV-2 S protein of a Wuhan strain;
(iii) three doses of an RNA vaccine that delivers a SARS-CoV-2 S protein of a Wuhan strain (where the first and the second dose were administered about 21 days apart and the third dose was administered about 28 days after the second dose) and at least one dose of a bivalent vaccine comprising a first RNA encoding a SARS-CoV-2 S protein of a Wuhan strain and a second RNA encoding a SARS-CoV-2 S protein of an Omicron BA.4/5 variant, where the bivalent composition was administered at least about 2 months after the most recent dose of a composition that delivers a SARS-CoV-2 S protein of a Wuhan strain;
(iv) three doses of an RNA vaccine that delivers a SARS-CoV-2 S protein of a Wuhan strain (where the first and the second dose were administered about 21 days apart and the third dose was administered at least about 2 months after the second dose) and at least one dose of a bivalent vaccine comprising a first RNA encoding a SARS-CoV-2 S protein of a Wuhan strain and a second RNA encoding a SARS-CoV-2 S protein of an Omicron BA.4/5 variant, where the bivalent composition was administered at least about 2 months after the most recent dose of a composition that delivers a SARS-CoV-2 S protein of a Wuhan strain.
(v) four doses of an RNA vaccine that delivers a SARS-CoV-2 S protein of a Wuhan strain (where the first and the second dose were administered about 21 days apart, the third dose was administered about 28 days after the second dose, and the fourth dose was administered at least about 2 months after the third dose) and at least one dose of a bivalent vaccine comprising a first RNA encoding a SARS-CoV-2 S protein of a Wuhan strain and a second RNA encoding a SARS-CoV-2 S protein of an Omicron BA.4/5 variant, where the bivalent composition was administered at least about 2 months after the most recent dose of a composition that delivers a SARS-CoV-2 S protein of a Wuhan strain; or four doses of an RNA vaccine that delivers a SARS-CoV-2 S protein of a Wuhan strain (where the first and the second dose were administered about 21 days apart, the third dose was administered at least about 2 months after the second dose, and the fourth dose was administered at least about 4 months after the third dose) and at least one dose of a bivalent vaccine comprising a first RNA encoding a SARS-CoV-2 S protein of a Wuhan strain and a second RNA encoding a SARS-CoV-2 S protein of an Omicron BA.4/5 variant, where the bivalent composition was administered at least about 2 months after the most recent dose of a composition that delivers a SARS-CoV-2 S protein of a Wuhan strain.

In some embodiments, a dose (e.g., a dose administered as part of a primary dosing regimen or a booster regimen) comprises about 30 µg of an RNA described herein. In some embodiments, a dose comprising about 30 µg of RNA described herein is administered to a subject who is 12 years or older.

In some embodiments, a dose (e.g., a dose administered as part of a primary dosing regimen or a booster regimen) comprises about 10 µg of an RNA described herein. In some embodiments, a dose comprising about 10 µg of RNA described herein is administered to a subject who is 5 years to less than 12 years old.

In some embodiments, a dose (e.g., a dose administered as part of a primary dosing regimen or a booster regimen)

comprises about 3 μg of an RNA described herein. In some embodiments, a dose comprising about 3 μg of RNA described herein is administered to a subject who is 6 months to less than 5 years old.

In some embodiments, a composition described herein is administered in a volume of between about 200 μl and about 300 μl (e.g., about 200 μl or about 300 μl).

In some embodiments, RNA in a pharmaceutical RNA preparation is diluted prior to administration (e.g., diluted to a concentration of about 0.05 mg/ml). In some embodiments, administration volumes are between about 200 μl and about 300 μl. In some embodiments, RNA in a pharmaceutical RNA preparation is formulated in about 10 mM Tris buffer, and about 10% sucrose.

In some embodiments, an RNA (e.g., mRNA) composition disclosed herein may be administered in conjunction with a vaccine targeting a different infectious agent. In some embodiments, the different infectious agent is one that increases the likelihood of a subject experiencing deleterious symptoms when coinfected with SARS-CoV-2 and the infectious agent. In some embodiments, the infectious agent is one that increases the infectivity of SARS-CoV-2 when a subject is coinfected with SARS-CoV-2 and the infectious agent. In some embodiments, at least one RNA (e.g., mRNA) composition described herein may be administered in combination with a vaccine that targets influenza. In some embodiments, at least two or more different drug products/formulations may comprise at least one RNA (e.g., mRNA) composition described herein and a vaccine targeting a different infectious agent (e.g., an influenza vaccine). In some embodiments, different drug products/formulations are separately administered. In some embodiments, such different drug product/formulations are separately administered at the same time (e.g., at the same vaccination session) at different sites of a subject (e.g., at different arms of the subject).

In one embodiment, the vaccination regimen comprises a first vaccination using at least two doses of the RNA described herein, e.g., two doses of the RNA described herein (wherein the second dose may be administered about 21 days following administration of the first dose), and a second vaccination using a single dose or multiple doses, e.g., two doses, of the RNA described herein. In various embodiments, the second vaccination is administered at least about 2 months after a previous dose (e.g., 3 to 24 months, 6 to 18 months, 6 to 12 months, or 5 to 7 months after administration of a previous vaccine, e.g., after an initial two-dose regimen or a booster dose). The amount of RNA used in each dose of the second vaccination may be equal or different to the amount of RNA used in each dose of the first vaccination. In one embodiment, the amount of RNA used in each dose of the second vaccination is equal to the amount of RNA used in each dose of the first vaccination. In one embodiment, the amount of RNA used in each dose of the second vaccination and the amount of RNA used in each dose of the first vaccination is about 30 μg per dose. In one embodiment, the same RNA as used for the first vaccination is used for the second vaccination.

In some embodiments, an RNA composition described herein is co-administered with one or more vaccines against a non-SARS-CoV-2 disease. In some embodiments, an RNA composition described herein is co-administered with one or more vaccines against a non-SARS-COV-2 viral disease. In some embodiments, an RNA composition described herein is co-administered with one or more vaccines against a non-SARS-CoV-2 respiratory disease. In some embodiments, the non-SARS-CoV-2 respiratory disease is a non-SARS-CoV-2 Coronavirus, an Influenza virus, a Pneumoviridae virus, or a Paramyxoviridae virus. In some embodiments, the Pneumoviridae virus is a Respiratory syncytial virus or a Metapneumovirus. In some embodiments, the Metapneumovirus is a human metapneumovirus (hMPV). In some embodiments, the Paramyxoviridae virus is a Parainfluenza virus or a Henipavirus. In some embodiments the parainfluenzavirus is PIV3. In some embodiments, the non-SARS-CoV-2 coronavirus is a betacoronavirus (e.g., SARS-CoV-1). In come embodiments the non-SARS-CoV-2 coronavirus is a Merbecovirus (e.g., a MERS-CoV virus).

In some embodiments, an RNA composition described herein is co-administered with an RSV vaccine (e.g., an RSV A or RSV B vaccine). In some embodiments, the RSV vaccine comprises an RSV fusion protein (F), an RSV attachment protein (G), an RSV small hydrophobic protein (SH), an RSV matrix protein (M), an RSV nucleoprotein (N), an RSV M2-1 protein, an RSV Large polymerase (L), and/or an RSV phosphoprotein (P), or an immunogenic fragment of immunogenic variant thereof, or a nucleic acid (e.g., RNA), encoding any one of the same.

Numerous RSV vaccines are known in the art, any one of which can be co-administered with an RNA composition described herein. See, for example, the list of RSV vaccines provided on the website of PATH, a global health organization (see http://www.path.org/resources/rsv-vaccine-and-mab-snapshot/), as well as in Mazur, Natalie I., et al, "The respiratory syncytial virus vaccine landscape: lessons from the graveyard and promising candidates," The Lancet Infectious Diseases 18.10 (2018): e295-e311, the contents of each of which is incorporated by reference herein. In some embodiments, an RNA composition described herein is co-administered with an RSV vaccine that has been previously published on (e.g., an RSV vaccine described on the PATH website page linked to above, or in Mazur et al.). In some embodiments, an RNA composition described herein is co-administered with a live-attenuated or chimeric vaccine (e.g., rBCG-N-hRSV (developed by Ponteificia Uinersidad Catolica de Chile), RSV D46 cp ΔM202 (developed by Sanofi Pasteur/LID/NIAD/NIH), RSV LID ΔM2-2 1030s (developed by Sanofi Pasteur/LID/NIAD/NIH), RSV ANS2 Δ1313/I1314L (developed by Sanofi Pasteur/LID/NIAD/NIH), RSV D46 ΔNS2 N ΔM2-2 HindIII (developed by Sanofi Pasteur/LID/NIAD/NIH) or RSV LID ΔM2-2 1030s (developed by Sanofi Pasteur/LID/NIAD/NIH), MV-012-968 (developed by Meissa Vaccines), SP0125 (developed by Sanofi), blb201 (developed by Blue lake), CodaVax™-RSV (developed by Cadagenix), RSVDeltaG (developed by Intravacc), or SeVRSV (developed by SIPL and St. Jude hospital), a particle based vaccine (e.g., RSV F nanoparticle (developed by Novavax) or SynGEM (developed by Mucosis), Icosavzx (developed by IVX-121), or V-306 (developed by Virometix)), a subunit vaccine (e.g., GSK RSV F (developed by GSK), Arexvy (developed by GSK), DPX-RSV (developed by Dalousie Univeristy, Immunovaccine, and VIB), RSV F DS-Cav1 (developed by NIH/NIAID/VRC), MEDI-7510 (developed by MedImmune), RSVpreF (developed by Pfizer), ADV110 (developed by Advaccine), VN-0200 (developed by Daiichi Sankyo, Inc.)), a vector vaccine (e.g., MVA-BN RSV (developed by Banarian Nordic), VXA-RSVf oral (developed by Vaxart), Ad26.RSV.pref (developed by Janssen), ChAd155-RSV (developed by GSK) Immunovaccine, DPX-RSV (developed by VIB), or DS-Cav1 (developed by NIH/NIAID/VRC) or a nucleic acid vaccine (e.g., an mRNA vaccine being developed by CureVac (currently unnamed) or mRNA-1345 (developed by Moderna), or SP0274 (developed by Sanofi)).

In some embodiments, an RNA composition described herein is co-administered with an influenza vaccine. In some embodiments, the influenza vaccine is an alpha-influenza virus, a beta-influenza virus, a gamma-influenza virus or a delta-influenza virus vaccine. In some embodiments the vaccine is an Influenza A virus, an Influenza B virus, an Influenza C virus, or an Influenza D virus vaccine. In some embodiments, the influenza A virus vaccine comprises a hemagglutinin selected from H1, H2, H3, H4, H5, H6, H7, H8, H9, H10, H11, H12, H13, H14, H15, H16, H17, and H18, or an immunogenic fragment or variant of the same, or a nucleic acid (e.g., RNA) encoding any one of the same. In some embodiments the influenza A vaccine comprises or encodes a neuraminidase (NA) selected from N1, N2, N3, N4, N5, N6, N7, N8, N9, N10, and N11, or an immunogenic fragment or variant of the same, or a nucleic acid (e.g., RNA) encoding any one of the same. In some embodiments, the influenza vaccine comprises at least one Influenza virus hemagglutinin (HA), neuraminidase (NA), nucleoprotein (NP), matrix protein 1 (M1), matrix protein 2 (M2), non-structural protein 1 (NS1), non-structural protein 2 (NS2), nuclear export protein (NEP), polymerase acidic protein (PA), polymerase basic protein PB1, PB1-F2, and/or polymerase basic protein 2 (PB2), or an immunogenic fragment or variant thereof, or a nucleic acid (e.g., RNA) encoding any of one of the same.

In some embodiments, an RNA composition described herein can be co-administered with a commercially approved influenza vaccine. In some embodiments, an RNA composition described herein can be co-administered with an inactivated influenza virus (e.g., Fluzone®, Fluzone high-dose Quadrivalent®, Fluzone Quadrivalent®, Fluzone intradermal Quardivalent®, Fluzone quadrivalent southern Hemisphere®, Fluad®, Fluad Quadrivalent®, Afluria Quardivalent®, Fluarix Quadrivalent®, FluLaval Quadrivalent®, or Flucelvax Quadrivalent®), a recombinant influenza vaccine (e.g., Flublok Quadrivalent®), a live attenuated influenza vaccine (e.g., FluMist Quadrivalent®), a non-adjuvanted influenza vaccine, an adjuvanted influenza vaccine, or a subunit or split vaccine.

In some embodiments, an RNA composition described herein is co-administered with an influenza vaccine and/or an RSV vaccine.

In one embodiment, a composition or medical preparation is a pharmaceutical composition.

In one embodiment, a composition or medical preparation is a vaccine.

EXAMPLES

Example 1: Further Studies of Variant-Adapted Bi- and Trivalent Vaccines in Vaccine-Experienced Mice The present Example describes a study to characterize immune responses induced by certain variant-adapted vaccines in vaccine-experienced subjects (mice in the present Example). In particular, the present Example describes an experiment to characterize immune responses induced in subjects previously administered (i) at least one dose of a composition that delivers a SARS-CoV-2 S protein of a Wuhan strain, and (ii) at least one dose of a bivalent composition comprising a first RNA that encodes a SARS-COV-2 S protein of a Wuhan strain and a second RNA that encodes a SARS-CoV-2 S protein of a BA.4/5 Omicron variant.

Figure 2:
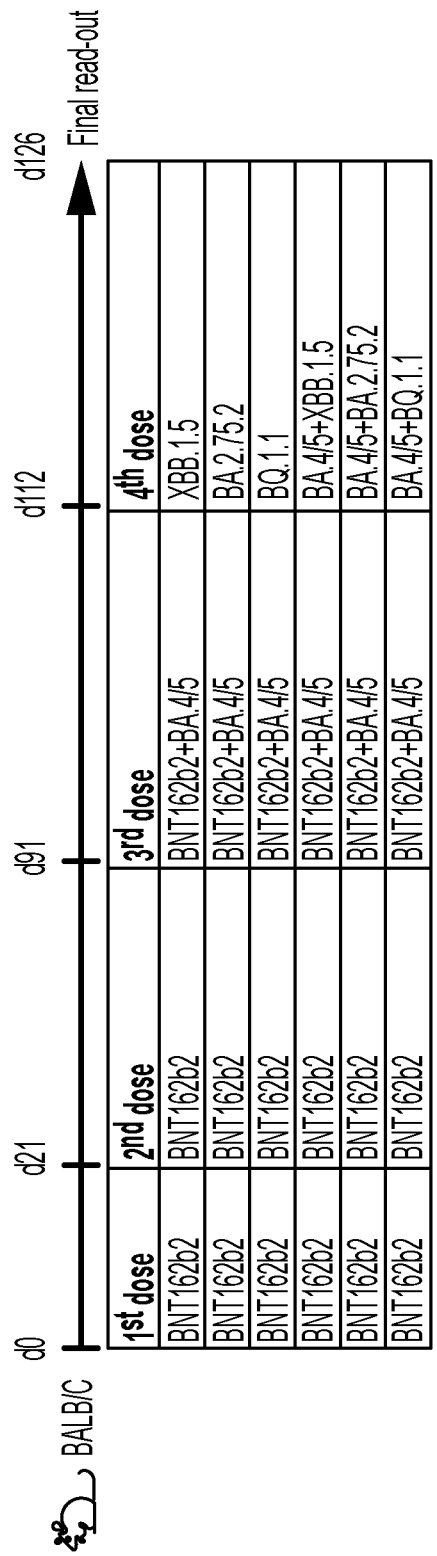
FIG. 2. Experimental design for a study to characterize variant-adapted vaccines in SARS-CoV-2 vaccine-experienced mice. Mice are split into 6 groups, each of which is administered a first and a second dose of an RNA encoding a SARS-CoV-2 S protein of a Wuhan strain (BNT162b2), followed by a third dose of a bivalent composition comprising a first RNA encoding a SARS-CoV-2 S protein of a Wuhan strain and a second RNA encoding a SARS-CoV-2 S protein of a BA.4/5 Omicron variant (BNT162b2+BA.4/5). Following the third dose, mice are administered a composition comprising an RNA encoding an SARS-CoV-2 S protein of a variant or strain or combination of strains/variants, as indicated in the Figure. The first and second doses are administered 21 days apart, the third dose is administered 70 days after the third dose, and the 4th dose is administered 21 days after the third dose. 126 days after administering the first dose, mice are sacrificed and the experiment concluded.

Two sets of experimental dosing regimens are summarized in FIGS. 1 and 2.

In a first set of experiments (summarized in FIG. 1), BALB/C mice are administered a first dose of an RNA vaccine encoding a SARS-CoV-2 S protein of a Wuhan variant (BNT162b2), and, 21 days later, a second dose of a bivalent vaccine comprising a first RNA encoding a SARS-CoV-2 S protein of a Wuhan strain and a second RNA encoding SARS-COV-2 S protein of a BA.4/5 Omicron variant. About 10 weeks after administered the second dose, mice are then administered one of the following compositions (comprising RNAs encoding SARS-CoV-2 S proteins from the listed strains/variants):

Wuhan+BA.4/5
XBB.1.5
BA.2.75.2
BQ.1.1
Wuhan+BA. 4/5+XBB.1.5
Wuhan+BA.4/5+BA.2.75.2
BA.4/5+XBB.1.5
BA.4/5+BA.2.75.2
BA.4/5+BQ.1.1

About 28 days after the third dose, mice are sacrificed and final neutralization titers are collected.

In a related experiment, neutralization titers are determined in mice administered two doses of a composition that delivers a Wuhan S protein, a third dose of a bivalent vaccine, and a fourth dose of one of the vaccines listed below (comprising RNAs encoding SARS-CoV-2 S proteins from the listed variants). The design of this experiment is summarized in FIG. 2.

XBB.1.5
BA.2.75.2
BQ.1.1
BA.4/5+XBB.1.5
BA.4/5+BA.2.75.2
BA.4/5+BQ.1.1

Figure 3:
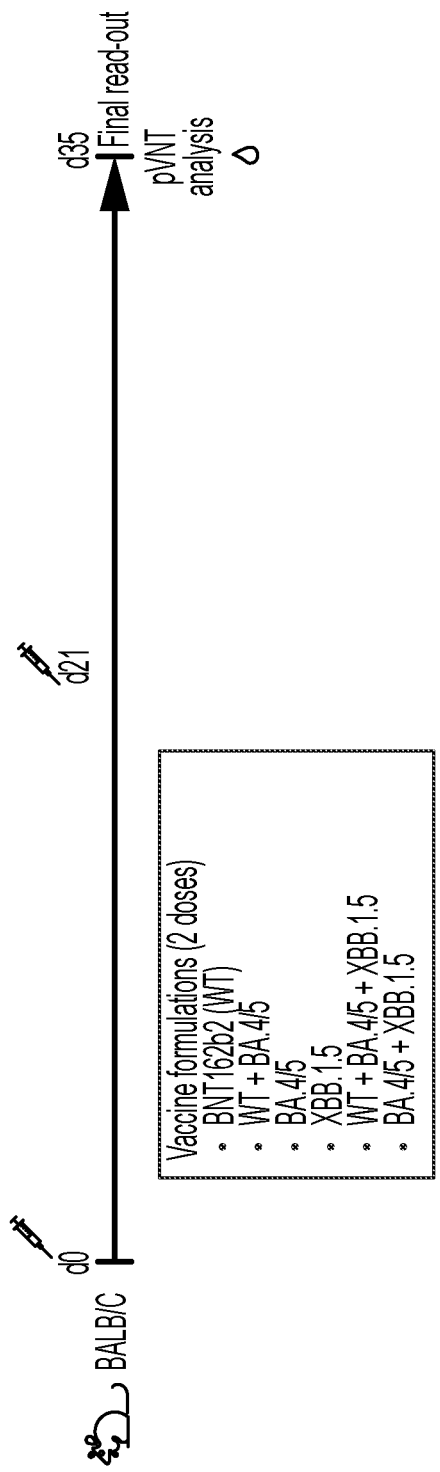
FIG. 3. Exemplary experimental protocol for testing variant-adapted vaccines as a primary series in mice. Two doses of a monovalent or bivalent vaccine composition comprising mRNA(s) encoding the SARS-CoV-2 S protein(s) of the strains/variants indicated in the figure were administered to mice 21 days apart. "WT" corresponds to RNA encoding a SARS-CoV-2 S protein from a Wuhan strain. Indicated in the figure is the mass of RNA (μg) administered to mice.

Example 2: Further Studies Investigating Variant-Adapted Vaccines Administered to Vaccine-Naïve Mice The present Example provides data characterizing certain monovalent and bivalent variant-adapted vaccines in vaccine naïve mice. The particular vaccines tested are shown in FIG. 3. As shown in the Figure, vaccines were administered vaccines on days 0 and 21 (the same vaccine composition and dose was administered on each day; dose amounts indicated in FIG. 3), and sera samples were collected on day 35 (14 days after the second dose of a vaccine).

Figure 4:
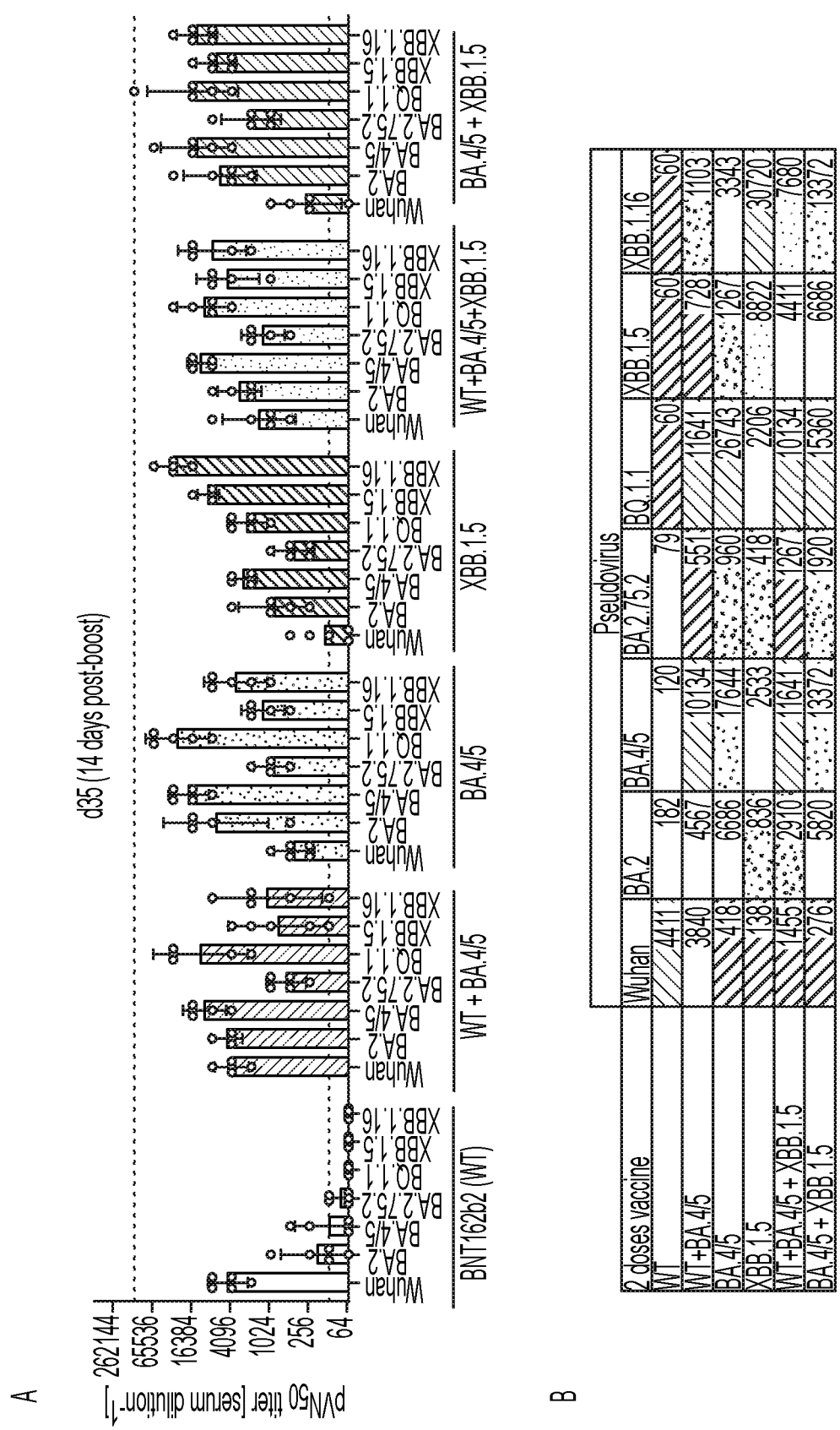
FIG. 4. A monovalent XBB.1.5-adapted vaccine, as a primary series, elicits higher neutralization titers against XBB.1.5 than a bivalent Wuhan+BA.4/5 vaccine. Shown are results collected in performing the experiment summarized in FIG. 3. (A) shows pseudovirus neutralization titers of serum samples collected at Day 35 of the experiment summarized in FIG. 3. (B) Lists neutralization titer values for the bar graph shown in panel (A).

Pseudovirus neutralization titers from sera samples collected on day 35 are shown in FIG. 4. As shown in the figure, each of the tested compositions can produce strong neutralization titers against the corresponding strain or variant. In particular, a monovalent composition comprising an RNA encoding an S protein of an XBB.1.5 Omicron variant was shown to induce high neutralization titers against XBB.1.5 when administered as a primary series. A bivalent composition comprising an RNA encoding an S protein of an XBB.1.5 Omicron variant and an RNA encoding an S protein of an Omicron BA.4/5 variant was also shown to induce high neutralization titers against XBB.1.5 when administered as a primary series, although titers were lower than those induced by an XBB.1.5 monovalent vaccine.

Each of the compositions comprising an RNA encoding an S protein of a SARS-CoV-2 variant (i.e., WT+BA.4/5, BA.4/5, XBB.1.5, and BA.4/5+XBB.1.5) was also found to induce broad cross-neutralization of other variants of concern. In particular, the BA.4/5+XBB.1.5 bivalent vaccine was found to induce high neutralization titers both against the XBB.1.5 variant as well as other strains. Neutralization titers against XBB.1.16 are expected to be similar to those induced against XBB.1.5, as neutralization data shows that the XBB.1.16 variant possesses no escape advantage relative to XBB.1.5 (see, e.g., FIG. 6). Similarly, neutralization titers for XBB.1.9.1/1.9.2 are expected to match those for XBB.1.5, as XBB.1.9.1/1.9.2 does not comprise any additional S protein mutations relative to XBB.1.5.

Figure 7:
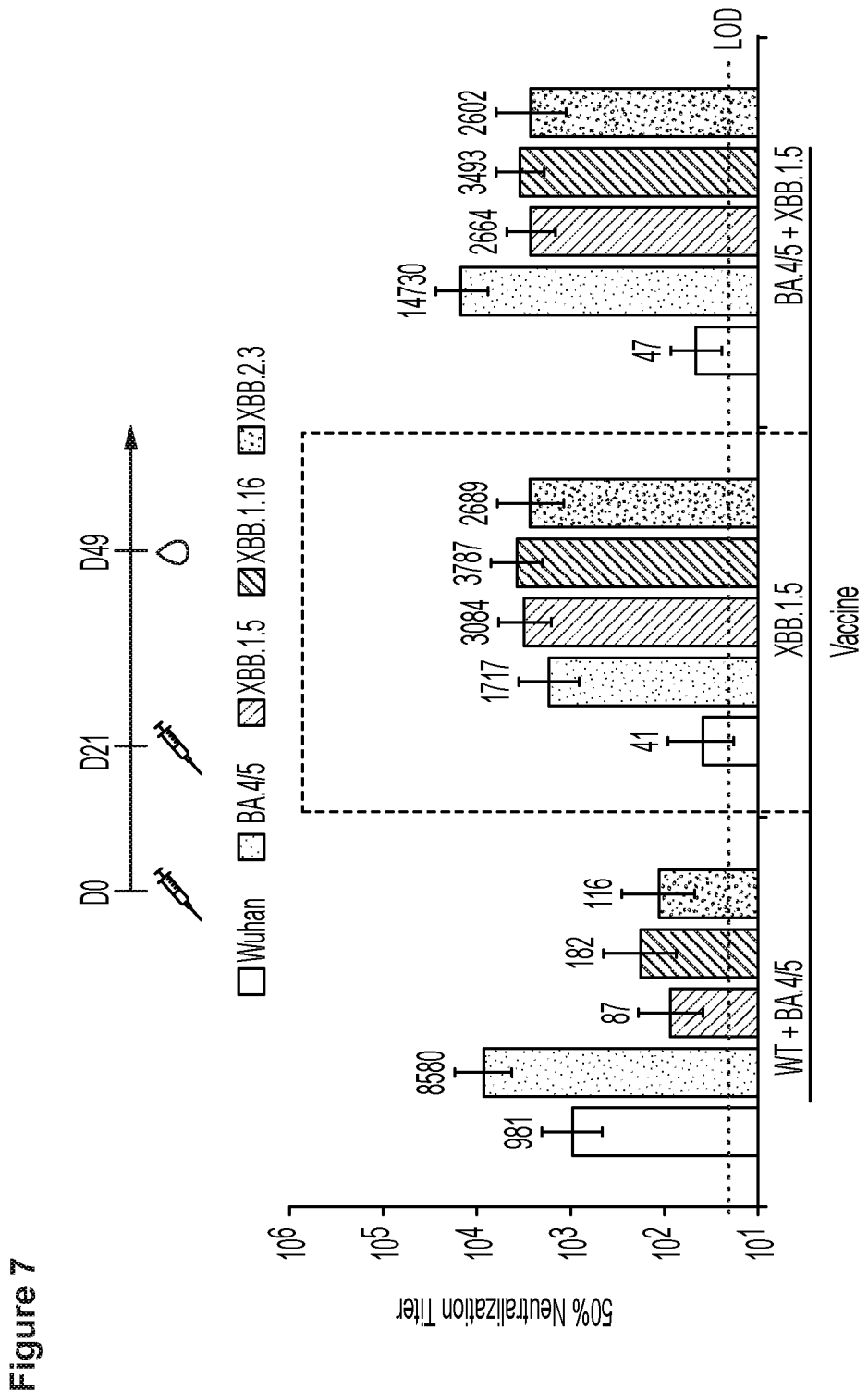
FIG. 7. Certain variant-adapted vaccines induce a neutralization response against Omicron XBB variants in vaccine-naïve mice. A summary of the experimental protocol is depicted at the top of the figure (syringes indicate days on which candidate vaccines were administered and the droplet indicates a day on which blood was collected). Vaccine naïve mice were administered two doses of the indicated candidate vaccines. Four weeks after receiving a second dose of vaccine, mice were bled and neutralization titers collected. As shown in the figure, neutralization titers were induced against each of the variants tested, with a monovalent XBB.1.5-adapted vaccine inducing the highest neutralization titers against each of the XBB variants tested.

A similar experiment (summarized in the schematic at the top of FIG. 7) was also performed in which vaccine-naïve mice were administered two doses of (i) a bivalent composition comprising RNA encoding a SARS-CoV-2 S protein of a Wuhan strain and RNA encoding a SARS-CoV-2 S protein of an Omicron BA.4/5 variant, (ii) a monovalent composition comprising RNA encoding a SARS-CoV-2 S protein of an XBB.1.5 variant, or (iii) a bivalent composition comprising RNA encoding a SARS-CoV-2 S protein of an Omicron BA.4/5 variant and RNA encoding a SARS-CoV-2 S protein of an XBB.1.5 variant. The two doses of RNA were administered 21 days apart, and neutralization titers were collected 4 weeks after administering the second dose. As shown in FIG. 7, an XBB.1.5-adapted monovalent vaccine (e.g., as described herein) induced the highest neutralization titers against each of an XBB.1.5 variant, an XBB.1.16 variant, and an XBB.2.3 variant as compared to the other compositions tested.

Example 3: Further Studies Investigating Variant-Adapted Vaccines Administered to Vaccine-Experienced Mice The present Example provides exemplary immune response data generated using certain monovalent and bivalent variant-adapted vaccines in vaccine-experienced mice. In particular, the present Example provides data demonstrating that vaccines (e.g., monovalent or bivalent vaccines) comprising an RNA encoding an XBB.1.5 S protein can induce strong neutralization titers against an XBB.1.5 Omicron variant in previously vaccinated subjects (e.g., subjects previously administered RNA encoding a SARS-CoV-2 S protein of a Wuhan strain and RNA encoding a SARS-CoV-2 S protein of an Omicron BA.4/5 variant, as in the present Example).

Figure 5:
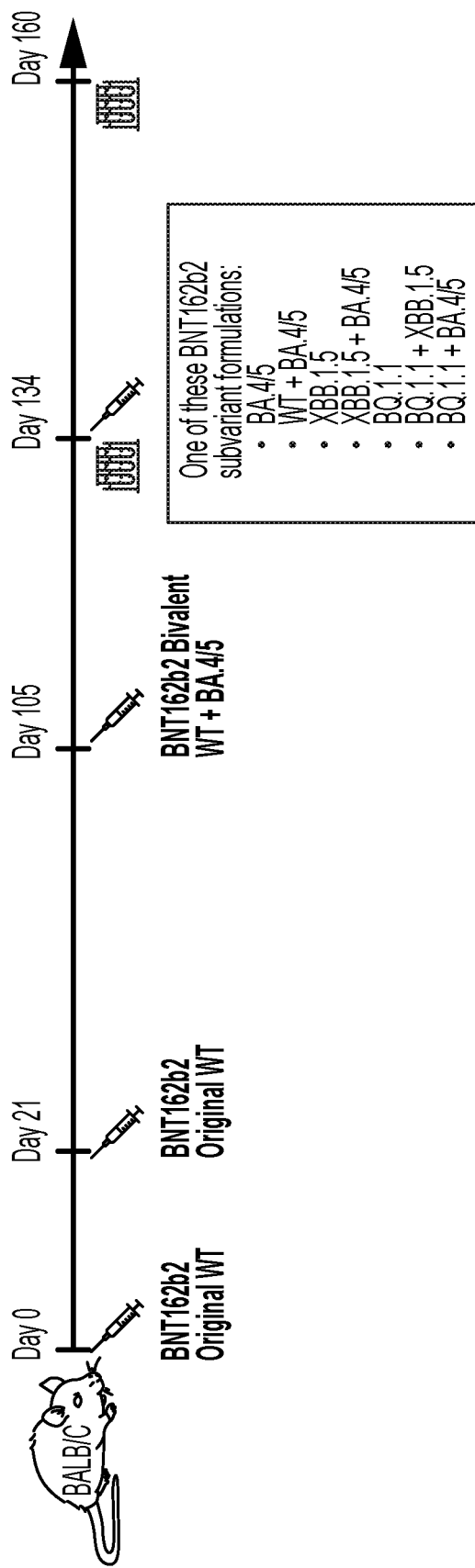
FIG. 5. Exemplary experimental protocol for testing variant-adapted vaccines as a fourth booster dose in mice. "BNT162b2 Original WT" corresponds to a monovalent mRNA vaccine encoding a SARS-CoV-2 S protein of a Wuhan strain, "BNT162b2 Bivalent WT+BA.4/5" corresponds to a bivalent vaccine comprising an RNA encoding an S protein of a Wuhan strain and an RNA encoding a SARS-CoV-2 S protein of an Omicron BA.4/5 variant. On day 134, mice were administered a monovalent or bivalent vaccine encoding one of the strains, variants, or combinations indicated in the figure. On days 134 and 160, blood samples were collected (represented by the test tube racks).

The particular vaccines tested are shown in FIG. 5. As shown in the Figure, mice in all groups were administered the following vaccines (listed in order of administration): (1) a first dose of a vaccine comprising RNA encoding a SARS-CoV-2 S protein of a Wuhan strain (BNT162b2 in the present example), (2) a second dose of a vaccine comprising an RNA encoding a SARS-CoV-2 S protein of a Wuhan strain (again, BNT162b2 in the present example; second dose administered about 21 days after the first dose), (3) a third dose of a bivalent vaccine comprising a first RNA encoding a SARS-CoV-2 S protein of a Wuhan strain and a second RNA encoding a SARS-CoV-2 S protein of an Omicron BA.4/5 variant (administered about 84 days after the second dose), and (4) a fourth dose of one of the monovalent or bivalent vaccines listed in the Figure (administered about 29 days after the third dose). Sera samples were collected 134 days after administration of the first dose of vaccine (immediately before administering the $4^{th}$ dose), and 160 days after administering the $1^{st}$ dose. Mice were administered 0.5 µg of each vaccine (for monovalent vaccines: 0.5 µg of an RNA, for bivalent vaccines: 0.25 µg of each RNA). On day 160, lymph nodes and spleen samples were also collected for T cell and B cell analysis.

Figure 6:
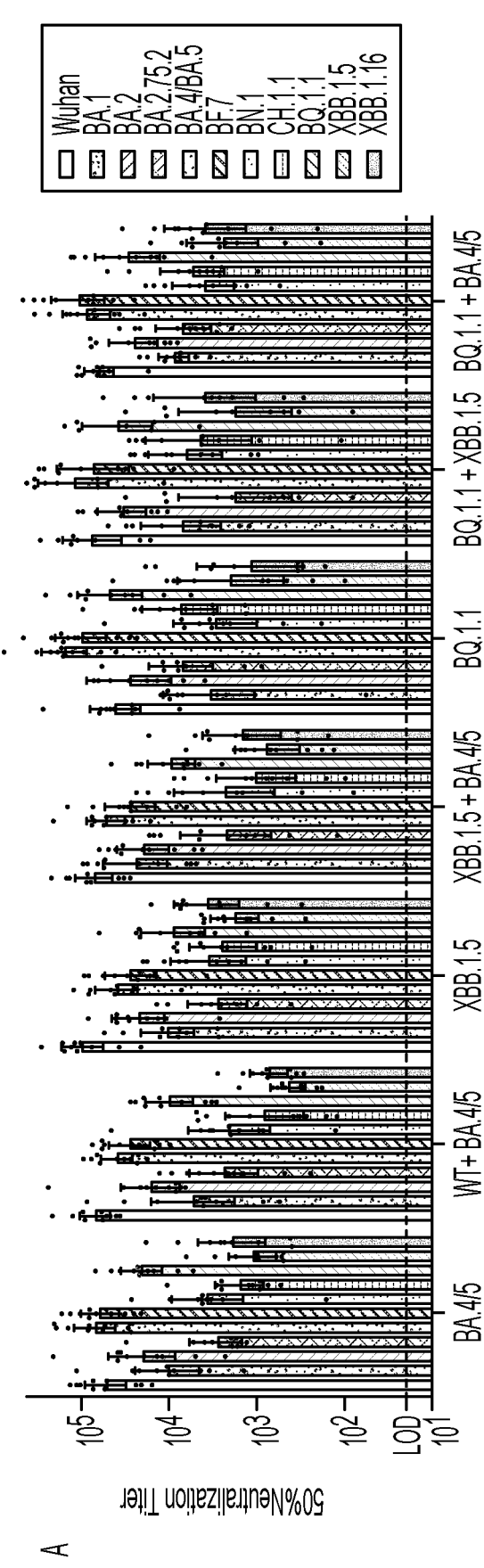
FIG. 6. An XBB.1.5-adapted booster vaccine elicits the highest neutralization titers against an XBB.1.5 and XBB.1.6 pseudovirus. Shown are results collected in performing the experiment summarized in FIG. 5. (A) shows neutralization titers collected for a panel of pseudoviruses (indicated in the figure legend). X-axis indicates vaccine administered. Titers collected at day 160. (B) shows neutralization titer values for the bar graph shown in panel (A). (C) Shows geometric mean ratios (GMR) of neutralization titers induced by the indicated vaccine relative to neutralization titers induced by a bivalent vaccine comprising an RNA encoding a SARS-CoV-2 S protein from a Wuhan strain (WT in the figure) and an RNA encoding a SARS-CoV-2 S protein from an Omicron BA.4/5 variant (GMR values calculated using neutralization titers at day 160). (D) provides GMR values for the bar graph shown in panel (C). (E) Shows GMR values comparing neutralization titers induced by the indicated vaccines relative to neutralization titers at day 135 (pre dose 4). (F) shows GMR values for the graph shown in panel (E). (G) shows neutralization titers against further SARS-CoV-2 variants (including XBB.2.3).
Figure 6:
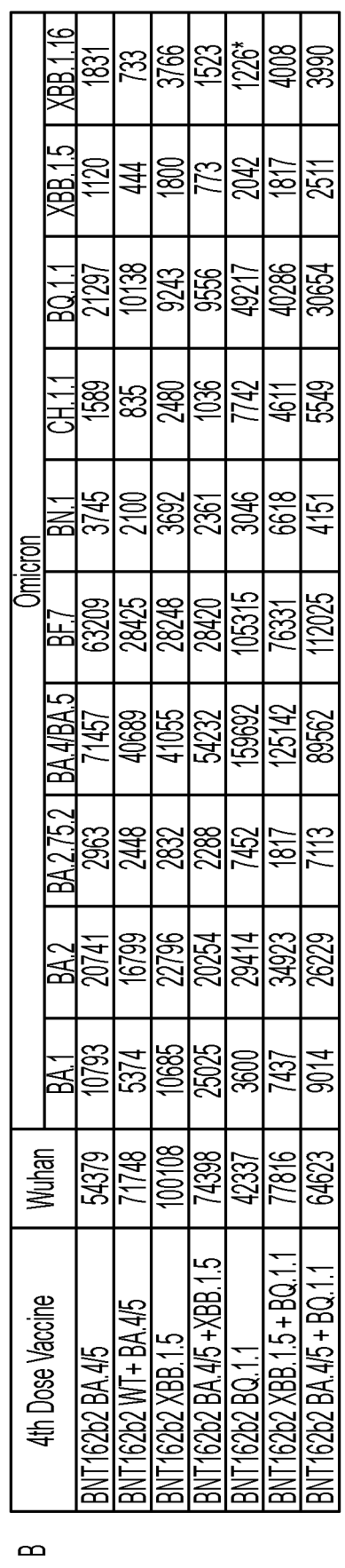
Figure 6:
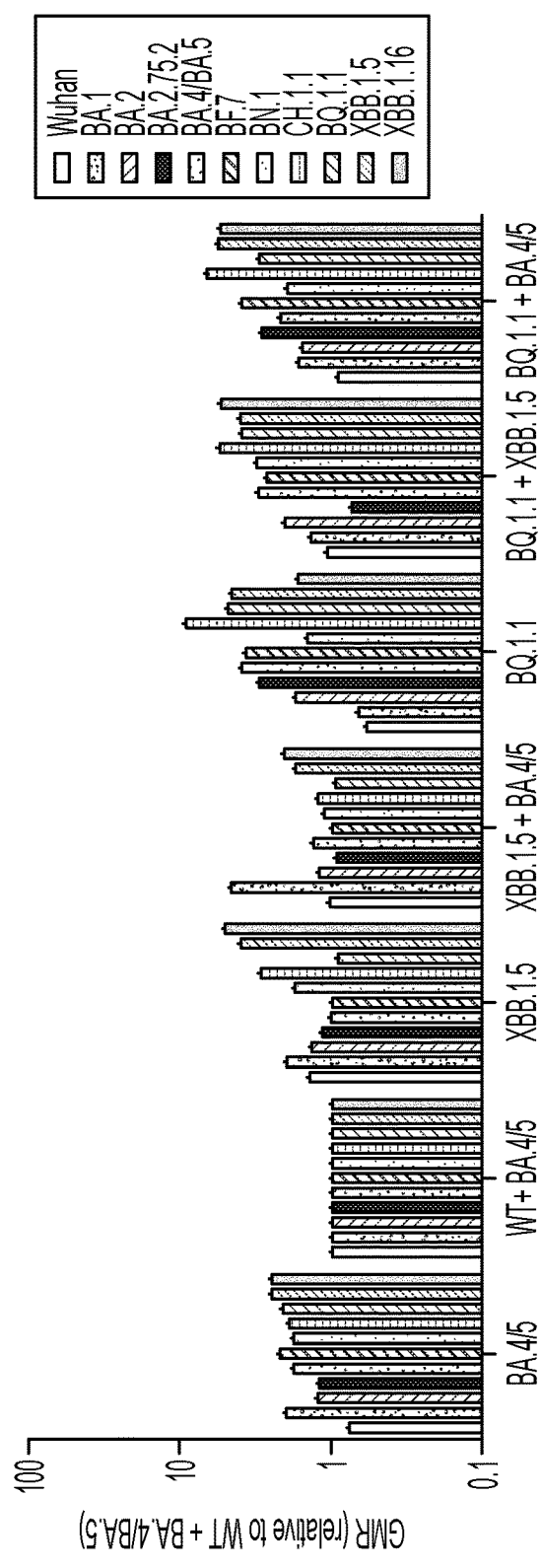
Figure 6:
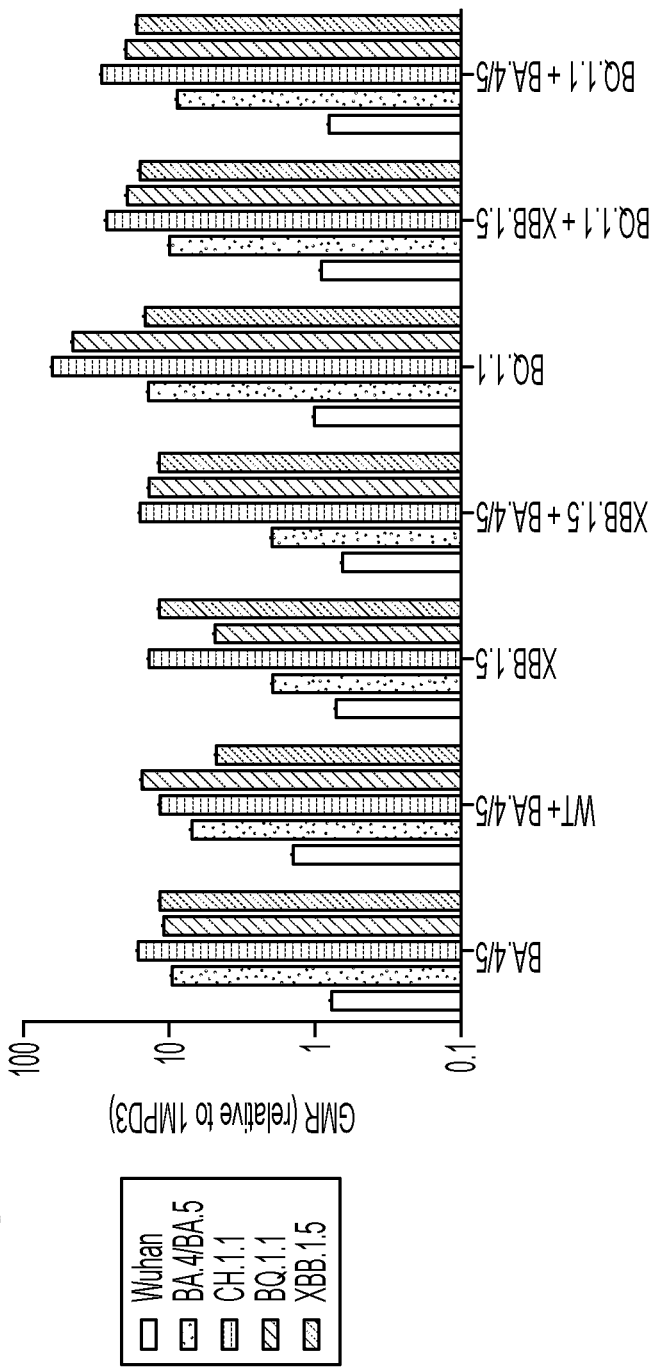
Figure 6:
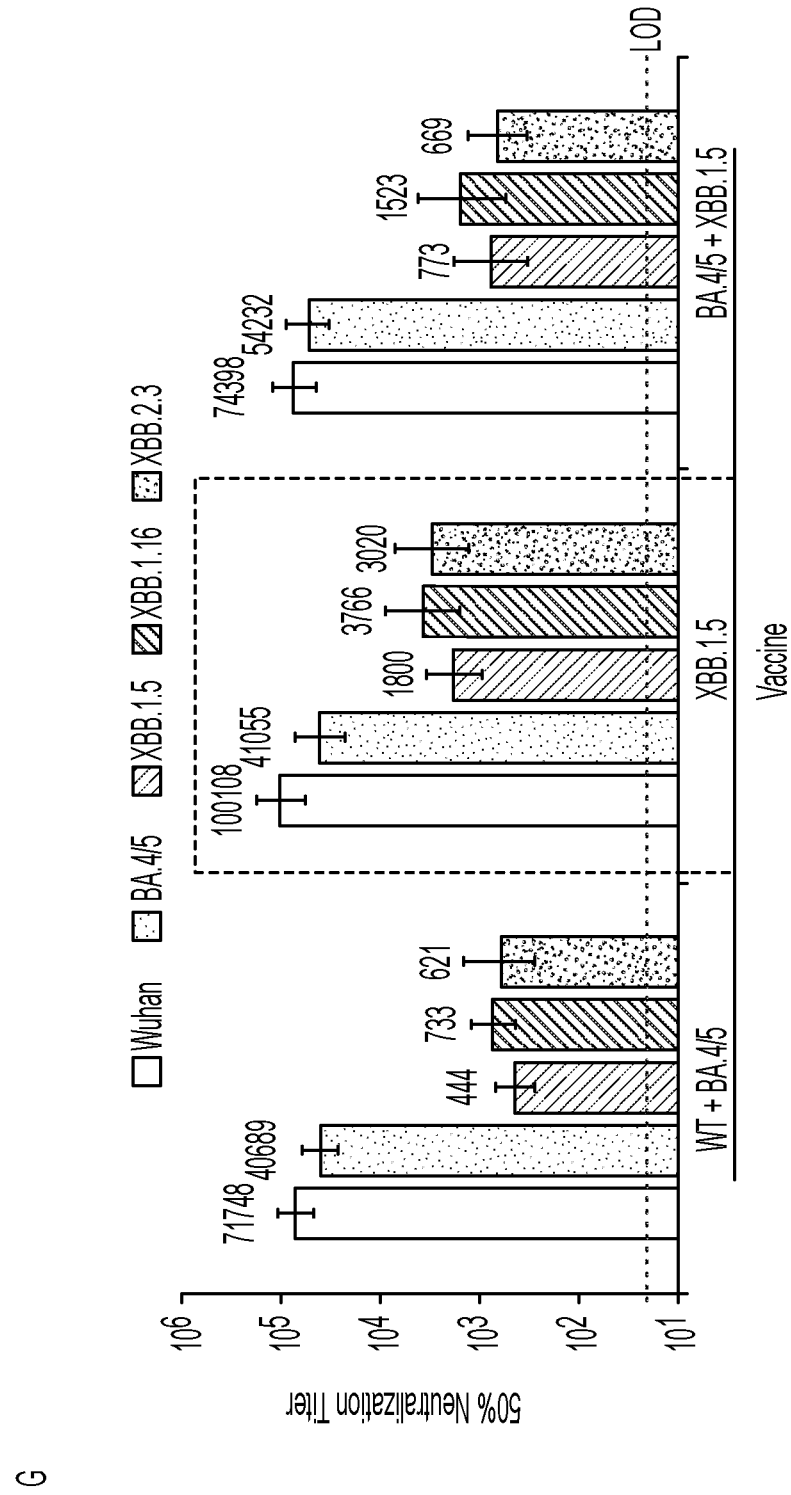

Pseudovirus neutralization titers are shown in FIG. 6. As shown in the figure, vaccines comprising an RNA encoding an XBB.1.5 S protein were found to induce a strong neutralization response when administered as either a monovalent or bivalent (e.g., BA.4/5+XBB.1.5) vaccine. In particular, the data demonstrates that such vaccines are especially effective when administered as a booster dose (e.g., to subjects previously administered one or more vaccines that deliver a SARS-CoV-2 S protein of a Wuhan strain and one or more bivalent vaccines (delivering a SARS-CoV-2 S protein of a Wuhan strain and an Omicron BA.4/5 variant), as tested in the present Example). In the present experiment, neutralization titers induced by an XBB.1.5 monovalent vaccine (in particular, neutralization titers against an XBB.1.5, XBB.1.16, and XBB.2.3-adapted pseudovirus) were found to be higher than those induced by a bivalent vaccine (BA.4/5+XBB.1.5). Other studies confirmed that monovalent or bivalent vaccine comprising an RNA encoding an XBB.1.5 S protein can induce a strong immune response against XBB variants (in particular, when administered as a booster), and further showed that, while a bivalent vaccine can induce higher neutralization titers at early time points, neutralization titers induced by a bivalent vaccine decreased faster than those induced by a monovalent vaccine, such that, 4 weeks after a booster dose, neutralization titers induced by a monovalent vaccine were higher than those induced by a bivalent vaccine (data not shown). As noted in previous Example 2, neutralization titers for XBB.1.9.1/1.9.2 are expected to match those induced for XBB.1.5, as XBB.1.9.1/1.9.2 does not comprise any additional S protein mutations relative to XBB.1.5.

Figure 8:
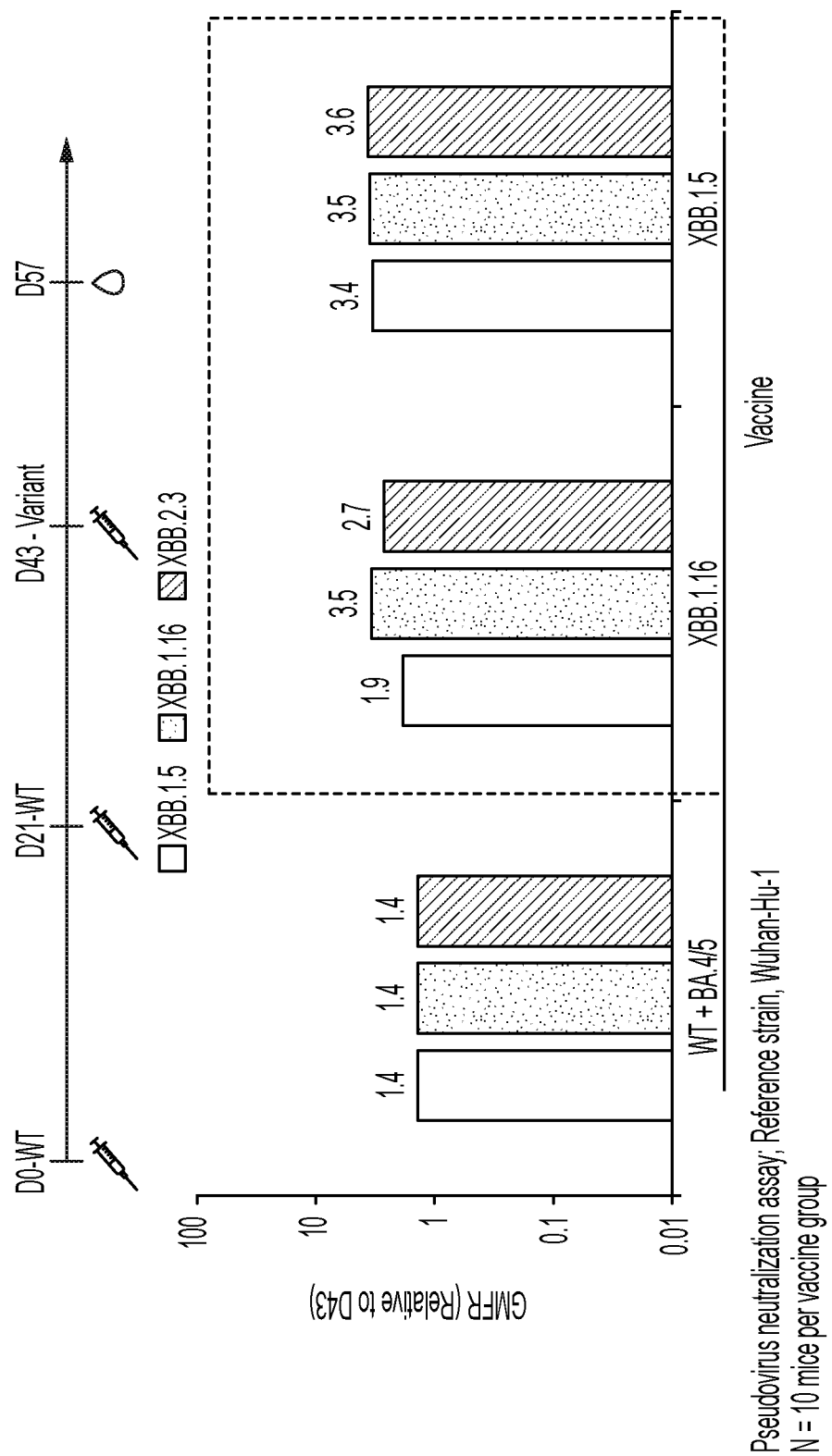
FIG. 8. Certain variant-adapted vaccines induce a neutralization response against Omicron XBB variants in vaccine-experienced mice. A summary of the experimental protocol is depicted at the top of the figure (syringes indicate days on which candidate vaccines were administered and the droplet indicates a day on which blood was collected). Mice were administered two doses of RNA encoding a SARS-CoV-2 S protein of a Wuhan strain (WT), followed by a dose of a candidate vaccine. Two weeks after receiving a dose of candidate vaccine, mice were bled and neutralization titers collected. As shown in the figure, neutralization titers were induced against each of the variants tested, with a monovalent XBB.1.5-adapted vaccine inducing the highest neutralization titers against each of the XBB variants tested.

A similar experiment was also performed to test the efficacy of an XBB.1.16-adapted vaccine (schematic summarizing the experimental protocol used is shown in FIG. 8). In short, mice were divided into groups of 10, and administered two doses (21 days apart) of an RNA encoding a SARS-CoV-2 S protein of a Wuhan strain (BNT162b2 in the present example), followed by a third dose (administered 14 days after the second dose) of a candidate vaccine encoding (i) a bivalent composition comprising a first RNA encoding a SARS-CoV-2 S protein of a Wuhan strain and a second RNA encoding a SARS-CoV-2 S protein of an Omicron BA.4/5 variant, (ii) a monovalent composition comprising an RNA encoding a SARS-CoV-2 S protein of an XBB.1.5 variant, (iii) a monovalent composition comprising an RNA encoding a SARS-CoV-2 S protein of an XBB.1.16 variant. 14 days after administering a third dose of vaccine, mice were bled and neutralization titers collected (e.g., using a pseudovirus neutralization assay described in one of the previous examples).

As shown in FIG. 8, a monovalent composition comprising an RNA encoding a SARS-CoV-2 S protein of an XBB.1.5 variant (e.g., an RNA described herein) induced the highest neutralization titers against each of the XBB.1.5, XBB.1.16, and XBB.2.3 variants. Surprisingly, an XBB.1.5 monovalent composition induced higher titers against an XBB.1.16 variant than a monovalent comprising an RNA encoding a SARS-CoV-2 S protein of an XBB.1.16 variant.

Example 4: Description of Sequences Provided in Sequence Listing

TABLE 2 below, provides a short description of sequences provided in the sequence listing submitted herewith.

| SEQ ID NO | Description |
|---|---|
| 1 | Amino acid sequence of a full length SARS-COV-2 S protein of a Wuhan strain |
| 2 | Exemplary RNA sequence encoding a full length SARS-CoV-2 S protein of a Wuhan strain |
| 3 | Exemplary amino acid sequence of a receptor binding domain (RBD) of a Wuhan SARS-COV-2 S protein |
| 4 | Exemplary RNA sequence encoding an RBD of a Wuhan SARS-COV-2 S protein |
| 5 | Exemplary amino acid sequence of an RBD of a Wuhan SARS-COV-2 S protein fused to a trimerization domain (fibritin) |
| 6 | Exemplary RNA sequence encoding an RBD of a Wuhan SARS-COV-2 strain fused to a trimerization domain (fibritin) |
| 7 | Exemplary amino acid sequence of a full length Wuhan SARS-COV-2 S protein comprising prefusion stablizing mutations (proline substitutions at positions 986 and 987) |
| 8 | Exemplary RNA sequence encoding a full length Wuhan SARS-COV-2 S protein comprising prefusion stablizing mutations (proline substitutions at positions 986 and 987) |
| 9 | Exemplary RNA sequence encoding a full length Wuhan SARS-COV-2 S protein comprising prefusion stablizing mutations (proline substitutions at positions 986 and 987) |
| 10 | Exemplary amino acid sequence of a "foldon" trimerization domain |
| 11 | Exemplary RNA sequence encoding a "foldon" trimerization domain |
| 12 | Exemplary 5' UTR sequence |
| 13 | Exemplary 3' UTR sequence |
| 14 | Exemplary polyA sequence |
| 15 | Exemplary RNA sequence encoding a full length SARS-CoV-2 S protein of a Wuhan strain comprising prefusion stabilizing mutations (proline substitutions at positions 986 and 987) |
| 16 | Exemplary RNA sequence encoding a full length SARS-CoV-2 S protein of a Wuhan strain comprising prefusion stabilizing mutations (proline substitutions at positions 986 and 987) |
| 17 | Exemplary RNA sequence encoding an RBD of a Wuhan SARS-COV-2 S protein fused to a trimerization domain (fibritin) |
| 18 | Exemplary amino acid sequence of an RBD of a Wuhan SARS-COV-2 S protein fused to a trimerization domain (fibritin) |
| 19 | Exemplary RNA sequence comprising a sequence encoding a full length, prefusion stabilized SARS-COV-2 S protein of a Wuhan strain, along with 5' UTR, 3' UTR, and polyA sequences |
| 20 | Exemplary RNA sequence comprising a sequence encoding a full length, prefusion stabilized SARS-COV-2 S protein of a Wuhan strain, along with 5' UTR, 3' UTR, and polyA sequences |
| 21 | Exemplary RNA sequence comprising a sequence encoding an RBD of a Wuhan SARS-COV-2 S protein fused to a trimerization domain (fibritin), along with 5' UTR, 3' UTR, and polyA sequences |
| 22 | Exemplary amino acid sequence of alphavirus nsp1-4 |
| 23 | Exemplary amino acid sequence of an alphavirus non-structural protein |
| 24 | Exemplary saRNA sequence encoding a full length SARS-CoV-2 S protein of a Wuhan strain comprising prefusion stablizing mutations (proline substitutions at positions 986 and 987) |
| 25 | Exemplary saRNA sequence encoding a full length SARS-CoV-2 S protein of a Wuhan strain comprising prefusion stablizing mutations (proline substitutions at positions 986 and 987) |
| 26 | Exemplary saRNA sequence encoding an RBD of a Wuhan strain fused to a trimerization domain (fibritin) |

TABLE 2-continued below, provides a short description of sequences provided in the sequence listing submitted herewith.

| SEQ ID NO | Description |
|---|---|
| 27 | Exemplary saRNA sequence encoding an RBD of a Wuhan SARS-COV-2 S protein fused to a trimerization domain (fibritin) and a transmembrane domain |
| 28 | Exemplary amino acid sequence of an RBD of a Wuhan SARS-COV-2 S protein fused to a trimerization domain (fibritin) and a transmembrane domain |
| 29 | Exemplary amino acid sequence of an RBD of a Wuhan SARS-COV-2 S protein fused to a trimerization domain (fibritin) and a transmembrane domain |
| 30 | Exemplary RNA sequence encoding an RBD of a Wuhan SARS-COV-2 S protein fused to a trimerization domain (fibritin) and a transmembrane domain |
| 31 | Exemplary amino acid sequence of an RBD of a Wuhan SARS-COV-2 S protein fused to a trimerization domain (fibritin) and a transmembrane domain |
| 32 | Exemplary RNA sequence encoding an RBD of a Wuhan SARS-COV-2 S protein fused to a trimerization domain (fibritin) and a transmembrane domain |
| 33 | Exemplary GS linker |
| 34 | Exemplary GS linker |
| 35-42, 142-145 | Exemplary T cell epitopes recognized by vaccine-induced T cells (e.g., CD8+ T cell) and presented by an MHC class I allele present in at least 50% of subjects in a population |
| 43-48, 138-141, 146-151 | Exemplary T cell epitope recognized by vaccine-induced T cells (e.g., CD8+ and/or CD4+ T cells) and presented by an MHC class I allele present in at least 50% of subjections in a population |
| 49 | Exemplary amino acid sequence of a prefusion-stabilized SARS-COV-2 S protein of a BA.1 Omicron variant |
| 50 | Exemplary RNA sequence encoding a prefusion-stabilized SARS-COV-2 S protein of a BA.1 Omicron variant |
| 51 | Exemplary RNA sequence comprising a sequence encoding a prefusion-stabilized SARS-COV-2 S protein of a BA.1 Omicron variant, along with 5' UTR, 3' UTR, and polyA sequences |
| 52 | Exemplary amino acid sequence of a prefusion-stabilized SARS-COV-2 S protein of a BA.1 Omicron variant |
| 53 | Exemplary RNA sequence encoding a prefusion-stabilized SARS-COV-2 S protein of a BA.1 Omicron variant |
| 54 | Exemplary RNA sequence comprising a sequence encoding a prefusion-stabilized SARS-COV-2 S protein of a BA.1 Omicron variant, along with 5' UTR, 3' UTR, and polyA sequences |
| 55 | Exemplary amino acid sequence of a prefusion-stabilized SARS-COV-2 S protein of a beta variant |
| 56 | Exemplary RNA sequence encoding a prefusion-stabilized SARS-COV-2 S protein of a beta variant |
| 57 | Exemplary RNA sequence comprising a sequence encoding a prefusion-stabilized SARS-COV-2 S protein of a beta variant, along with 5' UTR, 3' UTR, and polyA sequences |
| 58 | Exemplary amino acid sequence of a prefusion-stabilized SARS-COV-2 S protein of an alpha variant |
| 59 | Exemplary RNA sequence encoding a prefusion-stabilized SARS-COV-2 S protein of an alpha variant |
| 60 | Exemplary RNA sequence comprising a sequence encoding a prefusion-stabilized SARS-COV-2 S protein of an alpha variant, along with 5' UTR, 3' UTR, and polyA sequences |
| 61 | Exemplary amino acid sequence of a prefusion-stabilized SARS-COV-2 S protein of a delta variant |
| 62 | Exemplary DNA sequence encoding a prefusion-stabilized SARS-COV-2 S protein of a delta variant |
| 63 | Exemplary dNA sequence comprising a sequence encoding a prefusion-stabilized SARS-COV-2 S protein of a delta variant, along with 5' UTR, 3' UTR, and polyA sequences |
| 64 | Exemplary amino acid sequence of a prefusion-stabilized SARS-COV-2 S protein of an Omicron BA.2 variant |
| 65 | Exemplary RNA sequence encoding a prefusion-stabilized SARS-COV-2 S protein of an Omicron BA.2 variant |
| 66 | Exemplary DNA sequence encoding a prefusion-stabilized SARS-COV-2 S protein of an Omicron BA.2 variant |
| 67 | Exemplary RNA sequence comprising a sequence encoding a prefusion-stabilized SARS-COV-2 S protein of an Omicron BA.2 variant, along with 5' UTR, 3' UTR, and polyA sequences |

TABLE 2-continued below, provides a short description of sequences provided in the sequence listing submitted herewith.

| SEQ ID NO | Description |
|---|---|
| 68 | Exemplary DNA sequence comprising a sequence encoding a prefusion-stabilized SARS-COV-2 S protein of an Omicron BA.2 variant, along with 5' UTR, 3' UTR, and polyA sequences |
| 69 | Exemplary amino acid sequence of a prefusion-stabilized SARS-COV-2 S protein of an Omicron BA.4/5 variant |
| 70 | Exemplary RNA sequence encoding a prefusion-stabilized SARS-COV-2 S protein of an Omicron BA.4/5 variant |
| 71 | Exemplary DNA sequence encoding a prefusion-stabilized SARS-COV-2 S protein of an Omicron BA.4/5 variant |
| 72 | Exemplary RNA sequence comprising a sequence encoding a prefusion-stabilized SARS-COV-2 S protein of an Omicron BA.4/5 variant, along with 5' UTR, 3' UTR, and polyA sequences |
| 73 | Exemplary DNA sequence comprising a sequence encoding a prefusion-stabilized SARS-COV-2 S protein of an Omicron BA.4/5 variant, along with 5' UTR, 3' UTR, and polyA sequences |
| 74 | Exemplary amino acid sequence of a SARS-COV-2 S protein of a BA.4/5 variant, comprising prefusion-stabilizing mutations |
| 75 | Exemplary RNA sequence encoding a prefusion-stabilized SARS-COV-2 S protein of an Omicron BA.4/5 variant |
| 76 | Exemplary DNA sequence encoding a prefusion-stabilized SARS-COV-2 S protein of an Omicron BA.4/5 variant |
| 77 | Exemplary amino acid sequence of a SARS-COV-2 S protein of a BA.4/5 variant, comprising prefusion-stabilizing mutations |
| 78 | Exemplary RNA sequence encoding a prefusion-stabilized SARS-COV-2 S protein of an Omicron BA.4/5 variant |
| 79 | Exemplary DNA sequence encoding a prefusion-stabilized SARS-COV-2 S protein of an Omicron BA.4/5 variant |
| 80 | Exemplary amino acid sequence of a prefusion-stabilized SARS-COV-2 S protein of an Omicron BA.2.75 variant |
| 81 | Exemplary RNA sequence encoding a prefusion-stabilized SARS-COV-2 S protein of an Omicron BA.2.75 variant |
| 82 | Exemplary DNA sequence encoding a prefusion-stabilized SARS-COV-2 S protein of an Omicron BA.2.75 variant |
| 83 | Exemplary RNA sequence comprising a sequence encoding a prefusion-stabilized SARS-COV-2 S protein of an Omicron BA.2.75 variant, along with 5' UTR, 3' UTR, and polyA sequences |
| 84 | Exemplary DNA sequence comprising a sequence encoding a prefusion-stabilized SARS-COV-2 S protein of an Omicron BA.2.75 variant, along with 5' UTR, 3' UTR, and polyA sequences |
| 85 | Exemplary amino acid sequence of a prefusion-stabilized SARS-COV-2 S protein of an Omicron BA.2.75.2 variant |
| 86 | Exemplary RNA sequence encoding a prefusion-stabilized SARS-COV-2 S protein of an Omicron BA.2.75.2 variant |
| 87 | Exemplary DNA sequence encoding a prefusion-stabilized SARS-COV-2 S protein of an Omicron BA.2.75.2 variant |
| 88 | Exemplary RNA sequence comprising a sequence encoding a prefusion-stabilized SARS-COV-2 S protein of an Omicron BA.2.75.2 variant, along with 5' UTR, 3' UTR, and polyA sequences |
| 89 | Exemplary DNA sequence comprising a sequence encoding a prefusion-stabilized SARS-COV-2 S protein of an Omicron BA.2.75.2 variant, along with 5' UTR, 3' UTR, and polyA sequences |
| 90 | Exemplary amino acid sequence of a prefusion-stabilized SARS-COV-2 S protein of an Omicron BA.4.6/BF.7 variant |
| 91 | Exemplary RNA sequence encoding a prefusion-stabilized SARS-COV-2 S protein of an Omicron BA.4.6/BF.7 variant |
| 92 | Exemplary DNA sequence encoding a prefusion-stabilized SARS-COV-2 S protein of an Omicron BA.4.6/BF.7 variant |
| 93 | Exemplary RNA sequence comprising a sequence encoding a prefusion-stabilized SARS-COV-2 S protein of an Omicron BA.4.6/BF.7 variant, along with 5' UTR, 3' UTR, and polyA sequences |
| 94 | Exemplary DNA sequence comprising a sequence encoding a prefusion-stabilized SARS-COV-2 S protein of an Omicron BA.4.6/BF.7 variant, along with 5' UTR, 3' UTR, and polyA sequences |
| 95 | Exemplary amino acid sequence of a prefusion-stabilized SARS-COV-2 S protein of an Omicron XBB variant |
| 96 | Exemplary RNA sequence encoding a prefusion-stabilized SARS-COV-2 S protein of an Omicron XBB variant |
| 97 | Exemplary DNA sequence encoding a prefusion-stabilized SARS-COV-2 S protein of an Omicron XBB variant |
| 98 | Exemplary RNA sequence comprising a sequence encoding a prefusion-stabilized SARS-COV-2 S protein of an Omicron XBB variant, along with 5' UTR, 3' UTR, and polyA sequences |
| 99 | Exemplary DNA sequence comprising a sequence encoding a prefusion-stabilized SARS-COV-2 S protein of an Omicron XBB variant, along with 5' UTR, 3' UTR, and polyA sequences |
| 100 | Exemplary amino acid sequence of a prefusion-stabilized SARS-COV-2 S protein of an Omicron BQ.1.1 variant |
| 101 | Exemplary RNA sequence encoding a prefusion-stabilized SARS-COV-2 S protein of an Omicron BQ.1.1 variant |
| 102 | Exemplary DNA sequence encoding a prefusion-stabilized SARS-COV-2 S protein of an Omicron BQ.1.1 variant |
| 103 | Exemplary RNA sequence comprising a sequence encoding a prefusion-stabilized SARS-COV-2 S protein of an Omicron BQ.1.1 variant, along with 5' UTR, 3' UTR, and polyA sequences |
| 104 | Exemplary DNA sequence comprising a sequence encoding a prefusion-stabilized SARS-COV-2 S protein of an Omicron BQ.1.1 variant, along with 5' UTR, 3' UTR, and polyA sequences |
| 105 | Exemplary HSV-1 gD signal peptide |
| 106 | Exemplary HSV-2 gD signal peptide |
| 107 | Exemplary HSV-2 signal peptide |
| 108 | Exemplary SARS-COV-2 Spike signal peptide |
| 109 | Exemplary human Ig heavy chain signal peptide (huSec) |
| 110 | Exemplary HuIgGk signal peptide |
| 111 | Exemplary IgE heavy chain epsilon-1 signal peptide |
| 112 | Exemplary Japanese encephalitis PRM signal sequence |
| 113 | Exemplary VSVg protein signal sequence |
| 114-119 | Exemplary signal peptides |
| 120 | Exemplary nucleotide sequence encoding an HSV-1 gD signal peptide |
| 121 | Exemplary nucleotide sequence encoding an HSV-1 gD signal peptide |
| 122 | Exemplary nucleotide sequence encoding a SARS-COV-2 Spike signal peptide |
| 123 | Exemplary nucleotide sequence encoding a human Ig heavy chain signal peptide (huSec) |
| 124 | Exemplary epitope in a Wuhan SARS-COV-2 S protein |
| 125 | Exemplary epitope in a SARS-COV-2 S protein of a delta variant comprising an L452R mutation |
| 126 | Exemplary epitope in SARS-COV-2 Wuhan strain RBD |
| 127 | Exemplary epitope in an RBD of a delta variant of SARS-CoV-2 |
| 128 | Exemplary epitope in an RBD of Omicron BA.1 and BA.4/5 variant of SARS-COV-2 |
| 129 | Exemplary amino acid sequence of an RBD of a SARS-COV-2 alpha variant |
| 130 | Exemplary amino acid sequence of an RBD of a SARS-COV-2 beta variant |
| 131 | Exemplary amino acid sequence of an RBD of a SARS-COV-2 delta variant |
| 132 | Exemplary amino acid sequence of an RBD of a SARS-COV-2 Omicron BA.1 variant |
| 133 | Exemplary amino acid sequence of an RBD of a SARS-COV-2 Omicron BA.4/5 variant |
| 134 | Exemplary GS linker |
| 135 | Exemplary GS linker |
| 136 | Furin cleavage site in SARS-COV-2 S protein |
| 137 | Exemplary nucleotide sequence encodign a furin cleavage site in SARS-COV-2 S protein |
| 152 | Exemplary DNA sequence encoding a prefusion-stabilized SARS-COV-2 S protein of an Beta variant |
| 153 | Exemplary DNA sequence comprising a sequence encoding a prefusion-stabilized SARS-COV-2 S protein of a Beta variant, along with 5' UTR, 3' UTR, and polyA sequences |

TABLE 2-continued below, provides a short description of sequences provided in the sequence listing submitted herewith.

| SEQ ID NO | Description |
|---|---|
| 154 | Exemplary DNA sequence encoding a prefusion-stabilized SARS-COV-2 S protein of an Alpha variant |
| 155 | Exemplary DNA sequence comprising a sequence encoding a prefusion-stabilized SARS-COV-2 S protein of an Alpha variant, along with 5' UTR, 3' UTR, and polyA sequences |
| 156 | Exemplary RNA sequence encoding a prefusion-stabilized SARS-COV-2 S protein of a Delta variant |
| 157 | Exemplary RNA sequence comprising a sequence encoding a prefusion-stabilized SARS-COV-2 S protein of a Delta variant, along with 5' UTR, 3' UTR, and polyA sequences |
| 158 | Exemplary amino acid sequence of a prefusion-stabilized SARS-COV-2 S protein of an Omicron XBB.1.5 variant |
| 159 | Exemplary RNA sequence encoding a prefusion-stabilized SARS-COV-2 S protein of an Omicron XBB.1.5 variant |
| 160 | Exemplary DNA sequence encoding a prefusion-stabilized SARS-COV-2 S protein of an Omicron XBB.1.5 variant |
| 161 | Exemplary RNA sequence comprising a sequence encoding a prefusion-stabilized SARS-COV-2 S protein of an Omicron XBB.1.5 variant, along with 5' UTR, 3' UTR, and polyA sequences |
| 162 | Exemplary DNA sequence comprising a sequence encoding a prefusion-stabilized SARS-COV-2 S protein of an Omicron XBB.1.5 variant, along with 5' UTR, 3' UTR, and polyA sequences |
| 163 | Exemplary amino acid sequence of a prefusion-stabilized SARS-COV-2 S protein of an Omicron XBB.1.16 variant |
| 164 | Exemplary RNA sequence encoding a prefusion-stabilized SARS-COV-2 S protein of an Omicron XBB.1.16 variant |
| 165 | Exemplary DNA sequence encoding a prefusion-stabilized SARS-COV-2 S protein of an Omicron XBB.1.16 variant |
| 166 | Exemplary RNA sequence comprising a sequence encoding a prefusion-stabilized SARS-COV-2 S protein of an Omicron XBB.1.16 variant, along with 5' UTR, 3' UTR, and polyA sequences |
| 167 | Exemplary DNA sequence comprising a sequence encoding a prefusion-stabilized SARS-COV-2 S protein of an Omicron XBB.1.16 variant, along with 5' UTR, 3' UTR, and polyA sequences |
| 168 | Exemplary amino acid sequence of a prefusion-stabilized SARS-COV-2 S protein of an Omicron XBB.2.3 variant |
| 169 | Exemplary RNA sequence encoding a prefusion-stabilized SARS-COV-2 S protein of an Omicron XBB.2.3 variant |
| 170 | Exemplary DNA sequence encoding a prefusion-stabilized SARS-COV-2 S protein of an Omicron XBB.2.3 variant |
| 171 | Exemplary RNA sequence comprising a sequence encoding a prefusion-stabilized SARS-COV-2 S protein of an Omicron XBB.2.3 variant, along with 5' UTR, 3' UTR, and polyA sequences |
| 172 | Exemplary DNA sequence comprising a sequence encoding a prefusion-stabilized SARS-COV-2 S protein of an Omicron XBB.2.3 variant, along with 5' UTR, 3' UTR, and polyA sequences |
| 173 | Exemplary amino acid sequence of a prefusion-stabilized SARS-COV-2 S protein of an Omicron XBB.2.3.2 variant |
| 174 | Exemplary RNA sequence encoding a prefusion-stabilized SARS-COV-2 S protein of an Omicron XBB.2.3.2 variant |
| 175 | Exemplary DNA sequence encoding a prefusion-stabilized SARS-COV-2 S protein of an Omicron XBB.2.3.2 variant |
| 176 | Exemplary RNA sequence comprising a sequence encoding a prefusion-stabilized SARS-COV-2 S protein of an Omicron XBB.2.3.2 variant, along with 5' UTR, 3' UTR, and polyA sequences |
| 177 | Exemplary DNA sequence comprising a sequence encoding a prefusion-stabilized SARS-COV-2 S protein of an Omicron XBB.2.3.2 variant, along with 5' UTR, 3' UTR, and polyA sequences |

We claim:

1. A composition comprising an RNA molecule having:
   (a) a nucleotide sequence that is at least 99% identical to SEQ ID NO: 161; or
   (b) a nucleotide sequence that is at least 95% identical to SEQ ID NO: 161, and which encodes a SARS-CoV-2 S protein comprising the following substitutions relative to SEQ ID NO: 1: T19I, Δ24-26, A27S, V83A, G142D, Δ145, H146Q, Q183E, V213E, G252V, G339H, R346T, L368I, S371F, S373P, S375F, T376A, D405N, R408S, K417N, N440K, V445P, G446S, N460K, S477N, T478K, E484A, F486P, F490S, Q498R, N501Y, Y505H, D614G, H655Y, N679K, P681H, N764K, D796Y, Q954H, N969K, K986P, and V987P; and
   wherein the RNA molecule comprises:
   (i) a 5' cap; and
   (ii) a modified uridine in place of each uridine.

2. The composition of claim 1, wherein the modified uridine is N1-methyl-pseudouridine.

3. The composition of claim 1, wherein the 5' cap comprises $m_2^{7,3'-O}Gppp(m_1^{2'-O})ApG$.

4. The composition of claim 1, wherein the RNA molecule has a nucleotide sequence as set forth in SEQ ID NO: 161.

5. The composition of claim 1, wherein the RNA molecule is encapsulated in a lipid nanoparticle (LNP).

6. The composition of claim 5, wherein the LNP comprises molar ratios of 20-60% ionizable cationic lipid, 5-25% neutral lipid, 25-55% sterol, and 0.5-15% PEG-modified lipid.

7. The composition of claim 1, wherein the composition comprises one or more additional RNA molecules, each having a nucleotide sequence encoding an S protein of a SARS-CoV-2 strain or variant that is not XBB.1.5.

8. The composition of claim 7, wherein the one or more additional RNA molecules comprise a sequence that has at least 95% identical to SEQ ID NO: 20, 72, or 103.

9. A composition comprising an RNA molecule having a nucleotide sequence as set forth in SEQ ID NO: 161, wherein the RNA molecule comprises:
   (i) N1-methyl-pseudouridine in place of each uridine; and
   (ii) a 5' cap that comprises $m_2^{7,3'-O}Gppp(m_1^{2'-O})ApG$;
   wherein the RNA molecule is encapsulated in a lipid nanoparticle (LNP); and
   wherein the LNP comprises molar ratios of 20-60% ionizable cationic lipid, 5-25% neutral lipid, 25-55% sterol, and 0.5-15% PEG-modified lipid.

10. The composition of claim 9, comprising about 10 mM Tris buffer and about 10% sucrose.

11. The composition of claim 9, wherein the composition is formulated as a multi-dose formulation in a vial.

12. A method of inducing an immune response against coronavirus in a subject, comprising administering to a subject the composition of claim 1.

13. The method of claim 12, wherein the RNA molecule comprises N1-methyl-pseudouridine in place of each uridine.

14. The method of claim 12, wherein the 5' cap comprises $m_2^{7,3'-O}Gppp(m_1^{2'-O})ApG$.

15. The method of claim 12, wherein the RNA molecule is encapsulated in an LNP and wherein the LNP comprises molar ratios of 20-60% ionizable cationic lipid, 5-25% neutral lipid, 25-55% sterol, and 0.5-15% PEG-modified lipid.

16. The method of claim 15, wherein the subject is 12 years or older, and the composition comprises 30 μg of the RNA molecule.

17. The method of claim 15, wherein the subject is 5 years to less than 12 years old, and the composition comprises 10 μg of the RNA molecule.

18. The method of claim 15, wherein the subject is 6 months to less than 5 years old, and the composition comprises 3 μg of the RNA molecule.

19. The method of claim 15, wherein the composition is administered in a volume of about 200 μL to 300 μL.

20. The method of claim 15, wherein the subject was previously administered one or more doses of a SARS-CoV-2 vaccine.

21. The method of claim 20, wherein the subject was previously administered a complete dosing regimen of a SARS-CoV-2 vaccine.

22. The method of claim 15, wherein the subject was previously administered a first dose and a second dose of BNT162b2, wherein the first dose and the second dose were administered about 21 days apart.

23. The method of claim 22, wherein the subject was previously administered as a booster dose a bivalent vaccine that delivers (i) a SARS-CoV-2 S protein of an Omicron BA.4/5 variant and (ii) a SARS-CoV-2 S protein of a Wuhan strain.

24. The method of claim 15, further comprising co-administering one or more vaccines against a non-SARS-CoV-2 disease.

25. The method of claim 24, wherein the one or more vaccines comprise an RSV vaccine, an influenza vaccine, or a combination thereof.

26. A composition comprising at least one unit dose of LNP-encapsulated RNA molecules, wherein the composition comprises:
   a population of LNPs encapsulating RNA molecules, wherein:
      the LNPs comprise an ionizable cationic lipid, a neutral lipid, a sterol, and a PEG-modified lipid in molar ratios of 20-60%, 5-25%, 25-55%, and 0.5-15%, respectively; and
      each LNP in the population encapsulates at least an RNA molecule, wherein the RNA molecule comprises
         (a) a nucleotide sequence that is at least 99% identical to SEQ ID NO: 161; or
         (b) a nucleotide sequence that is at least 95% identical to SEQ ID NO: 161, and which comprises a nucleotide sequence that encodes a SARS-CoV-2 protein comprising the following substitutions relative to SEQ ID NO: 1: T19I, Δ24-26, A27S, V83A, G142D, Δ145, H146Q, Q183E, V213E, G252V, G339H, R346T, L368I, S371F, S373P, S375F, T376A, D405N, R408S, K417N, N440K, V445P, G446S, N460K, S477N, T478K, E484A, F486P, F490S, Q498R, N501Y, Y505H, D614G, H655Y, N679K, P681H, N764K, D796Y, Q954H, N969K, K986P, and V987P;
         (b) N1-methyl-pseudouridine in place of each uridine; and
         (c) a 5' cap that comprises $m_2^{7,3'-O}Gppp(m_1^{2'-O})ApG$.

27. The composition of claim 26, comprising about 10 mM Tris buffer and about 10% sucrose.

28. The composition of claim 26, wherein the unit dose comprises the RNA molecule in an amount of about 30 μg.

29. The composition of claim 26, wherein the unit dose comprises the RNA molecule in an amount of about 10 μg.

30. The composition of claim 26, wherein the unit dose comprises the RNA molecule in an amount of about 3 μg.

\* \* \* \* \*